(12) United States Patent
Heald et al.

(10) Patent No.: US 8,653,089 B2
(45) Date of Patent: Feb. 18, 2014

(54) HETEROCYCLIC COMPOUNDS AND METHODS OF USE

(75) Inventors: Robert Heald, Harlow (GB); Stephen Price, Harlow (GB); Brian Safina, South San Francisco, CA (US); Pascal Pierre Alexandre Savy, Harlow (GB); Eileen Mary Seward, Harlow (GB); Daniel P. Sutherlin, Burlingame, CA (US); Bohdan Waszkowycz, Harlow (GB)

(73) Assignee: F. Hoffmann-La Roche AG, Basel (CH)

( * ) Notice: Subject to any disclaimer, the term of this patent is extended or adjusted under 35 U.S.C. 154(b) by 0 days.

(21) Appl. No.: 13/369,016

(22) Filed: Feb. 8, 2012

(65) Prior Publication Data

US 2012/0202785 A1    Aug. 9, 2012

Related U.S. Application Data

(60) Provisional application No. 61/441,014, filed on Feb. 9, 2011.

(51) Int. Cl.
  *A61K 31/52* (2006.01)
  *C07D 473/00* (2006.01)

(52) U.S. Cl.
  USPC ..................... 514/263.21; 544/277

(58) Field of Classification Search
  USPC ........................................................ 544/277
  See application file for complete search history.

(56) References Cited

U.S. PATENT DOCUMENTS

| | | | |
|---|---|---|---|
| 4,146,716 A | 3/1979 | Cox et al. | |
| 4,714,764 A | 12/1987 | Sato et al. | |
| 4,740,230 A | 4/1988 | Takematsu et al. | |
| 4,818,761 A | 4/1989 | Sato et al. | |
| 4,932,998 A | 6/1990 | Takematsu et al. | |
| 6,696,437 B1 | 2/2004 | Lubisch et al. | |
| 7,129,244 B2 * | 10/2006 | Kasibhatla et al. | 514/261.1 |
| 7,138,402 B2 | 11/2006 | Kasibhatla et al. | |
| 7,285,558 B2 * | 10/2007 | Basarab et al. | 514/262.1 |
| 7,846,929 B2 | 12/2010 | Folkes et al. | |
| 8,158,625 B2 | 4/2012 | Castanedo et al. | |
| 8,173,650 B2 | 5/2012 | Castanedo et al. | |
| 2004/0019058 A1 | 1/2004 | Bridger et al. | |
| 2008/0076758 A1 | 3/2008 | Folkes et al. | |
| 2008/0076774 A1 * | 3/2008 | Anand et al. | 514/252.02 |
| 2008/0090861 A1 | 4/2008 | Barrett et al. | |
| 2011/0230464 A1 | 9/2011 | Goldsmith et al. | |
| 2011/0245257 A1 * | 10/2011 | Cushing et al. | 514/249 |

FOREIGN PATENT DOCUMENTS

| | | | | |
|---|---|---|---|---|
| WO | 2005/039506 A2 | 5/2005 | | |
| WO | 2006/020415 | 2/2006 | | |
| WO | 2008/039882 A1 | 4/2008 | | |
| WO | 2008/152394 A1 | 12/2008 | | |
| WO | 2009/034386 A1 | 3/2009 | | |
| WO | 2009/081112 A2 | 7/2009 | | |
| WO | WO 2009/143317 A1 * | 11/2009 | ........... | C07D 498/08 |
| WO | 2011/123751 A2 | 10/2011 | | |
| WO | 2011/163195 A1 | 12/2011 | | |

OTHER PUBLICATIONS

Wermuth, Camille. Molecular Variations Based on Isoteric Replacements. The Practice of Medicinal Chemistry. Academic Press, 1996. pp. 203-237.*
Che et al., "Synthesis of novel pyrimidine fused 8-membered heterocycles via iminium ion cyclization reactions" J Org Chem. 73(3):1147-9 (2008).
Danopoulos et al., "Cu(II) and Pd(II) complexes with adenine and histidine derivatives" Inorg. Chim. Acta 55:141-45 (1981).
Galal et al., "Synthesis and antitumor activity of novel benzimidazole-5-carboxylic acid derivatives and their transition metal complexes as topoisomerease II inhibitors" Eur J Med Chem. 45(12):5685-91 (2010).
Andricopulo et al., "Structure-activity relationships for a collection of structurally diverse inhibitors of purine nucleoside" Chem Pharm Bull 49(1):10-7 (2001).
Gadhachanda et al., "4-Aminopyrimidines as novel HIV-1 inhibitors" Bioorg Med Chem Lett. 17(1):260-5 (2007).
Yadava et al., "One-Pot Synthesis of Purinylpurine-2,6-Diones" Heterocycles 75(6):1489-92 (2008).

* cited by examiner

*Primary Examiner* — Noble Jarrell
*Assistant Examiner* — Laura Daniel
(74) *Attorney, Agent, or Firm* — Alex Andrus; Genentech, Inc.

(57) ABSTRACT

Formula I compounds, including stereoisomers, geometric isomers, tautomers, metabolites and pharmaceutically acceptable salts thereof, are useful for inhibiting the delta isoform of PI3K, and for treating disorders mediated by lipid kinases such as inflammation, immunological disorders, and cancer. Methods of using compounds of Formula I for in vitro, in situ, and in vivo diagnosis, prevention or treatment of such disorders in mammalian cells, or associated pathological conditions, are disclosed.

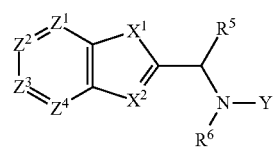

3 Claims, No Drawings

HETEROCYCLIC COMPOUNDS AND METHODS OF USE

CROSS REFERENCE TO RELATED APPLICATIONS

This non-provisional application filed under 37 CFR §1.53 (b), claims the benefit under 35 USC §119(e) of U.S. Provisional Application Ser. No. 61/441,014 filed on 9 Feb. 2011, which is incorporated by reference in entirety

FIELD OF THE INVENTION

The invention relates generally to compounds for treating disorders mediated by lipid kinases such as inflammation, immunological, and cancer, and more specifically to compounds which inhibit PI3 kinase activity. The invention also relates to methods of using the compounds for in vitro, in situ, and in vivo diagnosis or treatment of mammalian cells, or associated pathological conditions.

BACKGROUND OF THE INVENTION

Phosphatidylinositol (PI), a phospholipid found in cell membranes, plays an important role in intracellular signal transduction. Cell signaling via 3'-phosphorylated phosphoinositides has been implicated in a variety of cellular processes, e.g., malignant transformation, growth factor signaling, inflammation, and immunity (Rameh et al (1999) J. Biol Chem, 274:8347-8350). The enzyme responsible for generating these phosphorylated signaling products, phosphatidylinositol 3-kinase (also referred to as PI 3-kinase or PI3K), was originally identified as an activity associated with viral oncoproteins and growth factor receptor tyrosine kinases that phosphorylate phosphatidylinositol (PI) and its phosphorylated derivatives at the 3'-hydroxyl of the inositol ring (Panayotou et al (1992) Trends Cell Biol 2:358-60).

Phosphoinositide 3-kinases (PI3K) are lipid kinases that phosphorylate lipids at the 3-hydroxyl residue of the inositol ring of phosphoinositols (Whitman et al (1988) Nature, 332:664). The 3'-phosphorylated phospholipids (PIP3s) generated by PI3-kinases act as second messengers recruiting kinases with lipid binding domains (including plekstrin homology (PH) regions), such as Akt and phosphoinositide-dependent kinase-1 (PDK1). Binding of Akt to membrane PIP3s causes the translocation of Akt to the plasma membrane, bringing Akt into contact with PDK1, which is responsible for activating Akt. The tumor-suppressor phosphatase, PTEN, dephosphorylates PIP3 and therefore acts as a negative regulator of Akt activation. The PI3-kinases Akt and PDK1 are important in the regulation of many cellular processes including cell cycle regulation, proliferation, survival, apoptosis and motility and are significant components of the molecular mechanisms of diseases such as cancer, diabetes and immune inflammation (Vivanco et al (2002) Nature Rev. Cancer 2:489; Phillips et al (1998) Cancer 83:41).

PI3 kinase is a heterodimer consisting of p85 and p110 subunits (Otsu et al (1991) Cell 65:91-104; Hiles et al (1992) Cell 70:419-29). Four distinct Class I PI3Ks have been identified, designated PI3K α (alpha), β (beta), δ (delta), and γ (gamma), each consisting of a distinct 110 kDa catalytic subunit and a regulatory subunit. More specifically, three of the catalytic subunits, i.e., p110 alpha, p110 beta and p110 delta, each interact with the same regulatory subunit, p85; whereas p110 gamma interacts with a distinct regulatory subunit, p101. The patterns of expression of each of these PI3Ks in human cells and tissues are also distinct.

The p110 delta isoform has been implicated in biological functions related to immune-inflammatory diseases, including signaling from the B-cell receptor, T cell receptor, FcR signaling of mast cells and monocyte/macrophage, and osteoclast function/RANKL signaling (Berndt et al (2010) Nature Chemical Biology; Williams et al (2010) Chem. & Biol. 17:123-134; Chantry et al (1997) Jour. of Biol. Chem. 272 (31):19236-19241; Deane J and Fruman D A (2004) Annu Rev. Immunol. 2004. 22:563-98; Janas et al. (2008) The Journal of Immunology, 180:739-746; Marone R et al. (2007) Biochim. Biophy. Acta, 1784:159-185. Deletion of the PI3K delta gene or selective introduction of a catalytically inactive mutant of PI3K delta causes a nearly complete ablation of B cell proliferation and signaling, and impairment of signaling through T cells as well.

SUMMARY OF THE INVENTION

The invention relates to heterocyclic, including 4-substituted pyrimidine, compounds of Formula I with PI3 kinase inhibitory activity and selective binding to the p110 delta isoform relative to binding to the p110 alpha isoform.

Formula I compounds have the structures:

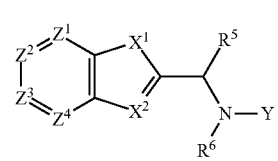

and stereoisomers, geometric isomers, tautomers, and pharmaceutically acceptable salts thereof. The various substituents are as defined herein.

Another aspect of the invention provides a pharmaceutical composition comprising a Formula I compound and a pharmaceutically acceptable carrier, glidant, diluent, or excipient.

Another aspect of the invention provides the pharmaceutical composition further comprising a chemotherapeutic agent.

Another aspect of the invention provides a process for making a pharmaceutical composition which comprises combining a compound of Formula I with a pharmaceutically acceptable carrier.

Another aspect of the invention provides the use of a Formula I compound in the manufacture of a medicament for treating a disease or disorder selected from cancer, immune disorders, cardiovascular disease, viral infection, inflammation, metabolism/endocrine function disorders and neurological disorders, and mediated by PI3 kinase including by selective inhibition of the p110 delta isoform.

The invention also relates to methods of using the Formula I compounds for in vitro, in situ, and in vivo diagnosis or treatment of mammalian cells, organisms, or associated pathological conditions, such as cancer, systemic and local inflammation, immune-inflammatory diseases such as rheumatoid arthritis, immune suppression, organ transplant rejection, allergies, ulcerative colitis, Crohn's disease, dermatitis, asthma, systemic lupus erythematosus, Sjögren's Syndrome, multiple sclerosis, scleroderma/systemic sclerosis, idiopathic thrombocytopenic purpura (ITP), anti-neutrophil cytoplasmic antibodies (ANCA) vasculitis, chronic obstructive pulmonary disease (COPD), psoriasis, and for general joint protective effects.

Another aspect of the invention provides a method of treating a disease or disorder which method comprises administering a Formula I compound to a patient with a disease or disorder selected from cancer, immune disorders, cardiovascular disease, viral infection, inflammation, metabolism/endocrine function disorders and neurological disorders, and mediated by the p110 delta, beta, or alpha isoform of PI3 kinase. In another aspect the disease or disorder is an immune disorder. The method may further comprise administering an additional therapeutic agent selected from a chemotherapeutic agent, an anti-inflammatory agent, an immunomodulatory agent, a neurotropic factor, an agent for treating cardiovascular disease, an agent for treating liver disease, an anti-viral agent, an agent for treating blood disorders, an agent for treating diabetes, and an agent for treating immunodeficiency disorders.

The methods of treating cancer include where the cancer is breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, pancreatic, myeloid disorders, lymphoma, hairy cells, buccal cavity, naso-pharyngeal, pharynx, lip, tongue, mouth, small intestine, colon-rectum, large intestine, rectum, brain and central nervous system, Hodgkin's, leukemia, bronchus, thyroid, liver and intrahepatic bile duct, hepatocellular, gastric, glioma/glioblastoma, endometrial, melanoma, kidney and renal pelvis, urinary bladder, uterine corpus, uterine cervix, multiple myeloma, acute myelogenous leukemia, chronic lymphoid leukemia, chronic myelogenous leukemia, lymphocytic leukemia, myeloid leukemia, oral cavity and pharynx, non-Hodgkin lymphoma, melanoma, or villous colon adenoma.

In another embodiment the disease or disorder is systemic and local inflammation, arthritis including rheumatoid arthritis, inflammation related to immune suppression, organ transplant rejection, allergies, ulcerative colitis, Crohn's disease, dermatitis, asthma, systemic lupus erythematosus, Sjögren's Syndrome, multiple sclerosis, scleroderma/systemic sclerosis, idiopathic thrombocytopenic purpura (ITP), anti-neutrophil cytoplasmic antibodies (ANCA) vasculitis, chronic obstructive pulmonary disease (COPD), psoriasis.

Another aspect of the invention provides a kit for treating a condition mediated by the p110 delta isoform of PI3 kinase, comprising a first pharmaceutical composition comprising a Formula I compound; and instructions for use.

Other aspects of the invention include: (i) method for preventing or treating conditions, disorders or diseases mediated by the activation of the PI3K kinase enzyme, in a subject in need of such treatment, which method comprises administering to said subject an effective amount of a compound of Formula I or a pharmaceutically acceptable salt thereof, in free form or in a pharmaceutically acceptable salt form as a pharmaceutical, in any of the methods as indicated herein; (ii) a compound of the Formula I in free form or in pharmaceutically acceptable salt form for use as a pharmaceutical in any of the methods described herein, in particular for the use in one or more phosphatidylinositol 3-kinase (PI3K) mediated diseases; (iii) the use of a compound of Formula I in free form or in pharmaceutically acceptable salt form in any of the methods as indicated herein, in particular for the treatment of one or more phosphatidylinositol 3-kinase mediated diseases; (iv) the use of a compound of Formula I in free form or in pharmaceutically acceptable salt form in any of the methods as indicated herein, in particular for the manufacture of a medicament for the treatment of one or more phosphatidylinositol 3-kinase mediated diseases.

DETAILED DESCRIPTION OF EXEMPLARY EMBODIMENTS

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

DEFINITIONS

The term "alkyl" as used herein refers to a saturated linear or branched-chain monovalent hydrocarbon radical of one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (1-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, 1-heptyl, 1-octyl, and the like.

The term "alkylene" as used herein refers to a saturated linear or branched-chain divalent hydrocarbon radical of one to twelve carbon atoms ($C_1$-$C_{12}$), wherein the alkylene radical may be optionally substituted independently with one or more substituents described below. In another embodiment, an alkylene radical is one to eight carbon atoms ($C_1$-$C_8$), or one to six carbon atoms ($C_1$-$C_6$). Examples of alkylene groups include, but are not limited to, methylene (—$CH_2$—), ethylene (—$CH_2CH_2$—), propylene (—$CH_2CH_2CH_2$—), and the like.

The term "alkenyl" refers to linear or branched-chain monovalent hydrocarbon radical of two to eight carbon atoms ($C_2$-$C_8$) with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH=$CH_2$), allyl (—$CH_2$CH=$CH_2$), and the like.

The term "alkenylene" refers to linear or branched-chain divalent hydrocarbon radical of two to eight carbon atoms ($C_2$-$C_8$) with at least one site of unsaturation, i.e., a carbon-carbon, $sp^2$ double bond, wherein the alkenyl radical may be optionally substituted, and includes radicals having "cis" and "trans" orientations, or alternatively, "E" and "Z" orientations. Examples include, but are not limited to, ethylenylene or vinylene (—CH=CH—), allyl (—$CH_2$CH=CH—), and the like.

The term "alkynyl" refers to a linear or branched monovalent hydrocarbon radical of two to eight carbon atoms ($C_2$-$C_8$) with at least one site of unsaturation, i.e., a carbon-carbon, sp triple bond, wherein the alkynyl radical may be optionally substituted independently with one or more substituents described herein. Examples include, but are not limited to, ethynyl (—C≡CH), propynyl (propargyl, —$CH_2$C≡CH), and the like.

The term "alkynylene" refers to a linear or branched divalent hydrocarbon radical of two to eight carbon atoms ($C_2$-$C_8$) with at least one site of unsaturation, i.e., a carbon-carbon, sp triple bond, wherein the alkynyl radical may be optionally. Examples include, but are not limited to, ethynylene (—C≡C—), propynylene (propargylene, —$CH_2$C≡C—), and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, adamantanyl, and the like.

"Aryl" means a monovalent aromatic hydrocarbon radical of 6-20 carbon atoms ($C_6$-$C_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

"Arylene" means a divalent aromatic hydrocarbon radical of 6-20 carbon atoms ($C_6$-$C_{20}$) derived by the removal of two hydrogen atom from a two carbon atoms of a parent aromatic ring system. Some arylene groups are represented in the exemplary structures as "Ar". Arylene includes bicyclic radicals comprising an aromatic ring fused to a saturated, partially unsaturated ring, or aromatic carbocyclic ring. Typical arylene groups include, but are not limited to, radicals derived from benzene (phenylene), substituted benzenes, naphthalene, anthracene, biphenylene, indenylene, indanylene, 1,2-dihydronaphthalene, 1,2,3,4-tetrahydronaphthyl, and the like. Arylene groups are optionally substituted.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, piperidonyl, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, dihydroisoquinolinyl, tetrahydroisoquinolinyl, pyrazolidinylimidazolinyl, imidazolidinyl, 2-oxa-5-azabicyclo[2.2.2]octane, 3-oxa-8-azabicyclo[3.2.1]octane, 8-oxa-3-azabicyclo[3.2.1]octane, 6-oxa-3-azabicyclo[3.1.1]heptane, 2-oxa-5-azabicyclo[2.2.1]heptane, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 1 or 2 ring carbon atoms are substituted with oxo (=O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Ring nitrogen atoms of the heterocycle or heteroaryl groups may be bonded with oxygen to form N-oxides.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, benzimidazole, position 2 of a isoindole, or isoindoline, position 4 of a morpholine, and position 9 of a carbazole, or β-carboline.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

"Inflammatory disorder" as used herein can refer to any disease, disorder, or syndrome in which an excessive or unregulated inflammatory response leads to excessive inflammatory symptoms, host tissue damage, or loss of tissue function. "Inflammatory disorder" also refers to a pathological state mediated by influx of leukocytes and/or neutrophil chemotaxis.

"Inflammation" as used herein refers to a localized, protective response elicited by injury or destruction of tissues, which serves to destroy, dilute, or wall off (sequester) both the injurious agent and the injured tissue. Inflammation is notably associated with influx of leukocytes and/or neutrophil chemotaxis. Inflammation can result from infection with pathogenic organisms and viruses and from noninfectious means such as trauma or reperfusion following myocardial infarction or stroke, immune response to foreign antigen, and autoimmune responses. Accordingly, inflammatory disorders amenable to treatment with Formula I compounds encompass disorders associated with reactions of the specific defense system as well as with reactions of the nonspecific defense system.

"Specific defense system" refers to the component of the immune system that reacts to the presence of specific antigens. Examples of inflammation resulting from a response of the specific defense system include the classical response to foreign antigens, autoimmune diseases, and delayed type hypersensitivity response mediated by T-cells. Chronic inflammatory diseases, the rejection of solid transplanted tissue and organs, e.g., kidney and bone marrow transplants, and graft versus host disease (GVHD), are further examples of inflammatory reactions of the specific defense system.

The term "nonspecific defense system" as used herein refers to inflammatory disorders that are mediated by leukocytes that are incapable of immunological memory (e.g., granulocytes, and macrophages). Examples of inflammation that result, at least in part, from a reaction of the nonspecific defense system include inflammation associated with conditions such as adult (acute) respiratory distress syndrome (ARDS) or multiple organ injury syndromes; reperfusion injury; acute glomerulonephritis; reactive arthritis; dermatoses with acute inflammatory components; acute purulent meningitis or other central nervous system inflammatory disorders such as stroke; thermal injury; inflammatory bowel disease; granulocyte transfusion associated syndromes; and cytokine-induced toxicity.

"Autoimmune disease" as used herein refers to any group of disorders in which tissue injury is associated with humoral or cell-mediated responses to the body's own constituents.

"Allergic disease" as used herein refers to any symptoms, tissue damage, or loss of tissue function resulting from allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies. "Transplant rejection" as used herein refers to any immune reaction directed against grafted tissue, such as organs or cells (e.g., bone marrow), characterized by a loss of function of the grafted and surrounding tissues, pain, swelling, leukocytosis, and thrombocytopenia. The therapeutic methods of the present invention include methods for the treatment of disorders associated with inflammatory cell activation.

"Inflammatory cell activation" refers to the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatibility antigens or cell adhesion molecules) in inflammatory cells (including but not limited to monocytes, macrophages, T lymphocytes, B lymphocytes, granulocytes (i.e., polymorphonuclear leukocytes such as neutrophils, basophils, and eosinophils), mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory disorder.

The term "NSAID" is an acronym for "non-steroidal anti-inflammatory drug" and is a therapeutic agent with analgesic, antipyretic (lowering an elevated body temperature and relieving pain without impairing consciousness) and, in higher doses, with anti-inflammatory effects (reducing inflammation). The term "non-steroidal" is used to distinguish these drugs from steroids, which (among a broad range of other effects) have a similar eicosanoid-depressing, anti-inflammatory action. As analgesics, NSAIDs are unusual in that they are non-narcotic. NSAIDs include aspirin, ibuprofen, and naproxen. NSAIDs are usually indicated for the treatment of acute or chronic conditions where pain and inflammation are present. NSAIDs are generally indicated for the symptomatic relief of the following conditions: rheumatoid arthritis, osteoarthritis, inflammatory arthropathies (e.g. ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic. Most NSAIDs act as non-selective inhibitors of the enzyme cyclooxygenase, inhibiting both the cyclooxygenase-1 (COX-1) and cyclooxygenase-2 (COX-2) isoenzymes. Cyclooxygenase catalyzes the formation of prostaglandins and thromboxane from arachidonic acid (itself derived from the cellular phospholipid bilayer by phospholipase $A_2$). Prostaglandins act (among other things) as messenger molecules in the process of inflammation. COX-2 inhibitors include celecoxib, etoricoxib, lumiracoxib, parecoxib, rofecoxib, rofecoxib, and valdecoxib.

The terms "cancer" refers to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, head and neck cancer, multiple myeloma, acute myelogenous leukemia, chronic lymphoid leukemia, chronic myelogenous leukemia, lymphocytic leukemia, myeloid leukemia, oral cavity and pharynx, non-Hodgkin lymphoma, melanoma, and villous colon adenoma A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy. Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, II), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gamma1I, calicheamicin omega1I (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG™, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the PI3K inhibitors of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

The term "hematopoietic malignancy" refers to a cancer or hyperproliferative disorder generated during hematopoiesis involving cells such as leukocytes, lymphocytes, natural killer cells, plasma cells, and myeloid cells such as neutrophils and monocytes. Hematopoietic Malignancies include the diseases listed in the WHO classification of Human Hematopoietic Malignancies; Tumors of Hematopoietic and Lymphoid Tissues (Jaffe E. S., Harris N. L., Stein H., Vardiman J. W. (Eds.) (2001): World Health Organization Classification of Tumours. Pathology and Genetics of Tumours of Hematopoietic and Lymphoid Tissues. IARC Press: Lyon) with the morphology code of the International Classification of Diseases (ICD-O). Behavior is coded/3 for malignant tumors and/1 for lesions of low or uncertain malignant potential.

Hematopoietic Malignancies Include:
I. CHRONIC MYELOPROLIFERATIVE DISEASES
  Chronic myelogenous leukemia—ICD-O 9875/3
  Chronic neutrophilic leukemia—ICD-O 9963/3
  Chronic eosinophilic leukemia/hypereosinophilic syndrome—ICD-O 9964/3
  Polycythemia vera—ICD-O 9950/3
  Chronic idiopathic myelofibrosis—ICD-O 9961/3
  Essential thrombocytemia—ICD-O 9962/3
  Chronic Myeloproliferative disease, unclassifiable—ICD-O 9975/3
II. MYELODYSPLASTIC/MYELOPROLIFERATIVE DISEASES
  Chronic myelomonocytic leukemia—ICD-O 9980/3
  Atypical chronic myelogenous leukemia—ICD-O 9876/3
  Juvenile myelomonocytic leukemia—ICD-O 9946/3

Myelodysplastic/myeloproliferative diseases, unclassifiable—ICD-O 9975/3

III. MYELODYSPLASTIC SYNDROMES

Refractory anemia—ICD-O 9980/3
Refractory anemia with ringed sideroblasts—ICD-O 9982/3
Refractory cytopenia with multilineage dysplasia—ICD-O 9985/3
Refractory anemia with excess blasts—ICD-O 9983/3
Myelodysplastic syndrome associated with isolated del (5q) chromosome abnormality—ICD-O 9986/3
Myelodysplastic syndrome, unclassifiable 9989/3

IV. ACUTE MYELOID LEUKEMIAS

Acute myeloid leukemias with recurrent cytogenetic abnormalities
AML with t(8;21)(q22;q22), AML1/ETO—ICD-O 9896/3
AML with inv(16)(p13q22) or t(16;16)(p13;q22), CBFb/MYH11—ICD-O 9871/3
Acute promyelocytic leukemia (AML with t(15;17)(q22;q12), PML-RARa and variants)—ICD-O 9866/3
AML with 11q23 (MLL) abnormalities—ICD-O 9897/3
Acute myeloid leukemia multilineage dysplasia—ICD-O 9895/3
Acute myeloid leukemia and myelodysplastic syndrome, therapy related—ICD-O 9920/3
Acute myeloid leukemia not otherwise categorised
Acute myeloid leukemia, minimally differentiated—ICD-O 9872/3
Acute myeloid leukemia, without maturation—ICD-O 9873/3
Acute myeloid leukemia, with maturation—ICD-O 9874/3
Acute myelomonocytic leukemia—ICD-O 9867/3
Acute monoblastic and monocytic leukemia—ICD-O 9891/3
Acute erythroid leukemia—ICD-O 9840/3
Acute megakaryoblastic leukemia—ICD-O 9910/3
Acute basophilic leukemia—ICD-O 9870/3
Acute panmyelosis with myelofibrosis—ICD-O 9931/3
Myeloid sarcoma—ICD-O 9930/3
Acute leukemia of ambiguous lineage—ICD-O 9805/3

V. B-CELL NEOPLASMS

Precursor hematopoietic neoplasm
Precursor B lymphoblastic leukemia/—ICD-O 9835/3
lymphoma—ICD-O 9728/3
Mature hematopoietic neoplasm
Chronic lymphocytic leukemia/—ICD-O 9823/3
small lymphocytic lymphoma—ICD-O 9670/3
hematopoietic prolymphocytic leukemia—ICD-O 9833/3
Lymphoplasmacytic lymphoma—ICD-O 9671/3
Splenic marginal zone lymphoma—ICD-O 9689/3
Hairy cell leukemia—ICD-O 9940/3
Plasma cell myeloma—ICD-O 9732/3
Solitary plasmacytoma of bone—ICD-O 9731/3
Extraosseous plasmacytoma—ICD-O 9734/3
Extranodal marginal zone hematopoietic lymphoma of mucosa-associated lymphoid tissue (MALT-lymphoma)—ICD-O 9699/3
Nodal marginal zone hematopoietic lymphoma—ICD-O 9699/3
Follicular lymphoma—ICD-O 9690/3
Mantle cell lymphoma—ICD-O 9673/3
Diffuse large hematopoietic lymphoma—ICD-O 9680/3
Mediastinal (thymic) large cell lymphoma—ICD-O 9679/3
Intravascular large hematopoietic lymphoma—ICD-O 9680/3
Primary effusion lymphoma—ICD-O 9678/3
Burkitt lymphoma/—ICD-O 9687/3
leukemia—ICD-O 9826/3
hematopoietic proliferations of uncertain malignant potential
Lymphomatoid granulomatosis—ICD-O 9766/1
Post-transplant lymphoproliferative disorder, pleomorphic—ICD-O 9970/1

VI. T-CELL AND NK-CELL NEOPLASMS

Precursor T-cell neoplasms
Precursor T lymphoblastic leukemia/—ICD-O 9837/3
lymphoma—ICD-O 9729/3
Blastic NK cell lymphoma—ICD-O 9727/3
Mature T-cell and NK-cell neoplasms
T-cell prolymphocytic leukemia—ICD-O 9834/3
T-cell large granular lymphocytic leukemia—ICD-O 9831/3
Aggressive NK cell leukemia—ICD-O 9948/3
Adult T-cell leukemia/lymphoma—ICD-O 9827/3
Extranodal NK/T cell lymphoma, nasal type—ICD-O 9719/3
Enteropathy type T-cell lymphoma—ICD-O 9717/3
Hepatosplenic T-cell lymphoma—ICD-O 9716/3
Subcutaneous panniculitis-like T-cell lymphoma—ICD-O 9708/3
Mycosis fungoides—ICD-O 9700/3
Sezary Syndrome—ICD-O 9701/3
Primary cutaneous anaplastic large cell lymphoma—ICD-O 9718/3
Peripheral T-cell lymphoma, unspecified—ICD-O 9702/3
Angioimmunoblastic T-cell lymphoma—ICD-O 9705/3
Anaplastic large cell lymphoma—ICD-O 9714/3
T-cell proliferation of uncertain malignant potential
Lymphomatoid papulosis—ICD-O 9718/1

VII. HODGKIN LYMPHOMA

Nodular lymphocyte predominant Hodgkin lymphoma—ICD-O 9659/3
Classical Hodgkin lymphoma—ICD-O 9650/3
Nodular sclerosis classical Hodgkin lymphoma—ICD-O 9663/3
Lymphocyte-rich classical Hodgkin lymphoma—ICD-O 9651/3
Mixed cellularity classical Hodgkin lymphoma—ICD-O 9652/3
Lymphocyte-depleted classical Hodgkin lymphoma—ICD-O 9653/3

VIII. HISTIOCYTIC AND DENDRITIC-CELL NEOPLASMS

Macrophage/histiocytic neoplasm
Histiocytic sarcoma—ICD-O 9755/3
Dendritic cell neoplasms
Langerhans cell histiocytosis—ICD-O 9751/1
Langerhans cell sarcoma—ICD-O 9756/3
Interdigitating dendritic cell sarcoma/tumor—ICD-O 9757/3/1
Follicular dendritic cell sarcoma/tumor—ICD-O 9758/3/1
Dendritic cell sarcoma, not otherwise specified—ICD-O 9757/3

IX. MASTOCYTOSIS

Cutaneous mastocytosis
Indolent systemic mastocytosis—ICD-O 9741/1
Systemic mastocytosis with associated clonal, hematological non-mast cell lineage disease—ICD-O 9741/3
Aggressive systemic mastocytosis—ICD-O 9741/3
Mast cell leukemia—ICD-O 9742/3
Mast cell sarcoma—ICD-O 9740/3
Extracutaneous mastocytoma—ICD-O 9740/1

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space. Stereoisomers include enantiomers and diastereomers.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography. Diastereomers include geometric isomers, cis/trans and E/Z isomers, and atropisomers.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center (s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethylacetate, acetic acid, and ethanolamine.

The terms "compound of this invention," and "compounds of the present invention" and "compounds of Formula I" include compounds of Formulas I and stereoisomers, tautomers, solvates, metabolites, and pharmaceutically acceptable salts and prodrugs thereof.

Any formula or structure given herein, including Formula I compounds, is also intended to represent hydrates, solvates, and polymorphs of such compounds, and mixtures thereof.

Any formula or structure given herein, including Formula I compounds, is also intended to represent isotopically labeled forms of the compounds as well as unlabeled forms. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as, but not limited to 2H (deuterium, D), 3H (tritium), 11C, 13C, 14C, 15N, 18F, 31P, 32P, 35S, 36Cl, and 125I. Various isotopically labeled compounds of the present invention, for example those into which radioactive isotopes such as 3H, 13C, and 14C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the formula (I). The concentration of such a heavier isotope, specifically deuterium, may be defined by an isotopic enrichment factor. In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this invention any atom specifically designated as a deuterium (D) is meant to represent deuterium.

Heterocyclic Compounds of the Invention

Formula I compounds include compounds having the formula:

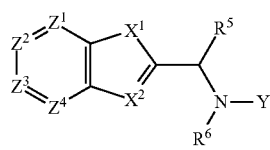

I and stereoisomers, geometric isomers, tautomers, and pharmaceutically acceptable salts thereof, wherein:

$Z^1$ is $CR^1$ or N;
$Z^2$ is $CR^2$ or N;
$Z^3$ is $CR^3$ or N;
$Z^4$ is $CR^4$ or N;
where none, one, or two of $Z^1$, $Z^2$, $Z^3$ and $Z^4$ are N;
where (i) $X^1$ is $NR^{10}$ and $X^2$ is N, (ii) $X^1$ is S and $X^2$ is $CR^{11}$, (iii) $X^1$ is O and $X^2$ is $CR^{11}$, or (iv) $X^1$ is $NR^{10}$ and $X^2$ is $CR^{11}$;
or $Z^1$ and $X^1$, wherein $X^1$ is N, form a five-membered, six-membered, or seven-membered heteroaryl or heterocyclyl ring, optionally substituted with one or more $R^{12}$ groups $R^5$ and $R^6$ are independently selected from H, $C_1$-$C_{12}$ alkyl, $C_2$-$C_8$ alkenyl, and $C_2$-$C_8$ alkynyl, where alkyl, alkenyl, and alkynyl are optionally substituted with one or more groups independently selected from F, Cl, Br, I, —CN, —$CO_2H$, —$COCH_3$, —$COC(CH_3)_3$, —$CO_2CH_3$, —$CONH_2$, —$CONHCH_3$, —$CON(CH_3)_2$, —$NO_2$, —$NH_2$, —$NHCH_3$, —$N(CH_3)_2$, —$NHCOCH_3$, —$NHS(O)_2CH_3$, —$N(CH_3)C(CH_3)_2CONH_2$, —$N(CH_3)CH_2CH_2S(O)_2CH_3$, =O, —OH, —$OCH_3$, —$OCH_2CH_3$, —$OCH(CH_3)_2$, —$S(O)_2N(CH_3)_2$, —$SCH_3$, and —$S(O)_2CH_3$;

or $R^5$ and $R^6$ form a five-membered or six-membered heteroaryl or heterocyclyl ring, optionally substituted with one or more $R^{12}$ groups;

$R^1$, $R^2$, $R^3$, $R^4$, and $R^{12}$ are independently selected from H, F, Cl, Br, I, —$CH_3$, —$CH_2CH_3$, —$C(CH_3)_3$, —$CH_2OH$, —$CH_2CH_2OH$, —$C(CH_3)_2OH$, —$CH_2OCH_3$, —CN, —$CF_3$, —$CO_2H$, —$COCH_3$, —$COC(CH_3)_3$, —$CO_2CH_3$, —$CONH_2$, —$CONHCH_3$, —$CON(CH_3)_2$, —$CONHCH_2CH_2OCH_3$, —$CON(CH_2CH_2)_2O$, —$CON(CH_2CH_2)_2N(CH_3)$, —$C(CH_3)_2CONH_2$, —$NO_2$, —$NH_2$, —$NHCH_3$, —$N(CH_3)_2$, —$NHCOCH_3$, —$NHS(O)_2CH_3$, —$N(CH_3)C(CH_3)_2CONH_2$, —$N(CH_3)CH_2CH_2S(O)_2CH_3$, =O, —OH, —$OCH_3$, —$OCF_3$, —$S(O)_2N(CH_3)_2$, —$SCH_3$, and —$S(O)_2CH_3$; or $R^1$, $R^2$, $R^3$, $R^4$, and $R^{12}$ are independently selected from $C_2$-$C_{20}$ heterocyclyl or $C_1$-$C_{20}$ heteroaryl optionally substituted with one or more groups selected from F, Cl, Br, I, —$CH_3$, —$CH_2CH_3$, —$C(CH_3)_3$, —$CH_2OH$, —$CH_2CH_2OH$, —$C(CH_3)_2OH$, —$CH_2OCH_3$, —CN, —$CF_3$, —$CO_2H$, —$COCH_3$, —$COC(CH_3)_3$, —$CO_2CH_3$, —$CONH_2$, —$CONHCH_3$, —$CON(CH_3)_2$, —$CONHCH_2CH_2OCH_3$, —$CON(CH_2CH_2)_2O$, —$CON(CH_2CH_2)_2N(CH_3)$, —$C(CH_3)_2CONH_2$, —$NO_2$, —$NH_2$, —$NHCH_3$, —$N(CH_3)_2$, —$NHCOCH_3$, —$NHS(O)_2CH_3$, —$N(CH_3)C(CH_3)_2CONH_2$, —$N(CH_3)CH_2CH_2S(O)_2CH_3$, =O, —OH, —$OCH_3$, —$OCF_3$, —$S(O)_2N(CH_3)_2$, —$SCH_3$, —$S(O)_2$ $CH_3$;

Y is $C_2$-$C_{20}$ heterocyclyl or $C_1$-$C_{20}$ heteroaryl optionally substituted with one or more groups selected from F, Cl, Br, I, —$CH_3$, —$CH_2CH_3$, —$C(CH_3)_3$, —$CH_2OH$, —$CH_2CH_2OH$, —$C(CH_3)_2OH$, —$CH_2OCH_3$, —CN, —$CF_3$, —$CO_2H$, —$COCH_3$, —$COC(CH_3)_3$, —$CO_2CH_3$, —$CONH_2$, —$CONHCH_3$, —$CON(CH_3)_2$, —$CONHCH_2CH_2OCH_3$, —$CON(CH_2CH_2)_2O$, —$CON(CH_2CH_2)_2N(CH_3)$, —$C(CH_3)_2CONH_2$, —$NO_2$, —$NH_2$, —$NHCH_3$, —$N(CH_3)_2$, —$NHCOCH_3$, —$NHS(O)_2CH_3$, —$N(CH_3)C(CH_3)_2CONH_2$, —$N(CH_3)CH_2CH_2S(O)_2CH_3$, =O, —OH, —$OCH_3$, —$OCF_3$, —$S(O)_2N(CH_3)_2$, —$SCH_3$, —$S(O)_2CH_3$, benzo[d]thiazol-2-yl optionally substituted with —$NHCOCH_3$, cyclopropyl, cyclobutyl, 1,1-dioxo-thiopyran-4-yl, indolyl, oxetanyl, morpholino, and phenyl optionally substituted with F, Cl, Br, I, —OH, —CN, or —$CH_3$;

or $R^6$ and Y form a five-membered or six-membered heteroaryl or heterocyclyl ring, optionally substituted with one or more $R^{12}$ groups;

$R^{10}$ is H, $C_1$-$C_{12}$ alkyl, $C_2$-$C_8$ alkenyl, $C_2$-$C_8$ alkynyl, $C_6$-$C_{20}$ aryl, $C_3$-$C_{12}$ carbocyclyl, $C_2$-$C_{20}$ heterocyclyl, $C_1$-$C_{20}$ heteroaryl, —($C_1$-$C_{12}$ alkylene)-($C_3$-$C_{12}$ carbocyclyl), —($C_1$-$C_{12}$ alkylene)-($C_2$-$C_{20}$ heterocyclyl), —($C_1$-$C_{12}$ alkylene)-C(═O)—($C_2$-$C_{20}$ heterocyclyl), —($C_1$-$C_{12}$ alkylene)-($C_6$-$C_{20}$ aryl), —($C_6$-$C_{20}$ aryl)-($C_1$-$C_{20}$ heteroaryl), —($C_6$-$C_{20}$ aryl)-($C_2$-$C_{20}$ heterocyclyl), and —($C_1$-$C_{12}$ alkylene)-($C_1$-$C_{20}$ heteroaryl), where alkyl, alkenyl, alkynyl, alkylene, carbocyclyl, heterocyclyl, aryl, and heteroaryl are optionally substituted with one or more groups independently selected from F, Cl, Br, I, —$CH_3$, —$CH_2CH_3$, —$CH(CH_3)_2$, —$C(CH_3)_3$, —$CH_2OH$, —$CH_2CH_2OH$, —$C(CH_3)_2OH$, —$CH_2OCH_3$, —CN, —$CH_2CH_2CN$, —$CH_2F$, —$CHF_2$, —$CH_2CONH_2$, —$CF_3$, —$CO_2H$, —$COCH_3$, —$COC(CH_3)_2$ OH, —$COCH_2N(CH_3)_2$, —$COC(CH_3)_3$, —$CO_2CH_3$, —$CO_2C(CH_3)_3$, —$CONH_2$, —$CONHCH_3$, —$CON(CH_3)_2$, —$C(CH_3)_2CONH_2$, —$NO_2$, —$NH_2$, —$NHCH_3$, —$N(CH_3)_2$, —$NHCOCH_3$, —$NHS(O)_2CH_3$, —$N(CH_3)C(CH_3)_2CONH_2$, —$N(CH_3)CH_2CH_2S(O)_2CH_3$, ═O, —OH, —$OCH_3$, —$S(O)_2N(CH_3)_2$, —$SCH_3$, —$S(O)_2CH_3$, cyclopropyl, cyclobutyl, oxetanyl, morpholino, and 1,1-dioxo-thiopyran-4-yl; and $R^{11}$ is H, F, Cl, Br, I, CN, —$N(R^5)_2$, —$OR^5$, $C_1$-$C_{12}$ alkyl, $C_2$-$C_8$ alkenyl, $C_2$-$C_8$ alkynyl, $C_6$-$C_{20}$ aryl, $C_3$-$C_{12}$ carbocyclyl, $C_2$-$C_{20}$ heterocyclyl, $C_1$-$C_{20}$ heteroaryl, —($C_1$-$C_{12}$ alkylene)-($C_3$-$C_{12}$ carbocyclyl), —($C_1$-$C_{12}$ alkylene)-($C_2$-$C_{20}$ heterocyclyl), —($C_1$-$C_{12}$ alkylene)-C(═O)—($C_2$-$C_{20}$ heterocyclyl), —($C_1$-$C_{12}$ alkylene)-($C_6$-$C_{20}$ aryl), and —($C_1$-$C_{12}$ alkylene)-($C_1$-$C_{20}$ heteroaryl), where alkyl, alkenyl, alkynyl, alkylene, carbocyclyl, heterocyclyl, aryl, and heteroaryl are optionally substituted with one or more groups independently selected from F, Cl, Br, I, —$CH_3$, —$CH_2CH_3$, —$C(CH_3)_3$, —$CH_2OH$, —$CH_2CH_2OH$, —$C(CH_3)_2OH$, —$CH_2OCH_3$, —CN, —$CH_2F$, —$CHF_2$, —$CF_3$, —$CO_2H$, —$COCH_3$, —$COC(CH_3)_3$, —$CO_2CH_3$, —$CONH_2$, —$CONHCH_3$, —$CON(CH_3)_2$, —$C(CH_3)_2CONH_2$, —$NO_2$, —$NH_2$, —$NHCH_3$, —$N(CH_3)_2$, —$NHCOCH_3$, —$NHS(O)_2CH_3$, —$N(CH_3)C(CH_3)_2CONH_2$, —$N(CH_3)CH_2CH_2S(O)_2CH_3$, ═O, —OH, —$OCH_3$, —$S(O)_2N(CH_3)_2$, —$SCH_3$, —$S(O)_2CH_3$, cyclopropyl, cyclobutyl, oxetanyl, morpholino, and 1,1-dioxo-thiopyran-4-yl.

Exemplary embodiments of Formula I compounds include wherein Y has the structure:

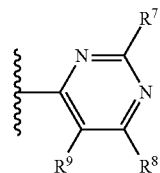

where the wavy line indicates the site of attachment;

$R^7$, $R^8$, and $R^9$ are independently selected from H, F, Cl, Br, I, —$CH_3$, —$CH_2CH_3$, —$C(CH_3)_3$, —$CH_2OH$, —$CH_2CH_2OH$, —$C(CH_3)_2OH$, —$CH_2OCH_3$, —CN, —$CF_3$, —$CO_2H$, —$COCH_3$, —$COC(CH_3)_3$, —$CO_2CH_3$, —$CONH_2$, —$CONHCH_3$, —$CON(CH_3)_2$, —$CONHCH_2CH_2OCH_3$, —$CON(CH_2CH_2)_2O$, —$CON(CH_2CH_2)_2N(CH_3)$, —$C(CH_3)_2CONH_2$, —$NO_2$, —$NH_2$, —$NHCH_3$, —$N(CH_3)_2$, —$NHCOCH_3$, —$NHS(O)_2CH_3$, —$N(CH_3)C(CH_3)_2CONH_2$, —$N(CH_3)CH_2CH_2S(O)_2CH_3$, ═O, —OH, —$OCH_3$, —$OCF_3$, —$S(O)_2N(CH_3)_2$, —$SCH_3$, —$S(O)_2CH_3$, cyclopropyl, cyclobutyl, oxetanyl, morpholino, and 1,1-dioxo-thiopyran-4-yl;

or: (iv) $R^6$ and $R^9$, or (v) $R^8$ and $R^9$ form a five-membered or six-membered heteroaryl or heterocyclyl ring, optionally substituted with one or more $R^{12}$ groups.

Exemplary embodiments of Formula I compounds include Formulas Ia-d:

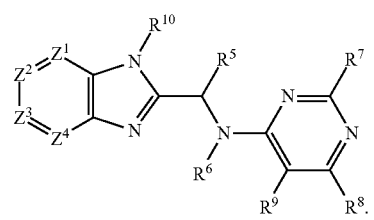

Ia

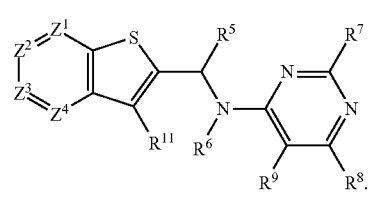

Ib

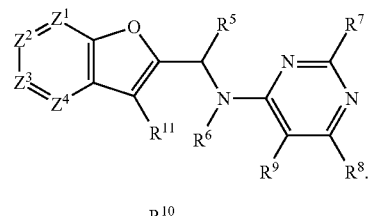

Ic

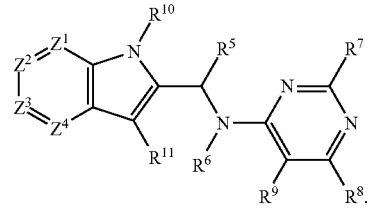

Id

Exemplary embodiments of Formula I compounds include wherein $Z^1$ is $CR^1$; $Z^2$ is $CR^2$; $Z^3$ is $CR^3$; and $Z^4$ is $CR^4$.

Exemplary embodiments of Formula I compounds include wherein $R^1$, $R^2$, $R^3$, and $R^4$ are independently selected from H, F, Cl, —$CH_3$, and —CN.

Exemplary embodiments of Formula I compounds include wherein one or more of $R^1$, $R^2$, $R^3$, and $R^4$ are F or Cl.

Exemplary embodiments of Formula I compounds include wherein $R^1$ is optionally substituted cyclopropyl, cyclobutyl, 1,1-dioxo-thiopyran-4-yl, indazolyl, oxetanyl, morpholino, phenyl, pyranyl, pyrazolyl or pyridinyl.

Exemplary embodiments of Formula I compounds include wherein $R^5$ is —$CH_3$ and $R^6$ is H.

Exemplary embodiments of Formula I compounds include wherein $R^7$ is H.

Exemplary embodiments of Formula I compounds include wherein Y is [1,3,5]triazine, pyridyl, or pyridazinone.

Exemplary embodiments of Formula I compounds include wherein $R^5$ and $R^6$ form a five-membered or six-membered heteroaryl or heterocyclyl ring, optionally substituted with one or more $R^{12}$ groups.

Exemplary embodiments of Formula I compounds include wherein $R^6$ and $R^9$ form a five-membered or six-membered heteroaryl or heterocyclyl ring, optionally substituted with one or more $R^{12}$ groups.

Exemplary embodiments of Formula I compounds include wherein $R^6$ and $R^9$ form an imidazolyl, piperidonyl, pyrrolidinyl, or pyrazolyl ring.

Exemplary embodiments of Formula I compounds include wherein $R^8$ and $R^9$ form a five-membered or six-membered heteroaryl or heterocyclyl ring, optionally substituted with one or more $R^{12}$ groups.

Exemplary embodiments of Formula I compounds include wherein $R^8$ and $R^9$ form an imidazolyl, piperidonyl, pyrrolidinyl, or pyrazolyl ring.

Exemplary embodiments of Formula I compounds include wherein $X^1$ is N and $Z^1$ is C, $X^1$ and $Z^1$ form a five-membered, six-membered, or seven-membered heteroaryl or heterocyclyl ring, optionally substituted with one or more $R^{12}$ groups.

Exemplary embodiments of Formula I compounds include wherein $R^{10}$ is phenyl, optionally substituted with one or more groups selected from F, Cl, and $CH_3$.

Exemplary embodiments of Formula I compounds include wherein $R^{10}$ is optionally substituted $C_2$-$C_{20}$ heterocyclyl.

Exemplary embodiments of Formula I compounds include:

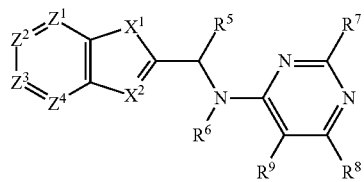

and stereoisomers, geometric isomers, tautomers, and pharmaceutically acceptable salts thereof, wherein:

$Z^1$ is $CR^1$ or N;
$Z^2$ is $CR^2$ or N;
$Z^3$ is $CR^3$ or N;
$Z^4$ is $CR^4$ or N;
where none, one, or two of $Z^1$, $Z^2$, $Z^3$ and $Z^4$ are N;
where (i) $X^1$ is $NR^{10}$ and $X^2$ is N, (ii) $X^1$ is S and $X^2$ is $CR^{11}$, (iii) $X^1$ is O and $X^2$ is $CR^{11}$, or (iv) $X^1$ is $NR^{10}$ and $X^2$ is $CR^{11}$;

$R^5$ and $R^6$ are independently selected from H, $C_1$-$C_{12}$ alkyl, $C_2$-$C_8$ alkenyl, and $C_2$-$C_8$ alkynyl, where alkyl, alkenyl, and alkynyl are optionally substituted with one or more groups independently selected from F, Cl, Br, I, —CN, —$CO_2$H, —$COCH_3$, —$COC(CH_3)_3$, —$CO_2CH_3$, —$CONH_2$, —$CONHCH_3$, —$CON(CH_3)_2$, —$NO_2$, —$NH_2$, —$NHCH_3$, —$N(CH_3)_2$, —$NHCOCH_3$, —$NHS(O)_2CH_3$, —$N(CH_3)C(CH_3)_2CONH_2$, —$N(CH_3)CH_2CH_2S(O)_2CH_3$, =O, —OH, —$OCH_3$, —$OCH_2CH_3$, —$OCH(CH_3)_2$, —$S(O)_2N(CH_3)_2$, —$SCH_3$, and —$S(O)_2CH_3$;

$R^1$, $R^2$, $R^3$, $R^4$, $R^7$, $R^8$, $R^9$, and $R^{12}$ are independently selected from H, F, Cl, Br, I, —$CH_3$, —$CH_2CH_3$, —$C(CH_3)_3$, —$CH_2OH$, —$CH_2CH_2OH$, —$C(CH_3)_2OH$, —$CH_2OCH_3$, —CN, —$CF_3$, —$CO_2H$, —$COCH_3$, —$COC(CH_3)_3$, —$CO_2CH_3$, —$CONH_2$, —$CONHCH_3$, —$CON(CH_3)_2$, —$C(CH_3)_2CONH_2$, —$NO_2$, —$NH_2$, —$NHCH_3$, —$N(CH_3)_2$, —$NHCOCH_3$, —$NHS(O)_2CH_3$, —$N(CH_3)C(CH_3)_2CONH_2$, —$N(CH_3)CH_2CH_2S(O)_2CH_3$, =O, —OH, —$OCH_3$, —$OCF_3$, —$S(O)_2N(CH_3)_2$, —$SCH_3$, —$S(O)_2CH_3$, cyclopropyl, cyclobutyl, oxetanyl, morpholino, and 1,1-dioxo-thiopyran-4-yl;

or $R^6$ and $R^9$, or $R^8$ and $R^9$ form a five-membered or six-membered heteroaryl or heterocyclyl ring, optionally substituted with one or more $R^{12}$ groups;

$R^{10}$ is H, $C_1$-$C_{12}$ alkyl, $C_2$-$C_8$ alkenyl, $C_2$-$C_8$ alkynyl, $C_6$-$C_{20}$ aryl, $C_3$-$C_{12}$ carbocyclyl, $C_2$-$C_{20}$ heterocyclyl, $C_1$-$C_{20}$ heteroaryl, —($C_1$-$C_{12}$ alkylene)-($C_3$-$C_{12}$ carbocyclyl), —($C_1$-$C_{12}$ alkylene)-($C_2$-$C_{20}$ heterocyclyl), —($C_1$-$C_{12}$ alkylene)-C(=O)—($C_2$-$C_{20}$ heterocyclyl), —($C_1$-$C_{12}$ alkylene)-($C_6$-$C_{20}$ aryl), —($C_6$-$C_{20}$ aryl)-($C_1$-$C_{20}$ heteroaryl), —($C_6$-$C_{20}$ aryl)-($C_2$-$C_{20}$ heterocyclyl), and —($C_1$-$C_{12}$ alkylene)-($C_1$-$C_{20}$ heteroaryl), where alkyl, alkenyl, alkynyl, alkylene, carbocyclyl, heterocyclyl, aryl, and heteroaryl are optionally substituted with one or more groups independently selected from F, Cl, Br, I, —$CH_3$, —$CH_2CH_3$, —$C(CH_3)_3$, —$CH_2OH$, —$CH_2CH_2OH$, —$C(CH_3)_2OH$, —$CH_2OCH_3$, —CN, —$CH_2F$, —$CHF_2$, —$CF_3$, —$CO_2H$, —$COCH_3$, —$COC(CH_3)_3$, —$CO_2CH_3$, —$CONH_2$, —$CONHCH_3$, —$CON(CH_3)_2$, —$C(CH_3)_2CONH_2$, —$NO_2$, —$NH_2$, —$NHCH_3$, —$N(CH_3)_2$, —$NHCOCH_3$, —$NHS(O)_2CH_3$, —$N(CH_3)C(CH_3)_2CONH_2$, —$N(CH_3)CH_2CH_2S(O)_2CH_3$, =O, —OH, —$OCH_3$, —$S(O)_2N(CH_3)_2$, —$SCH_3$, —$S(O)_2CH_3$, cyclopropyl, cyclobutyl, oxetanyl, morpholino, and 1,1-dioxo-thiopyran-4-yl; and $R^{11}$ is H, F, Cl, Br, I, CN, —$N(R^5)_2$, —$OR^5$, $C_1$-$C_{12}$ alkyl, $C_2$-$C_8$ alkenyl, $C_2$-$C_8$ alkynyl, $C_6$-$C_{20}$ aryl, $C_3$-$C_{12}$ carbocyclyl, $C_2$-$C_{20}$ heterocyclyl, $C_1$-$C_{20}$ heteroaryl, —($C_1$-$C_{12}$ alkylene)-($C_3$-$C_{12}$ carbocyclyl), —($C_1$-$C_{12}$ alkylene)-($C_2$-$C_{20}$ heterocyclyl), —($C_1$-$C_{12}$ alkylene)-C(=O)—($C_2$-$C_{20}$ heterocyclyl), —($C_1$-$C_{12}$ alkylene)-($C_6$-$C_{20}$ aryl), and —($C_1$-$C_{12}$ alkylene)-($C_1$-$C_{20}$ heteroaryl), where alkyl, alkenyl, alkynyl, alkylene, carbocyclyl, heterocyclyl, aryl, and heteroaryl are optionally substituted with one or more groups independently selected from F, Cl, Br, I, —$CH_3$, —$CH_2CH_3$, —$C(CH_3)_3$, —$CH_2OH$, —$CH_2CH_2OH$, —$C(CH_3)_2OH$, —$CH_2OCH_3$, —CN, —$CH_2F$, —$CHF_2$, —$CF_3$, —$CO_2H$, —$COCH_3$, —$COC(CH_3)_3$, —$CO_2CH_3$, —$CONH_2$, —$CONHCH_3$, —$CON(CH_3)_2$, —$C(CH_3)_2CONH_2$, —$NO_2$, —$NH_2$, —$NHCH_3$, —$N(CH_3)_2$, —$NHCOCH_3$, —$NHS(O)_2CH_3$, —$N(CH_3)C(CH_3)_2CONH_2$, —$N(CH_3)CH_2CH_2S(O)_2CH_3$, =O, —$OCH_3$, —$S(O)_2N(CH_3)_2$, —$SCH_3$, —$S(O)_2CH_3$, cyclopropyl, cyclobutyl, oxetanyl, morpholino, and 1,1-dioxo-thiopyran-4-yl.

Exemplary embodiments of Formula I compounds include compounds from Tables 1, 2, and 3.

Exemplary embodiments of Formula I compounds include wherein $R^{10}$ is $CH_3$ or optionally substituted phenyl and wherein phenyl is substituted with one or more groups selected from F, Cl, and $CH_3$.

Exemplary embodiments of Formula I compounds include wherein $R^{10}$ is optionally substituted $C_2$-$C_{20}$ heterocyclyl, and wherein $R^{10}$ is 4-piperidinyl.

The Formula I compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention.

In addition, the present invention embraces all geometric and positional isomers. For example, if a Formula I compound incorporates a double bond or a fused ring, the cis- and trans-forms, as well as mixtures thereof, are embraced within the scope of the invention. Both the single positional isomers and mixture of positional isomers are also within the scope of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embrace both solvated and unsolvated forms.

The compounds of the present invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The present invention also embraces isotopically-labeled compounds of the present invention which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^2$H, $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I and $^{125}$I. Certain isotopically-labeled compounds of the present invention (e.g., those labeled with $^3$H and $^{14}$C) are useful in compound and/or substrate tissue distribution assays. Tritiated ($^3$H) and carbon-14 ($^{14}$C) isotopes are useful for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C and $^{18}$F are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Biological Evaluation

The relative efficacies of Formula I compounds as inhibitors of an enzyme activity (or other biological activity) can be established by determining the concentrations at which each compound inhibits the activity to a predefined extent and then comparing the results. Typically, the preferred determination is the concentration that inhibits 50% of the activity in a biochemical assay, i.e., the 50% inhibitory concentration or "$IC_{50}$". Determination of $IC_{50}$ values can be accomplished using conventional techniques known in the art. In general, an $IC_{50}$ can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the $IC_{50}$ value. Analogously, other inhibitory concentrations can be defined through appropriate determinations of activity. For example, in some settings it can be desirable to establish a 90% inhibitory concentration, i.e., $IC_{90}$, etc.

Accordingly, a "selective PI3K delta inhibitor" can be understood to refer to a compound that exhibits a 50% inhibitory concentration ($IC_{50}$) with respect to PI3K delta that is at least at least 10-fold lower than the $IC_{50}$ value with respect to any or all of the other Class I PI3K family members.

Determination of the activity of PI3 kinase activity of Formula I compounds is possible by a number of direct and indirect detection methods. Certain exemplary compounds described herein were assayed for their ability to inhibit PI3K alpha, beta, gamma, and delta isoforms (Example 901). The range of $IC_{50}$ values for inhibition of PI3K delta was less than 1 nM (nanomolar) to about 10 µM (micromolar). Certain exemplary compounds of the invention had PI3K delta inhibitory $IC_{50}$ values less than 10 nM. The compounds are selective for the p110δ (delta) isoform, which is a class Ia PI3 kinase, over other class Ia PI3 kinases, and are thus selective for the p110δ isoform over both the p110α (alpha) isoform and the p110β (beta) isoform. In particular, they are selective for p110δ (delta) over p110α (alpha). The compounds are also selective for the p110δ isoform over p110γ (gamma), which is a class Ib kinase. The selectivity exhibited by Formula I compounds of the invention for p110δ (delta) over the p110α (alpha) isoform of PI3 kinase is at least 10 fold, as exemplified by the ratios of biochemical $IC_{50}$ values (Example 901).

Certain Formula I compounds may have antiproliferative activity to treat hyperproliferative disorders such as cancer. The Formula I compounds may inhibit tumor growth in mammals and may be useful for treating human cancer patients. Formula I compounds may be tested for in vitro cell proliferation activity and in vivo tumor growth inhibition according to the methods in WO 2006/046031; US 2008/0039459; US 2008/0076768; US 2008/0076758; WO 2008/070740; WO 2008/073785, which are incorporated by reference herein.

Evaluation of drug-induced immunosuppression by the compounds of the invention may be performed using in vivo functional tests, such as rodent models of induced arthritis and therapeutic or prophylactic treatment to assess disease score, T cell-dependent antibody response (TDAR), and delayed-type hypersensitivity (DTH). Other in vivo systems including murine models of host defense against infections or tumor resistance (Burleson G R, Dean J H, and Munson A E. *Methods in Immunotoxicology, Vol. 1.* Wiley-Liss, New York, 1995) may be considered to elucidate the nature or mechanisms of observed immunosuppression. The in vivo test systems can be complemented by well-established in vitro or ex vivo functional assays for the assessment of immune competence. These assays may comprise B or T cell proliferation in response to mitogens or specific antigens, measurement of signaling through the PI3K pathway in B or T cells or immortalized B or T cell lines, measurement of cell surface markers in response to B or T cell signaling, natural killer (NK) cell activity, mast cell activity, mast cell degranulation, macrophage phagocytosis or kill activity, and neutrophil oxidative burst and/or chemotaxis. In each of these tests determination of cytokine production by particular effector cells (e.g., lymphocytes, NK, monocytes/macrophages, neutrophils) may be included. The in vitro and ex vivo assays can be applied in both preclinical and clinical testing using lymphoid tissues and/or peripheral blood (House R V. "Theory and practice of cytokine assessment in immunotoxicology" (1999) Methods 19:17-27; Hubbard A K. "Effects of xenobiotics on macrophage function: evaluation in vitro" (1999) Methods; 19:8-16; Lebrec H, et al (2001) Toxicology 158:25-29).

Collagen-Induced Arthritis (CIA) 6-week detailed study using an autoimmune mechanism to mimic human arthritis; rat and mouse models (Example 902). Collagen-induced arthritis (CIA) is one of the most commonly used animal models of human rheumatoid arthritis (RA). Joint inflammation, which develops in animals with CIA, strongly resembles inflammation observed in patients with RA. Blocking tumor necrosis factor (TNF) is an efficacious treatment of CIA, just as it is a highly efficacious therapy in treatment of RA patients. CIA is mediated by both T-cells and antibodies (B-cells). Macrophages are believed to play an important role in mediating tissue damage during disease development. CIA is induced by immunizing animals with collagen emulsified in Complete Freund's Adjuvant (CFA). It is most commonly induced in the DBA/1 mouse strain, but the disease can also be induced in Lewis rats.

There is good evidence that B-cells play a key role in the pathogenesis of autoimmune and/or inflammatory disease. Protein-based therapeutics that deplete B cells such as Rituxan are effective against autoantibody-driven inflammatory diseases such as rheumatoid arthritis (Rastetter et al. (2004) Annu Rev Med 55:477). CD69 is the early activation marker in leukocytes including T cells, thymocytes, B cells, NK cells, neutrophils, and eosinophils. The CD69 human whole blood assay (Example 903) determines the ability of compounds to inhibit the production of CD69 by B lymphocytes in human whole blood activated by crosslinking surface IgM with goat F(ab')$_2$ anti-human IgM.

The T-cell Dependent Antibody Response (TDAR) is a predictive assay for immune function testing when potential immunotoxic effects of compounds need to be studied. The IgM-Plaque Forming Cell (TC) assay, using Sheep Red Blood Cells (SRBC) as the antigen, is currently a widely accepted and validated standard test. TDAR has proven to be a highly predictable assay for adult exposure immunotoxicity detection in mice based on the US National Toxicology Program (NTP) database (M. I. Luster et al (1992) Fundam. Appl. Toxicol. 18:200-210). The utility of this assay stems from the fact that it is a holistic measurement involving several important components of an immune response. A TDAR is dependent on functions of the following cellular compartments: (1) antigen-presenting cells, such as macrophages or dendritic cells; (2) T-helper cells, which are critical players in the genesis of the response, as well as in isotype switching; and (3) B-cells, which are the ultimate effector cells and are responsible for antibody production. Chemically-induced changes in any one compartment can cause significant changes in the overall TDAR (M. P. Holsapple In: G. R. Burleson, J. H. Dean and A. E. Munson, Editors, *Modern Methods in Immunotoxicology, Volume* 1, Wiley-Liss Publishers, New York, N.Y. (1995), pp. 71-108). Usually, this assay is performed either as an ELISA for measurement of soluble antibody (R. J. Smialowizc et al (2001) Toxicol. Sci. 61:164-175) or as a plaque (or antibody) forming cell assay (L. Guo et al (2002) Toxicol. Appl. Pharmacol. 181:219-227) to detect plasma cells secreting antigen specific antibodies. The antigen of choice is either whole cells (e.g. sheep erythrocytes) or soluble protein antigens (T. Miller et al (1998) Toxicol. Sci. 42:129-135).

Exemplary Formula I compounds in Tables 1, 2 and 3 were made, characterized, and tested for inhibition of PI3K delta and selectivity according to the methods of this invention, and have the following structures and corresponding names (ChemBioDraw Ultra, Version 11.0, CambridgeSoft Corp., Cambridge Mass.).

TABLE 1

| No. | Structure | Name |
|---|---|---|
| 101 | 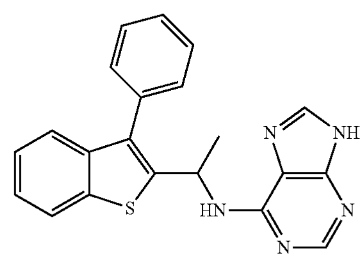 [SMILES: CC(Nc1ncnc2[nH]cnc12)c1sc2ccccc2c1-c1ccccc1] | N-(1-(3-phenylbenzo[b]thiophen-2-yl)ethyl)-9H-purin-6-amine |
| 102 | 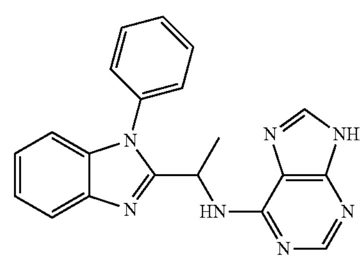 [SMILES: CC(Nc1ncnc2[nH]cnc12)c1nc2ccccc2n1-c1ccccc1] | N-(1-(1-phenyl-1H-benzo[d]imidazol-2-yl)ethyl)-9H-purin-6-amine |
| 103 | 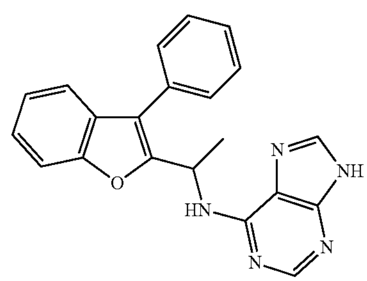 [SMILES: CC(Nc1ncnc2[nH]cnc12)c1oc2ccccc2c1-c1ccccc1] | N-(1-(3-phenylbenzofuran-2-yl)ethyl)-9H-purin-6-amine |

TABLE 1-continued

| No. | Structure | Name |
|---|---|---|
| 104 | 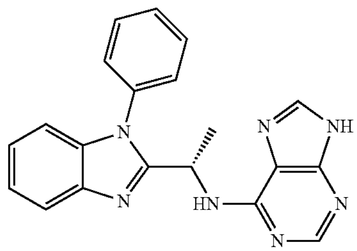 | (S)-N-(1-(1-phenyl-1H-benzo[d]imidazol-2-yl)ethyl)-9H-purin-6-amine |
| 105 | 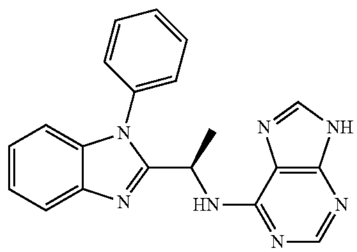 [SMILES: C[C@@H](Nc1ncnc2[nH]cnc12)c1nc2ccccc2n1-c1ccccc1] | (R)-N-(1-(1-phenyl-1H-benzo[d]imidazol-2-yl)ethyl)-9H-purin-6-amine |
| 106 | 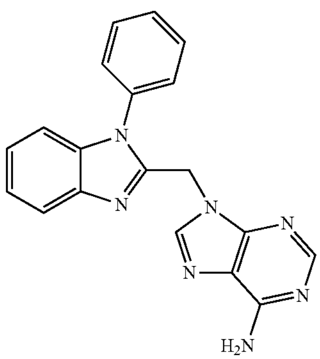 [SMILES: Nc1ncnc2c1ncn2Cc1nc2ccccc2n1-c1ccccc1] | 9-((1-phenyl-1H-benzo[d]imidazol-2-yl)methyl)-9H-purin-6-amine |
| 107 | 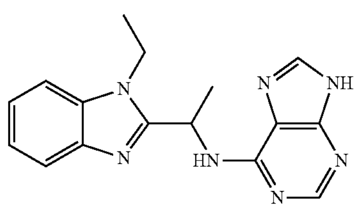 [SMILES: CCn1c(C(C)Nc2ncnc3[nH]cnc23)nc2ccccc21] | N-(1-(1-ethyl-1H-benzo[d]imidazol-2-yl)ethyl)-9H-purin-6-amine |
| 108 | 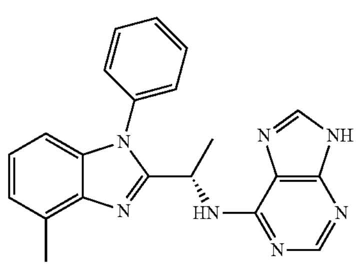 [SMILES: Cc1cccc2c1nc([C@H](C)Nc1ncnc3[nH]cnc13)n2-c1ccccc1] | (S)-N-(1-(4-methyl-1-phenyl-1H-benzo[d]imidazol-2-yl)ethyl)-9H-purin-6-amine |
| 109 | 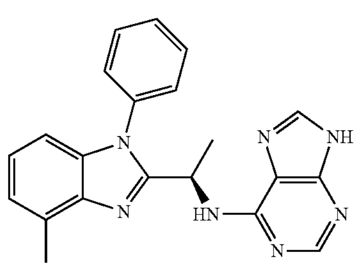 [SMILES: Cc1cccc2c1nc([C@@H](C)Nc1ncnc3[nH]cnc13)n2-c1ccccc1] | (R)-N-(1-(4-methyl-1-phenyl-1H-benzo[d]imidazol-2-yl)ethyl)-9H-purin-6-amine |

TABLE 1-continued

| No. | Structure | Name |
|---|---|---|
| 110 | 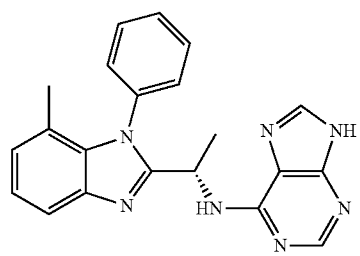 [SMILES: Cc1cccc2nc([C@H](C)Nc3ncnc4[nH]cnc34)n(-c3ccccc3)c12] | (S)-N-(1-(7-methyl-1-phenyl-1H-benzo[d]imidazol-2-yl)ethyl)-9H-purin-6-amine |
| 111 | 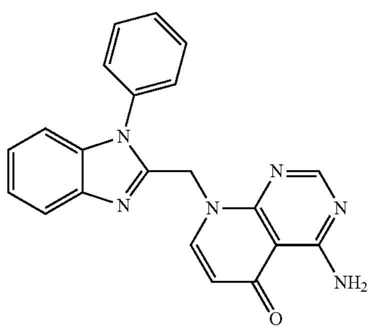 [SMILES: Nc1ncnc2c1c(=O)ccn2Cc1nc2ccccc2n1-c1ccccc1] | 4-amino-8-((1-phenyl-1H-benzo[d]imidazol-2-yl)methyl)pyrido[2,3-d]pyrimidin-5(8H)-one |
| 112 | 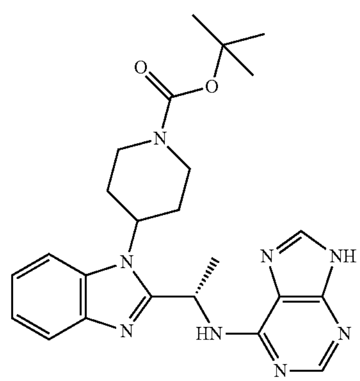 [SMILES: C[C@H](Nc1ncnc2[nH]cnc12)c1nc2ccccc2n1C1CCN(C(=O)OC(C)(C)C)CC1] | (S)-tert-butyl 4-(2-(1-(9H-purin-6-ylamino)ethyl)-1H-benzo[d]imidazol-1-yl)piperidine-1-carboxylate |
| 113 | 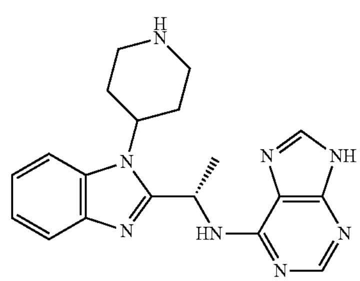 [SMILES: C[C@H](Nc1ncnc2[nH]cnc12)c1nc2ccccc2n1C1CCNCC1] | (S)-N-(1-(1-(piperidin-4-yl)-1H-benzo[d]imidazol-2-yl)ethyl)-9H-purin-6-amine |
| 114 | 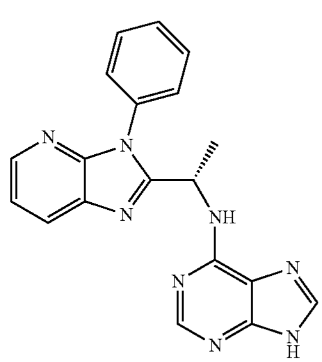 | (S)-N-(1-(3-phenyl-3H-imidazo[4,5-b]pyridin-2-yl)ethyl)-9H-purin-6-amine |

TABLE 1-continued

| No. | Structure | Name |
|---|---|---|
| 115 | 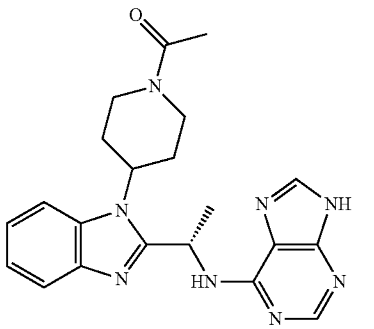 [SMILES: CC(=O)N1CCC(n2c([C@H](C)Nc3ncnc4[nH]cnc34)nc3ccccc32)CC1] | (S)-1-(4-(2-(1-(9H-purin-6-ylamino)ethyl)-1H-benzo[d]imidazol-1-yl)piperidin-1-yl)ethanone |
| 116 | 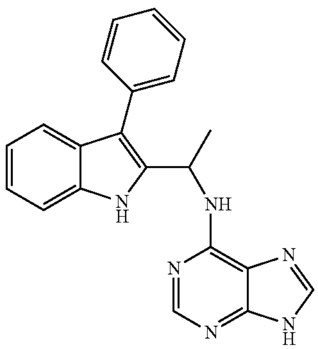 [SMILES: CC(Nc1ncnc2[nH]cnc12)c1[nH]c2ccccc2c1-c1ccccc1] | N-(1-(3-phenyl-1H-indol-2-yl)ethyl)-9H-purin-6-amine |
| 117 | 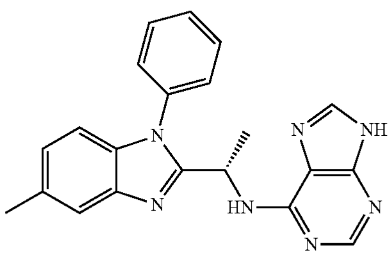 [SMILES: Cc1ccc2c(c1)nc([C@H](C)Nc1ncnc3[nH]cnc13)n2-c1ccccc1] | (S)-N-(1-(5-methyl-1-phenyl-1H-benzo[d]imidazol-2-yl)ethyl)-9H-purin-6-amine |
| 118 | 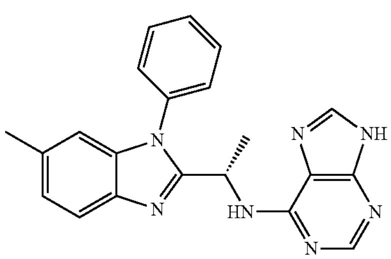 [SMILES: Cc1ccc2nc([C@H](C)Nc3ncnc4[nH]cnc34)n(-c3ccccc3)c2c1] | (S)-N-(1-(6-methyl-1-phenyl-1H-benzo[d]imidazol-2-yl)ethyl)-9H-purin-6-amine |
| 119 | 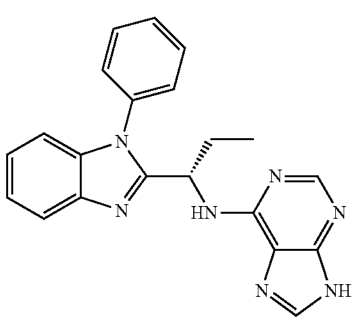 [SMILES: CC[C@H](Nc1ncnc2[nH]cnc12)c1nc2ccccc2n1-c1ccccc1] | (S)-N-(1-(1-phenyl-1H-benzo[d]imidazol-2-yl)propyl)-9H-purin-6-amine |

TABLE 1-continued

| No. | Structure | Name |
|---|---|---|
| 120 | 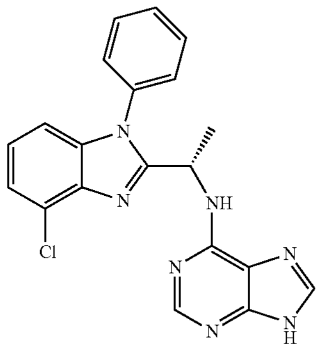 [SMILES: C[C@H](Nc1ncnc2[nH]cnc12)c1nc2c(Cl)cccc2n1-c1ccccc1] | (S)-N-(1-(4-chloro-1-phenyl-1H-benzo[d]imidazol-2-yl)ethyl)-9H-purin-6-amine |
| 121 | 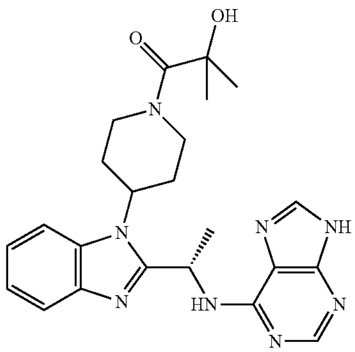 [SMILES: C[C@H](Nc1ncnc2[nH]cnc12)c1nc2ccccc2n1C1CCN(C(=O)C(C)(C)O)CC1] | (S)-1-(4-(2-(1-(9H-purin-6-ylamino)ethyl)-1H-benzo[d]imidazol-1-yl)piperidin-1-yl)-2-hydroxy-2-methylpropan-1-one |
| 122 | 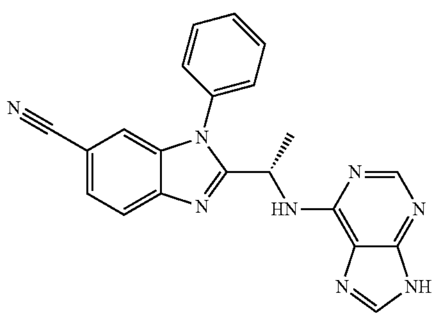 [SMILES: C[C@H](Nc1ncnc2[nH]cnc12)c1nc2ccc(C#N)cc2n1-c1ccccc1] | (S)-2-(1-(9H-purin-6-ylamino)ethyl)-1-phenyl-1H-benzo[d]imidazole-6-carbonitrile |
| 123 | 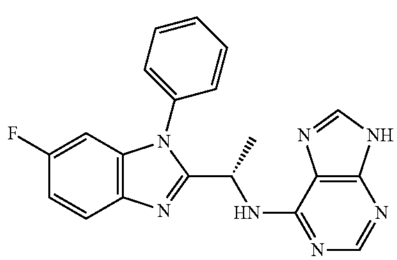 | (S)-N-(1-(6-fluoro-1-phenyl-1H-benzo[d]imidazol-2-yl)ethyl)-9H-purin-6-amine |
| 124 | 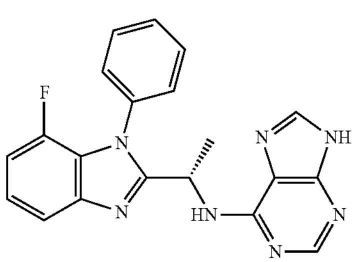 [SMILES: C[C@H](Nc1ncnc2[nH]cnc12)c1nc2cccc(F)c2n1-c1ccccc1] | (S)-N-(1-(7-fluoro-1-phenyl-1H-benzo[d]imidazol-2-yl)ethyl)-9H-purin-6-amine |

TABLE 1-continued

| No. | Structure | Name |
|-----|-----------|------|
| 125 | 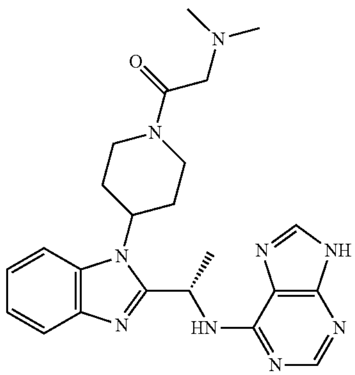 [SMILES: C[C@H](Nc1ncnc2[nH]cnc12)c1nc2ccccc2n1C1CCN(C(=O)CN(C)C)CC1] | (S)-1-(4-(2-(1-(9H-purin-6-ylamino)ethyl)-1H-benzo[d]imidazol-1-yl)piperidin-1-yl)-2-(dimethylamino)ethanone |
| 126 | 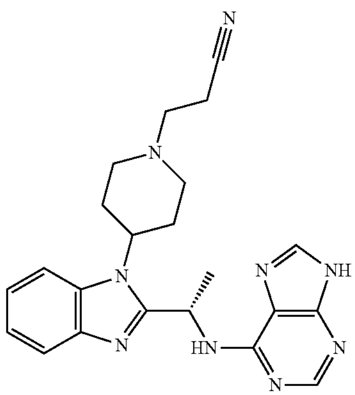 [SMILES: C[C@H](Nc1ncnc2[nH]cnc12)c1nc2ccccc2n1C1CCN(CCC#N)CC1] | (S)-3-(4-(2-(1-(9H-purin-6-ylamino)ethyl)-1H-benzo[d]imidazol-1-yl)piperidin-1-yl)propanenitrile |
| 127 | 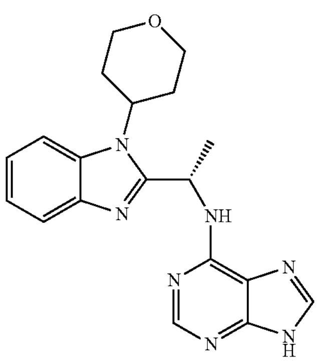 [SMILES: C[C@H](Nc1ncnc2[nH]cnc12)c1nc2ccccc2n1C1CCOCC1] | (S)-N-(1-(1-(tetrahydro-2H-pyran-4-yl-1H-benzo[d]imidazol-2-yl)ethyl)-9H-purin-6-amine |
| 128 | 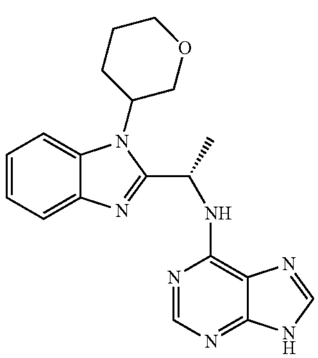 [SMILES: C[C@H](Nc1ncnc2[nH]cnc12)c1nc2ccccc2n1C1CCCOC1] | N-((1S)-1-(1-(tetrahydro-2H-pyran-3-yl-1H-benzo[d]imidazol-2-yl)ethyl)-9H-purin-6-amine |

TABLE 1-continued

| No. | Structure | Name |
|---|---|---|
| 129 | 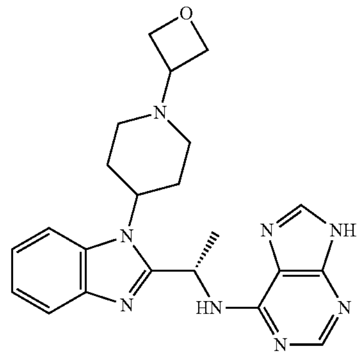 [SMILES: C[C@H](Nc1ncnc2[nH]cnc12)c1nc2ccccc2n1C1CCN(C2COC2)CC1] | (S)-N-(1-(1-(1-(oxetan-3-yl)piperidin-4-yl)-1H-benzo[d]imidazol-2-yl)ethyl)-9H-purin-6-amine |
| 130 | 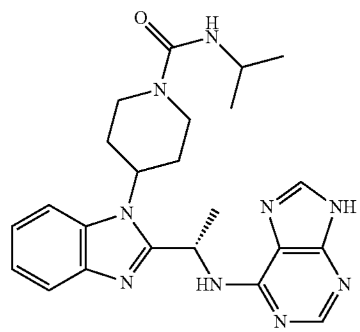 [SMILES: CC(C)NC(=O)N1CCC(n2c([C@H](C)Nc3ncnc4[nH]cnc34)nc3ccccc32)CC1] | (S)-4-(2-(1-(9H-purin-6-ylamino)ethyl)-1H-benzo[d]imidazol-1-yl)-N-isopropylpiperidine-1-carboxamide |
| 131 | 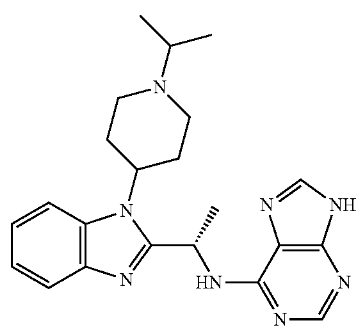 [SMILES: CC(C)N1CCC(n2c([C@H](C)Nc3ncnc4[nH]cnc34)nc3ccccc32)CC1] | (S)-N-(1-(1-(1-isopropylpiperidin-4-yl)-1H-benzo[d]imidazol-2-yl)ethyl)-9H-purin-6-amine |
| 132 | 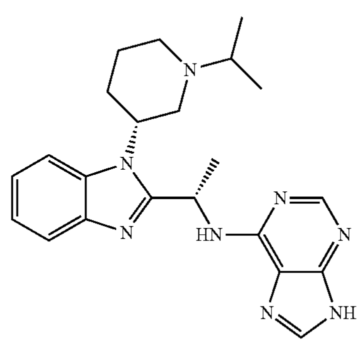 [SMILES: CC(C)N1CCC[C@@H](n2c([C@H](C)Nc3ncnc4[nH]cnc34)nc3ccccc32)C1] | N-((S)-1-(1-((R)-1-isopropylpiperidin-3-yl)-1H-benzo[d]imidazol-2-yl)ethyl)-9H-purin-6-amine |

TABLE 1-continued

| No. | Structure | Name |
|---|---|---|
| 133 | 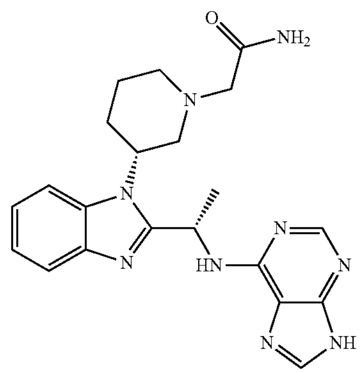 [SMILES: C[C@H](Nc1ncnc2[nH]cnc12)c1nc2ccccc2n1[C@@H]1CCCN(CC(N)=O)C1] | 2((R)-3-(2-((S)-1-(9H-purin-6-ylamino)ethyl)-1H-benzo[d]imidazol-1-yl)piperidin-1-yl)acetamide |
| 134 | 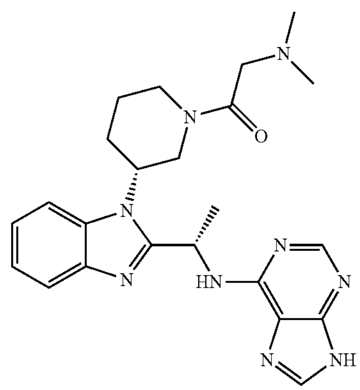 [SMILES: C[C@H](Nc1ncnc2[nH]cnc12)c1nc2ccccc2n1[C@@H]1CCCN(C(=O)CN(C)C)C1] | 1-((R)-3-(2-((S)-1-(9H-purin-6-ylamino)ethyl)-1H-benzo[d]imidazol-1-yl)piperidin-1-yl)-2-(dimethylamino)ethanone |
| 135 | 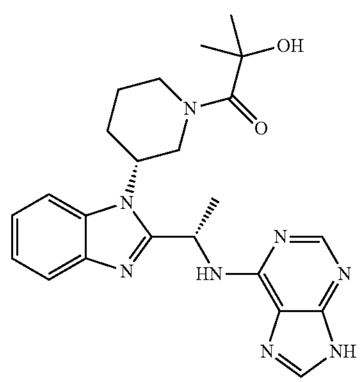 [SMILES: C[C@H](Nc1ncnc2[nH]cnc12)c1nc2ccccc2n1[C@@H]1CCCN(C(=O)C(C)(C)O)C1] | 1-((R)-3-(2-((S)-1-(9H-purin-6-ylamino)ethyl)-1H-benzo[d]imidazol-1-yl)piperidin-1-yl)-2-hydroxy-2-methylpropan-1-one |
| 136 | 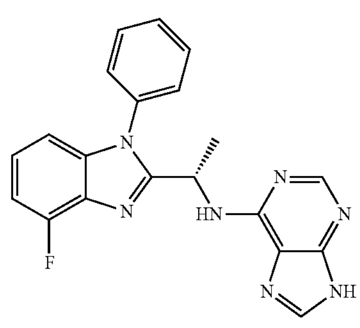 [SMILES: C[C@H](Nc1ncnc2[nH]cnc12)c1nc2c(F)cccc2n1-c1ccccc1] | (S)-N-(1-(4-fluoro-1-phenyl-1H-benzo[d]imidazol-2-yl)ethyl)-9H-purin-6-amine |

TABLE 1-continued

| No. | Structure | Name |
|---|---|---|
| 137 | 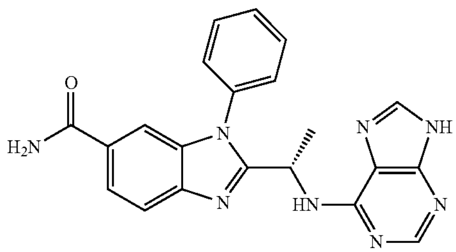 [SMILES: C[C@H](Nc1ncnc2[nH]cnc12)c1nc2ccc(C(N)=O)cc2n1-c1ccccc1] | (S)-2-(1-(9H-purin-6-ylamino)ethyl)-1-phenyl-1H-benzo[d]imidazole-6-carboxamide |
| 138 | 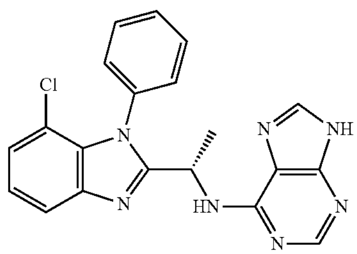 | (S)-N-(1-(7-chloro-1-phenyl-1H-benzo[d]imidazol-2-yl)ethyl)-9H-purin-6-amine |
| 139 | 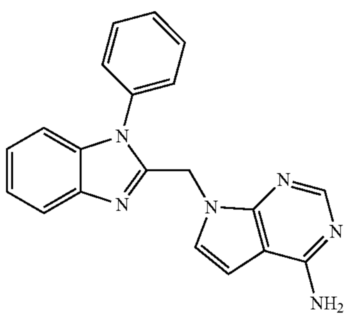 [SMILES: Nc1ncnc2c1ccn2Cc1nc2ccccc2n1-c1ccccc1] | 7((1-phenyl-1H-benzo[d]imidazol-2-yl)methyl)-7H-pyrrolo[2,3-d]pyrimidin-4-amine |
| 140 | 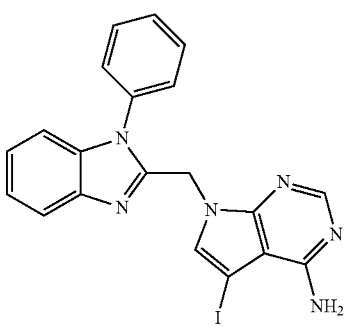 [SMILES: Nc1ncnc2c1c(I)cn2Cc1nc2ccccc2n1-c1ccccc1] | 5-iodo-7-((1-phenyl-1H-benzo[d]imidazol-2-yl)methyl)-7H-pyrrolo[2,3-d]pyrimidin-4-amine |
| 141 | 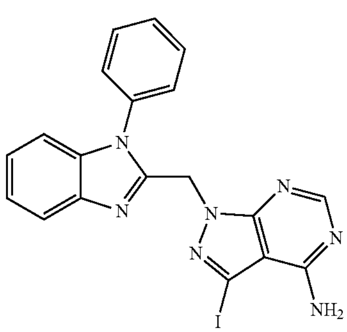 [SMILES: Nc1ncnc2c1c(I)nn2Cc1nc2ccccc2n1-c1ccccc1] | 3-iodo-1-((1-phenyl-1H-benzo[d]imidazol-2-yl)methyl)-1H-pyrazolo[3,4-d]pyrimidin-4-amine |

TABLE 1-continued

| No. | Structure | Name |
|---|---|---|
| 142 | 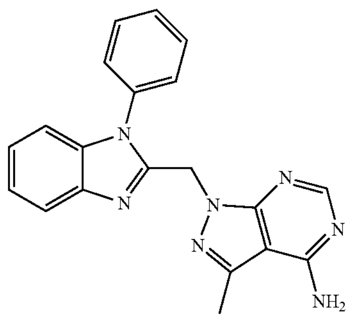 [SMILES: Cc1nn(Cc2nc3ccccc3n2-c2ccccc2)c2ncnc(N)c12] | 3-methyl-1-((1-phenyl-1H-benzo[d]imidazol-2-yl)methyl)-1H-pyrazolo[3,4-d]pyrimidin-4-amine |
| 143 | 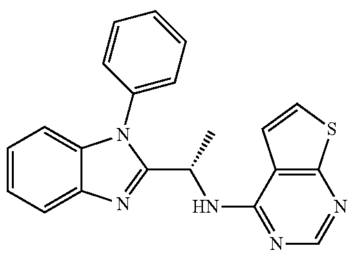 [SMILES: C[C@H](Nc1ncnc2sccc12)c1nc2ccccc2n1-c1ccccc1] | (S)-N-(1-(1-phenyl-1H-benzo[d]imidazol-2-yl)ethyl)thieno[2,3-d]pyrimidin-4-amine |
| 144 | 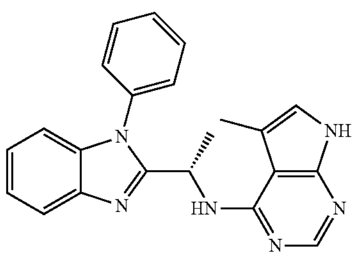 [SMILES: Cc1c[nH]c2ncnc(N[C@@H](C)c3nc4ccccc4n3-c3ccccc3)c12] | (S)-5-methyl-N-(1-(1-phenyl-1H-benzo[d]imidazol-2-yl)ethyl)-7H-pyrrolo[2,3-d]pyrimidin-4-amine |
| 145 | 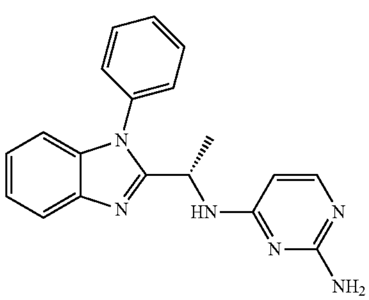 [SMILES: C[C@H](Nc1ccnc(N)n1)c1nc2ccccc2n1-c1ccccc1] | (S)-N4-(1-(1-phenyl-1H-benzo[d]imidazol-2-yl)ethyl)pyrimidine-2,4-diamine |
| 146 | 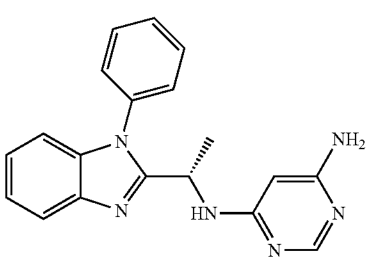 [SMILES: C[C@H](Nc1cc(N)ncn1)c1nc2ccccc2n1-c1ccccc1] | (S)-N4-(1-(1-phenyl-1H-benzo[d]imidazol-2-yl)ethyl)pyrimidine-4,6-diamine |

TABLE 1-continued

| No. | Structure | Name |
|---|---|---|
| 147 | 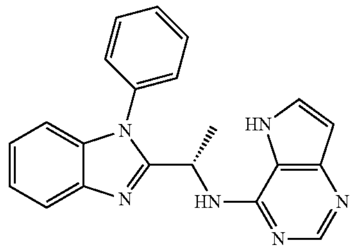 [SMILES: C[C@H](Nc1ncnc2cc[nH]c12)c1nc2ccccc2n1-c1ccccc1] | (S)-N-(1-(1-phenyl-1H-benzo[d]imidazol-2-yl)ethyl)-5H-pyrrolo[3,2-d]pyrimidine-4-amine |
| 148 | 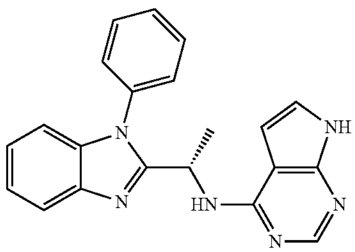 [SMILES: C[C@H](Nc1ncnc2[nH]ccc12)c1nc2ccccc2n1-c1ccccc1] | (S)-N-(1-(1-phenyl-1H-benzo[d]imidazol-2-yl)ethyl)-7H-pyrrolo[2,3-d]pyrimidine-4-amine |
| 149 | 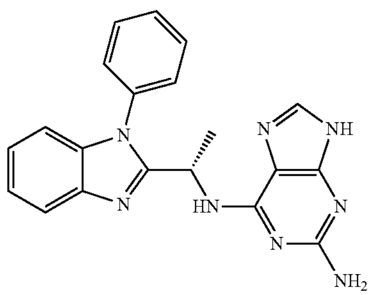 [SMILES: C[C@H](Nc1nc(N)nc2[nH]cnc12)c1nc2ccccc2n1-c1ccccc1] | (S)-N6-(1-(1-phenyl-1H-benzo[d]imidazol-2-yl)ethyl)-9H-purine-2,6-diamine |
| 150 | 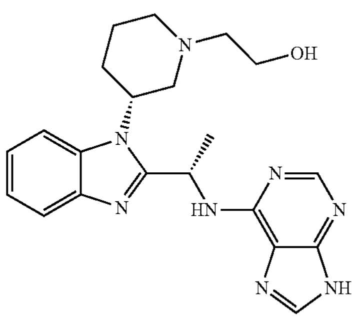 [SMILES: C[C@H](Nc1ncnc2[nH]cnc12)c1nc2ccccc2n1[C@@H]1CCCN(CCO)C1] | 2((R)-3-(2-((S)-1-(9H-purine-6-ylamino)ethyl)-1H-benzo[d]imidazol-1-yl)piperidin-1-yl)ethanol |
| 151 | 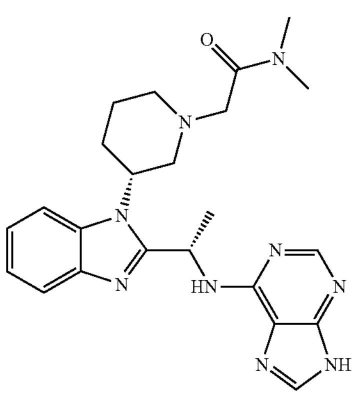 [SMILES: C[C@H](Nc1ncnc2[nH]cnc12)c1nc2ccccc2n1[C@@H]1CCCN(CC(=O)N(C)C)C1] | 2((R)-3-(2-((S)-1-(9H-purine-6-ylamino)ethyl)-1H-benzo[d]imidazol-1-yl)piperidin-1-yl)-N,N-dimethylacetamide |

TABLE 1-continued

| No. | Structure | Name |
| --- | --- | --- |
| 152 | 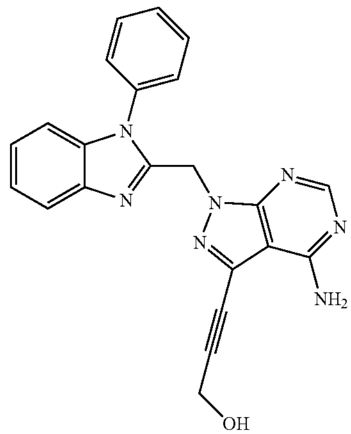 [SMILES: Nc1ncnc2c1c(C#CCO)nn2Cc1nc2ccccc2n1-c1ccccc1] | 3-(4-amino-1-((1-phenyl-1H-benzo[d]imidazol-2-yl)methyl)-1H-pyrazolo[3,4-d]pyrimidin-3-yl)prop-2-yn-1-ol |
| 153 | 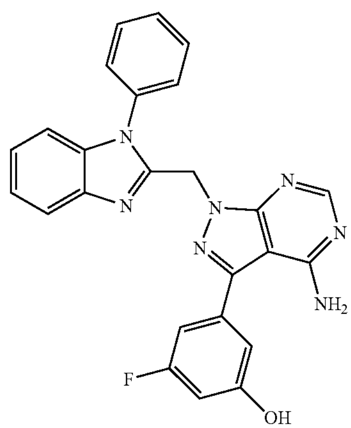 [SMILES: Nc1ncnc2c1c(-c1cc(O)cc(F)c1)nn2Cc1nc2ccccc2n1-c1ccccc1] | 3-(4-amino-1-((1-phenyl-1H-benzo[d]imidazol-2-yl)methyl)-1H-pyrazolo[3,4-d]pyrimidin-3-yl)-5-fluorophenol |
| 154 | 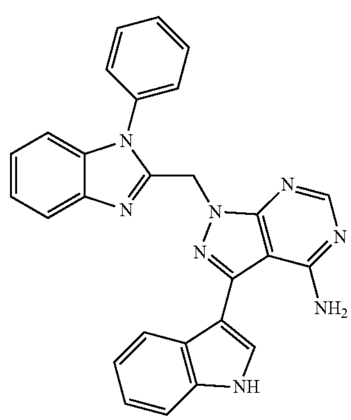 [SMILES: Nc1ncnc2c1c(-c1c[nH]c3ccccc13)nn2Cc1nc2ccccc2n1-c1ccccc1] | 3-(1H-indol-3-yl)-1-((1-phenyl-1H-benzo[d]imidazol-2-yl)methyl)-1H-pyrazolo[3,4-d]pyrimidin-4-amine |

TABLE 1-continued

| No. | Structure | Name |
|---|---|---|
| 155 | 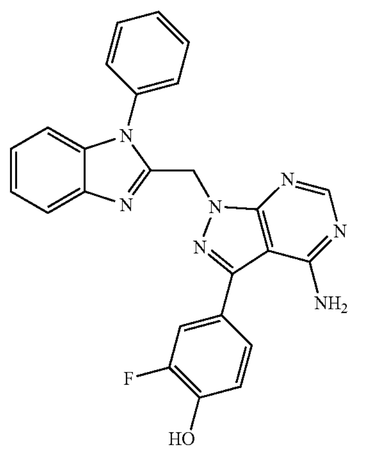 [SMILES: Nc1ncnc2c1c(-c1ccc(O)c(F)c1)nn2Cc1nc2ccccc2n1-c1ccccc1] | 4-(4-amino-1-((1-phenyl-1H-benzo[d]imidazol-2-yl)methyl)-1H-pyrazolo[3,4-d]pyrimidin-3-yl)-2-fluorophenol |
| 156 | 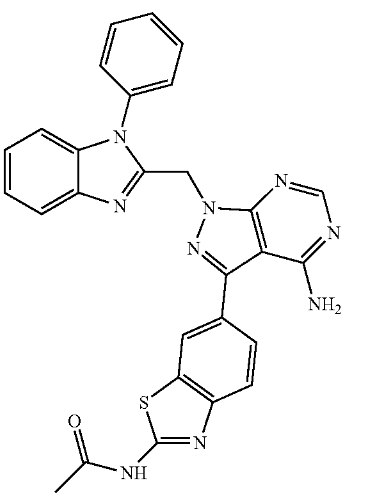 [SMILES: CC(=O)Nc1nc2ccc(-c3nn(Cc4nc5ccccc5n4-c4ccccc4)c4ncnc(N)c34)cc2s1] | N-(6-(4-amino-1-((1-phenyl-1H-benzo[d]imidazol-2-yl)methyl)-1H-pyrazolo[3,4-d]pyrimidin-3-yl)benzo[d]thiazol-2-yl)acetamide |
| 157 | 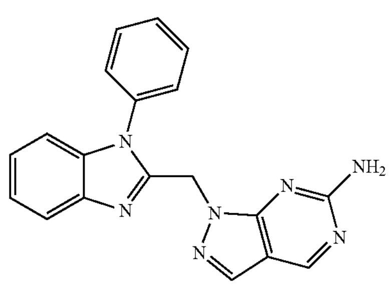 [SMILES: Nc1ncc2cnn(Cc3nc4ccccc4n3-c3ccccc3)c2n1] | 1-((1-phenyl-1H-benzo[d]imidazol-2-yl)methyl)-1H-pyrazolo[3,4-d]pyrimidin-6-amine |
| 158 | 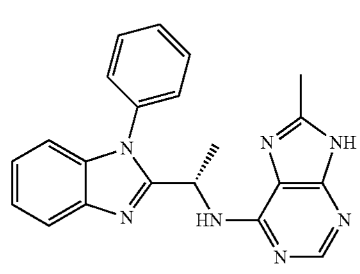 [SMILES: Cc1nc2c(N[C@@H](C)c3nc4ccccc4n3-c3ccccc3)ncnc2[nH]1] | (S)-8-methyl-N-(1-(1-phenyl-1H-benzo[d]imidazol-2-yl)ethyl)-9H-purin-6-amine |

TABLE 1-continued

| No. | Structure | Name |
|---|---|---|
| 159 | 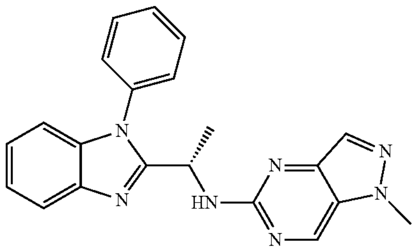 [SMILES: C[C@H](Nc1ncc2c(cnn2C)n1)c1nc2ccccc2n1-c1ccccc1] | (S)-1-methyl-N-(1-(1-phenyl-1H-benzo[d]imidazol-2-yl)ethyl)-1H-pyrazolo[4,3-d]pyrimidin-5-amine |
| 160 | 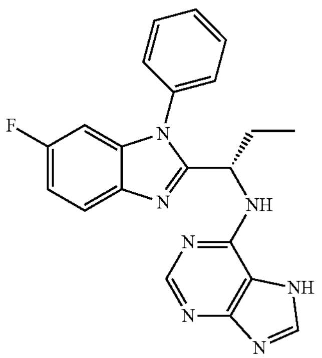 [SMILES: CC[C@H](Nc1ncnc2nc[nH]c12)c1nc2ccc(F)cc2n1-c1ccccc1] | (S)-N-(1-(6-fluoro-1-phenyl-1H-benzo[d]imidazol-2-yl)propyl)-7H-purin-6-amine |
| 161 | 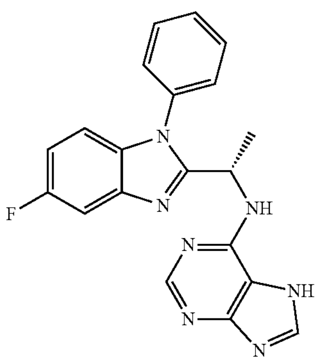 [SMILES: C[C@H](Nc1ncnc2nc[nH]c12)c1nc2cc(F)ccc2n1-c1ccccc1] | (S)-N-(1-(5-fluoro-1-phenyl-1H-benzo[d]imidazol-2-yl)ethyl)-7H-purin-6-amine |
| 162 | 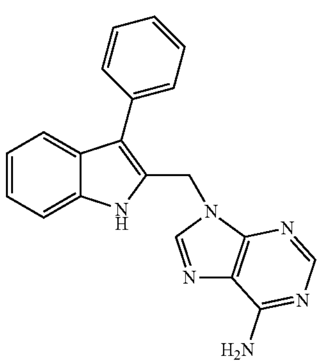 [SMILES: Nc1ncnc2c1ncn2Cc1[nH]c2ccccc2c1-c1ccccc1] | 9-((3-phenyl-1H-indol-2-yl)methyl)-9H-purin-6-amine |

TABLE 1-continued
| No. | Structure | Name |
|---|---|---|
| 163 | 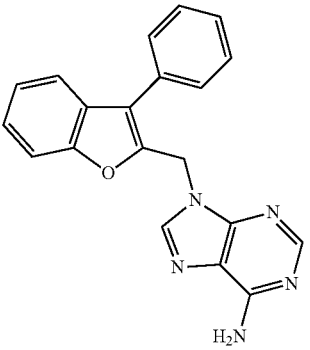 | 9-((3-phenylbenzofuran-2-yl)methyl)-9H-purin-6-amine |
| 164 | 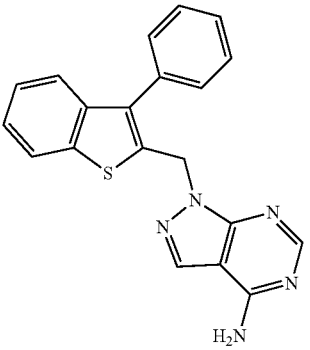 [SMILES: Nc1ncnc2c1cnn2Cc1sc2ccccc2c1-c1ccccc1] | 1-((3-phenylbenzo[b]thiophen-2-yl)methyl)-1H-pyrazolo[3,4-d]pyrimidin-4-amine |
| 165 | 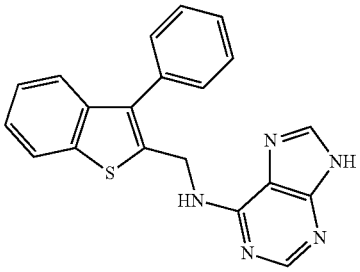 [SMILES: c1ccc(-c2c(CNc3ncnc4[nH]cnc34)sc3ccccc23)cc1] | N-((3-phenylbenzo[b]thiophen-2-yl)methyl)-9H-purin-6-amine |
| 166 | 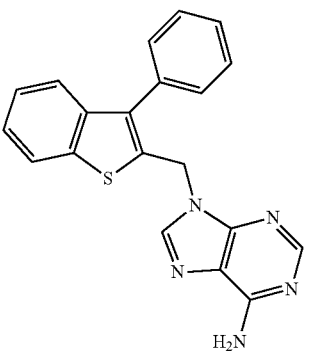 [SMILES: Nc1ncnc2c1ncn2Cc1sc2ccccc2c1-c1ccccc1] | 9-((3-phenylbenzo[b]thiophen-2-yl)methyl)-9H-purin-6-amine |

TABLE 1-continued

| No. | Structure | Name |
|---|---|---|
| 167 | 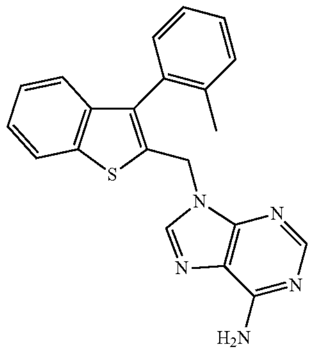 [SMILES: Cc1ccccc1-c1c(Cn2cnc3c(N)ncnc32)sc2ccccc12] | 9-((3-o-tolylbenzo[b]thiophen-2-yl)methyl)-9H-purin-6-amine |

TABLE 2

| No. | Structure | IUPAC_Name | CD69 Hu Blood FACS IC50 (μM) |
|---|---|---|---|
| 168 | 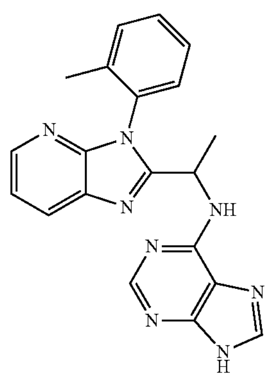 [SMILES: Cc1ccccc1-n1c(C(C)Nc2ncnc3[nH]cnc23)nc2cccnc21] | (9H-Purin-6-yl)-[1-(3-o-tolyl-3H-imidazo[4,5-b]pyridin-2-yl)-ethyl]-amine | |
| 169 | 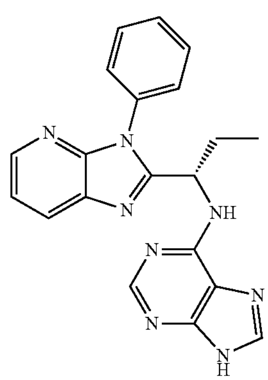 [SMILES: CC[C@H](Nc1ncnc2[nH]cnc12)c1nc2cccnc2n1-c1ccccc1] | [(S)-1-(3-Phenyl-3H-imidazo[4,5-b]pyridin-2-yl)-propyl]-(9H-purin-6-yl)-amine | |

TABLE 2-continued
| No. | Structure | IUPAC_Name | CD69 Hu Blood FACS IC50 (µM) |
|-----|-----------|------------|------|
| 170 | 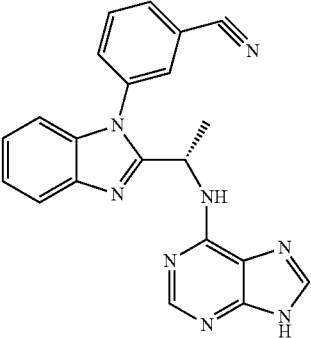 [SMILES: C[C@H](Nc1ncnc2[nH]cnc12)c1nc2ccccc2n1-c1cccc(C#N)c1] | 3-{2-[(S)-1-(9H-Purin-6-ylamino)-ethyl]benzoimidazol-1-yl}-benzonitrile | |
| 171 | 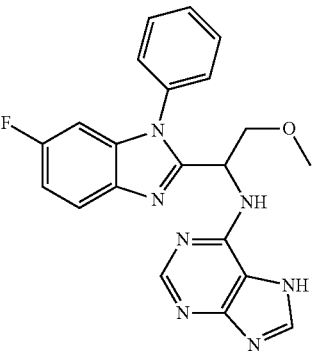 [SMILES: COCC(Nc1ncnc2nc[nH]c12)c1nc2ccc(F)cc2n1-c1ccccc1] | [1-(6-Fluoro-1-phenyl-1H-benzoimidazol-2-yl)-2-methoxy-ethyl]-(7H-purin-6-yl)-amine | 0.106 |
| 172 | 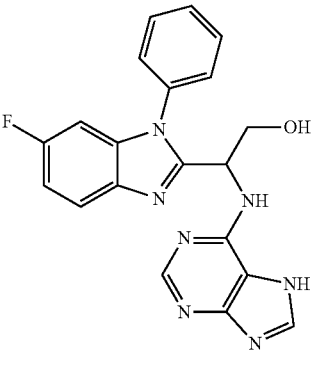 [SMILES: OCC(Nc1ncnc2nc[nH]c12)c1nc2ccc(F)cc2n1-c1ccccc1] | 2-(6-Fluoro-1-phenyl-1H-benzoimidazol-2-yl)-2-(7H-purin-6-ylamino)-ethanol | 0.175 |
| 173 | 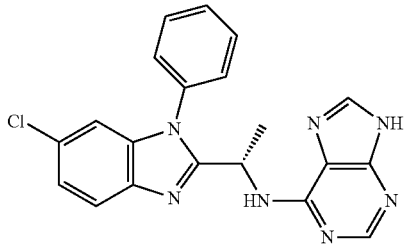 [SMILES: C[C@H](Nc1ncnc2[nH]cnc12)c1nc2ccc(Cl)cc2n1-c1ccccc1] | [(S)-1-(6-Chloro-1-phenyl-1H-benzoimidazol-2-yl)-ethyl]-(9H-purin-6-yl)-amine | 0.301 |

TABLE 2-continued

| No. | Structure | IUPAC_Name | CD69 Hu Blood FACS IC50 (μM) |
|---|---|---|---|
| 174 | 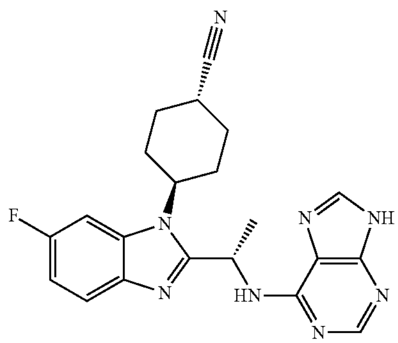 [SMILES: C[C@H](Nc1ncnc2[nH]cnc12)c1nc2ccc(F)cc2n1[C@H]1CC[C@H](C#N)CC1] | 4-{6-Fluoro-2-[(S)-1-(9H-purin-6-ylamino)-ethyl]-benzoimidazol-1-yl}-cyclohexanecarbonitrile | |
| 175 | 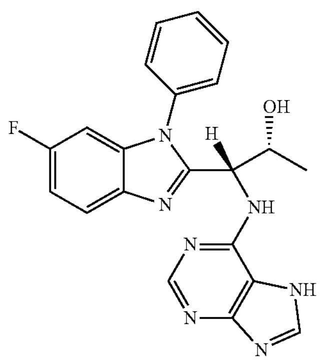 [SMILES: C[C@@H](O)[C@H](Nc1ncnc2nc[nH]c12)c1nc2ccc(F)cc2n1-c1ccccc1] | (1R,2R)-1-(6-Fluoro-1-phenyl-1H-benzoimidazol-2-yl)-1-(7H-purin-6-ylamino)-propan-2-ol | |
| 176 | 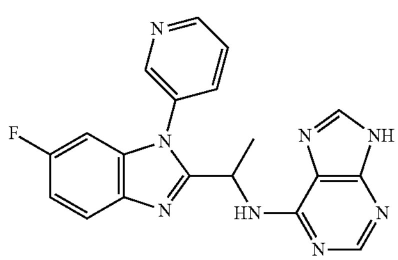 | [1-(6-Fluoro-1-pyridin-3-yl-1H-benzoimidazol-2-yl)-ethyl]-(9H-purin-6-yl)-amine | 0.0629 |
| 177 | 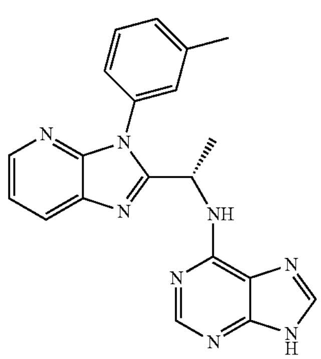 [SMILES: Cc1cccc(-n2c([C@H](C)Nc3ncnc4[nH]cnc34)nc3cccnc32)c1] | (9H-Purin-6-yl)-[(S)-1-(3-m-tolyl-3H-imidazo[4,5-b]pyridin-2-yl)-ethyl]-amine | |

TABLE 2-continued

| No. | Structure | IUPAC_Name | CD69 Hu Blood FACS IC50 (μM) |
|---|---|---|---|
| 178 | 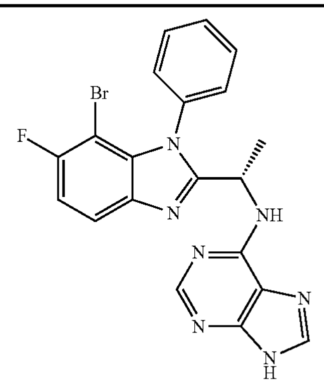 | [(S)-1-(7-Bromo-6-fluoro-1-phenyl-1H-benzoimidazol-2-yl)-ethyl]-(9H-purin-6-yl)-amine | 0.0806 |
| 179 | 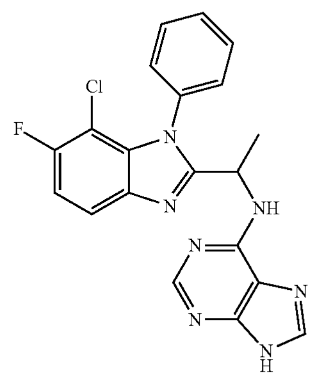 [SMILES: CC(Nc1ncnc2[nH]cnc12)c1nc2ccc(F)c(Cl)c2n1-c1ccccc1] | [1-(7-Chloro-6-fluoro-1-phenyl-1H-benzoimidazol-2-yl)-ethyl]-(9H-purin-6-yl)-amine | 0.146 |
| 180 | 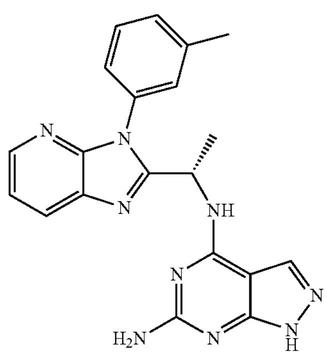 [SMILES: Cc1cccc(-n2c([C@H](C)Nc3nc(N)nc4[nH]ncc34)nc3cccnc32)c1] | N-4-[(S)-1-(3-m-Tolyl-3H-imidazo[4,5-b]pyridin-2-yl)-ethyl]-1H-pyrazolo[3,4-d]pyrimidine-4,6-diamine | |
| 181 | 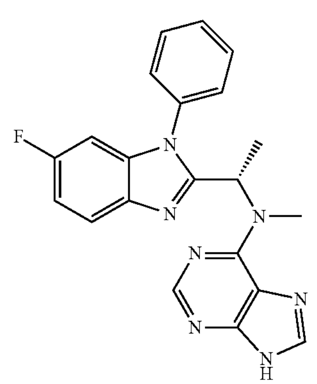 [SMILES: C[C@@H](c1nc2ccc(F)cc2n1-c1ccccc1)N(C)c1ncnc2[nH]cnc12] | [(S)-1-(6-Fluoro-1-phenyl-1H-benzoimidazol-2-yl)-ethyl]-methyl-(9H-purin-6-yl)-amine | |

TABLE 2-continued

| No. | Structure | IUPAC_Name | CD69 Hu Blood FACS IC50 (µM) |
|-----|-----------|------------|------------------------------|
| 182 | 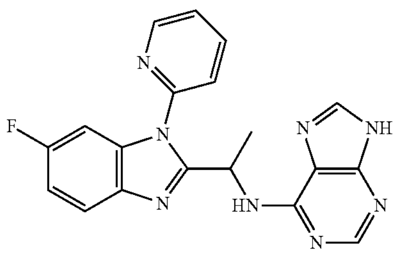 | [1-(6-Fluoro-1-pyridin-2-yl-1H-benzoimidazol-2-yl)-ethyl]-(9H-purin-6-yl)-amine | 0.0671 |
| 183 | 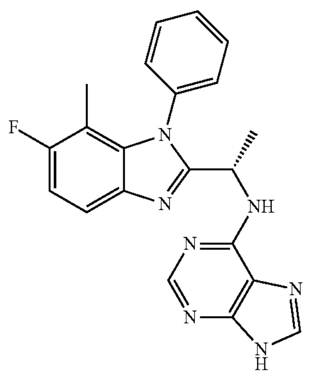 | [(S)-1-(6-Fluoro-7-methyl-1-phenyl-1H-benzoimidazol-2-yl)-ethyl]-(9H-purin-6-yl)-amine | 0.0262 |
| 184 | 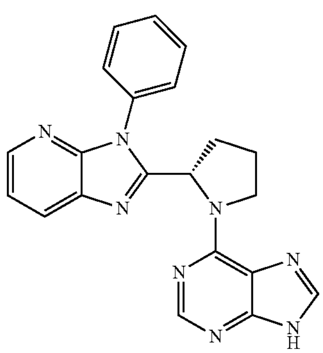 [SMILES: c1ccc(-n2c([C@@H]3CCCN3c3ncnc4[nH]cnc34)nc3cccnc32)cc1] | 6-[(S)-2-(3-Phenyl-3H-imidazo[4,5-b]pyridin-2-yl)-pyrrolidin-1-yl]-9H-purine | |
| 185 | 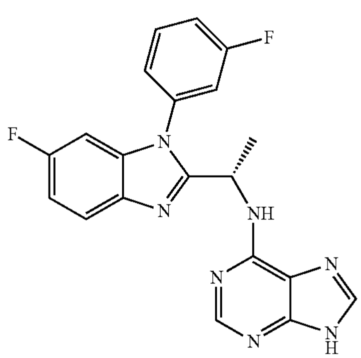 [SMILES: C[C@H](Nc1ncnc2[nH]cnc12)c1nc2ccc(F)cc2n1-c1cccc(F)c1] | {(S)-1-[6-Fluoro-1-(3-fluoro-phenyl)-1H-benzoimidazol-2-yl]-ethyl}-(9H-purine-6-yl)-amine | 0.0521 |

| No. | Structure | IUPAC_Name | CD69 Hu Blood FACS IC50 (μM) |
|---|---|---|---|
| 186 | 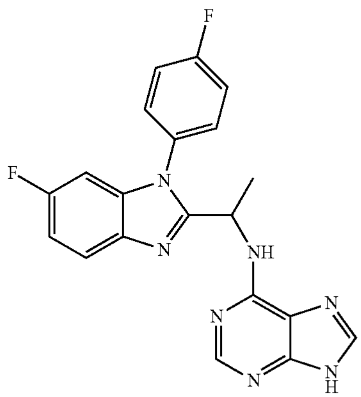 [SMILES: CC(Nc1ncnc2[nH]cnc12)c1nc2ccc(F)cc2n1-c1ccc(F)cc1] | {1-[6-Fluoro-1-(4-fluoro-phenyl)-1H-benzoimidazol-2-yl]-ethyl}-(9H-purin-6-yl)-amine | 0.134 |
| 187 | 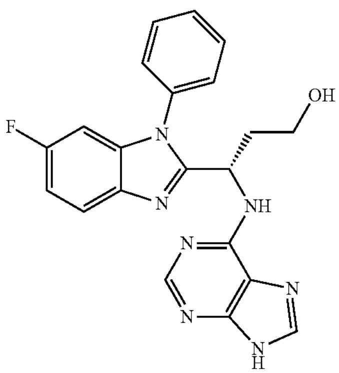 [SMILES: OCC[C@H](Nc1ncnc2[nH]cnc12)c1nc2ccc(F)cc2n1-c1ccccc1] | (S)-3-(6-Fluoro-1-phenyl-1H-benzoimidazol-2-yl)-3-(9H-purin-6-ylamino)-propan-1-ol | 0.119 |
| 188 | 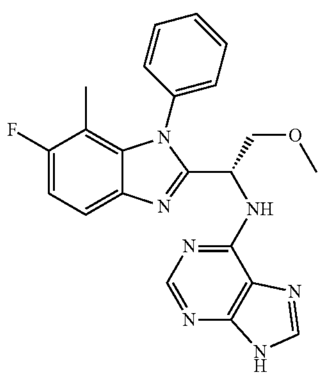 [SMILES: COC[C@H](Nc1ncnc2[nH]cnc12)c1nc2ccc(F)c(C)c2n1-c1ccccc1] | [(R)-1-(6-Fluoro-7-methyl-1-phenyl-1H-benzoimidazol-2-yl)-2-methoxy-ethyl]-(9H-purin-6-yl)-amine | 0.149 |
| 189 | 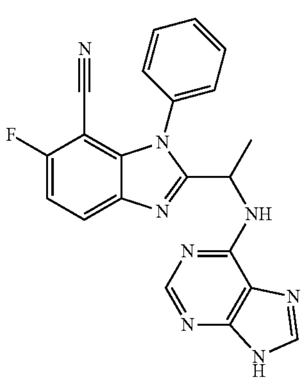 [SMILES: CC(Nc1ncnc2[nH]cnc12)c1nc2ccc(F)c(C#N)c2n1-c1ccccc1] | 5-Fluoro-3-phenyl-2-[1-(9H-purin-6-ylamino)-ethyl]-3H-benzoimidazole--4-carbonitrile | 0.0395 |

TABLE 2-continued

| No. | Structure | IUPAC_Name | CD69 Hu Blood FACS IC50 (μM) |
|---|---|---|---|
| 190 | 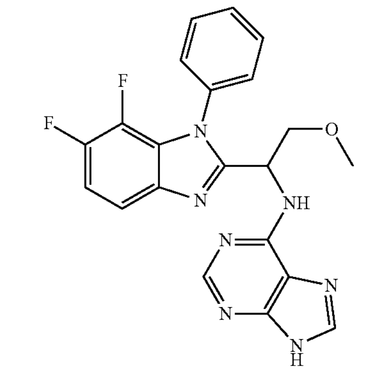 [SMILES: COCC(Nc1ncnc2[nH]cnc12)c1nc2ccc(F)c(F)c2n1-c1ccccc1] | [1-(6,7-Difluoro-1-phenyl-1H-benzoimidazol-2-yl)-2-methoxy-ethyl]-(9H-purin-6-yl)-amine | 0.247 |
| 191 | 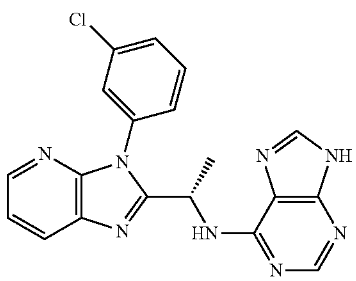 [SMILES: C[C@H](Nc1ncnc2[nH]cnc12)c1nc2cccnc2n1-c1cccc(Cl)c1] | {(S)-1-[3-(3-Chloro-phenyl)-3H-imidazo[4,5-b]pyridin-2-yl]-ethyl}-(9H-purin-6-yl)-amine | |
| 192 | 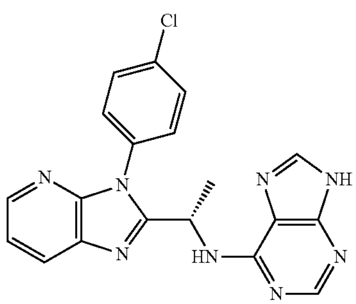 [SMILES: C[C@H](Nc1ncnc2[nH]cnc12)c1nc2cccnc2n1-c1ccc(Cl)cc1] | {(S)-1-[3-(4-Chloro-phenyl)-3H-imidazo[4,5-b]pyridin-2-yl]-ethyl}-(9H-purin-6-yl)-amine | |
| 193 | 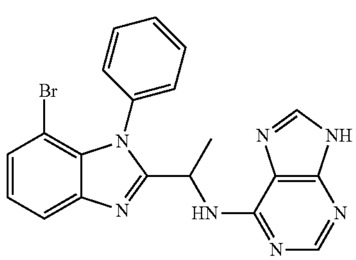 [SMILES: CC(Nc1ncnc2[nH]cnc12)c1nc2cccc(Br)c2n1-c1ccccc1] | [1-(7-Bromo-1-phenyl-1H-benzoimidazol-2-yl)-ethyl]-(9H-purin-6-yl)-amine | |
| 194 | 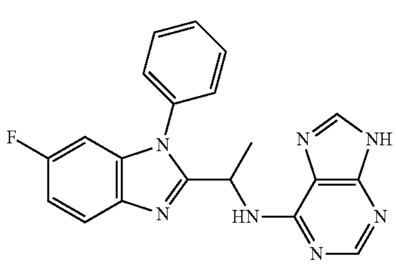 [SMILES: CC(Nc1ncnc2[nH]cnc12)c1nc2ccc(F)cc2n1-c1ccccc1] | [1-(6-Fluoro-1-phenyl-1H-benzoimidazol-2-yl)-ethyl]-(9H-purin-6-yl)-amine | 0.0508 |

TABLE 2-continued

| No. | Structure | IUPAC_Name | CD69 Hu Blood FACS IC50 (μM) |
|---|---|---|---|
| 195 | 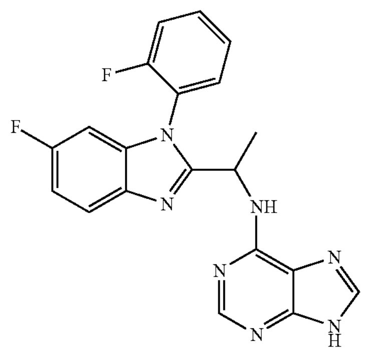 [SMILES: CC(Nc1ncnc2[nH]cnc12)c1nc2ccc(F)cc2n1-c1ccccc1F] | {1-[6-Fluoro-1-(2-fluoro-phenyl)-1H-benzoimidazol-2-yl]-ethyl}-(9H-purin-6-yl)-amine | 0.053 |
| 196 | 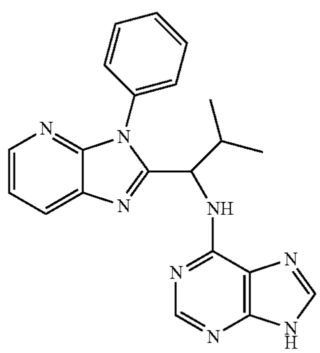 [SMILES: CC(C)C(Nc1ncnc2[nH]cnc12)c1nc2cccnc2n1-c1ccccc1] | [2-Methyl-1-(3-phenyl-3H-imidazo[4,5-b]pyridin-2-yl)-propyl]-(9H-purin-6-yl)-amine | |
| 197 | 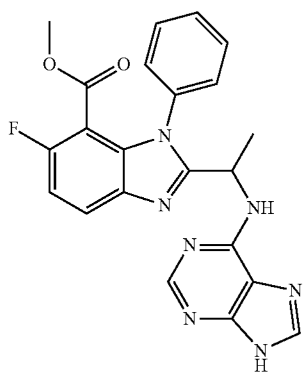 [SMILES: COC(=O)c1c(F)ccc2nc(C(C)Nc3ncnc4[nH]cnc34)n(-c3ccccc3)c12] | 5-Fluoro-3-phenyl-2-[1-(9H-purin-6-ylamino)-ethyl]-3H-benzoimidazole-4-carboxylic acid methyl esther | 0.0316 |
| 198 | 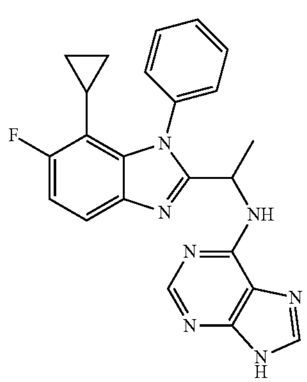 | [1-(7-Cyclopropyl-6-fluoro-1-phenyl-1H-benzoimidazol-2-yl)-ethyl]-(9H-purin-6-yl)-amine | 0.0109 |

TABLE 2-continued

| No. | Structure | IUPAC_Name | CD69 Hu Blood FACS IC50 (μM) |
|---|---|---|---|
| 199 | 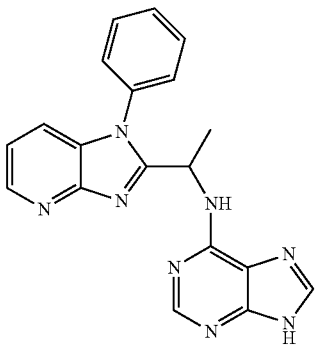 [SMILES: CC(Nc1ncnc2[nH]cnc12)c1nc2ncccc2n1-c1ccccc1] | [1-(1-Phenyl-1H-imidazo[4,5-b]pyridin-2-yl)-ethyl]-(9H-purin-6-yl)-amine | |
| 200 | 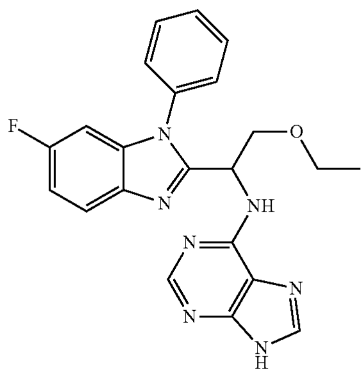 [SMILES: CCOCC(Nc1ncnc2[nH]cnc12)c1nc2ccc(F)cc2n1-c1ccccc1] | [2-Ethoxy-1-(6-fluoro-1-phenyl-1H-benzoimidazol-2-yl)-ethyl]-(9H-purin-6-yl)-amine | |
| 201 | 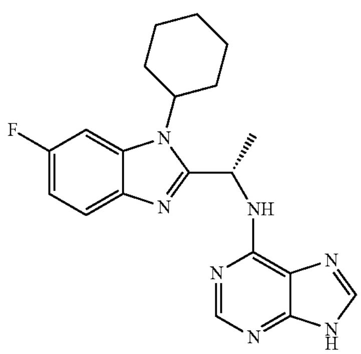 [SMILES: C[C@H](Nc1ncnc2[nH]cnc12)c1nc2ccc(F)cc2n1C1CCCCC1] | [(S)-1-(1-Cyclohexyl-6-fluoro-1H-benzoimidazol-2-yl)-ethyl]-(9H-purin-6-yl)-amine | 0.118 |
| 202 | 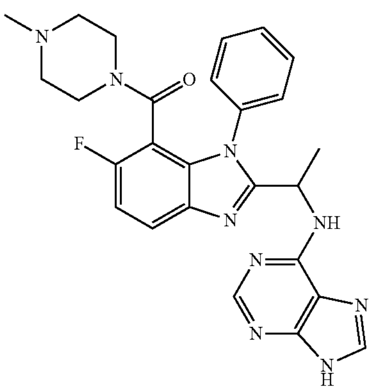 [SMILES: CC(Nc1ncnc2[nH]cnc12)c1nc2ccc(F)c(C(=O)N3CCN(C)CC3)c2n1-c1ccccc1] | {5-Fluoro-3-phenyl-2-[1-(9H-purin-6-ylamino)-ethyl]-3H-benzoimidazol-4-yl}-(4-methyl-piperazin-1-yl)-methanone | 0.0141 |

TABLE 2-continued

| No. | Structure | IUPAC_Name | CD69 Hu Blood FACS IC50 (μM) |
|---|---|---|---|
| 203 | 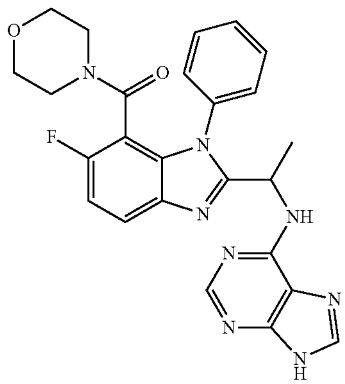 [SMILES: CC(Nc1ncnc2[nH]cnc12)c1nc2ccc(F)c(C(=O)N3CCOCC3)c2n1-c1ccccc1] | {5-Fluoro-3-phenyl-2-[1-(9H-purin-6-ylamino)-ethyl]-3-benzoimidazol-4-yl}-morpholin-4-yl-methanone | 0.00283 |
| 204 | 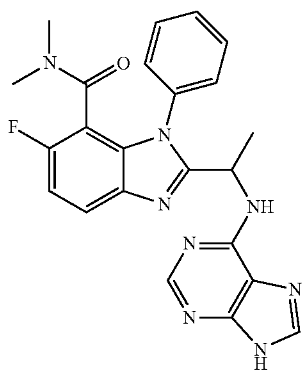 [SMILES: CC(Nc1ncnc2[nH]cnc12)c1nc2ccc(F)c(C(=O)N(C)C)c2n1-c1ccccc1] | 5-Fluoro-3-phenyl-2-[1-(9H-purin-6-ylamino)-ethyl]-3H-benzoimidazole-4-carboxylic acid dimethylamide | 0.0675 |
| 205 | 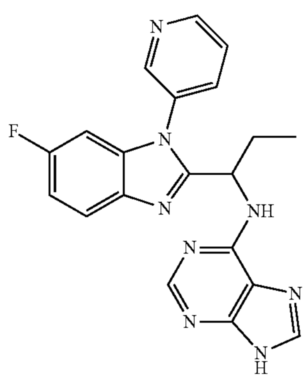 [SMILES: CCC(Nc1ncnc2[nH]cnc12)c1nc2ccc(F)cc2n1-c1cccnc1] | [1-(6-Fluoro-1-pyridin-3-yl-1H-benzoimidazol-2-yl)-propyl]-(9H-purin-6-yl)-amine | 0.0429 |
| 206 | 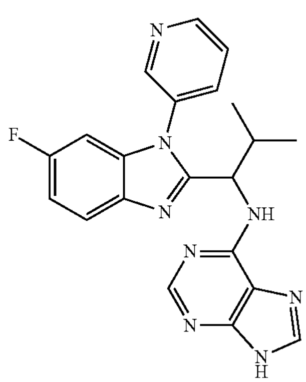 [SMILES: CC(C)C(Nc1ncnc2[nH]cnc12)c1nc2ccc(F)cc2n1-c1cccnc1] | [1-(6-Fluoro-1-pyridin-3-yl-1H-benzoimidazol-2-yl)-2-methyl-propyl]-(9H-purin-6-yl)-amine | 0.0547 |

TABLE 2-continued

| No. | Structure | IUPAC_Name | CD69 Hu Blood FACS IC50 (μM) |
|---|---|---|---|
| 207 | 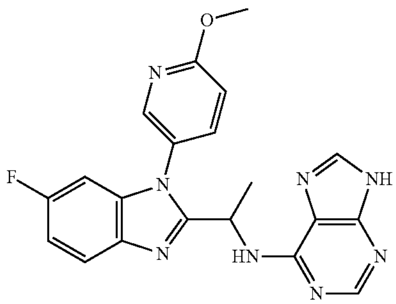 [SMILES: COc1ccc(-n2c(C(C)Nc3ncnc4[nH]cnc34)nc3ccc(F)cc32)cn1] | {1-[6-Fluoro-1-(6-methoxy-pyridin-3-yl)-1H-benzoimidazol-2-yl]-ethyl}-(9H-purin-6-yl)-amine | 0.798 |
| 208 | 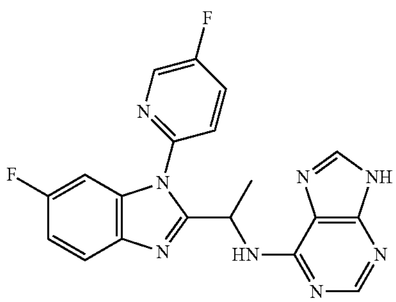 [SMILES: CC(Nc1ncnc2[nH]cnc12)c1nc2ccc(F)cc2n1-c1ccc(F)cn1] | {1-[6-Fluoro-1-(5-fluoro-pyridin-2-yl)-1H-benzoimidazol-2-yl]-ethyl}-(9H-purin-6-yl)-amine | 0.206 |
| 209 | 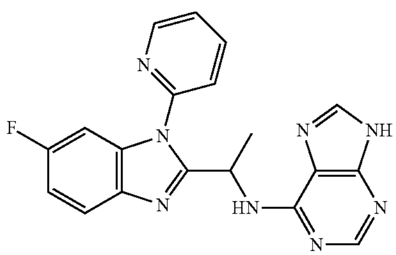 | [1-(6-Fluoro-1-pyridin-2-yl-1H-benzoimidazol-2-yl)-ethyl]-(9H-purin-6-yl)-amine | |
| 210 | 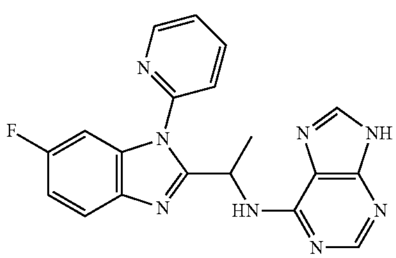 | [1-(6-Fluoro-1-pyridin-2-yl-1H-benzoimidazol-2-yl)-ethyl]-(9H-purin-6-yl)-amine | 0.0202 |
| 211 | 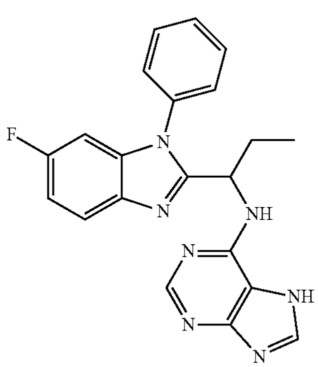 | [1-(6-Fluoro-1-phenyl-1H-benzoimidazol-2-yl)-propyl]-(7H-purin-6-yl)-amine | |

TABLE 2-continued

| No. | Structure | IUPAC_Name | CD69 Hu Blood FACS IC50 (μM) |
|---|---|---|---|
| 212 | 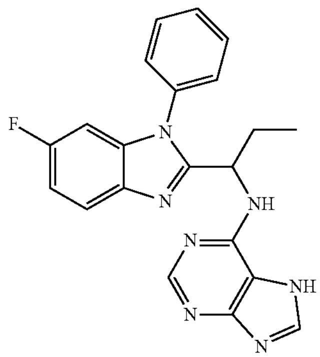 | [1-(6-Fluoro-1-phenyl-1H-benzoimidazol-2-yl)-propyl]-(7H-purin-6-yl)-amine | 0.0555 |
| 213 | 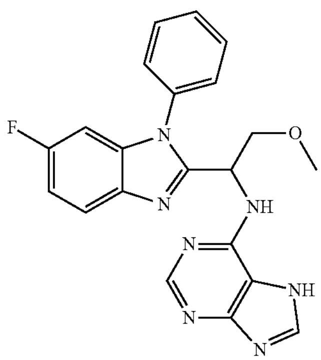 [SMILES: COCC(Nc1ncnc2nc[nH]c12)c1nc2ccc(F)cc2n1-c1ccccc1] | [1-(6-Fluoro-1-phenyl-1H-benzoimidazol-2-yl)-2-methyl-ethyl]-(7H-purin-6-yl)-amine | |
| 214 | 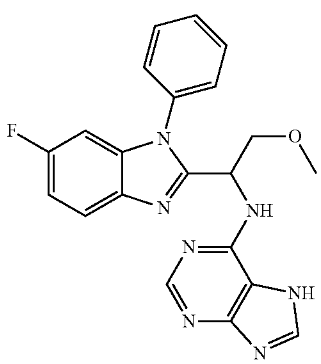 [SMILES: COCC(Nc1ncnc2nc[nH]c12)c1nc2ccc(F)cc2n1-c1ccccc1] | [1-(6-Fluoro-1-phenyl-1H-benzoimidazol-2-yl)-2-methyl-ethyl]-(7H-purin-6-yl)-amine | |
| 215 | 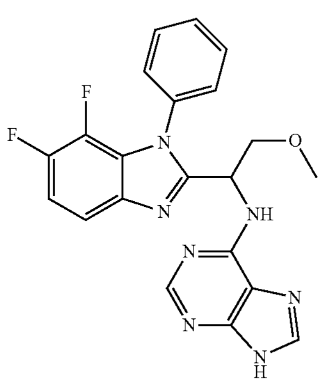 [SMILES: COCC(Nc1ncnc2[nH]cnc12)c1nc2ccc(F)c(F)c2n1-c1ccccc1] | [1-(6,7-Difluoro-1-phenyl-1H-benzoimidazol-2-yl)-2-methoxy-ethyl]-(9H-purin-6-yl)-amine | |

TABLE 2-continued

| No. | Structure | IUPAC_Name | CD69 Hu Blood FACS IC50 (μM) |
|---|---|---|---|
| 216 | 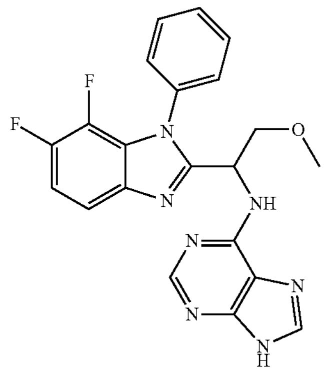 [SMILES: COCC(Nc1ncnc2[nH]cnc12)c1nc2ccc(F)c(F)c2n1-c1ccccc1] | [1-(6,7-Difluoro-1-phenyl-1H-benzoimidazol-2-yl)-2-methoxy-ethyl]-(9H-purin-6-yl)-amine | |
| 217 | 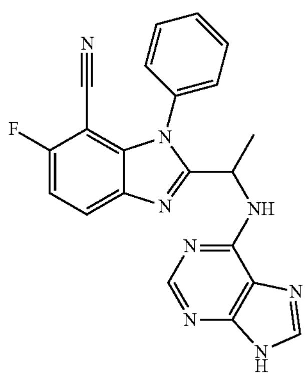 [SMILES: CC(Nc1ncnc2[nH]cnc12)c1nc2ccc(F)c(C#N)c2n1-c1ccccc1] | 5-Fluoro-3-phenyl-2-[1-(9H-purin-6-ylamino)-ethyl]-3H-benzoimidazole-4-carbonitrile | 0.0433 |
| 218 | 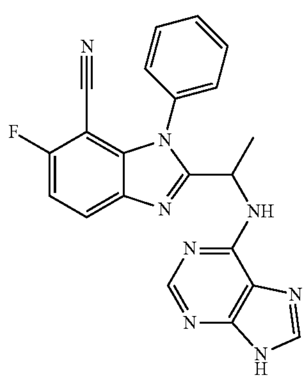 [SMILES: CC(Nc1ncnc2[nH]cnc12)c1nc2ccc(F)c(C#N)c2n1-c1ccccc1] | 5-Fluoro-3-phenyl-2-[1-(9H-purin-6-ylamino)-ethyl]-3H-benzoimidazole-4-carbonitrile | |
| 219 | 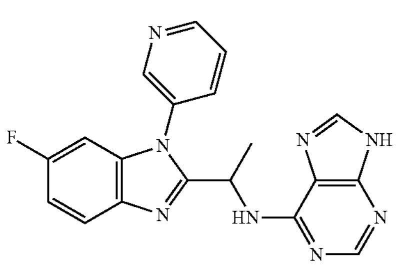 | [1-(6-Fluoro-1-pyridin-3-yl-1H-benzoimidazol-2-yl)-ethyl]-(9H-purin-6-yl)-amine | |

TABLE 2-continued

| No. | Structure | IUPAC_Name | CD69 Hu Blood FACS IC50 (μM) |
|---|---|---|---|
| 220 | 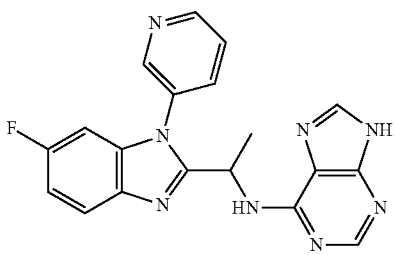 | [1-(6-Fluoro-1-pyridin-3-yl-1H-benzoimidazol-2-yl)-ethyl]-(9H-purin-6-yl)-amine | 0.0127 |
| 221 | 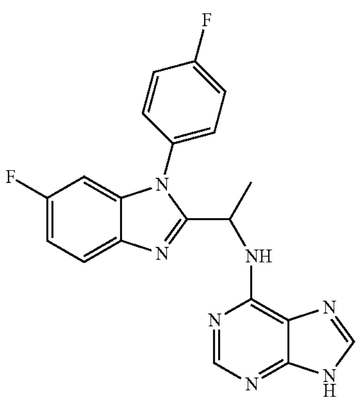 [SMILES: CC(Nc1ncnc2[nH]cnc12)c1nc2ccc(F)cc2n1-c1ccc(F)cc1] | {1-[6-Fluoro-1-(4-fluoro-phenyl)-1H-benzoimidazol-2-yl]-ethyl}-(9H-purin-6-yl)-amine | 0.152 |
| 222 | 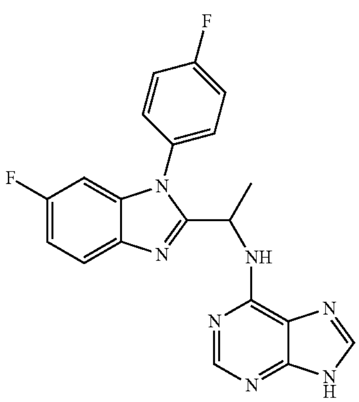 [SMILES: CC(Nc1ncnc2[nH]cnc12)c1nc2ccc(F)cc2n1-c1ccc(F)cc1] | {1-[6-Fluoro-1-(4-fluoro-phenyl)-1H-benzoimidazol-2-yl]-ethyl}-(9H-purin-6-yl)-amine | |
| 223 | 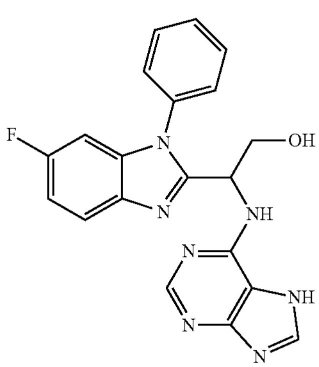 | 2-(6-Fluoro-1-phenyl-1H-benzoimidazol-2-yl)-2-(7H-purin-6-ylamino)-ethanol | |

TABLE 2-continued

| No. | Structure | IUPAC_Name | CD69 Hu Blood FACS IC50 (μM) |
|---|---|---|---|
| 224 | 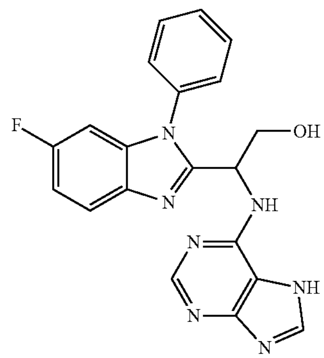 | 2-(6-Fluoro-1-phenyl-1H-benzoimidazol-2-yl)-2-(7H-purin-6-ylamino)-ethanol | 0.129 |
| 225 | 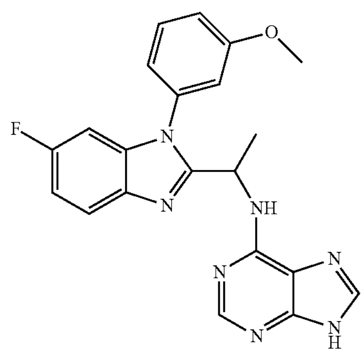 [SMILES: COc1cccc(-n2c(C(C)Nc3ncnc4[nH]cnc34)nc3ccc(F)cc32)c1] | {1-[6-Fluoro-1-(3-methoxy-phenyl)-1H-benzoimidazol-2-yl]-ethyl}-(9H-purin-6-yl)-amine | |
| 226 | 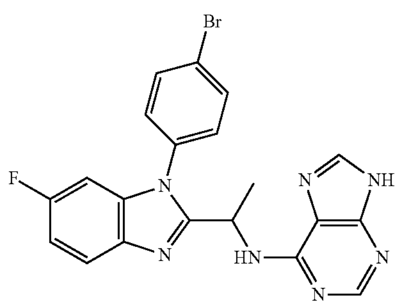 [SMILES: CC(Nc1ncnc2[nH]cnc12)c1nc2ccc(F)cc2n1-c1ccc(Br)cc1] | {1-[1-(4-Bromo-phenyl)-6-fluoro-1H-benzoimidazol-2-yl]-ethyl}-(9H-purin-6-yl)-amine | |
| 227 | 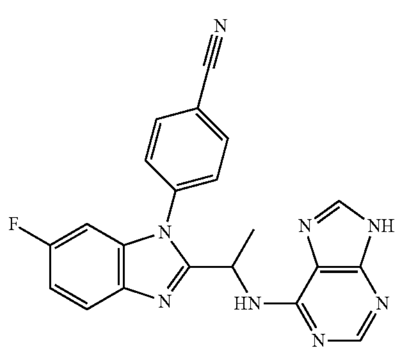 [SMILES: CC(Nc1ncnc2[nH]cnc12)c1nc2ccc(F)cc2n1-c1ccc(C#N)cc1] | 4-{6-Fluoro-2-[1-(9H-purin-6-ylamino)-ethyl]-benzoimidazol-1-yl}-benzonitrile | 0.0783 |

TABLE 2-continued

| No. | Structure | IUPAC_Name | CD69 Hu Blood FACS IC50 (μM) |
|---|---|---|---|
| 228 | 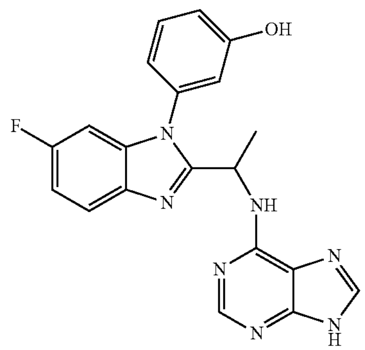 [SMILES: CC(Nc1ncnc2[nH]cnc12)c1nc2ccc(F)cc2n1-c1cccc(O)c1] | 3-{6-Fluoro-2-[1-(9H-purin-6-ylamino)-ethyl]-benzoimidazol-1-yl}-phenol | |
| 229 | 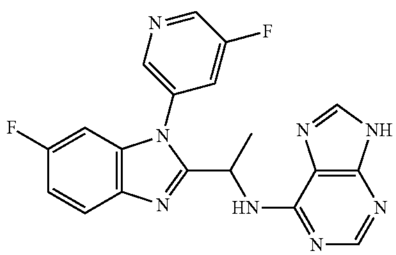 | {1-[6-Fluoro-1-(5-fluoro-pyridin-3-yl)-1H-benzoimidazol-2-yl]-ethyl}-(9H-purin-6-yl)-amine | |
| 230 | 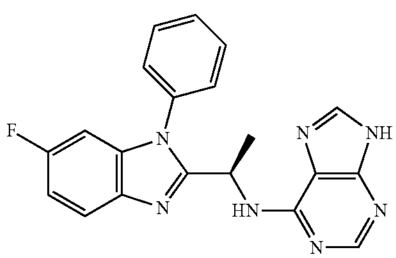 [SMILES: C[C@@H](Nc1ncnc2[nH]cnc12)c1nc2ccc(F)cc2n1-c1ccccc1] | [(R)-1-(6-Fluoro-1-phenyl-1H-benzoimidazol-2-yl)-ethyl]-(9H-purin-6-yl)-amine | |
| 231 | 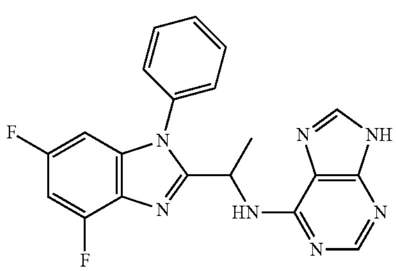 [SMILES: CC(Nc1ncnc2[nH]cnc12)c1nc2c(F)cc(F)cc2n1-c1ccccc1] | [1-(4,6-Difluoro-1-phenyl-1H-benzoimidazol-2-yl)-ethyl]-(9H-purin-6-yl)-amine | |
| 232 | 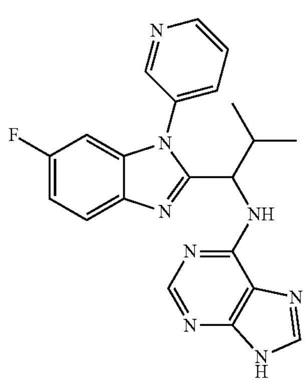 [SMILES: CC(C)C(Nc1ncnc2[nH]cnc12)c1nc2ccc(F)cc2n1-c1cccnc1] | [1-(6-Fluoro-1-pyridin-3-yl-1H-benzoimidazol-2-yl)-2-methyl-propyl]-(9H-purin-6-yl)-amine | |

TABLE 2-continued

| No. | Structure | IUPAC_Name | CD69 Hu Blood FACS IC50 (μM) |
|-----|-----------|------------|------|
| 233 | 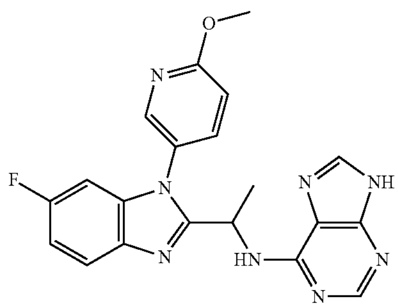 [SMILES: COc1ccc(-n2c(C(C)Nc3ncnc4[nH]cnc34)nc3ccc(F)cc32)cn1] | {1-[6-Fluoro-1-(6-methoxy-pyridin-3-yl)-1H-benzoimidazol-2-yl]-ethyl}-(9H-purin-6-yl)-amine | |
| 234 | 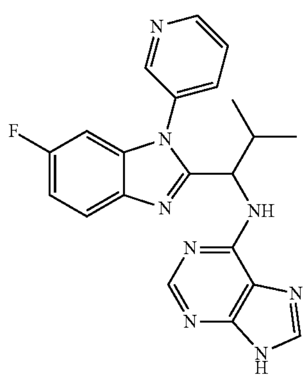 [SMILES: CC(C)C(Nc1ncnc2[nH]cnc12)c1nc2ccc(F)cc2n1-c1cccnc1] | [1-(6-Fluoro-1-pyridin-3-yl-1H-benzoimidazol-2-yl)-2-methyl-propyl]-(9H-purin-6-yl)-amine | |
| 235 | 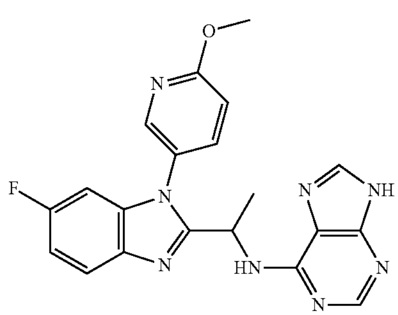 [SMILES: COc1ccc(-n2c(C(C)Nc3ncnc4[nH]cnc34)nc3ccc(F)cc32)cn1] | {1-[6-Fluoro-1-(6-methoxy-pyridin-3-yl)-1H-benzoimidazol-2-yl]-ethyl}-(9H-purin-6-yl)-amine | |
| 236 | 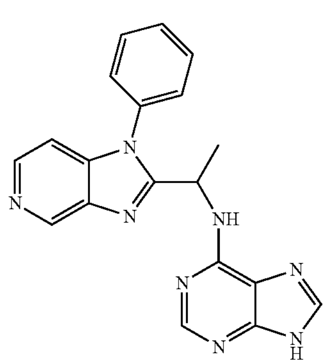 [SMILES: CC(Nc1ncnc2[nH]cnc12)c1nc2cnccc2n1-c1ccccc1] | [1-(1-Phenyl-1H-imidazo[4,5-c]pyridin-2-yl)-ethyl]-(9H-purin-6-yl)-amine | |

TABLE 2-continued

| No. | Structure | IUPAC_Name | CD69 Hu Blood FACS IC50 (μM) |
|---|---|---|---|
| 237 | 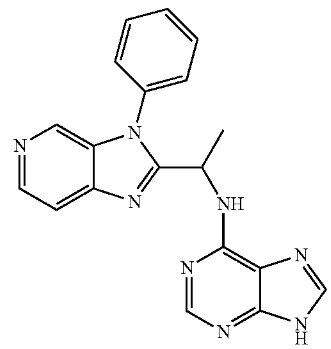 [SMILES: CC(Nc1ncnc2[nH]cnc12)c1nc2ccncc2n1-c1ccccc1] | [1-(3-Phenyl-3H-imidazo[4,5-c]pyridin-2-yl)-ethyl]-(9H-purin-6-yl)-amine | |
| 238 | 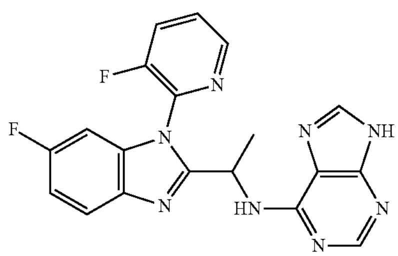 | {1-[6-Fluoro-1-(3-fluoro-pyridin-2-yl)-1H-benzoimidazol-2-yl]-ethyl}-(9H-purin-6-yl)-amine | |
| 239 | 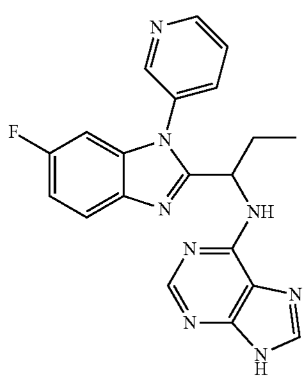 [SMILES: CCC(Nc1ncnc2[nH]cnc12)c1nc2ccc(F)cc2n1-c1cccnc1] | [1-(6-Fluoro-1-pyridin-3-yl-1H-benzoimidazol-2-yl)-propyl]-(9H-purin-6-yl)-amine | |
| 240 | 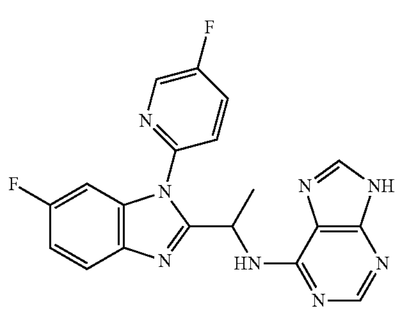 [SMILES: CC(Nc1ncnc2[nH]cnc12)c1nc2ccc(F)cc2n1-c1ccc(F)cn1] | {1-[6-Fluoro-1-(5-fluoro-pyridin-2-yl)-1H-benzoimidazol-2-yl]-ethyl}-(9H-purin-6-yl)-amine | |

TABLE 2-continued

| No. | Structure | IUPAC_Name | CD69 Hu Blood FACS IC50 (µM) |
|---|---|---|---|
| 241 | 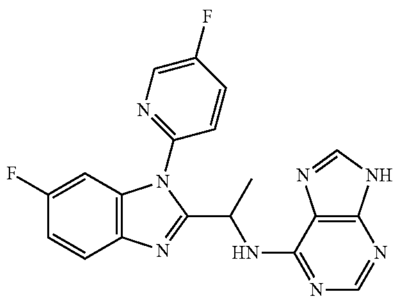 [SMILES: CC(Nc1ncnc2[nH]cnc12)c1nc2ccc(F)cc2n1-c1ccc(F)cn1] | {1-[6-Fluoro-1-(5-fluoro-pyridin-2-yl)-1H-benzoimidazol-2-yl]-ethyl}-(9H-purin-6-yl)-amine | |
| 242 | 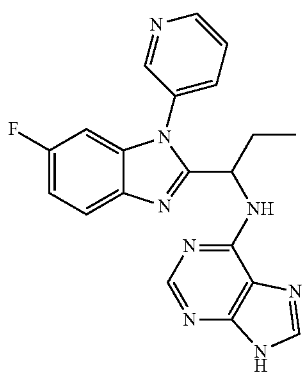 [SMILES: CCC(Nc1ncnc2[nH]cnc12)c1nc2ccc(F)cc2n1-c1cccnc1] | [1-(6-Fluoro-1-pyridin-3-yl-1H-benzoimidazol-2-yl)-propyl]-(9H-purin-6-yl)-amine | |
| 243 | 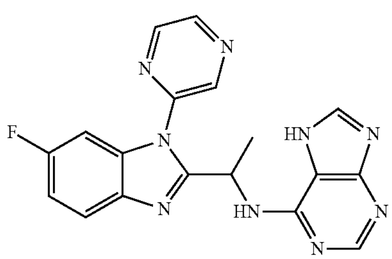 [SMILES: CC(Nc1ncnc2nc[nH]c12)c1nc2ccc(F)cc2n1-c1cnccn1] | [1-(6-Fluoro-1-pyrazin-2-yl 1H-benzoimidazol-2-yl)-ethyl]-(7H-purin-6-yl)-amine | |
| 244 | 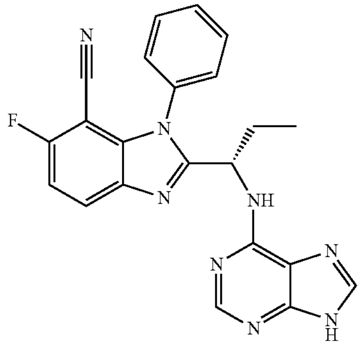 [SMILES: CC[C@H](Nc1ncnc2[nH]cnc12)c1nc2ccc(F)c(C#N)c2n1-c1ccccc1] | 5-Fluoro-3-phenyl-2-[(S)-1-(9H-purin-6-ylamino)-propyl]-3H-benzoimidazole-4-carbonitrile | 0.0793 |

TABLE 2-continued

| No. | Structure | IUPAC_Name | CD69 Hu Blood FACS IC50 (μM) |
|---|---|---|---|
| 245 | 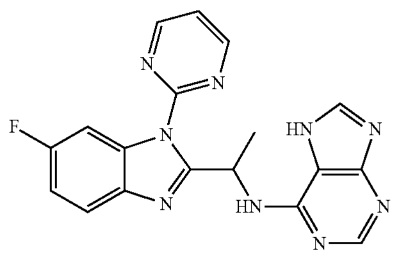 [SMILES: CC(Nc1ncnc2nc[nH]c12)c1nc2ccc(F)cc2n1-c1ncccn1] | [1-(6-Fluoro-1-pyrimidin-2-yl 1H-benzoimidazol-2-yl)-ethyl]-(7H-purin-6-yl)-amine | |
| 246 | 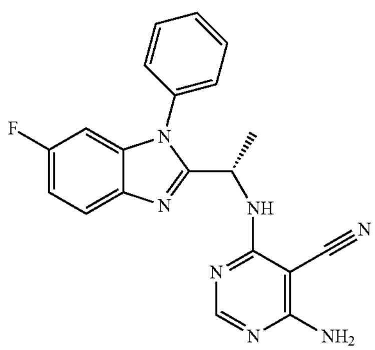 | 4-Amino-6-[(S)-1-(6-fluoro-1-phenyl-1H-benzoimidazol-2-yl)-ethylamino]-pyrimidine-5-carbonitrile | 0.0167 |
| 247 | 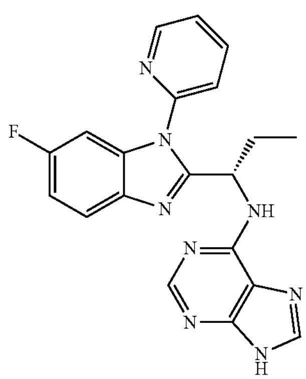 [SMILES: CC[C@H](Nc1ncnc2[nH]cnc12)c1nc2ccc(F)cc2n1-c1ccccn1] | [(S)-1-(6-Fluoro-1-pyrazin-2-yl-1H-benzoimidazol-2-yl)-propyl]-(9H-purin-6-yl)-amine | 0.405 |
| 248 | 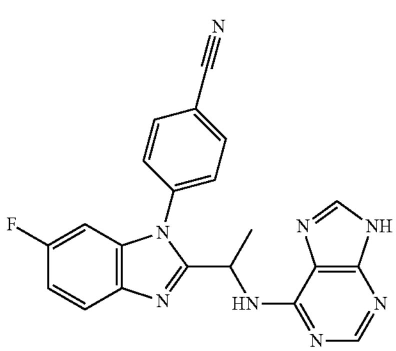 [SMILES: CC(Nc1ncnc2[nH]cnc12)c1nc2ccc(F)cc2n1-c1ccc(C#N)cc1] | 4-{6-Fluoro-2-[1-(9H-purin-6-ylamino)-ethyl]-benzoimidazol-1-yl}-benzonitrile | 0.0789 |

TABLE 2-continued

| No. | Structure | IUPAC_Name | CD69 Hu Blood FACS IC50 (μM) |
|---|---|---|---|
| 249 | 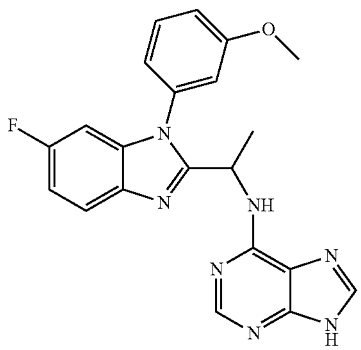 [SMILES: COc1cccc(-n2c(C(C)Nc3ncnc4[nH]cnc34)nc3ccc(F)cc32)c1] | {1-[6-Fluoro-1-(3-methoxy-phenyl)-1H-benzoimidazol-2-yl]-ethyl}-(9H-purin-6-yl)-amine | |
| 250 | 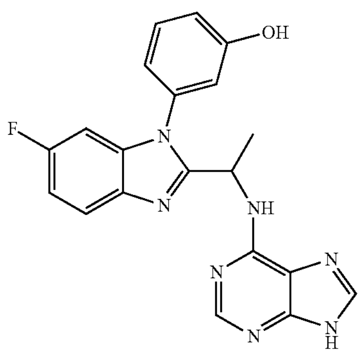 [SMILES: CC(Nc1ncnc2[nH]cnc12)c1nc2ccc(F)cc2n1-c1cccc(O)c1] | 3-{6-Fluoro-2-[1-(9H-purin-6-ylamino)-ethyl]-benzoimidazol-1-yl}-phenol | |
| 251 | 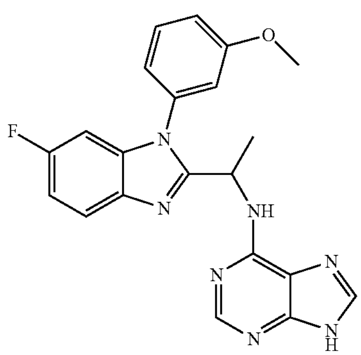 | {1-[6-Fluoro-1-(3-methoxy-phenyl)-1H-benzoimidazol-2-yl]-ethyl}-(9H-purin-6-yl)-amine | |
| 252 | 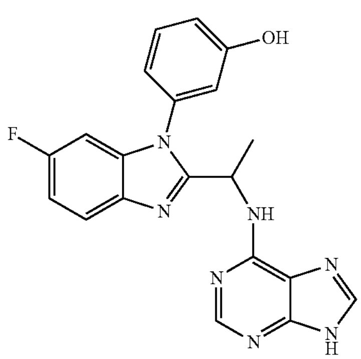 [SMILES: CC(Nc1ncnc2[nH]cnc12)c1nc2ccc(F)cc2n1-c1cccc(O)c1] | 3-{6-Fluoro-2-[1-(9H-purin-6-ylamino)-ethyl]-benzoimidazol-1-yl}-phenol | |

TABLE 2-continued

| No. | Structure | IUPAC_Name | CD69 Hu Blood FACS IC50 (μM) |
|---|---|---|---|
| 253 | 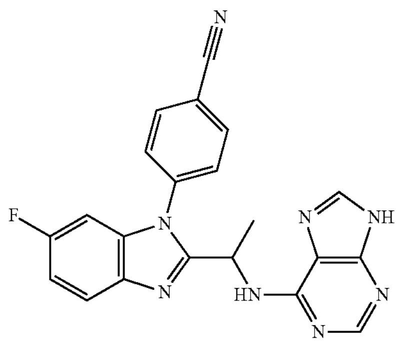 [SMILES: CC(Nc1ncnc2[nH]cnc12)c1nc2ccc(F)cc2n1-c1ccc(C#N)cc1] | 4-{6-Fluoro-2-[1-(9H-purin-6-ylamino)-ethyl]-benzoimidazol-1-yl}-benzonitrile | |
| 254 | 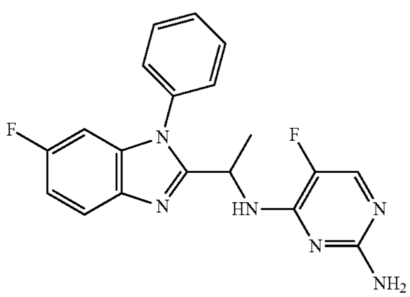 [SMILES: CC(Nc1nc(N)ncc1F)c1nc2ccc(F)cc2n1-c1ccccc1] | 5-Fluoro-N4-[1-(6-fluoro-1-phenyl-1H-benzoimidazol-2-yl)-ethyl]-pyrimidine-2,4-diamine | |
| 255 | 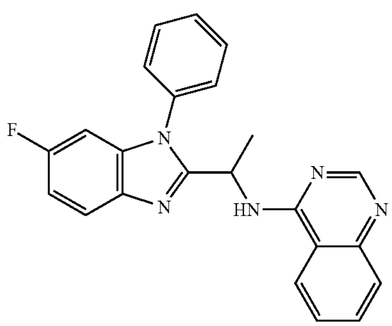 [SMILES: CC(Nc1ncnc2ccccc12)c1nc2ccc(F)cc2n1-c1ccccc1] | [1-(6-Fluoro-1-phenyl-1H-benzoimidazol-2-yl)-ethyl]-quinazolin-4-yl-amine | |
| 256 | 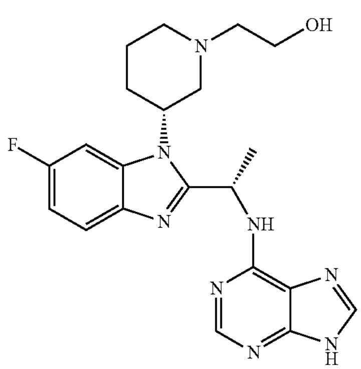 [SMILES: C[C@H](Nc1ncnc2[nH]cnc12)c1nc2ccc(F)cc2n1[C@@H]1CCCN(CCO)C1] | 2-((R)-3-{6-Fluoro-2-[(S)-1-(9H-purin-6-ylamino)-ethyl]-benzoimidazol-1-yl}-piperidin-1-yl)-ethanol | 0.0683 |

TABLE 2-continued

| No. | Structure | IUPAC_Name | CD69 Hu Blood FACS IC50 (μM) |
|---|---|---|---|
| 257 | 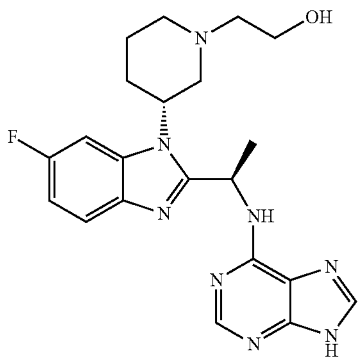 [SMILES: C[C@@H](Nc1ncnc2[nH]cnc12)c1nc2ccc(F)cc2n1[C@@H]1CCCN(CCO)C1] | 2-((R)-3-{6-Fluoro-2-[(R)-1-(9H-purin-6-ylamino)-ethyl]-benzoimidazol-1-yl}-piperidin-1-yl)-ethanol | |
| 258 | 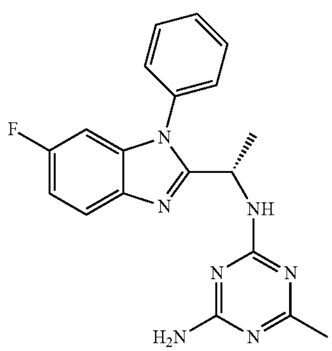 [SMILES: Cc1nc(N)nc(N[C@@H](C)c2nc3ccc(F)cc3n2-c2ccccc2)n1] | N-[(S)-1-(6-Fluoro-1-phenyl-1H-benzoimidazol-2-yl)-ethyl]-6-methyl-[1,3,5]triazine-2,4-diamine | 0.141 |
| 259 | 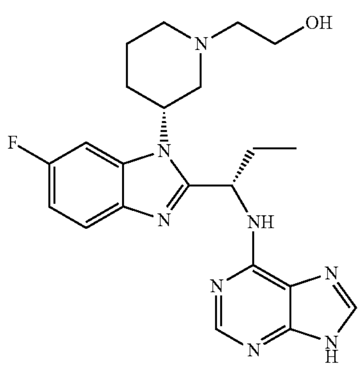 [SMILES: CC[C@H](Nc1ncnc2[nH]cnc12)c1nc2ccc(F)cc2n1[C@@H]1CCCN(CCO)C1] | 2-((R)-3-{6-Fluoro-2-[(S)-1-(9H-purin-6-ylamino)-propyl]-benzoimidazol-1-yl}-piperidin-1-yl)-ethanol | |
| 260 | 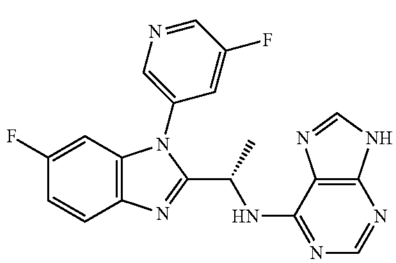 [SMILES: C[C@H](Nc1ncnc2[nH]cnc12)c1nc2ccc(F)cc2n1-c1cncc(F)c1] | {(S)-1-[6-Fluoro-1-(5-fluoro-pyridin-3-yl)-1H-benzoimidazol-2-yl]-ethyl}-(9H-purin-6-yl)-amine | 0.0257 |

TABLE 2-continued

| No. | Structure | IUPAC_Name | CD69 Hu Blood FACS IC50 (μM) |
|---|---|---|---|
| 261 | 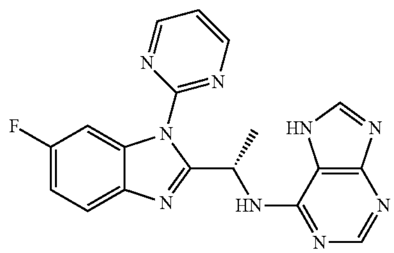 [SMILES: C[C@H](Nc1ncnc2nc[nH]c12)c1nc2ccc(F)cc2n1-c1ncccn1] | [(S)-1-(6-Fluoro-1-pyrimidin-2-yl-1H-benzoimidazol-2-yl)-ethyl]-(7H-purin-6-yl)-amine | |
| 262 | 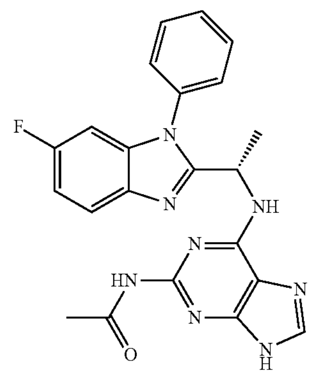 [SMILES: CC(=O)Nc1nc(N[C@@H](C)c2nc3ccc(F)cc3n2-c2ccccc2)c2nc[nH]c2n1] | N-{6-[(S)-1-(6-Fluoro-1-phenyl-1H-benzoimidazol-2-yl)-ethylamino]-9H-purin-2-yl}-acetamide | |
| 263 | 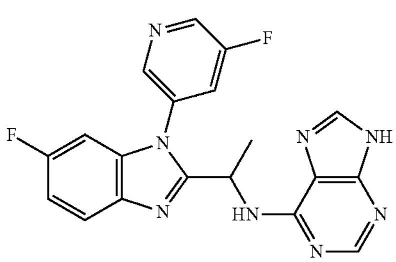 [SMILES: CC(Nc1ncnc2[nH]cnc12)c1nc2ccc(F)cc2n1-c1cncc(F)c1] | {1-[6-Fluoro-1-(5-fluoro-pyridin-3-yl)-1H-benzoimidazol-2-yl]-ethyl}-(9H-purin-6-yl)-amine | 0.0254 |
| 264 | 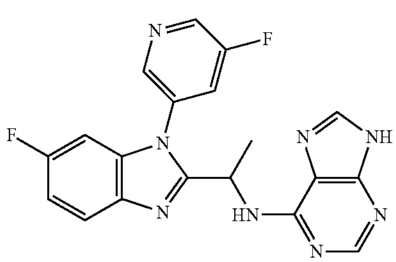 | {1-[6-Fluoro-1-(5-fluoro-pyridin-3-yl)-1H-benzoimidazol-2-yl]-ethyl}-(9H-purin-6-yl)-amine | |
| 265 | 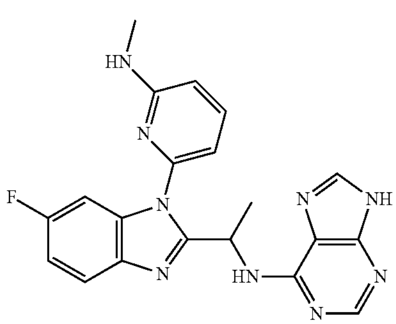 [SMILES: CNc1cccc(-n2c(C(C)Nc3ncnc4[nH]cnc34)nc3ccc(F)cc32)n1] | {1-[6-Fluoro-1-(6-methylamino-pyridin-2-yl)-1H-benzoimidazol-2-yl]-ethyl}-(9H-purin-6-yl)-amine | |

TABLE 2-continued

| No. | Structure | IUPAC_Name | CD69 Hu Blood FACS IC50 (μM) |
|---|---|---|---|
| 266 | 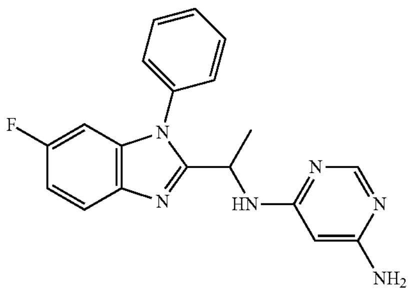 [SMILES: CC(Nc1cc(N)ncn1)c1nc2ccc(F)cc2n1-c1ccccc1] | N-[1-(6-Fluoro-1-phenyl-1H-benzoimidazol-2-yl)-ethyl]-pyrimidine-4,6-diamine | |
| 267 | 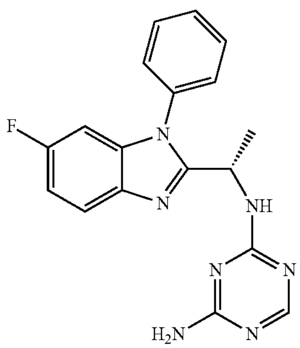 [SMILES: C[C@H](Nc1ncnc(N)n1)c1nc2ccc(F)cc2n1-c1ccccc1] | N-[(S-1-(6-Fluoro-1-phenyl-1H-benzoimidazol-2-yl)-ethyl]-[1,3,5]triazine-2,4-diamine | |
| 268 | 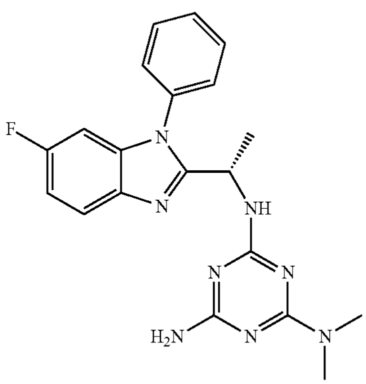 [SMILES: C[C@H](Nc1nc(N)nc(N(C)C)n1)c1nc2ccc(F)cc2n1-c1ccccc1] | N-[(S)1-(6-Fluoro-1-phenyl-1H-benzoimidazol-2-yl)-ethyl]-N',N',-dimethyl-[1,3,5]triazine-2,4,6-triamine | |
| 269 | 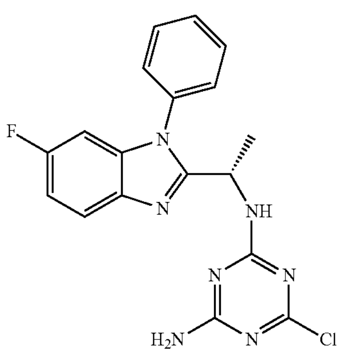 [SMILES: C[C@H](Nc1nc(N)nc(Cl)n1)c1nc2ccc(F)cc2n1-c1ccccc1] | 6-Chloro-N-[(S)-1-(6-fluoro-1-phenyl-1H-benzoimidazol-2-yl)-ethyl]-[1,3,5]triazine-2,4-diamine | |

TABLE 2-continued

| No. | Structure | IUPAC_Name | CD69 Hu Blood FACS IC50 (μM) |
|---|---|---|---|
| 270 | 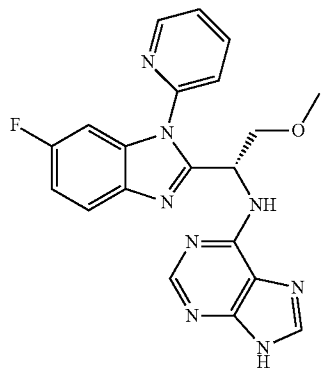 [SMILES: COC[C@H](Nc1ncnc2[nH]cnc12)c1nc2ccc(F)cc2n1-c1ccccn1] | [(R)-1-(6-Fluoro-1-pyridin-2-yl-1H-benzoimidazol-2-yl)-2-methoxy-ethyl]-(9H-purin-6-yl)-amine | 0.152 |
| 271 | 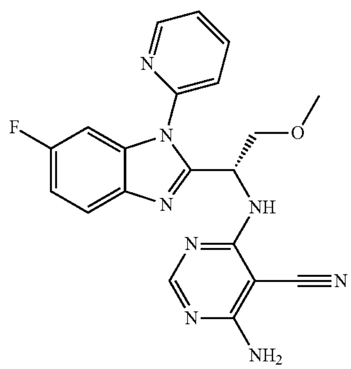 | 4-Amino-6-[(R)-1-(6-fluoro-1-pyridin-2-yl-1H-benzoimidazol-2-yl)-2-methoxy-ethylamino]-pyrimidine-5-carbonitrile | 0.0388 |
| 272 | 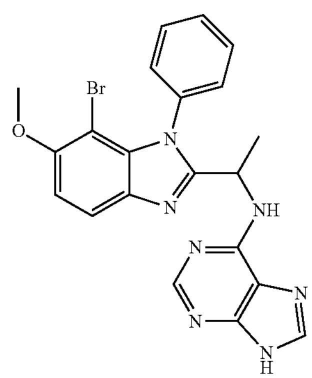 [SMILES: COc1ccc2nc(C(C)Nc3ncnc4[nH]cnc34)n(-c3ccccc3)c2c1Br] | [1-(7-Bromo-6-methoxy-1-phenyl-1H-benzoimidazol-2-yl)-ethyl]-(9H-purin-6-yl)-amine | |
| 273 | 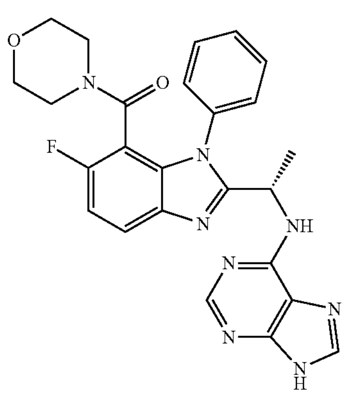 [SMILES: C[C@H](Nc1ncnc2[nH]cnc12)c1nc2ccc(F)c(C(=O)N3CCOCC3)c2n1-c1ccccc1] | {5-Fluoro-3-phenyl-2-[(S)-1-(9H-purin-6-ylamino)-ethyl]-3H-benzoimidazol-4-yl}-morpholin-4-yl-methanone | 0.0268 |

TABLE 2-continued

| No. | Structure | IUPAC_Name | CD69 Hu Blood FACS IC50 (μM) |
|---|---|---|---|
| 274 | 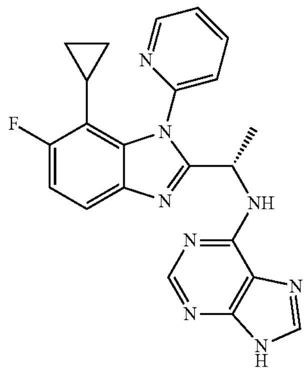 [SMILES: C[C@H](Nc1ncnc2[nH]cnc12)c1nc2ccc(F)c(C3CC3)c2n1-c1ccccn1] | [(S)-1-(7-Cyclopropyl-6-fluoro-1-pyridin-2-yl-1H-benzoimidazol-2-yl)-ethyl]-(9H-purin-6-yl)-amine | 0.0268 |
| 275 | 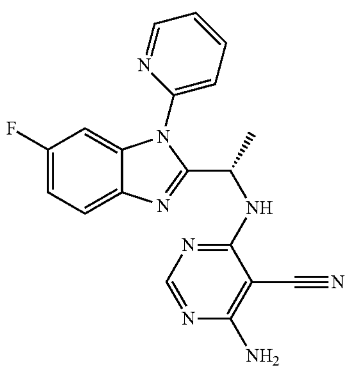 [SMILES: C[C@H](Nc1ncnc(N)c1C#N)c1nc2ccc(F)cc2n1-c1ccccn1] | 4-Amino-6-[(S)-1-(6-fluoro-1-pyridin-2-yl-1H-benzoimidazol-2-yl)-ethylamino]-pyrimidine-5-carbonitrile | 0.0275 |
| 276 | 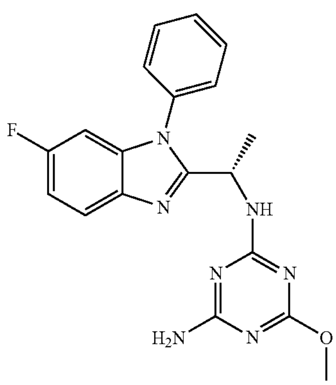 [SMILES: COc1nc(N)nc(N[C@@H](C)c2nc3ccc(F)cc3n2-c2ccccc2)n1] | N-[(S)-1-(6-Fluoro-1-phenyl-1H-benzoimidazol-2-yl)-ethyl]-6-methoxy-[1,3,5]triazine-2,4-diamine | |
| 277 | 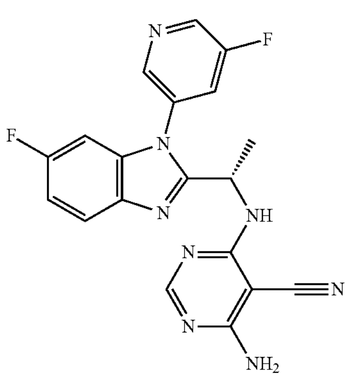 [SMILES: C[C@H](Nc1ncnc(N)c1C#N)c1nc2ccc(F)cc2n1-c1cncc(F)c1] | 4-Amino-6-{(S-1-[6-fluoro-1-(5-fluoro-pyridin-3-yl)-1H-benzoimidazol-2-yl]-ethylamino}-pyrimidine-5-carbonitrile | 0.018 |

TABLE 2-continued

| No. | Structure | IUPAC_Name | CD69 Hu Blood FACS IC50 (μM) |
|---|---|---|---|
| 278 | 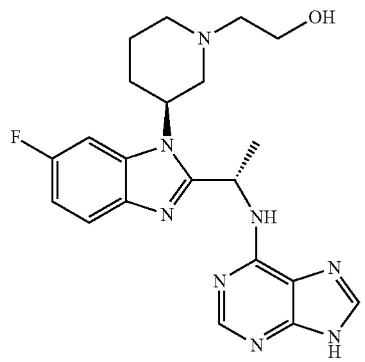 [SMILES: C[C@H](Nc1ncnc2[nH]cnc12)c1nc2ccc(F)cc2n1[C@H]1CCCN(CCO)C1] | 2-((S)-3-{6-Fluoro-2-[(S)-1-(9H-purin-6-ylamino)-ethyl]-benzoimidazol-1-yl}-piperidin-1-yl)-ethanol | 0.0166 |
| 279 | 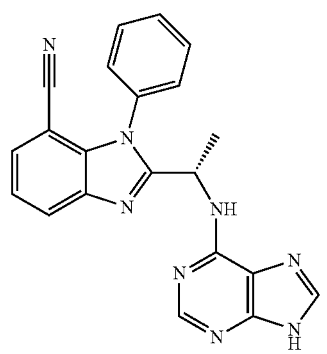 [SMILES: C[C@H](Nc1ncnc2[nH]cnc12)c1nc2cccc(C#N)c2n1-c1ccccc1] | 3-Phenyl-2-[(S)-1-(9H-purin-6-ylamino)-ethyl]-3H-benzoimidazole-4-carbonitrile | 0.184 |
| 280 | 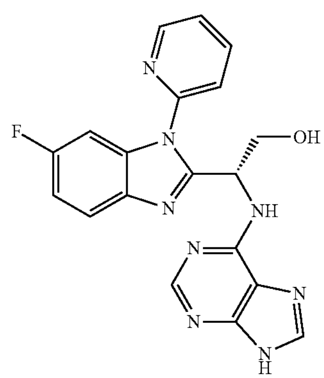 | (R)-2-(6-Fluoro-1-pyridin-2-yl-1H-benzoimidazol-2-yl)-2-(9H-purin-6-ylamino)-ethanol | 0.139 |
| 281 | 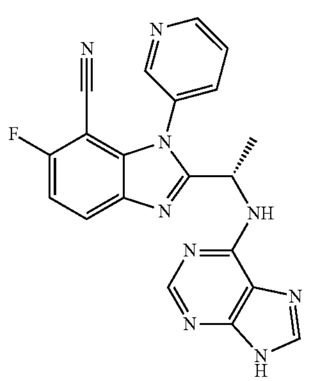 [SMILES: C[C@H](Nc1ncnc2[nH]cnc12)c1nc2ccc(F)c(C#N)c2n1-c1cccnc1] | 5-Fluoro-2-[(S)-1-(9H-purin-6-ylamino)-ethyl]-3-pyridin-3-yl-3H-benzoimidazole-4-carbonitrile | 0.11 |

TABLE 2-continued

| No. | Structure | IUPAC_Name | CD69 Hu Blood FACS IC50 (μM) |
|---|---|---|---|
| 282 | 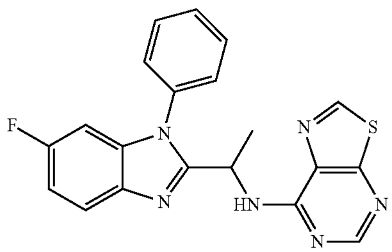 [SMILES: CC(Nc1ncnc2scnc12)c1nc2ccc(F)cc2n1-c1ccccc1] | [1-(6-Fluoro-1-phenyl-1H-benzoimidazol-2-yl)-ethyl]-thiazolo[5,4-d]pyrimidin-7-yl-amine | |
| 283 | 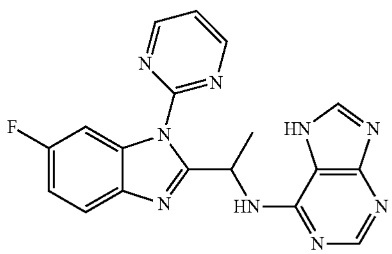 [SMILES: CC(Nc1ncnc2nc[nH]c12)c1nc2ccc(F)cc2n1-c1ncccn1] | [1-(6-Fluoro-1-pyrimidin-2-yl-1H-benzoimidazol-2-yl)-ethyl]-(7H-purin-6-yl)-amine | |
| 284 | 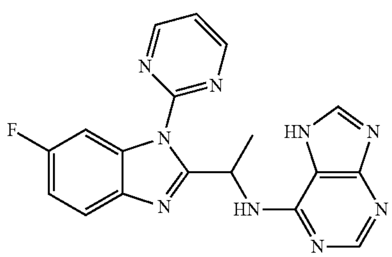 [SMILES: CC(Nc1ncnc2nc[nH]c12)c1nc2ccc(F)cc2n1-c1ncccn1] | [1-(6-Fluoro-1-pyrimidin-2-yl-1H-benzoimidazol-2-yl)-ethyl]-(7H-purin-6-yl)-amine | |
| 285 | 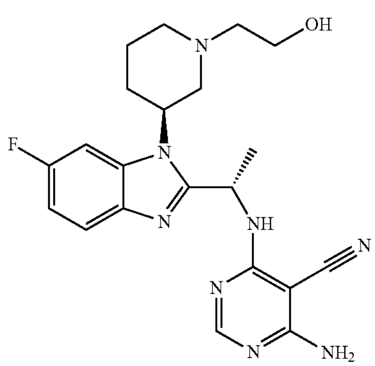 [SMILES: C[C@H](Nc1ncnc(N)c1C#N)c1nc2ccc(F)cc2n1[C@H]1CCCN(CCO)C1] | 4-Amino-6-((S)-1-{6-fluoro-1-[(S)-1-(2-hydroxy-ethyl)-piperidin-3-yl]-1H-benzoimidazol-2-yl}-ethylamino)-pyrimidine-5-carbonitrile | |
| 286 | 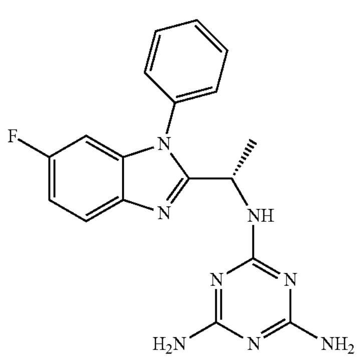 [SMILES: C[C@H](Nc1nc(N)nc(N)n1)c1nc2ccc(F)cc2n1-c1ccccc1] | N-[(S)-1-(6-Fluoro-1-phenyl-1H-benzoimidazol-2-yl)-ethyl]-[1,3,5]triazine-2,4,6-triamine | |

TABLE 2-continued

| No. | Structure | IUPAC_Name | CD69 Hu Blood FACS IC50 (μM) |
|---|---|---|---|
| 287 | 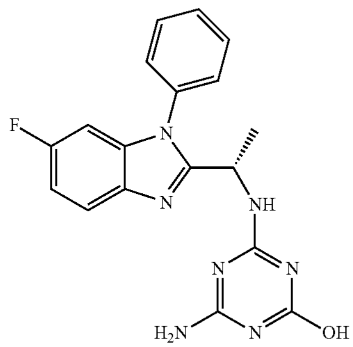 [SMILES: C[C@H](Nc1nc(N)nc(O)n1)c1nc2ccc(F)cc2n1-c1ccccc1] | 4-Amino-6-[(S)-1-(6-fluoro-1-phenyl-1H-benzoimidazol-2-yl)-ethylamino]-[1,3,5]triazin-2-ol | |
| 288 | 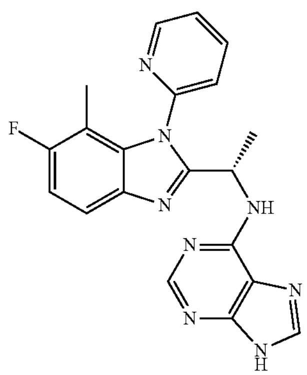 [SMILES: Cc1c(F)ccc2nc([C@H](C)Nc3ncnc4[nH]cnc34)n(-c3ccccn3)c12] | [(S)-1-(6-Fluoro-7-methyl-1-pyridin-2-yl-1H-benzoimidazol-2-yl)-ethyl]-(9H-purin-6-yl)-amine | |
| 289 | 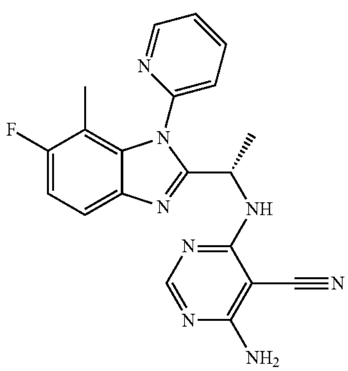 [SMILES: Cc1c(F)ccc2nc([C@H](C)Nc3ncnc(N)c3C#N)n(-c3ccccn3)c12] | 4-Amino-6-[(S)-1-(6-fluoro-7-methyl-1-pyridin-2-yl-1H-benzoimidazol-2-yl)-ethylamino]-pyrimidine-5-carbonitrile | 0.0483 |
| 290 | 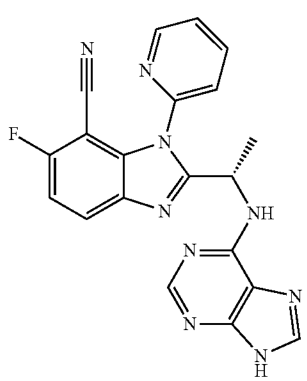 [SMILES: C[C@H](Nc1ncnc2[nH]cnc12)c1nc2ccc(F)c(C#N)c2n1-c1ccccn1] | 5-Fluoro-2-[(S)-1-(9H-purin-6-ylamino)-ethyl]-3-pyridin-2-yl-3H-benzoimidazole-4-carbonitrile | |

TABLE 2-continued

| No. | Structure | IUPAC_Name | CD69 Hu Blood FACS IC50 (μM) |
|---|---|---|---|
| 291 | 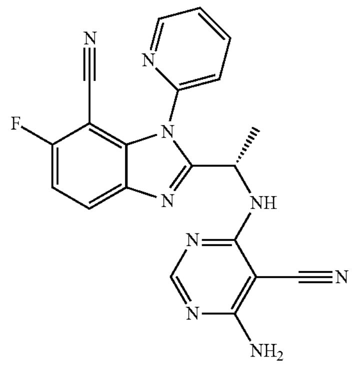 [SMILES: C[C@H](Nc1ncnc(N)c1C#N)c1nc2ccc(F)c(C#N)c2n1-c1ccccn1] | 2-[(S)-1-(6-Amino-5-cyano-pyrimidin-4-ylamino)-ethyl]-5-fluoro-3-pyridin-2-yl-3H-benzoimidazole-4-carbonitrile | 0.0972 |
| 292 | 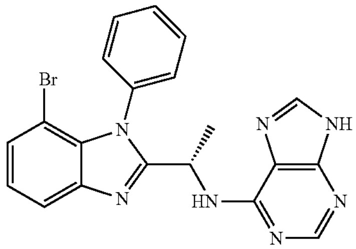 | [(S)-1-(7-Bromo-1-phenyl-1H-benzoimidazol-2-yl)-ethyl]-(9H-purin-6-yl)-amine | |
| 293 | 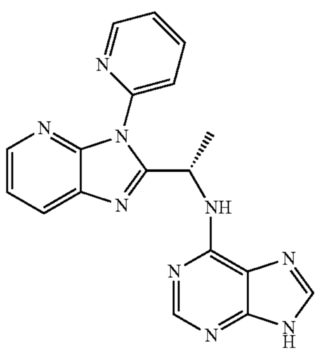 | (9H-Purin-6-yl)-[(S)-1-(3-pyridin-2-yl-3H-imidazo[4,5-b]pyridin-2-yl)-ethyl]-amine | |
| 294 | 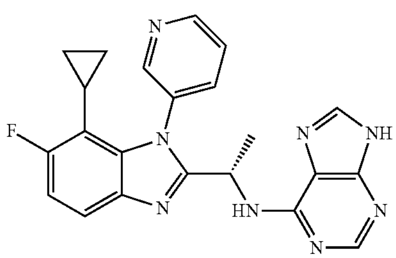 [SMILES: C[C@H](Nc1ncnc2[nH]cnc12)c1nc2ccc(F)c(C3CC3)c2n1-c1cccnc1] | [(S)-1-(7-Cyclopropyl-6-fluoro-1-pyridin-3-yl-1H-benzoimidazol-2-yl)-ethyl]-(9H-purin-6-yl)-amine | 0.0041 |
| 295 | 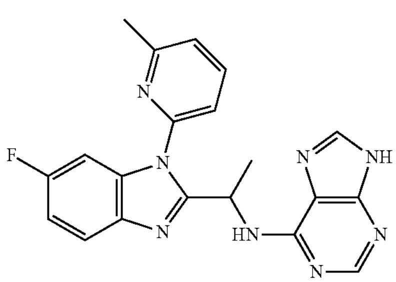 [SMILES: Cc1cccc(-n2c(C(C)Nc3ncnc4[nH]cnc34)nc3ccc(F)cc32)n1] | {1-[6-Fluoro-1-(6-methyl-pyridin-2-yl)-1H-benzoimidazol-2-yl]-ethyl}-(9H-purin-6-yl)-amine | |

TABLE 2-continued

| No. | Structure | IUPAC_Name | CD69 Hu Blood FACS IC50 (μM) |
|---|---|---|---|
| 296 | 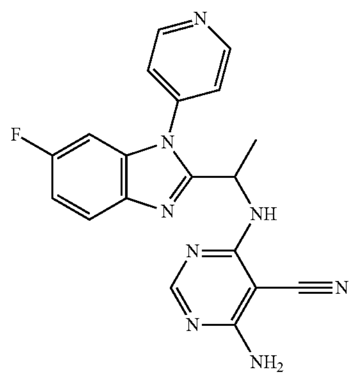 [SMILES: CC(Nc1ncnc(N)c1C#N)c1nc2ccc(F)cc2n1-c1ccncc1] | 4-Amino-6-[1-(6-fluoro-1-pyridin-4-yl-1H-benzoimidazol-2-yl)-ethylamino]-pyrimidine-5-carbonitrile | |
| 297 | 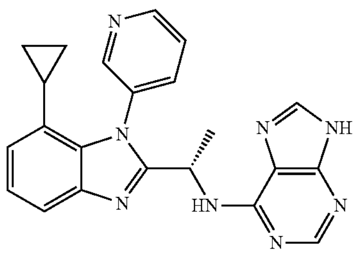 [SMILES: C[C@H](Nc1ncnc2[nH]cnc12)c1nc2cccc(C3CC3)c2n1-c1cccnc1] | [(S)-1-(7-Cyclopropyl-1-pyridin-3-yl-1H-benzoimidazol-2-yl)-ethyl]-(9H-purin-6-yl)-amine | |
| 298 | 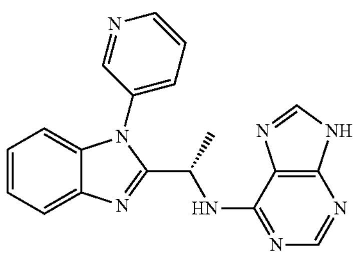 [SMILES: C[C@H](Nc1ncnc2[nH]cnc12)c1nc2ccccc2n1-c1cccnc1] | (9H-Purin-6-yl)-[(S)-1-(1-pyridin-3-yl-1H-benzoimidazol-2-yl)-ethyl]-amine | |
| 299 | 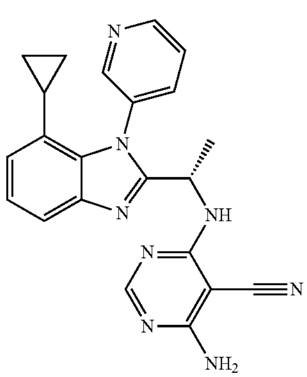 [SMILES: C[C@H](Nc1ncnc(N)c1C#N)c1nc2cccc(C3CC3)c2n1-c1cccnc1] | 4-Amino-6-[(S)-1-(7-cyclopropyl-1-pyridin-3-yl-1H-benzoimidazol-2-yl)-ethylamino]-pyrimidine-5-carbonitrile | 0.0355 |

TABLE 2-continued

| No. | Structure | IUPAC_Name | CD69 Hu Blood FACS IC50 (μM) |
|---|---|---|---|
| 300 | 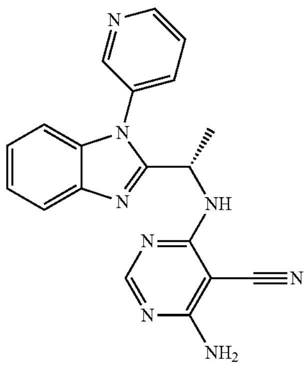 [SMILES: C[C@H](Nc1ncnc(N)c1C#N)c1nc2ccccc2n1-c1cccnc1] | 4-Amino-6-[(S)-1-(1-pyridin-3-yl-1H-benzoimidazol-2-yl)-ethylamino]-pyrimidine-5-carbonitrile | |
| 301 | 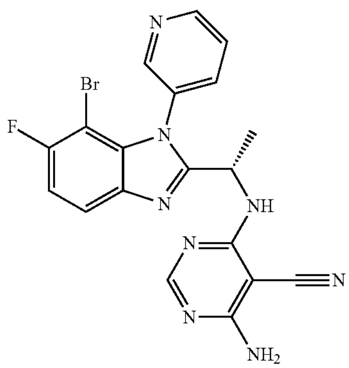 [SMILES: C[C@H](Nc1ncnc(N)c1C#N)c1nc2ccc(F)c(Br)c2n1-c1cccnc1] | 4-Amino-6-[(S)-1-(7-bromo-6-fluoro-1-pyridin-3-yl-1H-benzoimidazol-2-yl)-ethylamino]-pyrimidine-5-carbonitrile | 0.0341 |
| 302 | 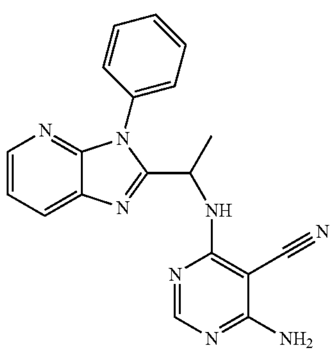 [SMILES: CC(Nc1ncnc(N)c1C#N)c1nc2cccnc2n1-c1ccccc1] | 4-Amino-6-[1-(3-phenyl-3H-imidazo[4,5-b]pyridin-2-yl)-ethylamino]-pyrimidine-5-carbonitrile | 0.189 |
| 303 | 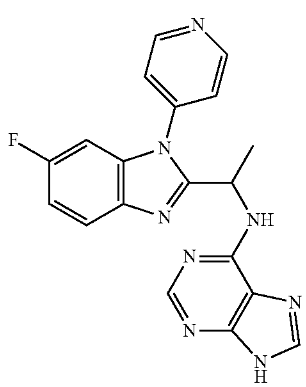 [SMILES: CC(Nc1ncnc2[nH]cnc12)c1nc2ccc(F)cc2n1-c1ccncc1] | [1-(6-Fluoro-1-pyridin-4-yl-1H-benzoimidazol-2-yl)-ethyl]-(9H-purin-6-yl)-amine | |

TABLE 2-continued

| No. | Structure | IUPAC_Name | CD69 Hu Blood FACS IC50 (μM) |
|---|---|---|---|
| 304 | 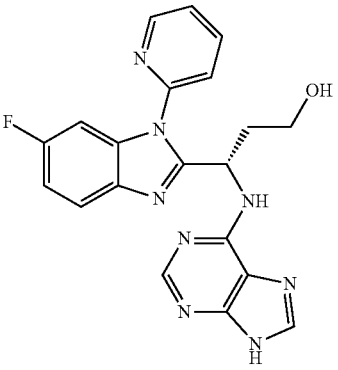 [SMILES: OCC[C@H](Nc1ncnc2[nH]cnc12)c1nc2ccc(F)cc2n1-c1ccccn1] | (S)-3-(6-Fluoro-1-pyridin-2-yl-1H-benzoimidazol-2-yl)-3-(9H-purin-6-ylamino)-propan-1-ol | 0.172 |
| 305 | 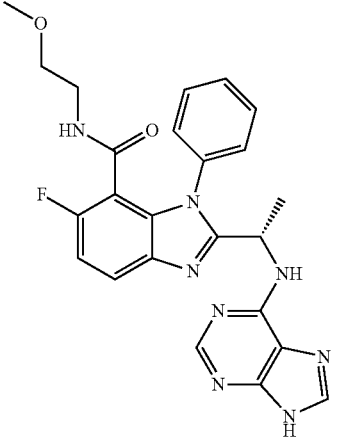 [SMILES: COCCNC(=O)c1c(F)ccc2nc([C@H](C)Nc3ncnc4[nH]cnc34)n(-c3ccccc3)c12] | 5-Fluoro-3-phenyl-2-[(S)-1-(9H-purin-6-ylamino)-ethyl]-3H-benzoimidazole-4-carboxylic acid (2-methoxy-ethyl)-amide | |
| 306 | 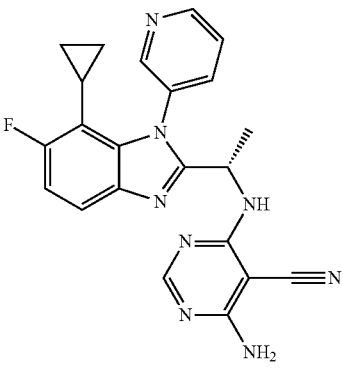 [SMILES: C[C@H](Nc1ncnc(N)c1C#N)c1nc2ccc(F)c(C3CC3)c2n1-c1cccnc1] | 4-Amino-6-[(S)-1-(7-cyclopropyl-6-fluoro-1-pyridin-3-yl-1H-benzoimidazol-2-yl)-ethylamino]-pyrimidine-5-carbonitrile | 0.00287 |
| 307 | 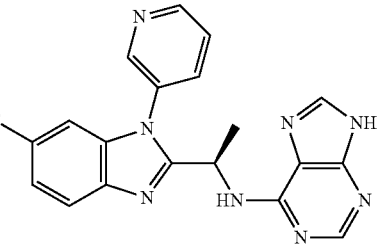 | [(R)-1-(6-Fluoro-1-pyridin-3-yl-1H-benzoimidazol-2-yl)-ethyl]-(9H-purin-6-yl)-amine | |

TABLE 2-continued

| No. | Structure | IUPAC_Name | CD69 Hu Blood FACS IC50 (μM) |
|---|---|---|---|
| 308 | 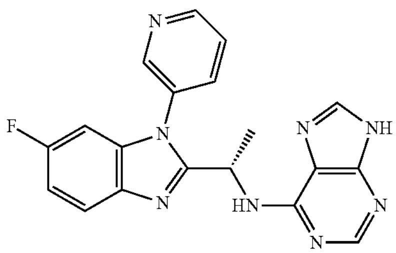 | [(S)-1-(6-Fluoro-1-pyridin-3-yl-1H-benzoimidazol-2-yl)-ethyl]-(9H-purin-6-yl)-amine | |
| 309 | 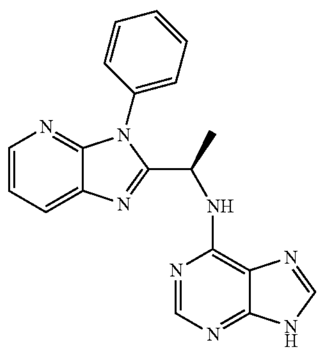 [SMILES: C[C@@H](Nc1ncnc2[nH]cnc12)c1nc2cccnc2n1-c1ccccc1] | [(R)-1-(3-Phenyl-3H-imidazo[4,5-b]pyridin-2-yl)-ethyl]-(9H-purin-6-yl)-amine | |
| 310 | 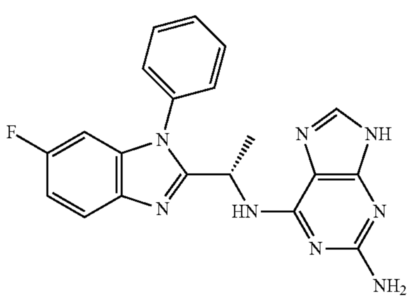 [SMILES: C[C@H](Nc1nc(N)nc2[nH]cnc12)c1nc2ccc(F)cc2n1-c1ccccc1] | (S)-N6-(1-(6-fluoro-1-phenyl-1H-benzo[d]imidazol-2-yl)ethyl)-9H-purine-2,6-diamine | |
| 311 | 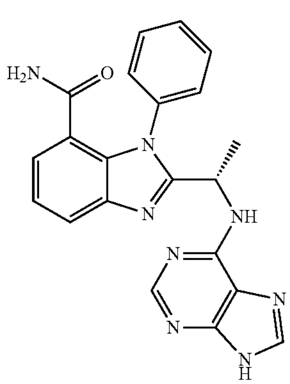 [SMILES: C[C@H](Nc1ncnc2[nH]cnc12)c1nc2cccc(C(N)=O)c2n1-c1ccccc1] | 3-Phenyl-2-[(S)-1-(9H-purin-6-ylamino)-ethyl]-3H-benzoimidazole-4-carboxylic acid amide | |

TABLE 2-continued

| No. | Structure | IUPAC_Name | CD69 Hu Blood FACS IC50 (µM) |
|---|---|---|---|
| 312 | 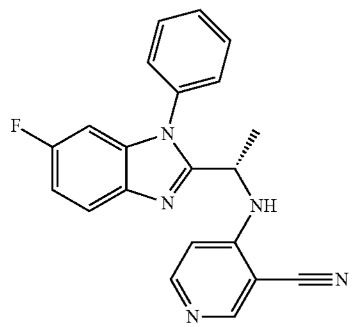 | 4-[(S)-1-(6-Fluoro-1-phenyl-1H-benzoimidazol-2-yl)-ethylamino]-nicotinonitrile | 3.9 |
| 313 | 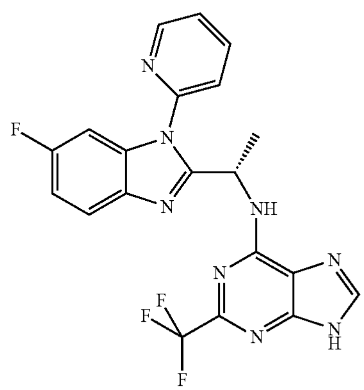 [SMILES: C[C@H](Nc1nc(C(F)(F)F)nc2[nH]cnc12)c1nc2ccc(F)cc2n1-c1ccccn1] | [(S)-1-(6-Fluoro-1-pyridin-2-yl-1H-benzoimidazol-2-yl)-ethyl]-(2-trifluoromethyl-9H-purin-6-yl)-amine | |
| 314 | 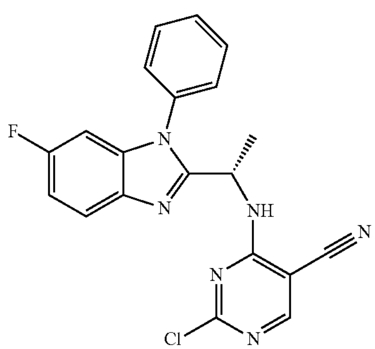 [SMILES: C[C@H](Nc1nc(Cl)ncc1C#N)c1nc2ccc(F)cc2n1-c1ccccc1] | 2-Chloro-4-[(S)-1-(6-fluoro-1-phenyl-1H-benzoimidazol-2-yl)-ethylamino]-pyrimidine-5-carbonitrile | |
| 315 | 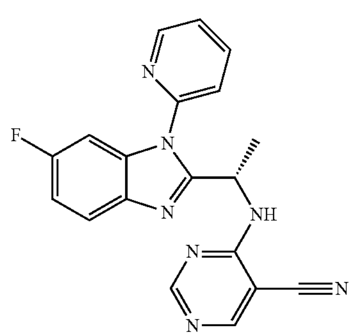 | 4-[(S)-1-(6-Fluoro-1-pyridin-2-yl-1H-benzoimidazol-2-yl)-ethylamino]-pyrimidine-5-carbonitrile | |

TABLE 2-continued

| No. | Structure | IUPAC_Name | CD69 Hu Blood FACS IC50 (μM) |
|---|---|---|---|
| 316 | 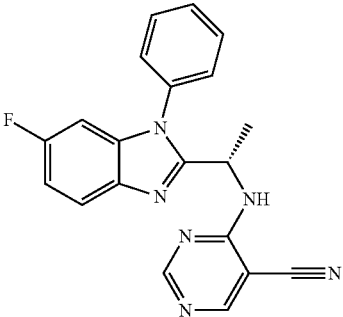 [SMILES: C[C@H](Nc1ncncc1C#N)c1nc2ccc(F)cc2n1-c1ccccc1] | 4-[(S)-1-(6-Fluoro-1-phenyl-1H-benzoimidazol-2-yl)-ethylamino]-pyrimidine-5-carbonitrile | 0.481 |
| 317 | 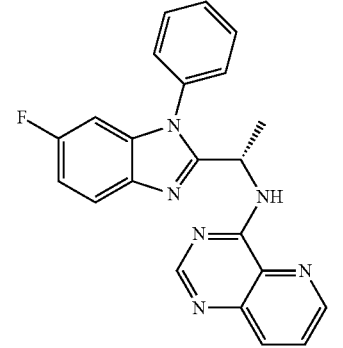 [SMILES: C[C@H](Nc1ncnc2cccnc12)c1nc2ccc(F)cc2n1-c1ccccc1] | [(S)-1-(6-Fluoro-1-phenyl-1H-benzoimidazol-2-yl)-ethyl]-pyrido[3,2-d]pyrimidin-4-yl-amine | |
| 318 | 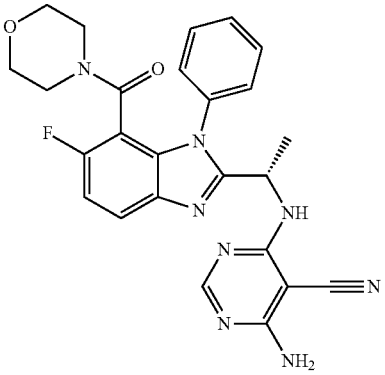 [SMILES: C[C@H](Nc1ncnc(N)c1C#N)c1nc2ccc(F)c(C(=O)N3CCOCC3)c2n1-c1ccccc1] | 4-Amino-6-{(S)-1-[6-fluoro-7-(morpholine-4-carbonyl)-1-phenyl-1H-benzoimidazol-2-yl]-ethylamino}-pyrimidine-5-carbonitrile | |
| 319 | 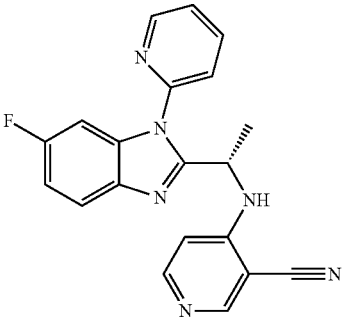 | 4-[(S)-1-(6-Fluoro-1-pyridin-2-yl-1H-benzoimidazol-2-yl)-ethylamino]-nicotinonitrile | |

TABLE 2-continued

| No. | Structure | IUPAC_Name | CD69 Hu Blood FACS IC50 (μM) |
|---|---|---|---|
| 320 | 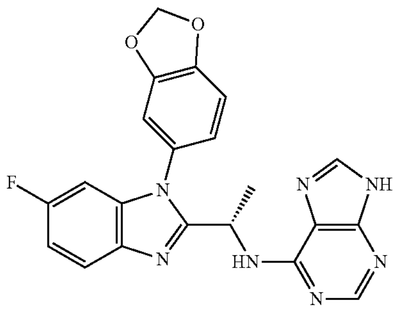 [SMILES: C[C@H](Nc1ncnc2[nH]cnc12)c1nc2ccc(F)cc2n1-c1ccc2c(c1)OCO2] | [(S)-1-(l-Benzo[1,3]dioxol-5-yl-6-fluoro-1H-benzoimidazol-2-yl)-ethyl]-(9H-purin-6-yl)-amine | 0.253 |
| 321 | 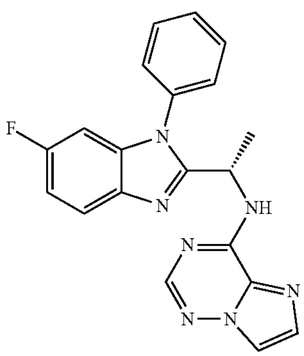 [SMILES: C[C@H](Nc1ncnn2ccnc12)c1nc2ccc(F)cc2n1-c1ccccc1] | [(S)-1-(6-Fluoro-1-phenyl-1H-benzoimidazol-2-yl)-ethyl]-imidazo[2,1-f][1,2,4]triazin-4-yl-amine | 0.0188 |
| 322 | 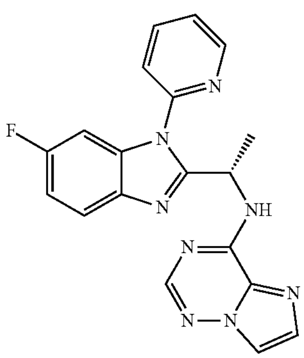 [SMILES: C[C@H](Nc1ncnn2ccnc12)c1nc2ccc(F)cc2n1-c1ccccn1] | [(S)-1-(6-Fluoro-1-pyridin-2-yl-1H-benzoimidazol-2-yl)-ethyl]-imidazo[2,1-f][1,2,4]triazin-4-yl-amine | 0.145 |
| 323 | 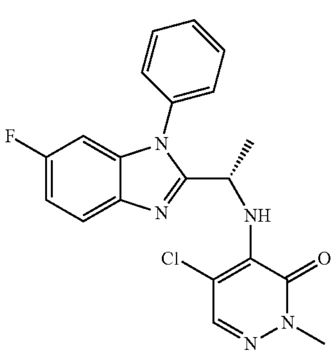 [SMILES: C[C@H](Nc1c(Cl)cnn(C)c1=O)c1nc2ccc(F)cc2n1-c1ccccc1] | 5-Chloro-4-[(S)-1-(6-fluoro-1-phenyl-1H-benzoimidazol-2-yl)-ethylamino]-2-methyl-2H-pyridazin-3-one | |

TABLE 2-continued

| No. | Structure | IUPAC_Name | CD69 Hu Blood FACS IC50 (μM) |
|---|---|---|---|
| 324 | 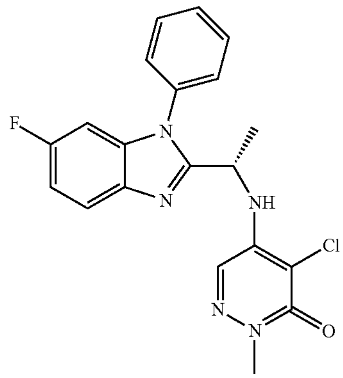 | 4-Chloro-5-[(S)-1-(6-fluoro-1-phenyl-1H-benzoimidazol-2-yl)-ethylamino]-2-methyl-2H-pyridazin-3-one | |
| 325 | 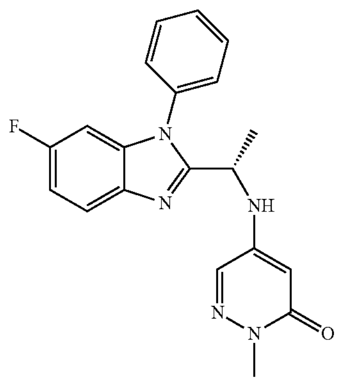 [SMILES: C[C@H](Nc1cnn(C)c(=O)c1)c1nc2ccc(F)cc2n1-c1ccccc1] | 5-[(S)-1-(6-Fluoro-1-phenyl-1H-benzoimidazol-2-yl)-ethylamino]-2-methyl-2H-pyridazin-3-one | |
| 326 | 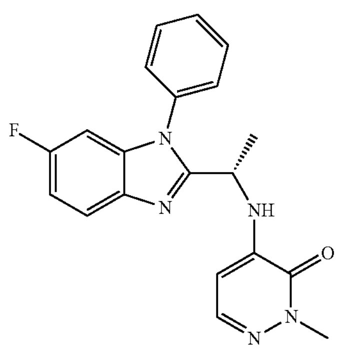 [SMILES: C[C@H](Nc1ccnn(C)c1=O)c1nc2ccc(F)cc2n1-c1ccccc1] | 4-[(S)-1-(6-Fluoro-1-phenyl-1H-benzoimidazol-2-yl)-ethylamino]-2-methyl-2H-pyridazin-3-one | |
| 327 | 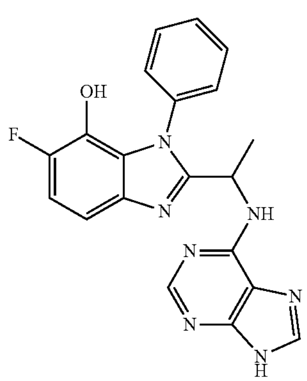 [SMILES: CC(Nc1ncnc2[nH]cnc12)c1nc2ccc(F)c(O)c2n1-c1ccccc1] | 5-Fluoro-3-phenyl-2-[1-(9H-purin-6-ylamino)-ethyl]-3H-benzoimidazol-4-ol | 0.196 |

TABLE 2-continued

| No. | Structure | IUPAC_Name | CD69 Hu Blood FACS IC50 (μM) |
|---|---|---|---|
| 328 | 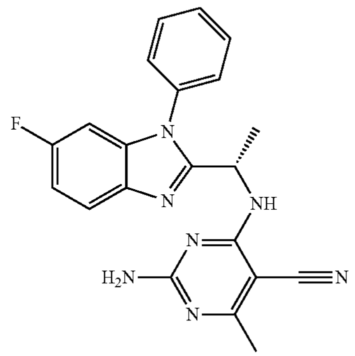 [SMILES: Cc1nc(N)nc(N[C@@H](C)c2nc3ccc(F)cc3n2-c2ccccc2)c1C#N] | 2-Amino-4-[(S)-1-(6-fluoro-1-phenyl-1H-benzoimidazol-2-yl)-ethylamino]-6-methyl-pyrimidine-5-carbonitrile | 0.00344 |
| 329 | 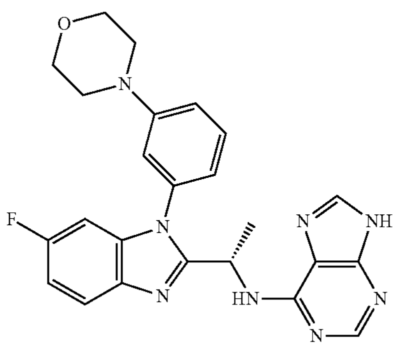 [SMILES: C[C@H](Nc1ncnc2[nH]cnc12)c1nc2ccc(F)cc2n1-c1cccc(N2CCOCC2)c1] | {(S)-1-[6-Fluoro-1-(3-morpholin-4-yl-phenyl)-1H-benzoimidazol-2-yl]-ethyl}-(9H-purin-6-yl)-amine | |
| 330 | 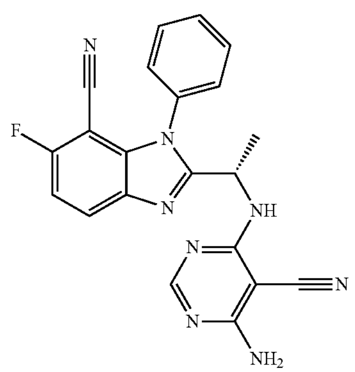 | 2-[(S)-1-(6-Amino-5-cyano-pyrimidin-4-ylamino)-ethyl]-5-fluoro-3-phenyl-3H-benzoimidazole-4-carbonitrile | 0.0129 |
| 331 | 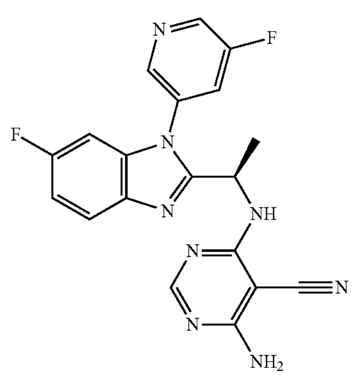 [SMILES: C[C@@H](Nc1ncnc(N)c1C#N)c1nc2ccc(F)cc2n1-c1cncc(F)c1] | 4-Amino-6-{(R)-1-[6-fluoro-1-(5-fluoro-pyridin-3-yl)-1H-benzoimidazol-2-yl]-ethylamino}-pyrimidine-5-carbonitrile | |

TABLE 2-continued

| No. | Structure | IUPAC_Name | CD69 Hu Blood FACS IC50 (μM) |
|---|---|---|---|
| 332 | 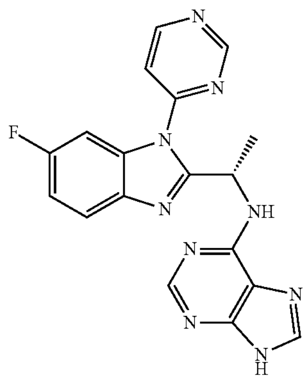 [SMILES: C[C@H](Nc1ncnc2[nH]cnc12)c1nc2ccc(F)cc2n1-c1ccncn1] | [(S)-1-(6-Fluoro-1-pyrimidin-4-yl-1H-benzoimidazol-2-yl)-ethyl]-(9H-purin-6-yl)-amine | 0.0817 |
| 333 | 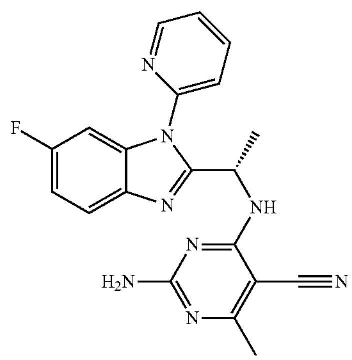 [SMILES: Cc1nc(N)nc(N[C@@H](C)c2nc3ccc(F)cc3n2-c2ccccn2)c1C#N] | 2-Amino-4-[(S)-1-(6-fluoro-1-pyridin-2-yl-1H-benzoimidazol-2-yl)-ethylamino]-6-methyl-pyrimidine-5-carbonitrile | 0.00492 |
| 334 | 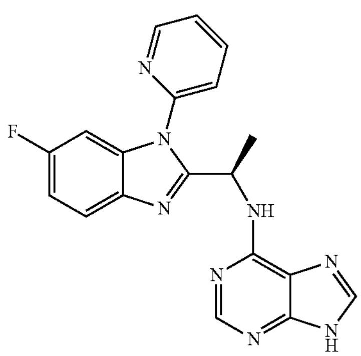 [SMILES: C[C@@H](Nc1ncnc2[nH]cnc12)c1nc2ccc(F)cc2n1-c1ccccn1] | [(R)-1-(6-Fluoro-1-pyridin-2-yl-1H-benzoimidazol-2-yl)-ethyl]-(9H-purin-6-yl)-amine | |
| 335 | 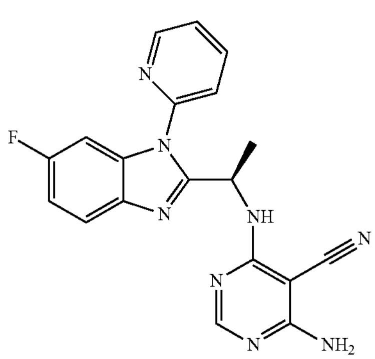 [SMILES: C[C@@H](Nc1ncnc(N)c1C#N)c1nc2ccc(F)cc2n1-c1ccccn1] | 4-Amino-6-[(R)-1-(6-fluoro-1-pyridin-2-yl-1H-benzoimidazol-2-yl)-ethylamino]-pyrimidine-5-carbonitrile | |

TABLE 2-continued

| No. | Structure | IUPAC_Name | CD69 Hu Blood FACS IC50 (μM) |
|---|---|---|---|
| 336 | 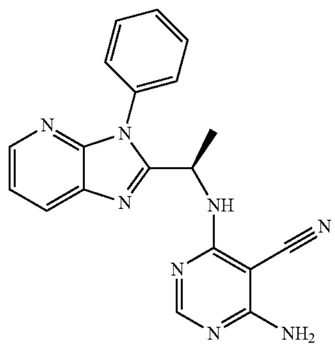 [SMILES: C[C@@H](Nc1ncnc(N)c1C#N)c1nc2cccnc2n1-c1ccccc1] | 4-Amino-6-[(R)-1-(3-phenyl-3H-imidazo[4,5-b]pyridin-2-yl)-cthylamino]-pyrimidine-5-carbonitrile | |
| 337 | 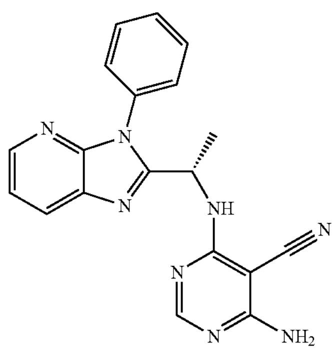 [SMILES: C[C@H](Nc1ncnc(N)c1C#N)c1nc2cccnc2n1-c1ccccc1] | 4-Amino-6-[(S)-1-(3-phenyl-3H-imidazo[4,5-b]pyridin-2-yl)-cthylamino]-pyrimidine-5-carbonitrile | 0.0966 |
| 338 | 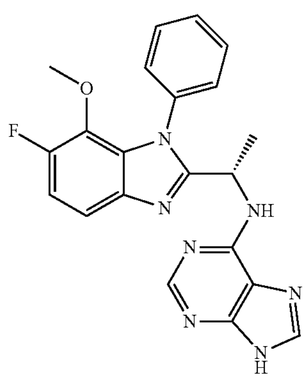 [SMILES: COc1c(F)ccc2nc([C@H](C)Nc3ncnc4[nH]cnc34)n(-c3ccccc3)c12] | [(S)-1-(6-Fluoro-7-methoxy-1-phenyl-1H-benzoimidazol-2-yl)-ethyl]-(9H-purin-6-yl)-amine | |
| 339 | 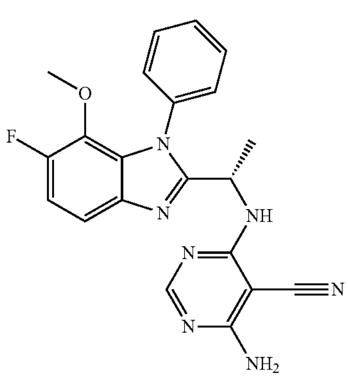 [SMILES: COc1c(F)ccc2nc([C@H](C)Nc3ncnc(N)c3C#N)n(-c3ccccc3)c12] | 4-Amino-6-[(S)-1-(6-fluoro-7-methoxy-1-phenyl-1H-benzoimidazol-2-yl)-ethylamino]-pyrimidine-5-carbonitrile | 0.00493 |

TABLE 2-continued

| No. | Structure | IUPAC_Name | CD69 Hu Blood FACS IC50 (μM) |
|---|---|---|---|
| 340 | 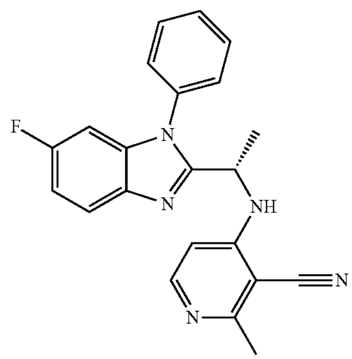 [SMILES: Cc1nccc(N[C@@H](C)c2nc3ccc(F)cc3n2-c2ccccc2)c1C#N] | 4-[(S)-1-(6-Fluoro-1-phenyl-1H-benzoimidazol-2-yl)-ethylamino]-2-methyl-nicotinonitrile | 0.606 |
| 341 | 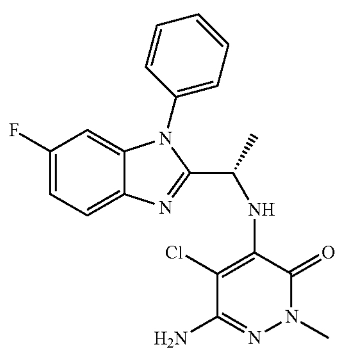 [SMILES: C[C@H](Nc1c(Cl)c(N)nn(C)c1=O)c1nc2ccc(F)cc2n1-c1ccccc1] | 6-Amino-5-chloro-4-[(S)-1-(6-fluoro-1-phenyl-1H-benzoimidazol-2-yl)-ethylamino]-2-methyl-2H-pyridazin-3-one | |
| 342 | 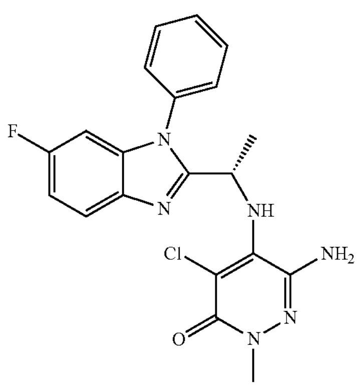 [SMILES: C[C@H](Nc1c(N)nn(C)c(=O)c1Cl)c1nc2ccc(F)cc2n1-c1ccccc1] | 6-Amino-5-chloro-4-[(S)-1-(6-fluoro-1-phenyl-1H-benzoimidazol-2-yl)-ethylamino]-2-methyl-2H-pyridazin-3-one | |
| 343 | 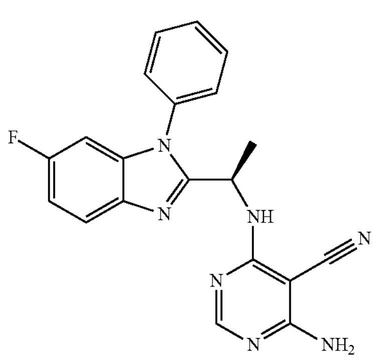 [SMILES: C[C@@H](Nc1ncnc(N)c1C#N)c1nc2ccc(F)cc2n1-c1ccccc1] | 4-Amino-6-[(R)-1-(6-fluoro-1-phenyl-1H-benzoimidazol-2-yl)-ethylamino]-pyrimidine-5-carbonitrile | |

TABLE 2-continued

| No. | Structure | IUPAC_Name | CD69 Hu Blood FACS IC50 (μM) |
|---|---|---|---|
| 344 | 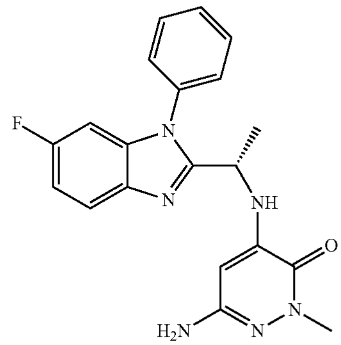 [SMILES: C[C@H](Nc1cc(N)nn(C)c1=O)c1nc2ccc(F)cc2n1-c1ccccc1] | 6-Amino-4-[(S)-1-(6-fluoro-1-phenyl-1H-benzoimidazol-2-yl)-ethylamino]-2-methyl-2H-pyridazin-3-one | |
| 345 | 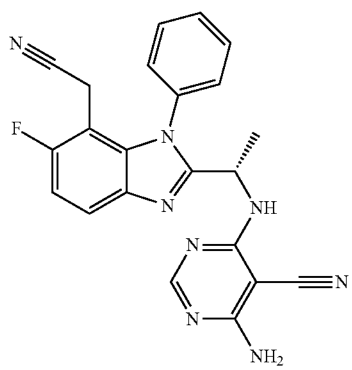 [SMILES: C[C@H](Nc1ncnc(N)c1C#N)c1nc2ccc(F)c(CC#N)c2n1-c1ccccc1] | 4-Amino-6-[(S)-1-(7-cyanomethyl-6-fluoro-1-phenyl-1H-benzoimidazol-2-yl)-ethylamino]-pyrimidine-5-carbonitrile | 0.00291 |
| 346 | 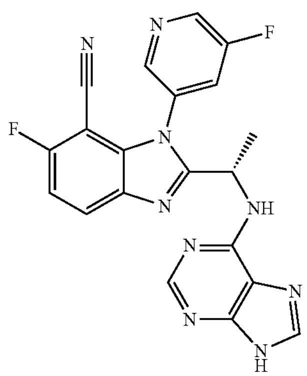 [SMILES: C[C@H](Nc1ncnc2[nH]cnc12)c1nc2ccc(F)c(C#N)c2n1-c1cncc(F)c1] | 5-Fluoro-3-(5-fluoro-pyridin-3-yl)-2-[(S)-1-(9H-purin-6-ylamino)-ethyl]-3H-benzoimidazole-4-carbonitrile | |
| 347 | 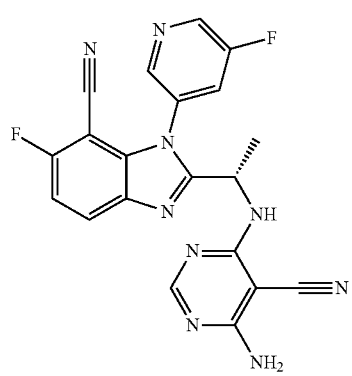 [SMILES: C[C@H](Nc1ncnc(N)c1C#N)c1nc2ccc(F)c(C#N)c2n1-c1cncc(F)c1] | 2-[(S)-1-(6-Amino-5-cyano-pyrimidin-4-ylamino)-ethyl]-5-fluoro-3-(5-fluoro-pyridin-3-yl)-3H-benzoimidazole-4-carbonitrile | 0.158 |

TABLE 2-continued

| No. | Structure | IUPAC_Name | CD69 Hu Blood FACS IC50 (μM) |
|---|---|---|---|
| 348 | 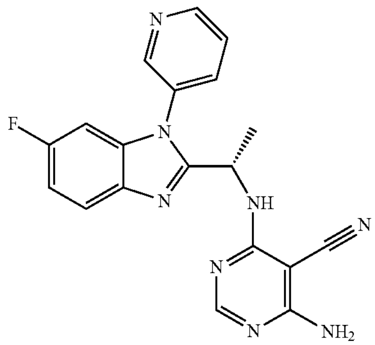 [SMILES: C[C@H](Nc1ncnc(N)c1C#N)c1nc2ccc(F)cc2n1-c1cccnc1] | 4-Amino-6-[(S)-1-(6-fluoro-1-pyridin-3-yl-1H-benzoimidazol-2-yl)-ethylamino]-pyrimidine-5-carbonitrile | |
| 349 | 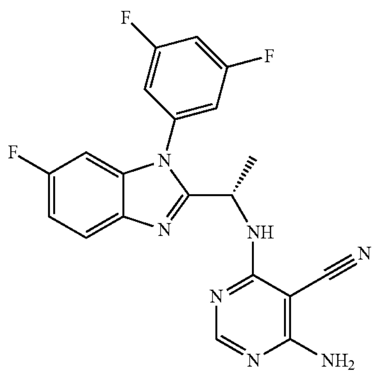 [SMILES: C[C@H](Nc1ncnc(N)c1C#N)c1nc2ccc(F)cc2n1-c1cc(F)cc(F)c1] | 4-Amino-6-{(S)-1-[1-(3,5-difluoro-phenyl)-6-fluoro-1H-benzoimidazol-2-yl]-ethylamino}-pyrimidine-5-carbonitrile | |
| 350 | 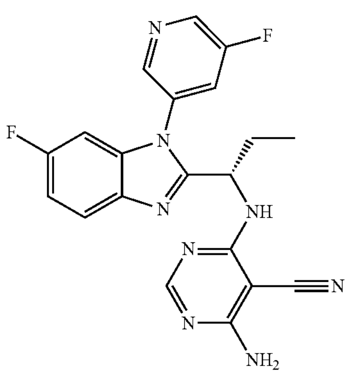 [SMILES: CC[C@H](Nc1ncnc(N)c1C#N)c1nc2ccc(F)cc2n1-c1cncc(F)c1] | 4-Amino-6-{(S)-1-[6-fluoro-1-(5-fluoro-pyridin-3-yl)-1H-benzoimidazol-2-yl]-propylamino}-pyrimidine-5-carbonitrile | 0.0839 |
| 351 | 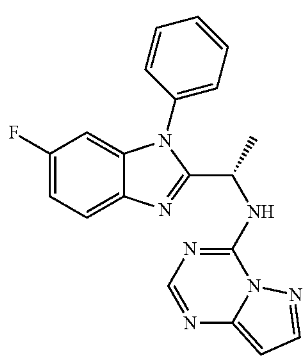 [SMILES: C[C@H](Nc1ncnc2ccnn12)c1nc2ccc(F)cc2n1-c1ccccc1] | [(S)-1-(6-Fluoro-1-phenyl-1H-benzoimidazol-2-yl)-ethyl]-pyrazolo[1,5-a] [1,3,5]triazin-4-yl-amine | |

TABLE 2-continued

| No. | Structure | IUPAC_Name | CD69 Hu Blood FACS IC50 (μM) |
|---|---|---|---|
| 352 | 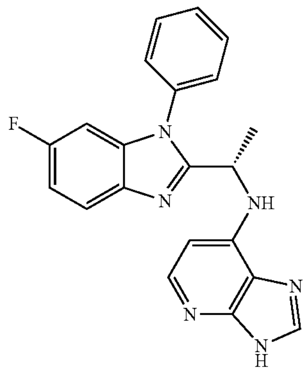 [SMILES: C[C@H](Nc1ccnc2[nH]cnc12)c1nc2ccc(F)cc2n1-c1ccccc1] | [(S)-1-(6-Fluoro-1-phenyl-1H-benzoimidazol-2-yl)-ethyl]-(3H-imidazo[4,5-b]pyridin-7-yl)-amine | |
| 353 | 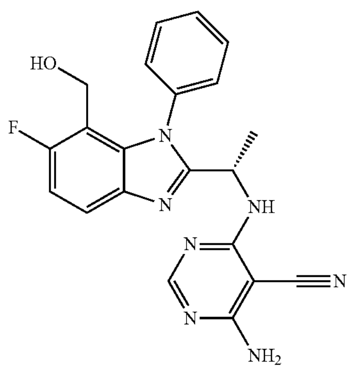 [SMILES: C[C@H](Nc1ncnc(N)c1C#N)c1nc2ccc(F)c(CO)c2n1-c1ccccc1] | 4-Amino-6-[(S)-1-(6-fluoro-7-hydroxymethyl-1-phenyl-1H-benzoimidazol-2-yl)-ethylamino]-pyrimidine-5-carbonitrile | |
| 354 | 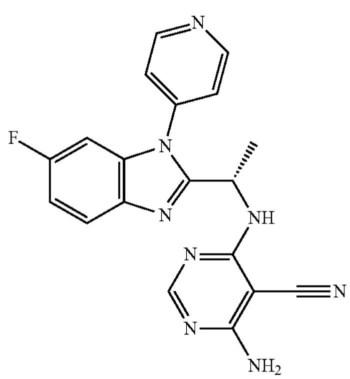 [SMILES: C[C@H](Nc1ncnc(N)c1C#N)c1nc2ccc(F)cc2n1-c1ccncc1] | 4-Amino-6-[(S)-1-(6-fluoro-1-pyridin-4-yl-1H-benzoimidazol-2-yl)-ethylamino]-pyrimidine-5-carbonitrile | 0.0484 |
| 355 | 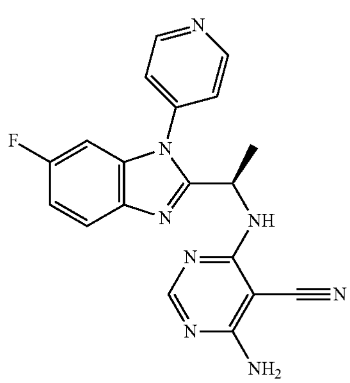 [SMILES: C[C@@H](Nc1ncnc(N)c1C#N)c1nc2ccc(F)cc2n1-c1ccncc1] | 4-Amino-6-[(R)-1-(6-fluoro-1-pyridin-4-yl-1H-benzoimidazol-2-yl)-ethylamino]-pyrimidine-5-carbonitrile | |

TABLE 2-continued

| No. | Structure | IUPAC_Name | CD69 Hu Blood FACS IC50 (μM) |
|---|---|---|---|
| 356 | 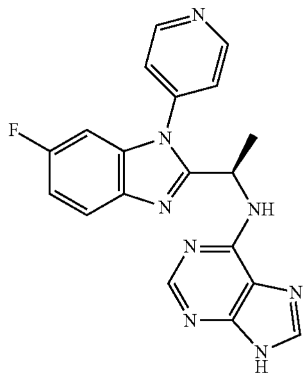 [SMILES: C[C@@H](Nc1ncnc2[nH]cnc12)c1nc2ccc(F)cc2n1-c1ccncc1] | [(R)-1-(6-Fluoro-1-pyridin-4-yl-1H-benzoimidazol-2-yl)-ethyl]-(9H-purin-6-yl)-amine | |
| 357 | 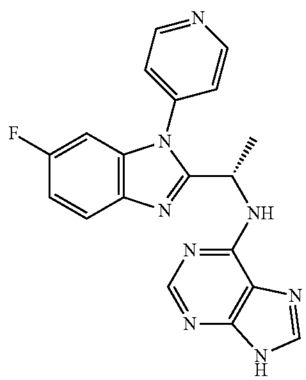 [SMILES: C[C@H](Nc1ncnc2[nH]cnc12)c1nc2ccc(F)cc2n1-c1ccncc1] | [(S)-1-(6-Fluoro-1-pyridin-4-yl-1H-benzoimidazol-2-yl)-ethyl]-(9H-purin-6-yl)-amine | |
| 358 | 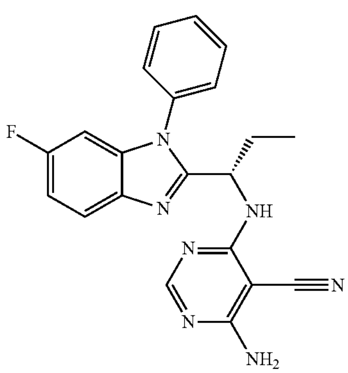 [SMILES: CC[C@H](Nc1ncnc(N)c1C#N)c1nc2ccc(F)cc2n1-c1ccccc1] | 4-Amino-6-[(S)-1-(6-fluoro-1-phenyl-1H-benzoimidazol-2-yl)-propylamino]-pyrimidine-5-carbonitrile | |
| 359 | 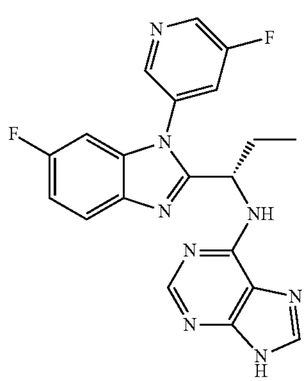 [SMILES: CC[C@H](Nc1ncnc2[nH]cnc12)c1nc2ccc(F)cc2n1-c1cncc(F)c1] | {(S)-1-[6-Fluoro-1-(5-fluoro-pyridin-3-yl)-1H-benzoimidazol-2-yl]-propyl}-(9H-purin-6-yl)-amine | |

TABLE 2-continued

| No. | Structure | IUPAC_Name | CD69 Hu Blood FACS IC50 (μM) |
|-----|-----------|------------|------------------------------|
| 360 | 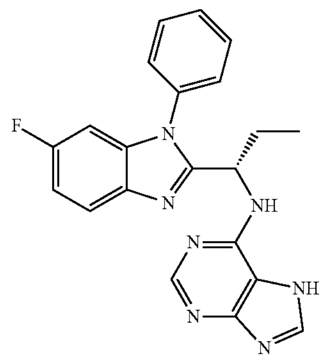 [SMILES: CC[C@H](Nc1ncnc2nc[nH]c12)c1nc2ccc(F)cc2n1-c1ccccc1] | [(S)-1-(6-Fluoro-1-phenyl-1H-benzoimidazol-2-yl)-propyl]-(7H-purin-6-yl)-amine | |
| 361 | 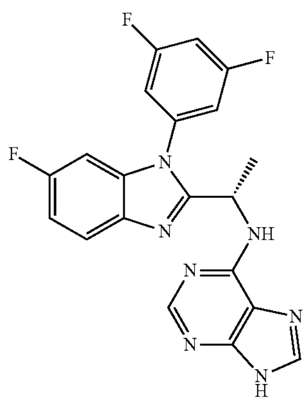 [SMILES: C[C@H](Nc1ncnc2[nH]cnc12)c1nc2ccc(F)cc2n1-c1cc(F)cc(F)c1] | {(S)-1-[1-(3,5-Difluoro-phenyl)-6-fluoro-1H-benzoimidazol-2-yl]-ethyl}-(9H-purin-6-yl)-amine | |
| 362 | 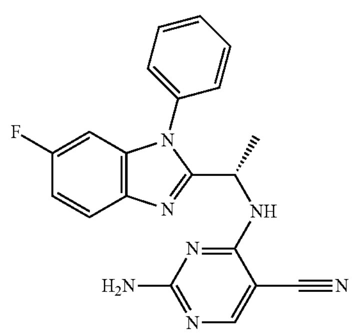 [SMILES: C[C@H](Nc1nc(N)ncc1C#N)c1nc2ccc(F)cc2n1-c1ccccc1] | 2-Amino-4-[(S)-1-(6-fluoro-1-phenyl-1H-benzoimidazol-2-yl)-ethylamino]-pyrimidine-5-carbonitrile | |
| 363 | 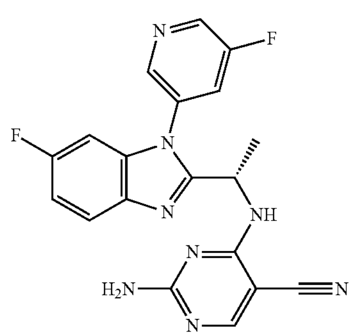 [SMILES: C[C@H](Nc1nc(N)ncc1C#N)c1nc2ccc(F)cc2n1-c1cncc(F)c1] | 2-Amino-4-{(S)-1-[6-fluoro-1-(5-fluoro-pyridin-3-yl)-1H-benzoimidazol-2-yl]-ethylamino}-pyrimidine-5-carbonitrile | |

TABLE 2-continued

| No. | Structure | IUPAC_Name | CD69 Hu Blood FACS IC50 (μM) |
|---|---|---|---|
| 364 | 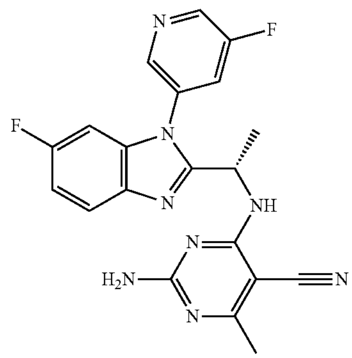 [SMILES: Cc1nc(N)nc(N[C@@H](C)c2nc3ccc(F)cc3n2-c2cncc(F)c2)c1C#N] | 2-Amino-4-{(S)-1-[6-fluoro-1-(5-fluoro-pyridin-3-yl)-1H-benzoimidazol-2-yl]-ethylamino}-6-methyl-pyrimidine-5-carbonitrile | |
| 365 | 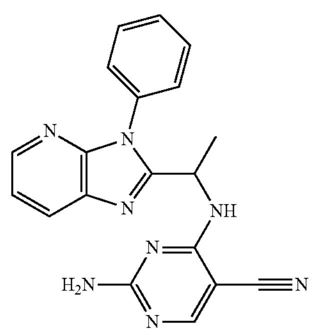 [SMILES: CC(Nc1nc(N)ncc1C#N)c1nc2cccnc2n1-c1ccccc1] | 2-Amino-4-[1-(3-phenyl-3H-imidazo[4,5-b]pyridin-2-yl)-ethylamino]-pyrimidine-5-carbonitrile | |
| 366 | 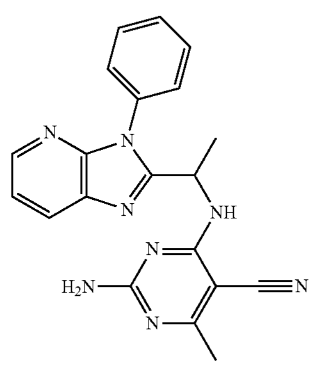 [SMILES: Cc1nc(N)nc(NC(C)c2nc3cccnc3n2-c2ccccc2)c1C#N] | 2-Amino-4-methyl-6-[1-(3-phenyl-3H-imidazo[4,5-b]pyridin-2-yl)-ethylamino]-pyrimidine-5-carbonitrile | |
| 367 | 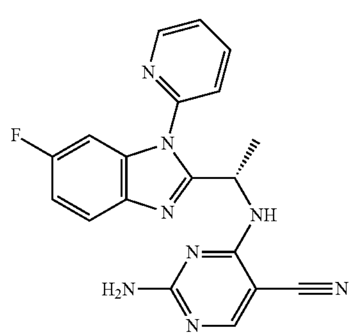 [SMILES: C[C@H](Nc1nc(N)ncc1C#N)c1nc2ccc(F)cc2n1-c1ccccn1] | 2-Amino-4-[(S)-1-(6-fluoro-1-pyridin-2-yl-1H-benzoimidazol-2-yl)-ethylamino]-pyrimidine-5-carbonitrile | |

TABLE 2-continued

| No. | Structure | IUPAC_Name | CD69 Hu Blood FACS IC50 (μM) |
|---|---|---|---|
| 368 | 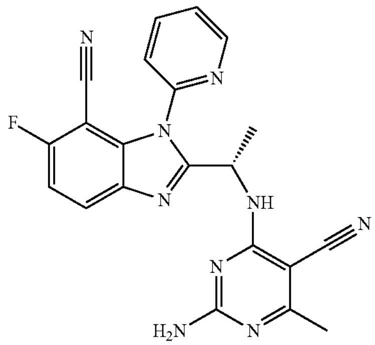 [SMILES: Cc1nc(N)nc(N[C@@H](C)c2nc3ccc(F)c(C#N)c3n2-c2ccccn2)c1C#N] | 2-[(S)-1-(2-Amino-5-cyano-6-methyl-pyrimidin-4-ylamino)-ethyl]-5-fluoro-3-pyridin-2-yl-3H-benzoimidazole-4-carbonitrile | |
| 369 | 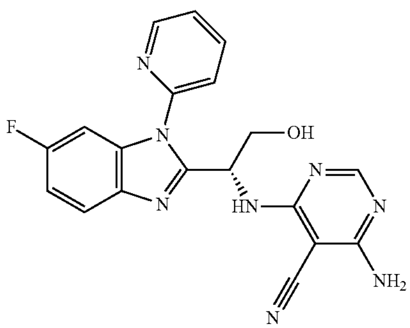 [SMILES: N#Cc1c(N)ncnc1N[C@@H](CO)c1nc2ccc(F)cc2n1-c1ccccn1] | 4-Amino-6-[(R)-1-(6-fluoro-1-pyridin-2-yl-1H-benzoimidazol-2-yl)-2-hydroxy-ethylamino]-pyrimidine-5-carbonitrile | |
| 370 | 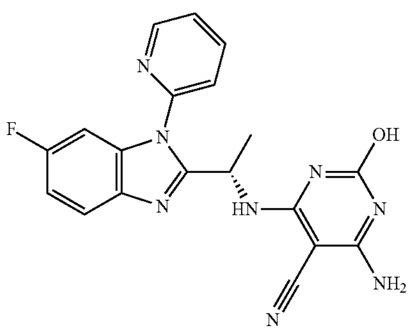 [SMILES: C[C@H](Nc1nc(O)nc(N)c1C#N)c1nc2ccc(F)cc2n1-c1ccccn1] | 4-Amino-6-[(S)-1-(6-fluoro-1-pyridin-2-yl-1H-benzoimidazol-2-yl)-ethylamino]-2-hydroxy-pyrimidine-5-carbonitrile | |
| 371 | 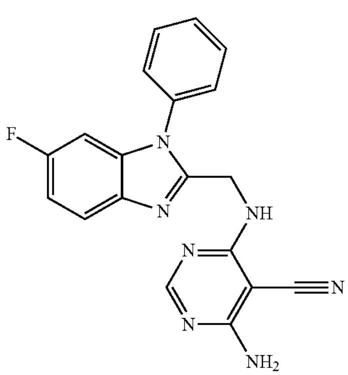 [SMILES: N#Cc1c(N)ncnc1NCc1nc2ccc(F)cc2n1-c1ccccc1] | 4-amino-6-((6-fluoro-1-phenyl-1H-benzo[d]imidazol-2-yl)methylamino)pyrimidine-5-carbonitrile | 0.514 |

TABLE 3
| No. | Structure | IUPAC Name | CD69 Hu Blood FACS IC50 (μM) |
|---|---|---|---|
| 372 | 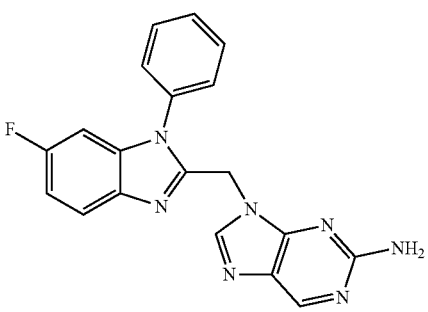 [SMILES: Nc1ncc2ncn(Cc3nc4ccc(F)cc4n3-c3ccccc3)c2n1] | 9-[(6-fluoro-1-phenyl-benzimidazol-2-yl)methyl]purin-2-amine | |
| 373 | 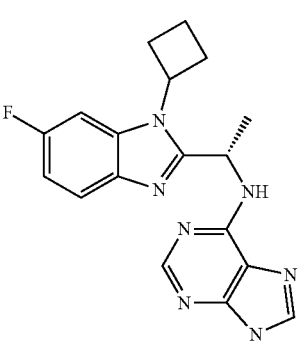 | N-[(1S)-1-(1-cyclobutyl-6-fluoro-benzimidazol-2-yl)ethyl]-9H-purin-6-amine | |
| 374 | 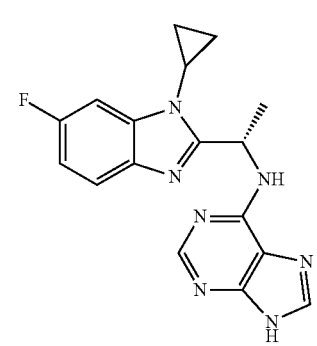 [SMILES: C[C@H](Nc1ncnc2[nH]cnc12)c1nc2ccc(F)cc2n1C1CC1] | N-[(1S)-1-(1-cyclopropyl-6-fluoro-benzimidazol-2-yl)ethyl]-9H-purin-6-amine | |
| 375 | 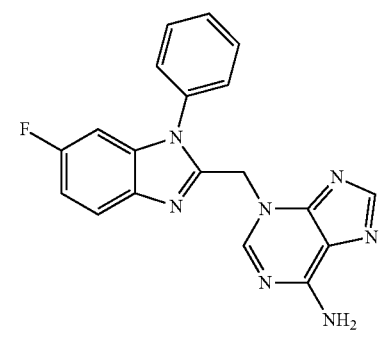 [SMILES: Nc1ncn(Cc2nc3ccc(F)cc3n2-c2ccccc2)c2ncnc1-2] | 3-[(6-fluoro-1-phenyl-benzimidazol-2-yl)methyl]purin-6-amine | |

TABLE 3-continued

| No. | Structure | IUPAC Name | CD69 Hu Blood FACS IC50 (μM) |
|---|---|---|---|
| 376 | 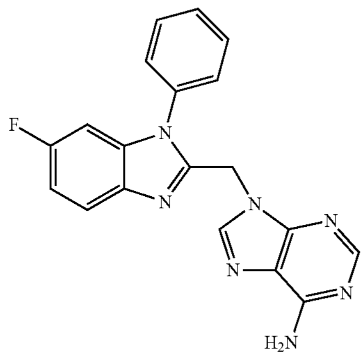 [SMILES: Nc1ncnc2c1ncn2Cc1nc2ccc(F)cc2n1-c1ccccc1] | 9-[(6-fluoro-1-phenyl-benzimidazol-2-yl)methyl]purin-6-amine | |
| 377 | 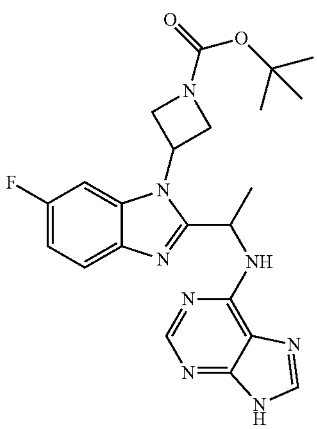 [SMILES: CC(Nc1ncnc2[nH]cnc12)c1nc2ccc(F)cc2n1C1CN(C(=O)OC(C)(C)C)C1] | tert-butyl 3-[6-fluoro-2-[1-(9H-purin-6-ylamino)ethyl]benzimidazol-1-yl]azetidine-1-carboxylate | |
| 378 | 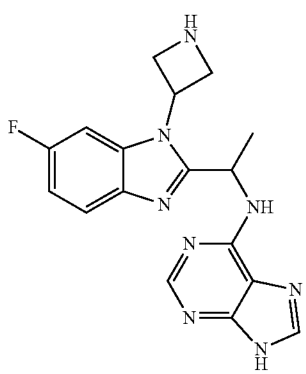 [SMILES: CC(Nc1ncnc2[nH]cnc12)c1nc2ccc(F)cc2n1C1CNC1] | N-[1-[1-(azetidin-3-yl)-6-fluoro-benzimidazol-2-yl)ethyl]-9H-purin-6-amine | |
| 379 | 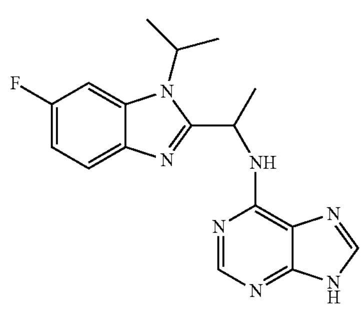 [SMILES: CC(Nc1ncnc2[nH]cnc12)c1nc2ccc(F)cc2n1C(C)C] | N-[1-(6-fluoro-1-isopropyl-benzimidazol-2-yl)ethyl]-9H-purin-6-amine | |

TABLE 3-continued

| No. | Structure | IUPAC Name | CD69 Hu Blood FACS IC50 (μM) |
|---|---|---|---|
| 380 | 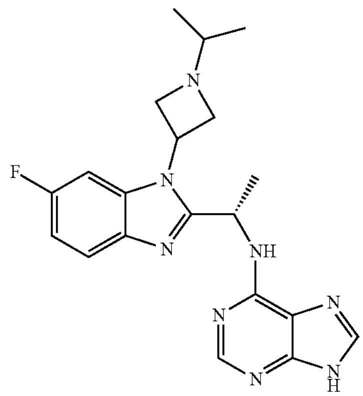 [SMILES: CC(C)N1CC(n2c([C@H](C)Nc3ncnc4[nH]cnc34)nc3ccc(F)cc32)C1] | N-[(1S)-1-[6-fluoro-1-(1-isopropylazetidin-3-yl)benzimidazol-2-yl]ethyl]-9H-purin-6-amine | 0.0582 |
| 381 | 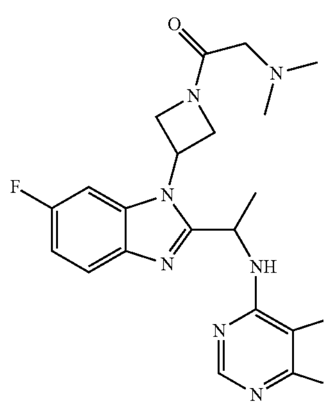 | 2-(dimethylamino)-1-[3-[6-fluoro-2-[1-(9H-purin-6-ylamino)ethyl]benzimidazol-1-yl]azetidin-1-yl]ethanone | |
| 382 | 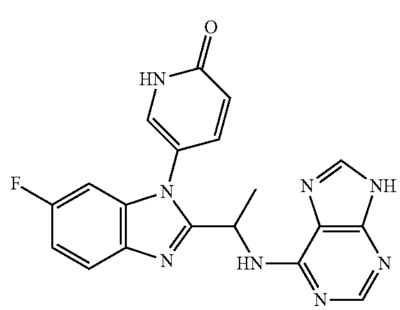 [SMILES: CC(Nc1ncnc2[nH]cnc12)c1nc2ccc(F)cc2n1-c1ccc(=O)[nH]c1] | 5-[6-fluoro-2-[1-(9H-purin-6-ylamino)ethyl]benzimidazol-1-yl]-1H-pyridin-2-one | |

TABLE 3-continued

| No. | Structure | IUPAC Name | CD69 Hu Blood FACS IC50 (μM) |
|---|---|---|---|
| 383 | 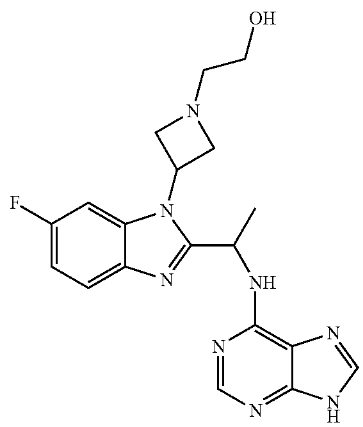 [SMILES: CC(Nc1ncnc2[nH]cnc12)c1nc2ccc(F)cc2n1C1CN(CCO)C1] | 2-[3-[6-fluoro-2-[1-(9H-purin-6-ylamino)ethyl]benzimidazol-1-yl]azetidin-1-yl]ethanol | |
| 384 | 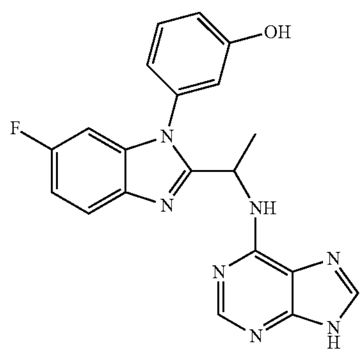 [SMILES: CC(Nc1ncnc2[nH]cnc12)c1nc2ccc(F)cc2n1-c1cccc(O)c1] | 3-[6-fluoro-2-[1-(9H-purin-6-ylamino)ethyl]benzimidazol-1-yl]phenol | |
| 385 | 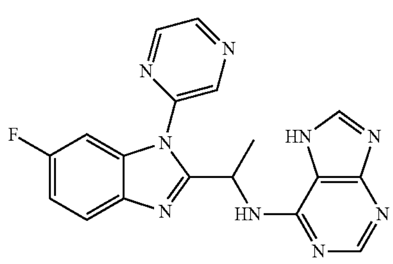 [SMILES: CC(Nc1ncnc2nc[nH]c12)c1nc2ccc(F)cc2n1-c1cnccn1] | N-[1-(6-fluoro-1-pyrazin-2-yl-benzimidazol-2-yl)ethyl]-7H-purin-6-amine | |
| 386 | 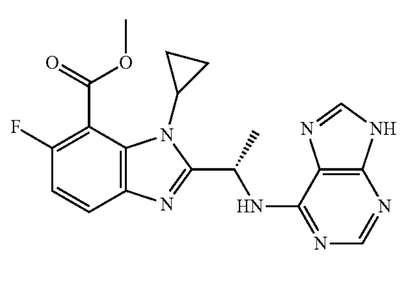 [SMILES: COC(=O)c1c(F)ccc2nc([C@H](C)Nc3ncnc4[nH]cnc34)n(C3CC3)c12] | methyl 3-cyclopropyl-5-fluoro-2-[(1S)-1-(9H-purin-6-ylamino)ethyl]benzimidazole-4-carboxylate | |

TABLE 3-continued

| No. | Structure | IUPAC Name | CD69 Hu Blood FACS IC50 (μM) |
|---|---|---|---|
| 387 | 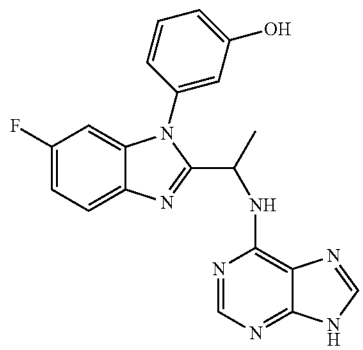 [SMILES: CC(Nc1ncnc2[nH]cnc12)c1nc2ccc(F)cc2n1-c1cccc(O)c1] | 3-[6-fluoro-2-[1-(9H-purin-6-ylamino)ethyl]benzimidazol-1-yl]phenol | |
| 388 | 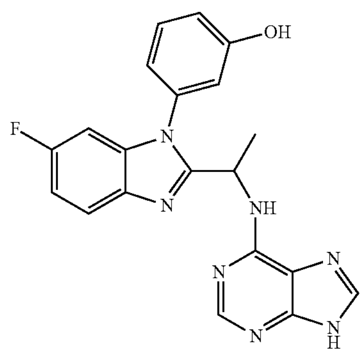 [SMILES: CC(Nc1ncnc2[nH]cnc12)c1nc2ccc(F)cc2n1-c1cccc(O)c1] | 3-[6-fluoro-2-[1-(9H-purin-6-ylamino)ethyl]benzimidazol-1-yl]phenol | |
| 389 | 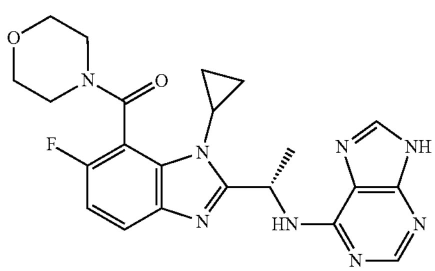 [SMILES: C[C@H](Nc1ncnc2[nH]cnc12)c1nc2ccc(F)c(C(=O)N3CCOCC3)c2n1C1CC1] | [3-cyclopropyl-5-fluoro-2-[(1S)-1-(9H-purin-6-ylamino)ethyl]benzimidazol-4-yl]-morpholino-methanone | 0.0119 |
| 390 | 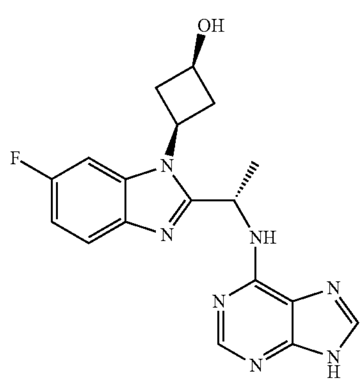 [SMILES: C[C@H](Nc1ncnc2[nH]cnc12)c1nc2ccc(F)cc2n1[C@H]1C[C@@H](O)C1] | 3-[6-fluoro-2-[(1S)-1-(9H-purin-6-ylamino)ethyl]benzimidazol-1-yl]cyclobutanol | 0.146 |

TABLE 3-continued

| No. | Structure | IUPAC Name | CD69 Hu Blood FACS IC50 (μM) |
|---|---|---|---|
| 391 | 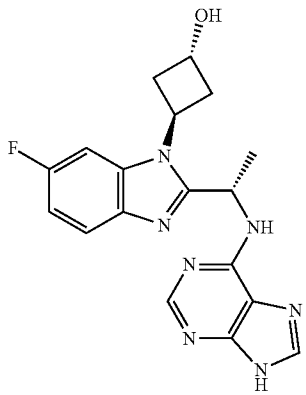 [SMILES: C[C@H](Nc1ncnc2[nH]cnc12)c1nc2ccc(F)cc2n1[C@H]1C[C@H](O)C1] | 3-[6-fluoro-2-[(1S)-1-(9H-purin-6-ylamino)ethyl]benzimidazol-1-yl]cyclobutanol | |
| 392 | 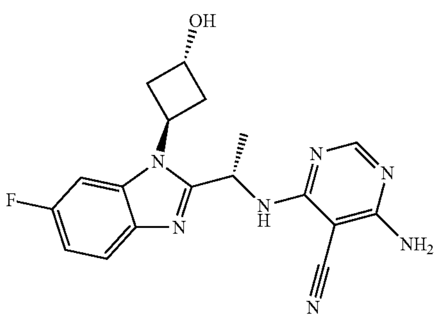 [SMILES: C[C@H](Nc1ncnc(N)c1C#N)c1nc2ccc(F)cc2n1[C@H]1C[C@H](O)C1] | 4-amino-6-[[(1S)-1-[6-fluoro-1-(3-hydroxycyclobutyl)benzimidazol-2-yl]ethyl]amino]pyrimidine-5-carbonitrile | |
| 393 | 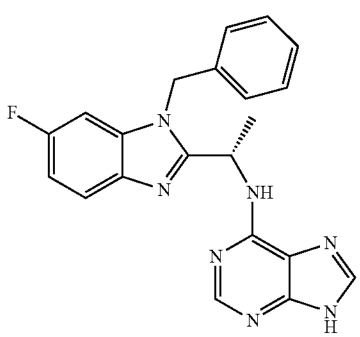 [SMILES: C[C@H](Nc1ncnc2[nH]cnc12)c1nc2ccc(F)cc2n1Cc1ccccc1] | N-[(1S)-1-(1-benzyl-6-fluoro-benzimidazol-2-yl)ethyl]-9H-purin-6-amine | |
| 394 | 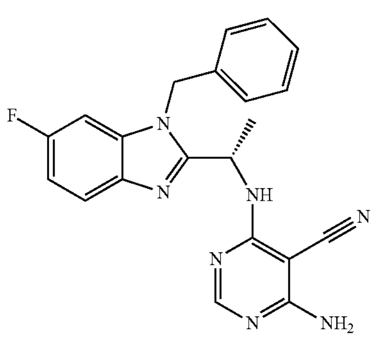 [SMILES: C[C@H](Nc1ncnc(N)c1C#N)c1nc2ccc(F)cc2n1Cc1ccccc1] | 4-amino-6-[[(1S)-1-(1-benzyl-6-fluoro-benzimidazol-2-yl)ethyl]amino)pyrimidine-5-carbonitrile | |

TABLE 3-continued

| No. | Structure | IUPAC Name | CD69 Hu Blood FACS IC50 (μM) |
|---|---|---|---|
| 395 | 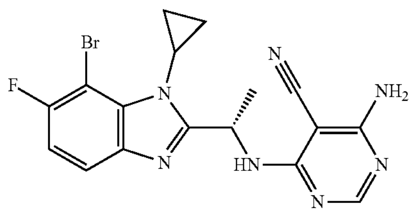 [SMILES: C[C@H](Nc1ncnc(N)c1C#N)c1nc2ccc(F)c(Br)c2n1C1CC1] | 4-amino-6-[[(1S)-1-(7-bromo-1-cyclopropyl-6-fluoro-benzimidazol-2-yl)ethyl]amino]pyrimidine-5-carbonitrile | |
| 396 | 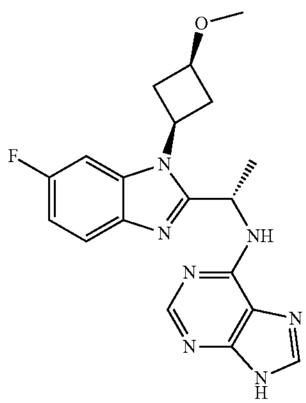 [SMILES: CO[C@H]1C[C@@H](n2c([C@H](C)Nc3ncnc4[nH]cnc34)nc3ccc(F)cc32)C1] | N-[(1S)-1-[6-fluoro-1-(3-methoxycyclobutyl)benzimidazol-2-yl]ethyl]-9H-purin-6-amine | |
| 397 | 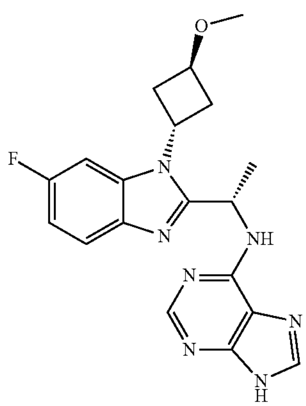 [SMILES: CO[C@H]1C[C@H](n2c([C@H](C)Nc3ncnc4[nH]cnc34)nc3ccc(F)cc32)C1] | N-[(1S)-1-[6-fluoro-1-(3-methoxycyclobutyl)benzimidazol-2-yl]ethyl]-9H-purin-6-amine | |
| 398 | 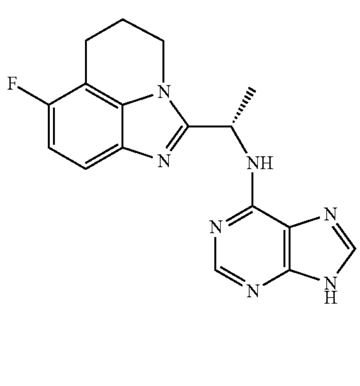 [SMILES: C[C@H](Nc1ncnc2[nH]cnc12)c1nc2ccc(F)c3c2n1CCC3] | (S)-N-(1-(7-fluoro-5,6-dihydro-4H-imidazo[4,5,1-ij]quinolin-2-yl)ethyl)-9H-purin-6-amine | |

TABLE 3-continued

| No. | Structure | IUPAC Name | CD69 Hu Blood FACS IC50 (µM) |
|---|---|---|---|
| 399 | 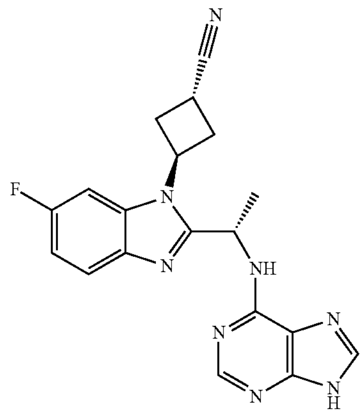 [SMILES: C[C@H](Nc1ncnc2[nH]cnc12)c1nc2ccc(F)cc2n1[C@H]1C[C@H](C#N)C1] | 3-[6-fluoro-2-[(1S)-1-(9H-purin-6-ylamino)ethyl]benzimidazol-1-yl]cyclobutanecarbonitrile | |
| 400 | 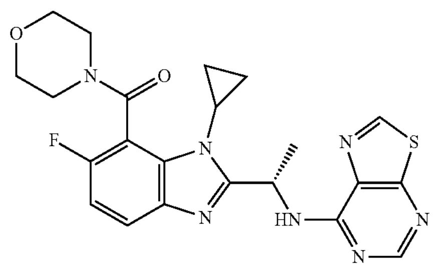 [SMILES: C[C@H](Nc1ncnc2scnc12)c1nc2ccc(F)c(C(=O)N3CCOCC3)c2n1C1CC1] | [3-cyclopropyl-5-fluoro-2-[(1S)-1-(thiazolo[5,4-d]pyrimidin-7-ylamino)ethyl]benzimidazol-4-yl]-morpholino-methanone | |
| 401 | 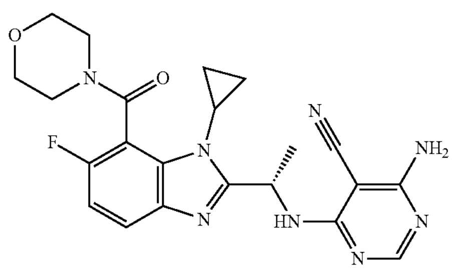 [SMILES: C[C@H](Nc1ncnc(N)c1C#N)c1nc2ccc(F)c(C(=O)N3CCOCC3)c2n1C1CC1] | 4-amino-6-[[(1S)-1-[1-cyclopropyl-6-fluoro-7-(morpholine-4-carbonyl)benzimidazol-2-yl]ethyl]amino]pyrimidine-5-carbonitrile | 0.0232 |
| 402 | 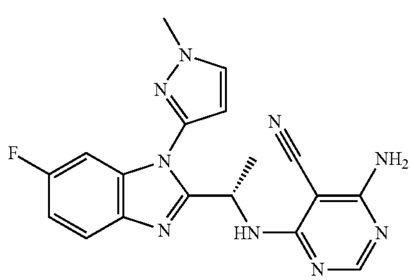 [SMILES: C[C@H](Nc1ncnc(N)c1C#N)c1nc2ccc(F)cc2n1-c1ccn(C)n1] | 4-amino-6-[[(1S)-1-[6-fluoro-1-(1-methylpyrazol-3-yl)benzimidazol-2-yl]ethyl]amino]pyrimidine-5-carbonitrile | 0.0647 |
| 403 | 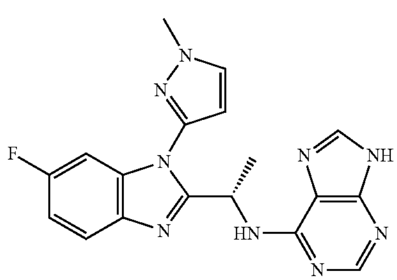 [SMILES: C[C@H](Nc1ncnc2[nH]cnc12)c1nc2ccc(F)cc2n1-c1ccn(C)n1] | N-[(1S)-1-[6-fluoro-1-(1-methylpyrazol-3-yl)benzimidazol-2-yl]ethyl]-9H-purin-6-amine | 0.163 |

TABLE 3-continued

| No. | Structure | IUPAC Name | CD69 Hu Blood FACS IC50 (μM) |
|---|---|---|---|
| 404 | 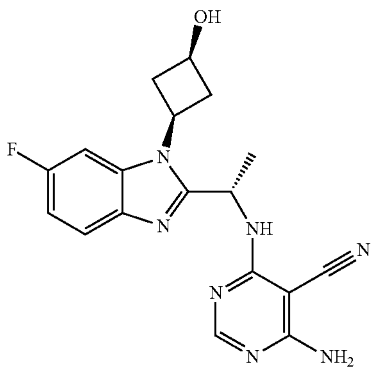 [SMILES: C[C@H](Nc1ncnc(N)c1C#N)c1nc2ccc(F)cc2n1[C@H]1C[C@@H](O)C1] | 4-amino-6-[[(1S)-1-[6-fluoro-1-(3-hydroxycyclobutyl)benzimidazol-2-yl]ethyl]amino]pyrimidine-5-carbonitrile | |
| 405 | 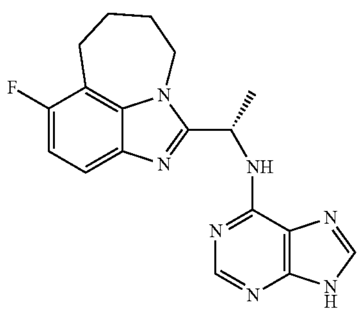 [SMILES: C[C@H](Nc1ncnc2[nH]cnc12)c1nc2ccc(F)c3c2n1CCCC3] | [(S)-1-(5-Fluoro-6,7,8,9-tetrahydro-2,9a-diazabenzo[cd]azulen-1-yl)ethyl]-(9H-purin-6-yl)amine | |
| 406 | 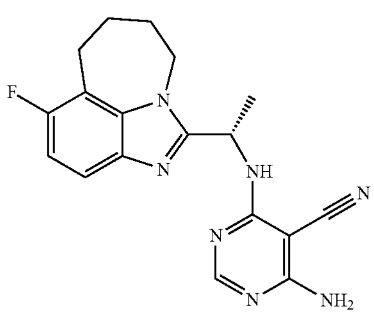 [SMILES: C[C@H](Nc1ncnc(N)c1C#N)c1nc2ccc(F)c3c2n1CCCC3] | 4-Amino-6-[(S)-1-(5-fluoro-6,7,8,9-tetrahydro-2,9a-diazabenzo[cd]azulen-1-yl)ethylamino]pyrimidine-5-carbonitrile | 0.0326 |
| 407 | 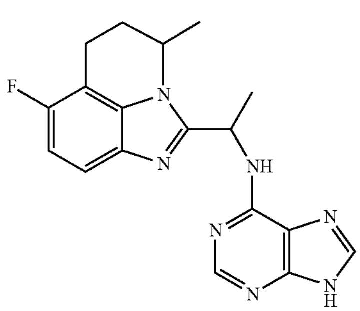 [SMILES: CC(Nc1ncnc2[nH]cnc12)c1nc2ccc(F)c3c2n1C(C)CC3] | [(S)-1-(7-Fluoro-4-methyl-5,6-dihydro-4H-imidazo[4,5,1-ij]quinolin-2-yl)ethyl]-(9H-purin-6-yl)amine | |

TABLE 3-continued

| No. | Structure | IUPAC Name | CD69 Hu Blood FACS IC50 (μM) |
|---|---|---|---|
| 408 | 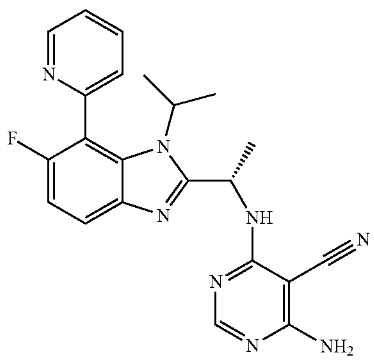 [SMILES: CC(C)n1c([C@H](C)Nc2ncnc(N)c2C#N)nc2ccc(F)c(-c3ccccn3)c21] | 4-amino-6-[[(1S)-1-[6-fluoro-1-isopropyl-7-(2-pyridyl)benzimidazol-2-yl]ethyl]amino]pyrimidine-5-carbonitrile | 0.163 |
| 409 | 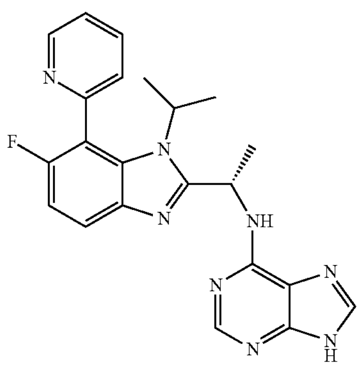 [SMILES: CC(C)n1c([C@H](C)Nc2ncnc3[nH]cnc23)nc2ccc(F)c(-c3ccccn3)c21] | N-[(1S)-1-[6-fluoro-1-isopropyl-7-(2-pyridyl)benzimidazol-2-yl]ethyl]-9H-purin-6-amine | 0.0642 |
| 410 | 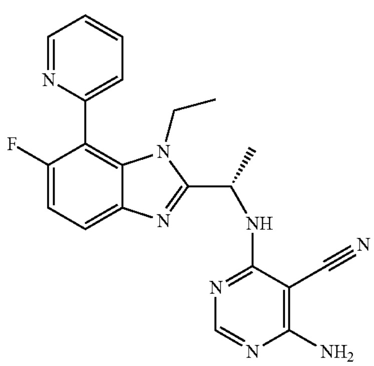 [SMILES: CCn1c([C@H](C)Nc2ncnc(N)c2C#N)nc2ccc(F)c(-c3ccccn3)c21] | 4-amino-6-[[(1S)-1-[1-ethyl-6-fluoro-7-(2-pyridyl)benzimidazol-2-yl]ethyl]amino]pyrimidine-5-carbonitrile | |
| 411 | 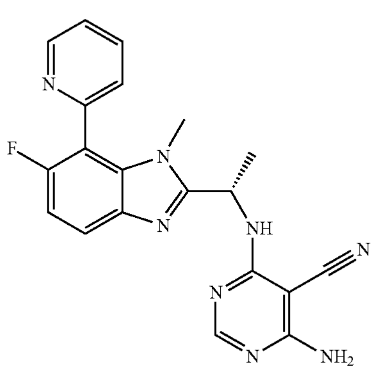 [SMILES: C[C@H](Nc1ncnc(N)c1C#N)c1nc2ccc(F)c(-c3ccccn3)c2n1C] | 4-amino-6-[[(1S)-1-[6-fluoro-1-methyl-7-(2-pyridyl)benzimidazol-2-yl]ethyl]amino]pyrimidine-5-carbonitrile | 0.895 |

TABLE 3-continued

| No. | Structure | IUPAC Name | CD69 Hu Blood FACS IC50 (μM) |
|---|---|---|---|
| 412 | 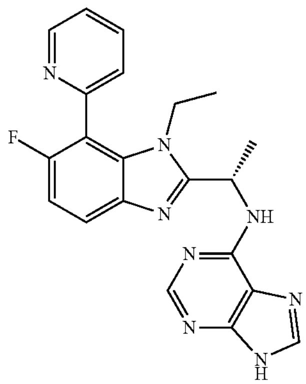 [SMILES: CCn1c([C@H](C)Nc2ncnc3[nH]cnc23)nc2ccc(F)c(-c3ccccn3)c21] | N-[(1S)-1-[1-ethyl-6-fluoro-7-(2-pyridyl)benzimidazol-2-yl]ethyl]-9H-purin-6-amine | |
| 413 | 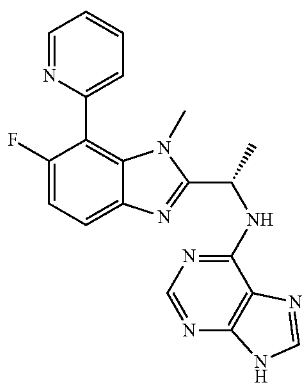 [SMILES: C[C@H](Nc1ncnc2[nH]cnc12)c1nc2ccc(F)c(-c3ccccn3)c2n1C] | N-[(1S)-1-[6-fluoro-1-methyl-7-(2-pyridyl)benzimidazol-2-yl]ethyl]-9H-purin-6-amine | |
| 414 | 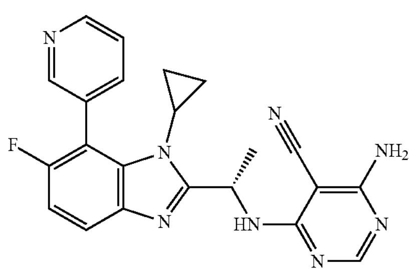 [SMILES: C[C@H](Nc1ncnc(N)c1C#N)c1nc2ccc(F)c(-c3ccccc3)c2n1C1CC1] | 4-amino-6-[[(1S)-1-[1-cyclopropyl-6-fluoro-7-(3-pyridyl)benzimidazol-2-yl]ethyl]amino]pyrimidine-5-carbonitrile | |
| 415 | 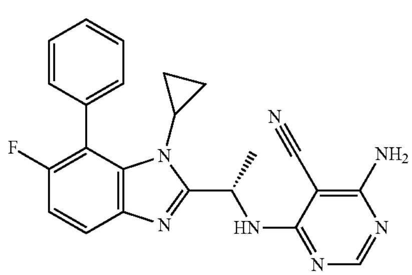 | 4-amino-6-[[(1S)-1-[1-cyclopropyl-6-fluoro-7-phenyl-benzimidazol-2-yl]ethyl]amino]pyrimidine-5-carbonitrile | 0.224 |

TABLE 3-continued

| No. | Structure | IUPAC Name | CD69 Hu Blood FACS IC50 (μM) |
|---|---|---|---|
| 416 | 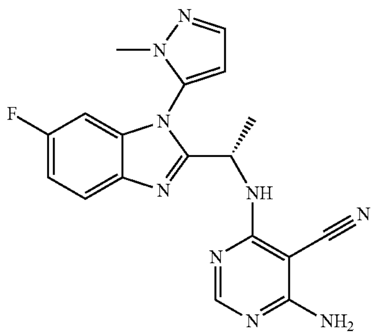 [SMILES: C[C@H](Nc1ncnc(N)c1C#N)c1nc2ccc(F)cc2n1-c1ccnn1C] | 4-amino-6-[[(1S)-1-[6-fluoro-1-(2-methylpyrazol-3-yl)benzimidazol-2-yl]ethyl]amino]pyrimidine-5-carbonitrile | 0.0678 |
| 417 | 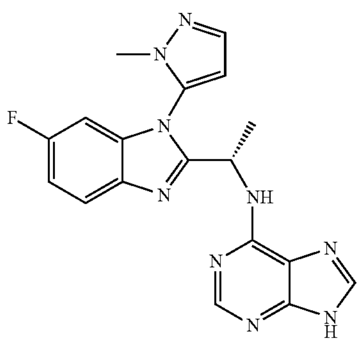 [SMILES: C[C@H](Nc1ncnc2[nH]cnc12)c1nc2ccc(F)cc2n1-c1ccnn1C] | N-[(1S)-1-[6-fluoro-1-(2-methylpyrazol-3-yl)benzimidazol-2-yl]ethyl]-9H-purin-6-amine | 0.140 |
| 418 | 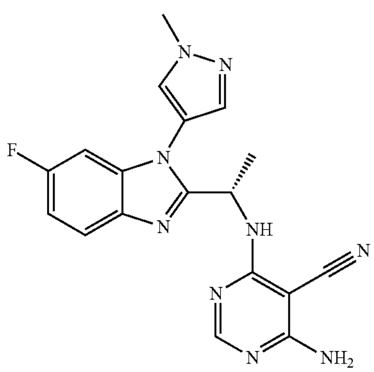 [SMILES: C[C@H](Nc1ncnc(N)c1C#N)c1nc2ccc(F)cc2n1-c1cnn(C)c1] | 4-amino-6-[[(1S)-1-[6-fluoro-1-(1-methylpyrazol-4-yl)benzimidazol-2-yl]ethyl]amino]pyrimidine-5-carbonitrile | 0.107 |
| 419 | 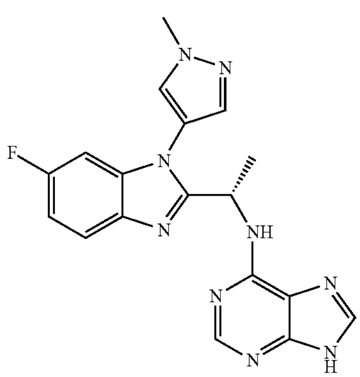 [SMILES: C[C@H](Nc1ncnc2[nH]cnc12)c1nc2ccc(F)cc2n1-c1cnn(C)c1] | N-[(1S)-1-[6-fluoro-1-(1-methylpyrazol-4-yl)benzimidazol-2-yl]ethyl]-9H-purin-6-amine | 0.0433 |

TABLE 3-continued

| No. | Structure | IUPAC Name | CD69 Hu Blood FACS IC50 (µM) |
|---|---|---|---|
| 420 | 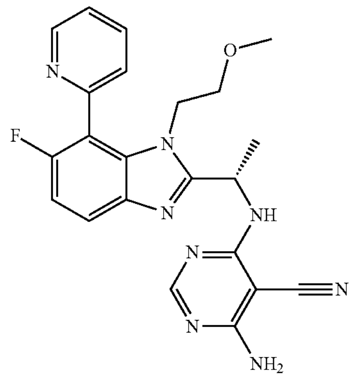 [SMILES: COCCn1c([C@H](C)Nc2ncnc(N)c2C#N)nc2ccc(F)c(-c3ccccn3)c21] | 4-amino-6-[[(1S)-1-[6-fluoro-1-(2-methoxyethyl)-7-(2-pyridyl)benzimidazol-2-yl]ethyl]amino]pyrimidine-5-carbonitrile | |
| 421 | 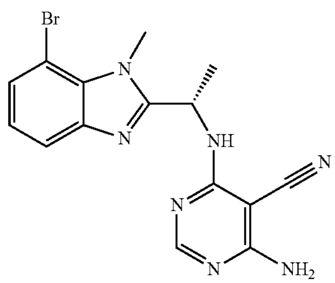 [SMILES: C[C@H](Nc1ncnc(N)c1C#N)c1nc2cccc(Br)c2n1C] | 4-amino-6-[[(1S)-1-(7-bromo-1-methyl-benzimidazol-2-yl)ethyl]amino]pyrimidine-5-carbonitrile | |
| 422 | 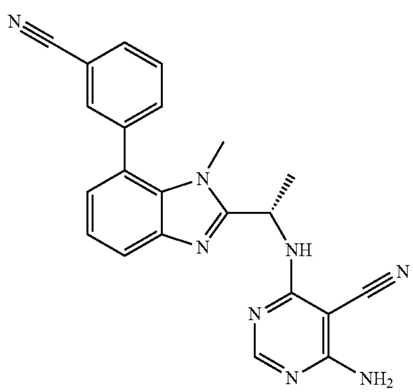 [SMILES: C[C@H](Nc1ncnc(N)c1C#N)c1nc2cccc(-c3cccc(C#N)c3)c2n1C] | 4-amino-6-[[(1S)-1-[7-(3-cyanophenyl)-1-methyl-benzimidazol-2-yl]ethyl]amino]pyrimidine-5-carbonitrile | |
| 423 | 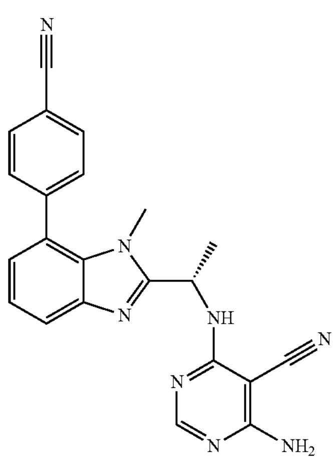 [SMILES: C[C@H](Nc1ncnc(N)c1C#N)c1nc2cccc(-c3ccc(C#N)cc3)c2n1C] | 4-amino-6-[[(1S)-1-[7-(4-cyanophenyl)-1-methyl-benzimidazol-2-yl]ethyl]amino]pyrimidine-5-carbonitrile | |

TABLE 3-continued

| No. | Structure | IUPAC Name | CD69 Hu Blood FACS IC50 (μM) |
|---|---|---|---|
| 424 | 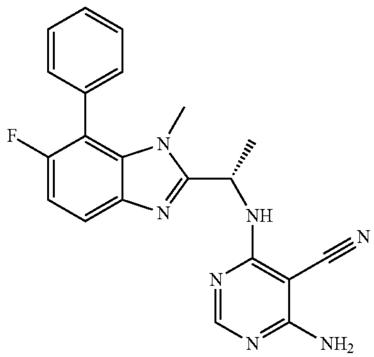 [SMILES: C[C@H](Nc1ncnc(N)c1C#N)c1nc2ccc(F)c(-c3ccccc3)c2n1C] | 4-amino-6-[[(1S)-1-(6-fluoro-1-methyl-7-phenyl-benzimidazol-2-yl]ethyl]amino]pyrimidine-5-carbonitrile | |
| 425 | 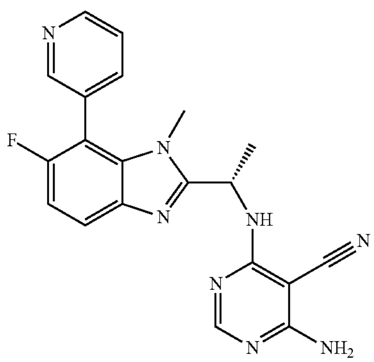 [SMILES: C[C@H](Nc1ncnc(N)c1C#N)c1nc2ccc(F)c(-c3cccnc3)c2n1C] | 4-amino-6-[[(1S)-1-[6-fluoro-1-methyl-7-(3-pyridyl)benzimidazol-2-yl]ethyl]amino]pyrimidine-5-carbonitrile | |
| 426 | 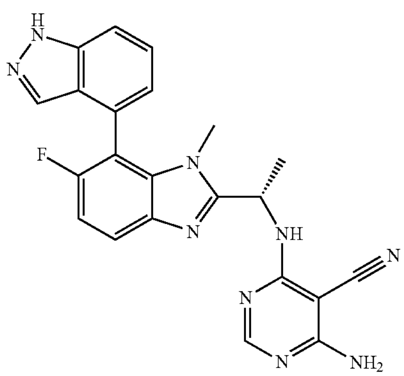 [SMILES: C[C@H](Nc1ncnc(N)c1C#N)c1nc2ccc(F)c(-c3cccc4[nH]ncc34)c2n1C] | 4-amino-6-[[(1S)-1-[6-fluoro-7-(1H-indazol-4-yl)-1-methyl-benzimidazol-2-yl]ethyl]amino]pyrimidine-5-carbonitrile | |
| 427 | 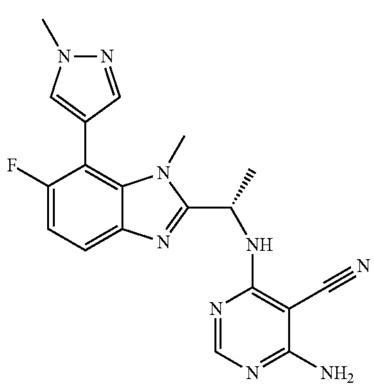 [SMILES: C[C@H](Nc1ncnc(N)c1C#N)c1nc2ccc(F)c(-c3cnn(C)c3)c2n1C] | 4-amino-6-[[(1S)-1-[6-fluoro-1-methyl-7-(1-methylpyrazol-4-yl)benzimidazol-2-yl]ethyl]amino]pyrimidine-5-carbonitrile | |

TABLE 3-continued

| No. | Structure | IUPAC Name | CD69 Hu Blood FACS IC50 (µM) |
|---|---|---|---|
| 428 | 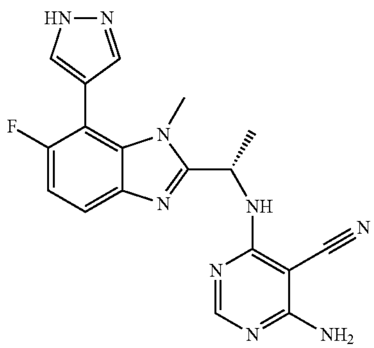 [SMILES: C[C@H](Nc1ncnc(N)c1C#N)c1nc2ccc(F)c(-c3cn[nH]c3)c2n1C] | 4-amino-6-[[(1S)-1-[6-fluoro-1-methyl-7-(1H-pyrazol-4-yl)benzimidazol-2-yl]ethyl]amino]pyrimidine-5-carbonitrile | |
| 429 | 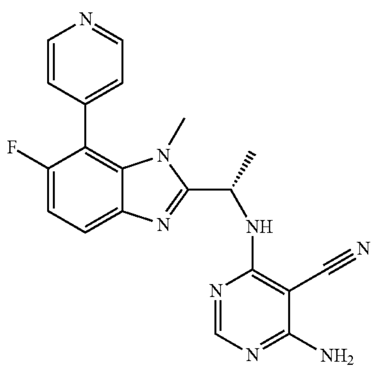 [SMILES: C[C@H](Nc1ncnc(N)c1C#N)c1nc2ccc(F)c(-c3ccncc3)c2n1C] | 4-amino-6-[[(1S)-1-[6-fluoro-1-methyl-7-(4-pyridyl)benzimidazol-2-yl]ethyl]amino]pyrimidine-5-carbonitrile | |
| 430 | 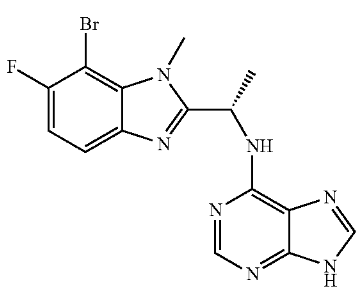 [SMILES: C[C@H](Nc1ncnc2[nH]cnc12)c1nc2ccc(F)c(Br)c2n1C] | N-[(1S)-1-(7-bromo-6-fluoro-1-methyl-benzimidazol-2-yl)ethyl]-9H-purin-6-amine | |
| 431 | 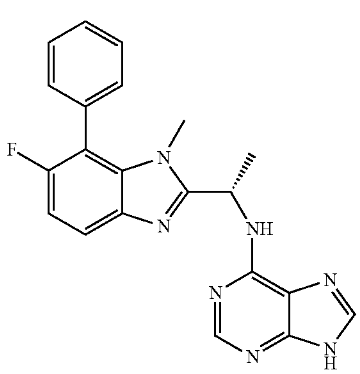 [SMILES: C[C@H](Nc1ncnc2[nH]cnc12)c1nc2ccc(F)c(-c3ccccc3)c2n1C] | N-[(1S)-1-(6-fluoro-1-methyl-7-phenyl-benzimidazol-2-yl)ethyl]-9H-purin-6-amine | |

TABLE 3-continued

| No. | Structure | IUPAC Name | CD69 Hu Blood FACS IC50 (μM) |
|---|---|---|---|
| 432 | 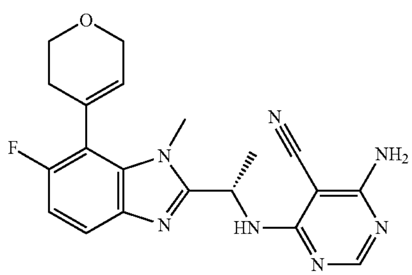 [SMILES: C[C@H](Nc1ncnc(N)c1C#N)c1nc2ccc(F)c(C3=CCOCC3)c2n1C] | 4-amino-6-[[(1S)-1-[7-(3,6-dihydro-2H-pyran-4-yl)-6-fluoro-1-methyl-benzimidazol-2-yl]ethyl]amino]pyrimidine-5-carbonitrile | |
| 433 | 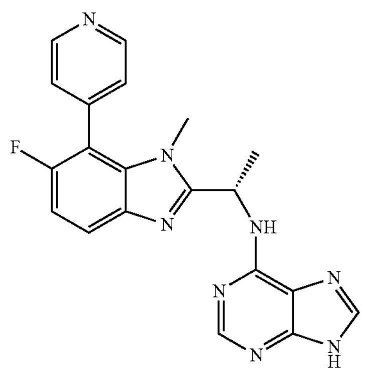 [SMILES: C[C@H](Nc1ncnc2[nH]cnc12)c1nc2ccc(F)c(-c3ccncc3)c2n1C] | N-[(1S)-1-[6-fluoro-1-methyl-7-(4-pyridyl)benzimidazol-2-yl]ethyl]-9H-purin-6-amine | |
| 434 | 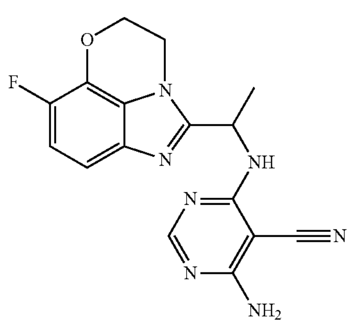 [SMILES: CC(Nc1ncnc(N)c1C#N)c1nc2ccc(F)c3c2n1CCO3] | 4-Amino-6-[1-(6-fluoro-3,4-dihydro-5-oxa-1,2a-diazaacenaphthylen-2-yl)ethylamino]pyrimidine-5-carbonitrile | |
| 435 | 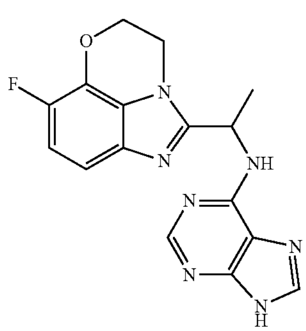 [SMILES: CC(Nc1ncnc2[nH]cnc12)c1nc2ccc(F)c3c2n1CCO3] | [1-(6-Fluoro-3,4-dihydro-5-oxa-1,2a-diazaacenaphthylen-2-yl)ethyl]-(9H-purin-6-yl)amine | |

TABLE 3-continued

| No. | Structure | IUPAC Name | CD69 Hu Blood FACS IC50 (μM) |
|---|---|---|---|
| 436 | 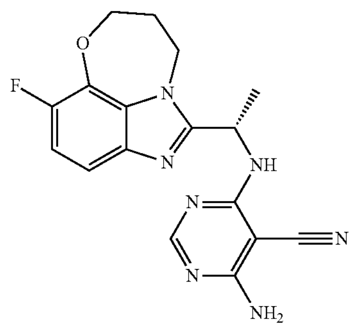 [SMILES: C[C@H](Nc1ncnc(N)c1C#N)c1nc2ccc(F)c3c2n1CCCO3] | 4-Amino-6-[(S)-1-(5-fluoro-8,9-dihydro-7H-6-oxa-2,9a-diazabenzo[c,d]azulen-1-yl)ethylamino]pyrimidine-5-carbonitrile | |
| 437 | 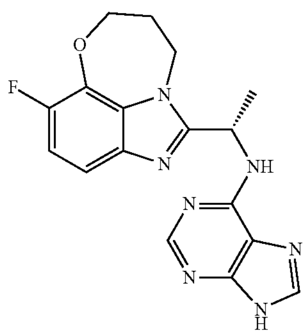 [SMILES: C[C@H](Nc1ncnc2[nH]cnc12)c1nc2ccc(F)c3c2n1CCCO3] | [(S)-1-(5-Fluoro-8,9-dihydro-7H-6-oxa-2,9a-diazabenzo[c,d]azulen-1-yl)ethyl]-(9H-purin-6-yl)amine | |
| 438 | 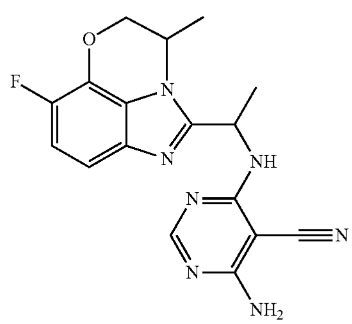 [SMILES: CC(Nc1ncnc(N)c1C#N)c1nc2ccc(F)c3c2n1C(C)CO3] | 4-Amino-6-[(S)-1-((R)-6-fluoro-3-methyl-3,4-dihydro-5-oxa-1,2a-diazaacenaphthylen-2-yl)ethylamino]pyrimidine-5-carbonitrile | |
| 439 | 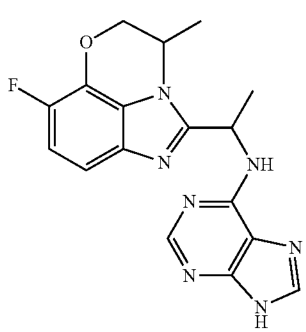 [SMILES: CC(Nc1ncnc2[nH]cnc12)c1nc2ccc(F)c3c2n1C(C)CO3] | [(S)-1-((R)-6-Fluoro-3-methyl-3,4-dihydro-5-oxa-1,2a-diazaacenaphthylen-2-yl)ethyl](9H-purin-6-yl)amine | |

TABLE 3-continued

| No. | Structure | IUPAC Name | CD69 Hu Blood FACS IC50 (µM) |
|---|---|---|---|
| 440 | 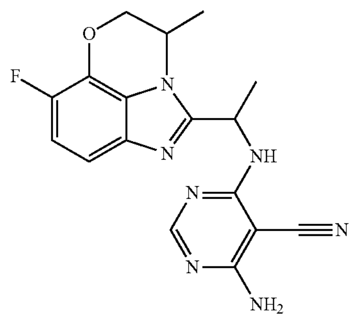 [SMILES: CC(Nc1ncnc(N)c1C#N)c1nc2ccc(F)c3c2n1C(C)CO3] | 4-Amino-6-[(S)-1-((S)-6-fluoro-3-methyl-3,4-dihydro-5-oxa-1,2a-diazaacenaphthylen-2-yl)ethylamino]pyrimidine-5-carbonitrile | |
| 441 | 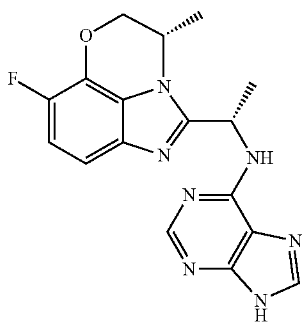 [SMILES: C[C@H](Nc1ncnc2[nH]cnc12)c1nc2ccc(F)c3c2n1[C@@H](C)CO3] | [(S)-1-((S)-6-Fluoro-3-methyl-3,4-dihydro-5-oxa-1,2a-diazaacenaphthylen-2-yl)ethyl](9H-purin-6-yl)amine | |
| 442 | 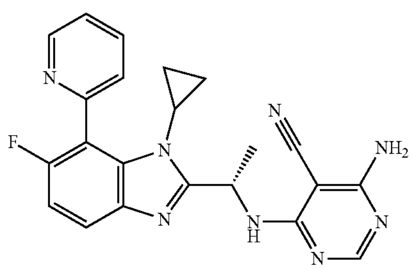 [SMILES: C[C@H](Nc1ncnc(N)c1C#N)c1nc2ccc(F)c(-c3ccccn3)c2n1C1CC1] | 4-Amino-6-[(S)-1-(1-cyclopropyl-6-fluoro-7-pyridin-2-yl-1H-benzoimidazol-2-yl)ethylamino]-pyrimidine-5-carbonitrile | 0.797 |
| 443 | 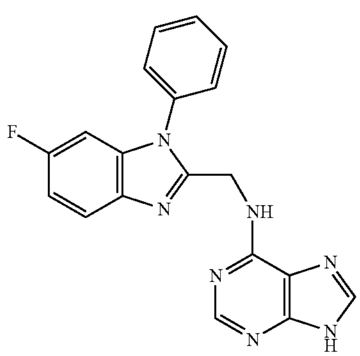 [SMILES: Fc1ccc2nc(CNc3ncnc4[nH]cnc34)n(-c3ccccc3)c2c1] | (6-Fluoro-1-phenyl-1H-benzoimidazol-2-ylmethyl)-(9H-purin-6-yl)amine | >5 |

Administration of Formula I Compounds

The Formula I compounds of the invention may be administered by a route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

A dose to treat human patients may range from about 10 mg to about 1000 mg of Formula I compound. A typical dose may be about 100 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Methods of Treatment with Formula I Compounds

Formula I compounds of the present invention are useful for treating a human or animal patient suffering from a disease or disorder arising from abnormal cell growth, function or behavior associated with PI3 kinase, in particular with the p110δ (delta) isoform of PI3 kinase such as an immune disorder, cardiovascular disease, viral infection, inflammation, a metabolism/endocrine disorder or a neurological disorder, may thus be treated by a method comprising the administration thereto of a compound of the present invention as defined above. A human or animal patient suffering from cancer may also be treated by a method comprising the administration thereto of a compound of the present invention as defined above. The condition of the patient may thereby be improved or ameliorated.

Formula I compounds may be useful for in vitro, in situ, and in vivo diagnosis or treatment of mammalian cells, organisms, or associated pathological conditions, such as systemic and local inflammation, immune-inflammatory diseases such as rheumatoid arthritis, immune suppression, organ transplant rejection, allergies, ulcerative colitis, Crohn's disease, dermatitis, asthma, systemic lupus erythematosus, Sjögren's Syndrome, multiple sclerosis, scleroderma/systemic sclerosis, idiopathic thrombocytopenic purpura (ITP), anti-neutrophil cytoplasmic antibodies (ANCA) vasculitis, chronic obstructive pulmonary disease (COPD), psoriasis, and for general joint protective effects.

Formula I compounds may be useful for treating such diseases as arthritic diseases, such as rheumatoid arthritis, monoarticular arthritis, osteoarthritis, gouty arthritis, spondylitis; Behcet disease; sepsis, septic shock, endotoxic shock, gram negative sepsis, gram positive sepsis, and toxic shock syndrome; multiple organ injury syndrome secondary to septicemia, trauma, or hemorrhage; ophthalmic disorders such as allergic conjunctivitis, vernal conjunctivitis, uveitis, and thyroid-associated ophthalmopathy; eosinophilic granuloma; pulmonary or respiratory disorders such as asthma, chronic bronchitis, allergic rhinitis, ARDS, chronic pulmonary inflammatory disease (e.g., chronic obstructive pulmonary disease), silicosis, pulmonary sarcoidosis, pleurisy, alveolitis, vasculitis, emphysema, pneumonia, bronchiectasis, and pulmonary oxygen toxicity; reperfusion injury of the myocardium, brain, or extremities; fibrosis such as cystic fibrosis; keloid formation or scar tissue formation; atherosclerosis; autoimmune diseases, such as systemic lupus erythematosus (SLE), autoimmune thyroiditis, multiple sclerosis, some forms of diabetes, and Reynaud's syndrome; and transplant rejection disorders such as GVHD and allograft rejection; chronic glomerulonephritis; inflammatory bowel diseases such as chronic inflammatory bowel disease (CIBD), Crohn's disease, ulcerative colitis, and necrotizing enterocolitis; inflammatory dermatoses such as contact dermatitis, atopic dermatitis, psoriasis, or urticaria; fever and myalgias due to infection; central or peripheral nervous system inflammatory disorders such as meningitis, encephalitis, and brain or spinal cord injury due to minor trauma; Sjogren's syndrome; diseases involving leukocyte diapedesis; alcoholic hepatitis; bacterial pneumonia; antigen-antibody complex mediated diseases; hypovolemic shock; Type I diabetes mellitus; acute and delayed hypersensitivity; disease states due to leukocyte dyscrasia and metastasis; thermal injury; granulocyte transfusion-associated syndromes; and cytokine-induced toxicity.

The methods of the invention can have utility in treating subjects who are or can be subject to reperfusion injury, i.e., injury resulting from situations in which a tissue or organ experiences a period of ischemia followed by reperfusion. The term "ischemia" refers to localized tissue anemia due to obstruction of the inflow of arterial blood. Transient ischemia followed by reperfusion characteristically results in neutrophil activation and transmigration through the endothelium of the blood vessels in the affected area. Accumulation of activated neutrophils in turn results in generation of reactive oxygen metabolites, which damage components of the involved tissue or organ. This phenomenon of "reperfusion injury" is commonly associated with conditions such as vascular stroke (including global and focal ischemia), hemorrhagic shock, myocardial ischemia or infarction, organ transplantation, and cerebral vasospasm. To illustrate, reperfusion injury occurs at the termination of cardiac bypass procedures or during cardiac arrest when the heart, once prevented from receiving blood, begins to reperfuse. It is expected that inhibition of PI3K delta activity may result in reduced amounts of reperfusion injury in such situations.

Methods of the invention include treating cancer with Formula I compounds where the cancer is breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, pancreatic, myeloid disorders, lymphoma, hairy cells, buccal cavity, naso-pharyngeal, pharynx, lip, tongue, mouth, small intestine, colon-rectum, large intestine, rectum, brain and central nervous system, Hodgkin's, leukemia, bronchus, thyroid, liver and intrahepatic bile duct, hepatocellular, gastric, glioma/glioblastoma, endometrial, melanoma, kidney and renal pelvis, urinary bladder, uterine corpus, uterine cervix, multiple myeloma, acute myelogenous leukemia, chronic lymphoid leukemia, chronic myelogenous leukemia, lymphocytic leukemia, myeloid leukemia, oral cavity and pharynx, non-Hodgkin lymphoma, melanoma, and villous colon adenoma.

Methods of the invention include administering a Formula I compound to treat a hematopoietic malignancy selected from leukemia, non-Hodgkin's lymphoma, diffuse large hematopoietic lymphoma, follicular lymphoma, mantle cell lymphoma, chronic lymphocytic leukemia (CLL), multiple myeloma, acute myeloid leukemia (AML), and myeloid cell leukemia (MCL).

The present invention also embraces the compound of Formula I for use as a medicament.

The present invention also embraces use of a compound of Formula I for treating a disease or disorder selected from cancer, immune disorders, cardiovascular disease, viral infection, inflammation, metabolism/endocrine function disorders and neurological disorders, and mediated by the p110 delta isoform of PI3 kinase.

The present invention also embraces the compound of Formula I for use in treating a disease or disorder selected from cancer, immune disorders, cardiovascular disease, viral infection, inflammation, metabolism/endocrine function disorders and neurological disorders, and mediated by the p110 delta isoform of PI3 kinase.

The present invention also embraces the use of a compound of Formula I in the manufacture of a medicament.

The present invention also embraces the use of a compound of Formula I in the manufacture of a medicament, wherein the medicament is for the treatment of cancer, immune disorders, cardiovascular disease, viral infection, inflammation, metabolism/endocrine function disorders and neurological disorders.

Pharmaceutical Formulations

In order to use a Formula I compound for the therapeutic treatment (including prophylactic treatment) of mammals including humans, it is normally formulated in accordance with standard pharmaceutical practice as a pharmaceutical composition. According to this aspect of the invention there is provided a pharmaceutical composition comprising a compound of this invention in association with a pharmaceutically acceptable diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a compound of Formula I having the desired degree of purity may optionally be mixed with pharmaceutically acceptable diluents, carriers, excipients or stabilizers (Remington's Pharmaceutical Sciences (1980) 16$^{th}$ edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compound ordinarily can be stored as a solid composition, a lyophilized formulation or as an aqueous solution.

The pharmaceutical compositions of the invention will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the hyperproliferative disorder.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences $16^{th}$ edition, Osol, A. Ed. (1980).

Sustained-release preparations of compounds of Formula I may be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula I suitable for oral administration may be prepared as discrete units such as pills, capsules, cachets or tablets each containing a predetermined amount of a compound of Formula I. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom. Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula I intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations may be applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs. The oily phase of the emulsions of this invention may be constituted from known ingredients in a known manner, including a mixture of at least one emulsifier with a fat or an oil, or with both a fat and an oil. A hydrophilic emulsifier included together with a lipophilic emulsifier acts as a stabilizer. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of Formula I compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula I may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formula I may be employed alone or in combination with other therapeutic agents for the treatment of a disease or disorder described herein, such as inflammation or a hyperproliferative disorder (e.g., cancer). In certain embodiments, a compound of Formula I is combined in a pharmaceutical combination formulation, or dosing regimen as combination therapy, with a second therapeutic compound that has anti-inflammatory or anti-hyperproliferative properties or that is useful for treating an inflammation, immune-response disorder, or hyperproliferative disorder (e.g., cancer). The second therapeutic agent may be an NSAID anti-inflammatory agent. The second therapeutic agent may be a chemotherapeutic agent. The second compound of the pharmaceutical combination formulation or dosing regimen preferably has complementary activities to the compound of Formula I such that they do not adversely affect each other. Such compounds are suitably present in combination in amounts that are effective for the purpose intended. In one embodiment, a composition of this invention comprises a compound of Formula I, or a stereoisomer, tautomer, or pharmaceutically acceptable salt or prodrug thereof, in combination with a therapeutic agent such as an NSAID.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other therapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combination therapy, effective dosages of two or more active ingredients are administered together.

In a particular embodiment of therapy, a compound of Formula I, or a stereoisomer, tautomer, or pharmaceutically acceptable salt or prodrug thereof, may be combined with other therapeutic, hormonal or antibody agents such as those described herein, as well as combined with surgical therapy and radiotherapy. Combination therapies according to the present invention thus comprise the administration of at least one compound of Formula I, or a stereoisomer, tautomer, or pharmaceutically acceptable salt or prodrug thereof, and the use of at least one other cancer treatment method. The amounts of the compound(s) of Formula I and the other pharmaceutically active chemotherapeutic agent(s) and the relative timings of administration will be selected in order to achieve the desired combined therapeutic effect.

Metabolites of Compounds of Formula I

Also falling within the scope of this invention are the in vivo metabolic products of Formula I described herein. Such products may result for example from the oxidation, reduction, hydrolysis, amidation, deamidation, esterification, deesterification, enzymatic cleavage, and the like, of the administered compound. Accordingly, the invention includes metabolites of compounds of Formula I, including compounds produced by a process comprising contacting a compound of this invention with a mammal for a period of time sufficient to yield a metabolic product thereof.

Metabolite products typically are identified by preparing a radiolabelled (e.g., $^{14}$C or $^{3}$H) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Articles of Manufacture

In another embodiment of the invention, an article of manufacture, or "kit", containing materials useful for the treatment of the diseases and disorders described above is provided. In one embodiment, the kit comprises a container comprising a compound of Formula I. The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula I or a formulation thereof which is effective for treating the condition and may have a sterile access port (for example, the container may be an intravenous solution bag or a vial having a stopper pierceable by a hypodermic injection needle). At least one active agent in the composition is a compound of Formula I. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a compound of Formula I can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I and, if present, the second pharmaceutical formulation. For example, if the kit comprises a first composition comprising a compound of Formula I and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula I, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of Formula I contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula I and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Preparation of Formula I Compounds

Heterocyclic compounds, e.g. 4-substituted pyrimidine compounds, of Formula I may be synthesized by synthetic routes that include processes analogous to those well-known in the chemical arts, particularly in light of the description contained herein, and those for other heterocycles described in: Comprehensive Heterocyclic Chemistry II, Editors Katritzky and Rees, Elsevier, 1997, e.g. Volume 3; Liebigs Annalen der Chemie, (9):1910-16, (1985); Helvetica Chimica Acta, 41:1052-60, (1958); Arzneimittel-Forschung, 40(12):1328-31, (1990), each of which are expressly incorporated by reference. Starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie*, 4, Aufl. ed. Springer-Verlag, Berlin, including supplements (also available via the Beilstein online database).

Synthetic chemistry transformations and protecting group methodologies (protection and deprotection) useful in synthesizing Formula I compounds and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, $3^{rd}$ Ed., John Wiley and Sons (1999); and L. Paquette, ed., Encyclopedia of Reagents for Organic Synthesis, John Wiley and Sons (1995) and subsequent editions thereof.

Compounds of Formula I may be prepared singly or as compound libraries comprising at least 2, for example 5 to 1,000 compounds, or 10 to 100 compounds. Libraries of compounds of Formula I may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds, or pharmaceutically acceptable salts thereof.

In preparing compounds of Formulas I, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

For illustrative purposes, Schemes 1-17 show general methods for preparing Formula I, such as 4-substituted pyrimidine compounds and key intermediates. For a more detailed description of the individual reaction steps, see the General Procedures and Examples sections. Those skilled in the art will appreciate that other synthetic routes may be used to synthesize the inventive compounds. Although specific starting materials and reagents are depicted and discussed in the General Procedures, Examples, and Schemes, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

In the following Schemes 1-17:

$Z_1$-$Z_4$=as defined previously $R^{13}$=appropriate group such as substituted alkyl or other $R^1$=appropriate group such as unsubstituted or substituted aromatic ring, acyclic or cyclic ether, alkyl or cycloalkyl, heteroaryl, piperidine, cyclic amine.

$R^2$=appropriate group such as a small alkyl, cycloalkyl, OH or ether.

$R^3$=appropriate group such as H, alkyl or $NH_2$.

Compounds of formula (I) may be obtained from compounds of formula (II) according to Scheme 1 by nucleophilic aromatic substitution reaction or other methods described in the literature. Typical reaction conditions consist of the use of halogenated heterocycles in the presence of a base, such as DIPEA, in a dipolar solvent, such as dioxane, n-butanol, and by heating at a temperature of between 90 and 140° C. under microwave irradiation or thermal heating.

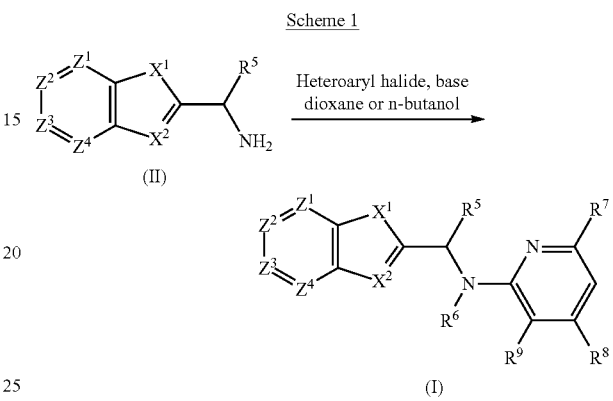

Scheme 1

Compounds of formula (Ia), wherein Het is 2-aminopyridyl may be obtained, or where $R^6$ and $R^9$ form a five- or six-membered heteroaryl or heterocyclic ring, according to Scheme 2; from compounds of formula (III), wherein X is a halogen such as bromide, chloride, iodide or a suitable leaving group, such as mesylate, by alkylation reaction or other methods described in the literature. Typical reaction conditions consist of the use of a base, such as $Cs_2CO_3$, $K_2CO_3$ or NaH, in an aprotic dipolar solvent, such as DMF or DMSO, at a temperature of between 0 and 140° C. under microwave irradiation or thermal heating.

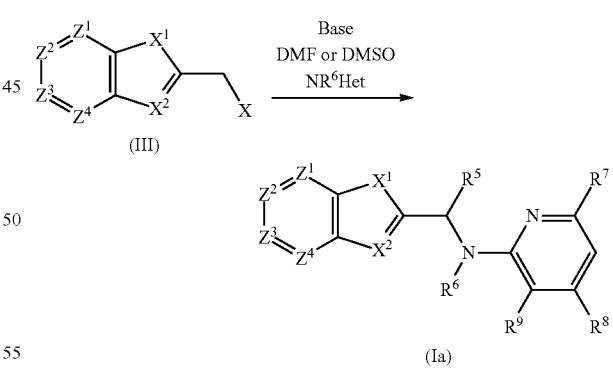

Scheme 2

Compounds of formula (Ib), wherein $X^1$ is $NR^{10}$, $X^2$ is N, $R^6$ is H and the N-linked heterocycle is purine, may be obtained according to Scheme 3 from compounds of formula (IIa) by nucleophilic aromatic substitution reaction or other methods described in the literature. Typical reaction conditions consist of the use of 6-chloro-9H-purine in the presence of a base, such as DIPEA, in a dipolar solvent, such as dioxane or n-butanol, and by heating at a temperature of between 100 and 140° C. under microwave irradiation or thermal heating. 6-Chloro-9H-purine bearing a N-protecting group at the 9 position, such as THP (tetrahydropyranyl) group, might also be used under the reaction conditions reported above. Removal of the THP group might be obtained during the work-up, for example by the use of strong cation cartridges (SCX-2).

Scheme 3

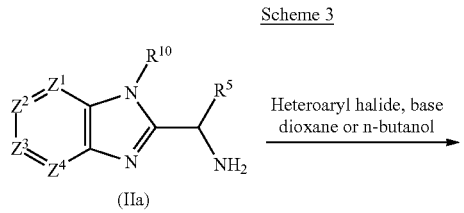

(IIa)

Heteroaryl halide, base
dioxane or n-butanol

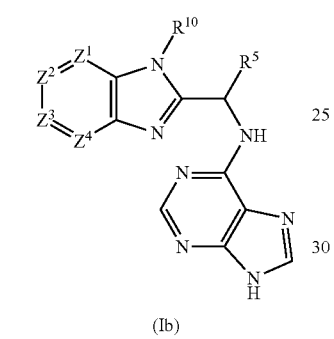

(Ib)

Compounds of formula (Ic), which are compounds of formula I wherein $R^{10}$ is a C-linked piperidine and $R^{13}$ is a substituted alkyl, may be obtained from compounds of formula (Id) according to Scheme 4 by reductive amination reaction or other methods described in the literature. The reaction may be performed by the use of the appropriate aldehyde or ketone, followed by addition of a reducing agent, such as sodium triacethoxyborohydride. Alternatively, substituted carboxylic acids, acid chlorides, halides, isocyanides may be reacted with compounds of formula (Id) under the appropriate reaction condition affording compounds of formula (Ic), wherein $R^{13}$ is an appropriate group as previously defined.

Scheme 4

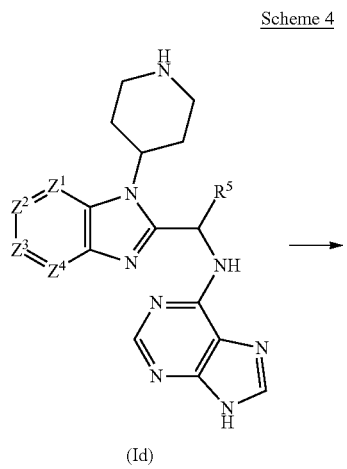

(Id)

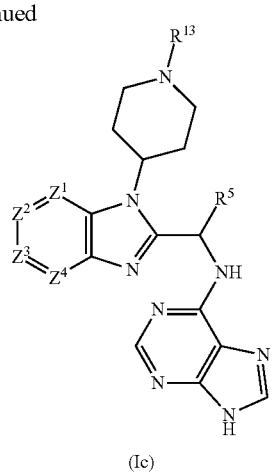

(Ic)

Compounds of formula (Id) may be obtained according to Scheme 5 from compounds of formula (Ie), wherein Pg is a suitable protecting group, such as Boc. Removal of the Boc group might be achieved, for example, by the use of TFA in DCM at a temperature of between 0° C. and RT.

Scheme 5

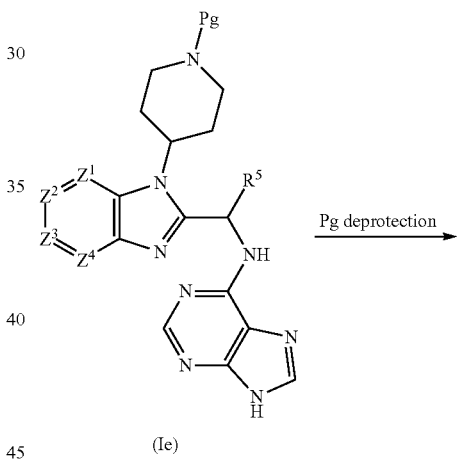

(Ie)

Pg deprotection

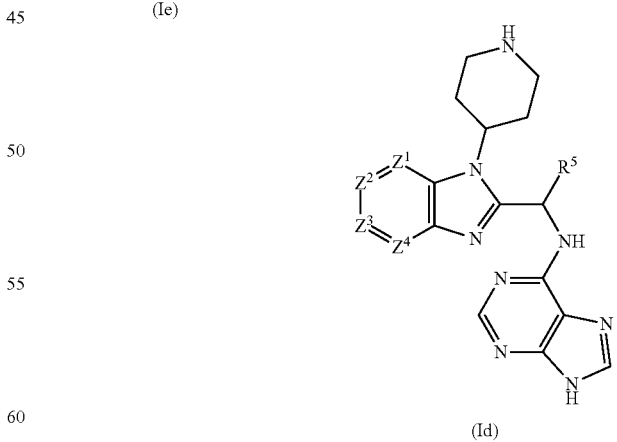

(Id)

Compounds of formula (If), which are equivalent to compounds of formula I wherein $R^{10}$ is a C-linked piperidine and $R^{13}$ is a substituted alkyl, may be obtained according to Scheme 6 from compounds of formula (Ig) by reductive amination by the use of the appropriate aldehyde or ketone, followed by addition of a reducing agent, such as sodium triacetoxyborohydride. Alternatively, substituted carboxylic acids, acid chlorides, halide and isocyanides might be reacted with compounds of formula (Ig) under the appropriate reaction condition described in the literature affording compounds of formula (If), wherein $R^{13}$ is an appropriate group as previously defined.

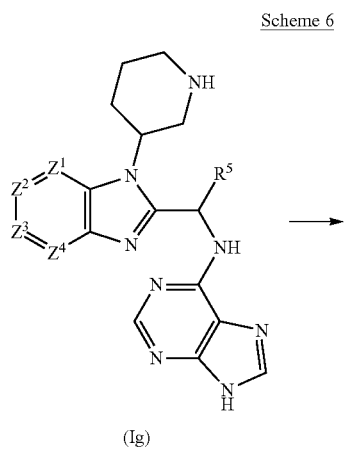

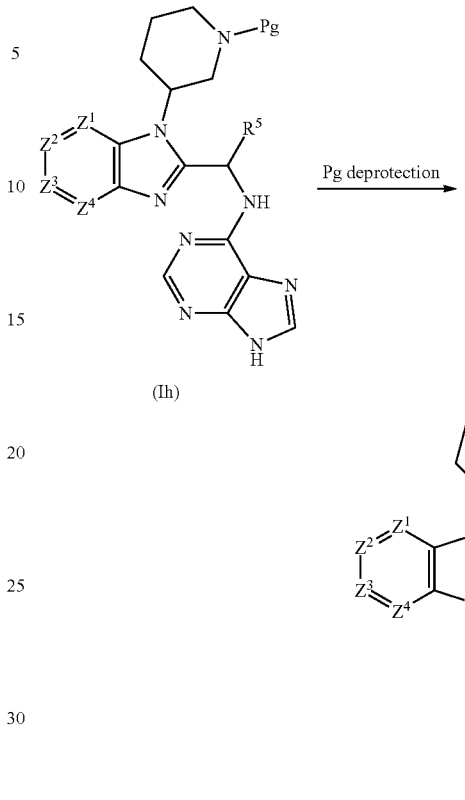

Compounds of formula (IIa) may be obtained, according to Scheme 8, from compounds of formula (III), wherein Pg is a suitable N-protecting group, typically Boc or CBZ through deprotection of N-Pg group. For examples, Boc groups might be removed by the use of TFA in DCM at a temperature of between 0° C. and RT. For example, CBZ groups might be removed by the use of Pd/C under a hydrogen atmosphere in the presence of HCl at RT using a protic solvent, such as EtOH or IMS.

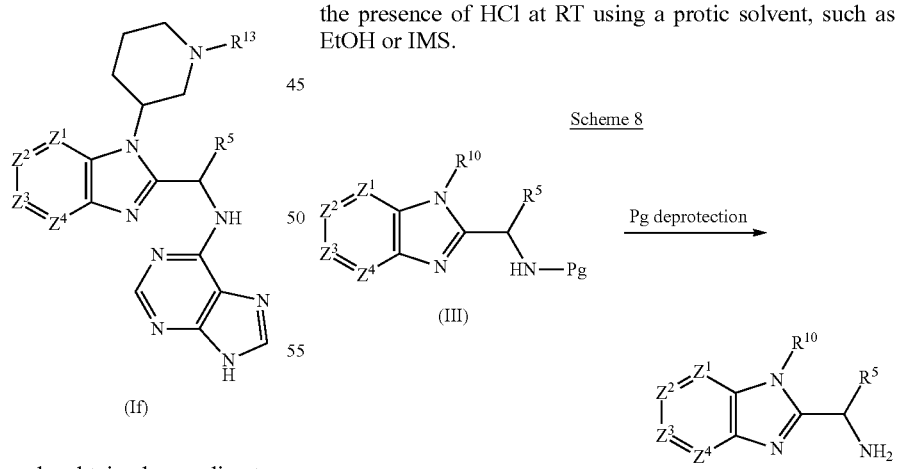

Compounds of formula (Ig) may be obtained according to Scheme 7 from compounds of formula (Ih), wherein Pg is a suitable protecting group, such as Boc or CBZ. Removal of the Boc group might be obtained, for example, by the use of TFA in DCM at a temperature of between 0° C. and RT. CBZ groups might be removed, for example, by the use of Pd/C under a hydrogen atmosphere in the presence of HCl at RT using a protic solvent, such as EtOH or IMS.

Compounds of formula (III), wherein Pg is a suitable N-protecting group, typically Boc or CBZ, may be obtained, according to Scheme 9, from compounds of formula (IV) by a cyclization reaction. Typical reaction conditions consist in the use of an acid, such as acetic acid, hydrochloric acid or p-toluensulfonic acid, by heating at a temperature of between 60 and 90° C. for a period of time varying from 2 h to 48 h.

Scheme 9

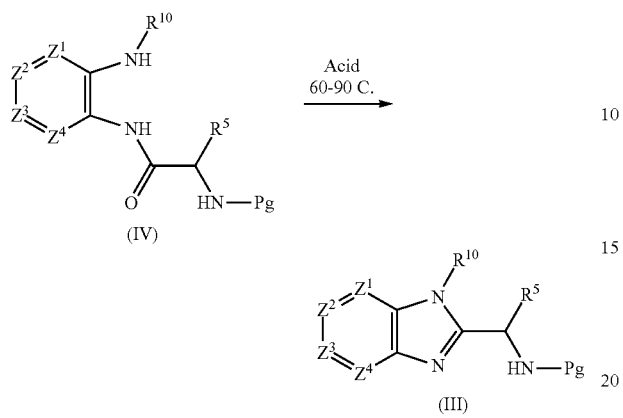

Compounds of formula (IV), wherein Pg is a suitable N-protecting group, typically Boc or CBZ, may be obtained, according to Scheme 10, from compounds of formula (V) by an amide coupling reaction or other methods described in the literature. Typical reaction conditions consist in the use of the appropriate amino acid bearing a suitable protecting group on the amino portion, such as Boc or CBZ, in the presence of a coupling reagent, such as HOBt or HOAt, of N-(3-dimethylaminopropyl)-N'-ethylcarbodiimide hydrochloride, and of a base, such as triethylamine or 4-methylmorpholine, in a dipolar aprotic solvent, such as DCM, at a temperature of between 0° C. and RT for a period of time varying from 2 h to 48 h.

Scheme 10

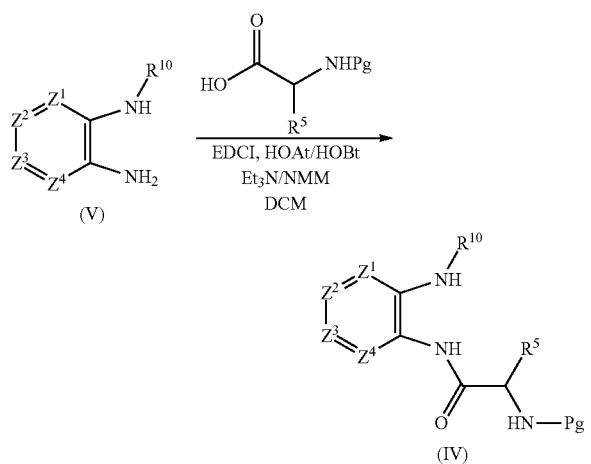

Compounds of formula (III), wherein Pg is a suitable N-protecting group, typically Boc or CBZ, may be obtained, according to Scheme 11, from compounds of formula (V) by amide coupling reaction followed by a cyclization reaction, without isolation of the open chain intermediate. Typical reaction conditions for the amide coupling step consist in the use of the appropriate amino acid bearing a suitable protecting group on the amino portion, such as Boc or CBZ, in the presence of a coupling reagent, such as HOBt or HOAt, of N-(3-dimethylaminopropyl)-N'-ethylcarbodiimide hydrochloride and of a base, such as triethylamine or 4-methylmorpholine, in a dipolar aprotic solvent, such a s DCM, at a temperature of between 0° C. and RT for a period of time varying from 2 h to 48 h. Typical reaction conditions for the cyclization step consist in the use of acetic acid by heating at a temperature of between 60 and 90° C. for a period of time varying from 2 h to 48 h.

Scheme 11

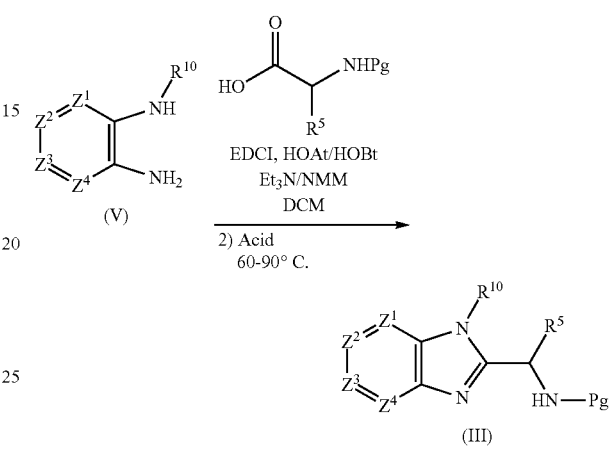

Compounds of formula (V) may be obtained, according to Scheme 12, from compounds of formula (VI) by reduction of a nitro-group. Typical reaction conditions consist in the use of a catalyst, such as Pd/C or PtO$_2$, under a hydrogen atmosphere in a solvent, such as IMS or EtOAc, at RT for a period of time varying from 2 h to 72 h. Alternative reaction conditions may be represented by the use of iron powder and ammonium chloride in a mixture of MeOH and water by heating to reflux temperature for a period of time varying from 2 h to 5 h.

Scheme 12

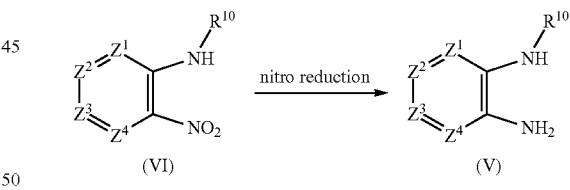

Compounds of formula (VI) may be obtained, according to Scheme 13, from compounds of formula (VII) by nucleophilic aromatic substitution or transition metal catalysed coupling reaction. Typical reaction conditions consist in the use of a base, such as potassium carbonate, triethylamine or sodium tert-butoxide, in a solvent such as DMF or NMP at RT or heating at a temperature of between 80 and 120° C. thermally or under microwave irradiation for a period of time varying from 2 h to 20 h. Alternative reaction conditions may be represented by the use LiHMDS as a base at −78° C. followed by addition of the appropriate primary amine NH$_2$R$^{10}$ in a solvent such as THF, or by the use of palladium-mediated reaction conditions, such as Pd(OAc)$_2$ as catalyst, (R)-BINAP or (S)-BINAP as ligand, NH$_2$R$^{10}$ in toluene heating at a temperature of between 90 and 140° C.

Scheme 13

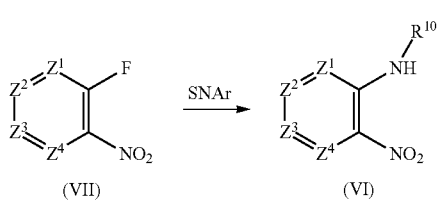

Compounds of formula (IIb), which are equivalent to compounds of formula II wherein $X^1$ is $CR^1$, may be obtained from compounds of formula (VIII) by reduction of an azide according to Scheme 14. Typical reaction conditions consist in the use of triphenylphosphine in a mixture THF/water as solvent at RT or heating at a temperature of between 60 and 80° C. for a period of time varying from 2 h to 8 h. Alternatively, reduction may be achieved by hydrogenation in the presence of a Pd catalyst, such as Pd/C, in a protic solvent, such as ethanol.

Scheme 14

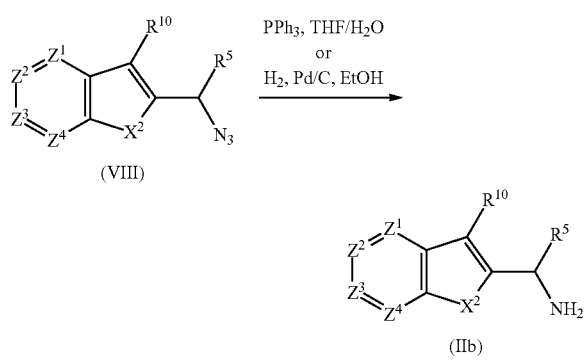

Compounds of formula (VIII) may be obtained, according to Scheme 15, from compounds of formula (IX) by converting an alcohol group into an azide group. Typical reaction conditions consist in reacting the appropriate alcohol under the Mitsunobu reaction conditions (DIAD, PPh$_3$ and diphenylphosphoryl azide) in a solvent such as dioxane. Alternatively, the transformation may be achieved by the use of a base, such as DBU, in the presence of diphenylphosphoryl azide in THF. Compounds of formula (VIII), wherein $R^5$ is H, may be obtained, according to Scheme 15, from compounds of formula (IX), wherein $R^5$ is H, by converting the alcohol functionality into a good leaving group, such as a mesylate, and subsequent reaction with sodium azide, as nucleophile.

Scheme 15

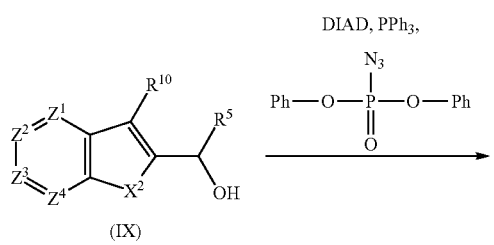

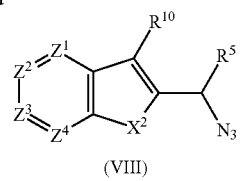

Compounds of formula (IX) may be obtained, according to Scheme 16, from compounds of formula (X) by addition of an organometallic species, such as a Grignard reagent, to an aldehyde group. Typical reaction conditions consist in the use of the organometallic species, in a solvent, such as THF or diethyl ether, at low temperature, typically −78° C.

Scheme 16

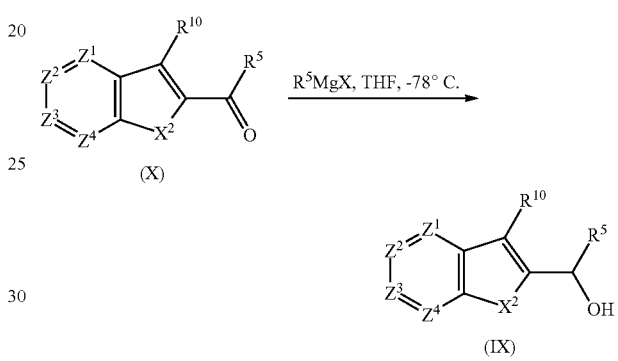

Compounds of formula (IXa), wherein $R^5$ is H, may be obtained, according to Scheme 17, from compounds of formula (X) by reduction of an aldehyde group. Typical reaction conditions consist in the use of tetrabutylammonium borohydride (nBu$_4$NBH$_4$), as a reducing agent, in THF as solvent.

Scheme 17

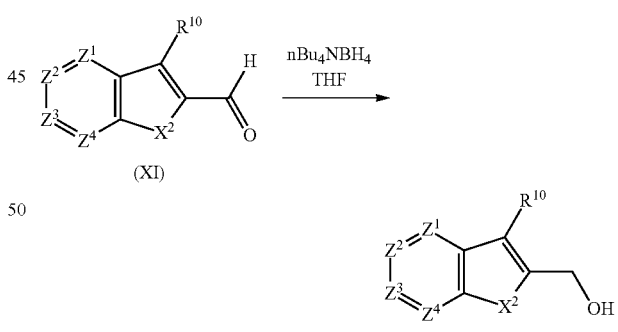

Methods of Separation

In the methods of preparing Formula I compounds, it may be advantageous to separate reaction products from one another and/or from starting materials. The desired products of each step or series of steps is separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like. Selection of appropriate methods of separation depends on the nature of the materials involved, such as, boiling point and molecular weight in distillation and sublimation, presence or absence of polar functional groups in chromatography, stability of materials in acidic and basic media in multiphase extraction, and the like.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. J. Org. Chem. (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

EXAMPLES

The chemical reactions described in the Examples may be readily adapted to prepare a number of other PI3K inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting reactive functional groups, by utilizing other suitable reagents known in the art other than those described, and/or by making routine modifications of reaction conditions. Alternatively, other reactions disclosed herein or known in the art will be recognized as having applicability for preparing other compounds of the invention.

$^1$H NMR spectra were recorded at ambient temperature using an NMR spectrometer, including a Varian Unity Inova (400 MHz) spectrometer with a triple resonance 5 mm probe. Chemical shifts are expressed in ppm relative to tetramethylsilane. The following abbreviations have been used: br=broad signal, s=singlet, d=doublet, dd=double doublet, t=triplet, q=quartet, m=multiplet.

High Pressure Liquid Chromatography/Mass Spectrometry (LCMS) experiments to determine retention times ($R_T$) and associated mass ions may be performed. The spectrometers may have an electrospray source operating in positive and negative ion mode. Additional detection is achieved using a evaporative light scattering detector.

Chiral SFC (supercritical fluid chromatography) may be used to separate enantiomers (Liu et al (2003) Chromatographia 58(11/12):775-779).

Microwave experiments were carried out using a CEM Explorer, Smith Synthesizer or a Biotage Initiator™, which uses a single-mode resonator and dynamic field tuning, both of which give reproducibility and control. Temperatures from 40-250° C. can be achieved and pressures of up to 20 bar can be reached.

Unless otherwise stated, all reactions were performed under an inert, i.e. argon or nitrogen, atmosphere.

The enantiomeric purity of the final compounds was assessed using three methods: Method A, Method B and Method C.

Method A involved the derivatisation of a sample of the precursor amine with a chiral aryl fluoride, (S)-2-(5-fluoro-2,4-dinitrophenylamino)propionamide, known as Marfey's Reagent. The % de of the resulting adduct was calculated by integration of the peak areas (identified by the mass spectra) in the UV trace of the LCMS of the crude sample. No erosion of chirality was observed upon $S_NAr$ reaction of the intermediate amine with a variety of hinge binder heteroaromatic chlorides as measured by chiral HPLC of the final compounds.

Method B measured the % ee of a number of final compounds by chiral HPLC (Chiral AGP 5 μm 150 mm×4.0 mm Column 426, T=35° C.; run time 40 min; isocratic–solvent=98% Water 2% Methanol 0.1% Formic Acid).

Method C measured the % ee of a number of final compounds by chiral SFC (Berger Analytical SFC with a Waters ZQ mass spectrometer. Column dimensions: 4.6 mm×50 mm, 3 micron. Columns screened: Chiralpak AD, Chiralpak IC, Chiralpak AS, Chiralcel OJ, Lux Cellulose-1, Lux Cellulose-4; Flow rate: 5 mL/min Mobile phase A: $CO_2$; Mobile phase B: Methanol (0.1% $NH_4OH$), ethanol (0.1% $NH_4OH$) or isopropanol (0.1% $NH_4OH$). Gradient: 10-65% in 1.8 minutes, hold for 0.7 minutes. UV: 254 nm Method D involved the derivatisation of samples of the precursor amine with both (R)- and (S)-methoxyphenylacetic acids. The % de values of the resulting amides were calculated by integration of the peak areas (identified by the mass spectra) in the UV trace of the LCMS of the sample.

Abbreviations

AcOH: Acetic acid; BINAP: 2,2'-Bis(diphenylphosphino)-1,1'-binaphthalene; $CH_3CN$: Acetonitrile; $Cs_2CO_3$: Cesium carbonate; CuI: Copper iodide; DBU: 1,8-Diazabicyclo[5.4.0]undec-7-ene; DCE; Dichloroethane; DIBAL-H: Diisobutylaluminum hydride; DCM: Dichloromethane; DIPEA: Diisopropylethylamine; DMAP: 4-Dimethylaminopyridine; DME: Dimethoxyethane; DMF: Dimethylformamide; DMSO: Dimethylsulfoxide; EDCl: 1-Ethyl-3-(3'-dimethylaminopropyl)carbodiimide; EtOAc: Ethyl acetate; $Et_3N$: Triethylamine; h or hr: Hour(s); HATU: (2-(7-Aza-1H-benzotriazole-1-yl)-1,1,3,3-tetramethyluronium hexafluorophosphate); HCl: Hydrochloric acid; $HCO_2H$: Formic acid; HOAt: 1-Hydroxy-7-azabenzotriazole; HOBt: Hydroxybenzotriazole; HM-N: Isolute® HM-N is a modified form of diatomaceous earth that can efficiently absorb aqueous samples; HPLC: High-performance liquid chromatography; IMS: Industrial methylated spirits; LCMS: Liquid chromatography mass spectrometry; LiHMDS: Lithium bis(trimethylsilyl)amide; M: Molar; min: Minute(s); mL: Milliliter; mCPBA: 3-Chloroperbenzoic acid; MeOH: Methanol; $MgSO_4$: Magnesium sulphate; $NaHCO_3$: Sodium bicarbonate; NaOH: Sodium hydroxide; $Na_2SO_4$: Sodium sulphate; NBS: N-Bromosuccinimide; $NH_3$: Ammonia; $NH_4Cl$: Ammonium chloride; NMP: N-methylpyrrolidone; NMR: Nuclear magnetic resonance; Pd/C: Palladium on carbon; $Pd_2dba_3$: Tris(dibenzylideneacetone)dipalladium(0); $Pd(OAc)_2$: Palladium(II) acetate; $Pd(PPh_3)_4$: Tetrakis(triphenylphosphine)palladium(0); $PdCl_2\{P^tBu_2(Ph\text{-}p\text{-}NMe_2)\}_2$: Bis(di-tert-butyl(4-dimethylaminophenyl)phosphine) dichloropalladium(II); PTFE: Polytetrafluoro ethylene; $PtO_2$: Platinum Oxide; RT: Room temperature; Si—PPC: Pre-packed silica flash chromatography cartridge: Isolute® SPE, Biotage SNAP® or ISCORedisep®; SCX-2 cartridge: Strong cation exchange cartridge; TBME: Tertbutyl methyl ether; TFA: Trifluoroacetic acid; THF: Tetrahydrofuran; Xantphos: 9,9-Dimethyl-4,5-bis(diphenylphosphino)xanthene Example 1

(S)-1-(7-Methyl-1-phenyl-1H-benzoimidazol-2-yl)ethylamine

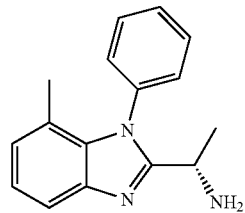 [SMILES: Cc1cccc2nc([C@H](C)N)n(-c3ccccc3)c12]

Step 1: (2-Methyl-6-nitrophenyl)phenylamine

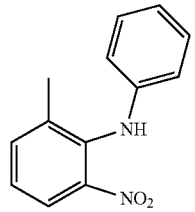

A mixture of 2-bromo-1-methyl-3-nitrobenzene (1.0 g, 4.63 mmol), phenylamine (506 μL, 5.56 mmol), $Cs_2CO_3$ (2.11 g, 6.48 mmol) and (R)-BINAP (5 mol %, 143 mg, 0.23 mmol) in toluene (10 mL) was degassed with a stream of nitrogen prior to addition of $Pd(OAc)_2$ (25 mg, 0.11 mmol) and was stirred at 110° C. under a nitrogen atmosphere for 20 h. After cooling to RT, the mixture was partitioned between EtOAc and water. The organic layer was washed with brine, then dried ($Na_2SO_4$) and concentrated in vacuo. The resulting residue was purified by column chromatography (Si—PCC, gradient 0-35% DCM in cyclohexane) affording (2-Methyl-6-nitrophenyl)phenylamine as a red solid (981 mg, 93%). LCMS: $R_T$ 3.88 min [M+H]$^+$ 229.1

Step 2: 3-Methyl-$N^2$-phenylbenzene-1,2-diamine

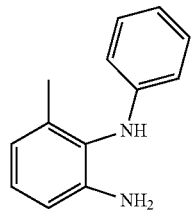 [SMILES: Cc1cccc([N+](=O)[O-])c1Nc1ccccc1]

A mixture of (2-methyl-6-nitrophenyl)phenylamine (981 mg, 4.3 mmol) and 10% Pd/C (981 mg) in EtOAc (20 mL) was degassed with a stream of nitrogen and then stirred at RT under a hydrogen atmosphere for 4 h. The suspension was then filtered through a PTFE frit and the filtrate was concentrated in vacuo affording 3-Methyl-$N^2$-phenylbenzene-1,2-diamine as a yellow solid (852 mg, 100%). LCMS: $R_T$ 3.02 min $[M+H]^+$ 199.0

Step 3: [(S)-1-(7-Methyl-1-phenyl-1H-benzoimidazol-2-yl)ethyl]carbamic acid benzyl ester

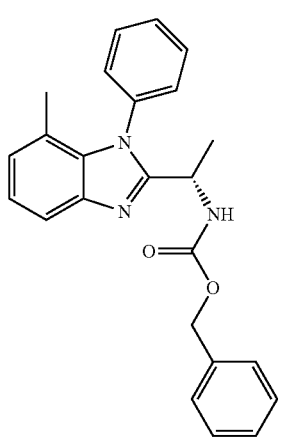 [SMILES: Cc1cccc2nc([C@H](C)NC(=O)OCc3ccccc3)n(-c3ccccc3)c12]

To a solution of 3-methyl-$N^2$-phenyl-benzene-1,2-diamine (852 mg, 4.3 mmol) in anhydrous DCM (20 mL) were added (S)-2-benzyloxycarbonylaminopropionic acid (1.44 g, 6.45 mmol), HOBt (639 mg, 4.73 mmol), 4-methylmorpholine (1.04 mL, 9.46 mmol) and N-(3-dimethylaminopropyl)-N'-ethylcarbodiimide hydrochloride (1.24 g, 6.45 mmol). The mixture was stirred at RT for 6.5 h and then partitioned between DCM (100 mL) and water. The organic layer was then washed with brine, dried (Na$_2$SO$_4$) and concentrated in vacuo. The resulting residue was dissolved in AcOH (10 mL) and heated to 65° C. for 18 h. After cooling to RT, volatiles were removed under reduced pressure and the residue diluted with EtOAc (100 mL). The organic layer was washed with a saturated solution of NaHCO$_3$, followed by brine, then dried (Na$_2$SO$_4$) and concentrated in vacuo affording [(S)-1-(7-Methyl-1-phenyl-1H-benzoimidazol-2-yl)ethyl]carbamic acid benzyl ester as brown foam (1.5 g, 90%). LCMS: $R_T$ 3.07 min $[M+H]^+$ 386.2.

Step 4

A mixture of [(S)-1-(7-methyl-1-phenyl-1H-benzoimidazol-2-yl)ethyl]carbamic acid benzyl ester (1.5 g, 3.89 mmol) and 10% Pd/C (150 mg) in IMS (25 mL) was degassed with a stream of nitrogen and, after addition of HCl (1M, 2.5 mL), was stirred at RT (room temperature) under a hydrogen atmosphere for 5.5 h. The suspension was then filtered through a pad of Celite® and the filtrate was concentrated in vacuo. The resulting residue was partitioned between DCM (dichloromethane) and water, the organic layer was then washed with a saturated solution of NaHCO$_3$, dried (Na$_2$SO$_4$) and concentrated in vacuo affording (S)-1-(7-Methyl-1-phenyl-1H-benzoimidazol-2-yl)ethylamine as a brown solid (1.41 g, 96%). LCMS: $R_T$ 2.07 min $[M-NH_2]^1$ 235.1

Example 2

(R)-1-(4-Methyl-1-phenyl-1H-benzoimidazol-2-yl)ethylamine

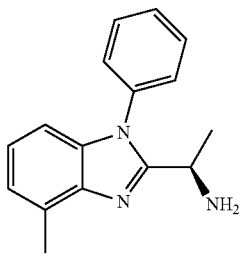 [SMILES: Cc1cccc2c1nc([C@@H](C)N)n2-c1ccccc1]

Step 1: (3-Methyl-2-nitrophenyl)phenylamine

A mixture of 1-bromo-3-methyl-2-nitrobenzene (1 g, 4.63 mmol), phenylamine (422 µL, 4.63 mmol), Cs$_2$CO$_3$ (2.11 g, 6.48 mmol) and (R)-BINAP (5 mol %, 143 mg, 0.23 mmol) in toluene (20 mL) was degassed with a stream of nitrogen prior to addition of Pd(OAc)$_2$ (25 mg, 0.11 mmol) and was stirred at 110° C. under a nitrogen atmosphere for 18 h. After cooling to RT, the mixture was partitioned between EtOAc and water. The organic layer was washed with brine, then dried (Na$_2$SO$_4$) and concentrated in vacuo. The resulting residue was purified by column chromatography (Si—PCC, gradient 0-35% DCM in cyclohexane) affording (3-Methyl-2-nitrophenyl)phenylamine as a red oil (931 mg, 88%). LCMS: $R_T$ 3.97 min $[M+H]^+$ 229.1.

Step 2: 3-M ethyl-$N^1$-phenylbenzene-1,2-diamine

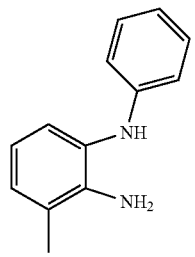

A mixture of (3-methyl-2-nitrophenyl)phenylamine (931 mg, 4.08 mmol) and 10% Pd/C (465 mg) in EtOAc (20 mL)

was degassed with a stream of nitrogen and stirred at RT under a hydrogen atmosphere for 4 h. The suspension was then filtered through a PTFE frit and the filtrate was concentrated in vacuo affording 3-Methyl-$N^1$-phenylbenzene-1,2-diamine as an off-white solid (763 mg, 94%). LCMS: $R_T$ 3.37 min $[M+H]^+$ 199.0.

Step 3: [(R)-1-(4-Methyl-1-phenyl-1H-benzoimidazol-2-yl)ethyl]carbamic acid tertbutyl ester

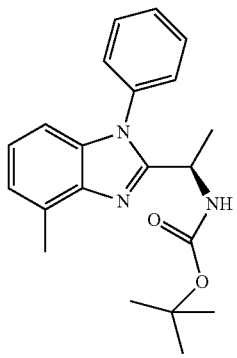 [SMILES: Cc1cccc2c1nc([C@@H](C)NC(=O)OC(C)(C)C)n2-c1ccccc1]

To a solution of 3-methyl-$N^1$-phenylbenzene-1,2-diamine (381 mg, 1.92 mmol) in anhydrous DCM (10 mL) were added (R)-2-tertbutoxycarbonylaminopropionic acid (399 mg, 2.11 mmol), HOBt (285 mg, 2.11 mmol), 4-methylmorpholine (464 µL, 4.22 mmol) and N-(3-dimethylaminopropyl)-N'-ethylcarbodiimide hydrochloride (404 mg, 2.11 mmol) and the mixture was stirred at RT for 2 h. After this period of time, additional amounts of (R)-2-tertbutoxycarbonylaminopropionic acid (145 mg, 0.77 mmol) and of N-(3-dimethylaminopropyl)-N'-ethylcarbodiimide hydrochloride (148 mg, 0.77 mmol) were added. Stirring was continued for 20 h and then additional amounts (R)-2-tertbutoxycarbonylaminopropionic acid (545 mg, 2.88 mmol), HOBt (285 mg, 2.11 mmol), 4-methylmorpholine (464 µL, 4.22 mmol) and N-(3-dimethylaminopropyl)-N'-ethylcarbodiimide hydrochloride (553 mg, 2.88 mmol) were added. Stirring was continued for 24 h and then the crude mixture was purified by column chromatography (Si—PCC, gradient 0-40% EtOAc in cyclohexane) affording [(R)-1-(2-methyl-6-phenylaminophenylcarbamoyl)ethyl]carbamic acid tertbutyl ester as an orange oil (456 mg, 64%). LCMS: $R_T$ 3.69 min $[M+H]^+$ 370.2

A solution of the product thus obtained (456 mg) in AcOH (5 mL) was heated to 70° C. for 2 h and 45 min then allowed to cool to RT and left standing for 18 h at RT. Volatiles were removed in vacuo and the residue was dissolved EtOAc (75 mL), washed with a saturated solution of NaHCO$_3$, then dried (Na$_2$SO$_4$) and concentrated in vacuo affording [(R)-1-(4-Methyl-1-phenyl-1H-benzoimidazol-2-yl)ethyl]carbamic acid tertbutyl ester (404 mg, 60%). LCMS: $R_T$ 3.11 min $[M+H]^+$ 352.2.

Step 4

To a solution of [(R)-1-(4-methyl-1-phenyl-1H-benzoimidazol-2-yl)ethyl]carbamic acid tertbutyl ester (404 mg, 1.15 mmol) in DCM (5 mL) was added TFA (1 mL) and the mixture was stirred at RT for 3 h. Additional TFA (0.5 mL) was added and stirring was continued for 30 min. Volatiles were then removed under reduced pressure and the residue was dissolved in a small amount of DCM and loaded onto an SCX-2 cartridge. The cartridge was initially washed with 10% MeOH in DCM and the product was eluted with 2M NH$_3$/MeOH affording (R)-1-(4-Methyl-1-phenyl-1H-benzoimidazol-2-yl)ethylamine as a brown solid (273 mg, 94%). LCMS: $R_T$ 2.14 $[M-NH_2]^+$ 235.1

Example 3

(S)-1-(4-Methyl-1-phenyl-1H-benzoimidazol-2-yl)ethylamine

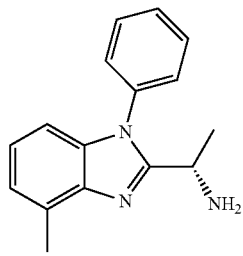 [SMILES: Cc1cccc2c1nc([C@H](C)N)n2-c1ccccc1]

Step 1: [(S)-1-(4-Methyl-1-phenyl-1H-benzoimidazol-2-yl)ethyl]carbamic acid tertbutyl ester

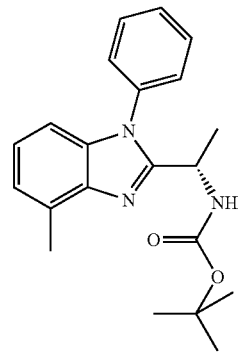 [SMILES: Cc1cccc2c1nc([C@H](C)NC(=O)OC(C)(C)C)n2-c1ccccc1]

To a solution of 3-methyl-$N^1$-phenylbenzene-1,2-diamine (381 mg, 1.92 mmol) in anhydrous DCM (10 mL) were added (S)-2-tertbutoxycarbonylaminopropionic acid (399 mg, 2.11 mmol), HOBt (285 mg, 2.11 mmol), 4-methylmorpholine (464 µL, 4.22 mmol) and N-(3-dimethylaminopropyl)-N'-ethylcarbodiimide hydrochloride (405 mg, 2.11 mmol). The mixture was stirred at RT for 2 h then additional amounts of (S)-2-tertbutoxycarbonylaminopropionic acid (145 mg, 0.77 mmol) and of N-(3-dimethylaminopropyl)-N'-ethylcarbodiimide hydrochloride (148 mg, 0.77 mmol) were added. Stirring was continued for 18 h and then additional amounts of (S)-2-tertbutoxycarbonylaminopropionic acid (545 mg, 2.88 mmol), HOBt (285 mg, 2.11 mmol), 4-methylmorpholine (464 µL, 4.22 mmol) and of N-(3-dimethylaminopropyl)-N'-ethylcarbodiimide hydrochloride (553 mg, 2.88 mmol) were added. Stirring was continued for 24 h and then the crude mixture was purified by column chromatography (Si—PCC, gradient 0-40% EtOAc in cyclohexane) affording [(S)-1-(2-methyl-6-phenylaminophenylcarbamoyl)ethyl]carbamic acid tertbutyl ester as an orange oil (395 mg, 56%). LCMS: $R_T$ 3.69 min $[M+H]^+$ 370.2.

A solution of the product thus obtained (395 mg) in AcOH (10 mL) was heated to 70° C. for 2 h and 45 min. After cooling to RT, volatiles were removed under reduced pressure and the residue was dissolved in EtOAc (75 mL) and washed with a saturated solution of NaHCO$_3$, then dried (Na$_2$SO$_4$) and concentrated in vacuo affording [(S)-1-(4-Methyl-1-phenyl-1H-benzoimidazol-2-yl)ethyl]carbamic acid tertbutyl ester (380 mg, 56%). LCMS: $R_T$ 3.15 min [M+H]$^+$ 352.2.

Step 2

To a solution of [(S)-1-(4-methyl-1-phenyl-1H-benzoimidazol-2-yl)ethyl]carbamic acid tertbutyl ester (380 mg, 1.08 mmol) in DCM (5 mL) was added TFA (1 mL) and the mixture was stirred at RT for 3 h. Additional TFA (0.5 mL) was added and stirring was continued for 30 min. Volatiles were then removed under reduced pressure and the residue was then dissolved in a small amount of DCM and loaded onto an SCX-2 cartridge which was initially washed with 10% MeOH in DCM. The product was eluted with 2M NH$_3$/MeOH affording (S)-1-(4-Methyl-1-phenyl-1H-benzoimidazol-2-yl)ethylamine as a brown solid (222 mg, 82%). LCMS: $R_T$ 2.16 [M-NH$_2$]$^+$ 235.1

Example 4

1-(1-phenyl-1H-benzo[d]imidazol-2-yl)ethanamine

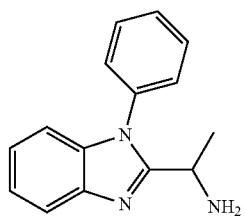 [SMILES: CC(N)c1nc2ccccc2n1-c1ccccc1]

Step 1:
[1-(2-Phenylaminophenylcarbamoyl)ethyl]carbamic acid tertbutyl ester

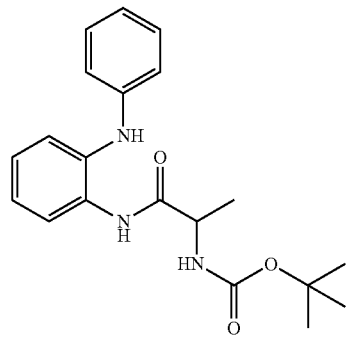 [SMILES: CC(NC(=O)OC(C)(C)C)C(=O)Nc1ccccc1Nc1ccccc1]

N-Phenylbenzene-1,2-diamine (1.84 g, 0.01 mol), racemic (R/S)-2-tertbutoxycarbonylaminopropionic acid (1.89 g, 0.01 mol), N-(3-dimethylaminopropyl)-N'-ethylcarbodiimide hydrochloride (1.92 g), 4-methylmorpholine (1.0 g, 0.01 mol), HOBt (1.53 g, 0.01 mol) were suspended in THF (10 mL) under a nitrogen atmosphere. The resulting mixture was stirred for 12 h at RT. After this period of time, additional amounts of N-(3-dimethylaminopropyl)-N'-ethylcarbodiimide hydrochloride (500 mg×3) and of (R/S)-2-tertbutoxycarbonylaminopropionic acid (500 mg) were added and the mixture was stirred for further 4 h. The reaction mixture was then partitioned between water and EtOAc. The organic layer was separated, dried (MgSO$_4$) and concentrated in vacuo and the resulting residue was purified by column chromatography (Si—PCC ISCO 24 g column, gradient 0-20% EtOAc in cyclohexane). The product containing fractions were combined and concentrated in vacuo affording [1-(2-Phenylaminophenylcarbamoyl)ethyl]carbamic acid tertbutyl ester as a white crystalline solid (3.07 g, 86%). LCMS: $R_T$ 3.61 min [M+H-$^t$Bu]$^+$ 300.1.

Step 2

[1-(2-Phenylaminophenylcarbamoyl)ethyl]carbamic acid tertbutyl ester (400 mg, 1.59 mmol) was suspended in AcOH (4 mL) and the resulting mixture was heated at 80° C. for 12 h whereupon the mixture clarified. The cooled solution was diluted with toluene and volatiles removed under reduced pressure. The resulting residue was stirred with TFA (4 mL) for 2 h and the resulting solution was loaded onto an SCX-2 cartridge which was initially washed with MeOH. The product was eluted with 2M NH$_3$/MeOH and further purified by column chromatography (Si—PCC, gradient 0-6% MeOH in DCM) affording 1-(1-phenyl-1H-benzo[d]imidazol-2-yl)ethanamine as a white crystalline solid (211 mg, 80%). LCMS: $R_T$ 0.27 min [M–NH$_2$]$^+$ 221.1. The enantiomers, (S)-1-(1-phenyl-1H-benzo[d]imidazol-2-yl)ethanamine and (R)-1-(1-phenyl-1H-benzo[d]imidazol-2-yl)ethanamine can be resolved and separated. Alternatively, (S)-1-(1-phenyl-1H-benzo[d]imidazol-2-yl)ethanamine can be prepared from enantiopure (S)-2-tertbutoxycarbonylaminopropionic acid.

Example 5

2-Bromomethyl-1-phenyl-1H-benzoimidazole

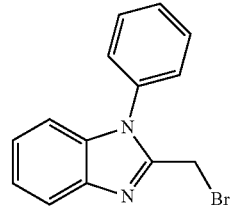 [SMILES: BrCc1nc2ccccc2n1-c1ccccc1]

To a stirred solution of (1-phenyl-1H-benzoimidazol-2-yl)methanol (240 mg, 1.02 mmol) and triphenylphosphine (295 mg, 1.12 mmol) in DCM (10 mL) was added NBS (200 mg, 1.12 mmol) and the mixture was stirred at RT for 3 h. Volatiles were evaporated under reduced pressure and the residue was purified by column chromatography (Si—PCC, gradient 0-5% MeOH in DCM) affording 2-Bromomethyl-1-phenyl- 1H-benzoimidazole as a colourless oil (0.636 g, quantitative yield). LCMS: $R_T$ 3.31 min [M+H]$^+$ 386.8/388.8

Example 6

4-[2-((S)-1-Aminoethyl)benzoimidazol-1-yl]piperidine-1-carboxylic acid tertbutyl ester

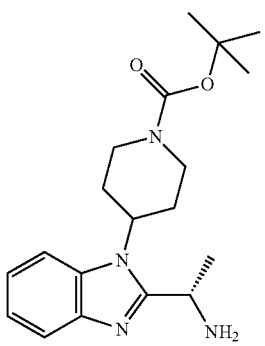 [SMILES: C[C@H](N)c1nc2ccccc2n1C1CCN(C(=O)OC(C)(C)C)CC1]

Step 1: 4-[2-((S)-1-Benzyloxycarbonylaminoethyl)benzoimidazol-1-yl]piperidine-1-carboxylic acid tertbutyl ester

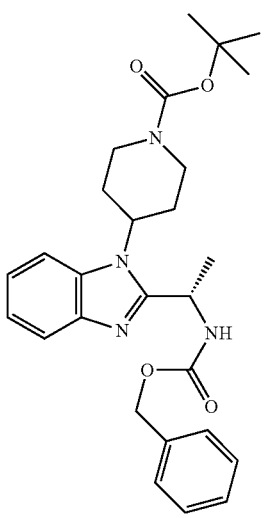 [SMILES: C[C@H](NC(=O)OCc1ccccc1)c1nc2ccccc2n1C1CCN(C(=O)OC(C)(C)C)CC1]

A mixture of (S)-2-benzyloxycarbonylaminopropionic acid (230 mg, 1.03 mmol), 4-(2-aminophenylamino)piperidine-1-carboxylic acid tertbutyl ester (200 mg, 0.686 mmol), HOBt (102 mg, 0.755 mmol), 4-methylmorpholine (166 μL, 1.51 mmol) and N-(3-dimethylaminopropyl)-N'-ethylcarbodiimide hydrochloride (197 mg, 1.03 mmol) in DCM (7 mL) was stirred at RT for 3 h. The reaction mixture was then diluted with additional DCM and the organic layer was washed with water, then dried and concentrated in vacuo affording 4-[2-((S)-2-benzyloxycarbonylaminopropionylamino)phenylamino]piperidine-1-carboxylic acid tertbutyl ester as a purple/brown oil (436 mg, quantitative). LCMS: $R_T$ 3.66 min [M+H]$^+$ 497.2.

A solution of the compound thus obtained (0.686 mmol) in AcOH (5 mL) was stirred for 18 h at 60° C. After cooling to RT, volatiles were evaporated under reduced pressure and the residue was partitioned between EtOAc and a saturated solution of NaHCO$_3$. The organic layer was washed with brine, dried (Na$_2$SO$_4$) and then concentrated in vacuo. The resulting residue was purified by column chromatography (Si—PCC, gradient 0-100% EtOAc in cyclohexane) affording 4-[2-((S)-1-Benzyloxycarbonylaminoethyl)benzoimidazol-1-yl]piperidine-1-carboxylic acid tertbutyl ester as a pale orange oil (308 mg, 94% over two steps). LCMS: $R_T$ 3.06 min [M+H]$^+$ 479.1.

Step 2

To a nitrogen purged solution of 4-[2-((S)-1-benzyloxycarbonylaminoethyl)benzoimidazol-1-yl]piperidine-1-carboxylic acid tertbutyl ester (308 mg, 0.644 mmol) in IMS (10 mL) was added 10% Pd/C (32 mg) and the reaction mixture was stirred at RT under a hydrogen atmosphere for 2 h. Additional quantities of 10% Pd/C were subsequently added (41 mg after 2 h and 33 mg after 4 h) and the reaction mixture was stirred at RT under a hydrogen atmosphere for 17 h. The suspension was filtered through a PTFE frit and washed with additional IMS. The filtrate was concentrated in vacuo affording 4-[2-((S)-1-Aminoethyl)benzoimidazol-1-yl]piperidine-1-carboxylic acid tertbutyl ester as a pale yellow oil (202 mg). LCMS: $R_T$ 2.34 min [M+H]$^+$ 345.2

Example 7

(S)-1-(7-Fluoro-1-phenyl-1H-benzoimidazol-2-yl)ethylamine (S)-1-(7-Fluoro-1-phenyl-1H-benzoimidazol-2-yl)ethylamine

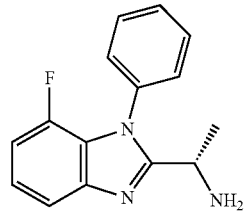 [SMILES: C[C@H](N)c1nc2cccc(F)c2n1-c1ccccc1]

Step 1: (2-Fluoro-6-nitrophenyl)phenylamine

A mixture of 1,2-difluoro-3-nitrobenzene (690 μL, 6.29 mmol), phenylamine (600 μL, 6.60 mmol) and potassium carbonate (1.74 g, 12.57 mmol) in DMSO (3 mL) was stirred at RT for 3 h and then heated to 90° C. for 4 h. After cooling to RT, the reaction mixture was partitioned between EtOAc and water. The organic layer was then washed with brine, dried (Na$_2$SO$_4$) and concentrated in vacuo and the resulting residue was purified by column chromatography (Si—PCC, gradient 0-20% EtOAc in cyclohexane) followed by (Si—PCC, gradient 0-50% DCM in cyclohexane) affording (2-Fluoro-6-nitrophenyl)phenylamine as a orange/red oil (563 mg, 39%). $^1$H NMR (CDCl$_3$, 400 MHz): δ 8.70 (1H, s), 8.00 (1H, d, J=8.66 Hz), 7.36-7.23 (3H, m), 7.09 (1H, t, J=7.41 Hz), 7.03-6.89 (3H, m).

Step 2: 3-Fluoro-N$^2$-phenylbenzene-1,2-diamine

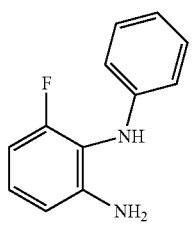

A mixture of (2-fluoro-6-nitrophenyl)phenylamine (558 mg, 6.57 mmol) and 10% Pd/C (115 mg) in IMS (20 mL) was degassed with a stream of nitrogen and stirred at RT under a hydrogen atmosphere for 2 h. The suspension was then filtered through a PTFE frit and the filtrate was concentrated in vacuo affording 3-Fluoro-N$^2$-phenylbenzene-1,2-diamine as a white solid (468 mg, 96%). $^1$H NMR (CDCl$_3$, 400 MHz): δ 7.24-7.16 (2H, m), 7.04-6.96 (1H, m), 6.83 (1H, t, J=7.37 Hz), 6.66 (2H, d, J=7.95 Hz), 6.59-6.48 (2H, m), 5.16 (1H, bs), 3.96 (2H, s).

Step 3: [(S)-1-(7-Fluoro-1-phenyl-1H-benzoimidazol-2-yl)ethyl]carbamic acid tertbutyl ester

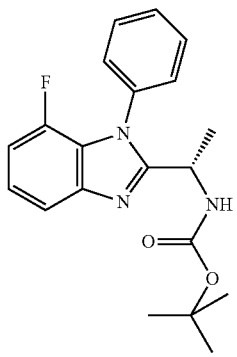

A mixture of (S)-2-tertbutoxycarbonylaminopropionic acid (480 mg, 2.53 mmol), 3-fluoro-N$^2$-phenylbenzene-1,2-diamine (466 mg, 2.30 mmol), HOAt (345 mg, 2.53 mmol), 4-methylmorpholine (560 μL, 5.07 mmol) and N-(3-dimethylaminopropyl)-N'-ethylcarbodiimide hydrochloride (486 mg, 2.53 mmol) in DCM (15 mL) was stirred at RT for 2 h. The reaction mixture was then partitioned between additional DCM and an aqueous solution of NaHCO$_3$. The organic layer was dried and concentrated in vacuo and the resulting residue (1.0 g) was dissolved in AcOH (20 mL) and stirred for 18 h at 70° C. After cooling to RT, volatiles were evaporated under reduced pressure and the residue was partitioned between EtOAc and a saturated solution of NaHCO$_3$. The organic layer was washed with water, followed by brine, then dried (Na$_2$SO$_4$) and concentrated in vacuo. The resulting residue was purified by column chromatography (Si—PCC, gradient 0-30% EtOAc in DCM) affording [(S)-1-(7-Fluoro-1-phenyl-1H-benzoimidazol-2-yl)ethyl]carbamic acid tertbutyl ester as a yellow/orange oil (631 mg, 77%). LCMS: R$_T$ 3.64 min [M+H]$^+$ 356.0.

Step 4

To a solution of [(S)-1-(7-fluoro-1-phenyl-1H-benzoimidazol-2-yl)ethyl]carbamic acid tertbutyl ester (625 mg) in DCM (3 mL) was added TFA (3 mL) and the resulting mixture was stirred at RT for 3 h. The crude reaction mixture was loaded onto an Isolute® SCX-2 cartridge. The cartridge was washed with MeOH and the product eluted with 2M NH$_3$/MeOH. The product containing fractions were combined and concentrated in vacuo affording (S)-1-(7-Fluoro-1-phenyl-1H-benzoimidazol-2-yl)ethylamine as a pale orange oil (372 mg, 83%). LCMS: R$_T$ 1.97 and 2.11 min [M+H]$^+$ 255.9.

Example 8

(S)-1-(6-Fluoro-1-phenyl-1H-benzoimidazol-2-yl)ethylamine

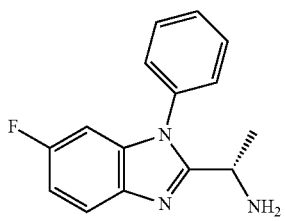 [SMILES: C[C@H](N)c1nc2ccc(F)cc2n1-c1ccccc1]

Step 1: (5-Fluoro-2-nitrophenyl)phenylamine

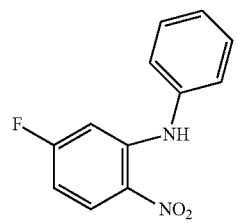 [SMILES: O=[N+]([O-])c1ccc(F)cc1Nc1ccccc1]

LiHMDS (1.0M in THF, 12.57 mL) was added dropwise to a stirred solution of phenylamine (600 μL, 6.60 mmol) in ahydrous THF (10 mL) under a nitrogen atmosphere at −78° C. After 30 min, a solution of 2,4-difluoro-1-nitrobenzene (690 μL, 6.29 mmol) in THF (10 mL) was added and stirring was continued for 1 h. The solution was poured into an aqueous solution of NH$_4$Cl (100 mL) and extracted with EtOAc (×3). The combined organic layers were dried and concentrated in vacuo and the resulting residue was purified by column chromatography (Si—PCC, gradient 0-30% EtOAc in cyclohexane) affording (5-Fluoro-2-nitrophenyl)phenylamine as a yellow/orange solid (1.37 g, 94%). $^1$H NMR (CDCl$_3$, 400 MHz): δ 9.66 (1H, s), 8.28 (1H, dd, J=9.48, 6.01

Hz), 7.47 (2H, t, J=7.63 Hz), 7.36-7.24 (3H, m), 6.82 (1H, dd, J=11.38, 2.61 Hz), 6.53-6.44 (1H, m).

Step 2: 4-Fluoro-N²-phenylbenzene-1,2-diamine

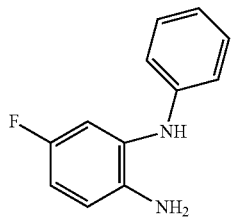

A mixture of (5-fluoro-2-nitrophenyl)phenylamine (1.37 g, 5.90 mmol) in IMS (50 mL) and EtOAc (50 mL) was degassed with a stream of nitrogen prior to addition of 10% Pd/C (138 mg) and was stirred at RT under a hydrogen atmosphere for 4 h. The suspension was then filtered through a PTFE frit and the filtrate was concentrated in vacuo affording 4-Fluoro-N²-phenylbenzene-1,2-diamine as a red oil (1.19 g, quantitative). LCMS: $R_T$ 2.87 min [M+H]⁺ 203.1.

Step 3: [(S)-1-(6-Fluoro-1-phenyl-1H-benzoimidazol-2-yl)ethyl]carbamic acid tertbutyl ester

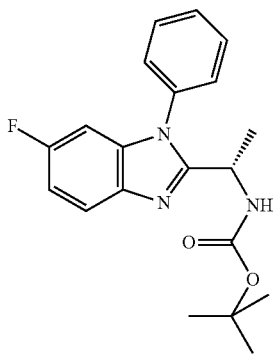 [SMILES: C[C@H](NC(=O)OC(C)(C)C)c1nc2ccc(F)cc2n1-c1ccccc1]

A mixture of 4-fluoro-N²-phenylbenzene-1,2-diamine (1.19 g, 5.88 mmol), (S)-2-tertbutoxycarbonylaminopropionic acid (1.22 g, 6.47 mmol), HOAt (881 mg, 6.47 mmol), 4-methylmorpholine (1.42 mL, 12.95 mmol) and N-(3-dimethylaminopropyl)-N'-ethylcarbodiimide hydrochloride (1.24 g, 6.47 mmol) in DCM (30 mL) was stirred at RT for 21 h. The reaction mixture was then partitioned between additional DCM and an aqueous solution of NaHCO₃. The organic layer was dried and concentrated in vacuo and the resulting residue (2.40 g) was dissolved in AcOH (50 mL) and stirred for 48 h at 60° C. After cooling to RT, volatiles were evaporated under reduced pressure and the residue was partitioned between EtOAc and a saturated solution of NaHCO₃. The organic layer was washed with brine, dried (Na₂SO₄) and then concentrated in vacuo. The resulting residue was purified by column chromatography (Si—PCC, gradient 0-50% EtOAc in DCM) affording [(S)-1-(6-Fluoro-1-phenyl-1H-benzoimidazol-2-yl)ethyl]carbamic acid tertbutyl ester as a yellow foam (1.20 g, 57%). LCMS: $R_T$ 3.50 min [M+H]⁺ 356.2

Step 4

To a solution of [(S)-1-(6-fluoro-1-phenyl-1H-benzoimidazol-2-yl)ethyl]carbamic acid tertbutyl ester (1.20 g, 3.38 mmol) in DCM (5 mL) was added TFA (5 mL) and the resulting mixture was stirred at RT for 1.5 h. The crude reaction mixture was loaded onto an Isolute® SCX-2 cartridge. The cartridge was washed with MeOH and the product eluted with 2M NH₃/MeOH. The product containing fractions were combined and concentrated in vacuo affording (S)-1-(6-Fluoro-1-phenyl-1H-benzoimidazol-2-yl)ethylamine as a yellow oil (861 mg, quantitative). LCMS: $R_T$ 1.97 and 2.19 min [M+H]⁺ 256.2

Example 9

(S)-1-(4-Chloro-1-phenyl-1H-benzoimidazol-2-yl)ethylamine

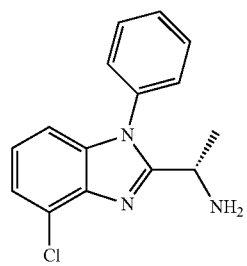

Step 1: (3-Chloro-2-nitrophenyl)phenylamine

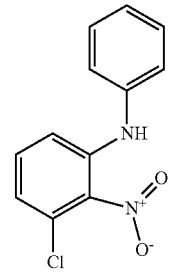 [SMILES: O=[N+]([O-])c1c(Cl)cccc1Nc1ccccc1]

LiHMDS (1.0M in THF, 23 mL) was added to a stirred solution of phenylamine (1.12 g, 12.0 mmol) in THF (15 mL) at −78° C. under a nitrogen atmosphere. Stirring was continued for 30 min then 1-chloro-3-fluoro-2-nitrobenzene (1.92 g, 10.9 mmol) in THF (15 mL) was added. The reaction mixture was stirred at −78° C. for 30 min, then slowly warmed to RT and stirred at RT for 2 h. The reaction mixture was poured into a saturated solution of NH₄Cl and then extracted with EtOAc (×2). The combined organic layers were washed with brine, then dried (Na₂SO₄) and concentrated in vacuo affording (3-Chloro-2-nitrophenyl)phenylamine as a dark brown oil (2.85 g, quantitative). $^1$H NMR (CDCl$_3$, 400 MHz): δ 7.41-7.25 (3H, m), 7.23-7.12 (5H, m), 6.96-6.91 (1H, m).

Step 2: 3-Chloro-N$^1$-phenylbenzene-1,2-diamine

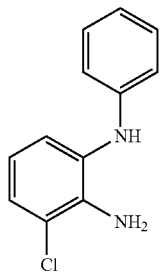 [SMILES: Nc1c(Cl)cccc1Nc1ccccc1]

To a mixture of (3-chloro-2-nitrophenyl)phenylamine (0.0109 mol) in MeOH (150 mL) and water (50 mL) were added NH$_4$Cl (3.51 g, 0.0656 mol) and iron powder (2.45 g, 0.0438 mol) and the reaction mixture was heated to reflux temperature for 3 h. After cooling to RT, the solid was filtered through a pad of Celite® and washed with additional MeOH. The filtrate was concentrated in vacuo and then partitioned between EtOAc and water. The aqueous phase was further extracted with EtOAc and the combined organic layers were washed with brine, then dried (Na$_2$SO$_4$) and concentrated in vacuo affording 3-Chloro-N$^1$-phenylbenzene-1,2-diamine as a light brown solid (2.61 g, quantitative). LCMS: R$_T$ 3.72 min [M+H]$^+$ 219.0

Step 3: [(S)-1-(2-Chloro-6-phenylaminophenylcarbamoyl)ethyl]carbamic acid tertbutyl ester

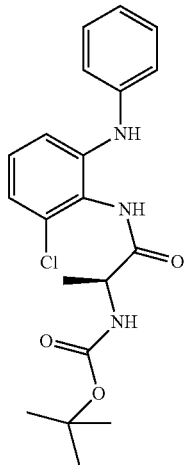 [SMILES: C[C@H](NC(=O)OC(C)(C)C)C(=O)Nc1c(Cl)cccc1Nc1ccccc1]

To a mixture of 3-chloro-N$^1$-phenylbenzene-1,2-diamine (1.72 g, 7.87 mmol), (S)-2-tertbutoxycarbonylaminopropionic acid (1.64 g, 8.65 mmol), HOAt (1.18 g, 8.65 mmol) and N-(3-dimethylaminopropyl)-N'-ethylcarbodiimide hydrochloride (1.66 g, 8.65 mmol) in DCM (40 mL) cooled to 0° C. under a nitrogen atmosphere was added Et$_3$N (3.3 mL, 0.0236 mol). The reaction mixture was stirred at 0° C. for 5 min, then slowly warmed to RT and stirring was continued for 16 h. The resulting mixture was partitioned between DCM and a saturated solution of NaHCO$_3$. The organic layer was washed with brine, then dried (Na$_2$SO$_4$) and concentrated in vacuo. The residue thus obtained was purified column chromatography (Si—PCC, gradient 0-2% 2M NH$_3$/MeOH in DCM) affording [(S)-1-(2-Chloro-6-phenylaminophenylcarbamoyl)ethyl]carbamic acid tertbutyl ester as an off-white solid (1.60 g, 52% over three steps). LCMS: R$_T$ 3.75 min [M+H]$^+$ 390.2.

Step 4: [(S)-1-(4-Chloro-1-phenyl-1H-benzoimidazol-2-yl)ethyl]carbamic acid tertbutyl ester

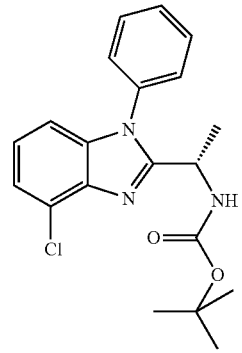 [SMILES: C[C@H](NC(=O)OC(C)(C)C)c1nc2c(Cl)cccc2n1-c1ccccc1]

A solution of [(S)-1-(2-chloro-6-phenylaminophenylcarbamoyl)ethyl]carbamic acid tertbutyl ester (1.58 g, 4.05 mmol) in AcOH (25 mL) was stirred for 18 h at 65° C. After cooling to RT, volatiles were evaporated under reduced pressure and the residue was partitioned between EtOAc and a saturated solution of NaHCO$_3$. The aqueous phase was further extracted with EtOAc and the combined organic layers were washed with brine, then dried (Na$_2$SO$_4$) and concentrated in vacuo. The resulting residue was purified by column chromatography (Si—PCC, gradient 0-2% 2M NH$_3$/MeOH in DCM) affording [(S)-1-(4-Chloro-1-phenyl-1H-benzoimidazol-2-yl)ethyl]carbamic acid tertbutyl ester as an off-white solid (1.41 g, 93%). LCMS: R$_T$ 3.90 min [M+H]$^+$ 372.2.

Step 5

To a solution of [(S)-1-(4-chloro-1-phenyl-1H-benzoimidazol-2-yl)ethyl]carbamic acid tertbutyl ester (1.40 g, 3.76 mmol) in DCM (20 mL) was added TFA (20 mL) and the resulting mixture was stirred at RT for 20 min. Volatiles were removed under reduced pressure and the resulting residue was partitioned between DCM and a saturated solution of NaHCO$_3$. The aqueous layer was further extracted with DCM and the combined organic layers were then dried (Na$_2$SO$_4$) and concentrated in vacuo. The resulting residue was purified by column chromatography (Si—PCC, gradient 0-8% 2M NH$_3$/MeOH in DCM) affording (S)-1-(4-Chloro-1-phenyl- 1H-benzoimidazol-2-yl)ethylamine as a white solid (680 mg, 67%). LCMS: $R_T$ 2.23 min [M+H]$^+$ 272.1

Example 10

(S)-1-(3-Phenyl-3H-imidazo[4,5-b]pyridin-2-yl)ethylamine

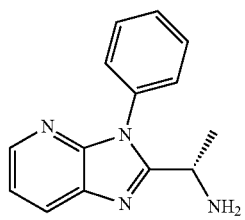

Step 1: (3-Nitropyridin-2-yl)phenylamine

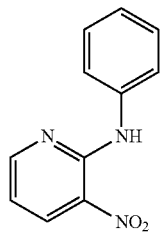

A mixture of 2-chloro-3-nitropyridine (3.49 g, 22.0 mmol), phenylamine (2 mL, 22.0 mmol) and Et$_3$N (3.1 mL, 22.0 mmol) in NMP (7 mL) was stirred at 100° C. for 1.5 h under a nitrogen atmosphere. Additional amounts of Et$_3$N (0.2 mL) and of phenylamine (0.1 mL) were added and the stirring was continued for further 30 min. The mixture was then partitioned between EtOAc and water. The aqueous phase was further extracted with EtOAc and the combined organic layers were washed with brine, then dried (Na$_2$SO$_4$) and concentrated in vacuo. The resulting residue was purified by column chromatography (Si—PCC, gradient 10-100% DCM in pentane) affording (3-Nitropyridin-2-yl)phenylamine as a red crystalline solid (2.49 g, 58%). LCMS: $R_T$ 3.53 min [M+H]$^+$ 216.0.

Step 2: N$^2$-Phenylpyridine-2,3-diamine

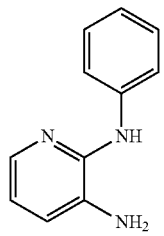

A mixture of (3-nitropyridin-2-yl)phenylamine (2.49 g, 0.0116 mol) and 10% Pd/C (40 mg) in EtOAc (100 mL) was degassed with a stream of nitrogen and then stirred at RT under a hydrogen atmosphere for 16 h. The suspension was then filtered through a pad of Celite® and then the filtrate was concentrated in vacuo affording N$^2$-Phenylpyridine-2,3-diamine as a white solid (2.06 g, 96%). LCMS: $R_T$ 1.15 min [M+H]$^+$ 186.0.

Step 3: [(S)-1-(3-Phenyl-3H-imidazo[4,5-b]pyridin-2-yl)ethyl]carbamic acid tertbutyl ester

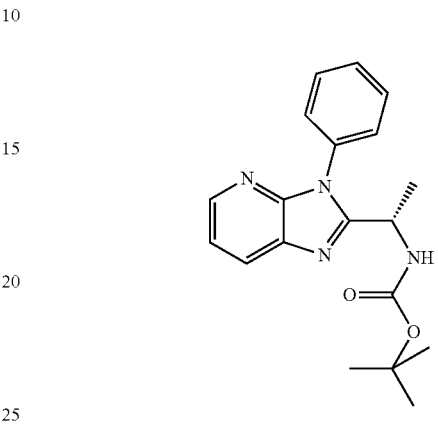

To a mixture of N$^2$-phenylpyridine-2,3-diamine (2.00 g, 0.011 mol), (S)-2-tertbutoxycarbonylaminopropionic acid (3.06 g, 0.0162 mol), HOBt (2.19 g, 0.0162 mol) and N-(3-dimethylaminopropyl)-N'-ethylcarbodiimide hydrochloride (3.10 g, 0.0162 mol) in DCM (80 mL) cooled to 0° C. under a nitrogen atmosphere was added Et$_3$N (4.5 mL, 0.0324 mol). The reaction mixture was stirred at 0° C. for 5 min, then slowly warmed to RT and stirring was continued for 20 h. The resulting mixture was partitioned between EtOAc and a saturated solution of NaHCO$_3$. The aqueous phase was further extracted with EtOAc and the combined organic layers were washed with brine, then dried (Na$_2$SO$_4$) and concentrated in vacuo. The residue thus obtained was purified column chromatography (Si—PCC, gradient 0-5% 2M NH$_3$/MeOH in DCM) affording [(S)-1-(2-phenylaminopyridin-3-ylcarbamoyl)ethyl]carbamic acid tertbutyl ester as a pale pink solid (2.05 g, 4.56 mmol). LCMS: $R_T$ 3.75 min [M+H]$^+$ 390.2

A solution of the compound thus obtained (4.56 mmol) in AcOH (8 mL) was stirred for 5 h at 65° C. After cooling to RT, volatiles were evaporated under reduced pressure and the residue was partitioned between DCM and a saturated solution of NaHCO$_3$. The aqueous phase was further extracted with DCM and the combined organic layers were washed with brine, dried (Na$_2$SO$_4$) and then concentrated in vacuo. The resulting residue was purified by column chromatography (Si—PCC, gradient 0-5% 2M NH$_3$/MeOH in DCM) affording [(S)-1-(3-Phenyl-3H-imidazo[4,5-b]pyridin-2-yl)ethyl]carbamic acid tertbutyl ester as a pink foam (1.78 g). LCMS: $R_T$ 3.02 min [M+H-$^t$Bu]$^+$ 283.1

Step 4

To a solution of [(S)-1-(3-phenyl-3H-imidazo[4,5-b]pyridin-2-yl)ethyl]carbamic acid tertbutyl ester (1.77 g) in DCM (4 mL) was added TFA (20 mL) and the resulting mixture was stirred at RT for 15 min. Volatiles were removed under reduced pressure and the resulting residue was partitioned between DCM and a saturated solution of NaHCO$_3$. The aqueous phase was further extracted with DCM and then the combined organic layers were dried (Na$_2$SO$_4$) and then concentrated in vacuo. The resulting residue was purified by column chromatography (Si—PCC, gradient 0-8% 2M NH₃/MeOH in DCM) affording (S)-1-(3-Phenyl-3H-imidazo[4,5-b]pyridin-2-yl)ethylamine as colourless gum (540 mg, 20% over three steps). LCMS: $R_T$ 1.65 min [M–NH₂]⁺ 222.0.

Example 11

2-((S)-1-Aminoethyl)-3-phenyl-3H-benzoimidazole-5-carbonitrile

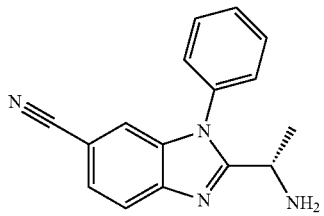 [SMILES: C[C@H](N)c1nc2ccc(C#N)cc2n1-c1ccccc1]

Step 1: 4-Nitro-3-phenylaminobenzonitrile

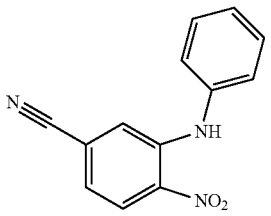 [SMILES: N#Cc1ccc([N+](=O)[O-])c(Nc2ccccc2)c1]

A suspension of 3-fluoro-4-nitrobenzonitrile (1.66 g, 10.0 mmol) in DMSO (5 mL) was purged with a stream of argon prior to addition of phenylamine (1.82 mL, 20.0 mmol) and then the mixture was stirred at 120° C. for 1 h under an argon atmosphere. After cooling to RT, the reaction mixture was partitioned between EtOAc (75 mL) and an aqueous solution of KHSO₄ (100 mL). The organic layer was then washed with brine, dried (Na₂SO₄) and concentrated in vacuo. The resulting residue was triturated with diethyl ether affording 4-Nitro-3-phenylaminobenzonitrile as red crystals (2.35 g, 98%). ¹H NMR (CDCl₃, 400 MHz): δ 9.48 (1H, bs), 8.29 (1H, d, J=8.76 Hz), 7.53-7.40 (3H, m), 7.35 (1H, t, J=7.52 Hz), 7.29-7.22 (2H, m), 6.97 (1H, d, J=8.79 Hz).

Step 2: 4-Amino-3-phenylaminobenzonitrile

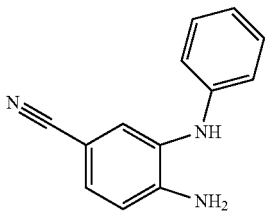 [SMILES: N#Cc1ccc(N)c(Nc2ccccc2)c1]

A solution of 4-nitro-3-phenylaminobenzonitrile (560 mg, 2.34 mmol) in EtOAc (30 mL) was degassed with a stream of nitrogen, prior to addition of PtO₂ (44 mg), and was stirred at RT under a hydrogen atmosphere for 2 h. The suspension was then filtered through a pad of Celite® and the filtrate was concentrated in vacuo affording 4-Amino-3-phenylaminobenzonitrile as a purple solid (500 mg, quantitative). LCMS: $R_T$ 3.20 min [M+H]⁺ 210.1.

Step 3: [(S)-1-(4-Cyano-2-phenylaminophenylcarbamoyl)ethyl]carbamic acid tertbutyl ester

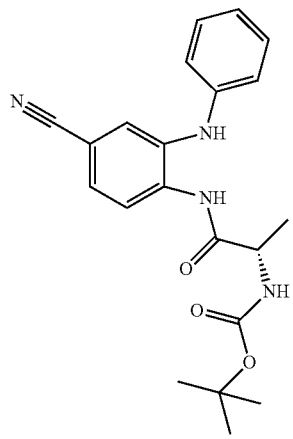 [SMILES: C[C@H](NC(=O)OC(C)(C)C)C(=O)Nc1ccc(C#N)cc1Nc1ccccc1]

A mixture of 4-amino-3-phenylaminobenzonitrile (490 mg, 2.34 mmol), (S)-2-tertbutoxycarbonylaminopropionic acid (490 mg, 2.57 mol), HOAt (380 mg, 2.79 mmol), N-(3-dimethylaminopropyl)-N'-ethylcarbodiimide hydrochloride (540 mg, 2.81 mol) and 4-methylmorpholine (560 μL, 5.15 mmol) in THF (5 mL) was stirred at RT for 48 h under an argon atmosphere. The crude reaction mixture was then partitioned between EtOAc and a saturated solution of NaHCO₃. The aqueous phase was further extracted with EtOAc and the combined organic layers were washed with brine, then dried (Na₂SO₄) and concentrated in vacuo. The resulting residue was purified by column chromatography (Si—PCC, gradient 0-10% EtOAc in DCM) affording [(S)-1-(4-Cyano-2-phenylaminophenylcarbamoyl)ethyl]carbamic acid tertbutyl ester as a cream foam (800 mg, 89%). LCMS: $R_T$ 3.62 min [M+H]⁺ 381.2.

Step 4

A solution of [(S)-1-(4-cyano-2-phenylaminophenylcarbamoyl)ethyl]carbamic acid tertbutyl ester (750 mg, 1.97 mmol) in AcOH (3 mL) was stirred for 18 h at 80° C. After cooling to RT, volatiles were evaporated under reduced pressure affording [(S)-1-(6-cyano-1-phenyl-1H-benzoimidazol-2-yl)ethyl]carbamic acid tertbutyl ester (1.97 mmol) which was used without any further purification in the following step. LCMS: $R_T$ 3.55 min [M+H]⁺ 363.2.

A solution of [(S)-1-(6-cyano-1-phenyl-1H-benzoimidazol-2-yl)ethyl]carbamic acid tertbutyl ester (1.97 mmol) in TFA (3 mL) was stirred at RT for 30 min. Volatiles were removed under reduced pressure and the resulting residue was loaded onto an Isolute® SCX-2 cartridge. The cartridge was washed with MeOH and the product eluted with 2M NH₃/MeOH. The product was further purified by column chromatography (Si—PCC, gradient 0-10% MeOH in DCM) affording 2-((S)-1-Aminoethyl)-3-phenyl-3H-benzoimida-

Example 12

(S)-1-(1-Phenyl-1H-benzoimidazol-2-yl)propylamine

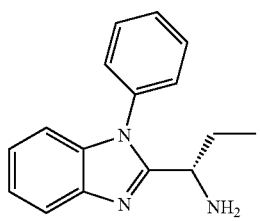

Step 1: [(S)-1-(1-Phenyl-1H-benzoimidazol-2-yl)propyl]carbamic acid tertbutyl ester

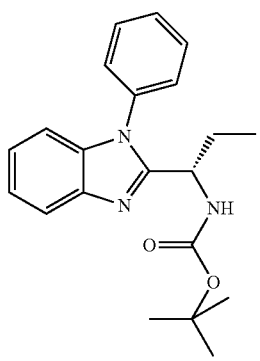 [SMILES: CC[C@H](NC(=O)OC(C)(C)C)c1nc2ccccc2n1-c1ccccc1]

A mixture of N-phenylbenzene-1,2-diamine (1.0 g, 5.43 mmol), (S)-2-tertbutoxycarbonylaminobutyric acid (1.21 g, 5.97 mmol), HOAt (813 mg, 5.97 mmol), N-(3-dimethylaminopropyl)-N'-ethylcarbodiimide hydrochloride (1.15 g, 5.97 mmol) and 4-methylmorpholine (1.31 mL, 11.95 mmol) in DCM (20 mL) was stirred at RT for 2 h. The crude reaction mixture was diluted with DCM (100 mL), then washed with a saturated solution of NaHCO$_3$, followed by brine, dried (Na$_2$SO$_4$) and concentrated in vacuo. The resulting residue was dissolved in AcOH (20 mL) and heated to 70° C. for 18 h. After cooling to RT, volatiles were evaporated under reduced pressure and the residue was dissolved in EtOAc (150 mL) and washed with a saturated solution of NaHCO$_3$. The organic layer was then washed with brine, dried (Na$_2$SO$_4$) and then concentrated in vacuo. The resulting residue was absorbed onto HM-N and purified twice by column chromatography (Si—PCC, gradient 0-50% EtOAc in cyclohexane) affording [(S)-1-(1-Phenyl-1H-benzoimidazol-2-yl)propyl]carbamic acid tertbutyl ester (1.76 g). LCMS: R$_T$ 3.23 min [M+H-$^t$Bu]$^+$ 352.2

Step 2

To a solution of [(S)-1-(1-phenyl-1H-benzoimidazol-2-yl)propyl]carbamic acid tertbutyl ester (1.76 g) in DCM (10 mL) was added TFA (7.5 mL) and the mixture was stirred at RT for 4 h. Volatiles were removed under reduced pressure and the resulting residue was dissolved in DCM and washed with a saturated solution of NaHCO$_3$. The two phase system was stirred for 20 min, then the organic layer was dried (Na$_2$SO$_4$) and concentrated in vacuo affording (S)-1-(1-Phenyl-1H-benzoimidazol-2-yl)propylamine as a brown oil (1.1 g, 81% over three steps). LCMS: R$_T$ 2.02 min [M+H]$^+$ 252.2

Example 13

(S)-1-(6-Methyl-1-phenyl-1H-benzoimidazol-2-yl)ethylamine

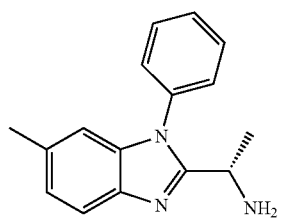

Step 1: (5-Methyl-2-nitrophenyl)phenylamine

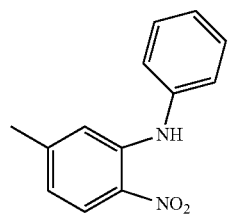 [SMILES: Cc1ccc([N+](=O)[O-])c(Nc2ccccc2)c1]

A solution of 2-fluoro-4-methyl-1-nitrobenzene (1.0 g, 6.45 mmol) in DMSO (3 mL) was purged with a stream of nitrogen prior to addition of phenylamine (1.18 mL, 12.9 mmol) and then stirred in a sealed tube at 100° C. for 20 h. After cooling to RT, the reaction mixture was partitioned between EtOAc (125 mL) and water (150 mL). The organic layer was then washed with water (150 mL×3), followed by brine, then dried (Na$_2$SO$_4$) and concentrated in vacuo affording (5-Methyl-2-nitrophenyl)phenylamine as a red solid (1.5 g, quantitative). $^1$H NMR (DMSO, 400 MHz): δ 9.40 (1H, s), 8.03 (1H, d, J=8.70 Hz), 7.45-7.39 (2H, m), 7.35-7.30 (2H, m), 7.21 (1H, t, J=7.33 Hz), 6.98 (1H, s), 6.72-6.68 (1H, m), 2.24 (3H, s).

Step 2: 4-Methyl-N$^2$-phenylbenzene-1,2-diamine

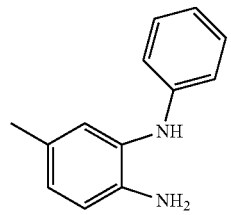

A mixture of (5-methyl-2-nitrophenyl)phenylamine (1.5 g, 6.57 mmol) and 10% Pd/C (750 mg) in EtOAc (25 mL) was degassed with a stream of nitrogen and stirred at RT under a hydrogen atmosphere for 5 h. The suspension was then filtered through a PTFE frit and the filtrate was concentrated in vacuo affording 4-Methyl-$N^2$-phenylbenzene-1,2-diamine as a brown solid (1.29 g, 99%). LCMS: $R_T$ 2.61 min [M+H]$^+$ 199.2.

Step 3: [(S)-1-(6-Methyl-1-phenyl-1H-benzoimidazol-2-yl)ethyl]carbamic acid tertbutyl ester

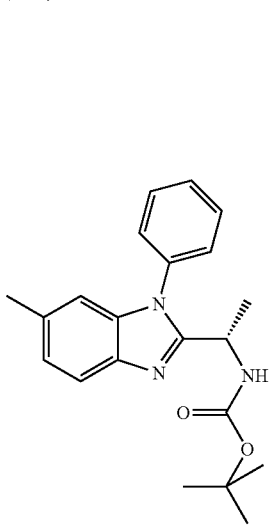

A mixture of 4-methyl-$N^2$-phenylbenzene-1,2-diamine (600 mg, 3.03 mmol), (S)-2-tertbutoxycarbonylaminopropionic acid (861 mg, 4.55 mmol), HOAt (453 mg, 3.33 mmol), N-(3-dimethylaminopropyl)-N'-ethylcarbodiimide hydrochloride (874 mg, 4.55 mmol) and 4-methylmorpholine (0.74 mL, 6.67 mmol) in anhydrous DCM (20 mL) was stirred at RT for 1.5 h. Volatiles were removed under reduced pressure and the resulting residue was dissolved in AcOH (10 mL) and heated to 70° C. for 20 h. After cooling to RT, volatiles were removed in vacuo and the residue was dissolved in EtOAc (100 mL) and washed with a saturated solution of NaHCO$_3$ (2×100 mL). The organic layer was then washed with brine, dried (Na$_2$SO$_4$) and then concentrated in vacuo. The resulting residue was absorbed onto HM-N and the solvent was removed in vacuo. The product was purified by column chromatography (Si—PCC, gradient 10-60% EtOAc in cyclohexane) affording [(S)-1-(6-Methyl-1-phenyl-1H-benzoimidazol-2-yl)ethyl]carbamic acid tertbutyl ester (969 mg, 92%). LCMS: $R_T$ 3.10 min [M+H-$^t$Bu]$^+$ 352.1.

Step 4

To a solution of [(S)-1-(6-methyl-1-phenyl-1H-benzoimidazol-2-yl)ethyl]carbamic acid tertbutyl ester (969 mg, 2.76 mmol) in DCM (7.5 mL) was added TFA (2.5 mL) and the mixture was stirred at RT for 20 h. Volatiles were removed under reduced pressure and the resulting residue was dissolved in DCM (30 mL) and washed with a saturated solution of NaHCO$_3$ (40 mL). The two phase system was stirred for 10 min, then the organic layer was dried (Na$_2$SO$_4$) and concentrated in vacuo affording (S)-1-(6-Methyl-1-phenyl-1H-benzoimidazol-2-yl)ethylamine as a brown solid (583 mg, 84%). LCMS: $R_T$ 3.02 min [M+H]$^+$ 252.2

Example 14

(S)-1-(5-Methyl-1-phenyl-1H-benzoimidazol-2-yl)ethylamine

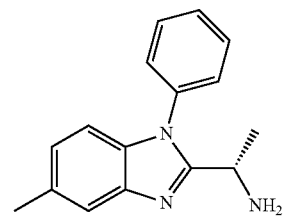 [SMILES: Cc1ccc2c(c1)nc([C@H](C)N)n2-c1ccccc1]

Step 1: (4-Methyl-2-nitrophenyl)phenylamine

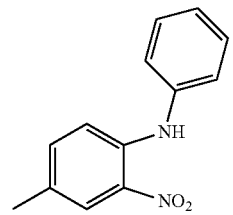

A solution of 1-fluoro-4-methyl-2-nitrobenzene (1.0 g, 6.45 mmol) in DMSO (3 mL) was purged with a stream of nitrogen prior to addition of phenylamine (1.18 mL, 12.9 mmol) and then stirred in a sealed tube at 100° C. for 20 h. After cooling to RT, the reaction mixture was partitioned between EtOAc (200 mL) and water (150 mL). The organic layer was then washed with water (150 mL×3), followed by brine, then dried (Na$_2$SO$_4$) and concentrated in vacuo and the resulting residue was purified by column chromatography (Si—PCC, gradient 0-40% DCM in cyclohexane) affording (4-Methyl-2-nitrophenyl)phenylamine as a red oil (1.41 g, 96%). $^1$H NMR (DMSO, 400 MHz): δ 9.21 (1H, s), 7.94-7.91 (1H, m), 7.43-7.26 (5H, m), 7.19-7.12 (2H, m), 2.27 (3H, s).

Step 2: 4-Methyl-$N^1$-phenylbenzene-1,2-diamine

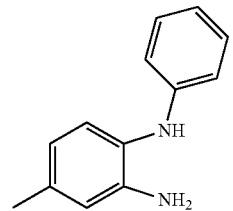 [SMILES: Cc1ccc(Nc2ccccc2)c([N+](=O)[O-])c1]

A mixture of (4-methyl-2-nitrophenyl)phenylamine (1.41 g, 6.18 mmol) and 10% Pd/C (140 mg) in EtOAc (30 mL) was degassed with a stream of nitrogen and stirred at RT under a hydrogen atmosphere for 5 h. The suspension was then filtered through a PTFE frit and the filtrate was concentrated in vacuo affording 4-Methyl-N¹-phenylbenzene-1,2-diamine as an off-white solid (1.18 g, 96%). LCMS: $R_T$ 3.08 min [M+H]⁺ 199.1.

Step 3: [(S)-1-(5-Methyl-1-phenyl-1H-benzoimidazol-2-yl)ethyl]carbamic acid tertbutyl ester

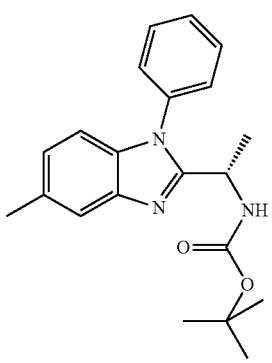 [SMILES: Cc1ccc2c(c1)nc([C@H](C)NC(=O)OC(C)(C)C)n2-c1ccccc1]

A mixture of 4-methyl-N¹-phenylbenzene-1,2-diamine (500 mg, 2.52 mmol), (S)-2-tertbutoxycarbonylaminopropionic acid (524 mg, 2.77 mmol), HOAt (377 mg, 2.77 mmol), N-(3-dimethylaminopropyl)-N'-ethylcarbodiimide hydrochloride (532 mg, 2.77 mmol) and 4-methylmorpholine (0.609 mL, 5.54 mmol) in anhydrous DCM (20 mL) was stirred at RT for 20 h. The reaction mixture was diluted with DCM (100 mL) and washed with a saturated solution of NaHCO₃. The organic layer was then dried and concentrated in vacuo. The resulting residue was dissolved in AcOH (10 mL) and heated to 70° C. for 20 h. After cooling to RT, volatiles were removed in vacuo and the residue was dissolved in EtOAc and washed with a saturated solution of NaHCO₃ (2×100 mL). The organic layer was then washed with brine, dried (Na₂SO₄) and then concentrated in vacuo. The resulting residue was purified by column chromatography (Si—PCC, gradient 10-60% EtOAc in cyclohexane) affording [(S)-1-(5-Methyl-1-phenyl-1H-benzoimidazol-2-yl)ethyl]carbamic acid tertbutyl ester (912 mg, quantitative). LCMS: $R_T$ 3.02 min [M+H-$^t$Bu]⁺ 352.1.

Step 4

To a solution of [(S)-1-(5-methyl-1-phenyl-1H-benzoimidazol-2-yl)ethyl]carbamic acid tertbutyl ester (912 mg, 2.59 mmol) in DCM (10 mL) was added TFA (5 mL) and the mixture was stirred at RT for 2 h. Volatiles were removed under reduced pressure and the resulting residue was dissolved in DCM (40 mL) and washed with a saturated solution of NaHCO₃ (50 mL). The two phase system was stirred for 10 min, then the organic layer was dried (Na₂SO₄) and concentrated in vacuo affording (S)-1-(5-Methyl-1-phenyl-1H-benzoimidazol-2-yl)ethylamine (617 mg, 95%). LCMS: $R_T$ 2.10 and 2.23 min [M−NH₂] 252.0.

Example 15

(S)-1-(4-Fluoro-1-phenyl-1H-benzoimidazol-2-yl)ethylamine

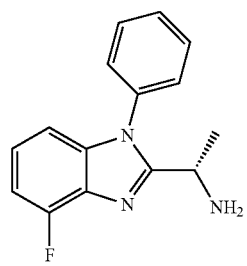 [SMILES: C[C@H](N)c1nc2c(F)cccc2n1-c1ccccc1]

Step 1: (3-Fluoro-2-nitrophenyl)phenylamine

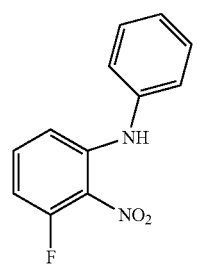 [SMILES: O=[N+]([O-])c1c(F)cccc1Nc1ccccc1]

Sodium tertbutoxide (1.2 g, 12.58 mmol) was added portionwise to a stirred solution of 1,3-difluoro-2-nitrobenzene (1 g, 6.29 mmol) and phenylamine (1.15 mL, 12.58 mmol) in a hydrous DMF (5 mL) under a nitrogen atmosphere at RT and stirring was continued for 20 h. The mixture was poured into an aqueous solution of NH₄Cl and extracted with EtOAc (150 mL). The organic layer was washed with brine, then dried and concentrated in vacuo and the resulting residue was purified by column chromatography (Si—PCC, gradient 0-15% EtOAc in cyclohexane) affording (3-Fluoro-2-nitrophenyl)phenylamine as a red solid (1.06 g, 73%). LCMS: $R_T$ 3.80 min.

Step 2: 3-Fluoro-N¹-phenylbenzene-1,2-diamine

A mixture of (3-fluoro-2-nitrophenyl)phenylamine (1.06 g, 4.56 mmol) and 10% Pd/C (100 mg) in EtOAc (20 mL) was degassed with a stream of nitrogen and stirred at RT under a hydrogen atmosphere for 7 h. The suspension was then filtered through a PTFE frit and the filtrate was concentrated in vacuo. The resulting residue was purified by column chromatography (Si—PCC, gradient 0-20% EtOAc in cyclohexane) affording 3-Fluoro-N[1]-phenylbenzene-1,2-diamine (440 mg, 48%). LCMS: $R_T$ 3.46 min [M+H]$^+$ 203.1.

Step 3

A mixture of 3-fluoro-N[1]-phenylbenzene-1,2-diamine (440 mg, 2.18 mmol), (S)-2-tertbutoxycarbonylaminopropionic acid (454 mg, 2.40 mmol), HOAt (327 mg, 2.40 mmol), N-(3-dimethylaminopropyl)-N'-ethylcarbodiimide hydrochloride (460 mg, 2.40 mmol) and 4-methylmorpholine (0.527 mL, 4.79 mmol) in anhydrous DCM (20 mL) was stirred at RT for 2 h. The reaction mixture was diluted with DCM (100 mL) and washed with a saturated solution of NaHCO$_3$. The organic layer was then dried and concentrated in vacuo. The resulting residue was dissolved in AcOH (10 mL) and heated to 70° C. for 2 h and then to 80° C. for 20 h. After cooling to RT, TFA (20 mL) was added and the mixture was stirred at RT for 1 h and 20 min. Volatiles were then removed in vacuo and the residue was dissolved in DCM (100 mL) and washed with a saturated solution of NaHCO$_3$. The organic layer was then washed with brine, dried (Na$_2$SO$_4$) and then concentrated in vacuo. The resulting residue was purified by column chromatography (Si—PCC, gradient 0-10% MeOH in TBME) affording (S)-1-(4-Fluoro-1-phenyl-1H-benzoimidazol-2-yl)ethylamine as a brown oil (396 mg, 71%). LCMS: $R_T$ 2.01 min [M–NH$_2$]$^+$ 239.1.

Example 16

[(S)-1-((R)-1-Piperidin-3-yl-1H-benzoimidazol-2-yl)ethyl]-(9H-purin-6-yl)amine

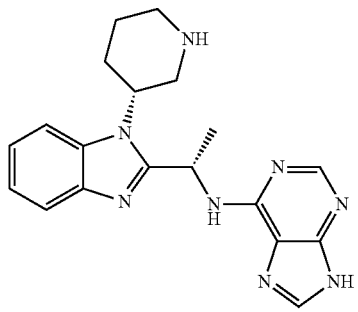 [SMILES: C[C@H](Nc1ncnc2[nH]cnc12)c1nc2ccccc2n1[C@@H]1CCCNC1]

Step 1:
(R)-3-(2-Nitrophenylamino)piperidine-1-carboxylic acid tertbutyl ester

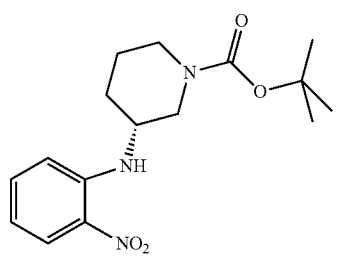

A mixture of 1-fluoro-2-nitrobenzene (1.41 g, 10.0 mmol), (R)-3-aminopiperidine-1-carboxylic acid tertbutyl ester (2 g, 10.0 mmol) and potassium carbonate (152 mg, 11.0 mmol) in DMF (18 mL) was heated to 120° C. under microwave irradiation for 30 min. The reaction mixture was partitioned between EtOAc (150 mL) and water. The organic layer was washed with brine, dried (Na$_2$SO$_4$) and then concentrated in vacuo. The resulting residue was purified by column chromatography (Si—PCC, eluant 10% EtOAc in DCM) affording (R)-3-(2-Nitrophenylamino)piperidine-1-carboxylic acid tertbutyl ester as an orange oil (2.48 g, 77%). LCMS: $R_T$ 3.95 min [M+H-$^t$Bu]$^+$ 266.2.

Step 2:
(R)-3-(2-Aminophenylamino)piperidine-1-carboxylic acid tertbutyl ester

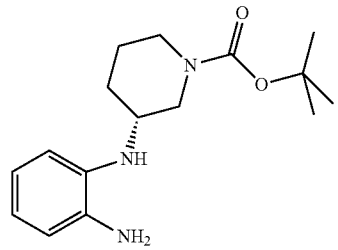 [SMILES: CC(C)(C)OC(=O)N1CCC[C@@H](Nc2ccccc2N)C1]

A mixture of (R)-3-(2-nitrophenylamino)piperidine-1-carboxylic acid tertbutyl ester (2.48 g, 7.72 mmol) and 10% Pd/C (250 mg) in EtOAc (50 mL) was degassed with a stream of nitrogen and stirred at RT under a hydrogen atmosphere for 20 h. The suspension was then filtered through a PTFE frit and the filtrate was concentrated in vacuo affording (R)-3-(2-Aminophenylamino)piperidine-1-carboxylic acid tertbutyl ester as a clear glass (2.25 g, quantitative). LCMS: $R_T$ 2.64 min [M+H-Boc]$^+$ 192.1.

Step 3: (R)-3-[2-((S)-1-Benzyloxycarbonylaminoethyl)benzoimidazol-1-yl]piperidine-1-carboxylic acid tertbutyl ester

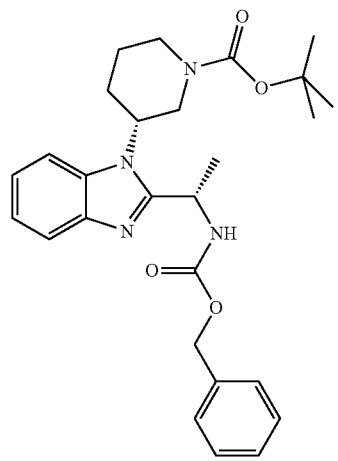 [SMILES: C[C@H](NC(=O)OCc1ccccc1)c1nc2ccccc2n1[C@@H]1CCCN(C(=O)OC(C)(C)C)C1]

A mixture of (R)-3-(2-aminophenylamino)piperidine-1-carboxylic acid tertbutyl ester (2.25 g, 7.72 mmol), (S)-2-benzyloxycarbonylaminopropionic acid (1.9 g, 8.49 mmol), HOAt (1.16 g, 8.49 mmol), N-(3-dimethylaminopropyl)-N'-ethylcarbodiimide hydrochloride (1.63 g, 8.49 mmol) and 4-methylmorpholine (1.87 mL, 16.98 mmol) in anhydrous DCM (50 mL) was stirred at RT for 1.5 h. The reaction mixture was diluted with DCM (200 mL) and washed with a 10% citric acid solution, followed by a saturated solution of NaHCO₃ and then brine. The organic layer was then dried and concentrated in vacuo. The resulting residue was dissolved in AcOH (20 mL) and heated at 70° C. for 20 h and then at 80° C. for 2 h. After cooling to RT, volatiles were then removed in vacuo and the residue was dissolved in EtOAc (200 mL) and washed with a saturated solution of NaHCO₃ (100 mL×2). The organic layer was then washed with brine, dried (Na₂SO₄) and then concentrated in vacuo. The resulting residue was purified by column chromatography (Si—PCC, gradient 0-50% EtOAc in cyclohexane) affording (R)-3-[2-((S)-1-Benzyloxycarbonylaminoethyl)benzoimidazol-1-yl]piperidine-1-carboxylic acid tertbutyl ester as a white foam (2.75 g, 74%). LCMS: R$_T$ 3.16 min [M+H]⁺ 479.1.

Step 4: (R)-3-[2-((S)-1-Aminoethyl)benzoimidazol-1-yl]piperidine-1-carboxylic acid tertbutyl ester A mixture of (R)-3-[2-((S)-1-benzyloxycarbonylaminoethyl)benzoimidazol-1-yl]piperidine-1-carboxylic acid tertbutyl ester (2.75 g, 5.75 mmol) 10% Pd/C (275 mg) and AcOH (4 mL) in EtOAc (40 mL) was purged with a stream of nitrogen and then was stirred at RT for 20 h under an hydrogen atmosphere. The suspension was then filtered through a PTFE frit and the filtrate was concentrated in vacuo. The resulting residue was purified by column chromatography (Si—PCC, gradient 0-10% 2M NH₃/MeOH in DCM) affording (R)-3-[2-((S)-1-Aminoethyl)benzoimidazol-1-yl]piperidine-1-carboxylic acid tertbutyl ester as a white foam (1.65 g, 83%). LCMS: R$_T$ 2.30 min [M+H-$^t$Bu]⁺ 289.2.

Step 5: (R)-3-(2-{(S)-1-[9-(Tetrahydropyran-2-yl)-9H-purin-6-ylamino]ethyl}benzoimidazol-1-yl)piperidine-1-carboxylic acid tertbutyl ester

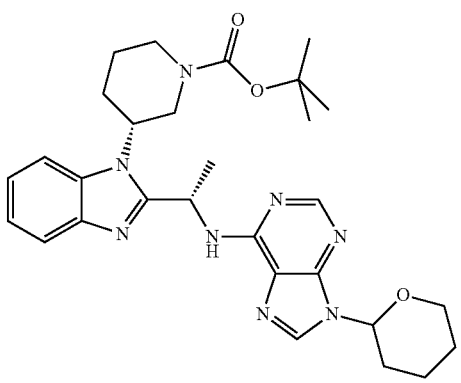 [SMILES: C[C@H](Nc1ncnc2c1ncn2C1CCCCO1)c1nc2ccccc2n1[C@@H]1CCCN(C(=O)OC(C)(C)C)C1]

A mixture of (R)-3-[2-((S)-1-aminoethyl)benzoimidazol-1-yl]piperidine-1-carboxylic acid tertbutyl ester (1.65 g, 4.79 mmol), 6-chloro-9-(tetrahydropyran-2-yl)-9H-purine (1.14 g, 4.79 mmol), and DIPEA (2.5 mL, 14.4 mmol) in IMS (10 mL) was stirred in a sealed vial for 48 h at 90° C. After cooling to RT, volatiles were removed under reduced pressure and the resulting residue was purified by column chromatography (Si—PCC, gradient 0-10% MeOH in EtOAc). The product containing fractions were concentrated in vacuo affording (R)-3-(2-{(S)-1-[9-(Tetrahydropyran-2-yl)-9H-purin-6-ylamino]ethyl}benzoimidazol-1-yl)piperidine-1-carboxylic acid tertbutyl ester as a white foam (2.27 g, 87%). LCMS: R$_T$ 2.88 min [M+H]⁺ 547.1.

Step 6

To a solution of (R)-3-(2-{(S)-1-[9-(tetrahydropyran-2-yl)-9H-purin-6-ylamino]ethyl}benzoimidazol-1-yl)piperidine-1-carboxylic acid tertbutyl ester (2.27 g, 4.15 mmol) in DCM (25 mL) was added TFA (15 mL) and the mixture was stirred at RT for 1 h. Volatiles were removed under reduced pressure and the resulting residue was loaded onto an Isolute® SCX-2 cartridge. The cartridge was washed with a 1:1 mixture MeOH:DCM and the product was eluted with 2M NH₃/MeOH (100 mL) in DCM (150 mL). The product containing fractions were combined and concentrated in vacuo affording [(S)-1-((R)-1-Piperidin-3-yl-1H-benzoimidazol-2- yl)ethyl]-(9H-purin-6-yl)amine as a pale yellow solid (1.53 g, quantitative). LCMS: $R_T$ 1.63 min [M+H]$^+$ 363.2.

Example 17

(S)-1-[1-(Tetrahydropyran-4-yl)-1H-benzoimidazol-2-yl]ethylamine

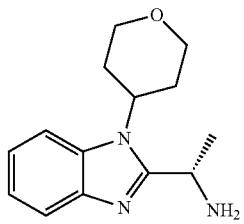 [SMILES: C[C@H](N)c1nc2ccccc2n1C1CCOCC1]

Step 1: (2-Nitrophenyl)(tetrahydropyran-4-yl)amine

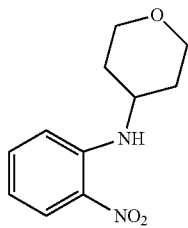

A solution of tetrahydropyran-4-ylamine (0.75 g, 7.44 mmol) in DMF (2 mL) was added to a mixture of 1-fluoro-2-nitrobenzene (1.00 g, 7.09 mmol) and potassium carbonate (2.94 g, 21.3 mmol) in DMF (10 mL). The reaction mixture was heated for 1 h at 135° C. under microwave irradiation and then volatiles were removed in vacuo. The resulting residue was partitioned between EtOAc and water. The aqueous phase was further extracted with EtOAc (×2) and the combined organic layers were washed with brine, then dried (Na$_2$SO$_4$) and concentrated in vacuo affording (2-Nitrophenyl)(tetrahydropyran-4-yl)amine as a yellow solid (1.58 g, quantitative). $^1$H NMR (CDCl$_3$, 400 MHz): δ 8.18 (1H, d, J=8.65 Hz), 8.09 (1H, s), 7.42 (1H, t, J=7.81 Hz), 6.87 (1H, d, J=8.70 Hz), 6.64 (1H, t, J=7.72), 4.06-3.98 (2H, m), 3.79-3.68 (1H, m), 3.57 (2H, t, J=11.32 Hz), 2.14-2.01 (2H, m), 1.74-1.61 (2H, m).

Step 2: N-(Tetrahydropyran-4-yl)benzene-1,2-diamine

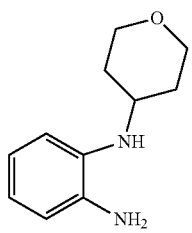 [SMILES: Nc1ccccc1NC1CCOCC1]

A mixture of (2-nitrophenyl)(tetrahydropyran-4-yl)amine (1.58 g, 7.09 mmol) and 10% Pd/C (400 mg) in EtOAc (30 mL) was degassed with a stream of nitrogen and stirred at RT under a hydrogen atmosphere for 3 days. The suspension was then filtered through a pad of celite and the filtrate was concentrated in vacuo affording N-(Tetrahydropyran-4-yl)benzene-1,2-diamine as a colourless oil (quantitative). $^1$H NMR (CDCl$_3$, 400 MHz): δ 6.83-6.64 (4H, m), 4.01 (2H, d, J=11.69 Hz), 3.57-3.41 (3H, m), 3.40-3.19 (3H, bs), 2.08-1.99 (2H, m), 1.59-1.46 (2H, m).

Step 3: {(S)-1-[2-(Tetrahydropyran-4-ylamino)phenylcarbamoyl]ethyl}carbamic acid tertbutyl ester

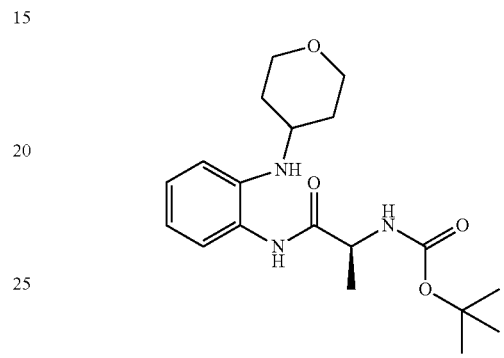

Et$_3$N (2.6 mL, 18.9 mmol) was added to a stirred mixture of N-(tetrahydropyran-4-yl)benzene-1,2-diamine (1.21 g, 6.29 mmol), (S)-2-tertbutoxycarbonylaminopropionic acid (1.31 g, 6.92 mmol), HOAt (0.94 g, 6.92 mmol) and N-(3-dimethylaminopropyl)-N'-ethylcarbodiimide hydrochloride (1.33 g, 6.92 mmol) in anhydrous DCM (30 mL) at 0° C. under a nitrogen atmosphere. Stirring was continued for 10 min at 0° C. then the mixture was slowly warmed to RT and stirred at RT for 4 h. The reaction mixture was partitioned between DCM and a saturated solution of NaHCO$_3$. The aqueous phase was further extracted with DCM and the combined organic layers were then washed with brine, dried (Na$_2$SO$_4$) and concentrated in vacuo. The resulting residue was purified by column chromatography (Si—PCC, gradient 0-4% 2M NH$_3$/MeOH in DCM) affording {(S)-1-[2-(Tetrahydropyran-4-ylamino)phenylcarbamoyl]ethyl}carbamic acid tertbutyl ester as a white solid (1.91 g, 83%). LCMS: $R_T$ 2.78 min [M+H-$^t$Bu]$^+$ 308.1.

Step 4: {(S)-1-[1-(Tetrahydropyran-4-yl)-1H-benzoimidazol-2-yl]ethyl}carbamic acid tertbutyl ester

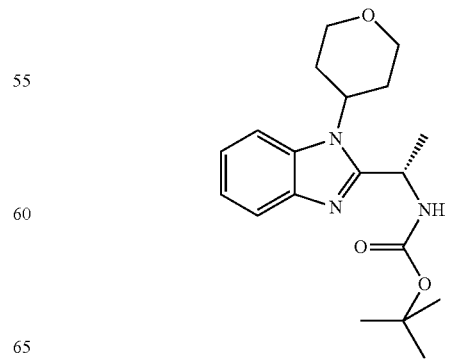

{(S)-1-[2-(Tetrahydropyran-4-ylamino)phenylcarbamoyl]ethyl}carbamic acid tertbutyl ester (1.90 g, 5.23 mmol) was dissolved in AcOH (30 mL) and heated to 70° C. for 18 h. Volatiles were then removed in vacuo and the residue was partitioned between DCM and a saturated solution of NaHCO$_3$. The aqueous phase was further extracted with DCM (×2) and the combined organic layers were then washed with brine, dried (Na$_2$SO$_4$) and concentrated in vacuo. The resulting residue was purified by column chromatography (Si—PCC, gradient 0-4% 2M NH$_3$/MeOH in DCM) affording {(S)-1-[1-(Tetrahydropyran-4-yl)-1H-benzoimidazol-2-yl]ethyl}carbamic acid tertbutyl ester as a white foam (1.40 g, 77%). LCMS: R$_T$ 2.23 min [M+H-$^t$Bu]$^+$ 290.1.

Step 5

To a solution of {(S)-1-[1-(tetrahydropyran-4-yl)-1H-benzoimidazol-2-yl]ethyl}carbamic acid tertbutyl ester (1.80 g, 5.22 mmol) in DCM (25 mL) was added TFA (10 mL) and the mixture was stirred at RT for 1 h. Volatiles were removed under reduced pressure and the resulting residue was partitioned between DCM and a saturated solution of NaHCO$_3$. The aqueous phase was further extracted with DCM (×2) and the combined organic layers were dried (Na$_2$SO$_4$) and concentrated in vacuo. The resulting residue was purified by column chromatography (Si—PCC, gradient 0-10% 2M NH$_3$/MeOH in DCM). The product containing fractions were concentrated in vacuo affording (S)-1-[1-(Tetrahydropyran-4-yl)-1H-benzoimidazol-2-yl]ethylamine as a light yellow solid (415 mg, 32%). LCMS: R$_T$ 0.27 min [M+Na]$^+$ 268.1.

Example 18

(S)-1-[1-(Tetrahydropyran-3-yl)-1H-benzoimidazol-2-yl]ethylamine

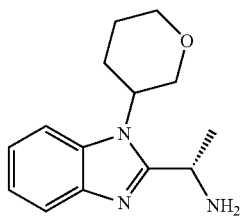 [SMILES: C[C@H](N)c1nc2ccccc2n1C1CCCOC1]

Step 1: (2-Nitrophenyl)(tetrahydropyran-3-yl)amine

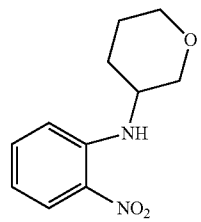 [SMILES: O=[N+]([O-])c1ccccc1NC1CCCOC1]

A solution of tetrahydropyran-3-ylamine (0.43 g, 4.05 mmol) in DMF (2 mL) was added to a mixture of 1-fluoro-2-nitrobenzene (0.57 g, 4.05 mmol) and potassium carbonate (1.68 g, 12.1 mmol) in DMF (10 mL). The reaction mixture was heated for 1 h at 135° C. under microwave irradiation. Additional tetrahydropyran-3-ylamine (40 mg) was added and microwave irradiation at 135° C. was continued for further 30 min. Volatiles were then removed in vacuo and the resulting residue was partitioned between EtOAc and water. The aqueous phase was further extracted with EtOAc (×2) and the combined organic layers were washed with brine, then dried (Na$_2$SO$_4$) and concentrated in vacuo. The resulting residue was purified by column chromatography (Si—PCC, gradient 0-2% MeOH in DCM) affording (2-Nitrophenyl)(tetrahydropyran-3-yl)amine as an orange oil (0.73 g, 81%). LCMS: R$_T$ 3.31 min [M+H]$^+$ 223.2.

Step 2:
N-(Tetrahydropyran-3-yl)benzene-1,2-diamine

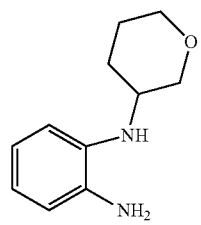

A mixture of (2-nitrophenyl)(tetrahydropyran-3-yl)amine (0.72 g, 3.24 mmol) and 10% Pd/C (200 mg) in EtOAc (30 mL) was degassed with a stream of nitrogen and stirred at RT under a hydrogen atmosphere for 3 days. The suspension was then filtered through a pad of celite and the filtrate was concentrated in vacuo affording N-(Tetrahydropyran-3-yl)benzene-1,2-diamine as a colourless oil (quantitative). $^1$H NMR (CDCl$_3$, 400 MHz): δ 6.80 (1H, t, J=7.55 Hz), 6.75-6.62 (3H, m), 4.00 (1H, d, J=11.24 Hz), 3.84-3.71 (1H, m), 3.67-3.16 (6H, m), 2.07-1.92 (1H, m), 1.87-1.73 (1H, m), 1.72-1.56 (2H, m).

Step 3: {(S)-1-[2-(Tetrahydropyran-3-ylamino)phenylcarbamoyl]ethyl}carbamic acid tertbutyl ester

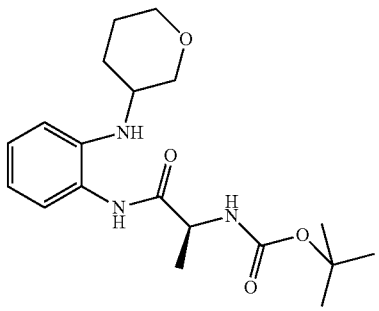 [SMILES: C[C@H](NC(=O)OC(C)(C)C)C(=O)Nc1ccccc1NC1CCCOC1]

Et$_3$N (1.6 mL, 11.3 mmol) was added to a stirred mixture of N-(tetrahydropyran-3-yl)benzene-1,2-diamine (0.61 g, 3.17 mmol), (S)-2-tertbutoxycarbonylaminopropionic acid (0.78 g, 4.14 mmol), HOAt (0.56 g, 4.14 mmol) and N-(3-dimethylaminopropyl)-N'-ethylcarbodiimide hydrochloride (0.79 g, 4.14 mmol) in anhydrous DCM (20 mL) at 0° C. under a nitrogen atmosphere. Stirring was continued for 10 min at 0° C. then the mixture was slowly warmed to RT and stirred at RT for 3 h. The reaction mixture was partitioned between DCM and a saturated solution of NaHCO$_3$. The aqueous phase was further extracted with DCM (×2) and the combined organic layers were washed with brine, then dried (Na₂SO₄) and concentrated in vacuo. The resulting residue was purified by column chromatography (Si—PCC, gradient 0-4% 2M NH₃/MeOH in DCM) affording {(S)-1-[2-(Tetrahydropyran-3-ylamino)phenylcarbamoyl]ethyl}carbamic acid tertbutyl ester as a white solid (0.96 g, 70%). LCMS: $R_T$ 3.00 min [M+H]⁺ 364.1.

Step 4: {(S)-1-[1-(Tetrahydropyran-3-yl)-1H-benzoimidazol-2-yl]ethyl}carbamic acid tertbutyl ester

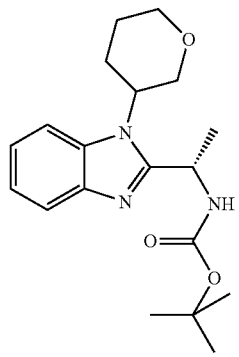 [SMILES: C[C@H](NC(=O)OC(C)(C)C)c1nc2ccccc2n1C1CCCOC1]

{(S)-1-[2-(Tetrahydropyran-3-ylamino)phenylcarbamoyl]ethyl}carbamic acid tertbutyl ester (0.95 g, 2.61 mmol) was dissolved in AcOH (20 mL) and heated to 70° C. for 38 h. Volatiles were then removed in vacuo and the residue was partitioned between DCM and a saturated solution of NaHCO₃. The aqueous phase was further extracted with DCM (×2) and the combined organic layers were then washed with brine, dried (Na₂SO₄) and concentrated in vacuo. The resulting residue was purified by column chromatography (Si—PCC, gradient 0-4% 2M NH₃/MeOH in DCM) affording {(S)-1-[1-(Tetrahydropyran-3-yl)-1H-benzoimidazol-2-yl]ethyl}carbamic acid tertbutyl ester as a light brown solid (0.73 g, 81%). LCMS: $R_T$ 2.35 min [M+H-$^t$Bu]⁺ 290.0.

Step 5

To a solution of {(S)-1-[1-(tetrahydropyran-3-yl)-1H-benzoimidazol-2-yl]ethyl}carbamic acid tertbutyl ester (720 mg, 2.08 mmol) in DCM (5 mL) was added TFA (15 mL) and the mixture was stirred at RT for 20 min. Volatiles were removed under reduced pressure and the resulting residue was partitioned between DCM and a saturated solution of NaHCO₃. The aqueous phase was further extracted with DCM (×2) and the combined organic layers were dried (Na₂SO₄) and concentrated in vacuo. The resulting residue was purified by column chromatography (Si—PCC, gradient 0-10% 2M NH₃/MeOH in DCM). The product containing fractions were concentrated in vacuo affording (S)-1-[1-(Tetrahydropyran-3-yl)-1H-benzoimidazol-2-yl]ethylamine as an oil (305 mg, 60%). LCMS: $R_T$ 1.85 min [M–NH₂]⁺ 229.1.

Example 19

(S)-1-(7-Chloro-1-phenyl-1H-benzoimidazol-2-yl)ethylamine

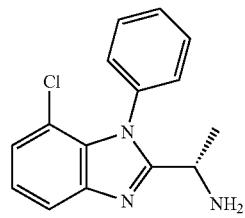

Step 1: (2-Chloro-6-nitrophenyl)phenylamine

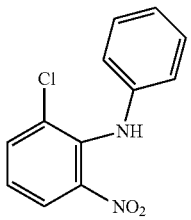 [SMILES: O=[N+]([O-])c1cccc(Cl)c1Nc1ccccc1]

A solution of 1-chloro-2-fluoro-3-nitrobenzene (983 mg, 5.60 mmol) in DMSO (3 mL) was purged with a stream of nitrogen prior to addition of phenylamine (1.0 mL, 11.2 mmol) and then stirred in a sealed tube at 100° C. for 3 h. After cooling to RT, the reaction mixture was partitioned between EtOAc and water. The organic layer was then washed with a saturated solution of KHSO₄ (×3), then with water, followed by brine, dried (Na₂SO₄) and concentrated in vacuo affording (2-Chloro-6-nitrophenyl)phenylamine as a dark orange oil (1.35 g, 97%). ¹H NMR (CDCl₃, 400 MHz): δ 8.15 (1H, s), 8.03 (1H, dd, J=8.40, 1.49 Hz), 7.63 (1H, d, J=7.90 Hz), 7.32-7.23 (2H, m), 7.08-6.99 (2H, m), 6.86 (2H, d, J=7.90 Hz).

Step 2: 3-Chloro-N²-phenylbenzene-1,2-diamine

To a mixture of (2-chloro-6-nitrophenyl)phenylamine (676 mg, 2.72 mmol) in MeOH (45 mL) and water (15 mL) were added NH₄Cl (872 mg, 16.31 mol) and iron powder (607 mg, 10.87 mmol) and the reaction mixture was heated to reflux temperature for 4 h. After cooling to RT, the solid was filtered through a pad of Celite® and washed with additional MeOH. The filtrate was concentrated in vacuo and then partitioned between EtOAc and water. The aqueous phase was further extracted with EtOAc and the combined organic layers were washed with brine, then dried ($Na_2SO_4$) and concentrated in vacuo. The resulting residue was purified by column chromatography (Si—PCC, gradient 50-100% DCM in cyclohexane). The product containing fractions were concentrated in vacuo affording 3-Chloro-$N^2$-phenylbenzene-1,2-diamine as a pale orange solid (500 mg, 84%). LCMS: $R_T$ 3.45 min $[M+H]^+$ 219.1.

Step 3: [(S)-1-(7-Chloro-1-phenyl-1H-benzoimidazol-2-yl)ethyl]carbamic acid tertbutyl ester

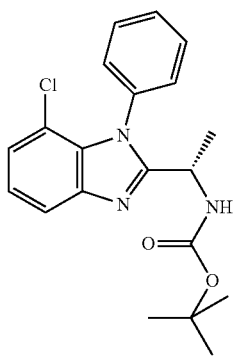 [SMILES: C[C@H](NC(=O)OC(C)(C)C)c1nc2cccc(Cl)c2n1-c1ccccc1]

A mixture of 3-chloro-$N^2$-phenylbenzene-1,2-diamine (495 mg, 2.26 mmol), (S)-2-tertbutoxycarbonylaminopropionic acid (470 mg, 2.48 mmol), HOAt (338 mg, 2.48 mmol), N-(3-dimethylaminopropyl)-N'-ethylcarbodiimide hydrochloride (477 mg, 2.48 mmol) and 4-methylmorpholine (0.550 mL, 4.97 mmol) in anhydrous DCM (15 mL) was stirred at RT for 19 h. The reaction mixture was diluted with DCM (100 mL) and washed with a saturated solution of $NaHCO_3$. The organic layer was then dried and concentrated in vacuo. The resulting residue was dissolved in AcOH (20 mL) and heated at 70° C. for 22 h. After cooling to RT, volatiles were removed in vacuo and the residue was purified by column chromatography (Si—PCC, gradient 0-30% EtOAc in DCM) affording [(S)-1-(7-Chloro-1-phenyl-1H-benzoimidazol-2-yl)ethyl]carbamic acid tertbutyl ester as pale yellow oil (quantitative). LCMS: $R_T$ 3.83 min $[M+H-^tBu]^+$ 316.0.

Step 4

To a solution of [(S)-1-(7-chloro-1-phenyl-1H-benzoimidazol-2-yl)ethyl]carbamic acid tertbutyl ester (2.26 mmol) in DCM (5 mL) was added TFA (5 mL) and the mixture was stirred at RT for 3 h. The crude reaction mixture was loaded onto an Isolute® SCX-2 cartridge which was washed with MeOH and the product was eluted with 2M $NH_3$/MeOH. The product containing fractions were combined and concentrated in vacuo affording (S)-1-(7-Chloro-1-phenyl-1H-benzoimidazol-2-yl)ethylamine as a pale orange oil (482 mg, 78%). LCMS: $R_T$ 2.11 and 2.24 min $[M+H]^+$ 271.9

Example 20

4-chloro-5H-pyrrolo[3,2-d]pyrimidine

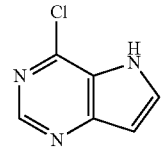

Step 1: diethyl 2-(2-cyanovinylamino)malonate

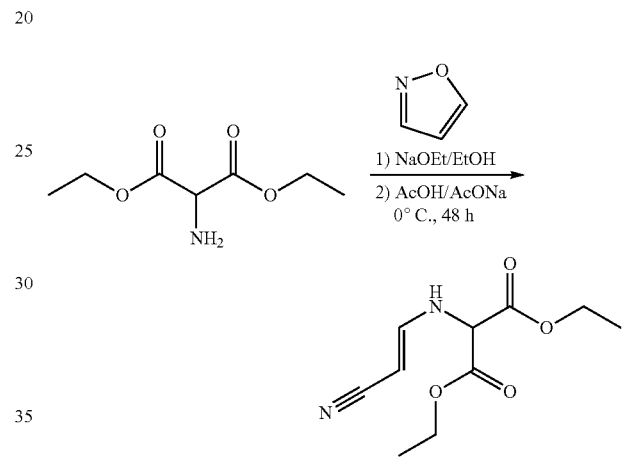

Into a 500-mL round-bottom flask was placed isoxazole (25 g, 354.76 mmol, 1.00 equiv, 98%) in ethanol (100 mL) and sodium ethanolate (124 mL, 21%). The resulting solution was stirred at 0° C. for 30 min. Then acetic acid (6.9 mL, 98%), sodium acetate (20.5 g, 244.91 mmol, 0.69 equiv, 98%) and diethyl 2-aminomalonate hydrochloride (48 g, 222.26 mmol, 0.63 equiv, 98%) were added. The resulting solution was allowed to react, with stirring, for an additional 48 h at room temperature, concentrated under vacuum, dissolved in 200 mL of dichloromethane, washed with 2×100 mL of water, dried over anhydrous sodium sulfate and concentrated to afford 30 g (37%) of diethyl 2-(2-cyanovinylamino)malonate as a yellow oil Step 2: ethyl 3-amino-1H-pyrrole-2-carboxylate

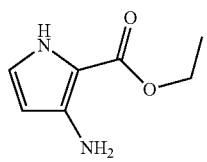

Into a 1000-mL round-bottom flask was placed a solution of diethyl 2-(2-cyanovinylamino)malonate (30 g, 119.3 mmol, 1.00 equiv, 90%) in ethanol (420 mL) and sodium ethanolate (80 mL, 21%). The resulting solution was stirred for 3 days at room temperature. After the addition of acetic acid (15 ml), the resulting mixture was concentrated under vacuum, dissolved in 200 mL of dichloromethane, washed with 2×100 mL of saturated aqueous sodium bicarbonate and 1×100 mL of brine, dried over anhydrous sodium sulfate and concentrated. The residue was dried in HV to afford 10 g (49%) of ethyl 3-amino-1H-pyrrole-2-carboxylate as an orange syrup.

Step 3: 3H-pyrrolo[3,2-d]pyrimidin-4(5H)-one

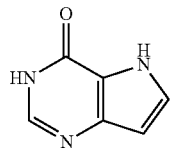

Into a 250-mL round-bottom flask was placed a solution of ethyl 3-amino-1H-pyrrole-2-carboxylate (10 g, 58.38 mmol, 1.00 equiv, 90%) in ethanol (150 mL) and formamidine acetate (10 g, 94.13 mmol, 1.61 equiv, 98%). The resulting solution was stirred at reflux for 16 h. The precipitates were collected by filtration, washed with ethanol and dried under reduced pressure to afford 5 g (61%) of 3H-pyrrolo[3,2-d]pyrimidin-4(5H)-one as a gray solid Step 4

Into a 50-mL round-bottom flask was placed a solution of 3H-pyrrolo[3,2-d]pyrimidin-4(5H)-one (5 g, 35.52 mmol, 1.00 equiv, 96%) in trichlorophosphate (20 mL). The resulting solution was stirred at reflux for 1 h, concentrated under vacuum, dissolved in 100 mL of ethyl acetate, washed with 2×100 mL of 10% aqueous sodium bicarbonate and 1×100 mL of brine, dried over anhydrous sodium sulfate and concentrated under vacuum. The residue was applied onto a silica gel column eluted with ethyl acetate/petroleum ether (1:8) to afford 2 g (36%) of 4-chloro-5H-pyrrolo[3,2-d]pyrimidine as a yellow solid.

Example 21

N-(1-(3-phenyl-1-tosyl-1H-indol-2-yl)ethyl)-9H-purin-6-amine

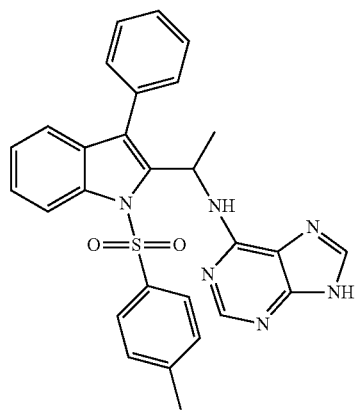 [SMILES: Cc1ccc(S(=O)(=O)n2c(C(C)Nc3ncnc4[nH]cnc34)c(-c3ccccc3)c3ccccc32)cc1]

Step 1: 3-Phenyl-1-(toluene-4-sulfonyl)-1H-indole-2-carboxylic acid ethyl ester

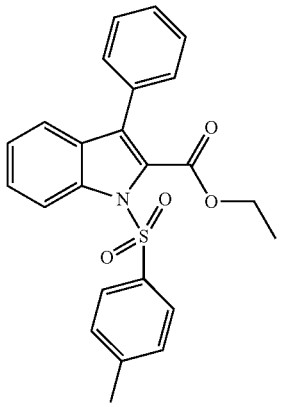 [SMILES: CCOC(=O)c1c(-c2ccccc2)c2ccccc2n1S(=O)(=O)c1ccc(C)cc1]

To a stirred solution of 3-phenyl-1H-indole-2-carboxylic acid ethyl ester (3.99 g, 15.0 mmol) in DMF (25 mL) cooled to 0° C. and under a nitrogen atmosphere was added NaH (60% in mineral oil, 720 mg, 18.0 mmol). After stirring for 10 min at RT, the reaction mixture was cooled to 0° C. and 4-methylbenzenesulfonyl chloride (3.44 g, 18.0 mmol) in DMF (15 mL) was added. Stirring was continued for 16 h at RT then the mixture was poured into 1.0M HCl and extracted with EtOAc (×2). The combined organic layers were washed with water, then dried ($Na_2SO_4$) and concentrated in vacuo. The resulting residue was purified by column chromatography (Si—PCC, gradient 30-100% DCM in pentane) affording 3-Phenyl-1-(toluene-4-sulfonyl)-1H-indole-2-carboxylic acid ethyl ester as a colourless oil (3.25 g, 52%). $^1$H NMR ($CDCl_3$, 400 MHz): δ 8.08 (1H, d, J=8.43 Hz), 7.92 (2H, d, J=8.37 Hz), 7.53-7.36 (7H, m), 7.28-7.21 (3H, m), 4.35 (2H, q, J=7.15 Hz), 2.36 (3H, s), 1.25 (3H, t, J=7.14 Hz).

Step 2: [3-Phenyl-1-(toluene-4-sulfonyl)-1H-indol-2-yl]methanol

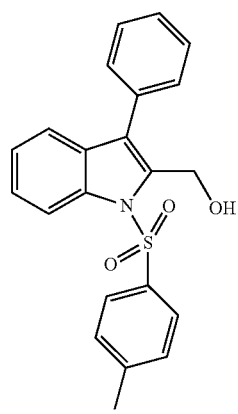 [SMILES: Cc1ccc(S(=O)(=O)n2c(CO)c(-c3ccccc3)c3ccccc32)cc1]

To a stirred solution of 3-phenyl-1-(toluene-4-sulfonyl)-1H-indole-2-carboxylic acid ethyl ester (3.24 g, 7.72 mmol) in toluene (40 mL) cooled to −78° C. and under a nitrogen atmosphere was added 1.0M DIBAL-H in toluene (23.2 mL, 23.2 mmol). The reaction mixture was stirred at −78° C. for 15 min and then at −10° C. for 30 min. After re-cooling to −78° C., the reaction mixture was quenched with water (20 mL) and then allowed to warm to RT. The mixture was partitioned between EtOAc and 1.0M HCl and the aqueous phase was extracted with additional EtOAc (×3). The combined organic layers were washed with water, then dried (Na₂SO₄) and concentrated in vacuo. The resulting residue was purified by column chromatography (Si—PCC, gradient 30-100% DCM in pentane) affording [3-Phenyl-1-(toluene-4-sulfonyl)-1H-indol-2-yl]methanol as a white foam (2.49 g, 85%). LCMS: $R_T$ 4.77 min [M+Na]⁺ 400.1.

Step 3: 3-Phenyl-1-(toluene-4-sulfonyl)-1H-indole-2-carbaldehyde

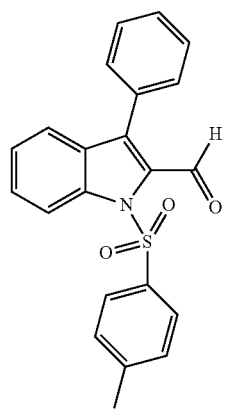 [SMILES: Cc1ccc(S(=O)(=O)n2c(C=O)c(-c3ccccc3)c3ccccc32)cc1]

To a stirred solution of oxalyl chloride (1.37 g, 10.8 mmol) in DCM (30 mL) cooled to −78° C. and under a nitrogen atmosphere was added DMSO (1.50 mL, 21.6 mmol). After stirring for 10 min at −78° C., a solution of [3-phenyl-1-(toluene-4-sulfonyl)-1H-indol-2-yl]methanol (2.27 g, 6.01 mmol) in DCM (20 mL) was added and stirring was continued for 1.5 h. Triethylamine was then added and, after stirring for 10 min at −78° C., the mixture was slowly warmed to RT. The reaction mixture was then poured into a 1.0M aq HCl solution and extracted with DCM (×3). The combined organic layers were washed with water, then with brine, dried (Na₂SO₄) and concentrated in vacuo affording 3-Phenyl-1-(toluene-4-sulfonyl)-1H-indole-2-carbaldehyde as a gum which then solidified on standing to give an off-white solid (2.26 g, 100%). ¹H NMR (CDCl₃, 400 MHz): δ 10.22 (1H, s), 8.31 (1H, d, J=8.56 Hz), 7.86-7.81 (2H, m), 7.60-7.41 (7H, m), 7.33-7.21 (3H, m), 2.37 (3H, s).

Step 4: 1-[3-Phenyl-1-(toluene-4-sulfonyl)-1H-indol-2-yl]ethanol

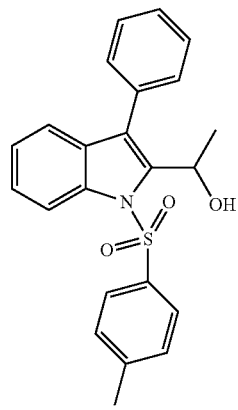 [SMILES: Cc1ccc(S(=O)(=O)n2c(C(C)O)c(-c3ccccc3)c3ccccc32)cc1]

To a solution of 3-phenyl-1-(toluene-4-sulfonyl)-1H-indole-2-carbaldehyde (2.11 g, 5.62 mmol) in THF (30 mL) cooled to −78° C. and under a nitrogen atmosphere, was added 3.0M MeMgBr in diethyl ether (2.6 mL). The mixture was stirred at 0° C. for 30 min and then additional 3.0M MeMgBr in diethyl ether (0.3 mL) was added. After 15 min stirring, the reaction mixture was poured into a saturated solution of NH₄Cl and extracted with EtOAc (×2). The combined organic layers were washed with water, then dried (Na₂SO₄) and concentrated in vacuo. The crude material was combined with a second portion of crude reaction mixture obtained following the same method (starting from 140 mg, 3.73 mmol of 3-phenyl-1-(toluene-4-sulfonyl)-1H-indole-2-carbaldehyde) and the combined batches were purified by column chromatography (Si—PCC, gradient 20-100% DCM in pentane) affording the title compound as a gum which then solidified on standing (2.02 g, 86%). ¹H NMR (CDCl₃, 400 MHz): δ 8.07 (1H, d, J=8.35), 7.80-7.75 (2H, m), 7.51-7.38

(5H, m), 7.33-7.26 (2H, m), 7.20-7.14 (3H, m), 5.25-5.15 (1H, m), 4.06 (1H, d, J=11.01 Hz), 2.31 (3H, s), 1.70 (3H, d, J=6.88 Hz).

Step 5: 2-(1-Azidoethyl)-3-phenyl-1-(toluene-4-sulfonyl)-1H-indole

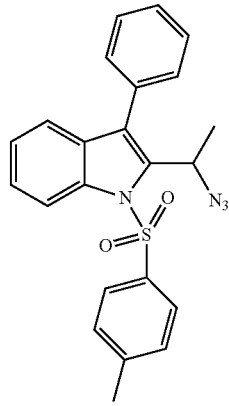 [SMILES: Cc1ccc(S(=O)(=O)n2c(C(C)N=[N+]=[N-])c(-c3ccccc3)c3ccccc32)cc1]

A solution of DIAD (1.80 g, 8.89 mmol) in dioxane (5 mL) was added to a solution of triphenylphosphine (2.33 g, 8.89 mmol) in dioxane (20 mL) at 0° C. under a nitrogen atmosphere. After 10 min stirring, 1-[3-phenyl-1-(toluene-4-sulfonyl)-1H-indol-2-yl]ethanol (1.74 g, 4.44 mmol) in dioxane (15 mL) was added followed by diphenylphosphoryl azide (1.47 g, 5.53 mmol) in dioxane (5 mL). Stirring at 20° C. was continued for 16 h and then the crude reaction mixture was diluted with DCM and purified by column chromatography (Si—PCC, gradient 10-100% DCM in pentane) affording 2-(1-Azidoethyl)-3-phenyl-1-(toluene-4-sulfonyl)-1H-indole as a gum (1.39 g, 75%). LCMS: $R_T$ 4.77 min [M-N$_3$]$^+$ 374.1.

Step 6: 1-[3-Phenyl-1-(toluene-4-sulfonyl)-1H-indol-2-yl]ethylamine

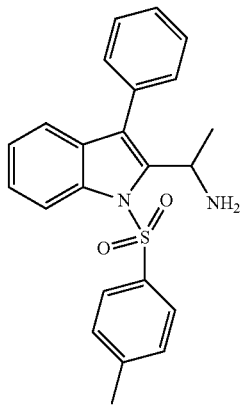 [SMILES: Cc1ccc(S(=O)(=O)n2c(C(C)N)c(-c3ccccc3)c3ccccc32)cc1]

A mixture of 2-(1-azidoethyl)-3-phenyl-1-(toluene-4-sulfonyl)-1H-indole (1.34 g, 3.22 mmol) and 10% Pd/C (200 mg) in EtOAc (80 mL) was degassed with a stream of nitrogen and stirred at RT under a hydrogen atmosphere for 20 h. The suspension was then filtered and the filtrate was concentrated in vacuo. The resulting residue was purified by column chromatography (Si—PCC, gradient 0-10% MeOH in DCM) affording 1-[3-Phenyl-1-(toluene-4-sulfonyl)-1H-indol-2-yl]ethylamine as a white solid (960 mg, 76%). $^1$H NMR (CDCl$_3$, 400 MHz): δ 8.18 (1H, d, J=8.44 Hz), 7.73 (2H, d, J=8.44 Hz), 7.49-7.15 (10H, m), 4.72 (1H, q, J=6.96 Hz), 2.35 (3H, s), 1.45 (3H, d, J=7.40 Hz)

Step 7

A mixture of 1-[3-phenyl-1-(toluene-4-sulfonyl)-1H-indol-2-yl]ethylamine (294 mg, 0.753 mmol), 6-chloro-9H-purine (140 mg, 0.903 mmol) and DIPEA (0.20 mL, 1.13 mmol) in n-butanol (1.5 mL) was stirred in a sealed tube for 56 h at 120° C. After cooling to RT, the crude reaction mixture was loaded onto an Isolute® SCX-2 cartridge which was washed with MeOH and the product eluted with 2M NH$_3$/MeOH. The product containing fractions were combined and concentrated under reduced pressure. The resulting residue was purified by column chromatography (Si—PCC, gradient 0-7% 2M NH$_3$/MeOH in DCM) affording N-(1-(3-phenyl-1-tosyl-1H-indol-2-yl)ethyl)-9H-purin-6-amine as a yellow solid (350 mg, 91%). LCMS: $R_T$ 3.31 min [M+H]$^+$ 509.1

Example 22

9-((3-phenyl-1-tosyl-1H-indol-2-yl)methyl)-9H-purin-6-amine

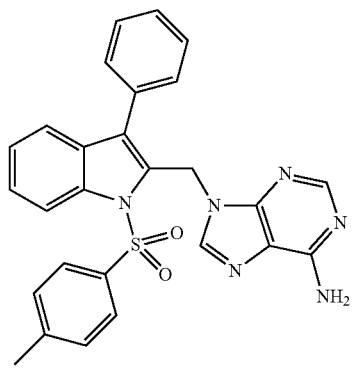 [SMILES: Cc1ccc(S(=O)(=O)n2c(Cn3cnc4c(N)ncnc43)c(-c3ccccc3)c3ccccc32)cc1]

Step 1: 2-Bromomethyl-3-phenyl-1-(toluene-4-sulfonyl)-1H-indole

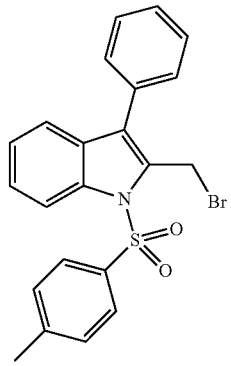 [SMILES: Cc1ccc(S(=O)(=O)n2c(CBr)c(-c3ccccc3)c3ccccc32)cc1]

To a solution of [3-phenyl-1-(toluene-4-sulfonyl)-1H-indol-2-yl]methanol (1.31 g, 3.47 mmol) and triphenylphosphine (1.09 g, 4.16 mmol) in DCM (30 mL) at RT under a nitrogen atmosphere was added NBS (240 mg, 4.16 mmol) and stirring was continued for 2 h. Volatiles were removed under reduced pressure and the resulting residue was purified by column chromatography (Si—PCC, gradient 30-100% DCM in pentane) affording 2-Bromomethyl-3-phenyl-1-(toluene-4-sulfonyl)-1H-indole as a gum (440 mg, 29%). $^1$H NMR (CDCl$_3$, 400 MHz): δ 8.16 (1H, dt, J=8.48, 0.84 Hz), 7.92-7.88 (2H, m), 7.60-7.49 (4H, m), 7.48-7.37 (3H, m), 7.28-7.22 (3H, m), 5.05 (2H, s), 2.38 (3H, s).

Step 2

To a stirred mixture of 9H-purin-6-ylamine (130 mg, 0.976 mmol) in DMF (5 mL) under an argon atmosphere was added NaH (60% in mineral oil, 40 mg, 0.976 mmol). After stirring for 10 min at RT, 2-bromomethyl-3-phenyl-1-(toluene-4-sulfonyl)-1H-indole (430 mg, 0.976 mmol) in DMF (10 mL) was added and stirring was continued for 15 min. The crude reaction mixture was loaded onto an Isolute® SCX-2 cartridge which was washed with MeOH and the product eluted with 2M NH$_3$/MeOH. The product containing fractions were combined and concentrated under reduced pressure. The resulting residue was purified by column chromatography (Si—PCC, gradient 0-10% MeOH in DCM) affording 9-((3-phenyl-1-tosyl-1H-indol-2-yl)methyl)-9H-purin-6-amine as a white solid (370 mg, 77%). LCMS: R$_T$ 3.16 min [M+H]$^+$ 495.1

Example 23

1-(3-phenylbenzo[b]thiophen-2-yl)ethanamine

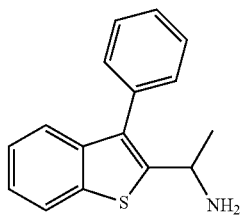 [SMILES: CC(N)c1sc2ccccc2c1-c1ccccc1]

Step 1: 1-(3-phenylbenzo[b]thiophen-2-yl)ethanol

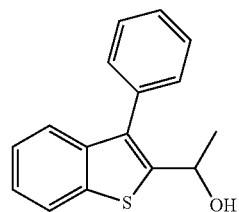 [SMILES: CC(O)c1sc2ccccc2c1-c1ccccc1]

To a solution of 3-phenylbenzo[b]thiophene-2-carbaldehyde (430 mg, 1.87 mmol) in THF (10 mL) cooled to −78° C. and under a nitrogen atmosphere was added 3.0M MeMgBr in diethyl ether (1.24 mL) and stirring was continued for 30 min. The reaction mixture was quenched with a saturated solution of NH$_4$Cl (20 mL) and slowly warmed to RT. The mixture was extracted with EtOAc (×2) and the combined organic layers were washed with water, then dried (Na$_2$SO$_4$) and concentrated in vacuo affording 1-(3-phenylbenzo[b]thiophen-2-yl)ethanol as a white solid (472 mg, quantitative). $^1$H NMR (CDCl$_3$, 400 MHz): δ 7.88-7.84 (1H, m), 7.52-7.28 (8H, m), 5.21 (1H, q, J=6.35 Hz), 2.03 (1H, s), 1.59 (3H, d, J=6.63 Hz).

Step 2: 2-(1-Azidoethyl)-3-phenylbenzo[b]thiophene

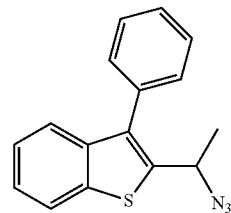 [SMILES: CC(N=[N+]=[N-])c1sc2ccccc2c1-c1ccccc1]

DIAD (556 mg, 2.75 mmol) was added to a solution of triphenylphosphine (722 mg, 2.75 mmol) in dioxane (5 mL) at 0° C. under a nitrogen atmosphere. After 10 min stirring, 1-(3-phenylbenzo[b]thiophen-2-yl)ethanol (350 mg, 1.37 mmol) was added followed by diphenylphosphoryl azide (454 mg, 1.65 mmol). Stirring at 20° C. was continued for 16 h and then volatiles were concentrated in vacuo. The crude reaction mixture was purified by column chromatography (Si—PCC, gradient 0-20% DCM in cyclohexane) affording 2-(1-Azidoethyl)-3-phenylbenzo[b]thiophene as a colourless oil (211 mg, 55%). $^1$H NMR (CDCl$_3$, 400 MHz): δ 7.88 (1H, d, J=7.87 Hz), 7.54-7.42 (4H, m), 7.41-7.29 (4H, m), 4.97 (1H, q, J=6.80 Hz), 1.58 (3H, d, J=6.80 Hz).

Step 3

2-(1-Azidoethyl)-3-phenylbenzo[b]thiophene (211 mg, 0.756 mmol) was dissolved in a mixture THF (4 mL) and water (0.27 mL) and triphenylphosphine (237 mg, 0.91 mmol) was added. The mixture was stirred at RT for 1 h and then additional triphenylphosphine (237 mg) was added. Stirring was continued for 1 h and the crude reaction mixture was loaded onto an Isolute® SCX-2 cartridge which was washed with MeOH and the product eluted with 2M NH$_3$/MeOH. The product containing fractions were combined and concentrated under reduced pressure. The resulting residue was purified by column chromatography (Si—PCC, gradient 0-8% MeOH in DCM) affording 1-(3-phenylbenzo[b]thiophen-2-yl)ethanamine as a white solid (160 mg, 83%). $^1$H NMR (CDCl$_3$, 400 MHz): δ 7.84 (1H, dd, J=7.63, 1.55 Hz), 7.52-7.27 (8H, m), 4.56-4.44 (1H, br), 1.76 (2H, s), 1.47 (3H, d, J=6.21 Hz).

Example 24

1-(3-phenylbenzofuran-2-yl)ethanamine

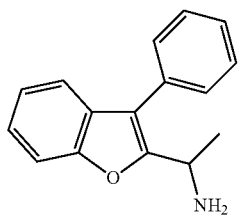 [SMILES: CC(N)c1oc2ccccc2c1-c1ccccc1]

Step 1: 1-(3-phenylbenzofuran-2-yl)ethanol

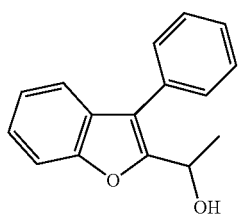 [SMILES: CC(O)c1oc2ccccc2c1-c1ccccc1]

Tetrabutylammonium borohydride (nBu$_4$NBH$_4$) (750 mg, 2.91 mmol) was added to a solution of 1-(3-phenylbenzofuran-2-yl)ethanone (459 mg, 1.94 mmol) in THF (9 mL) and IMS (1 mL) and the mixture was stirred at RT for 1 h. The reaction mixture was then quenched by addition of MeOH and volatiles were removed under reduced pressure. The resulting residue was purified by column chromatography (Si—PCC, gradient 0-40% EtOAc in cyclohexane) affording 1-(3-phenylbenzofuran-2-yl)ethanol as an oil (452 mg, 98%). LCMS: R$_T$ 3.57 min [M−OH]$^+$ 221.1

Step 2: 2-(1-Azidoethyl)-3-phenylbenzofuran

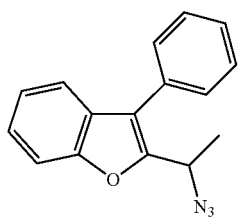

DBU (155 μL, 1.04 mmol) was added dropwise to a solution of 1-(3-phenylbenzofuran-2-yl)ethanol (206 mg, 0.864 mmol) and diphenyl phosphoryl azide (255 μL, 1.04 mmol) in anhydrous THF (7 mL) at 0° C. under a nitrogen atmosphere. After 30 min stirring at 0° C., the mixture was slowly warmed to RT and stirring was continued for 1.5 h. Additional diphenyl phosphoryl azide (255 μL, 1.04 mmol) and DBU (155 μL, 1.04 mmol) were added and stirring was continued for 18 h. Volatiles were removed under reduced pressure and the resulting residues was purified by column chromatography (Si—PCC, gradient 0-30% EtOAc in cyclohexane) affording the title compound as an oil (186 mg, 82%). LCMS: R$_T$ 4.48 min [M+H-N$_2$]$^+$ 236.1.

Step 3

Triphenylphosphine (231 mg, 0.883 mmol) was added to a solution of 2-(1-azidoethyl)-3-phenylbenzofuran (186 mg, 0.706 mmol) in THF (9 mL) and water (1 mL). The mixture was heated at 60° C. for 2 h and then cooled to RT. Volatiles were removed under reduced pressure and the resulting residue was purified by column chromatography (Si—PCC, gradient 0-10% MeOH in EtOAc) affording 1-(3-phenylbenzofuran-2-yl)ethanamine as an oil (327 mg, quantitative). LCMS: R$_T$ 2.21 min [M−NH$_2$]$^+$ 221.1

Example 25

(3-phenylbenzofuran-2-yl)methyl methanesulfonate

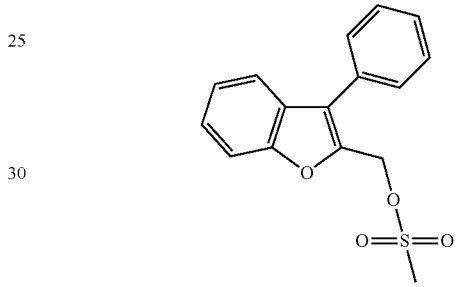

Methanesulfonyl chloride (160 μL, 2.05 mmol) was added dropwise to a solution of (3-phenylbenzofuran-2-yl)methanol (367 mg, 1.64 mmol) and DIPEA (343 μL, 1.97 mmol) in anhydrous DCM (10 mL) at 0° C. Stirring at 0° C. was continued for 15 min, then the mixture was slowly warmed to RT. After 2 h stirring at RT, additional amounts of methanesulfonyl chloride (80 μL, 1.03 mmol) and DIPEA (172 μL, 0.99 mmol) were added and stirring was continued for 1.5 h. The reaction mixture was diluted with DCM and the organic layer was washed with water, then dried (Na$_2$SO$_4$) and concentrated in vacuo affording (3-phenylbenzofuran-2-yl)methyl methanesulfonate as an oil (443 mg, 89%). $^1$H NMR (DMSO, 400 MHz): δ 7.71-7.64 (2H, m), 7.62-7.56 (4H, m), 7.52-7.41 (2H, m), 7.37-7.32 (1H, m), 4.98 (2H, s), 3.89 (3H, s)

Example 26

(3-phenylbenzo[b]thiophen-2-yl)methanamine

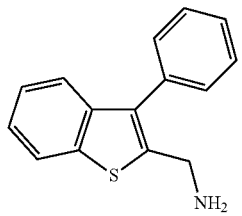 [SMILES: NCc1sc2ccccc2c1-c1ccccc1]

Step 1: (3-phenylbenzo[b]thiophen-2-yl)methyl methanesulfonate

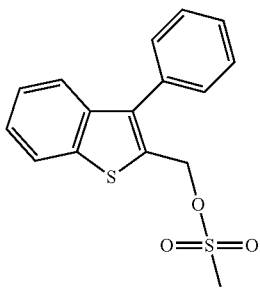 [SMILES: CS(=O)(=O)OCc1sc2ccccc2c1-c1ccccc1]

Methanesulfonyl chloride (127 μL, 1.63 mmol) was added dropwise to a solution of (3-phenylbenzo[b]thiophen-2-yl)methanol (356 mg, 1.48 mmol) and DIPEA (322 μL, 1.85 mmol) in anhydrous DCM (10 mL) at 0° C. Stirring at 0° C. was continued for 15 min, then the mixture was slowly warmed to RT. After 2.5 h stirring at RT, additional methanesulfonyl chloride (1 drop) was added and stirring was continued for 1 h. The reaction mixture was diluted with DCM and the organic layer was washed with water, then dried ($Na_2SO_4$) and concentrated in vacuo affording (3-phenylbenzo[b]thiophen-2-yl)methyl methanesulfonate as a yellow oil (408 mg, 87%). $^1$H NMR (DMSO, 400 MHz): δ 8.07-8.02 (1H, m), 7.62-7.56 (2H, m), 7.55-7.37 (6H, m), 4.96 (2H, s), 3.33 (3H, s).

Step 2: 2-Azidomethyl-3-phenylbenzo[b]thiophene

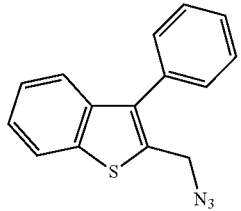 [SMILES: [N-]=[N+]=NCc1sc2ccccc2c1-c1ccccc1]

Sodium azide (179 mg, 2.76 mmol) was added to a solution of methanesulfonic acid 3-phenylbenzo[b]thiophen-2-ylmethyl ester (828 mg, 1.84 mmol) in DMF (10 mL) and the mixture was stirred at RT for 18 h. The reaction mixture was diluted with water and extracted with EtOAc. The organic layer was washed with brine, then dried ($Na_2SO_4$) and concentrated in vacuo and the resulting residue was purified by column chromatography (Si—PCC, gradient 0-35% DCM in cyclohexane) affording 2-azidomethyl-3-phenylbenzo[b]thiophene as a clear oil (244 mg, 50%). LCMS: $R_T$ 4.46 min [M+H-$N_2$]$^+$ 237.8.

Step 3

A solution of 2-azidomethyl-3-phenylbenzo[b]thiophene (244 mg, 0.92 mmol) in THF (10 mL) was treated with a solution of triphenylphosphine (302 mg, 1.15 mmol) in water (1 mL) under a nitrogen atmosphere. The mixture was heated to 60° C. for 2 h and then cooled to RT. Volatile were removed under reduced pressure and the resulting residue was loaded onto an Isolute® SCX-2 cartridge which was washed with MeOH and the product eluted with 2M $NH_3$/MeOH. The product containing fractions were combined and concentrated in vacuo affording (3-phenylbenzo[b]thiophen-2-yl)methanamine (288 mg, quantitative). LCMS: $R_T$ 2.15 min [M-$N_3$]$^+$ 223.0

Example 27

(3-o-tolylbenzo[b]thiophen-2-yl)methyl methanesulfonate

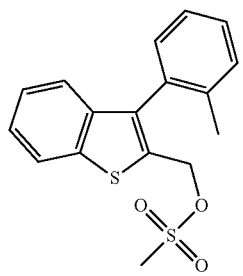 [SMILES: Cc1ccccc1-c1c(COS(C)(=O)=O)sc2ccccc12]

Step 1: 3-o-tolylbenzo[b]thiophene-2-carbaldehyde

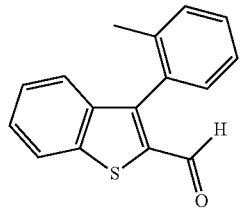 [SMILES: Cc1ccccc1-c1c(C=O)sc2ccccc12]

A mixture of 3-bromobenzo[b]thiophene-2-carbaldehyde (500 mg, 2.07 mmol), 2-methylphenylboronic acid (394 mg, 2.90 mmol), Pd(PPh$_3$)$_4$ (243 mg, 0.21 mmol), $Cs_2CO_3$ (2.02 g, 6.21 mmol) in dioxane (12 mL) and water (4 mL) was degassed with a stream of nitrogen and then was heated at 130° C. in a sealed tube using microwave irradiation for 45 min. The reaction mixture was extracted with EtOAc, then the organic layer was washed with water, followed by brine, dried ($Na_2SO_4$) and concentrated in vacuo. The resulting residue was purified by column chromatography (Si—PCC, gradient 0-70% DCM in cyclohexane) affording the title compound (quantitative yield). LCMS: $R_T$ 4.16 min.

Step 2: (3-o-Tolylbenzo[b]thiophen-2-yl)methanol

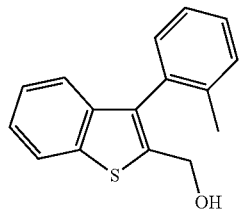 [SMILES: Cc1ccccc1-c1c(CO)sc2ccccc12]

Tetrabutylammonium borohydride (nBu$_4$NBH$_4$) (800 mg, 3.10 mmol) was added at RT to a solution of 3-o-tolylbenzo

[b]thiophene-2-carbaldehyde (2.07 mmol) in THF (10 mL) and IMS (1 mL) and the mixture was stirred at RT for 1 h. The reaction mixture was then quenched by addition of MeOH and volatiles were removed under reduced pressure. The resulting residues was purified by column chromatography (Si—PCC, gradient 0-30% EtOAc in cyclohexane) affording the title compound as an oil (432 mg, 82% over 2 steps). LCMS: $R_T$ 3.74 min [M-OH]$^+$ 237.1.

Step 3

Methanesulfonyl chloride (158 µL, 2.04 mmol) was added dropwise to a solution of (3-o-tolylbenzo[b]thiophen-2-yl)methanol (432 mg, 1.70 mmol) and DIPEA (385 µL, 2.21 mmol) in anhydrous DCM (10 mL) at RT. Stirring at RT was continued for 18 h then the reaction mixture was washed with water, then dried (Na$_2$SO$_4$) and concentrated in vacuo affording (3-o-tolylbenzo[b]thiophen-2-yl)methyl methanesulfonate as a brown oil (424 mg, 75%). $^1$H NMR (DMSO, 400 MHz): δ 8.05 (1H, d, J=8.04 Hz), 7.45-7.40 (3H, m), 7.38-7.32 (2H, m), 7.21 (1H, d, J=7.40 Hz), 7.12 (1H, d, J=7.98 Hz), 4.82 (1H, d, J=12.41 Hz), 4.76 (1H, d, J=12.41 Hz), 3.32 (3H, s), 1.99 (3H, s)

Example 28

(S)-1-(6-fluoro-1-phenyl-1H-benzo[d]imidazol-2-yl)propan-1-amine

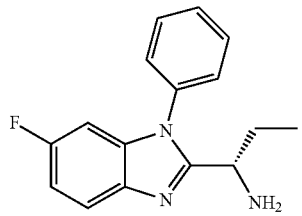

Step 1: (S)-tert-butyl 1-(6-fluoro-1-phenyl-1H-benzo[d]imidazol-2-yl)propylcarbamate

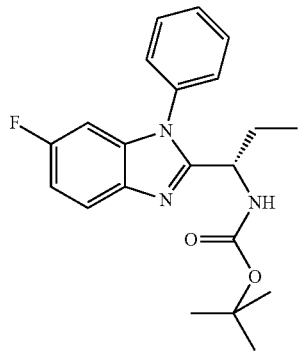 [SMILES: CC[C@H](NC(=O)OC(C)(C)C)c1nc2ccc(F)cc2n1-c1ccccc1]

A mixture of 4-fluoro-N$^2$-phenylbenzene-1,2-diamine from Example 8 (199 mg, 0.984 mmol), (S)-2-tertbutoxycarbonylaminobutyric acid (219 mg, 1.08 mmol), HOAt (147 mg, 1.08 mmol), 4-methylmorpholine (0.238 mL, 2.16 mmol) and N-(3-dimethylaminopropyl)-N'-ethylcarbodiimide hydrochloride (207 mg, 1.08 mmol) in DCM (5 mL) was stirred at RT for 2 h. The reaction mixture was then partitioned between DCM (50 mL) and a saturated solution of NaHCO$_3$. The organic layer was dried (Na$_2$SO$_4$) and concentrated in vacuo and the resulting residue was dissolved in AcOH (10 mL) and stirred for 18 h at 70° C. After cooling to RT, volatiles were evaporated in vacuo and the residue was partitioned between DCM (50 mL) and a saturated solution of NaHCO$_3$. The organic layer was washed with brine, dried (Na$_2$SO$_4$) and then concentrated in vacuo. The resulting residue was purified by column chromatography (Si—PCC, gradient 0-50% EtOAc in cyclohexane) affording (S)-tert-butyl 1-(6-fluoro-1-phenyl-1H-benzo[d]imidazol-2-yl)propylcarbamate as a beige solid (234 mg, 64%). LCMS: $R_T$ 3.82 min [M+H]$^+$ 370.5

Step 2

To a solution of (S)-tert-butyl 1-(6-fluoro-1-phenyl-1H-benzo[d]imidazol-2-yl)propylcarbamate (234 mg, 0.63 mmol) in DCM (3 mL) was added TFA (1.5 mL) and the mixture was stirred at RT for 2 h. Volatiles were removed under reduced pressure and the resulting residue was partitioned between DCM (20 mL) and a saturated solution of NaHCO$_3$. The two phase system was stirred for 10 min, then the organic layer was dried (MgSO$_4$) and concentrated in vacuo. The resulting residue was purified by column chromatography (Si—PCC, gradient 0-10% MeOH in DCM) affording (S)-1-(6-fluoro-1-phenyl-1H-benzo[d]imidazol-2-yl)propan-1-amine as a colourless oil (42 mg, 25%). LCMS: $R_T$ 1.90 min [M−NH$_2$] 253.0

Example 29

(S)-1-(5-fluoro-1-phenyl-1H-benzo[d]imidazol-2-yl)ethanamine

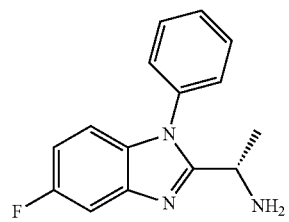 [SMILES: C[C@H](N)c1nc2cc(F)ccc2n1-c1ccccc1]

Step 1: (S)-tert-butyl 1-(5-fluoro-2-(phenylamino)phenylamino)-1-oxopropan-2-ylcarbamate

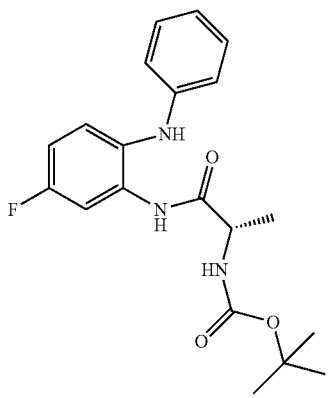 [SMILES: C[C@H](NC(=O)OC(C)(C)C)C(=O)Nc1cc(F)ccc1Nc1ccccc1]

A mixture of 4-fluoro-N$^1$-phenylbenzene-1,2-diamine (866 mg, 4.3 mmol), (S)-2-tertbutoxycarbonylaminopropionic acid (890 mg, 4.7 mmol), HOAt (640 mg, 4.7 mmol), 4-methylmorpholine (1.0 mL, 9.5 mmol) and N-(3-dimethylaminopropyl)-N'-ethylcarbodiimide hydrochloride (900 mg, 4.7 mmol) in DCM (20 mL) was stirred at RT for 2 h. The reaction mixture was then partitioned between DCM (50 mL) and a saturated solution of NaHCO$_3$. The organic layer was washed with brine, then dried (MgSO$_4$) and concentrated in vacuo affording (S)-tert-butyl 1-(5-fluoro-2-(phenylamino)phenylamino)-1-oxopropan-2-ylcarbamate as a yellow-orange solid (quantitative), used in the following step without further purification. LCMS: R$_T$ 3.83 min [M+H]$^+$ 374.1

Step 2: (S)-tert-butyl 1-(5-fluoro-1-phenyl-1H-benzo[d]imidazol-2-yl)ethylcarbamate

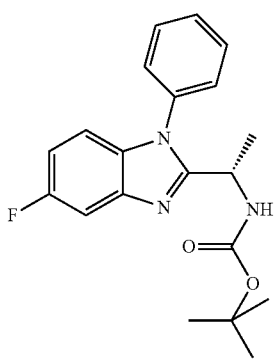 [SMILES: C[C@H](NC(=O)OC(C)(C)C)c1nc2cc(F)ccc2n1-c1ccccc1]

A solution of (S)-tert-butyl 1-(5-fluoro-2-(phenylamino)phenylamino)-1-oxopropan-2-ylcarbamate (2.15 mmol) in AcOH (10 mL) was stirred for 18 h at 70° C. After cooling to RT, volatiles were evaporated under reduced pressure and the residue was partitioned between EtOAc and a saturated solution of NaHCO$_3$. The organic layer was washed with brine, dried (MgSO$_4$) and then concentrated in vacuo. The resulting residue was purified by column chromatography (Si—PCC, gradient 0-40% EtOAc in cyclohexane) affording (S)-tert-butyl 1-(5-fluoro-1-phenyl-1H-benzo[d]imidazol-2-yl)ethylcarbamate as an orange oil (661 mg, 86% over two steps). LCMS: R$_T$ 3.52 min [M+H]$^+$ 356.1

Step 3

To a solution of (S)-tert-butyl 1-(5-fluoro-1-phenyl-1H-benzo[d]imidazol-2-yl)ethylcarbamate (661 mg, 1.9 mmol) in DCM (9 mL) was added TFA (4.5 mL) and the mixture was stirred at RT for 2 h. Volatiles were removed under reduced pressure and the resulting residue was partitioned between DCM (20 mL) and a saturated solution of NaHCO$_3$ (40 mL). The two phase system was stirred for 10 min, then the organic layer was dried (MgSO$_4$) and concentrated in vacuo. The resulting residue was purified by column chromatography (Si—PCC, gradient 0-10% MeOH in DCM) affording (S)-1-(5-fluoro-1-phenyl-1H-benzo[d]imidazol-2-yl)ethanamine as a yellow oil (379 mg, 78%). LCMS: R$_T$ 1.77 min [M+H]$^+$ 256.2

Intermediates

The following intermediates are also useful in the synthesis of compounds of the invention:

(5-Fluoro-2-nitrophenyl)phenylamine (Alternative Prep)

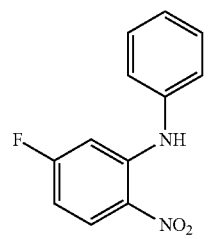 [SMILES: O=[N+]([O-])c1ccc(F)cc1Nc1ccccc1]

To a solution of aniline (30.1 mL, 0.33 mol) in THF (300 mL) at −78° C. was added LiHMDS (408 mL, 1 M in THF, 0.41 mmol) at such a rate that T ≤ −65° C. The reaction mixture was stirred at −78° C. for 30 min and was then added to a solution of 2,4-difluoronitrobenzene (50 g, 0.31 mol) in THF (200 mL) at −78° C. at such a rate that T ≤ −65° C. The mixture was stirred at −78° C. for 2 h. The reaction mixture was diluted with water (300 mL) and EtOAc (300 mL) and the emulsion which formed filtered through Celite®. The layers were separated and the aqueous fraction extracted with EtOAc (3×100 mL). The combined organic extracts were washed with brine, dried (MgSO$_4$) and concentrated in vacuo. The resultant residue was stirred with pentane (300 mL) for 16 h then filtered to give the title compound as a tan solid. (50 g, 68%). $^1$H NMR 400 MHz (CDCl$_3$) δ: 9.64 (1H, br s), 8.26

(1H, dd, J=9.5, 6.0 Hz), 7.49-7.42 (2H, m), 7.32-7.25 (3H, m), 6.80 (1H, dd, J=11.3, 2.5 Hz), 6.51-6.45 (1H, m)

4-Fluoro-N-2-phenylbenzene-1,2-diamine (Alternative Prep)

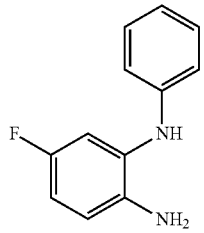

To a solution of (5-fluoro-2-nitrophenyl)phenylamine (50 g, 0.22 mol) in EtOAc (500 mL) was added palladium on carbon (10% by wt, 5 g). The reaction mixture was stirred at RT under an atmosphere of hydrogen for 48 h. The mixture was filtered through Celite® and the filtrate concentrated in vacuo to give the title compound as a purple solid (40.1 g, 92%). $^1$H NMR 400 MHz (CDCl$_3$) δ: 7.28-7.21 (2H, m), 6.93-6.83 (4H, m), 6.72 (1H, dd, J=8.6, 5.6 Hz), 6.68-6.62 (1H, m), 5.29 (1H, br s), 3.49 (2H, br s).

[(S)-1-(4-Fluoro-2-phenylaminophenylcarbamoyl) ethyl]carbamic acid tert-butyl ester (Alternative Prep)

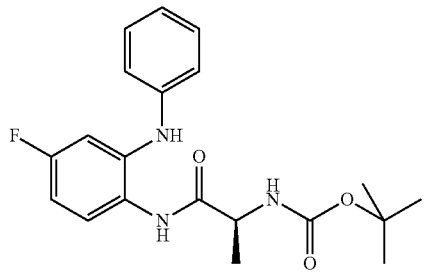 [SMILES: C[C@H](NC(=O)OC(C)(C)C)C(=O)Nc1ccc(F)cc1Nc1ccccc1]

To a solution of 4-fluoro-N-2-phenylbenzene-1,2-diamine (50 g, 0.25 mol), L-Boc-ala-OH (46.8 g, 0.25 mol) and HOAT (33.7 g, 0.25 mol) in DCM (500 mL) at 0° C. was added piece-wise EDC at such a rate that T≤2° C., the reaction mixture was then stirred at 0° C. for 30 min. Water (500 mL) was added causing a white precipitate to form. The mixture was filtered and the filtrate extracted with DCM (3×100 mL). The combined organic fractions were washed with citric acid solution (10% by wt, 100 mL), then sat. aq. NaHCO$_3$, then brine, dried (MgSO$_4$) and concentrated in vacuo. The residue was triturated with pentane to give the title compound as a purple solid (79 g, 86%). $^1$H NMR 400 MHz (CDCl$_3$) δ: 8.03 (1H, br s), 7.44 (1H, dd, J=8.9, 6.0 Hz), 7.29-7.23 (2H, m), 7.03-6.92 (4H, m), 6.64 (1H, td, J=8.7, 2.9 Hz), 6.21 (1H, br s), 4.93 (1H, d, J=6.2 Hz), 4.22 (1H, quintet, 6.8 Hz), 1.44-1.38 (12H, m). LCMS: R$_T$=3.68 min, [M+H-$^t$Bu]$^+$=318

(S)-1-(6-Fluoro-1-phenyl-1H-benzoimidazol-2-yl) ethylamine dihydrochloride (Alternative Prep)

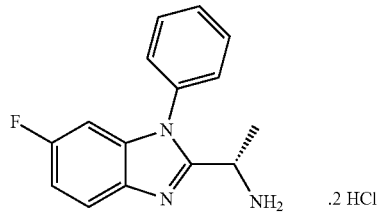 [SMILES: C[C@H](N)c1nc2ccc(F)cc2n1-c1ccccc1]

[(S)-1-(4-Fluoro-2-phenylaminophenylcarbamoyl)ethyl] carbamic acid tert-butyl ester (40 g, 0.11 mol) was dissolved in HCl in dioxane (4N, 135 mL) and the reaction mixture heated at 60° C. for 3 h. The reaction mixture was cooled to RT and seeded with a crystal of the desired product causing the product to crystallise. The product was collected by filtration and dried in vacuo to give the title compound as a purple solid (31.2 g, 89%). $^1$H NMR 400 MHz (DMSO-d$_6$) δ: 8.94 (3H, br s), 7.81 (1H, dd, J=8.8, 4.9 Hz), 7.74-7.62 (5H, m), 7.25-7.18 (1H, m), 6.98 (1H, dd, J=9.0, 2.4), 4.41 (1H, quintet, J=6.3 Hz), 1.45 (3H, d, J=6.4 Hz). LCMS: R$_T$=2.02 min, [M+H]$^+$=256 (10%) [M−NH$_2$]=239 (100%).

[(S)-1-(6-Fluoro-1-phenyl-1H-benzoimidazol-2-yl) ethyl]-[9-(tetrahydropyran-2-yl)-9H-purin-6-yl] amine

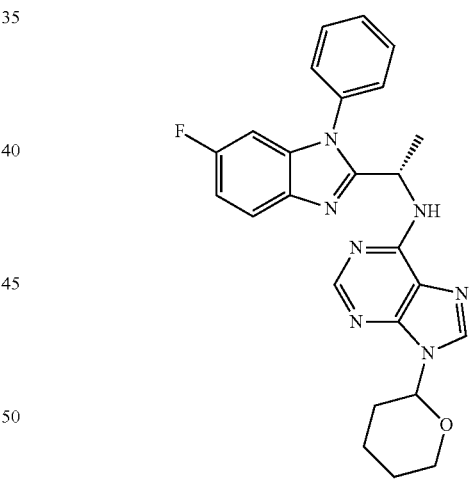

To a solution of (S)-1-(6-fluoro-1-phenyl-1H-benzoimidazol-2-yl)ethylamine dihydrochloride (30.7 g, 93.7 mmol) in IPA (300 mL) was added 6-chloro-9-(tetrahydropyran-2-yl)-9H-purine (26.9 g, 112.5 mmol) and DIPEA (48 mL, 281.2 mmol) and the reaction mixture heated at 80° C. for 16 h. The reaction mixture was concentrated in vacuo and the residue dissolved in EtOAc (600 mL). The solution was washed with water and the organic fraction separated. The organic fraction was washed with brine, dried (MgSO$_4$) and concentrated in vacuo. The resultant residue was subjected to flash chromatography (SiO$_2$, eluting with 0-10% methanol in EtOAc) to yield the title compound as a yellow oil (30 g, 70%) $^1$H NMR 400 MHz (CDCl$_3$) δ 8.25 (1H, s), 7.96 (1H, s), 7.70 (1H, qn, J=4.1 Hz), 7.37-7.58 (5H, m), 6.98-6.82 (1H, m), 6.52-6.66

(1H, m), 5.60-5.77 (2H, m), 4.12-4.19 (1H, m), 3.76 (1H, td, J 11.3, 2.5 Hz), 1.91-2.13 (4H, m), 1.68-1.84 (2H, m), 1.60-1.68 (3H, m)

3-Phenyl-1-(toluene-4-sulfonyl)-1H-indole-2-carboxylic acid ethyl ester

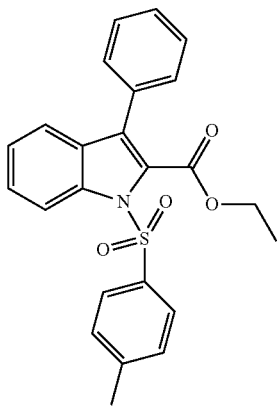 [SMILES: CCOC(=O)c1c(-c2ccccc2)c2ccccc2n1S(=O)(=O)c1ccc(C)cc1]

To a stirred solution of 3-phenyl-1H-indole-2-carboxylic acid ethyl ester (3.99 g, 15.0 mmol) in DMF (25 mL) cooled to 0° C. and under a nitrogen atmosphere was added NaH (60% in mineral oil, 720 mg, 18.0 mmol). After stirring for 10 min at RT, the reaction mixture was cooled to 0° C. and 4-methylbenzenesulfonyl chloride (3.44 g, 18.0 mmol) in DMF (15 mL) added. Stirring was continued for 16 h at RT then the mixture was poured into 1.0M HCl and extracted with EtOAc (×2). The combined organic fractions were washed with water, dried (Na$_2$SO$_4$) and concentrated in vacuo. The resulting residue was purified by column chromatography (Si—PCC, gradient 30-100% DCM in pentane) affording the title compound as a colourless oil (3.25 g, 52%). $^1$H NMR (CDCl$_3$, 400 MHz): δ 8.08 (1H, d, J=8.43 Hz), 7.92 (2H, d, J=8.37 Hz), 7.53-7.36 (7H, m), 7.28-7.21 (3H, m), 4.35 (2H, q, J=7.15 Hz), 2.36 (3H, s), 1.25 (3H, t, J=7.14 Hz)

[3-Phenyl-1-(toluene-4-sulfonyl)-1H-indol-2-yl]methanol

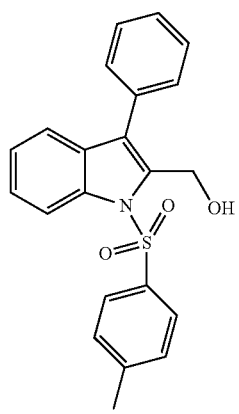 [SMILES: Cc1ccc(S(=O)(=O)n2c(CO)c(-c3ccccc3)c3ccccc32)cc1]

To a stirred solution of 3-phenyl-1-(toluene-4-sulfonyl)-1H-indole-2-carboxylic acid ethyl ester (3.24 g, 7.72 mmol) in toluene (40 mL) at −78° C. and under a nitrogen atmosphere was added 1.0M DIBAL-H in toluene (23.2 mL, 23.2 mmol). The reaction mixture was stirred at −78° C. for 15 min then at −10° C. for 30 min. After re-cooling to −78° C., the reaction mixture was quenched with water (20 mL) then allowed to warm to RT. The mixture was partitioned between EtOAc and 1.0M HCl and the aqueous phase was extracted with additional EtOAc (×3). The combined organic fractions were washed with water, dried (Na$_2$SO$_4$) and concentrated in vacuo. The resulting residue was purified by column chromatography (Si—PCC, gradient 30-100% DCM in pentane) affording the title compound as a white foam (2.49 g, 85%). LCMS (Method C): R$_T$ 4.77 min [M+Na]$^+$ 400.1

3-Phenyl-1-(toluene-4-sulfonyl)-1H-indole-2-carbaldehyde

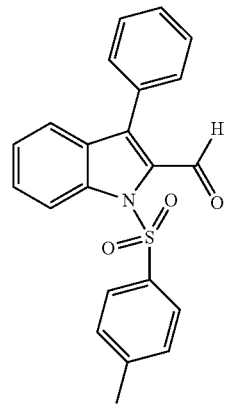 [SMILES: Cc1ccc(S(=O)(=O)n2c(C=O)c(-c3ccccc3)c3ccccc32)cc1]

To a stirred solution of oxalyl chloride (1.37 g, 10.8 mmol) in DCM (30 mL) at −78° C. and under a nitrogen atmosphere was added DMSO (1.50 mL, 21.6 mmol). After stirring for 10 min at −78° C., a solution of [3-phenyl-1-(toluene-4-sulfonyl)-1H-indol-2-yl]methanol (2.27 g, 6.01 mmol) in DCM (20 mL) was added and stirring was continued for 1.5 h. Triethylamine was added and, after stirring for 10 min at −78° C., the mixture was slowly warmed to RT. The reaction mixture was poured into a 1.0M aq HCl solution and extracted with DCM (×3). The combined organic layers were washed with water, then brine, dried (Na$_2$SO$_4$) and concentrated in vacuo affording the title compound as a gum which then solidified on standing to give an off-white solid (2.26 g, 100%). $^1$H NMR (CDCl$_3$, 400 MHz): δ 10.22 (1H, s), 8.31

(1H, d, J=8.56 Hz), 7.86-7.81 (2H, m), 7.60-7.41 (7H, m), 7.33-7.21 (3H, m), 2.37 (3H, s)

1-[3-Phenyl-1-(toluene-4-sulfonyl)-1H-indol-2-yl]ethanol

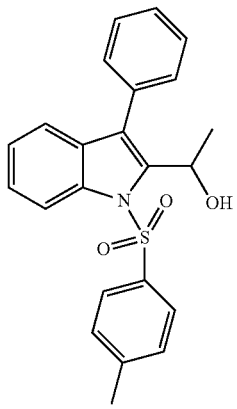 [SMILES: Cc1ccc(S(=O)(=O)n2c(C(C)O)c(-c3ccccc3)c3ccccc32)cc1]

To a solution of 3-phenyl-1-(toluene-4-sulfonyl)-1H-indole-2-carbaldehyde (2.11 g, 5.62 mmol) in THF (30 mL) at −78° C. and under a nitrogen atmosphere, was added 3.0M methylmagnesium bromide in diethyl ether (2.6 mL). The mixture was stirred at 0° C. for 30 min then additional 3.0M methylmagnesium bromide in diethyl ether (0.3 mL) added. After 15 min, the reaction mixture was poured into a saturated solution of NH$_4$Cl and extracted with EtOAc (×2). The combined organic fractions were washed with water, dried (Na$_2$SO$_4$) and concentrated in vacuo. The crude material was combined with a second portion of crude reaction mixture obtained following the same method (starting from 140 mg, 3.73 mmol of 3-phenyl-1-(toluene-4-sulfonyl)-1H-indole-2-carbaldehyde) and the combined batches were purified by column chromatography (Si—PCC, gradient 20-100% DCM in pentane) affording the title compound as a gum which solidified on standing (2.02 g, 86%). $^1$H NMR (CDCl$_3$, 400 MHz): δ 8.07 (1H, d, J=8.35), 7.80-7.75 (2H, m), 7.51-7.38 (5H, m), 7.33-7.26 (2H, m), 7.20-7.14 (3H, m), 5.25-5.15 (1H, m), 4.06 (1H, d, J=11.01 Hz), 2.31 (3H, s), 1.70 (3H, d, J=6.88 Hz)

2-(1-Azidoethyl)-3-phenyl-1-(toluene-4-sulfonyl)-1H-indole

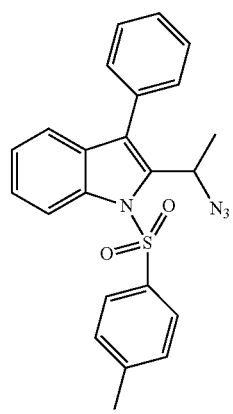 [SMILES: Cc1ccc(S(=O)(=O)n2c(C(C)N=[N+]=[N-])c(-c3ccccc3)c3ccccc32)cc1]

A solution of DIAD (1.80 g, 8.89 mmol) in dioxane (5 mL) was added to a solution of triphenylphosphine (2.33 g, 8.89 mmol) in dioxane (20 mL) at 0° C. under a nitrogen atmosphere. After 10 min stirring, 1-[3-phenyl-1-(toluene-4-sulfonyl)-1H-indol-2-yl]ethanol (1.74 g, 4.44 mmol) in dioxane (15 mL) was added followed by diphenylphosphoryl azide (1.47 g, 5.53 mmol) in dioxane (5 mL). The reaction mixture was stirred at 20° C. for 16 h then the reaction mixture was diluted with DCM and purified by column chromatography (Si—PCC, gradient 10-100% DCM in pentane) affording the title compound as a gum (1.39 g, 75%). LCMS (Method C): R$_T$ 4.77 min [M-N$_3$]$^+$ 374.1.

1-[3-Phenyl-1-(toluene-4-sulfonyl)-1H-indol-2-yl]ethylamine

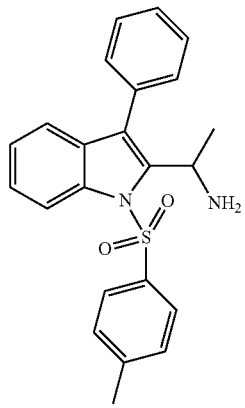 [SMILES: Cc1ccc(S(=O)(=O)n2c(C(C)N)c(-c3ccccc3)c3ccccc32)cc1]

A mixture of 2-(1-azidoethyl)-3-phenyl-1-(toluene-4-sulfonyl)-1H-indole (1.34 g, 3.22 mmol) and 10% Pd/C (200 mg) in EtOAc (80 mL) was degassed with a stream of nitrogen and stirred at RT under a hydrogen atmosphere for 20 h. The suspension was filtered and the filtrate concentrated in vacuo. The resulting residue was purified by column chromatography (Si—PCC, gradient 0-10% MeOH in DCM) affording the title compound as a white solid (960 mg, 76%). $^1$H NMR (CDCl$_3$, 400 MHz): δ 8.18 (1H, d, J=8.44 Hz), 7.73 (2H, d, J=8.44 Hz), 7.49-7.15 (10H, m), 4.72 (1H, q, J=6.96 Hz), 2.35 (3H, s), 1.45 (3H, d, J=7.40 Hz).

1-[3-Phenyl-1-(toluene-4-sulfonyl)-1H-indol-2-yl]ethyl}-(9H-purin-6-yl)amine

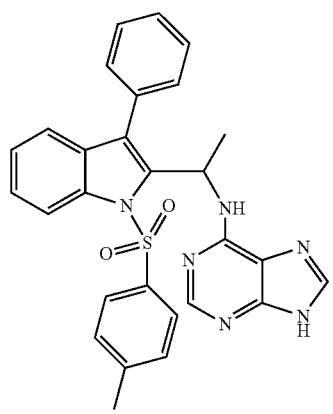 [SMILES: Cc1ccc(S(=O)(=O)n2c(C(C)Nc3ncnc4[nH]cnc34)c(-c3ccccc3)c3ccccc32)cc1]

A mixture of 1-[3-phenyl-1-(toluene-4-sulfonyl)-1H-indol-2-yl]ethylamine (294 mg, 0.75 mmol), 6-chloro-9H-purine (140 mg, 0.90 mmol) and DIPEA (0.20 mL, 1.13 mmol) in n-butanol (1.5 mL) was stirred in a sealed tube for 56 h at 120° C. After cooling to RT, the crude reaction mixture was loaded onto an Isolute® SCX-2 cartridge then washed with MeOH and the product eluted with 2M $NH_3$/MeOH. The product containing fractions were combined and concentrated in vacuo. The resulting residue was purified by column chromatography (Si—PCC, gradient 0-7% 2M $NH_3$/MeOH in DCM) affording the title compound as a yellow solid (350 mg, 91%). LCMS (Method C): $R_T$ 3.31 min [M+H]$^+$ 509.1.

2-Bromomethyl-3-phenyl-1-(toluene-4-sulfonyl)-1H-indole

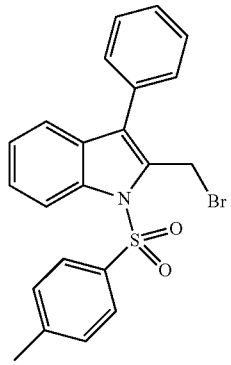 [SMILES: Cc1ccc(S(=O)(=O)n2c(CBr)c(-c3ccccc3)c3ccccc32)cc1]

To a solution of [3-phenyl-1-(toluene-4-sulfonyl)-1H-indol-2-yl]methanol (1.31 g, 3.47 mmol) and triphenylphosphine (1.09 g, 4.16 mmol) in DCM (30 mL) at RT under a nitrogen atmosphere was added NBS (240 mg, 4.16 mmol) and stirring was continued for 2 h. Volatiles were removed under reduced pressure and the resulting residue purified by column chromatography (Si—PCC, gradient 30-100% DCM in pentane) affording the title compound as a gum (440 mg, 29%). $^1$H NMR (CDCl$_3$, 400 MHz): δ 8.16 (1H, dt, J=8.48, 0.84 Hz), 7.92-7.88 (2H, m), 7.60-7.49 (4H, m), 7.48-7.37 (3H, m), 7.28-7.22 (3H, m), 5.05 (2H, s), 2.38 (3H, s)

9-[3-Phenyl-1-(toluene-4-sulfonyl)-1H-indol-2-ylmethyl]-9H-purin-6-ylamine

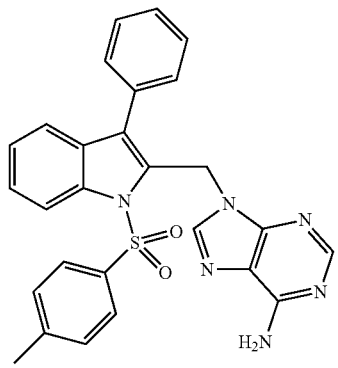 [SMILES: Cc1ccc(S(=O)(=O)n2c(Cn3cnc4c(N)ncnc43)c(-c3ccccc3)c3ccccc32)cc1]

To a stirred mixture of 9H-purin-6-ylamine (130 mg, 0.98 mmol) in DMF (5 mL) under an argon atmosphere was added NaH (60% in mineral oil, 40 mg, 0.98 mmol). After stirring for 10 min at RT, 2-bromomethyl-3-phenyl-1-(toluene-4-sulfonyl)-1H-indole (430 mg, 0.98 mmol) in DMF (10 mL) was added and stirring continued for 15 min. The crude reaction mixture was loaded onto an Isolute® SCX-2 cartridge then washed with MeOH and the product eluted with 2M $NH_3$/MeOH. The product containing fractions were combined and concentrated under reduced pressure. The resulting residue was purified by column chromatography (Si—PCC, gradient 0-10% MeOH in DCM) affording the title compound as a white solid (370 mg, 77%). LCMS (Method C): $R_T$ 3.16 min [M+H]$^+$ 495.1.

1-(3-Phenylbenzo[b]thiophen-2-yl)ethanol

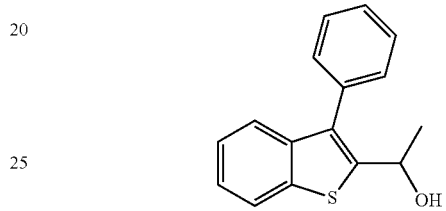

To a solution of 3-phenylbenzo[b]thiophene-2-carbaldehyde (430 mg, 1.87 mmol) in THF (10 mL) at −78° C. and under a nitrogen atmosphere was added 3.0M methylmagnesium bromide in diethyl ether (1.24 mL) and stirring continued for 30 min. The reaction mixture was quenched with a saturated solution of NH$_4$Cl (20 mL) and slowly warmed to RT. The mixture was extracted with EtOAc (×2) and the combined organic fractions washed with water, dried (Na$_2$SO$_4$) and concentrated in vacuo affording the title compound as a white solid (472 mg, quantitative). $^1$H NMR (CDCl$_3$, 400 MHz): δ 7.88-7.84 (1H, m), 7.52-7.28 (8H, m), 5.21 (1H, q, J=6.35 Hz), 2.03 (1H, s), 1.59 (3H, d, J=6.63 Hz)

2-(1-Azidoethyl)-3-phenylbenzo[b]thiophene

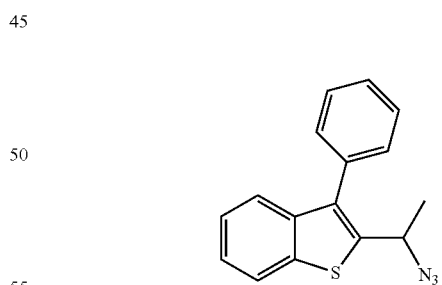

DIAD (556 mg, 2.75 mmol) was added to a solution of triphenylphosphine (722 mg, 2.75 mmol) in dioxane (5 mL) at 0° C. under a nitrogen atmosphere. After 10 min, 1-(3-phenylbenzo[b]thiophen-2-yl)ethanol (350 mg, 1.37 mmol) was added followed by diphenylphosphoryl azide (454 mg, 1.65 mmol). The reaction mixture was stirred 20° C. for 16 h then concentrated in vacuo. The crude reaction mixture was purified by column chromatography (Si—PCC, gradient 0-20% DCM in cyclohexane) affording the title compound as a colourless oil (211 mg, 55%). $^1$H NMR (CDCl$_3$, 400 MHz):

δ 7.88 (1H, d, J=7.87 Hz), 7.54-7.42 (4H, m), 7.41-7.29 (4H, m), 4.97 (1H, q, J=6.80 Hz), 1.58 (3H, d, J=6.80 Hz).

1-(3-Phenylbenzo[b]thiophen-2-yl)ethylamine

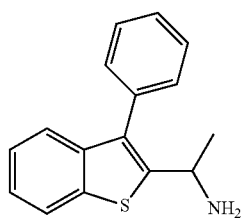 [SMILES: CC(N)c1sc2ccccc2c1-c1ccccc1]

2-(1-Azidoethyl)-3-phenylbenzo[b]thiophene (211 mg, 0.76 mmol) was dissolved in a mixture THF (4 mL) and water (0.27 mL) and triphenylphosphine (237 mg, 0.91 mmol) added. The mixture was stirred at RT for 1 h then additional triphenylphosphine (237 mg) was added. The reaction mixture was stirred at RT for 1 h then the reaction mixture was loaded onto an Isolute® SCX-2 cartridge and washed with MeOH and the product eluted with 2M NH$_3$/MeOH. The product containing fractions were combined and concentrated in vacuo. The resulting residue was purified by column chromatography (Si—PCC, gradient 0-8% MeOH in DCM) affording the title compound as a white solid (160 mg, 83%). $^1$H NMR (CDCl$_3$, 400 MHz): δ 7.84 (1H, dd, J=7.63, 1.55 Hz), 7.52-7.27 (8H, m), 4.56-4.44 (1H, br), 1.76 (2H, s), 1.47 (3H, d, J=6.21 Hz).

1-(3-Phenylbenzofuran-2-yl)ethanol

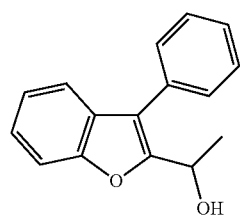 [SMILES: CC(O)c1oc2ccccc2c1-c1ccccc1]

Tetrabutylammonium borohydride (750 mg, 2.91 mmol) was added to a solution of 1-(3-phenylbenzofuran-2-yl)ethanone (459 mg, 1.94 mmol) in THF (9 mL) and IMS (1 mL) and the mixture stirred at RT for 1 h. The reaction mixture was quenched by addition of MeOH and volatiles were removed in vacuo. The resulting residue was purified by column chromatography (Si—PCC, gradient 0-40% EtOAc in cyclohexane) affording the title compound as an oil (452 mg, 98%). LCMS (Method C): R$_T$ 3.57 min [M-OH]$^+$ 221.1

2-(1-Azidoethyl)-3-phenylbenzofuran

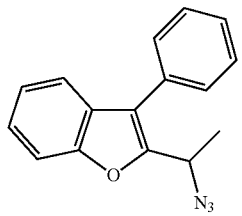

DBU (155 μL, 1.04 mmol) was added dropwise to a solution of 1-(3-phenylbenzofuran-2-yl)ethanol (206 mg, 0.86 mmol) and diphenyl phosphoryl azide (255 μL, 1.04 mmol) in anhydrous THF (7 mL) at 0° C. under a nitrogen atmosphere. After 30 min 0° C., the mixture was slowly warmed to RT and stirring was continued for 1.5 h. Additional diphenyl phosphoryl azide (255 μL, 1.04 mmol) and DBU (155 μL, 1.04 mmol) were added and stirring continued for 18 h. The volatiles were removed in vacuo and the resulting residue purified by column chromatography (Si—PCC, gradient 0-30% EtOAc in cyclohexane) affording the title compound as an oil (186 mg, 82%). LCMS (Method C): R$_T$ 4.48 min [M+H-N$_2$]$^+$ 236.1

1-(3-Phenylbenzofuran-2-yl)ethylamine

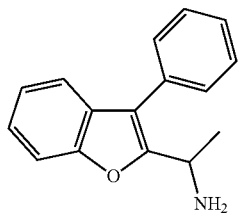 [SMILES: CC(N)c1oc2ccccc2c1-c1ccccc1]

Triphenylphosphine (231 mg, 0.88 mmol) was added to a solution of 241-azidoethyl)-3-phenylbenzofuran (186 mg, 0.71 mmol) in THF (9 mL) and water (1 mL). The mixture was heated at 60° C. for 2 h then cooled to RT. The volatiles were removed in vacuo and the resulting residue purified by column chromatography (Si—PCC, gradient 0-10% MeOH in EtOAc) affording the title compound as an oil (327 mg, quantitative). LCMS (Method C): $R_T$ 2.21 min [M−NH$_2$]$^+$ 221.1

Methanesulfonic acid 3-phenylbenzofuran-2-ylmethyl ester

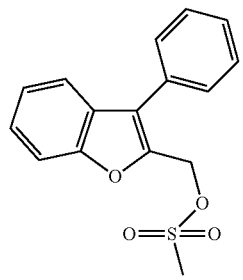

Methanesulfonyl chloride (160 μL, 2.05 mmol) was added dropwise to a solution of (3-phenylbenzofuran-2-yl)methanol (367 mg, 1.64 mmol) and DIPEA (343 μL, 1.97 mmol) in anhydrous DCM (10 mL) at 0° C. Stirring at 0° C. was continued for 15 min, then the mixture slowly warmed to RT. After 2 h at RT, additional amounts of methanesulfonyl chloride (80 μL, 1.03 mmol) and DIPEA (172 μL, 0.99 mmol) were added and stirring continued for 1.5 h. The reaction mixture was diluted with DCM and the organic fraction washed with water, dried (Na$_2$SO$_4$) and concentrated in vacuo affording the title compound as an oil (443 mg, 89%). $^1$H NMR (DMSO-d$_6$, 400 MHz): δ 7.71-7.64 (2H, m), 7.62-7.56 (4H, m), 7.52-7.41 (2H, m), 7.37-7.32 (1H, m), 4.98 (2H, s), 3.89 (3H, s)

Methanesulfonic acid 3-phenylbenzo[b]thiophen-2-ylmethyl ester

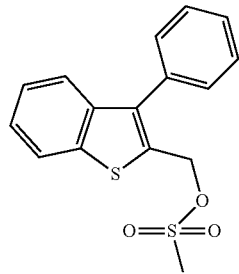 [SMILES: CS(=O)(=O)OCc1sc2ccccc2c1-c1ccccc1]

Methanesulfonyl chloride (127 μL, 1.63 mmol) was added dropwise to a solution of (3-phenylbenzo[b]thiophen-2-yl)methanol (356 mg, 1.48 mmol) and DIPEA (322 μL, 1.85 mmol) in anhydrous DCM (10 mL) at 0° C. Stirring at 0° C. was continued for 15 min, then the mixture was slowly warmed to RT. After 2.5 h at RT, additional methanesulfonyl chloride (1 drop) was added and stirring was continued for 1 h. The reaction mixture was diluted with DCM and the organic fraction washed with water, dried (Na$_2$SO$_4$) and concentrated in vacuo affording the title compound as a yellow oil (408 mg, 87%). $^1$H NMR (DMSO-d$_6$, 400 MHz): δ 8.07-8.02 (1H, m), 7.62-7.56 (2H, m), 7.55-7.37 (6H, m), 4.96 (2H, s), 3.33 (3H, s)

2-Azidomethyl-3-phenylbenzo[b]thiophene

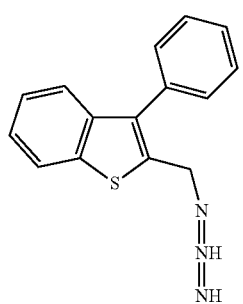

Sodium azide (179 mg, 2.76 mmol) was added to a solution of methanesulfonic acid 3-phenylbenzo[b]thiophen-2-ylmethyl ester (828 mg, 1.84 mmol) in DMF (10 mL) and the mixture stirred at RT for 18 h. The reaction mixture was diluted with water and extracted with EtOAc. The organic fraction was washed with brine, dried (Na$_2$SO$_4$) and concentrated in vacuo and the resulting residue purified by column chromatography (Si—PCC, gradient 0-35% DCM in cyclohexane) affording the title compound as a clear oil (244 mg, 50%). LCMS (Method C): $R_T$ 4.46 min [M+H-N$_2$]$^+$ 237.8

(3-Phenylbenzo[b]thiophen-2-yl)methylamine

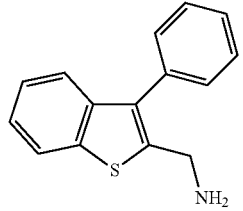

A solution of 2-azidomethyl-3-phenylbenzo[b]thiophene (244 mg, 0.92 mmol) in THF (10 mL) was treated with a solution of triphenylphosphine (302 mg, 1.15 mmol) in water (1 mL) under a nitrogen atmosphere. The mixture was heated at 60° C. for 2 h then cooled to RT. The volatiles were removed in vacuo and the resulting residue loaded onto an Isolute® SCX-2 cartridge then washed with MeOH and the product eluted with 2M NH$_3$/MeOH. The product containing fractions were combined and concentrated in vacuo affording the title compound (288 mg, quantitative). LCMS (Method C): $R_T$ 2.15 min [M−N$_3$]$^+$ 223.0.

3-o-Tolylbenzo[b]thiophene-2-carbaldehyde

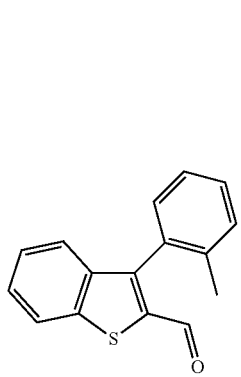 [SMILES: Cc1ccccc1-c1c(C=O)sc2ccccc12]

A mixture of 3-bromobenzo[b]thiophene-2-carbaldehyde (500 mg, 2.07 mmol), 2-methylphenylboronic acid (394 mg, 2.90 mmol), Pd(PPh$_3$)$_4$ (243 mg, 0.21 mmol), Cs$_2$CO$_3$ (2.02 g, 6.21 mmol) in dioxane (12 mL) and water (4 mL) was degassed with a stream of nitrogen then heated at 130° C. in a sealed tube using microwave irradiation for 45 min. The reaction mixture was extracted with EtOAc, and the organic fraction washed with water, followed by brine, dried (Na$_2$SO$_4$) and concentrated in vacuo. The resulting residue was purified by column chromatography (Si—PCC, gradient 0-70% DCM in cyclohexane) affording the title compound (quantitative yield). LCMS (Method C): $R_T$ 4.16 min

(3-o-Tolylbenzo[b]thiophen-2-yl)methanol

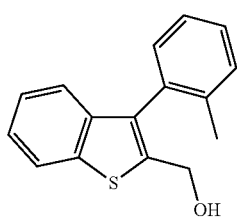 [SMILES: Cc1ccccc1-c1c(CO)sc2ccccc12]

Tetrabutylammonium borohydride (800 mg, 3.10 mmol) was added at RT to a solution of 3-o-tolylbenzo[b]thiophene-2-carbaldehyde (2.07 mmol) in THF (10 mL) and IMS (1 mL) and the mixture stirred at RT for 1 h. The reaction mixture was quenched by addition of MeOH and volatiles were removed under reduced pressure. The resulting residues was purified by column chromatography (Si—PCC, gradient 0-30% EtOAc in cyclohexane) affording the title compound as an oil (432 mg, 82% over 2 steps). LCMS (Method C): $R_T$ 3.74 min [M-OH]$^+$ 237.1.

Methanesulfonic acid 3-o-tolylbenzo[b]thiophen-2-ylmethyl ester

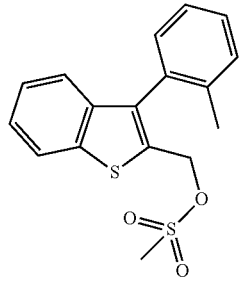 [SMILES: Cc1ccccc1-c1c(COS(C)(=O)=O)sc2ccccc12]

Methanesulfonyl chloride (158 µL, 2.04 mmol) was added dropwise to a solution of (3-o-tolylbenzo[b]thiophen-2-yl)methanol (432 mg, 1.70 mmol) and DIPEA (385 µL, 2.21 mmol) in anhydrous DCM (10 mL) at RT. Stirring at RT was continued for 18 h then the reaction mixture was washed with water, dried (Na$_2$SO$_4$) and concentrated in vacuo affording the title compound as a brown oil (424 mg, 75%). $^1$H NMR (DMSO-d$_6$, 400 MHz): δ 8.05 (1H, d, J=8.04 Hz), 7.45-7.40 (3H, m), 7.38-7.32 (2H, m), 7.21 (1H, d, J=7.40 Hz), 7.12 (1H, d, J=7.98 Hz), 4.82 (1H, d, J=12.41 Hz), 4.76 (1H, d, J=12.41 Hz), 3.32 (3H, s), 1.99 (3H, s)

(3-Nitropyridin-2-yl)-o-tolylamine

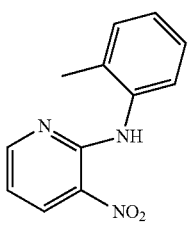

A mixture of 2-chloro-3-nitropyridine (4.13 g, 26.1 mmol), o-tolylamine (3.4 mL, 31.3 mmol) and Et$_3$N (4.4 mL, 31.3 mmol) in DMF (10 mL) was stirred at 90° C. for 1 h under a nitrogen atmosphere. Additional o-tolylamine (2 mL, 18.2 mmol) was added and stirring continued for 16 h. The mixture was partitioned between DCM and water. The aqueous phase was further extracted with DCM (×3) and the combined organic fractions washed with brine, dried (Na$_2$SO$_4$) and concentrated in vacuo. The resulting residue was purified by column chromatography (Si—PCC, gradient 20-100% DCM in cyclohexane) to afford the title compound as an orange solid (3.96 g, 66%). LCMS (Method C): $R_T$ 3.60 min $[M+H]^+$ 230.3

$N^2$-o-Tolylpyridine-2,3-diamine

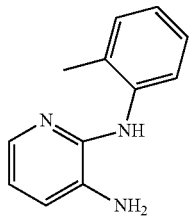 [SMILES: Cc1ccccc1Nc1ncccc1[N+](=O)[O-]]

A mixture of (3-nitropyridin-2-yl)-o-tolylamine (3.96 g, 17.3 mmol) in EtOAc (200 mL) was degassed with a stream of nitrogen prior to addition of 10% Pd/C (700 mg) and was stirred at RT under a hydrogen atmosphere for 16 h. The suspension was filtered and the filtrate was concentrated in vacuo to afford the title compound as a white solid (2.02 g, 59%). $^1$H NMR (CDCl$_3$, 400 MHz): δ 7.83 (1H, d, J=4.94 Hz), 7.28-7.11 (3H, m), 7.01 (1H, d, J=7.64 Hz), 6.93 (1H, t, J=7.41 Hz), 6.79 (1H, dd, J=7.63, 4.96 Hz), 5.97 (1H, s), 3.43 (2H, s), 2.30 (3H, s).

[(S)-1-(2-o-Tolylaminopyridin-3-ylcarbamoyl)ethyl]carbamic acid tert-butyl ester

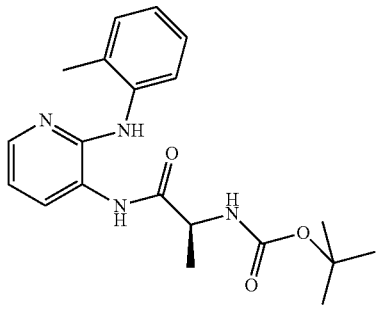 [SMILES: Cc1ccccc1Nc1ncccc1NC(=O)[C@H](C)NC(=O)OC(C)(C)C]

Triethylamine (1.05 mL, 7.53 mmol) was added to a mixture of $N^2$-o-tolylpyridine-2,3-diamine (500 mg, 2.51 mmol), (S)-2-tertbutoxycarbonylaminopropionic acid (520 mg, 2.76 mmol), HOAt (380 mg, 2.76 mmol) and N-(3-dimethylaminopropyl)-N'-ethylcarbodiimide hydrochloride (530 mg, 2.76 mmol) in anhydrous DCM (20 mL) at 0° C. under a nitrogen atmosphere. The reaction mixture was stirred at 0° C. for 10 min and then slowly warmed to RT. Stirring at RT was continued for 16 h. The resulting mixture was partitioned between DCM and a saturated aqueous solution of NaHCO$_3$. The aqueous phase was further extracted with DCM and the combined organic fractions were washed with water, dried (Na$_2$SO$_4$) and concentrated in vacuo to afford the title compound. The crude material was used without further purification in the following step. Yield assumed to be quantitative. LCMS (Method J): $R_T$ 2.19 min $[M+H]^+$ 371.1.

(S)-1-(3-o-Tolyl-3H-imidazo[4,5-b]pyridin-2-yl)ethylamine

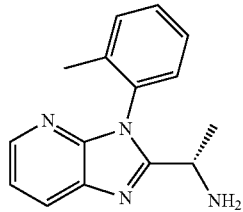 [SMILES: Cc1ccccc1-n1c([C@H](C)N)nc2cccnc21]

A solution of [(S)-1-(2-o-tolylaminopyridin-3-ylcarbamoyl)ethyl]carbamic acid tert-butyl ester (2.51 mmol) in AcOH (20 mL) was heated at 70° C. for 6 h. After cooling to RT, the volatiles were removed under reduced pressure and the residue partitioned between DCM and a saturated aqueous solution of NaHCO$_3$. The aqueous phase was extracted with DCM and the combined organic fractions washed with water, dried (Na$_2$SO$_4$) and concentrated in vacuo to afford [(S)-1-(3-o-tolyl-3H-imidazo[4,5-b]pyridin-2-yl)ethyl]carbamic acid tert-butyl ester as a brown oil (quantitative). To a solution of the compound thus obtained (2.51 mmol) in DCM (25 mL) was added TFA (10 mL) and the mixture stirred at RT for 15 min. The volatiles were removed in vacuo and the resulting residue dissolved in DCM and washed with a saturated aqueous solution of NaHCO$_3$ (40 mL). The aqueous phase was further extracted with DCM (×3) and the combined organic fractions dried (Na$_2$SO$_4$) and concentrated in vacuo. The resulting residue was purified by column chromatography (Si—PCC, gradient 0-8% 2M NH$_3$/MeOH in DCM) to afford the title compound as an oil (340 mg, 54% over 3 steps). $^1$H NMR (CDCl$_3$, 400 MHz): δ 8.33 (1H, d, J=4.83 Hz), 8.09 (1H, d, J=8.00 Hz), 7.52-7.37 (3H, m), 7.33-7.21 (2H, m), 4.08 (0.5H, q, J=6.75 Hz), 3.99 (0.5H, q, J=6.72 Hz), 2.02 (3H, s), 1.50 (1.5H, d, J=6.75 Hz), 1.41 (1.5H, d, J=6.75 Hz). Signals split due to presence of rotamers/tautomers.

[(S)-1-(2-Phenylaminopyridin-3-ylcarbamoyl)propyl]carbamic acid tert-butyl ester

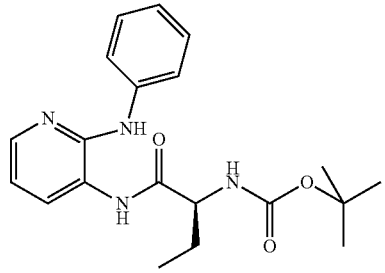 [SMILES: CC[C@H](NC(=O)OC(C)(C)C)C(=O)Nc1cccnc1Nc1ccccc1]

Triethylamine (1.8 mL, 13.0 mmol) was added to a mixture of $N^2$-phenylpyridine-2,3-diamine (800 mg, 4.32 mmol), (S)-2-tertbutoxycarbonylaminobutyric acid (960 mg, 4.75 mmol), HOAt (650 mg, 4.75 mmol) and N-(3-dimethylaminopropyl)-N'-ethylcarbodiimide hydrochloride (910 mg, 4.75 mmol) in anhydrous DCM (25 mL) at 0° C. under a nitrogen atmosphere. The reaction mixture was stirred at 0°

C. for 10 min then slowly warmed to RT. Stirring at RT was continued for 16 h. After re-cooling to 0° C., additional amounts of (S)-2-tertbutoxycarbonylaminobutyric acid (610 mg), N-(3-dimethylaminopropyl)-N'-ethylcarbodiimide hydrochloride (580 mg), HOAt (410 mg) and triethylamine (1.0 mL) were added and stirring at RT continued for 1 h. The reaction mixture was then partitioned between DCM and a saturated aqueous solution of NaHCO$_3$. The aqueous phase was further extracted with DCM (×3) and the combined organic fractions washed with water, dried (Na$_2$SO$_4$) and concentrated in vacuo to afford the title compound as a dark oil. The crude material was used without further purification in the following step. Yield assumed to be quantitative. LCMS (Method J): R$_T$ 2.67 min [M+H]$^+$ 371.2.

[(S)-1-(3-Phenyl-3H-imidazo[4,5-b]pyridin-2-yl)propyl]carbamic acid tert-butyl ester

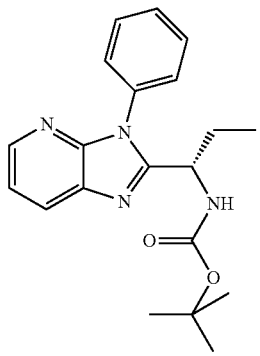 [SMILES: CC[C@H](NC(=O)OC(C)(C)C)c1nc2cccnc2n1-c1ccccc1]

A solution of [(S)-1-(2-phenylaminopyridin-3-ylcarbamoyl)propyl]carbamic acid tert-butyl ester (4.32 mmol) in AcOH (30 mL) was heated at 70° C. for 3 h. After cooling to RT, the volatiles were removed under reduced pressure and the residue partitioned between DCM and a saturated aqueous solution of NaHCO$_3$. The aqueous phase was extracted with DCM (×3) and the combined organic fractions washed with water, dried (Na$_2$SO$_4$) and concentrated in vacuo to afford the title compound as an oil (1.27 g, crude material). LCMS (Method C): R$_T$ 3.24 min [M+H]$^+$ 353.4.

(S)-1-(3-Phenyl-3H-imidazo[4,5-b]pyridin-2-yl)propylamine

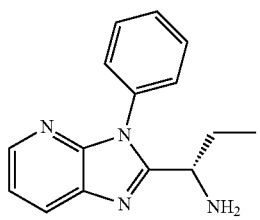 [SMILES: CC[C@H](N)c1nc2cccnc2n1-c1ccccc1]

To a solution of [(S)-1-(3-phenyl-3H-imidazo[4,5-b]pyridin-2-yl)propyl]carbamic acid tert-butyl ester (1.27 g, 3.60 mmol) in DCM (25 mL) was added TFA (10 mL) and the mixture stirred at RT for 15 min. The volatiles were removed in vacuo and the resulting residue dissolved in DCM and washed with a saturated solution of NaHCO$_3$. The aqueous phase was extracted with DCM (×3) and the combined organic fractions dried (Na$_2$SO$_4$) and concentrated in vacuo. The resulting residue was purified by column chromatography (Si—PCC, gradient 0-8% 2M NH$_3$/MeOH in DCM) to afford the title compound as a brown oil (440 mg, 40% over 3 steps). $^1$H NMR (CDCl$_3$, 400 MHz): δ 8.34 (1H, d, J=4.82 Hz), 8.08 (1H, d, J=8.00 Hz), 7.67-7.52 (3H, m), 7.45 (2H, d, J=7.60 Hz), 7.30-7.22 (1H, m), 3.99 (1H, t, J=6.70 Hz), 2.02-1.87 (1H, m), 1.83-1.69 (3H, m), 0.89 (3H, t, J=7.40 Hz).

[(S)-1-(6-Fluoro-1-phenyl-1H-benzoimidazol-2-yl)propyl]carbamic acid tert-butyl ester

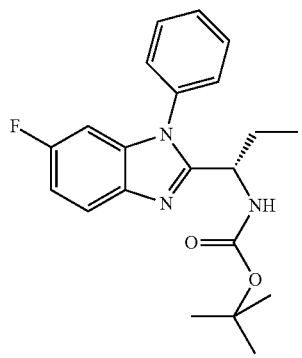 [SMILES: CC[C@H](NC(=O)OC(C)(C)C)c1nc2ccc(F)cc2n1-c1ccccc1]

A mixture of 4-fluoro-N$^2$-phenylbenzene-1,2-diamine (199 mg, 0.98 mmol), (S)-2-tertbutoxycarbonylaminobutyric acid (219 mg, 1.08 mmol), HOAt (147 mg, 1.08 mmol), 4-methylmorpholine (0.238 mL, 2.16 mmol) and N-(3-dimethylaminopropyl)-N'-ethylcarbodiimide hydrochloride (207 mg, 1.08 mmol) in DCM (5 mL) was stirred at RT for 2 h. The reaction mixture was partitioned between DCM (50 mL) and a saturated solution of NaHCO$_3$. The organic layer was dried (Na$_2$SO$_4$), concentrated in vacuo and the resulting residue dissolved in AcOH (10 mL) and stirred for 18 h at 70° C. After cooling to RT, the volatiles were evaporated under reduced pressure and the residue was partitioned between DCM (50 mL) and a saturated aqueous solution of NaHCO$_3$. The organic layer was washed with brine, dried (Na$_2$SO$_4$) and then concentrated in vacuo. The resulting residue was purified by column chromatography (Si—PCC, gradient 0-50% EtOAc in cyclohexane) to afford the title compound as a beige solid (234 mg, 64%). LCMS (Method C): R$_T$ 3.82 min [M+H]$^+$ 370.5.

(S)-1-(6-Fluoro-1-phenyl-1H-benzoimidazol-2-yl)propylamine

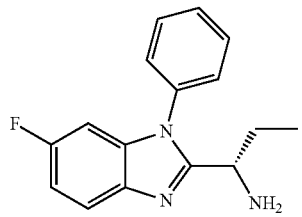 [SMILES: CC[C@H](N)c1nc2ccc(F)cc2n1-c1ccccc1]

To a solution of [(S)-1-(6-fluoro-1-phenyl-1H-benzoimidazol-2-yl)propyl]carbamic acid tert-butyl ester (234 mg, 0.63 mmol) in DCM (3 mL) was added TFA (1.5 mL) and the mixture stirred at RT for 2 h. The volatiles were removed in vacuo and the resulting residue partitioned between DCM (20 mL) and a saturated aqueous solution of NaHCO$_3$. The two phase system was stirred for 10 min, then the organic fraction dried (MgSO$_4$) and concentrated in vacuo. The resulting residue was purified by column chromatography (Si—PCC, gradient 0-10% MeOH in DCM) to afford the title compound as a colourless oil (42 mg, 25%). LCMS (Method B): R$_T$ 1.90 min [M−NH$_2$]$^+$ 253.0.

[(S)-1-(5-Fluoro-2-phenylaminophenylcarbamoyl) ethyl]carbamic acid tert-butyl ester

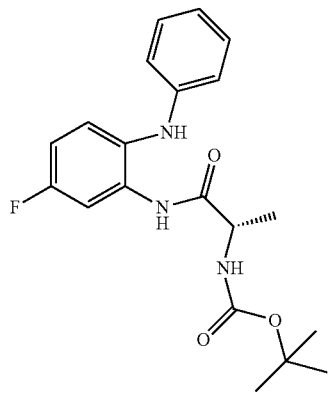 [SMILES: C[C@H](NC(=O)OC(C)(C)C)C(=O)Nc1cc(F)ccc1Nc1ccccc1]

A mixture of 4-fluoro-N$^1$-phenylbenzene-1,2-diamine (866 mg, 4.3 mmol), (S)-2-tertbutoxycarbonylaminopropionic acid (890 mg, 4.7 mmol), HOAt (640 mg, 4.7 mmol), 4-methylmorpholine (1.0 mL, 9.5 mmol) and N-(3-dimethylaminopropyl)-N'-ethylcarbodiimide hydrochloride (900 mg, 4.7 mmol) in DCM (20 mL) was stirred at RT for 2 h. The reaction mixture was partitioned between DCM and a saturated aqueous solution of NaHCO$_3$. The organic fraction was washed with brine, dried (MgSO$_4$) and concentrated in vacuo to afford the title compound as a yellow-orange solid (quantitative). The crude product was used in the following step without further purification. LCMS (Method B): R$_T$ 3.83 min [M+H]$^+$ 374.1.

[(S)-1-(5-Fluoro-1-phenyl-1H-benzoimidazol-2-yl) ethyl]carbamic acid tert-butyl ester

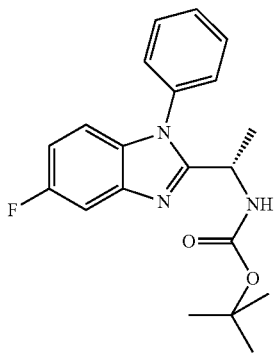 [SMILES: C[C@H](NC(=O)OC(C)(C)C)c1nc2cc(F)ccc2n1-c1ccccc1]

A solution of [(S)-1-(5-fluoro-2-phenylaminophenylcarbamoyl)ethyl]carbamic acid tert-butyl ester (2.15 mmol) in AcOH (10 mL) was stirred for 18 h at 70° C. After cooling to RT, the volatiles were evaporated in vacuo and the residue partitioned between EtOAc and a saturated aqueous solution of NaHCO$_3$. The organic fraction was washed with brine, dried (MgSO$_4$) and concentrated in vacuo. The resulting residue was purified by column chromatography (Si—PCC, gradient 0-40% EtOAc in cyclohexane) to afford the title compound as an orange oil (661 mg, 86% over two steps). LCMS (Method J): R$_T$ 3.52 min [M+H]$^+$ 356.1.

(S)-1-(5-Fluoro-1-phenyl-1H-benzoimidazol-2-yl) ethylamine

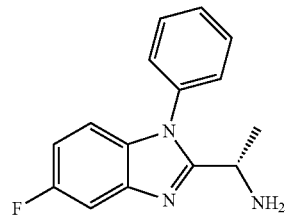 [SMILES: C[C@H](N)c1nc2cc(F)ccc2n1-c1ccccc1]

To a solution of [(S)-1-(5-fluoro-1-phenyl-1H-benzoimidazol-2-yl)ethyl]carbamic acid tert-butyl ester (661 mg, 1.9 mmol) in DCM (9 mL) was added TFA (4.5 mL) and the mixture stirred at RT for 2 h. The volatiles were removed in vacuo and the resulting residue partitioned between DCM (20 mL) and a saturated aqueous solution of NaHCO$_3$ (40 mL). The two phase system was stirred for 10 min, then the organic fraction was dried (MgSO$_4$) and concentrated in vacuo. The resulting residue was purified by column chromatography (Si—PCC, gradient 0-10% MeOH in DCM) to afford the title compound as a yellow oil (379 mg, 78%). LCMS (Method J): R$_T$ 1.77 min [M+H]$^+$ 256.2.

3-(2-Aminophenylamino)benzonitrile

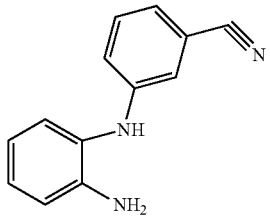 [SMILES: N#Cc1cccc(Nc2ccccc2N)c1]

A mixture of 1-fluoro-2-nitrobenzene (2.00 g, 14.2 mmol), 3-aminobenzonitrile (3.35 g, 28.3 mmol) and potassium carbonate (5.88 g, 42.5 mmol) in DMF (30 mL) was stirred at 135° C. for 16 h under a nitrogen atmosphere. After cooling to RT, the reaction mixture was partitioned between DCM and water. The aqueous phase was extracted with DCM (×3) and the combined organic fractions dried (Na$_2$SO$_4$) and concentrated in vacuo. The resulting residue was purified by column chromatography (Si—PCC, gradient 25-100% DCM in cyclohexane) then loaded onto an SCX-2 cartridge and washed with DCM to afford 3-(2-nitrophenylamino)benzonitrile as a bright orange foam (2.02 g, 60%).

To a mixture of 3-(2-nitrophenylamino)benzonitrile (2.0 g, 8.40 mmol) in a 3:1 mixture MeOH:water (120 mL) were added NH$_4$Cl (2.70 g, 0.05 mol) and iron powder (1.88 g, 0.03 mol) and the reaction mixture heated at reflux temperature for 1 h. After cooling to RT, the solid was filtered through a pad of Celite® and washed with additional MeOH. The filtrate was concentrated in vacuo and the resulting residue partitioned between DCM and water. The aqueous phase was further extracted with DCM (×3) and the combined organic fractions were washed with brine, dried (Na$_2$SO$_4$) and concentrated in vacuo. The resulting residue was purified by column chromatography (Si—PCC, gradient 0-2% MeOH in DCM) to afford the title compound as a yellow solid (185 mg, 11%). LCMS (Method J): R$_T$ 2.99 min [M+H]$^+$ 210.0.

{(S)-1-[2-(3-Cyanophenylamino)phenylcarbamoyl]ethyl}carbamic acid tert-butyl ester

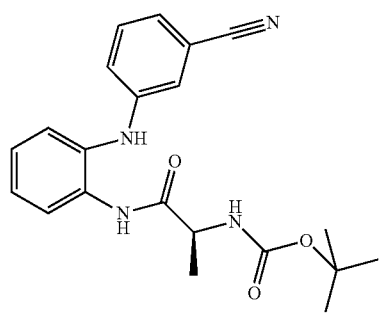 [SMILES: C[C@H](NC(=O)OC(C)(C)C)C(=O)Nc1ccccc1Nc1cccc(C#N)c1]

Triethylamine (0.35 mL, 2.59 mmol) was added to a mixture of 3-(2-aminophenylamino)benzonitrile (177 mg, 0.85 mmol), (S)-2-tertbutoxycarbonylaminopropionic acid (190 mg, 1.02 mmol), HOAt (140 mg, 1.02 mmol) and N-(3-dimethylaminopropyl)-N'-ethylcarbodiimide hydrochloride (190 mg, 1.02 mmol) in anhydrous DCM (10 mL) at 0° C. under a nitrogen atmosphere. The reaction mixture was stirred at 0° C. for 10 min then slowly warmed to RT. Stirring at RT was continued for 16 h. The reaction mixture was then partitioned between DCM and a saturated aqueous solution of NaHCO$_3$. The aqueous phase was further extracted with DCM (×3) and the combined organic fractions were washed with water, dried (Na$_2$SO$_4$) and concentrated in vacuo. The resulting residue was purified by column chromatography (Si—PCC, gradient 0-2% 2M NH$_3$/MeOH in DCM) to afford the title compound as a yellow oil (290 mg, 90%). Material still impure, taken forward in the next step without further purification. LCMS (Method J): R$_T$ 3.54 min [M+H]$^+$ 380.8

{(S)-1-[1-(3-Cyanophenyl)-1H-benzoimidazol-2-yl]ethyl}carbamic acid tert-butyl ester

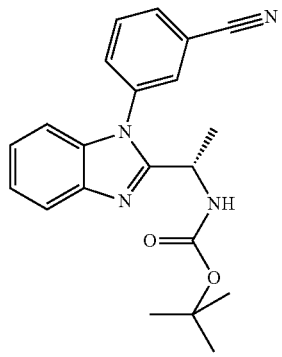 [SMILES: C[C@H](NC(=O)OC(C)(C)C)c1nc2ccccc2n1-c1cccc(C#N)c1]

A solution of {(S)-1-[2-(3-cyanophenylamino)phenylcarbamoyl]ethyl}carbamic acid tert-butyl ester (289 mg, 0.75 mmol) in AcOH (3 mL) was heated at 80° C. for 16 h. After cooling to RT, the volatiles were removed in vacuo and the residue dissolved in DCM and washed with a saturated aqueous solution of NaHCO$_3$. The aqueous phase was further extracted with DCM (×3) and the combined organic fractions were dried (Na$_2$SO$_4$) and concentrated in vacuo. The resulting residue was purified by column chromatography (Si—PCC, gradient 0-2% 2M NH$_3$/MeOH in DCM) to afford the title compound (232 mg, 86%). The material was still impure and taken forward in the next step without further purification. LCMS (Method C): R$_T$ 3.54 min [M+H]$^+$ 363.4

3-[2-((S)-1-Aminoethyl)benzoimidazol-1-yl]benzonitrile

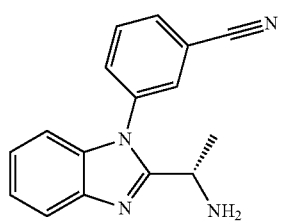 [SMILES: C[C@H](N)c1nc2ccccc2n1-c1cccc(C#N)c1]

To a solution of {(S)-1-[1-(3-cyanophenyl)-1H-benzoimidazol-2-yl]ethyl}carbamic acid tert-butyl ester (200 mg, 0.55 mmol) in DCM (2 mL) was added TFA (5 mL) and the mixture was stirred at RT for 15 min. The volatiles were removed in vacuo and the resulting residue dissolved in DCM and washed with a saturated aqueous solution of NaHCO$_3$. The aqueous phase was further extracted with DCM (×3) and the combined organic fractions were dried (Na$_2$SO$_4$) and concentrated in vacuo. The resulting residue was purified by column chromatography (Si—PCC, gradient 0-7% 2M NH$_3$/MeOH in DCM) to afford the title compound (58 mg, 40%).

¹H NMR (CDCl₃, 400 MHz): δ 7.93-7.66 (6H, m), 7.39-7.21 (3H, m), 7.08 (1H, d, J=7.94 Hz), 4.16-4.05 (1H, m), 1.51 (3H, d, J=7.36 Hz)

(5-Chloro-2-nitrophenyl)phenylamine

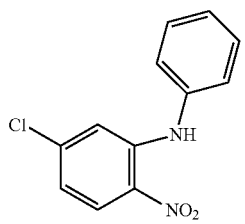 [SMILES: O=[N+]([O-])c1ccc(Cl)cc1Nc1ccccc1]

A mixture of 4-chloro-2-fluoro-1-nitrobenzene (983 mg, 5.60 mmol) and aniline (1.0 mL, 11.20 mmol) in DMSO (3 mL) was heated at 110° C. for 4 h. After cooling to RT, the reaction mixture was partitioned between EtOAc and water. The organic layer was washed with a saturated aqueous solution of KHSO₄ (×3), followed by brine, then dried (Na₂SO₄) and concentrated in vacuo to afford the title compound as an orange solid (1.37 g, 98%). ¹H NMR (CDCl₃, 400 MHz): δ 9.54 (1H, s), 8.16 (1H, d, J=9.13 Hz), 7.46 (2H, t, J=7.61 Hz), 7.32-7.22 (3H, m), 7.14 (1H, d, J=2.14 Hz), 6.72 (1H, dd, J=9.12, 2.15 Hz)

4-Chloro-N²-phenylbenzene-1,2-diamine

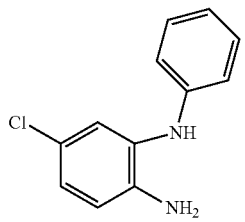 [SMILES: Nc1ccc(Cl)cc1Nc1ccccc1]

To a mixture of (5-chloro-2-nitrophenyl)phenylamine (1.36 g, 5.47 mmol) in a 3:1 mixture of MeOH:water (120 mL) were added NH₄Cl (1.76 g, 32.81 mmol) and iron powder (1.22 g, 21.88 mmol) and the reaction mixture heated at 90° C. for 2 h. After cooling to RT, the solid was filtered through a pad of Celite® and washed with additional MeOH. The filtrate was concentrated in vacuo and the resulting residue partitioned between EtOAc and water. The aqueous phase was further extracted with EtOAc and the combined organic fractions washed with brine, dried (Na₂SO₄) and concentrated in vacuo. The resulting residue was purified by column chromatography (Si—PCC, gradient 0-100% DCM in cyclohexane) to afford the title compound as a brown oil (980 mg, 82%). LCMS (Method C): R_T 3.57 min [M+H]⁺ 219.0

[(S)-1-(6-Chloro-1-phenyl-1H-benzoimidazol-2-yl) ethyl]carbamic acid tert-butyl ester

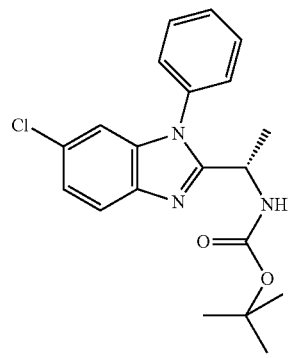 [SMILES: C[C@H](NC(=O)OC(C)(C)C)c1nc2ccc(Cl)cc2n1-c1ccccc1]

A mixture of 4-chloro-N²-phenylbenzene-1,2-diamine (975 mg, 4.46 mmol), (S)-2-tertbutoxycarbonylaminopropionic acid (928 mg, 4.90 mmol), HOAt (668 mg, 4.90 mmol), 4-methylmorpholine (1.08 mL, 9.81 mmol) and N-(3-dimethylaminopropyl)-N'-ethylcarbodiimide hydrochloride (940 mg, 4.90 mmol) in DCM (30 mL) was stirred at RT for 19 h. The reaction mixture was partitioned between DCM and a saturated aqueous solution of NaHCO₃. The organic layer was washed with brine, dried and concentrated in vacuo to afford [(S)-1-(4-chloro-2-phenylaminophenylcarbamoyl) ethyl]carbamic acid tert-butyl ester as a purple solid (quantitative). A solution of the compound thus obtained (4.46 mmol) in AcOH (30 mL) was heated at 70° C. for 22 h. After cooling to RT, the volatiles were removed in vacuo and the resulting residue partitioned between EtOAc and a saturated aqueous solution of NaHCO₃. The organic layer was washed with water, followed by brine, then dried (Na₂SO₄) and concentrated in vacuo. The resulting residue was purified by column chromatography (Si—PCC, gradient 0-30% EtOAc in DCM) to afford the title compound as a yellow solid (1.20 g, 72% over two steps). LCMS (Method C): R_T 3.82 min [M+H]⁺ 372.3

(S)-1-(6-Chloro-1-phenyl-1H-benzoimidazol-2-yl) ethylamine

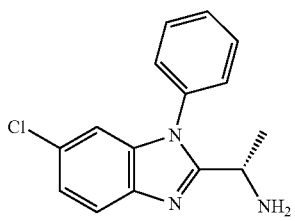 [SMILES: C[C@H](N)c1nc2ccc(Cl)cc2n1-c1ccccc1]

To a solution of [(S)-1-(6-chloro-1-phenyl-1H-benzoimidazol-2-yl)ethyl]carbamic acid tert-butyl ester (1.20 g, 3.23 mmol) in DCM (5 mL) was added TFA (5 mL) and the mixture stirred at RT for 3 h. The crude mixture was loaded into an Isolute® SCX-2 cartridge then washed with MeOH followed by 2M NH₃/MeOH. The basic fractions were combined and concentrated in vacuo to afford (S)-1-(6-chloro-1-phenyl-1H-benzoimidazol-2-yl)ethylamine as a yellow oil (796 mg, 91%).

LCMS (Method C): $R_T$ 2.35 min [M+H]$^+$ 272.2

(5-Fluoro-2-nitrophenyl)pyridin-3-ylamine

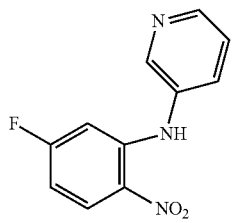

LiHMDS (1.0M in THF, 12.6 mL, 12.6 mmol) was added dropwise to a stirred solution of pyridin-3-ylamine (621 mg, 6.60 mmol) in anhydrous THF (10 mL) under a nitrogen atmosphere at −78° C. After 45 min stirring at −78° C., a solution of 2,4-difluoro-1-nitrobenzene (690 μL, 6.29 mmol) in THF (10 mL) was added and stirring continued for 1 h. The solution was poured into an aqueous solution of NH$_4$Cl (100 mL) and extracted with EtOAc (×3). The combined organic fractions were washed with water, followed by brine, dried (Na$_2$SO$_4$) and concentrated in vacuo. The resulting residue was triturated with EtOAc to afford the title compound as a dark orange solid (638 mg). The mother liquours were concentrated under reduced pressure to afford the title compound as a dark orange solid (648 mg, 87% for the combined batches). $^1$H NMR (CDCl$_3$, 400 MHz): δ 9.60 (1H, br s), 8.63 (1H, s), 8.56 (1H, d, J=4.76 Hz), 8.35-8.27 (1H, m), 7.65 (1H, d, J=8.20 Hz), 7.45-7.38 (1H, m), 6.75 (1H, d, J=11.14 Hz), 6.57 (1H, t, J=8.24 Hz)

4-Fluoro-N$^2$-pyridin-3-ylbenzene-1,2-diamine

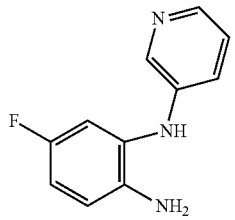 [SMILES: Nc1ccc(F)cc1Nc1cccnc1]

A mixture of (5-fluoro-2-nitrophenyl)pyridin-3-ylamine (1.28 g, 5.49 mmol) in EtOAc (60 mL) was degassed with a stream of nitrogen prior to addition of 10% Pd/C (107 mg) and was stirred at RT under a hydrogen atmosphere for 2 h. The resulting suspension was diluted with IMS (10 mL) and stirred under a hydrogen atmosphere for 56 h. The reaction mixture was filtered through a phase separator and the filtrate concentrated in vacuo. The resulting residue was purified by column chromatography (Si—PCC, gradient 0-20% MeOH in DCM) to afford the title compound as a brown solid (1.03 g, 92%). $^1$H NMR (CDCl$_3$, 400 MHz): δ 8.24 (1H, d, J=2.67 Hz), 8.14 (1H, d, J=4.50 Hz), 7.20-7.05 (2H, m), 6.86 (1H, dd, J=9.62, 2.63 Hz), 6.79-6.65 (2H, m), 5.42 (1H, s), 3.50 (2H, s)

{(S)-1-[4-Fluoro-2-(pyridin-3-ylamino)phenylcarbamoyl]ethyl}carbamic acid tert-butyl ester

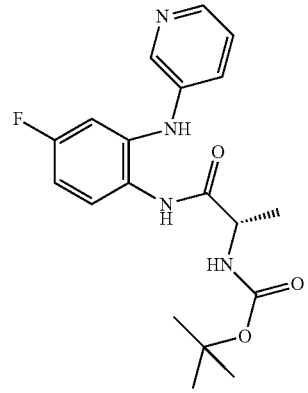 [SMILES: C[C@H](NC(=O)OC(C)(C)C)C(=O)Nc1ccc(F)cc1Nc1cccnc1]

A mixture of 4-fluoro-N$^2$-pyridin-3-ylbenzene-1,2-diamine (1.03 g, 5.07 mmol), (S)-2-tertbutoxycarbonylaminopropionic acid (1.05 g, 5.58 mmol), HOAt (759 mg, 5.58 mmol), 4-methylmorpholine (1.23 mL, 11.15 mmol) and N-(3-dimethylaminopropyl)-N'-ethylcarbodiimide hydrochloride (1.07 g, 5.58 mmol) in DCM (30 mL) was stirred at RT for 2 h. The reaction mixture was then partitioned between DCM and a saturated solution of NaHCO$_3$. A precipitate was present in the organic fraction which was filtered off to afford the title compound as a pale yellow solid (503 mg). The filtrate was dried (MgSO$_4$) and concentrated in vacuo and the resulting residue was triturated with DCM to afford a second batch of the title compound as a yellow solid (765 mg; 67% yield for the combined batches). LCMS (Method C): $R_T$ 2.06 min [M+H]$^+$ 375.3

N—[(S)-1-(6-Fluoro-1-pyridin-3-yl-1H-benzoimidazol-2-yl)ethyl]acetamide

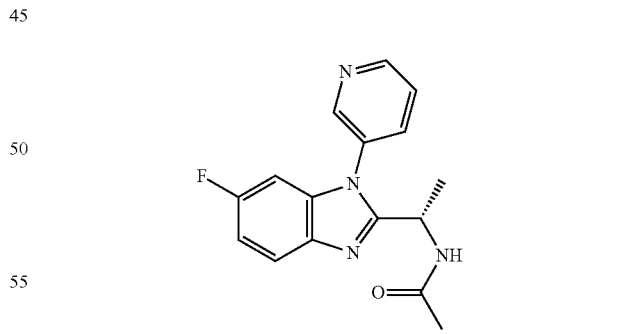

A solution of {(S)-1-[4-fluoro-2-(pyridin-3-ylamino)phenylcarbamoyl]ethyl}carbamic acid tert-butyl ester (47 mg, 0.126 mmol) in AcOH (1 mL) was heated at 100° C. for 28 h in a sealed tube. In a separate vial, {(S)-1-[4-fluoro-2-(pyridin-3-ylamino)phenylcarbamoyl]ethyl}carbamic acid tert-butyl ester (228 mg, 0.61 mmol) was dissolved in AcOH (2 mL) and heated at 100° C. for 17 h. After cooling to RT, the two reaction mixtures were combined and the volatiles were removed in vacuo. The resulting residue was partitioned between EtOAc and a saturated aqueous solution of NaHCO$_3$. The organic fraction was washed with water, followed by brine, dried (Na$_2$SO$_4$) and concentrated in vacuo. The resulting residue was purified by column chromatography (Si—PCC, gradient 0-10% MeOH in DCM) to afford the title compound as an orange oil (126 mg, 57%). LCMS (Method C): R$_T$ 2.16 min [M+H]$^+$ 299.3. $^1$H NMR (CDCl$_3$, 400 MHz): δ 8.84 (1H, dd, J=4.82, 1.02 Hz), 8.75 (1H, s), 7.95 (1H, s), 7.72-7.57 (2H, m), 7.47 (1H, s), 7.07 (1H, td, J=9.15, 2.31 Hz), 6.80 (1H, d, J=8.61 Hz), 5.21-5.09 (1H, m), 1.96 (3H, s), 1.50 (3H, d, J=6.99 Hz)

(S)-1-(6-Fluoro-1-pyridin-3-yl-1H-benzoimidazol-2-yl)ethylamine

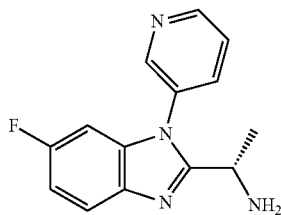 [SMILES: C[C@H](N)c1nc2ccc(F)cc2n1-c1cccnc1]

A mixture of N—[(S)-1-(6-fluoro-1-pyridin-3-yl-1H-benzoimidazol-2-yl)ethyl]acetamide (126 mg) and 6N HCl (2 mL) was heated at 100° C. in a sealed vial for 1 h. After cooling to RT, the crude reaction mixture was partitioned between EtOAc and a saturated aqueous solution of NaHCO$_3$. The organic fraction was washed with water, followed by brine, dried (Na$_2$SO$_4$) and concentrated in vacuo to afford 10 mg of crude material as an orange oil. The aqueous phase was re-extracted with DCM (×3) and the combined organic fractions were washed with brine, dried (Na$_2$SO$_4$) and concentrated in vacuo to afford 71 mg of crude material as a colourless oil. The crude materials were combined to afford the title compound as a pale orange oil (81 mg, 75%). $^1$H NMR (CDCl$_3$, 400 MHz): δ 8.82 (1H, d, J=5.43 Hz), 8.75 (1H, s), 7.83 (1H, d, J=8.06 Hz), 7.73 (1H, dd, J=8.85, 4.75 Hz), 7.61-7.56 (1H, m), 7.06 (1H, t, J=9.26 Hz), 6.77 (1H, d, J=8.49 Hz), 4.14-4.04 (1H, m), 1.50 (3H, d, J=6.65 Hz)

[(R)-1-(6-Fluoro-1-phenyl-1H-benzoimidazol-2-yl)-2-methoxyethyl]carbamic acid tert-butyl ester

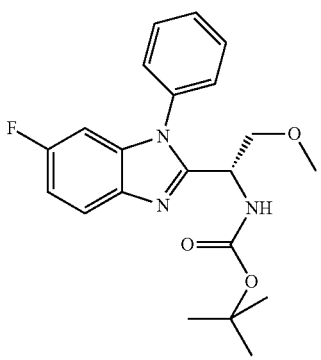 [SMILES: COC[C@H](NC(=O)OC(C)(C)C)c1nc2ccc(F)cc2n1-c1ccccc1]

A mixture of 4-fluoro-N$^2$-phenylbenzene-1,2-diamine (450 mg, 2.2 mmol), (S)-2-tertbutoxycarbonylamino-3-methoxypropionic acid (525 mg, 2.4 mmol), HOAt (330 mg, 2.4 mmol), 4-methylmorpholine (0.53 mL, 4.8 mmol) and N-(3-dimethylaminopropyl)-N'-ethylcarbodiimide hydrochloride (460 mg, 2.4 mmol) in DCM (10 mL) was stirred at RT for 18 h. The reaction mixture was partitioned between DCM and a saturated aqueous solution of NaHCO$_3$. The organic phase was washed with brine, dried (MgSO$_4$) concentrated in vacuo and the resulting residue was purified by column chromatography (Si—PCC, gradient 0-30% EtOAc in cyclohexane) to afford [(S)-1-(4-fluoro-2-phenylaminophenylcarbamoyl)-2-methoxyethyl]carbamic acid tert-butyl ester (0.655 g, 74%). A solution of the compound thus obtained (0.655 g) in AcOH (10 mL) was heated at 70° C. for 56 h. After cooling to RT, the volatiles were removed in vacuo and the resulting residue partitioned between DCM and a saturated aqueous solution of NaHCO$_3$. The organic layer was washed with brine, dried (MgSO$_4$) and concentrated in vacuo. The resulting residue was purified by column chromatography (Si—PCC, gradient 0-30% EtOAc in cyclohexane) to afford the title compound (227 mg, 28%). LCMS (Method J): R$_T$ 3.59 and 3.70 min [M+H]$^+$ 386.2

(R)-1-(6-Fluoro-1-phenyl-1H-benzoimidazol-2-yl)-2-methoxyethylamine

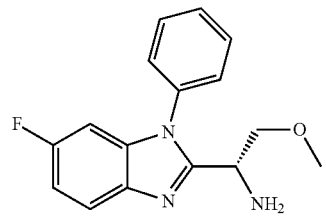

To a solution of [(R)-1-(6-fluoro-1-phenyl-1H-benzoimidazol-2-yl)-2-methoxyethyl]carbamic acid tert-butyl ester (0.227 g, 0.59 mmol) in DCM (4.5 mL) was added TFA (2.5 mL) and the mixture stirred at RT for 2 h. The volatiles were removed in vacuo and the resulting residue partitioned between DCM and a saturated aqueous solution of NaHCO$_3$. The two phase system was stirred for 10 min, then the organic fraction was dried (MgSO$_4$) and concentrated in vacuo. The resulting residue was purified by column chromatography (Si—PCC, gradient 0-10% MeOH in DCM) to afford the title compound as a colourless oil (110 mg, 65%). LCMS (Method B): R$_T$ 1.90 min [M+H]$^+$ 286.0.

[(1R,2R)-2-Benzyloxy-1-(6-fluoro-1-phenyl-1H-benzoimidazol-2-yl)propyl]carbamic acid tert-butyl ester

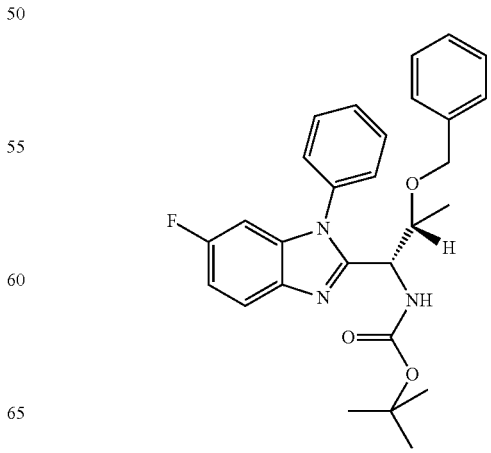

A mixture of 4-fluoro-N²-phenylbenzene-1,2-diamine (525 mg, 2.6 mmol), (2S,3R)-3-benzyloxy-2-tertbutoxycarbonylaminobutyric acid (880 mg, 2.9 mmol), HOAt (390 mg, 2.9 mmol), 4-methylmorpholine (0.60 mL, 5.7 mmol) and N-(3-dimethylaminopropyl)-N'-ethylcarbodiimide hydrochloride (560 mg, 2.9 mmol) in DCM (13 mL) was stirred at RT for 18 h. The reaction mixture was partitioned between DCM and a saturated aqueous solution of NaHCO₃. The organic phase was washed with brine, dried (MgSO₄), concentrated in vacuo and the resulting residue purified by column chromatography (Si—PCC, gradient 0-30% EtOAc in cyclohexane) to afford [(1S,2R)-2-benzyloxy-1-(4-fluoro-2-phenylaminophenylcarbamoyl)propyl]carbamic acid tert-butyl ester (1.32 g). LCMS (Method B): $R_T$ 4.32 min [M+H]⁺ 494.3.

A solution of the compound thus obtained (1.32 g) in AcOH (13 mL) was heated at 70° C. for 18 h. After cooling to RT, the volatiles were removed in vacuo and the resulting residue partitioned between DCM and a saturated aqueous solution of NaHCO₃. The organic fraction was washed with brine, dried (MgSO₄) and concentrated in vacuo. The resulting residue was purified by column chromatography (Si—PCC, gradient 0-30% EtOAc in cyclohexane) to afford the title compound as a yellow solid (971 mg, 79%), still impure and used in the following step without further purification. LCMS (Method J): $R_T$ 4.28 min [M+H]⁺ 476.2.

(1R,2R)-2-Benzyloxy-1-(6-fluoro-1-phenyl-1H-benzoimidazol-2-yl)propylamine

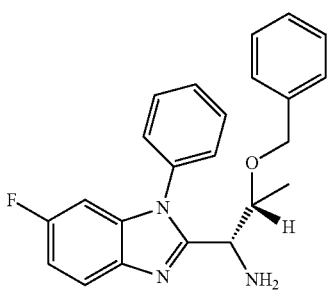 [SMILES: C[C@@H](OCc1ccccc1)[C@H](N)c1nc2ccc(F)cc2n1-c1ccccc1]

To a solution of [(1R,2R)-2-benzyloxy-1-(6-fluoro-1-phenyl-1H-benzoimidazol-2-yl)propyl]carbamic acid tert-butyl ester (0.971 g, 2.0 mmol) in DCM (15 mL) was added TFA (8 mL) and the mixture stirred at RT for 2 h. The volatiles were removed in vacuo and the resulting residue partitioned between DCM and a saturated aqueous solution of NaHCO₃. The two phase system was stirred for 10 min, then the organic fraction was dried (MgSO₄) and concentrated in vacuo. The resulting residue was purified by column chromatography (Si—PCC, gradient 0-10% MeOH in DCM) to afford the title compound (100 mg, 13%). LCMS (Method C): $R_T$ 2.59 min [M+H]⁺ 376.4.

[(1R,2R)-2-Benzyloxy-1-(6-fluoro-1-phenyl-1H-benzoimidazol-2-yl)propyl]-(7H-purin-6-yl)amine

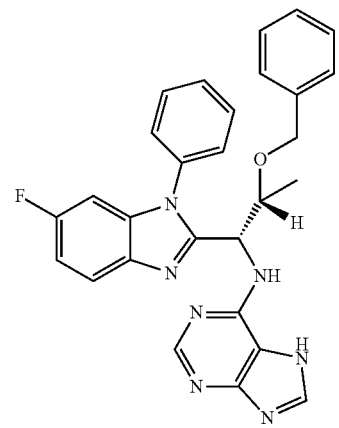 [SMILES: C[C@@H](OCc1ccccc1)[C@H](Nc1ncnc2nc[nH]c12)c1nc2ccc(F)cc2n1-c1ccccc1]

A mixture of (1R,2R)-2-benzyloxy-1-(6-fluoro-1-phenyl-1H-benzoimidazol-2-yl)propylamine (100 mg, 0.27 mmol), 6-chloro-9-(tetrahydropyran-2-yl)-9H-purine (65 mg, 0.27 mmol) and DIPEA (240 µL, 1.35 mmol) in n-butanol (1 mL) was heated at 90° C. in a sealed vial for 18 h. After cooling to RT, the volatiles were removed in vacuo and the resulting residue loaded onto an Isolute® SCX-2 cartridge then washed with MeOH followed by 2M NH₃/MeOH. The product containing fractions were combined and concentrated in vacuo. The resulting residue was purified by column chromatography (Si—PCC, gradient 0-10% 2M NH₃/MeOH in DCM) to afford the title compound (128 mg, 96%). LCMS (Method J): $R_T$ 3.19 min [M+H]⁺ 494.1.

[(R)-2-Benzyloxy-1-(6-fluoro-1-phenyl-1H-benzoimidazol-2-yl)ethyl]carbamic acid tert-butyl ester

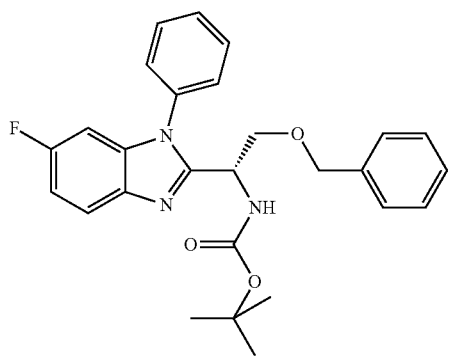 [SMILES: CC(C)(C)OC(=O)N[C@@H](COCc1ccccc1)c1nc2ccc(F)cc2n1-c1ccccc1]

A mixture of 4-fluoro-N²-phenylbenzene-1,2-diamine (550 mg, 2.7 mmol), (S)-3-benzyloxy-2-tertbutoxycarbonylaminopropionic acid (880 mg, 3.0 mmol), HOAt (410 mg, 3.0 mmol), 4-methylmorpholine (0.65 mL, 5.9 mmol) and N-(3-dimethylaminopropyl)-N'-ethylcarbodiimide hydrochloride (580 mg, 3.0 mmol) in DCM (13 mL) was stirred at RT for 18 h. The reaction mixture was partitioned between DCM and a saturated aqueous solution of NaHCO$_3$. The organic fraction was washed with brine, dried (MgSO$_4$), concentrated in vacuo and the resulting residue purified by column chromatography (Si—PCC, gradient 0-30% EtOAc in cyclohexane) to afford [(S)-2-benzyloxy-1-(4-fluoro-2-phenylaminophenylcarbamoyl)ethyl]carbamic acid tert-butyl ester as a red oil (1.1 g, 83%).

A solution of the compound thus obtained (1.1 g) in AcOH (10 mL) was heated at 70° C. for 96 h. After cooling to RT, the volatiles were removed in vacuo and the resulting residue partitioned between DCM and a saturated aqueous solution of NaHCO$_3$. The organic fraction was washed with brine, dried (MgSO$_4$) and concentrated in vacuo. The resulting residue was purified by column chromatography (Si—PCC, gradient 0-30% EtOAc in cyclohexane) to afford the title compound as an orange oil (797 mg, 74%). LCMS (Method J): R$_T$ 4.14 min [M+H]$^+$ 462.3.

(R)-2-Benzyloxy-1-(6-fluoro-1-phenyl-1H-benzoimidazol-2-yl)ethylamine

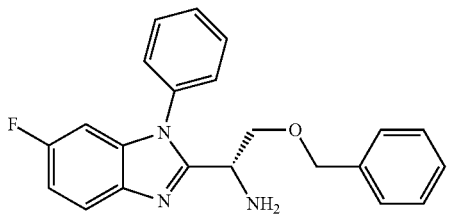 [SMILES: N[C@@H](COCc1ccccc1)c1nc2ccc(F)cc2n1-c1ccccc1]

To a solution of [(R)-2-benzyloxy-1-(6-fluoro-1-phenyl-1H-benzoimidazol-2-yl)ethyl]carbamic acid tert-butyl ester (0.797 g, 1.7 mmol) in DCM (9 mL) was added TFA (5 mL) and the mixture was stirred at RT for 2 h. The volatiles were removed under reduced pressure and the resulting residue partitioned between DCM and a saturated aqueous solution of NaHCO$_3$. The two phase system was stirred for 10 min, then the organic fraction was dried (MgSO$_4$) and concentrated in vacuo. The resulting residue was purified by column chromatography (Si—PCC, gradient 0-10% MeOH in DCM) to afford the title compound (298 mg, 49%). LCMS (Method J): R$_T$ 2.02 min [M+H]$^+$ 362.2.

[(R)-2-Benzyloxy-1-(6-fluoro-1-phenyl-1H-benzoimidazol-2-yl)ethyl]-(7H-purin-6-yl)amine

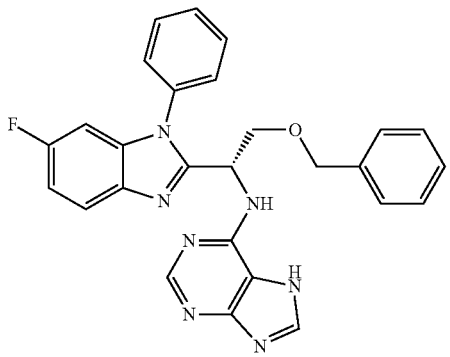 [SMILES: Fc1ccc2nc([C@H](COCc3ccccc3)Nc3ncnc4nc[nH]c34)n(-c3ccccc3)c2c1]

A mixture of (R)-2-benzyloxy-1-(6-fluoro-1-phenyl-1H-benzoimidazol-2-yl)ethylamine (298 mg, 0.83 mmol), 6-chloro-9-(tetrahydropyran-2-yl)-9H-purine (200 mg, 0.83 mmol) and DIPEA (700 µL, 4.2 mmol) in n-butanol (5 mL) was heated at 90° C. in a sealed vial for 48 h. After cooling to RT, the volatiles were removed in vacuo and the resulting residue loaded onto an Isolute® SCX-2 cartridge then washed with MeOH followed by 2M NH$_3$/MeOH. The product containing fractions were combined and concentrated in vacuo. The resulting residue was purified by column chromatography (Si—PCC, gradient 0-10% 2M NH$_3$/MeOH in DCM) to afford the title compound as a colourless oil (256 mg, 64%). LCMS (Method B): R$_T$ 3.26 min [M+H]$^+$ 480.2.

(2-Bromo-3-fluoro-6-nitrophenyl)phenylamine

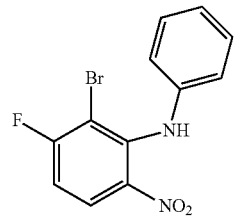

LiHMDS (1.0M in THF, 16.8 mL, 16.8 mmol) was added dropwise to a stirred solution of aniline (821 mg, 8.80 mmol) in anhydrous THF (20 mL) under a nitrogen atmosphere at −78° C. After 10 min stirring at −78° C., a solution of 2-bromo-1,3-difluoro-4-nitrobenzene (2.0 g, 8.40 mmol) in THF (10 mL) was added and stirring at −78° C. was continued for 30 min. The reaction mixture was quenched by addition of water and extracted with EtOAc (×3). The combined organic fractions were washed with brine, dried (MgSO$_4$), concentrated in vacuo and the resulting residue purified by column chromatography (Si—PCC, gradient 0-100% DCM in cyclohexane) to afford the title compound (2.4 g, 91%). $^1$H NMR (CDCl$_3$, 400 MHz): δ 8.48 (1H, s), 8.19-7.12 (1H, m), 7.33-7.25 (2H, m), 7.09 (1H, t, J=7.41 Hz), 6.93-6.83 (3H, m).

3-Bromo-4-fluoro-N$^2$-phenylbenzene-1,2-diamine

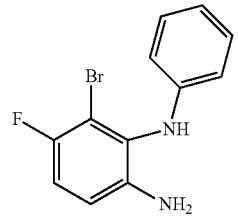 [SMILES: Nc1ccc(F)c(Br)c1Nc1ccccc1]

To a mixture of (2-bromo-3-fluoro-6-nitrophenyl)phenylamine (2.4 g, 7.7 mmol) in MeOH (40 mL) and water (15 mL) were added NH$_4$Cl (2.38 g, 46.3 mmol) and iron powder (1.72 g, 30.9 mmol) and the reaction mixture heated at 90° C. for 1 h. After cooling to RT, the crude mixture was filtered through a pad of Celite® and the filtrate concentrated in vacuo. The resulting residue was partitioned between EtOAc and water. The aqueous phase was extracted with EtOAc (×3) and the combined organic fractions washed with brine, dried (MgSO$_4$) and concentrated in vacuo to afford the title compound (1.95 g, 90%). LCMS (Method C): R$_T$ 3.48 min [M+H]$^+$ 281.1/283.1.

(S)-1-(7-Bromo-6-fluoro-1-phenyl-1H-benzoimidazol-2-yl)ethylamine

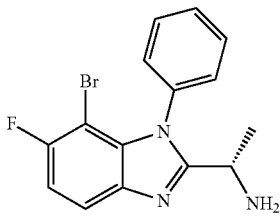 [SMILES: C[C@H](N)c1nc2ccc(F)c(Br)c2n1-c1ccccc1]

A mixture of 3-bromo-4-fluoro-N²-phenylbenzene-1,2-diamine (500 mg, 1.79 mmol), (S)-2-tertbutoxycarbonylaminopropionic acid (370 mg, 1.95 mmol), HOAt (266 mg, 1.95 mmol), 4-methylmorpholine (0.43 mL, 3.91 mmol) and N-(3-dimethylaminopropyl)-N'-ethylcarbodiimide hydrochloride (376 mg, 1.95 mmol) in DCM (5 mL) was stirred at RT for 2 h. The reaction mixture was diluted with water and extracted with DCM (×3). The combined organic fractions were washed with brine, dried (MgSO$_4$) and concentrated in vacuo. The resulting residue was dissolved in dioxane (10 mL) and HCl (12N, 1.5 mL) added. The reaction mixture was stirred at RT for 18 h then made basic by addition of 1N NaOH. The aqueous phase was extracted with EtOAc (×3) and the combined organic fractions washed with brine, dried (MgSO$_4$) and concentrated under reduced pressure. The resulting residue was purified by column chromatography (Si—PCC, gradient 0-10% MeOH in DCM) to afford (S)-1-(7-bromo-6-fluoro-1-phenyl-1H-benzoimidazol-2-yl)ethylamine (102 mg, 17%). LCMS (Method C): R$_T$ 2.28 min [M+H]$^+$ 334.1/336.1. Chromatography purification afforded also (S)-2-amino-N-(3-bromo-4-fluoro-2-phenylaminophenyl)propionamide (384 mg) which was dissolved in 4N HCl in dioxane (10 mL) and heated at 70° C. for 3 h. The volatiles were removed in vacuo to afford (S)-1-(7-bromo-6-fluoro-1-phenyl-1H-benzoimidazol-2-yl)ethylamine dihydrochloride salt (434 mg, 60%). $^1$H NMR (DMSO-d$_6$, 400 MHz): δ 8.84 (2H, s), 7.83 (1H, dd, J=8.80, 4.57 Hz), 7.71-7.58 (5H, m), 7.38 (1H, dd, J=9.65, 8.80 Hz), 4.17-4.07 (1H, m), 3.56 (2H, s), 1.42 (3H, d, J=6.80 Hz)

[(S)-1-(7-Bromo-6-fluoro-1-phenyl-1H-benzoimidazol-2-yl)ethyl]-[9-(tetrahydropyran-2-yl)-9H-purin-6-yl]amine

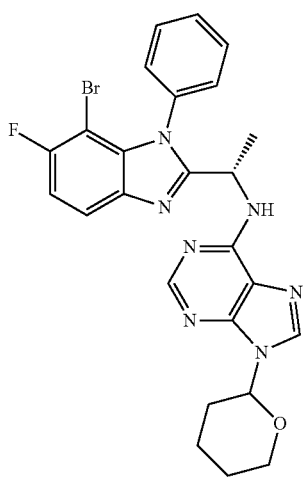 [SMILES: C[C@H](Nc1ncnc2c1ncn2C1CCCCO1)c1nc2ccc(F)c(Br)c2n1-c1ccccc1]

A mixture of (S)-1-(7-bromo-6-fluoro-1-phenyl-1H-benzoimidazol-2-yl)ethylamine (102 mg, 0.31 mmol), 6-chloro-9-(tetrahydropyran-2-yl)-9H-purine (80 mg, 0.34 mmol) and DIPEA (104 µL, 0.61 mmol) in n-butanol (2 mL) was heated at 90° C. in a sealed vial for 18 h. After cooling to RT, the volatiles were removed in vacuo and the resulting residue purified by column chromatography (Si—PCC, gradient 0-10% MeOH in EtOAc) to afford the title compound (128 mg, 78%). LCMS (Method C): R$_T$ 3.57 min [M+H]$^+$ 536.3/538.3.

(2-Chloro-3-fluoro-6-nitrophenyl)phenylamine

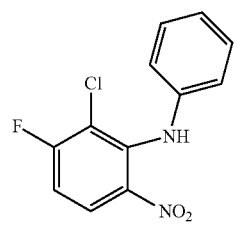

LiHMDS (1.0M in THF, 10.3 mL, 10.3 mmol) was added dropwise to a stirred solution of aniline (505 mg, 5.43 mmol) in anhydrous THF (10 mL) under a nitrogen atmosphere at −78° C. After 10 min stirring at −78° C., a solution of 2-chloro-1,3-difluoro-4-nitrobenzene (1.0 g, 5.17 mmol) in THF (5 mL) was added and stirring at −78° C. was continued for 30 min. The reaction mixture was quenched by addition of water then extracted with EtOAc (×3). The combined organic fractions were washed with brine, dried (MgSO$_4$), concentrated in vacuo and the resulting residue purified by column chromatography (Si—PCC, gradient 0-70% EtOAc in cyclohexane) to afford the title compound (1.28 g, 93%). $^1$H NMR (CDCl$_3$, 400 MHz): δ 8.70 (1H, s), 8.15 (1H, dd, J=9.44, 5.61 Hz), 7.36-7.28 (2H, m), 7.12 (1H, t, J=7.44 Hz), 6.98-6.86 (3H, m).

3-Chloro-4-fluoro-N²-phenylbenzene-1,2-diamine

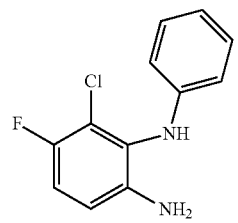

To a mixture of (2-chloro-3-fluoro-6-nitrophenyl)phenylamine (1.28 g, 4.8 mmol) in MeOH (45 mL) and water (15 mL) were added NH₄Cl (1.48 g, 28.8 mmol) and iron powder (1.07 g, 19.2 mmol) and the reaction mixture heated at 90° C. for 2 h. After cooling to RT, the crude mixture was filtered through a pad of Celite® and the filtrate concentrated in vacuo. The resulting residue was partitioned between EtOAc and water. The aqueous phase was extracted with EtOAc (×3) and the combined organic fractions washed with brine, dried (MgSO₄) and concentrated in vacuo. The resulting residue was purified by column chromatography (Si—PCC, gradient 0-100% DCM in cyclohexane) to afford the title compound (918 mg, 81%). LCMS (Method C): $R_T$ 3.46 min [M+H]⁺ 237.1/239.1.

(S)-1-(7-Chloro-6-fluoro-1-phenyl-1H-benzoimidazol-2-yl)ethylamine dihydrochloride

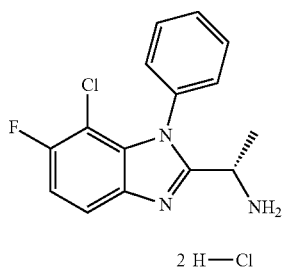

A mixture of 3-chloro-4-fluoro-N²-phenylbenzene-1,2-diamine (300 mg, 1.26 mmol), (S)-2-tertbutoxycarbonylaminopropionic acid (264 mg, 1.39 mmol), HOAt (190 mg, 1.39 mmol), 4-methylmorpholine (0.31 mL, 2.79 mmol) and N-(3-dimethylaminopropyl)-N'-ethylcarbodiimide hydrochloride (270 mg, 1.39 mmol) in DCM (5 mL) was stirred at RT for 18 h. The reaction mixture was diluted with a saturated aqueous solution of NaHCO₃ and extracted with DCM (×3). The combined organic fractions were washed with brine, dried (MgSO₄) and concentrated in vacuo. The resulting residue was dissolved in AcOH (5 mL) and the solution heated at 70° C. for 36 h. The volatiles were removed in vacuo and the resulting residue purified by column chromatography (Si—PCC, gradient 0-100% EtOAc in cyclohexane) to afford impure [(S)-1-(7-chloro-6-fluoro-1-phenyl-1H-benzoimidazol-2-yl)ethyl]carbamic acid tert-butyl ester. The product thus obtained was dissolved in 4N HCl in dioxane (7 mL) and heated at 70° C. for 2 h. The volatiles were removed in vacuo to afford (S)-1-(7-chloro-6-fluoro-1-phenyl-1H-benzoimidazol-2-yl)ethylamine dihydrochloride as an off-white foam (368 mg, 80% over three steps). LCMS (Method C): $R_T$ 2.28 min [M+H]⁺ 290.2.

[(S)-1-(7-Chloro-6-fluoro-1-phenyl-1H-benzoimidazol-2-yl)ethyl]-[9-(tetrahydropyran-2-yl)-9H-purin-6-yl]amine

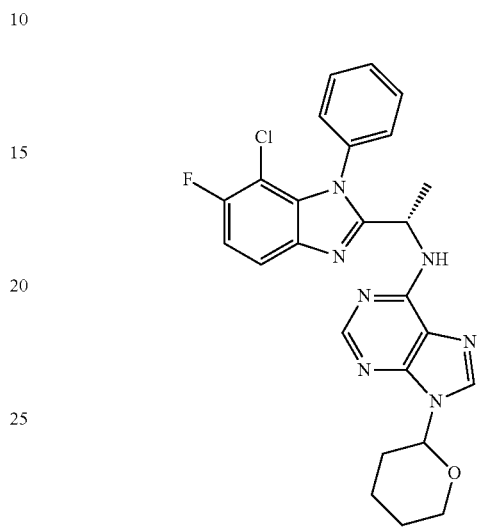

A mixture of (S)-1-(7-chloro-6-fluoro-1-phenyl-1H-benzoimidazol-2-yl)ethylamine dihydrochloride (150 mg, 0.41 mmol), 6-chloro-9-(tetrahydropyran-2-yl)-9H-purine (118 mg, 0.49 mmol) and DIPEA (280 μL, 1.65 mmol) in n-butanol (3 mL) was heated at 90° C. in a sealed vial for 18 h. After cooling to RT, the volatiles were removed under reduced pressure and the resulting residue purified by column chromatography (Si—PCC, gradient 0-10% MeOH in EtOAc) to afford the title compound (166 mg, 82%). LCMS (Method B): $R_T$ 3.57 min [M+H]⁺ 492.0/493.8.

(3-Nitropyridin-2-yl)-m-tolylamine

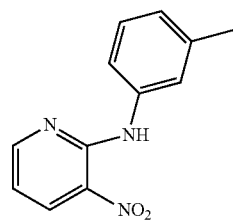 [SMILES: Cc1cccc(Nc2ncccc2[N+](=O)[O-])c1]

A mixture of 2-chloro-3-nitropyridine (2.28 g, 14.4 mmol), m-tolylamine (2.78 g, 25.9 mmol) and Et₃N (3.6 mL, 25.9 mmol) in DMF (10 mL) was stirred at 90° C. for 16 h under a nitrogen atmosphere. The reaction mixture was partitioned between DCM and water. The aqueous phase was extracted with DCM (×3) and the combined organic layers were dried (Na₂SO₄) and concentrated in vacuo. The resulting residue was purified by column chromatography (Si—PCC, gradient 30-100% DCM in cyclohexane) to afford the title compound as an orange solid (2.31 g, 70%). LCMS (Method C): $R_T$ 3.81 min [M+H]$^+$ 230.1.

N$^2$-m-Tolylpyridine-2,3-diamine

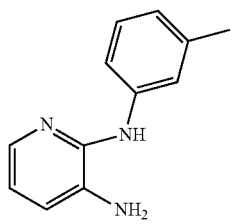

A mixture of (3-nitropyridin-2-yl)-m-tolylamine (2.30 g, 10.0 mmol) in EtOAc (150 mL) was degassed with a stream of nitrogen prior to addition of 10% Pd/C (400 mg) and was stirred at RT under a hydrogen atmosphere for 16 h. The suspension was filtered and the filtrate was concentrated in vacuo to afford the title compound as a white solid (1.88 g, 94%). LCMS (Method C): $R_T$ 1.60 min [M+H]$^+$ 200.1.

[(S)-1-(2-m-Tolylaminopyridin-3-ylcarbamoyl)ethyl] carbamic acid tert-butyl ester

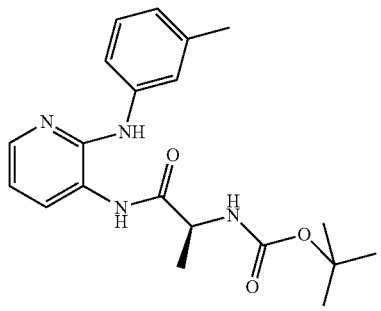 [SMILES: Cc1cccc(Nc2ncccc2NC(=O)[C@H](C)NC(=O)OC(C)(C)C)c1]

Triethylamine (1.7 mL, 12.0 mmol) was added to a mixture of N$^2$-m-tolylpyridine-2,3-diamine (600 mg, 3.01 mmol), (S)-2-tertbutoxycarbonylaminopropionic acid (1.03 g, 5.42 mmol), HOAt (740 mg, 5.42 mmol) and N-(3-dimethylaminopropyl)-N'-ethylcarbodiimide hydrochloride (1.04 g, 5.42 mmol) in anhydrous DCM (25 mL) at 0° C. under a nitrogen atmosphere. The reaction mixture was stirred at 0° C. for 15 min then slowly warmed to RT. Stirring at RT was continued for 16 h. After re-cooling the mixture to 0° C., additional amounts of (S)-2-tertbutoxycarbonylaminopropionic acid (220 mg, 1.20 mmol), HOAt (160 mg, 1.20 mmol), N-(3-dimethylaminopropyl)-N'-ethylcarbodiimide hydrochloride (230 mg, 1.20 mmol) and triethylamine (0.41 mL, 3.01 mmol) were added. The reaction mixture was stirred at 0° C. for 15 min then slowly warmed to RT. Stirring at RT was continued for 72 h. The reaction mixture was partitioned between DCM and a saturated solution of NaHCO$_3$. The aqueous phase was extracted with DCM (×3) and the combined organic fractions were washed with water, dried (Na$_2$SO$_4$) and concentrated in vacuo to afford the title compound as an off-white foam. The crude material was used without further purification in the following step. Yield assumed to be quantitative. LCMS (Method C): $R_T$ 2.70 min [M+H]$^+$ 371.3.

[(S)-1-(3-m-Tolyl-3H-imidazo[4,5-b]pyridin-2-yl) ethyl]carbamic acid tert-butyl ester

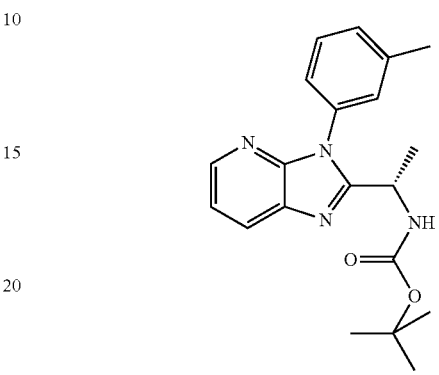

A solution of [(S)-1-(2-m-tolylaminopyridin-3-ylcarbamoyl)ethyl]carbamic acid tert-butyl ester (3.01 mmol) in AcOH (20 mL) was heated at 70° C. for 2 h under a nitrogen atmosphere. After cooling to RT, the volatiles were removed in vacuo and the resulting residue partitioned between DCM and a saturated aqueous solution of NaHCO$_3$. The aqueous phase was extracted with DCM (×3) and the combined organic fractions washed with water, dried (Na$_2$SO$_4$) and concentrated in vacuo to afford the title compound as an off-white foam (quantitative). LCMS (Method C): $R_T$ 3.23 min [M+H]$^+$ 353.4.

(S)-1-(3-m-Tolyl-3H-imidazo[4,5-b]pyridin-2-yl) ethylamine

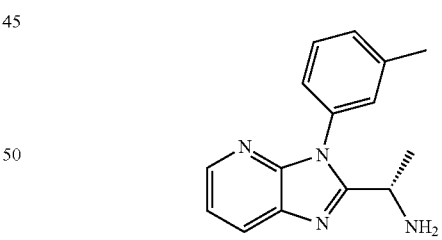

To a solution of [(S)-1-(3-m-tolyl-3H-imidazo[4,5-b]pyridin-2-yl)ethyl]carbamic acid tert-butyl ester (3.01 mmol) in DCM (25 mL) was added TFA (10 mL) and the mixture stirred at RT for 15 min. The volatiles were removed in vacuo and the resulting residue partitioned between DCM and a saturated solution of NaHCO$_3$. The aqueous phase was extracted with DCM (×3) and the combined organic fractions dried (Na$_2$SO$_4$) and concentrated in vacuo. The resulting residue was purified by column chromatography (Si—PCC, gradient 0-8% 2M NH$_3$/MeOH in DCM) to afford the title compound as a colourless oil (700 mg, 92% over three steps). LCMS (Method C): $R_T$ 1.91 min [M+H]$^+$ 253.2.

2-Chloro-N-(4-fluoro-2-phenylaminophenyl)acetamide

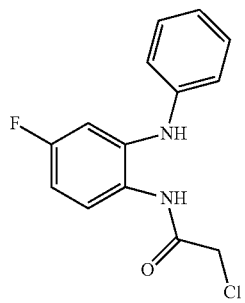 [SMILES: O=C(CCl)Nc1ccc(F)cc1Nc1ccccc1]

Chloroacetyl chloride (0.68 mL, 8.58 mmol) was added dropwise to a stirred solution of 4-fluoro-N$^2$-phenylbenzene-1,2-diamine (1.24 g, 6.13 mmol) and pyridine (2.0 mL, 24.5 mmol) in DCM (8 mL) at 0° C. under a nitrogen atmosphere. After stirring at 0° C. for 20 min, the mixture was slowly warmed to RT and stirring at RT was continued for 2 h. The mixture was partitioned between DCM and aqueous HCl (1M, 50 mL) cooled at 0° C. and the aqueous phase was further extracted with DCM (×3). The combined organic fractions were washed with water, dried (Na$_2$SO$_4$) and concentrated in vacuo. The resulting residue was purified by column chromatography (Si—PCC, gradient 30-100% DCM in cyclohexane) to afford the title compound as a white crystalline solid (750 mg, 44%). LCMS (Method C): $R_T$ 3.42 min [M+H]$^+$ 279.2.

2-Chloromethyl-6-fluoro-1-phenyl-1H-benzoimidazole

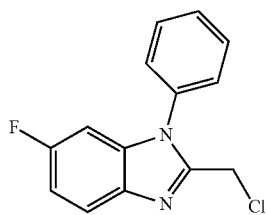 [SMILES: Fc1ccc2nc(CCl)n(-c3ccccc3)c2c1]

2-Chloro-N-(4-fluoro-2-phenylaminophenyl)acetamide (740 mg, 2.62 mmol) was dissolved in AcOH (20 mL) and the mixture heated at 70° C. under a nitrogen atmosphere for 5 h. The volatiles were removed in vacuo and the resulting residue partitioned between DCM and a saturated aqueous solution of NaHCO$_3$. The aqueous phase was extracted with DCM (×3). The combined organic fractions were washed with water, dried (Na$_2$SO$_4$) and concentrated in vacuo. The resulting residue was purified by column chromatography (Si—PCC, gradient 0-5% MeOH in DCM) to afford the title compound as a brown oil which crystallised on standing (570 mg, 84%). LCMS (Method C): $R_T$ 3.40 min [M+H]$^+$ 261.2. $^1$H NMR (CDCl$_3$, 400 MHz): δ 7.75 (1H, dd, J=8.87, 4.76 Hz), 7.66-7.54 (3H, m), 7.47 (2H, d, J=7.38 Hz), 7.07 (1H, td, J=9.21, 2.41 Hz), 6.84 (1H, dd, J=8.54, 2.41 Hz), 4.66 (2H, s). 1

(5-Fluoro-2-nitrophenyl)pyridin-2-yl-amine

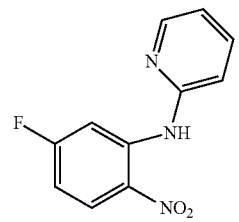 [SMILES: O=[N+]([O-])c1ccc(F)cc1Nc1ccccn1]

LiHMDS (1.0M in THF, 4.8 mL, 4.8 mmol) was added dropwise to a stirred solution of pyridin-2-ylamine (269 mg, 2.86 mmol) in anhydrous THF (10 mL) under a nitrogen atmosphere at −78° C. After 30 min stirring at −78° C., 2,4-difluoro-1-nitrobenzene (298 μL, 2.72 mmol) was added and stirring at −78° C. was continued for 30 min. The reaction mixture was slowly warmed to RT and after 30 min quenched by addition of an aqueous solution of NH$_4$Cl (50 mL). The mixture was partitioned between EtOAc and water, then filtered through Celite®. The organic fraction was dried (Na$_2$SO$_4$), concentrated in vacuo and the resulting residue was purified by column chromatography (Si—PCC, gradient 0-40% EtOAc in cyclohexane) to afford the title compound as an orange solid (258 mg, 41%). $^1$H NMR (CDCl$_3$, 400 MHz): δ 10.48 (1H, s), 8.82 (1H, dd, J=12.32, 2.77 Hz), 8.38 (1H, dd, J=5.03, 1.87 Hz), 8.34-8.25 (1H, m), 7.70-7.64 (1H, m), 7.03-6.94 (2H, m), 6.68-6.61 (1H, m).

4-Fluoro-N$^2$-pyridin-2-ylbenzene-1,2-diamine

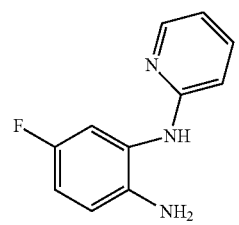 [SMILES: Nc1ccc(F)cc1Nc1ccccn1]

A mixture of (5-fluoro-2-nitrophenyl)pyridin-2-yl-amine (255 mg, 1.09 mmol) in EtOAc (20 mL) was degassed with a stream of nitrogen prior to addition of 10% Pd/C (28 mg) and was stirred at RT under a hydrogen atmosphere for 18 h. The suspension was filtered through a phase separator and the filtrate concentrated in vacuo to afford the title compound as a black solid (241 mg, quantitative). $^1$H NMR (CDCl$_3$, 400

MHz): δ 8.20-8.16 (1H, m), 7.51-7.44 (1H, m), 7.12-7.07 (1H, m), 6.78-6.72 (3H, m), 6.55 (1H, dt, J=8.39, 0.93 Hz), 6.22 (1H, s), 3.63 (2H, s).

(S)-2-Amino-N-[4-fluoro-2-(pyridin-2-ylamino)phenyl]propionamide

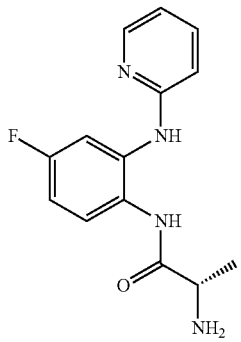 [SMILES: C[C@H](N)C(=O)Nc1ccc(F)cc1Nc1ccccn1]

A mixture of 4-fluoro-$N^2$-pyridin-2-ylbenzene-1,2-diamine (241 mg, 1.19 mmol), (S)-2-tertbutoxycarbonylaminopropionic acid (247 mg, 1.30 mmol), HOAt (178 mg, 1.30 mmol), 4-methylmorpholine (0.287 mL, 2.61 mmol) and N-(3-dimethylaminopropyl)-N'-ethylcarbodiimide hydrochloride (250 mg, 1.30 mmol) in DCM (10 mL) was stirred at RT for 2 h. The reaction mixture was diluted with a saturated aqueous solution of NaHCO$_3$ and extracted with DCM (×3). The combined organic fractions were passed through a phase separator and concentrated in vacuo to afford {(S)-1-[4-fluoro-2-(pyridin-2-ylamino)phenylcarbamoyl]ethyl}carbamic acid tert-butyl ester as a pale red solid (505 mg, quantitative). LCMS (Method B): $R_T$ 2.30 min [M+H]$^+$ 375.0.

A portion of the compound thus obtained (391 mg) was treated with 4M HCl in dioxane (5 mL) and the mixture heated at 70° C. in a sealed vial for 2 h. The volatiles were removed in vacuo and the resulting residue partitioned between DCM and a saturated aqueous solution of NaHCO$_3$. The organic layer was passed through a phase separator and concentrated in vacuo to afford the title compound as a brown oil (190 mg, 66%). $^1$H NMR (CDCl$_3$, 400 MHz): δ 9.61 (1H, s), 8.20-8.17 (1H, m), 7.68 (1H, dd, J=8.93, 5.91 Hz), 7.48 (1H, ddd, J=8.35, 7.22, 1.93 Hz), 7.32 (1H, dd, J=9.79, 2.61 Hz), 6.96 (1H, s), 6.87-6.81 (1H, m), 6.78-6.73 (1H, m), 6.58 (1H, dt, J=8.35, 0.92 Hz), 3.59 (1H, q, J=7.16 Hz), 1.39 (3H, d, J=7.01 Hz).

(S)—N-[4-Fluoro-2-(pyridin-2-ylamino)phenyl]-2-(9H-purin-6-ylamino)propionamide

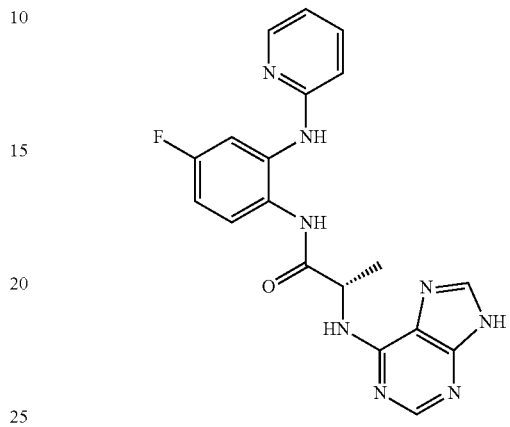

A mixture of (S)-2-amino-N-[4-fluoro-2-(pyridin-2-ylamino)phenyl]propionamide (190 mg, 0.69 mmol), 6-chloro-9-(tetrahydropyran-2-yl)-9H-purine (186 mg, 0.78 mmol) and DIPEA (380 μL, 2.22 mmol) in n-butanol (1.5 mL) was heated at 90° C. in a sealed vial for 65 h. After cooling to RT, the volatiles were removed in vacuo and the resulting residue loaded into an Isolute® SCX-2 cartridge then washed with MeOH followed by 2M NH$_3$/MeOH. The product containing fractions were combined and concentrated in vacuo to afford the title compound as an orange/brown oil (263 mg, 97%). LCMS (Method C): $R_T$ 1.67 min [M+H]$^+$ 393.3.

4-trans-(5-Fluoro-2-nitrophenylamino)cyclohexanecarbonitrile

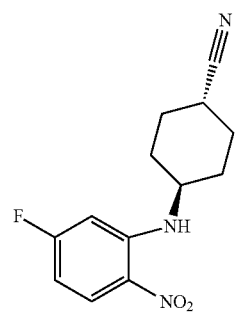

A mixture of 2,4-difluoro-1-nitrobenzene (505 mg, 3.17 mmol), 4-aminocyclohexanecarbonitrile hydrochloride (510 mg, 3.17 mmol) and NaHCO$_3$ (780 mg, 9.3 mmol) in DMSO (5 mL) was heated at 60° C. in a sealed vial for 1 h. The reaction mixture was diluted with water and extracted with EtOAc (×3). The combined organic fractions were washed with brine, dried and concentrated in vacuo. The resulting residue was purified by column chromatography (Si—PCC, gradient 0-25% EtOAc in cyclohexane) to afford the title compound as a pale brown solid (500 mg, 61%). $^1$H NMR (CDCl₃, 400 MHz): δ 8.29-8.10 (2H, m), 6.47 (1H, dd, J=11.40, 2.52 Hz), 6.42-6.34 (1H, m), 3.55-3.44 (1H, m), 2.66-2.55 (1H, m), 2.27-2.13 (4H, m), 1.87-1.72 (2H, m), 1.55-1.41 (2H, m).

4-trans-(2-Amino-5-fluorophenylamino)cyclohexanecarbonitrile

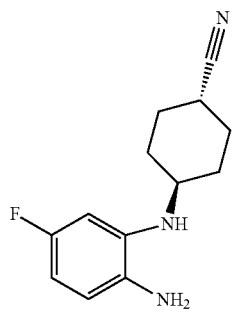 [SMILES: N#C[C@H]1CC[C@H](Nc2cc(F)ccc2[N+](=O)[O-])CC1]

A solution of 4-trans-(5-fluoro-2-nitrophenylamino)cyclohexanecarbonitrile (500 mg, 1.89 mmol) in EtOAc (3 mL) and EtOH (3 mL) was degassed with a stream of argon prior to addition of PtO₂ (50 mg) and was stirred at RT under a hydrogen atmosphere for 24 h. The suspension was filtered and the filtrate was concentrated in vacuo. The resulting residue was purified by column chromatography (Si—PCC, gradient 0-80% EtOAc in cyclohexane) to afford the title compound (195 mg, 44%). LCMS (Method J): $R_T$ 2.07 min [M+H]⁺ 234.2.

{(S)-1-[2-(Trans-4-cyanocyclohexylamino)-4-fluorophenylcarbamoyl]ethyl}carbamic acid tert-butyl ester

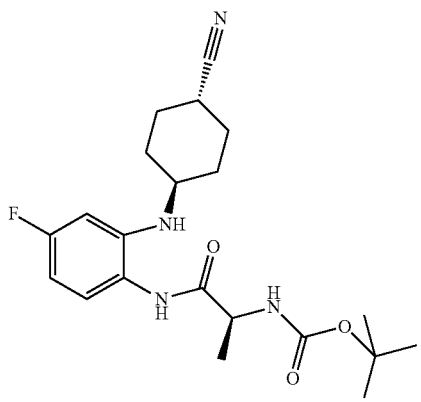 [SMILES: C[C@H](NC(=O)OC(C)(C)C)C(=O)Nc1ccc(F)cc1N[C@H]1CC[C@H](C#N)CC1]

A mixture of trans-4-(2-amino-5-fluorophenylamino)cyclohexanecarbonitrile (195 mg, 0.83 mmol), (S)-2-tertbutoxycarbonylaminopropionic acid (174 mg, 0.92 mmol), HOAt (125 mg, 0.92 mmol), 4-methylmorpholine (0.20 mL, 1.83 mmol) and N-(3-dimethylaminopropyl)-N'-ethylcarbodiimide hydrochloride (192 mg, 1.0 mmol) in THF (3 mL) was stirred at RT for 18 h under a nitrogen atmosphere. The reaction mixture was partitioned between EtOAc and water. The organic fraction was washed with brine, dried (MgSO₄), concentrated in vacuo and the resulting residue purified by column chromatography (Si—PCC, gradient 0-50% EtOAc in cyclohexane) to afford the title compound as a white foam (199 mg, 60%). LCMS (Method B): $R_T$ 3.37 [M+H]⁺ 405.2

Trans-4-[2-((S)-1-Aminoethyl)-6-fluorobenzoimidazol-1-yl]cyclohexanecarbonitrile

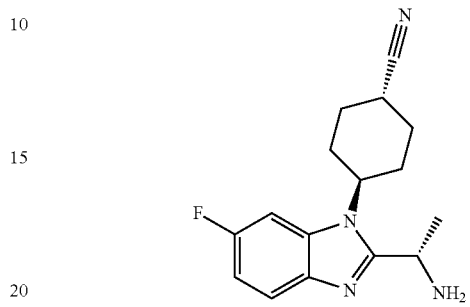

A mixture of {(S)-1-[2-(trans-4-cyanocyclohexylamino)-4-fluorophenylcarbamoyl]ethyl}carbamic acid tert-butyl ester (195 mg, 0.48 mmol) in AcOH (2 mL) was heated at 80° C. under a nitrogen atmosphere for 1 h, then at 90° C. for 2 h and finally at 110° C. for 16 h. The volatiles were removed under reduced pressure and the resulting residue dissolved in 6N HCl (5 mL) and heated at reflux temperature for 2 h. The volatiles were removed in vacuo and the resulting residue dissolved in an aqueous solution of NaHCO₃ and extracted with EtOAc (×3). The combined organic fractions were washed with water, dried and concentrated in vacuo to afford the title compound as a brown solid (100 mg, 72%). LCMS (Method C): $R_T$ 2.01 min [M+H]⁺ 287.1.

N²-Cyclobutyl-4-fluorobenzene-1,2-diamine

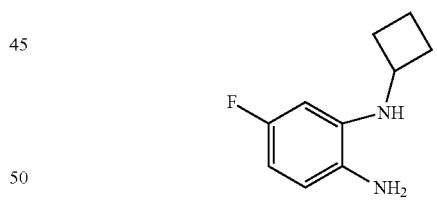

To a solution of 2,4-difluoro-1-nitrobenzene (0.7 mL, 6.3 mmol) in CH₃CN (10 mL) were added cyclobutylamine (0.54 mL, 6.3 mmol) and DIPEA (1.1 mL, 6.3 mmol). The reaction mixture was stirred at RT for 18 h then concentrated in vacuo. The resulting residue was purified by column chromatography (Si—PCC, gradient 0-10% EtOAc in cyclohexane) to afford cyclobutyl-(5-fluoro-2-nitrophenyl)amine as a yellow oil (1.38 g, quantitative). To a solution of the product thus obtained (6.3 mmol) in EtOAc (60 mL) was added 10% Pd/C (150 mg) and the reaction mixture stirred at RT for 18 h under a hydrogen atmosphere. The suspension was filtered through a pad of Celite® and the filtrate concentrated in vacuo to afford the title compound as an orange oil (1.1 g, quantitative). ¹H NMR (CDCl₃, 300 MHz): δ 6.63-6.56 (1H, m), 6.35-6.19 (2H, m), 3.92-3.78 (1H, m), 3.66-2.91 (2H, m), 2.53-2.36 (2H, m), 1.94-1.73 (4H, m).

[(S)-1-(1-Cyclobutyl-6-fluoro-1H-benzoimidazol-2-yl)ethyl]carbamic acid tert-butyl ester

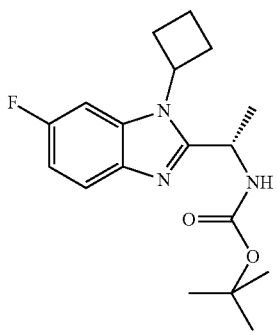 [SMILES: C[C@H](NC(=O)OC(C)(C)C)c1nc2ccc(F)cc2n1C1CCC1]

A mixture of N²-cyclobutyl-4-fluorobenzene-1,2-diamine (0.63 g, 3.5 mmol), (S)-2-tertbutoxycarbonylaminopropionic acid (0.73 g, 3.9 mmol), HOAt (0.53 g, 3.9 mmol), 4-methylmorpholine (0.85 mL, 7.7 mmol) and N-(3-dimethylaminopropyl)-N'-ethylcarbodiimide hydrochloride (0.75 g, 3.9 mmol) in DCM (12 mL) was stirred at RT for 18 h. The reaction mixture was partitioned between DCM and a saturated aqueous solution of NaHCO₃. The organic fraction was washed with brine, dried (MgSO₄), concentrated in vacuo and the resulting residue purified by column chromatography (Si—PCC, gradient 0-30% EtOAc in cyclohexane) to afford [(S)-1-(2-cyclobutylamino-4-fluorophenylcarbamoyl)ethyl]carbamic acid tert-butyl ester (853 mg, 69%). LCMS (Method J): $R_T$ 3.54 min [M+H]⁺ 352.2.

The compound thus obtained was dissolved in AcOH (12 mL) and heated at 70° C. for 18 h. After cooling to RT, the volatiles were evaporated in vacuo and the residue partitioned between DCM and a saturated aqueous solution of NaHCO₃. The organic fraction was washed with brine, dried (MgSO₄) then concentrated in vacuo. The resulting residue was purified by column chromatography (Si—PCC, gradient 0-30% EtOAc in cyclohexane) to afford the title compound as a yellow oil (728 mg, 62%). LCMS (Method B): $R_T$ 2.96 min [M+H]⁺ 334.2.

(S)-1-(1-Cyclobutyl-6-fluoro-1H-benzoimidazol-2-yl)ethylamine

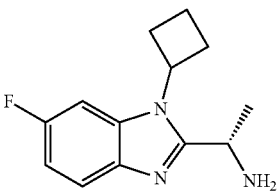 [SMILES: C[C@H](N)c1nc2ccc(F)cc2n1C1CCC1]

To a solution of [(S)-1-(1-cyclobutyl-6-fluoro-1H-benzoimidazol-2-yl)ethyl]carbamic acid tert-butyl ester (728 mg, 2.2 mmol) in DCM (15 mL) was added TFA (8 mL) and the mixture stirred at RT for 1 h. The volatiles were removed in vacuo and the resulting residue partitioned between DCM and a saturated aqueous solution of NaHCO₃. The two phase system was stirred for 10 min and the organic layer dried (MgSO₄) and concentrated in vacuo. The resulting residue was purified by column chromatography (Si—PCC, gradient 0-10% MeOH in DCM) to afford the title compound as a white solid (251 mg, 49%). LCMS (Method C): $R_T$ 2.07 min [M+H]⁺ 234.1.

Cyclopropyl-(5-fluoro-2-nitrophenyl)amine

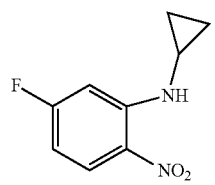

To a solution of 2,4-difluoro-1-nitrobenzene (0.7 mL, 6.3 mmol) in anhydrous CH₃CN (10 mL) were added cyclopropylamine (0.4 mL, 6.3 mmol) and DIPEA (1.1 mL, 6.3 mmol). The reaction mixture was stirred at RT for 18 h then evaporated in vacuo. The resulting residue was purified by column chromatography (Si—PCC, gradient 0-10% EtOAc in cyclohexane) to afford the title compound as a yellow solid (6.3 mmol, quantitative). ¹H NMR (CDCl₃, 300 MHz): δ 8.26-8.09 (2H, m), 6.95 (1H, dd, J=11.43, 2.68 Hz), 6.46-6.35 (1H, m), 2.60-2.50 (1H, m), 0.98-0.89 (2H, m), 0.71-0.63 (2H, m).

N²-Cyclopropyl-4-fluorobenzene-1,2-diamine

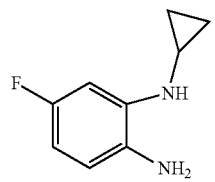

To a solution of cyclopropyl-(5-fluoro-2-nitrophenyl)amine (6.3 mmol) in EtOAc (60 mL) was added 10% Pd/C (150 mg) and the reaction mixture was stirred at RT under a hydrogen atmosphere for 5 h. The suspension was filtered through a pad of Celite® and the filtrate concentrated in vacuo to afford the title compound as a brown oil (1.1 g, quantitative). ¹H NMR (CDCl₃, 300 MHz): δ 6.76 (1H, dd, J=10.85, 2.76 Hz), 6.60 (1H, dd, J=8.38, 5.56 Hz), 6.34 (1H, td, J=8.45, 2.82 Hz), 4.15 (1H, br s), 3.03 (2H, br s), 2.45-2.36 (1H, m), 0.80-0.72 (2H, m), 0.56-0.49 (2H, m).

[(S)-1-(1-Cyclopropyl-6-fluoro-1H-benzoimidazol-2-yl)ethyl]carbamic acid tert-butyl ester

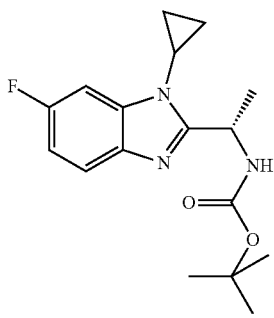 [SMILES: C[C@H](NC(=O)OC(C)(C)C)c1nc2ccc(F)cc2n1C1CC1]

A mixture of N²-cyclopropyl-4-fluorobenzene-1,2-diamine (0.724 g, 4.4 mmol), (S)-2-tertbutoxycarbonylaminopropionic acid (0.91 g, 4.8 mmol), HOAt (0.65 g, 4.8 mmol), 4-methylmorpholine (1.1 mL, 9.7 mmol) and N-(3-dimethylaminopropyl)-N'-ethylcarbodiimide hydrochloride (0.92 g, 4.8 mmol) in DCM (15 mL) was stirred at RT for 18 h. The reaction mixture was partitioned between DCM and a saturated aqueous solution of NaHCO₃. The organic fraction was washed with brine, dried (MgSO₄), concentrated in vacuo and the resulting residue purified by column chromatography (Si—PCC, gradient 0-30% EtOAc in cyclohexane) to afford [(S)-1-(2-cyclopropylamino-4-fluorophenylcarbamoyl)ethyl]carbamic acid tert-butyl ester as a brown oil (1.07 g, 72%). LCMS (Method B): $R_T$ 3.40 min $[M+H]^+$ 338.2. 110180243

The compound thus obtained (1.07 g) was dissolved in AcOH (15 mL) and heated at 70° C. for 18 h. After cooling to RT, the volatiles were evaporated in vacuo and the resulting residue partitioned between DCM and a saturated aqueous solution of NaHCO₃. The organic layer was washed with brine, dried (MgSO₄) and then concentrated in vacuo. The resulting residue was purified by column chromatography (Si—PCC, gradient 0-30% EtOAc in cyclohexane) to afford the title compound as a colourless oil (414 mg, 29%). LCMS (Method C): $R_T$ 2.81 min $[M+H]^+$ 320.2.

(S)-1-(1-Cyclopropyl-6-fluoro-1H-benzoimidazol-2-yl)ethylamine

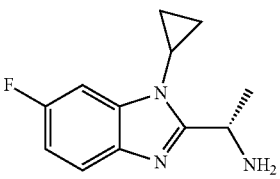 [SMILES: C[C@H](N)c1nc2ccc(F)cc2n1C1CC1]

To a solution of [(S)-1-(1-cyclopropyl-6-fluoro-1H-benzoimidazol-2-yl)ethyl]carbamic acid tert-butyl ester (414 mg, 1.3 mmol) in DCM (7 mL) was added TFA (3 mL) and the mixture stirred at RT for 1 h. The volatiles were removed in vacuo and the resulting residue partitioned between DCM and a saturated aqueous solution of NaHCO₃. The two phase system was stirred for 10 min and then the organic layer was dried (MgSO₄) and concentrated in vacuo. The resulting residue was purified by column chromatography (Si—PCC, gradient 0-10% MeOH in DCM) to afford the title compound as a yellow oil (166 mg, 58%). LCMS (Method C): $R_T$ 1.66 min $[M+H]^+$ 220.1.

[(S)-1-(6-Fluoro-1-phenyl-1H-benzoimidazol-2-yl)ethyl]methylcarbamic acid tert-butyl ester

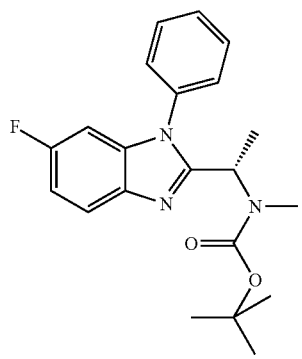 [SMILES: C[C@@H](c1nc2ccc(F)cc2n1-c1ccccc1)N(C)C(=O)OC(C)(C)C]

A mixture of 4-fluoro-N²-phenylbenzene-1,2-diamine (450 mg, 2.2 mmol), (S)-2-(tertbutoxycarbonylmethylamino)propionic acid (0.50 g, 2.4 mmol), HOAt (0.33 g, 2.4 mmol), 4-methylmorpholine (0.5 mL, 4.8 mmol) and N-(3-dimethylaminopropyl)-N'-ethylcarbodiimide hydrochloride (0.46 g, 2.4 mmol) in DCM (10 mL) was stirred at RT for 2 h. The reaction mixture was partitioned between DCM and a saturated aqueous solution of NaHCO₃. The organic layer was washed with brine, dried (MgSO₄), concentrated in vacuo and the resulting residue purified by column chromatography (Si—PCC, gradient 0-30% EtOAc in cyclohexane) to afford [(S)-1-(4-fluoro-2-phenylaminophenylcarbamoyl)ethyl]methylcarbamic acid tert-butyl ester (0.781 g, 92%). LCMS (Method J): $R_T$ 3.92 min $[M+H]^+$ 388.1.

The compound thus obtained (0.781 g) was dissolved in AcOH (10 mL) and heated at 70° C. for 18 h. After cooling to RT, the volatiles were evaporated in vacuo and the residue partitioned between DCM and a saturated aqueous solution of NaHCO₃. The organic fraction was washed with brine, dried (MgSO₄) and concentrated in vacuo. The resulting residue was purified by column chromatography (Si—PCC, gradient 0-30% EtOAc in cyclohexane) to afford the title compound as an orange solid (264 mg, 33%). LCMS (Method B): $R_T$ 3.82 min $[M+H-^tBu]^+$ 314.0.

[(S)-1-(6-Fluoro-1-phenyl-1H-benzoimidazol-2-yl)ethyl]methylamine

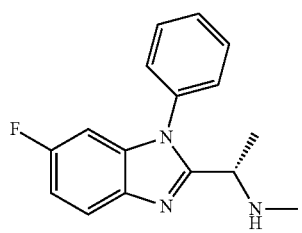 [SMILES: CN[C@@H](C)c1nc2ccc(F)cc2n1-c1ccccc1]

To a solution of [(S)-1-(6-fluoro-1-phenyl-1H-benzoimidazol-2-yl)ethyl]methylcarbamic acid tert-butyl ester (0.264 g, 0.72 mmol) in DCM (8 mL) was added TFA (4 mL) and the mixture stirred at RT for 1.5 h. The volatiles were removed under in vacuo and the resulting residue partitioned between DCM and a saturated aqueous solution of NaHCO$_3$. The two phase system was stirred for 10 minutes and then the aqueous phase extracted with DCM. The combined organic fractions were dried (MgSO$_4$) and concentrated in vacuo to afford the title compound as a colourless oil (102 mg, 53%). LCMS (Method J): R$_T$ 1.80 min [M+H]$^+$ 270.2.

[(S)-3-Benzyloxy-1-(4-fluoro-2-phenylaminophenylcarbamoyl)propyl]carbamic acid tert-butyl ester

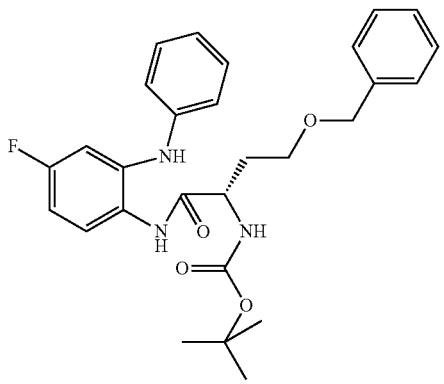 [SMILES: CC(C)(C)OC(=O)N[C@@H](CCOCc1ccccc1)C(=O)Nc1ccc(F)cc1Nc1ccccc1]

A mixture of 4-fluoro-N$^2$-phenylbenzene-1,2-diamine (614 mg, 3.04 mmol), (S)-4-benzyloxy-2-tertbutoxycarbonylaminobutyric acid (1.0 g, 3.3 mmol), HOAt (0.450 g, 3.3 mmol), 4-methylmorpholine (0.7 mL, 6.7 mmol) and N-(3-dimethylaminopropyl)-N'-ethylcarbodiimide hydrochloride (0.63 g, 3.3 mmol) in DCM (15 mL) was stirred at RT for 18 h. The reaction mixture was partitioned between DCM and a saturated aqueous solution of NaHCO$_3$. The organic fraction was washed with brine, dried (MgSO$_4$), concentrated in vacuo and the resulting residue purified by column chromatography (Si—PCC, gradient 0-30% EtOAc in cyclohexane) to afford the title compound as a yellow oil (1.22 g, 82%). LCMS (Method J): R$_T$ 4.17 min [M+H]$^+$ 494.1.

(S)-3-Benzyloxy-1-(6-fluoro-1-phenyl-1H-benzoimidazol-2-yl)propylamine

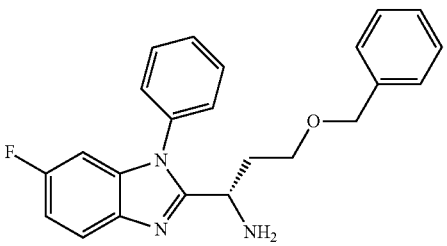 [SMILES: N[C@@H](CCOCc1ccccc1)c1nc2ccc(F)cc2n1-c1ccccc1]

A solution of [(S)-3-benzyloxy-1-(4-fluoro-2-phenylaminophenylcarbamoyl)propyl]carbamic acid tert-butyl ester (1.22 g, 2.5 mmol) in 4M HCl in dioxane (10 mL) was heated at 70° C. for 2 h. After cooling to RT, the volatiles were concentrated in vacuo and the residue partitioned between DCM and a saturated aqueous solution of NaHCO$_3$. The organic fraction was washed with brine, dried (MgSO$_4$) and then concentrated in vacuo. The resulting residue was purified by column chromatography (Si—PCC, gradient 0-10% MeOH in DCM) to afford the title compound as a colourless oil (639 mg, 68%). LCMS (Method B): R$_T$ 2.11 and 2.55 min [M+H]$^+$ 376.2.

[(S)-3-Benzyloxy-1-(6-fluoro-1-phenyl-1H-benzoimidazol-2-yl)propyl]-(9H-purin-6-yl)amine

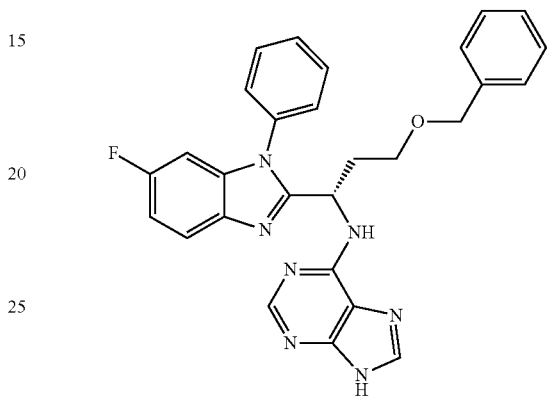

A mixture of (S)-3-benzyloxy-1-(6-fluoro-1-phenyl-1H-benzoimidazol-2-yl)propylamine (639 mg, 1.7 mmol), 6-chloro-9-(tetrahydropyran-2-yl)-9H-purine (410 mg, 1.7 mmol) and DIPEA (1.5 mL, 8.5 mmol) in n-butanol (6 mL) was heated at 100° C. for 18 h. After cooling to RT, the volatiles were removed in vacuo and the resulting residue loaded onto an Isolute® SCX-2 cartridge. The cartridge was washed with MeOH followed by 2M NH$_3$/MeOH. The basic fractions were combined and concentrated in vacuo and the resulting residue purified by column chromatography (Si—PCC, gradient 0-10% 2M NH$_3$/MeOH in DCM) to afford the title compound as a white solid (703 mg, 84%). LCMS (Method C): R$_T$ 3.10 min [M+H]$^+$ 494.3.

(S)-2-Amino-3-methyl-N-(2-phenylaminopyridin-3-yl)butyramide

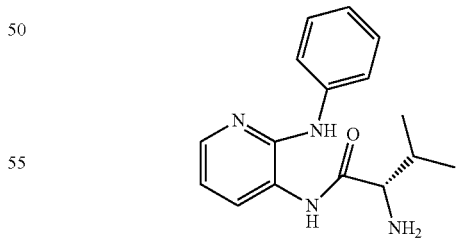

A mixture of N$^2$-phenylpyridine-2,3-diamine (556 mg, 3.0 mmol), (S)-2-tertbutoxycarbonylamino-3-methylbutyric acid (0.72 g, 3.3 mmol), HOAt (0.450 g, 3.3 mmol), 4-methylmorpholine (0.73 mL, 6.6 mmol) and N-(3-dimethylaminopropyl)-N'-ethylcarbodiimide hydrochloride (0.63 g, 3.3 mmol) in DCM (15 mL) was stirred at RT for 18 h. The reaction mixture was partitioned between DCM and a saturated aqueous solution of NaHCO$_3$. The organic layer was washed with brine, dried (MgSO₄), concentrated in vacuo and the resulting residue purified by column chromatography (Si—PCC, gradient 0-30% EtOAc in cyclohexane) to afford [(S)-2-methyl-1-(2-phenylaminopyridin-3-ylcarbamoyl)propyl]carbamic acid tert-butyl ester as a white solid (1.13 g, quantitative).

A mixture of the compound thus obtained in 4M HCl in dioxane (10 mL) was heated at 70° C. for 2 h. After cooling to RT the volatiles were removed under reduced pressure. The resulting residue was partitioned between DCM and a saturated aqueous solution of NaHCO₃. The two phase system was stirred for 10 min. then the organic fraction was washed with brine, dried (MgSO₄) and concentrated in vacuo to afford the title compound (quantitative). LCMS (Method C): $R_T$ 1.17 min [M+H]⁺ 285.3.

(S)-3-Methyl-N-(2-phenylaminopyridin-3-yl)-2-(9H-purin-6-ylamino)butyramide

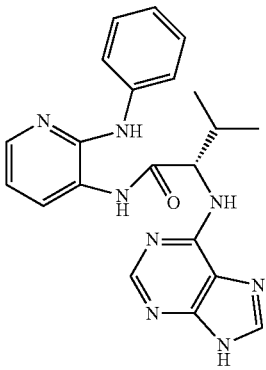 [SMILES: CC(C)[C@H](Nc1ncnc2[nH]cnc12)C(=O)Nc1cccnc1Nc1ccccc1]

A mixture of (S)-2-amino-3-methyl-N-(2-phenylaminopyridin-3-yl)butyramide (3.0 mmol), 6-chloro-9-(tetrahydropyran-2-yl)-9H-purine (720 mg, 3.0 mmol) and DIPEA (2.6 mL, 15.0 mmol) in n-butanol (12 mL) was heated at 100° C. for 18 h in a sealed vial. After cooling to RT, the volatiles were removed in vacuo and the resulting residue loaded onto an Isolute® SCX-2 cartridge. The cartridge was washed with MeOH followed by 2M NH₃/MeOH. The basic fractions were combined, concentrated in vacuo and the resulting residue was purified by column chromatography (Si—PCC, gradient 0-10% 2M NH₃/MeOH in DCM) to afford the title compound (821 mg, 68% over two steps). LCMS (Method J): $R_T$ 1.75 min [M+H]⁺ 403.2.

(5-Fluoro-2-nitrophenyl)pyridin-3-yl-amine

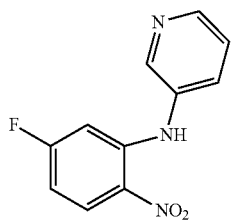 [SMILES: O=[N+]([O-])c1ccc(F)cc1Nc1cccnc1]

LiHMDS (1.0M in THF, 50 mL, 50 mmol) was added dropwise to a stirred solution of pyridin-3-ylamine (2.5 g, 26.4 mmol) in anhydrous THF (20 mL) under a nitrogen atmosphere at −70° C. After 10 min stirring at −78° C., a solution of 2,4-difluoro-1-nitrobenzene (4.0 g, 25.1 mmol) in THF (40 mL) was added dropwise at −78° C. The reaction mixture was slowly warmed to RT. After 4 h stirring at RT, the crude mixture was quenched by addition of an aqueous solution of NH₄Cl and the aqueous fraction extracted with EtOAc. The combined organic fractions were washed with brine, dried (MgSO₄) and concentrated in vacuo to afford the title compound as a red solid (quantitative). ¹H NMR (CDCl₃, 300 MHz): δ 9.58 (1H, br s), 8.61 (1H, d, J=2.64 Hz), 8.55 (1H, d, J=4.76 Hz), 8.29 (1H, dd, J=9.47, 5.92 Hz), 7.66-7.61 (1H, m), 7.40 (1H, dd, J=8.19, 4.75 Hz), 6.74 (1H, dd, J=10.95, 2.62 Hz), 6.60-6.51 (1H, m).

4-Fluoro-N²-pyridin-3-ylbenzene-1,2-diamine

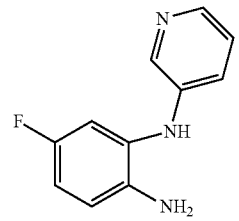

To a mixture of (5-fluoro-2-nitrophenyl)pyridin-3-yl-amine (25 mmol) in EtOH (300 mL) was added 10% Pd/C (1.0 g) and the reaction mixture stirred at RT under a hydrogen atmosphere for 18 h. Additional Pd/C (1.0 g) was added and stirring at RT under a hydrogen atmosphere continued for 2 h. The suspension was filtered through a pad of Celite® and the filtrate was concentrated in vacuo to afford the title compound as a brown solid (quantitative). ¹H NMR (CDCl₃, 300 MHz): δ 8.27 (1H, dd, J=2.64, 0.91 Hz), 8.15 (1H, dd, J=4.41, 1.71 Hz), 7.20-7.09 (2H, m), 6.87 (1H, dd, J=9.61, 2.59 Hz), 6.80-6.68 (2H, m), 5.50 (1H, br s), 2.96 (2H, br s)

(S)-1-(6-Fluoro-1-pyridin-3-yl-1H-benzoimidazol-2-yl)-2-methylpropylamine

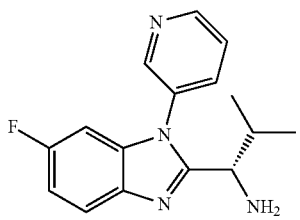

To a solution of 4-fluoro-N²-pyridin-3-ylbenzene-1,2-diamine (685 mg, 3.0 mmol) in DCM (18 mL) at 0° C. were added (S)-2-tertbutoxycarbonylamino-3-methylbutyric acid (720 mg, 3.3 mmol), HOAt (0.450 g, 3.3 mmol) and N-(3-dimethylaminopropyl)-N'-ethylcarbodiimide hydrochloride (0.63 g, 3.3 mmol) and the resulting mixture stirred at 0° C. for 2 h. The reaction mixture was partitioned between DCM and a saturated aqueous solution of NaHCO₃. The organic layer was dried (MgSO₄), concentrated in vacuo and the resulting residue purified by column chromatography (Si—PCC, gradient 0-60% EtOAc in cyclohexane) to afford {(S)-1-[4-fluoro-2-(pyridin-3-ylamino)phenylcarbamoyl]-2- methylpropyl}carbamic acid tert-butyl ester (790 mg). LCMS (Method J): $R_T$ 2.10 min [M+H]$^+$ 403.3

A solution of the compound thus obtained (790 mg) in AcOH (15 mL) was heated at 100° C. for 72 h then the volatiles were removed in vacuo. The resulting residue was partitioned between DCM and a saturated aqueous solution of NaHCO$_3$. The two phase system was vigorously stirred for 10 minutes then the organic fraction dried (MgSO$_4$) and concentrated in vacuo. The resulting residue was purified by column chromatography (Si—PCC, gradient 0-10% MeOH in DCM) and the relevant fractions combined and concentrated in vacuo. The resulting residue (251 mg) was dissolved in 6M HCl (6 mL) and heated at 100° C. for 1 h in a sealed tube. The crude mixture was partitioned between DCM and a saturated aqueous solution of NaHCO$_3$. The two phase system was vigorously stirred for 10 minutes then the organic fraction was dried (MgSO$_4$) and concentrated in vacuo to afford the title compound (135 mg, 16% over four steps). LCMS (Method J): $R_T$ 1.75 min [M+H]$^+$ 285.2

(R)-2-Ethoxy-1-(6-fluoro-1-phenyl-1H-benzoimidazol-2-yl)ethylamine

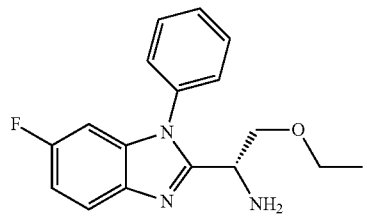

To a solution of 4-fluoro-N$^2$-phenylbenzene-1,2-diamine (562 mg, 2.8 mmol) in DCM (18 mL) at 0° C. were added (S)-2-tertbutoxycarbonylamino-3-ethoxypropionic acid (720 mg, 3.1 mmol), HOAt (0.420 g, 3.1 mmol) and N-(3-dimethylaminopropyl)-N'-ethylcarbodiimide hydrochloride (0.59 g, 3.1 mmol) and the resulting mixture stirred at 0° C. for 1 h. The reaction mixture was partitioned between DCM and a saturated aqueous solution of NaHCO$_3$. The organic fraction was washed with brine, dried (MgSO$_4$), concentrated in vacuo and the resulting residue purified by column chromatography (Si—PCC, gradient 0-30% EtOAc in cyclohexane) to afford [(S)-2-ethoxy-1-(4-fluoro-2-phenylaminophenylcarbamoyl)ethyl]carbamic acid tert-butyl ester (770 mg, 66%). LCMS (Method B): $R_T$ 3.87 min [M+H]$^+$ 418.3

A solution of the compound thus obtained (770 mg) in 4N HCl in dioxane (10 mL) was heated at 70° C. for 2 h then the volatiles were removed in vacuo. The resulting residue was purified by column chromatography (Si—PCC, gradient 0-10% MeOH in DCM) to afford the title compound as an oil (510 mg, 92%). LCMS (Method B): $R_T$ 1.94 min [M+H]$^+$ 300.1

[(S)-1-(7-Cyclopropyl-6-fluoro-1-phenyl-1H-benzoimidazol-2-yl)ethyl]-[9-(tetrahydropyran-2-yl)-9H-purin-6-yl]amine

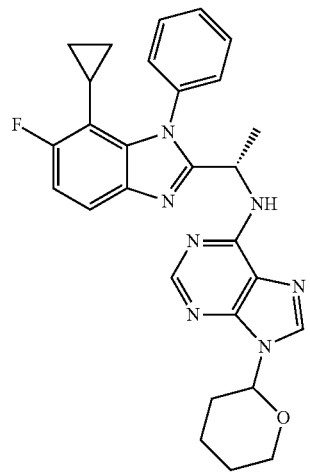 [SMILES: C[C@H](Nc1ncnc2c1ncn2C1CCCCO1)c1nc2ccc(F)c(C3CC3)c2n1-c1ccccc1]

A mixture of [(S)-1-(7-bromo-6-fluoro-1-phenyl-1H-benzoimidazol-2-yl)ethyl]-[9-(tetrahydropyran-2-yl)-9H-purin-6-yl]amine (50 mg, 0.09 mmol), cyclopropylboronic acid (10 mg, 0.12 mmol) and Cs$_2$CO$_3$ (46 mg, 0.14 mmol) in a 4:1 mixture dioxane:water (2.5 mL) was degassed with a stream of argon prior to addition of Pd(PPh$_3$)$_4$ (5 mg) and was heated at 100° C. for 18 h in a sealed vial. Additional cyclopropylboronic acid (10 mg, 0.12 mmol) and Pd(PPh$_3$)$_4$ (5 mg) in dioxane (0.25 mL) were added and stirring at 100° C. in a sealed vial was continued for 3 h. The reaction mixture was diluted with water and extracted with EtOAc (×3). The combined organic fractions were washed with brine, dried (MgSO$_4$) and concentrated in vacuo. The resulting residue was purified by reverse phase HPLC (Phenomenex Gemini 5 μm C18 on a 25 min gradient 10-90%, 0.1% HCO$_2$H in acetonitrile/water) to afford the title compound (20 mg, 43%). LCMS (Method C): $R_T$ 3.32 min [M+H]$^+$ 498.1.

6-Fluoro-3-nitro-2-phenylaminobenzonitrile

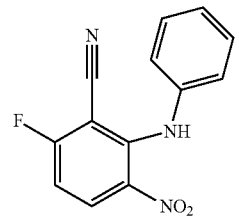

LiHMDS (1.0M in THF, 38 mL, 38.0 mmol) was added dropwise to a stirred solution of aniline (1.86 g, 19.9 mmol) in anhydrous THF (30 mL) under a nitrogen atmosphere at −78° C. After 10 min stirring at −78° C., a solution of 2,6-difluoro-3-nitrobenzonitrile (3.5 g, 19.0 mmol) in THF (15 mL) was added and stirring at −78° C. continued for 30 min. The crude mixture was quenched with water and diluted with EtOAc. The resulting emulsion was filtered through a pad of Celite® and the organic fraction separated, washed with brine, dried (MgSO₄) and concentrated in vacuo. The resulting residue was purified by column chromatography (Si—PCC, gradient 0-100% EtOAc in cyclohexane) to afford the title compound (2.7 g, 55%). $^1$H NMR (CDCl$_3$, 400 MHz): δ 9.94 (1H, br s), 8.51 (1H, dd, J=9.50, 5.88 Hz), 7.51-7.21 (5H, m), 6.68 (1H, dd, J=9.50, 7.46 Hz).

3-Amino-6-fluoro-2-phenylaminobenzonitrile

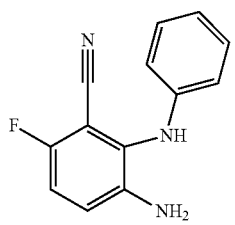

To a mixture of 6-fluoro-3-nitro-2-phenylaminobenzonitrile (2.7 g, 10.5 mmol) in a mixture of MeOH (50 mL) and water (20 mL) were added NH₄Cl (3.23 g, 62.9 mmol) and iron powder (2.3 g, 41.9 mmol) and the reaction mixture was heated at 90° C. for 1 h. After cooling to RT, the solid was filtered through a pad of Celite® and the filtrate concentrated in vacuo. The resulting residue was partitioned between EtOAc and water and the aqueous phase was extracted with EtOAc (×3). The combined organic fractions were washed with brine, dried (MgSO₄) and concentrated in vacuo. The resulting residue was purified by column chromatography (Si—PCC, gradient 0-100% EtOAc in cyclohexane) to afford the title compound (930 mg, 39%). LCMS (Method B): R$_T$ 3.27 min [M+H]⁺ 227.8.

[(S)-1-(7-Cyano-6-fluoro-1-phenyl-1H-benzoimidazol-2-yl)ethyl]carbamic acid tert-butyl ester

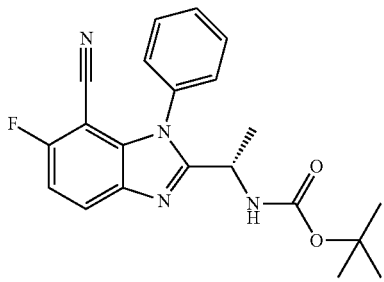 [SMILES: C[C@H](NC(=O)OC(C)(C)C)c1nc2ccc(F)c(C#N)c2n1-c1ccccc1]

To a suspension of ((S)-1-carbamoylethyl)carbamic acid tert-butyl ester (1.12 g, 6.0 mmol) in DCM (7 mL) was added triethyloxonium tetrafluoroborate (969 mg, 5.1 mmol) and the reaction mixture stirred at RT for 3 h, during which time the solids dissolved. The reaction mixture was concentrated in vacuo and the residue dissolved in ethanol (7 mL). 3-Amino-6-fluoro-2-phenylaminobenzonitrile (400 mg, 1.8 mmol) was added and the reaction was heated at 75° C. for 1 h. The reaction mixture was concentrated in vacuo, the residue dissolved in water and the product extracted with EtOAc (3×20 mL). The combined organic extracts were washed with brine, dried (MgSO₄) and concentrated in vacuo. The resultant residue was subjected to flash chromatography (SiO₂, eluting with 0-100% EtOAc in cyclohexane) to yield the title compound as a white solid (411 mg, 61%). LCMS (Method C): R$_T$=3.55 min, [M+H]+=381.

(S)-1-(6-Fluoro-1-pyridin-3-yl-1H-benzoimidazol-2-yl)propylamine

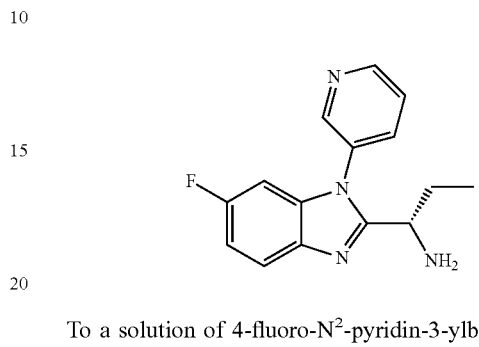

To a solution of 4-fluoro-N²-pyridin-3-ylbenzene-1,2-diamine (0.594 g, 2.9 mmol) in DCM (18 mL) at 0° C. were added (S)-2-tertbutoxycarbonylaminobutyric acid (650 mg, 3.2 mmol), HOAt (440 mg, 3.2 mmol) and N-(3-dimethylaminopropyl)-N'-ethylcarbodiimide hydrochloride (610 mg, 3.2 mmol) and the reaction mixture stirred at 0° C. for 2 h. The crude mixture was partitioned between DCM and a saturated aqueous solution of NaHCO₃. The organic phase was washed with brine, dried (MgSO₄), concentrated in vacuo and the resulting residue purified by column chromatography (Si—PCC, gradient 0-60% EtOAc in cyclohexane) to afford {(S)-1-[4-fluoro-2-(pyridin-3-ylamino)phenylcarbamoyl]propyl}carbamic acid tert-butyl ester (839 mg, 75%). LCMS (Method J): R$_T$ 0.69 min [M+H]⁺ 389.2.

A solution of the compound thus obtained (839 mg, 2.2 mmol) in AcOH (15 mL) was heated at 100° C. for 18 h then the volatiles were removed in vacuo. The resulting residue was partitioned between DCM and a saturated aqueous solution of NaHCO₃. The two phase system was stirred at RT for 10 min, then the organic fraction was separated, dried (MgSO₄) and concentrated in vacuo. The resulting residue was purified by column chromatography (Si—PCC, gradient 0-10% MeOH in DCM) to afford 292 mg of a brown solid. The compound thus obtained was dissolved in 6N aq. HCl (6 mL) and the solution heated at 100° C. for 1 h in a sealed vial. After cooling to RT, the reaction mixture was partitioned between DCM and a saturated aqueous solution of NaHCO₃. The two phase system was stirred at RT for 10 min, then the organic fraction was separated, dried (MgSO₄) and concentrated in vacuo to afford the title compound (243 mg, 41%). LCMS (Method J): R$_T$ 1.57 min [M+H]⁺ 271.3.

(2-Nitropyridin-3-yl)phenylamine

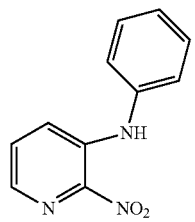

A mixture of 3-fluoro-2-nitropyridine (1.07 g, 6.75 mmol), aniline (1.8 mL, 20.2 mmol) and Et₃N (2.8 mL, 20.2 mmol) in DMF (10 mL) was stirred at 100° C. for 16 h under a nitrogen atmosphere. After cooling to RT, the volatiles were removed under reduced pressure. The resulting residue was partitioned between DCM and water. The aqueous phase was further extracted with DCM (×3) and the combined organic fractions dried (Na₂SO₄) and concentrated in vacuo. The resulting residue was purified by column chromatography (Si—PCC, gradient 0-4% MeOH in DCM) to afford the title compound as a red oil (2.24 g, quantitative). LCMS (Method C): R$_T$ 3.03 min [M+H]⁺ 216.2.

N³-Phenylpyridine-2,3-diamine

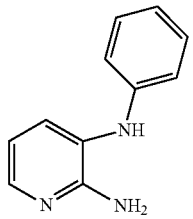 [SMILES: O=[N+]([O-])c1ncccc1Nc1ccccc1]

A mixture of (2-nitropyridin-3-yl)phenylamine (6.75 mmol) in EtOAc (40 mL) was degassed with a stream of nitrogen prior to addition of 10% Pd/C (200 mg) and was stirred at RT under a hydrogen atmosphere for 16 h. The suspension was filtered and the filtrate was concentrated in vacuo. The resulting residue was purified by column chromatography (Si—PCC, gradient 0-10% MeOH in DCM) to afford the title compound as a white solid (520 mg, 42% over two steps). ¹H NMR (CDCl₃, 400 MHz): δ 7.92 (1H, dd, J=4.98, 1.64 Hz), 7.36 (1H, ddd, J=7.62, 1.65, 0.69 Hz), 7.26-7.20 (2H, m), 6.90-6.85 (1H, m), 6.78-6.73 (2H, m), 6.68 (1H, dd, J=7.61, 4.98 Hz), 5.13 (1H, br s), 4.57 (2H, br s).

[(S)-1-(3-Phenylaminopyridin-2-ylcarbamoyl)ethyl] carbamic acid tert-butyl ester

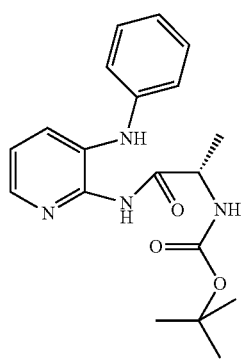 [SMILES: C[C@H](NC(=O)OC(C)(C)C)C(=O)Nc1ncccc1Nc1ccccc1]

Triethylamine (1.5 mL, 11.0 mmol) was added to a mixture of N³-phenylpyridine-2,3-diamine (510 mg, 2.75 mmol), (S)-2-tertbutoxycarbonylaminopropionic acid (0.94 g, 4.96 mmol), HOAt (670 mg, 4.96 mmol) and N-(3-dimethylaminopropyl)-N'-ethylcarbodiimide hydrochloride (0.95 g, 4.96 mmol) in anhydrous DCM (30 mL) at 0° C. under a nitrogen atmosphere. The reaction mixture was stirred at 0° C. for 10 min then slowly warmed to RT. Stirring at RT was continued for 18 h. The reaction mixture was partitioned between DCM and a saturated aqueous solution of NaHCO₃. The aqueous phase was further extracted with DCM (×3) and the combined organic fractions washed with water, dried (Na₂SO₄) and concentrated in vacuo to afford the title compound as a light brown foam (1.17 g, quantitative). LCMS (Method C): R$_T$ 3.04 min [M+H]⁺ 357.3.

[(S)-1-(1-Phenyl-1H-imidazo[4,5-b]pyridin-2-yl) ethyl]carbamic acid tert-butyl ester

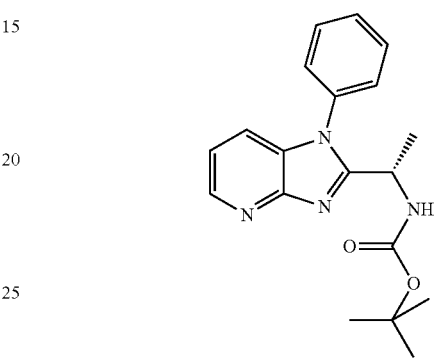

A mixture of [(S)-1-(3-phenylaminopyridin-2-ylcarbamoyl)ethyl]carbamic acid tert-butyl ester (980 mg, 2.75 mmol) in AcOH (25 mL) was heated for 10 h at 75° C. under a nitrogen atmosphere. The volatiles were removed in vacuo and the resulting residue partitioned between DCM and a saturated aqueous solution of NaHCO₃. The aqueous phase was further extracted with DCM (×3) and the combined organic fractions washed with water, followed by brine, then dried (Na₂SO₄) and concentrated in vacuo to afford the title compound as a light brown foam (920 mg, 99%). LCMS (Method C): R$_T$ 2.88 min [M+H]⁺ 339.3.

(S)-1-(1-Phenyl-1H-imidazo[4,5-b]pyridin-2-yl) ethylamine

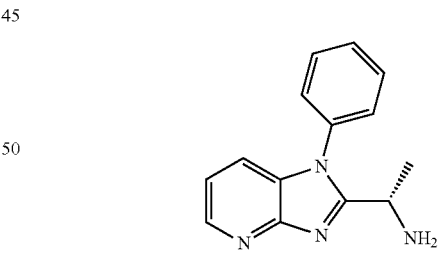

To a solution of [(S)-1-(1-phenyl-1H-imidazo[4,5-b]pyridin-2-yl)ethyl]carbamic acid tert-butyl ester (910 mg, 2.69 mmol) in DCM (5 mL) was added TFA (15 mL) and the mixture stirred at RT for 15 min. The volatiles were removed in vacuo and the resulting residue dissolved in DCM and washed with a saturated aqueous solution of NaHCO₃. The aqueous phase was further extracted with DCM (×3) and the combined organic fractions dried (Na₂SO₄) and concentrated in vacuo. The resulting residue was purified by column chromatography (Si—PCC, gradient 0-10% 2M NH₃/MeOH in DCM) to afford the title compound as a brown solid (340 mg, 53%). ¹H NMR (CDCl₃, 400 MHz): δ 8.55 (1H, dd, J=4.78, 1.56 Hz), 7.65-7.53 (3H, m), 7.45-7.37 (3H, m), 7.15 (1H, dd, J=8.04, 4.78 Hz), 4.18 (1H, q, J=6.71 Hz), 3.49 (2H, s), 1.48 (3H, d, J=6.71 Hz).

6-Fluoro-3-nitro-2-phenylaminobenzoic acid

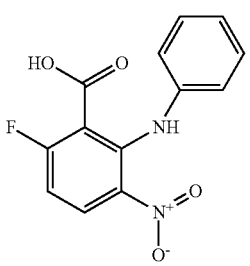 [SMILES: O=C(O)c1c(F)ccc([N+](=O)[O-])c1Nc1ccccc1]

To a solution of 2,6-difluoro-3-nitrobenzoic acid (5 g, 24.6 mmol) in EtOH (25 mL) and water (25 mL) at 0° C. were added Et$_3$N (6.2 mL, 44.3 mmol) and aniline (2.3 g, 24.6 mmol). The reaction mixture was heated at 70° C. for 4 h under a nitrogen atmosphere. After cooling to RT, the pH of the solution was adjusted to 1 by addition of 1N HCl. A precipitate formed and this solid was collected by filtration, washed with water to afford the title compound (6.0 g, 88%). $^1$H NMR (DMSO-d$_6$, 400 MHz): δ 9.02 (1H, s), 8.18 (1H, dd, J=9.29, 5.78 Hz), 7.25-7.16 (2H, m), 7.05 (1H, t, J=9.07 Hz), 7.00-6.91 (3H, m)

6-Fluoro-3-nitro-2-phenylaminobenzoic acid methyl ester

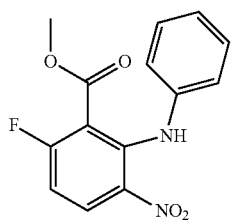 [SMILES: COC(=O)c1c(F)ccc([N+](=O)[O-])c1Nc1ccccc1]

Trimethylsilyldiazomethane (2M in hexane, 7.24 mL, 14.5 mmol) was added dropwise to a solution of 6-fluoro-3-nitro-2-phenylaminobenzoic acid (2.0 g, 7.24 mmol) in MeOH (5 mL) and DCM (40 mL) at RT. The solution was stirred at RT for 45 min then the volatiles were removed under reduced pressure to afford the title compound (2.1 g, quantitative). $^1$H NMR (CDCl$_3$, 400 MHz): δ 9.67 (1H, br s), 8.32 (1H, dd, J=9.47, 5.75 Hz), 7.36-7.30 (2H, m), 7.23-7.07 (3H, m), 6.64 (1H, dd, J=9.47, 8.33 Hz), 3.27 (3H, s)

3-Amino-6-fluoro-2-phenylaminobenzoic acid methyl ester

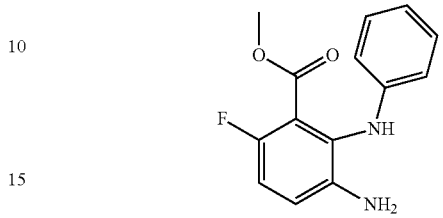

To a mixture of 6-fluoro-3-nitro-2-phenylaminobenzoic acid methyl ester (2.1 g, 7.24 mmol) in a mixture of MeOH (50 mL) and water (15 mL) were added NH$_4$Cl (2.23 g, 43.4 mmol) and iron powder (1.61 g, 28.9 mmol) and the reaction mixture heated at 90° C. for 3 h. After cooling to RT, the suspension was filtered through a pad of Celite® washing with additional MeOH. The filtrate was concentrated in vacuo to remove the organic solvent and the resulting aqueous residue extracted with EtOAc (×3). The combined organic fractions were washed with brine, dried (MgSO$_4$) and concentrated in vacuo to afford the title compound as an orange oil which solidified on standing (2.0 g, quantitative). $^1$H NMR (CDCl$_3$, 400 MHz): δ 7.23-7.18 (2H, m), 7.13 (1H, br s), 6.89-6.80 (3H, m), 6.69-6.64 (2H, m), 3.83 (3H, s)

2-((S)-1-tert-Butoxycarbonylaminoethyl)-5-fluoro-3-phenyl-3H-benzoimidazole-4-carboxylic acid methyl ester

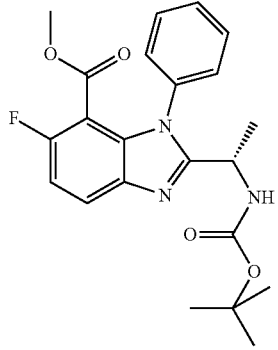 [SMILES: COC(=O)c1c(F)ccc2nc([C@H](C)NC(=O)OC(C)(C)C)n(-c3ccccc3)c12]

A mixture of 3-amino-6-fluoro-2-phenylaminobenzoic acid methyl ester (2.0 g, 7.7 mmol), (S)-2-tertbutoxycarbonylaminopropionic acid (1.6 g, 8.45 mmol), HOAt (760 mg, 8.45 mmol), 4-methylmorpholine (1.86 mL, 16.9 mmol) and N-(3-dimethylaminopropyl)-N'-ethylcarbodiimide hydrochloride (1.07 g, 8.45 mmol) in DCM (20 mL) was stirred at RT for 2 h. The reaction mixture was then partitioned between DCM and a saturated aqueous solution of NaHCO$_3$. The organic layer was washed with brine, dried (MgSO$_4$) and concentrated in vacuo. The resulting residue was purified by column chromatography (Si—PCC, gradient 0-100% EtOAc in cyclohexane) to afford 3-((S)-2-tertbutoxycarbonylamino-propionylamino)-6-fluoro-2-phenylaminobenzoic acid methyl ester. LCMS (Method B): R$_T$ 3.65 min [M+H]$^+$ 432.3.

A solution of the compound thus obtained in AcOH (15 mL) was heated at 80° C. for 48 h. After cooling to RT, the volatiles were concentrated in vacuo and the residue partitioned between EtOAc and a saturated aqueous solution of NaHCO₃. The aqueous phase was further extracted with EtOAc and the combined organic fractions were washed with brine, dried (MgSO₄) and then concentrated in vacuo. The resulting residue was purified by column chromatography (Si—PCC, gradient 0-100% EtOAc in cyclohexane) to afford the title compound (1.1 g, 32%). LCMS (Method C): $R_T$ 3.47 min [M+H]⁺ 414.2.

5-Fluoro-3-phenyl-2-{(S)-1-[9-(tetrahydropyran-2-yl)-9H-purin-6-ylamino]ethyl}-3H-benzoimidazole-4-carboxylic acid methyl ester

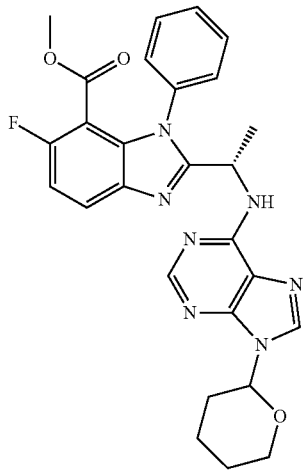 [SMILES: COC(=O)c1c(F)ccc2nc([C@H](C)Nc3ncnc4c3ncn4C3CCCCO3)n(-c3ccccc3)c12]

To a solution of 2-((S)-1-tertbutoxycarbonylaminoethyl)-5-fluoro-3-phenyl-3H-benzoimidazole-4-carboxylic acid methyl ester (1.1 g, 2.7 mmol) in MeOH (20 mL) was added 4N HCl in dioxane (5 mL) and the reaction mixture was heated at 45° C. for 3 h. The volatiles were removed under reduced pressure and the resulting residue was treated with 6-chloro-9-(tetrahydropyran-2-yl)-9H-purine (825 mg, 3.46 mmol) and DIPEA (1.8 mL, 10.6 mmol) in n-butanol (10 mL). The reaction mixture was heated in a sealed vial for 16 h at 90° C. After cooling to RT, the volatiles were removed under reduced pressure and the resulting residue purified by column chromatography (Si—PCC, gradient 0-10% MeOH in EtOAc) to afford the title compound (1.2 g, 87%). LCMS (Method C): $R_T$ 3.11 min [M+H]⁺ 516.2.

5-Fluoro-3-phenyl-2-{(S)-1-[9-(tetrahydropyran-2-yl)-9H-purin-6-ylamino]ethyl}-3H-benzoimidazole-4-carboxylic acid

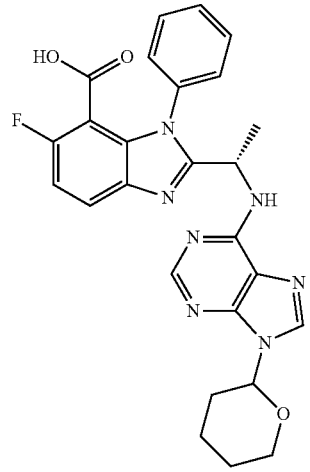 [SMILES: C[C@H](Nc1ncnc2c1ncn2C1CCCCO1)c1nc2ccc(F)c(C(=O)O)c2n1-c1ccccc1]

A solution of 5-fluoro-3-phenyl-2-{(S)-1-[9-(tetrahydropyran-2-yl)-9H-purin-6-ylamino]ethyl}-3H-benzoimidazole-4-carboxylic acid methyl ester (580 mg, 1.13 mmol) and LiOH.H₂O (94 mg, 2.25 mmol) in MeOH (20 mL) and water (2 mL) was heated at 45° C. for 3 h. Additional LiOH.H₂O (94 mg) was added and the mixture heated at 80° C. for 16 h. After further addition of LiOH.H₂O (94 mg), stirring at 75° C. was continued for 18 h. After cooling to RT, the pH of the mixture was adjusted to 4 by addition of 1N HCl. The organic solvent was removed under reduced pressure and EtOAc was added to the crude mixture. After sonication of the suspension, the organic solvent was removed in vacuo. The solid was collected by filtration and dried in vacuo to afford the title compound (412 mg, 73%). LCMS (Method C): $R_T$ 2.40 min [M+H]⁺ 502.0.

(3-Fluoro-2-methyl-6-nitrophenyl)phenylamine

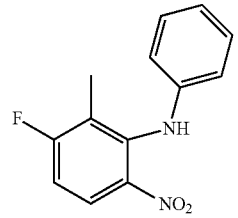 [SMILES: Cc1c(F)ccc([N+](=O)[O-])c1Nc1ccccc1]

LiHMDS (1.0M in THF, 12.9 mL, 12.9 mmol) was added dropwise to a stirred solution of aniline (633 mg, 6.79 mmol) in anhydrous THF (10 mL) under a nitrogen atmosphere at −78° C. After 10 min stirring at −78° C., a solution of 1,3-difluoro-2-methyl-4-nitrobenzene (1.12 g, 6.47 mmol) in THF (5 mL) was added and stirring was continued for 30 min. The reaction mixture was quenched by addition of water and was diluted with EtOAc. The resulting emulsion was filtered through Celite® and the organic fraction separated, washed with brine and dried (MgSO$_4$). The volatiles were removed in vacuo and the resulting residue purified by column chromatography (Si—PCC, gradient 0-100% EtOAc in cyclohexane) to afford the title compound (1.5 g, 94%). $^1$H NMR (CDCl$_3$, 400 MHz): δ 8.74 (1H, br s), 8.07 (1H, dd, J=9.34, 5.86 Hz), 7.30-7.23 (2H, m), 7.03 (1H, t, J=7.41 Hz), 6.85-6.78 (3H, m), 1.92 (3H, d, J=2.87 Hz).

4-Fluoro-3-methyl-N$^2$-phenylbenzene-1,2-diamine

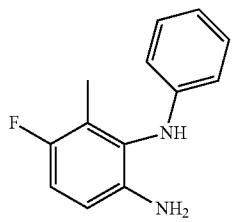 [SMILES: Cc1c(F)ccc(N)c1Nc1ccccc1]

To a mixture of (3-fluoro-2-methyl-6-nitrophenyl)phenylamine (1.5 g, 6.1 mmol) in a 3:1 mixture of MeOH:water (40 mL) were added NH$_4$Cl (1.88 g, 36.5 mmol) and iron powder (1.36 g, 24.4 mmol) and the reaction mixture heated at 90° C. for 1 h. After cooling to RT, the solid was filtered through a pad of Celite® and washed with additional MeOH. The filtrate was concentrated in vacuo and the resulting residue partitioned between EtOAc and water. The aqueous phase was further extracted with EtOAc (×3) and the combined organic fractions were washed with brine, dried (MgSO$_4$) and concentrated in vacuo to afford the title compound as a pink solid (1.16 g, 88%). $^1$H NMR (CDCl$_3$, 400 MHz): δ 7.22-7.15 (2H, m), 6.88-6.77 (2H, m), 6.64-6.55 (3H, m), 5.03 (1H, br s), 3.68 (2H, br s), 2.11 (3H, d, J=2.24 Hz).

(S)-1-(6-Fluoro-7-methyl-1-phenyl-1H-benzoimidazol-2-yl)ethylamine dihydrochloride

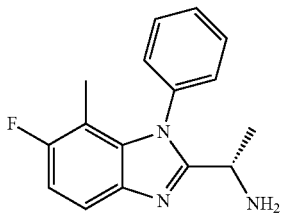

A mixture of 4-fluoro-3-methyl-N$^2$-phenylbenzene-1,2-diamine (600 mg, 2.77 mmol), (S)-2-tertbutoxycarbonylaminopropionic acid (577 mg, 3.05 mmol), HOAt (415 mg, 3.05 mmol), 4-methylmorpholine (0.67 mL, 6.1 mmol) and N-(3-dimethylaminopropyl)-N'-ethylcarbodiimide hydrochloride (586 mg, 3.05 mmol) in DCM (10 mL) was stirred at RT for 1 h. The reaction mixture was diluted with water and extracted with DCM (×3). The combined organic fractions were washed with brine, dried (MgSO$_4$) and concentrated in vacuo.

The resulting residue was dissolved in 4N HCl in dioxane (15 mL) and the solution heated at 70° C. for 2 h. The volatiles were removed in vacuo and the resulting residue partitioned between EtOAc and a saturated aqueous solution of NaHCO$_3$. The aqueous phase was further extracted with EtOAc and the combined organic fractions washed with water, then brine and dried (MgSO$_4$). The volatiles were removed in vacuo and the resulting residue purified by column chromatography (Si—PCC, gradient 0-10% MeOH in DCM) to afford the title compound (662 mg, 89%). $^1$H NMR (CDCl$_3$, 400 MHz): δ 7.63-7.52 (4H, m), 7.46-7.36 (2H, m), 7.05-6.97 (1H, m), 3.93 (1H, q, J=6.72 Hz), 1.77 (3H, d, J=2.06 Hz), 1.44 (3H, d, J=6.40 Hz).

(R)-1-(6-Fluoro-7-methyl-1-phenyl-1H-benzoimidazol-2-yl)-2-methoxyethylamine

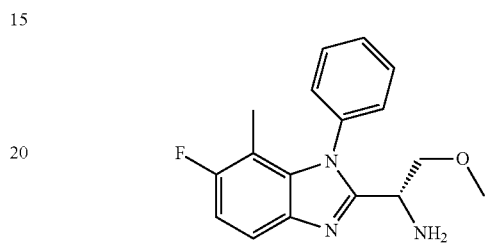

A mixture of 4-fluoro-3-methyl-N$^2$-phenylbenzene-1,2-diamine (560 mg, 2.59 mmol), (S)-2-tertbutoxycarbonylamino-3-methoxypropionic acid (624 mg, 2.85 mmol), HOAt (388 mg, 2.85 mmol), 4-methylmorpholine (626 μL, 5.69 mmol) and N-(3-dimethylaminopropyl)-N'-ethylcarbodiimide hydrochloride (547 mg, 2.85 mmol) in DCM (10 mL) was stirred at RT for 1 h. The reaction mixture was partitioned between DCM and water. The aqueous phase was further extracted with DCM and the combined organic fractions washed with brine, dried (MgSO$_4$) and concentrated in vacuo. The resulting residue was dissolved in 4N HCl in dioxane (5 mL) and the mixture heated at 70° C. for 2 h. The volatiles were removed in vacuo and the resulting residue partitioned between EtOAc and a saturated aqueous solution of NaHCO$_3$. The aqueous phase was further extracted with EtOAc and the combined organic fractions were washed with brine, dried (MgSO$_4$) and concentrated in vacuo. The resulting residue was purified by column chromatography (Si—PCC, gradient 0-10% MeOH in DCM) to afford the title compound (545 mg, 70%). LCMS (Method C): R$_T$ 3.95 min [M+H]$^+$ 300.2.

(3-Chlorophenyl)-(3-nitropyridin-2-yl)amine

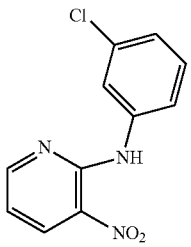

A mixture of 2-chloro-3-nitropyridine (317 mg, 2.0 mmol), 3-chlorophenylamine (0.212 mL, 2.0 mmol) and potassium carbonate (829 mg, 6.0 mmol) in DMF (3 mL) was heated at 140° C. for 30 min using microwave irradiation. After cooling to RT, the reaction mixture was partitioned between EtOAc and water. The aqueous phase was extracted with EtOAc (×3) and the combined organic fractions were washed with brine, dried (Na₂SO₄) and concentrated in vacuo. The resulting brown oil (370 mg) was purified by column chromatography (Si—PCC, gradient 0-100% DCM in cyclohexane) to afford the title compound as a red solid (111 mg, 22%). LCMS (Method B): R$_T$ 3.95 min [M+H]⁺ 250.0.

N²-(3-Chlorophenyl)pyridine-2,3-diamine

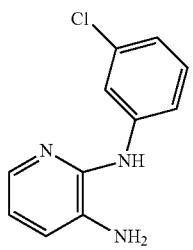 [SMILES: O=[N+]([O-])c1cccnc1Nc1cccc(Cl)c1]

To a mixture of (3-chlorophenyl)-(3-nitropyridin-2-yl)amine (111 mg, 0.45 mmol) in a 3:1 mixture MeOH:water (20 mL) were added NH₄Cl (154 mg, 2.88 mmol) and iron powder (107 mg, 1.92 mmol) and the reaction mixture heated at 90° C. for 3 h. After cooling to RT, the solid was filtered through a pad of Celite® and the filtrate concentrated in vacuo. The resulting residue was partitioned between EtOAc and water. The aqueous phase was further extracted with EtOAc (×3) and the combined organic fractions washed with brine, dried (Na₂SO₄) and concentrated in vacuo. The resulting brown oil was purified by column chromatography (Si—PCC, gradient 0-10% MeOH in DCM) to afford the title compound as a brown solid (29 mg, 30%). LCMS (Method C): R$_T$ 1.84 min [M+H]⁺ 220.1.

{(S)-1-[3-(3-Chlorophenyl)-3H-imidazo[4,5-b]pyridin-2-yl]ethyl}carbamic acid tert-butyl ester

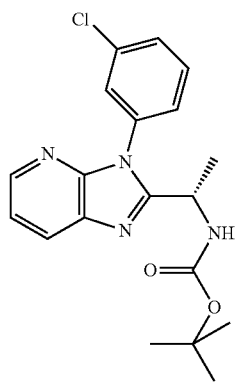 [SMILES: C[C@H](NC(=O)OC(C)(C)C)c1nc2cccnc2n1-c1cccc(Cl)c1]

A mixture of N²-(3-chlorophenyl)pyridine-2,3-diamine (29 mg, 0.13 mmol), (S)-2-tertbutoxycarbonylaminopropionic acid (27 mg, 0.15 mmol), HOAt (20 mg, 0.15 mmol), 4-methylmorpholine (32 µL, 0.29 mmol) and N-(3-dimethylaminopropyl)-N'-ethylcarbodiimide hydrochloride (28 mg, 0.15 mmol) in DCM (5 mL) was stirred at RT for 1 h then left standing at RT for 64 h. The reaction mixture was partitioned between DCM and a saturated solution of NaHCO₃. The organic fraction was washed with brine, dried (Na₂SO₄) and concentrated in vacuo. The resulting {(S)-1-[2-(3-chlorophenylamino)pyridin-3-ylcarbamoyl]ethyl}carbamic acid tert-butyl ester, as a brown oil (44 mg), was dissolved in AcOH (3 mL) and heated at 70° C. for 4 h. After cooling to RT, the volatiles were removed in vacuo. The resulting residue was partitioned between EtOAc and a saturated aqueous solution of NaHCO₃. The organic fraction was washed water, followed by brine, then dried (Na₂SO₄) and concentrated in vacuo. The resulting brown oil was purified by column chromatography (Si—PCC, gradient 0-5% MeOH in DCM) to afford the title compound as an orange/brown oil (35 mg, 72% over two steps). LCMS (Method C): R$_T$ 3.34 min [M+H]⁺ 373.2.

{(S)-1-[3-(4-Chlorophenyl)-3H-imidazo[4,5-b]pyridin-2-yl]ethyl}carbamic acid tert-butyl ester

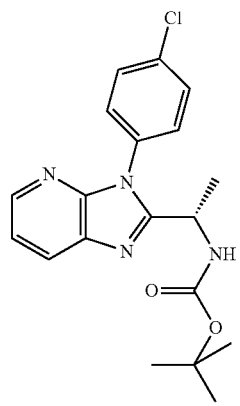 [SMILES: C[C@H](NC(=O)OC(C)(C)C)c1nc2cccnc2n1-c1ccc(Cl)cc1]

A mixture of N²-(4-chlorophenyl)pyridine-2,3-diamine (64 mg, 0.291 mmol), (S)-2-tertbutoxycarbonylaminopropionic acid (61 mg, 0.32 mmol), HOAt (44 mg, 0.32 mmol), 4-methylmorpholine (70 µL, 0.641 mmol) and N-(3-dimethylaminopropyl)-N'-ethylcarbodiimide hydrochloride (61 mg, 0.32 mmol) in DCM (10 mL) was stirred at RT for 1 h then left standing at RT for 64 h. The reaction mixture was partitioned between DCM and a saturated aqueous solution of NaHCO₃. The organic fraction was washed with brine, dried and concentrated in vacuo. The resulting {(S)-1-[2-(4-chlorophenylamino)pyridin-3-ylcarbamoyl]ethyl}carbamic acid tert-butyl ester, as a brown oil (136 mg), was dissolved in AcOH (5 mL) and heated at 70° C. for 4 h. After cooling to RT, the volatiles were removed under reduced pressure. The resulting residue was partitioned between EtOAc and a saturated aqueous solution of NaHCO₃. The organic fraction was washed with water, followed by brine, dried (Na₂SO₄) and concentrated in vacuo. The resulting brown oil was purified by column chromatography (Si—PCC, gradient 0-5% MeOH in DCM) to afford the title compound as an orange/brown oil (99 mg, 91% over two steps). LCMS (Method C): $R_T$ 3.33 min $[M+H]^+$ 373.2.

(5-Fluoro-2-nitrophenyl)-(6-fluoropyridin-3-yl)amine

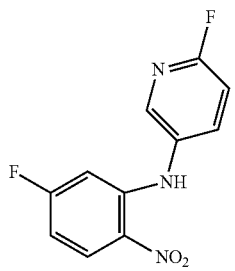 [SMILES: O=[N+]([O-])c1ccc(F)cc1Nc1ccc(F)nc1]

LiHMDS (1.0M in THF, 5.0 mL, 5.0 mmol) was added dropwise to a stirred solution of 6-fluoropyridin-3-ylamine (294 mg, 2.63 mmol) in anhydrous THF (5 mL) under a nitrogen atmosphere at −78° C. After 30 min stirring at −78° C., a solution of 2,4-difluoro-1-nitrobenzene (275 µL, 2.50 mmol) in THF (5 mL) was added and stirring at −78° C. continued for 1 h. The solution was poured into an aqueous solution of NH₄Cl and extracted with EtOAc (×3). The combined organic fractions were washed with brine, dried (Na₂SO₄) and concentrated in vacuo. The resulting residue was purified by column chromatography (Si—PCC, gradient 0-100% DCM in cyclohexane) to afford the title compound as a yellow solid (571 mg, 91%). LCMS (Method C): $R_T$ 3.33 min $[M+H]^+$ 252.1.

4-Fluoro-$N^2$-(6-fluoropyridin-3-yl)benzene-1,2-diamine

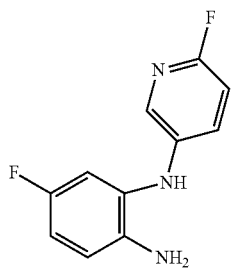

A mixture of (5-fluoro-2-nitrophenyl)-(6-fluoropyridin-3-yl)amine (571 mg, 2.27 mmol) in EtOAc (40 mL) was degassed with a stream of nitrogen prior to addition of 10% Pd/C (57 mg) and was stirred at RT under a hydrogen atmosphere for 22 h. The mixture was filtered through a phase separator and the filtrate concentrated in vacuo to afford the title compound as a dark oil (524 mg, quantitative). LCMS (Method C): $R_T$ 2.39 min $[M+H]^+$ 222.2.

{(S)-1-[4-Fluoro-2-(6-fluoropyridin-3-ylamino)phenylcarbamoyl]ethyl}carbamic acid tert-butyl ester

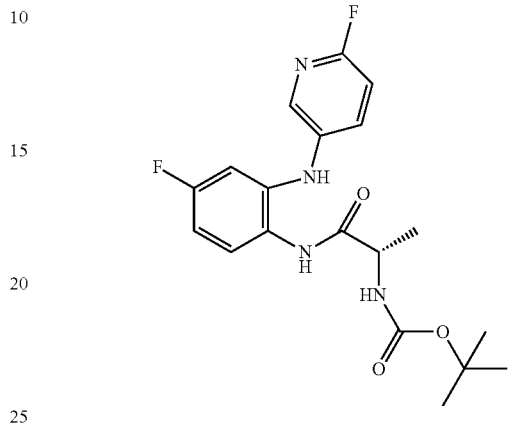

A mixture of 4-fluoro-$N^2$-(6-fluoropyridin-3-yl)benzene-1,2-diamine (524 mg, 2.37 mmol), (S)-2-tertbutoxycarbonylaminopropionic acid (493 mg, 2.61 mmol), HOAt (355 mg, 2.61 mmol), 4-methylmorpholine (575 µL, 5.21 mmol) and N-(3-dimethylaminopropyl)-N'-ethylcarbodiimide hydrochloride (500 mg, 2.61 mmol) in DCM (20 mL) was stirred at RT for 3 h. The reaction mixture was partitioned between DCM and a saturated aqueous solution of NaHCO₃. The organic layer was washed with brine, dried (Na₂SO₄) and concentrated in vacuo to afford the title compound as a yellow solid (973 mg, quantitative). LCMS (Method C): $R_T$ 3.25 min $[M+H]^+$ 393.3.

(S)-2-Amino-N-[4-fluoro-2-(6-fluoropyridin-3-ylamino)phenyl]propionamide

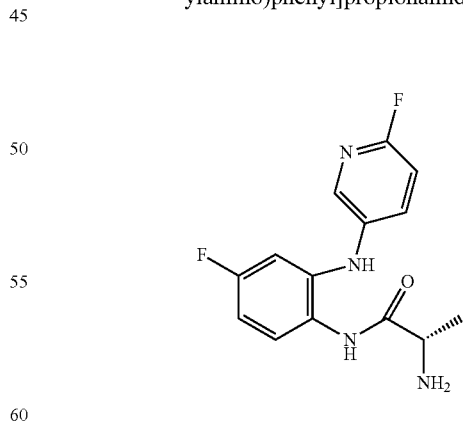

A mixture of {(S)-1-[4-fluoro-2-(6-fluoropyridin-3-ylamino)phenylcarbamoyl]ethyl}carbamic acid tert-butyl ester (276 mg, 0.70 mmol) in DCM (1 mL) and TFA (1 mL) was stirred at RT for 3 h. The reaction mixture was loaded onto an Isolute® SCX-2 cartridge then washed with MeOH followed by 2M NH₃/MeOH. The basic fractions were combined and concentrated in vacuo to afford the title compound as a yellow oil (193 mg, 94%). LCMS (Method C): $R_T$ 0.29 and 1.93 min [M+H]$^+$ 293.2.

(S)—N-[4-Fluoro-2-(6-fluoropyridin-3-ylamino)phenyl]-2-(9H-purin-6-ylamino)propionamide

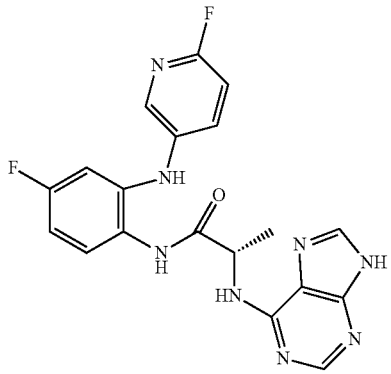 [SMILES: C[C@H](Nc1ncnc2[nH]cnc12)C(=O)Nc1ccc(F)cc1Nc1ccc(F)nc1]

A mixture of (S)-2-amino-N-[4-fluoro-2-(6-fluoropyridin-3-ylamino)phenyl]propionamide (193 mg, 0.66 mmol), 6-chloro-9-(tetrahydropyran-2-yl)-9H-purine (165 mg, 0.69 mmol) and DIPEA (0.34 mL, 1.98 mmol) in n-butanol (1 mL) was heated at 100° C. in a sealed vial for 16 h. After cooling to RT, the volatiles were removed in vacuo and the resulting residue loaded onto an Isolute® SCX-2 cartridge then washed with MeOH followed by 2M NH$_3$/MeOH. The basic fractions were combined and concentrated in vacuo to afford the title compound as a red solid (255 mg, 94%). LCMS (Method C): $R_T$ 2.40 min [M+H]$^+$ 411.2.

{(S)-1-[6-Fluoro-1-(6-methoxypyridin-3-yl)-1H-benzoimidazol-2-yl]ethyl}carbamic acid tert-butyl ester

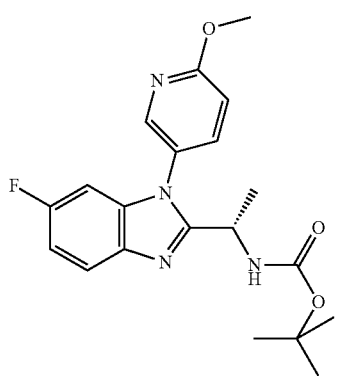 [SMILES: COc1ccc(-n2c([C@H](C)NC(=O)OC(C)(C)C)nc3ccc(F)cc32)cn1]

A suspension of {(S)-1-[4-fluoro-2-(6-fluoropyridin-3-ylamino)phenylcarbamoyl]ethyl}carbamic acid tert-butyl ester (196 mg, 0.50 mmol) in 0.5M NaOMe in MeOH (2.0 mL, 1.0 mmol) was heated at 120° C. using microwave irradiation for 15 min. The crude reaction mixture was diluted with MeOH and loaded onto an Isolute®SCX-2 cartridge then washed with MeOH followed by 2M NH$_3$/MeOH. The basic fractions were combined and concentrated in vacuo and the resulting residue was purified by column chromatography (Si—PCC, gradient 0-5% MeOH in DCM) to afford the title compound as a pink oil (52 mg, 27%). LCMS (Method C): $R_T$ 3.42 min [M+H]$^+$ 387.2.

(5-Fluoro-2-nitrophenyl)-(5-fluoropyridin-2-yl)amine

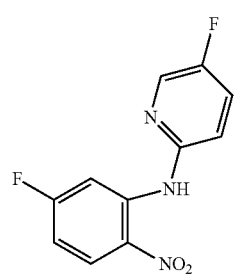 [SMILES: O=[N+]([O-])c1ccc(F)cc1Nc1ccc(F)cn1]

LiHMDS (1.0M in THF, 4.0 mL, 4.0 mmol) was added dropwise to a stirred solution of 5-fluoropyridin-2-ylamine (224 mg, 2.0 mmol) in anhydrous THF (5 mL) under a nitrogen atmosphere at −78° C. After 15 min stirring at −78° C., a solution of 2,4-difluoro-1-nitrobenzene (0.22 mL, 2.0 mmol) in THF (5 mL) was added and stirring at −78° C. was continued for 30 min. The mixture was slowly warmed to 0° C. then the reaction mixture poured into a saturated solution of NH$_4$Cl (50 mL). The aqueous phase was extracted with EtOAc (×3) and the combined organic fractions washed with water, followed by brine, dried (Na$_2$SO$_4$) and concentrated in vacuo. The resulting residue was purified by column chromatography (Si—PCC, gradient 0-40% EtOAc in cyclohexane) to afford the title compound as an orange solid (34 mg, 7%). LCMS (Method C): $R_T$ 3.81 min [M+H]$^+$ 252.1.

4-Fluoro-N$^2$-(5-fluoropyridin-2-yl)benzene-1,2-diamine

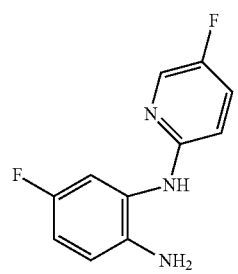 [SMILES: Nc1ccc(F)cc1Nc1ccc(F)cn1]

A mixture of (5-fluoro-2-nitrophenyl)-(5-fluoropyridin-2-yl)amine (34 mg, 0.14 mmol) in EtOAc (5 mL) was degassed with a stream of nitrogen prior to addition of 10% Pd/C (10 mg) and was stirred at RT under a hydrogen atmosphere for 3 h. The mixture was filtered through a phase separator and the filtrate concentrated in vacuo to afford the title compound as a dark oil (30 mg, quantitative). LCMS (Method C): $R_T$ 1.95 min [M+H]$^+$ 222.2.

{(S)-1-[6-Fluoro-1-(5-fluoropyridin-2-yl)-1H-benzoimidazol-2-yl]ethyl}carbamic acid tert-butyl ester

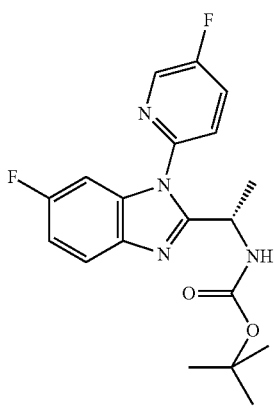 [SMILES: C[C@H](NC(=O)OC(C)(C)C)c1nc2ccc(F)cc2n1-c1ccc(F)cn1]

A mixture of 4-fluoro-N$^2$-(5-fluoropyridin-2-yl)benzene-1,2-diamine (30 mg, 0.136 mmol), (S)-2-tertbutoxycarbonylaminopropionic acid (28 mg, 0.15 mmol), HOAt (20 mg, 0.15 mmol) and N-(3-dimethylaminopropyl)-N'-ethylcarbodiimide hydrochloride (29 mg, 0.15 mmol) in DCM (5 mL) was stirred at 0° C. for 1 h. Additional (S)-2-tertbutoxycarbonylaminopropionic acid (5 mg), HOAt (4 mg) and N-(3-dimethylaminopropyl)-N'-ethylcarbodiimide hydrochloride (5 mg) were added and stirring continued for 30 min. The reaction mixture was partitioned between DCM and a saturated aqueous solution of NaHCO$_3$. The organic layer was dried and concentrated in vacuo to afford {(S)-1-[4-fluoro-2-(5-fluoropyridin-2-ylamino)phenylcarbamoyl]ethyl}carbamic acid tert-butyl ester as an orange oil. LCMS (Method C): $R_T$ 3.51 min [M+H]$^+$ 393.1.

A mixture of the compound thus obtained in AcOH (5 mL) was heated at 70° C. for 16 h. The volatiles were removed under reduced pressure and the resulting residue partitioned between EtOAc and a saturated aqueous solution of NaHCO$_3$. The organic fraction was washed with water, followed by brine, then dried (Na$_2$SO$_4$) and concentrated in vacuo. The resulting oil was purified by column chromatography (Si—PCC, gradient 0-5% MeOH in DCM) to afford the title compound as an orange oil (33 mg, 65%). LCMS (Method C): $R_T$ 3.38 min [M+H]$^+$ 375.2.

3-(5-Fluoro-2-nitrophenylamino)azetidine-1-carboxylic acid tert-butyl ester

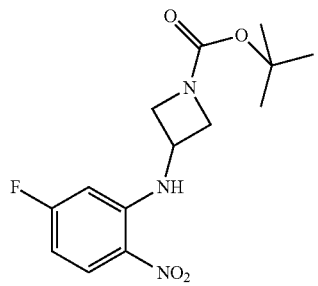 [SMILES: CC(C)(C)OC(=O)N1CC(Nc2cc(F)ccc2[N+](=O)[O-])C1]

A mixture of 2,4-difluoro-1-nitrobenzene (3.69 g, 23.2 mmol), 3-aminoazetidine-1-carboxylic acid tert-butyl ester (4.0 g, 23.2 mmol) and DIPEA (3.97 mL, 23.2 mmol) in CH$_3$CN (37 mL) was stirred at RT for 18 h under an argon atmosphere. The volatiles were removed in vacuo and the resulting residue purified by column chromatography (Si—PCC, gradient 0-40% EtOAc in cyclohexane) to afford the title compound as a yellow solid (4.84 g, 67%). LCMS (Method B): $R_T$ 3.80 min [M+H]$^+$ 312.1.

3-(2-Amino-5-fluorophenylamino)azetidine-1-carboxylic acid tert-butyl ester

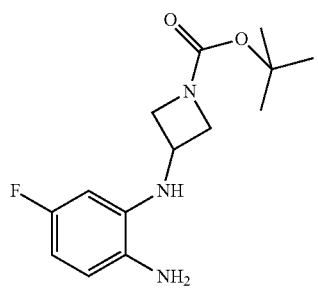 [SMILES: CC(C)(C)OC(=O)N1CC(Nc2cc(F)ccc2N)C1]

A mixture of 3-(5-fluoro-2-nitrophenylamino)azetidine-1-carboxylic acid tert-butyl ester (4.84 g, 15.54 mmol) in EtOAc (100 mL) was degassed with a stream of nitrogen prior to addition of 10% Pd/C (500 mg) and was stirred at RT under a hydrogen atmosphere for 16 h. Additional 10% Pd/C (500 mg) was added and stirring under a hydrogen atmosphere continued for 6 h. The mixture was filtered and the filtrate concentrated in vacuo to afford the title compound as a brown foam (4.4 g, quantitative). LCMS (Method J): $R_T$ 2.39 and 2.60 min [M+H]$^+$ 282.1.

3-[2-((S)-2-Benzyloxycarbonylaminopropionylamino)-5-fluoro-phenylamino]azetidine-1-carboxylic acid tert-butyl ester

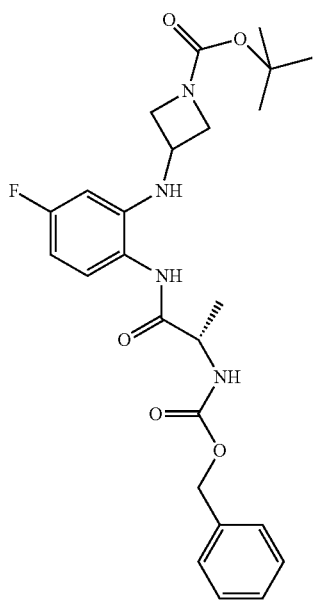 [SMILES: C[C@H](NC(=O)OCc1ccccc1)C(=O)Nc1ccc(F)cc1NC1CN(C(=O)OC(C)(C)C)C1]

A mixture of 3-(2-amino-5-fluorophenylamino)azetidine-1-carboxylic acid tert-butyl ester (15.5 mmol), (S)-2-benzyloxycarbonylaminopropionic acid (3.81 g, 17.1 mmol), HOAt (2.32 g, 17.1 mmol), 4-methylmorpholine (3.75 mL, 34.1 mmol) and N-(3-dimethylaminopropyl)-N'-ethylcarbodiimide hydrochloride (3.27 g, 17.1 mmol) in DCM (53 mL) was stirred at RT for 2 h. The reaction mixture was partitioned between EtOAc and a saturated aqueous solution of NaHCO$_3$. The aqueous phase was further extracted with EtOAc (×3) and the combined organic fractions were washed with water, followed by brine, then dried (Na$_2$SO$_4$) and concentrated in vacuo to afford the title compound as a yellow oil (quantitative). LCMS (Method B): $R_T$ 3.63 min [M+H]$^+$ 487.3.

3-[2-((S)-1-Benzyloxycarbonylaminoethyl)-6-fluorobenzoimidazol-1-yl]azetidine-1-carboxylic acid tert-butyl ester

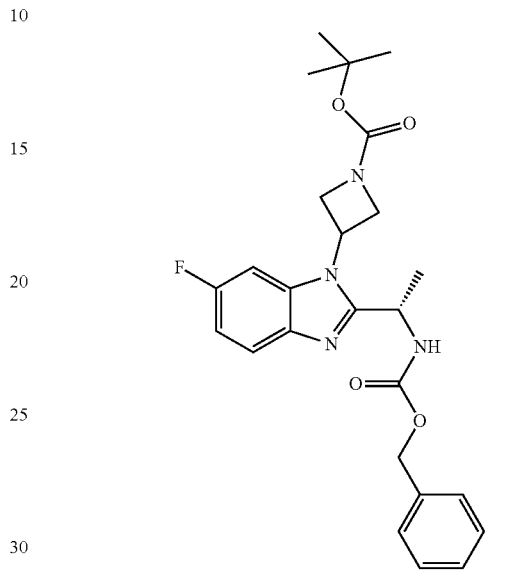

A mixture of 3-[2-((S)-2-benzyloxycarbonylaminopropionylamino)-5-fluoro-phenylamino]azetidine-1-carboxylic acid tert-butyl ester (15.52 mmol) in AcOH (110 mL) was heated at 60° C. for 18 h, at 70° C. for 24 h and then at 80° C. for 6 h. The volatiles were removed in vacuo and the resulting residue partitioned between EtOAc and a saturated aqueous solution of NaHCO$_3$. The aqueous phase was further extracted with EtOAc (×3) and the combined organic fractions washed with water, followed by brine, then dried (Na$_2$SO$_4$) and concentrated in vacuo. The resulting residue was purified by column chromatography (Si—PCC, gradient 0-60% EtOAc in cyclohexane) to afford the title compound as a yellow oil (3.23 g, 44%). LCMS (Method J): $R_T$ 3.60 min [M+H]$^+$ 469.1.

3-[2-((S)-1-Aminoethyl)-6-fluorobenzoimidazol-1-yl]azetidine-1-carboxylic acid tert-butyl ester

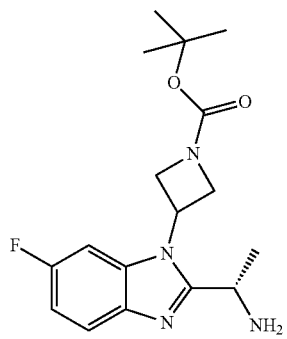 [SMILES: C[C@H](N)c1nc2ccc(F)cc2n1C1CN(C(=O)OC(C)(C)C)C1]

A mixture of 3-[2-((S)-1-benzyloxycarbonylaminoethyl)-6-fluorobenzoimidazol-1-yl]azetidine-1-carboxylic acid tert-butyl ester (524 mg, 1.12 mmol) in IMS (18 mL) was degassed with a stream of nitrogen prior to addition of 10% Pd/C (100 mg) and was stirred at RT under a hydrogen atmosphere for 64 h. The mixture was filtered washing with IMS and the filtrate concentrated in vacuo. The same process was repeated using 3-[2-((S)-1-benzyloxycarbonylaminoethyl)-6-fluorobenzoimidazol-1-yl]azetidine-1-carboxylic acid tert-butyl ester (2.11 g, 4.5 mmol) and the two residues combined. The product was purified by column chromatography (Si—PCC, gradient 0-10% MeOH in DCM) to afford the title compound as a yellow foam (1.17 g, 62%). $^1$H NMR (CDCl$_3$, 300 MHz): δ 7.68 (1H, dd, J=8.85, 4.93 Hz), 7.45 (1H, dd, J=9.04, 2.37 Hz), 7.04 (1H, td, J=9.19, 2.31 Hz), 5.67-5.54 (1H, m), 4.56-4.43 (4H, m), 4.30 (1H, q, J=6.64 Hz), 1.68 (2H, br s), 1.60-1.49 (12H, m). 327301

2-Chloro-N-(4-fluoro-2-phenylaminophenyl)acetamide

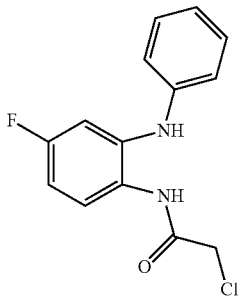 [SMILES: O=C(CCl)Nc1ccc(F)cc1Nc1ccccc1]

Chloroacetyl chloride (0.68 mL, 8.58 mmol) was added dropwise to a stirred solution of 4-fluoro-N$^2$-phenylbenzene-1,2-diamine (1.24 g, 6.13 mmol) and pyridine (2.0 mL, 24.5 mmol) in DCM (8 mL) at 0° C. under a nitrogen atmosphere. Stirring at 0° C. was continued for 20 min then at RT for 2 h. The reaction mixture was partitioned between aq. 1M HCl (50 mL) cooled to 0° C. and DCM. The aqueous phase was further extracted with DCM (×3) and the combined organic fractions were washed with water, dried (Na$_2$SO$_4$) and concentrated in vacuo. The resulting residue was purified by column chromatography (Si—PCC, gradient 30-100% DCM in cyclohexane) to afford the title compound as a white crystalline solid (750 mg, 44%). LCMS (Method C): R$_T$ 3.39 min [M+H]$^+$ 279.2.

2-Chloromethyl-6-fluoro-1-phenyl-1H-benzoimidazole

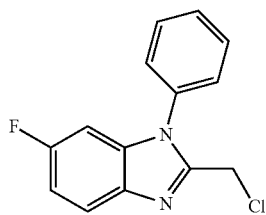 [SMILES: Fc1ccc2nc(CCl)n(-c3ccccc3)c2c1]

A mixture of 2-chloro-N-(4-fluoro-2-phenylaminophenyl) acetamide (740 mg, 2.62 mmol) in AcOH (20 mL) was heated at 70° C. for 5 h under a nitrogen atmosphere. The volatiles were removed in vacuo and the resulting residue partitioned between DCM and a saturated aqueous solution of NaHCO$_3$. The aqueous phase was further extracted with DCM (×3) and the combined organic fractions washed with water, dried (Na$_2$SO$_4$) and concentrated in vacuo. The resulting residue was purified by column chromatography (Si—PCC, gradient 0-5% MeOH in DCM) to afford the title compound as a brown oil which crystallised on standing (570 mg, 84%). LCMS (Method C): R$_T$ 3.40 min [M+H]$^+$ 261.2.

(5-Fluoro-2-nitrophenyl)pyridin-2-yl-amine (Prep 1)

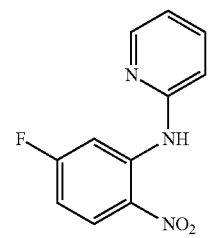 [SMILES: O=[N+]([O-])c1ccc(F)cc1Nc1ccccn1]

LiHMDS (1.0M in THF, 62 mL, 6.2 mmol) was added dropwise to a stirred solution of pyridin-2-ylamine (3.1 g, 33 mmol) in anhydrous THF (50 mL) under a nitrogen atmosphere at –78° C. After 30 min stirring at –78° C., 2,4-difluoro-1-nitrobenzene (3.4 mL, 31 mmol) was added and stirring at –78° C. continued for 30 min. The reaction mixture was slowly warmed to RT and after 5 h quenched by addition of a saturated aqueous solution of NH$_4$Cl (150 mL). The mixture was partitioned between EtOAc and water, then filtered through Celite®. The organic fraction was dried (MgSO$_4$), concentrated in vacuo and the resulting residue purified by column chromatography (Si—PCC, gradient 0-50% DCM in cyclohexane) to afford the title compound as an orange solid (3.9 g, 54%). $^1$H NMR (CDCl$_3$, 400 MHz): δ 10.48 (1H, s), 8.82 (1H, dd, J=12.32, 2.77 Hz), 8.38 (1H, dd, J=5.03, 1.87 Hz), 8.34-8.25 (1H, m), 7.70-7.64 (1H, m), 7.03-6.94 (2H, m), 6.68-6.61 (1H, m).

Prep 2: Sodium hydride (48.6 g, 60% by wt, 1.22 mol) was added piecewise to a solution of 2-aminopyridine (57.2 g, 0.61 mol) in THF (400 mL) at 0° C. at such a rate that T≤18° C. The reaction mixture was stirred at 0° C. for 10 min. then added via cannula to a solution of 2,4-difluoronitrobenzene in THF (350 mL) at –20° C. at such a rate that T≤10° C. The reaction was stirred at –40° C. for 1 h then allowed to warm to RT. As the reaction reached RT the temperature rose rapidly to 35° C. and effervescence was observed. The reaction mixture was poured onto ice (~2 L) and the solid which formed collected by filtration. The solid was washed with pentane and dried in vacuo to give the (5-fluoro-2-nitrophenyl)pyridin-2-yl-amine as a bright orange solid (139.3 g, 94%).

4-Fluoro-N²-pyridin-2-yl-benzene-1,2-diamine

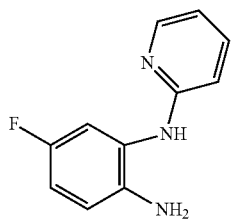 [SMILES: Nc1ccc(F)cc1Nc1ccccn1]

A mixture of (5-fluoro-2-nitrophenyl)pyridin-2-yl-amine (3.92 g, 17 mmol) in EtOAc (150 mL) was degassed with a stream of nitrogen prior to addition of 10% Pd/C (500 mg) and was stirred at RT under a hydrogen atmosphere for 18 h. The suspension was filtered through a phase separator and the filtrate concentrated in vacuo to afford the title compound as a black solid (3.5 g, quantitative).

[(S)-1-(6-Fluoro-1-pyridin-2-yl-1H-benzoimidazol-2-yl)ethyl]carbamic acid tert-butyl ester (Prep 1)

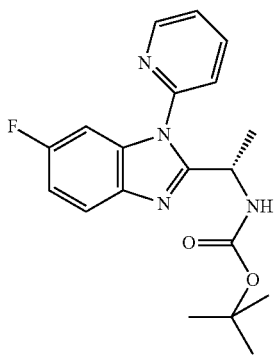 [SMILES: C[C@H](NC(=O)OC(C)(C)C)c1nc2ccc(F)cc2n1-c1ccccn1]

To a solution of (S)-Boc-alaninamide (1.5 g, 7.9 mmol) in anhydrous THF (20 mL) was added triethyloxonium tetrafluoroborate (1.6 g, 8.3 mmol) in one portion under a nitrogen atmosphere. The resulting mixture was left to stir at RT for 2 h. The volatiles were removed in vacuo and the resulting residue redissolved in absolute EtOH (20 mL). To the mixture was added 4-fluoro-N²-pyridin-2-yl-benzene-1,2-diamine (1.0 g, 4.9 mmol) and the mixture stirred at 75° C. for 16 h. The volatiles were removed in vacuo and the resulting residue partitioned between DCM and a saturated aqueous solution of NaHCO₃. The aqueous phase was further extracted with DCM and the combined organic fractions washed with water, dried (MgSO₄) and concentrated in vacuo. The resulting residue was purified by column chromatography (Si—PCC, gradient 0-40% EtOAc in cHex) to afford the title compound as an orange oil (1.6 g, 92%). LCMS (Method B): $R_T$ 3.21 min [M+H]⁺ 357.0.

(Prep 2) To a suspension of (S)-Boc-alaninamide (79.4 g, 0.42 mol) in DCM (750 mL) was added triethyloxonium tetrafluoroborate (69.5 g, 0.37 mol) and the reaction mixture stirred at RT for 2 h, during which the solids dissolved. The reaction mixture was concentrated in vacuo and the residue dissolved in ethanol (750 mL). (5-Fluoro-2-nitrophenyl)pyridin-2-yl-amine (57.1 g, 0.28 mol) was added and the reaction heated at 70° C. for 1 h. The reaction mixture was concentrated in vacuo, the residue dissolved in water and the product extracted with EtOAc (3×150 mL). The combined organic extracts were washed with brine, dried (MgSO₄) and concentrated in vacuo. The resultant residue was subjected to flash chromatography (SiO₂, eluting with 0-100% EtOAc in cyclohexane) to yield the title compound as a white foam (60.3 mg, 60%).

(S)-1-(6-Fluoro-1-pyridin-2-yl-1H-benzoimidazol-2-yl)ethylamine

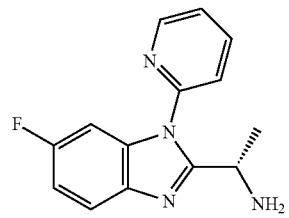

To a solution of [(S)-1-(6-fluoro-1-pyridin-2-yl-1H-benzoimidazol-2-yl)ethyl]carbamic acid tert-butyl ester (1.6 g, 4.5 mmol) in DCM (24 mL) was added TFA (12 mL) and the mixture stirred at RT for 1 h. The volatiles were removed in vacuo and the resulting residue loaded onto an Isolute® SCX-2 cartridge. The cartridge was washed with MeOH followed by 2M NH₃/MeOH. The basic fractions were combined and concentrated in vacuo to give the crude material as yellow oil (764 mg, 66%) which was used without further purification. LCMS (Method B): $R_T$ 1.63 min [M+H]⁺ 256.9.

((S)-1-Carbamoylpropyl)carbamic acid tert-butyl ester

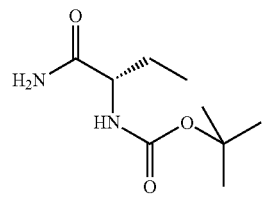

To a solution of (S)-2-tertbutoxycarbonylamino butyric acid (1.2 g, 5.8 mmol) in anhydrous THF (20 mL) cooled to −15° C. was added N-methylmorpholine (0.64 mL, 5.8 mmol) and isobutylchloroformate (0.75 mL, 5.8 mmol) under an atmosphere of nitrogen. After 2 minutes, 33% aqueous ammonia (0.5 mL, 8.7 mmol) was added and the resulting mixture stirred at this −15° C. for 2 h. The reaction mixture was left to warm to RT then partitioned between EtOAc and a saturated aqueous solution of NaHCO₃. The combined organic fractions were washed with aqueous 5% NaHCO₃, water, dried (MgSO₄) and concentrated in vacuo. The resulting white solid was used without further purification (1.0 g, 85%). ¹H NMR (CDCl₃, 300 MHz): δ 6.15 (1H, br s), 5.63

(1H, br s), 5.08 (1H, br s), 4.05 (1H, br s), 1.95-1.80 (1H, m), 1.70-1.53 (1H, m), 1.40 (9H, s), 0.95 (3H, d, J=6.71 Hz). 327997

[(S)-1-(6-Fluoro-1-pyridin-2-yl-1H-benzoimidazol-2-yl)propyl]carbamic acid tert-butyl ester

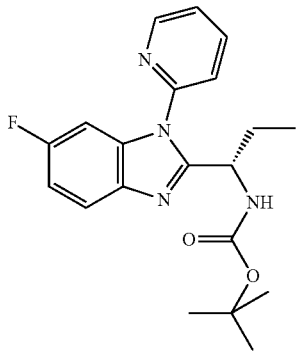 [SMILES: CC[C@H](NC(=O)OC(C)(C)C)c1nc2ccc(F)cc2n1-c1ccccn1]

To a solution of ((S)-1-carbamoyl-propyl)carbamic acid tert-butyl ester (510 mg, 2.5 mmol) in anhydrous THF (8 mL) was added triethyloxonium tetrafluoroborate (520 mg, 2.7 mmol) in one portion under a nitrogen atmosphere. The resulting mixture left to stir at RT for 2 h. The volatiles were removed in vacuo and the resulting residue redissolved in absolute EtOH (8 mL). To the mixture was added 4-fluoro-N-2-pyridin-2-yl-benzene-1,2-diamine (318 mg, 1.6 mmol) and the mixture stirred at 75° C. for 16 h. The volatiles were removed under reduced pressure and the resulting residue partitioned between DCM and a saturated aqueous solution of NaHCO$_3$. The aqueous phase was further extracted with DCM and the combined organic fractions washed with water, dried (MgSO$_4$) and concentrated in vacuo. The resulting residue was purified by column chromatography (Si—PCC, gradient 0-40% EtOAc in cHex) to afford the title compound as an orange oil (0.557 g, 94%). LCMS (Method B): R$_T$ 3.45 min [M+H]$^+$ 371.1.

(S)-1-(6-Fluoro-1-pyridin-2-yl-1H-benzoimidazol-2-yl)propylamine

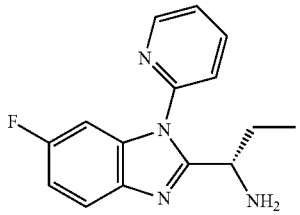 [SMILES: CC[C@H](N)c1nc2ccc(F)cc2n1-c1ccccn1]

To a solution of [(S)-1-(6-fluoro-1-pyridin-2-yl-1H-benzoimidazol-2-yl)propyl]carbamic acid tert-butyl ester (557 mg, 1.5 mmol) in DCM (8 mL) was added TFA (4 mL) and the mixture stirred at RT for 1 h. The volatiles were removed in vacuo and the resulting residue loaded onto an Isolute® SCX-2 cartridge. The cartridge was washed with MeOH followed by 2M NH$_3$/MeOH. The basic fractions were combined and concentrated in vacuo. The crude material was used in the following step without further purification. Yellow oil (349 mg, 86%). LCMS (Method B): R$_T$ 1.75 min [M+H]$^+$ 270.92.

((S)-1-Carbamoyl-2-methoxyethyl)carbamic acid tert-butyl ester

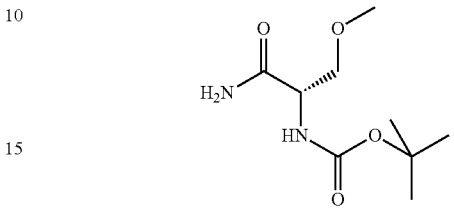

To a solution of (S)-2-tertbutoxycarbonylamino-3-methoxypropionic acid (1.13 g, 5.2 mmol) in anhydrous THF (20 mL) at −15° C. was added N-methylmorpholine (0.57 mL, 5.2 mmol) and isobutylchloroformate (0.67 mL, 5.2 mmol) under a nitrogen atmosphere. After 2 minutes, 33% aqueous ammonia (0.45 mL, 7.8 mmol) was added and the resulting mixture was stirred at −15° C. for 2 h. The reaction mixture was allowed to warm to RT and was partitioned between EtOAc and a saturated aqueous solution of NaHCO$_3$. The combined organic fractions were washed with aqueous 5% NaHCO$_3$, water, then dried (MgSO$_4$) and concentrated in vacuo. The resulting pink oil was used without further purification (1.03 g, 91%). $^1$H NMR (CDCl$_3$, 300 MHz): δ 6.42 (1H, br s), 5.48 (2H, br s), 4.25 (1H, br s), 3.83-3.74 (1H, m), 3.52-3.41 (1H, m), 3.40 (3H, s), 1.42 (9H, s).

[(R)-1-(6-Fluoro-1-pyridin-2-yl-1H-benzoimidazol-2-yl)-2-methoxyethyl]carbamic acid tert-butyl ester

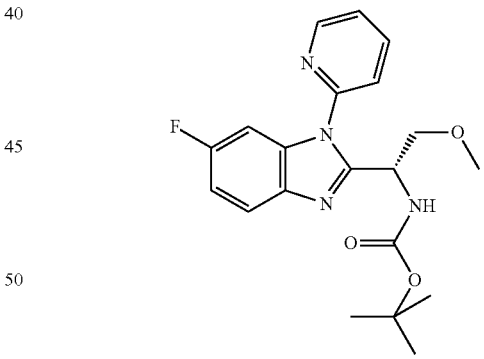

To a solution of ((S)-1-carbamoyl-2-methoxyethyl)carbamic acid tert-butyl ester (340 mg, 1.7 mmol) in anhydrous THF (8 mL) was added triethyloxonium tetrafluoroborate (550 mg, 2.9 mmol) in one portion under a nitrogen atmosphere. The resulting mixture stirred at RT for 2 h. The volatiles were removed in vacuo and the resulting residue redissolved in absolute EtOH (8 mL). To the mixture was added 4-fluoro-N-2-pyridin-2-yl-benzene-1,2-diamine (340 mg, 1.7 mmol) and the mixture stirred at 75° C. for 16 h. The volatiles were removed under reduced pressure and the resulting residue partitioned between DCM and a saturated aqueous solution of NaHCO$_3$. The aqueous phase was further extracted with DCM and the combined organic fractions washed with water, dried (MgSO$_4$) and concentrated in vacuo. The resulting residue was purified by column chromatography (Si—PCC, gradient 0-50% EtOAc in cHex) to afford the title compound as an orange oil (557 mg, 64%). LCMS (Method B): R$_T$ 3.32 min [M+H]$^+$ 387.1.

(R)-1-(6-Fluoro-1-pyridin-2-yl-1H-benzoimidazol-2-yl)-2-methoxyethylamine

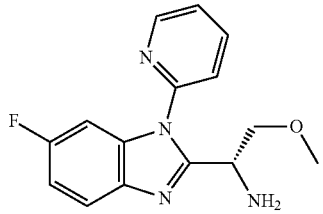 [SMILES: COC[C@H](N)c1nc2ccc(F)cc2n1-c1ccccn1]

To a solution of [(R)-1-(6-fluoro-1-pyridin-2-yl-1H-benzoimidazol-2-yl)-2-methoxyethyl]carbamic acid tert-butyl ester (419 mg, 1 mmol) in DCM (6 mL) was added TFA (3 mL) and the mixture was stirred at RT for 2 h. The volatiles were removed in vacuo and the resulting residue loaded onto an Isolute® SCX-2 cartridge. The cartridge was washed with MeOH followed by 2M NH$_3$/MeOH. The basic fractions were combined and concentrated in vacuo. The crude material was used in the following step without further purification: yellow oil (135 mg, 47%). LCMS (Method B): R$_T$ 1.71 min [M+H]$^+$ 287.01.

((S)-2-Benzyloxy-1-carbamoylethyl)carbamic acid tert-butyl ester

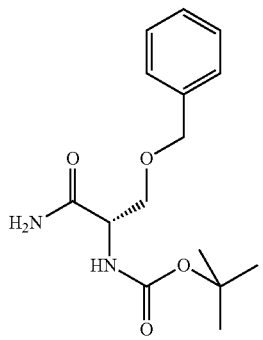 [SMILES: CC(C)(C)OC(=O)N[C@@H](COCc1ccccc1)C(N)=O]

To a solution of (S)-3-benzyloxy-2-(tert butoxycarbonylamino)propionic acid (0.98 g, 3.3 mmol) in anhydrous THF (13 mL) at −15° C. was added N-methylmorpholine (0.4 mL, 3.3 mmol) and isobutylchloroformate (0.4 mL, 3.3 mmol) under a nitrogen atmosphere. After 2 minutes, 33% aqueous ammonia (0.3 mL, 5 mmol) was added and the resulting mixture stirred at −15° C. for 2 h. The reaction mixture was allowed to warm to RT and was partitioned between EtOAc and a saturated aqueous solution of NaHCO$_3$. The combined organic fractions were washed with aqueous 5% NaHCO$_3$, water, dried (MgSO$_4$) and concentrated in vacuo. The resulting white solid was used without further purification (quant. yield). $^1$H NMR (CDCl$_3$, 300 MHz): δ 7.41-7.25 (5H, m), 6.42 (1H, br s), 5.48 (2H, br s), 4.55 (2H, dd, J=22., 12 Hz), 4.30 (1H, br s), 3.95-3.85 (1H, dd, J=9.5, 3.9 Hz), 3.55 (1H, dd, J=9.5, 6.7 Hz), 1.42 (9H, s).

[(R)-2-Benzyloxy-1-(6-fluoro-1-pyridin-2-yl-1H-benzoimidazol-2-yl)ethyl]carbamic acid tert-butyl ester

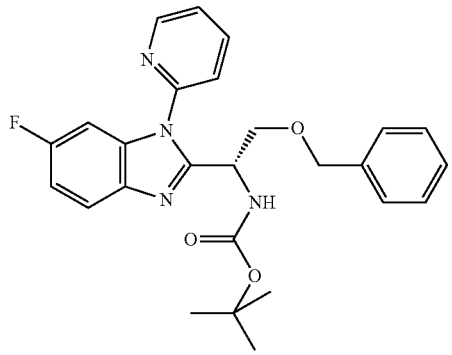 [SMILES: CC(C)(C)OC(=O)N[C@@H](COCc1ccccc1)c1nc2ccc(F)cc2n1-c1ccccn1]

To a solution of ((S)-2-benzyloxy-1-carbamoylethyl)carbamic acid tert-butyl ester (820 mg, 2.8 mmol) in anhydrous THF (10 mL) was added triethyloxonium tetrafluoroborate (550 mg, 2.9 mmol) in one portion under a nitrogen atmosphere. The resulting mixture was stirred at RT for 2 h. The volatiles were removed in vacuo and the resulting residue redissolved in absolute EtOH (10 mL). To the mixture was added 4-fluoro-N$^2$-pyridin-2-yl-benzene-1,2-diamine (355 mg, 1.7 mmol) and the mixture stirred at 75° C. for 16 h. The volatiles were removed in vacuo and the resulting residue partitioned between DCM and a saturated aqueous solution of NaHCO$_3$. The aqueous phase was further extracted with DCM and the combined organic fractions washed with water, dried (MgSO$_4$) and concentrated in vacuo. The resulting residue purified by column chromatography (Si—PCC, gradient 0-30% EtOAc in cHex) to afford the title compound as a yellow oil (420 mg, 53%). LCMS (Method B): R$_T$ 3.95 min [M+H]$^+$ 463.1.

(R)-2-Benzyloxy-1-(6-fluoro-1-pyridin-2-yl-1H-benzoimidazol-2-yl)ethylamine

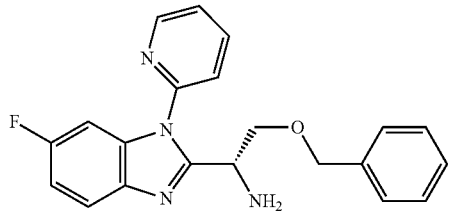 [SMILES: N[C@@H](COCc1ccccc1)c1nc2ccc(F)cc2n1-c1ccccn1]

To a solution of [(R)-2-benzyloxy-1-(6-fluoro-1-pyridin-2-yl-1H-benzoimidazol-2-yl)ethyl]carbamic acid tert-butyl ester (420 mg, 0.91 mmol) in DCM (6 mL) was added TFA (3 mL) and the mixture stirred at RT for 2 h. The volatiles were removed in vacuo and the resulting residue loaded onto an Isolute® SCX-2 cartridge. The cartridge was washed with MeOH followed by 2M NH$_3$/MeOH. The basic fractions were combined and concentrated in vacuo. The crude material was used in the following step without further purification. Yellow oil (284 mg, 86%). LCMS (Method B): $R_T$ 2.16 min [M+H]$^+$ 363.20.

[(R)-2-Benzyloxy-1-(6-fluoro-1-pyridin-2-yl-1H-benzoimidazol-2-yl)ethyl](7H-Aurin-6-yl)amine

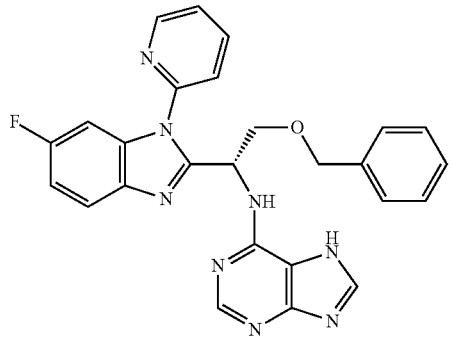 [SMILES: Fc1ccc2nc([C@H](COCc3ccccc3)Nc3ncnc4nc[nH]c34)n(-c3ccccn3)c2c1]

A mixture of (R)-2-benzyloxy-1-(6-fluoro-1-pyridin-2-yl-1H-benzoimidazol-2-yl)ethylamine (284 mg, 0.78 mmol), 6-chloro-9-(tetrahydropyran-2-yl)-9H-purine (190 mg, 0.78 mmol) and DIPEA (0.7 mL, 3.9 mmol) in IPA (1.5 mL) was heated for 72 h at 90° C. After cooling to RT, the volatiles were removed in vacuo and the resulting residue loaded onto an Isolute® SCX-2 cartridge. The cartridge was washed with MeOH followed by 2M NH$_3$/MeOH. The basic fractions were combined and concentrated in vacuo and the resulting residue purified by column chromatography (Si—PCC, gradient 0-2.5% MeOH in DCM) to afford the title compound as a white solid (336 mg, 90%). LCMS (Method B): $R_T$ 2.94 min [M+H]$^+$ 481.1.

((S)-3-Benzyloxy-1-carbamoylpropyl)carbamic acid tert-butyl ester

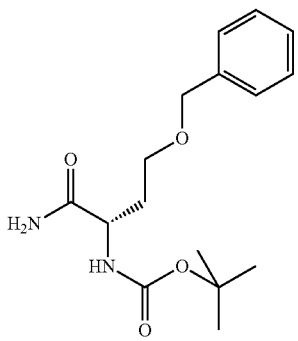 [SMILES: CC(C)(C)OC(=O)N[C@@H](CCOCc1ccccc1)C(N)=O]

To a solution of (S)-4-benzyloxy-2-tert butoxycarbonylamino butyric acid (1.16 g, 3.7 mmol) in anhydrous THF (15 mL) at −15° C. was added N-methylmorpholine (0.41 mL, 3.7 mmol) and isobutylchloroformate (0.51 mL, 3.7 mmol) under a nitrogen atmosphere. After 2 minutes, 33% aqueous ammonia (0.34 mL, 5.6 mmol) was added and the resulting mixture stirred at −15° C. for 2 h. The reaction mixture was left to warm to RT and was partitioned between EtOAc and a saturated aqueous solution of NaHCO$_3$. The combined organic fractions were washed with aqueous 5% NaHCO$_3$, water, dried (MgSO$_4$) and concentrated in vacuo. The resulting white solid was used without further purification (quant. yield). $^1$H NMR (CDCl$_3$, 300 MHz): δ 7.41-7.25 (5H, m), 6.38 (1H, br s), 5.75 (1H, br s), 5.38 (1H, br s), 4.55-4.45 (2H, m), 4.30 (1H, br s), 3.75-3.52 (2H, m), 2.10-2.00 (2H, m), 1.42 (9H, s).

[(S)-3-Benzyloxy-1-(6-fluoro-1-pyridin-2-yl-1H-benzoimidazol-2-yl)propyl]carbamic acid tert-butyl ester

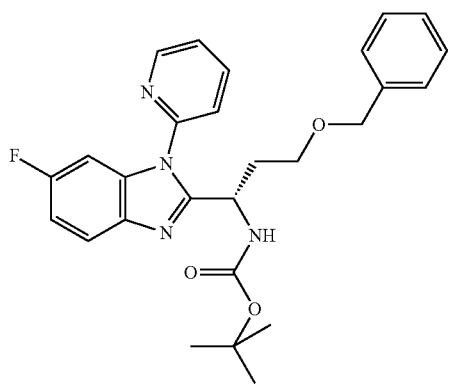 [SMILES: CC(C)(C)OC(=O)N[C@@H](CCOCc1ccccc1)c1nc2ccc(F)cc2n1-c1ccccn1]

To a solution of ((S)-3-benzyloxy-1-carbamoylpropyl)carbamic acid tert-butyl ester (840 mg, 2.7 mmol) in anhydrous DCM (10 mL) was added triethyloxonium tetrafluoroborate (550 mg, 2.9 mmol) in one portion under a nitrogen atmosphere. The resulting mixture was left to stir at RT for 2 h. The volatiles were removed in vacuo and the resulting residue redissolved in absolute EtOH (10 mL). To the mixture was added 4-fluoro-N-2-pyridin-2-yl-benzene-1,2-diamine (345 mg, 1.7 mmol) and the mixture was stirred at 75° C. for 16 h. The volatiles were removed in vacuo and the resulting residue partitioned between DCM and a saturated aqueous solution of NaHCO$_3$. The aqueous phase was further extracted with DCM and the combined organic fractions washed with water, dried (MgSO$_4$) and concentrated in vacuo. The resulting residue was purified by column chromatography (Si—PCC, gradient 0-30% EtOAc in cHex) to afford the title compound as a yellow oil (546 mg, 67%). LCMS (Method B): $R_T$ 3.89 min [M+H]$^+$ 477.2.

(S)-3-Benzyloxy-1-(6-fluoro-1-pyridin-2-yl-1H-benzoimidazol-2-yl)propylamine

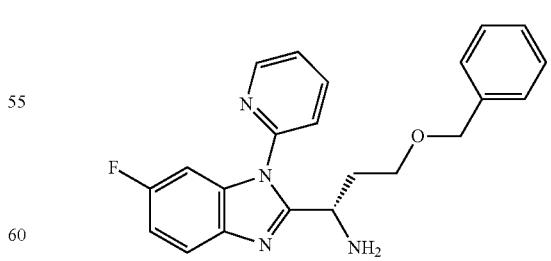

To a solution of [(S)-3-benzyloxy-1-(6-fluoro-1-pyridin-2-yl-1H-benzoimidazol-2-yl)propyl]carbamic acid tert-butyl ester (546 mg, 1.1 mmol) in DCM (10 mL) was added TFA (5 mL) and the mixture was stirred at RT for 1 h. The volatiles were removed under reduced pressure and the resulting residue loaded onto an Isolute® SCX-2 cartridge. The cartridge was washed with MeOH followed by 2M NH₃/MeOH. The basic fractions were combined and concentrated in vacuo. The crude material was used in the following step without further purification. Colourless oil (355 mg, 86%). LCMS (Method B): R$_T$ 1.89 min [M+H]⁺ 377.3.

[(S)-3-Benzyloxy-1-(6-fluoro-1-pyridin-2-yl-1H-benzoimidazol-2-yl)propyl](7H-purin-6-yl)amine

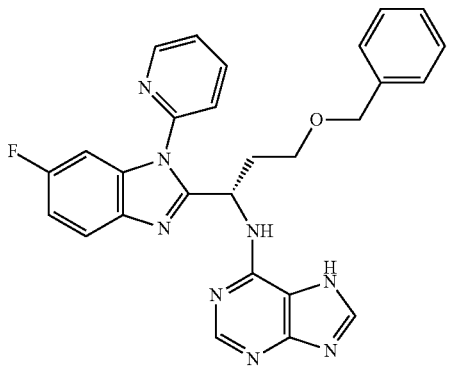 [SMILES: Fc1ccc2nc([C@H](CCOCc3ccccc3)Nc3ncnc4nc[nH]c34)n(-c3ccccn3)c2c1]

A mixture of (S)-3-benzyloxy-1-(6-fluoro-1-pyridin-2-yl-1H-benzoimidazol-2-yl)propylamine (355 mg, 0.94 mmol), 6-chloro-9-(tetrahydropyran-2-yl)-9H-purine (230 mg, 0.94 mmol) and DIPEA (0.82 mL, 4.7 mmol) in IPA (2 mL) was heated for 16 h at 90° C. After cooling to RT, the volatiles were removed in vacuo and the resulting residue loaded onto an Isolute® SCX-2 cartridge. The cartridge was washed with MeOH followed by 2M NH₃/MeOH. The basic fractions were combined, concentrated in vacuo and the resulting residue purified by column chromatography (Si—PCC, gradient 0-5% MeOH in DCM) to afford the title compound as a yellow solid (465 mg, 86%). LCMS (Method B): R$_T$ 3.56 min [M+H]⁺ 495.1.

2,2-Dimethylpropionic acid 2-bromoethyl ester

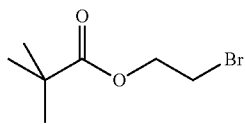

2,2-Dimethylpropionyl chloride (10 mL, 81.2 mmol) was added over 10 min to an ice-cooled solution of 2-bromoethanol (5.48 mL, 77.4 mmol) and DIPEA (20.8 mL, 121.8 mmol) in DCM (150 mL). The reaction mixture was stirred in the ice bath for a further 15 min, then at RT for 16 h. The reaction mixture was washed successively with 1M HCl, saturated aqueous NaHCO₃ and water. The organic fraction was dried (Na₂SO₄) then concentrated in vacuo. The resulting residue was purified by column chromatography (Si—PCC, eluant 1-6% EtOAc in cyclohexane) affording the title compound as a colourless oil (10.58 g, 65%). ¹H NMR (CDCl₃, 300 MHz): 4.37 (2H, t, J=6.0 Hz), 3.52 (2H, t, J=6.0 Hz), 1.23 (9H, s).

2,2-Dimethylpropionic acid 2-((R)-3-tert-butoxycarbonylaminopiperidin-1-yl)ethyl ester

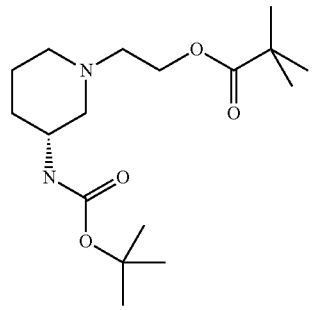 [SMILES: CC(C)(C)OC(=O)N[C@@H]1CCCN(CCOC(=O)C(C)(C)C)C1]

A mixture of 2,2-dimethylpropionic acid 2-bromoethyl ester (2.3 g, 11 mmol), (R)-piperidin-3-ylcarbamic acid tert-butyl ester (2 g, 10.0 mmol), potassium carbonate (4.15 g, 30 mmol) and sodium iodide (0.15 g, 1 mmol) in DMF (20 mL) was stirred at RT for 2 days. The reaction mixture was partitioned between water and EtOAc. The aqueous phase was extracted with EtOAc and the combined organic fractions washed with water, followed by brine, then dried (Na₂SO₄) and concentrated in vacuo. The resulting residue was purified by column chromatography (Si—PCC, eluant 10-40% EtOAc in cyclohexane) affording the title compound as a colourless oil (2.884 g, 88%). ¹H NMR (CDCl₃, 300 MHz): 5.09 (1H, bs), 4.25-4.07 (2H, m), 3.73 (1H, bs), 2.63-2.52 (3H, m), 2.49 (1H, bs), 2.31-2.24 (1H, m), 1.74-1.61 (1H, m), 1.59-1.49 (3H, m), 1.44 (9H, s), 1.21 (9H, s).

2,2-Dimethylpropionic acid 2-((R)-3-aminopiperidin-1-yl)ethyl ester

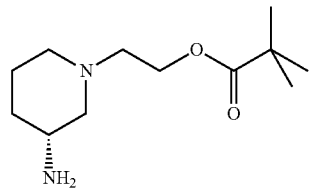 [SMILES: CC(C)(C)C(=O)OCCN1CCC[C@@H](N)C1]

To an ice-cooled solution of 2,2-dimethylpropionic acid 2-((R)-3-tert-butoxycarbonylaminopiperidin-1-yl)ethyl ester (2.86 g, 8.72 mmol) in DCM (100 mL) was added TFA (25 mL) and the mixture stirred at RT for 3 h. Toluene was added and volatiles were removed in vacuo. The resulting residue was dissolved in MeOH and loaded onto an Isolute® SCX-2 cartridge. The cartridge was washed with MeOH and the product eluted with 1M NH₃/MeOH. The product containing fractions were combined and concentrated in vacuo affording the title compound as a colourless oil (1.678 g, 84%). ¹H NMR (CDCl₃, 300 MHz): 4.18 (2H, t, J=6.0 Hz), 2.89-2.77 (2H, m), 2.68-2.59 & 2.62 (3H, m & t, J=6.0 Hz), 2.19-2.11

(1H, m), 2.00-1.94 (1H, m), 1.84-1.65 (2H, m), 1.60-1.46 (1H, m), 1.23 (2H, bs), 1.20 (9H, s), 1.15-1.03 (1H, m).

2,2-Dimethylpropionic acid 2-[(R)-3-(5-fluoro-2-nitrophenylamino)piperidin-1-yl]ethyl ester

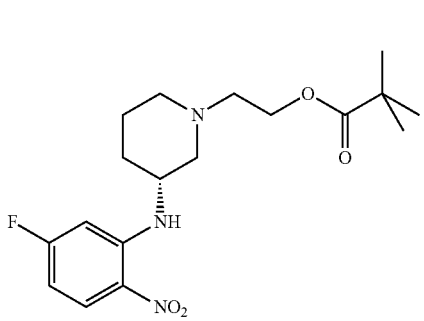 [SMILES: CC(C)(C)C(=O)OCCN1CCC[C@@H](Nc2cc(F)ccc2[N+](=O)[O-])C1]

To an ice-cooled solution of 2,2-dimethylpropionic acid 2-((R)-3-aminopiperidin-1-yl)ethyl ester (1.675 g, 7.33 mmol) in DMF (30 mL) was added 2,4-difluoronitrobenzene (1.517 g, 9.54 mmol) and potassium carbonate (2.03 g, 14.7 mmol). The reaction mixture was stirred at RT for 16 h, then partitioned between water and EtOAc. The aqueous phase was extracted with EtOAc and the combined organic fractions washed with water, followed by brine, then dried ($Na_2SO_4$) and concentrated in vacuo. The resulting residue was purified by column chromatography (Si—PCC, eluant 10-40% EtOAc in cyclohexane) affording the title compound as a yellow oil (2.533 g, 94%). LCMS (Method J): $R_T$ 2.31 min $[M+H]^+$ 368.

2,2-Dimethylpropionic acid 2-[(R)-3-(2-amino-5-fluorophenylamino)piperidin-1-yl]ethyl ester

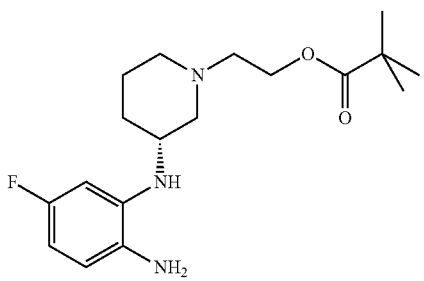

To a solution of 2,2-dimethylpropionic acid 2-[(R)-3-(5-fluoro-2-nitrophenylamino)piperidin-1-yl]ethyl ester (2.53 g, 6.88 mmol) in EtOAC (100 mL) was added a slurry of 10% Pd/C (200 mg) in IMS (20 mL) and the reaction mixture stirred at RT under a hydrogen atmosphere for 18 h. The suspension was filtered through a pad of Celite® and the filtrate concentrated in vacuo affording the title compound as a purple oil (2.33 g, 100%). LCMS (Method J): $R_T$ 1.75 min $[M+H]^+$ 338.

2,2-Dimethylpropionic acid 2-{(R)-3-[2-((S)-2-tert-butoxycarbonylaminopropionylamino)-5-fluoro-phenylamino]piperidin-1-yl}ethyl ester

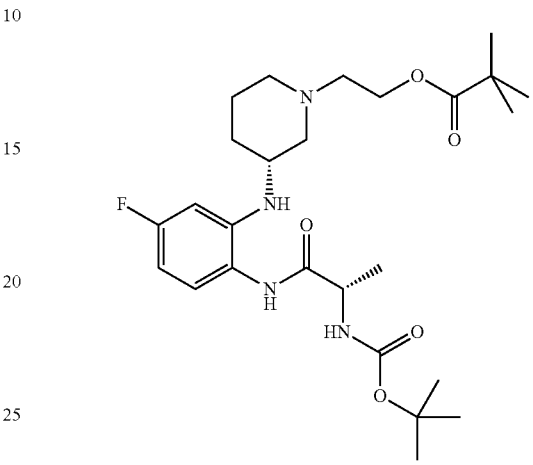

To an ice-cooled mixture of 2,2-dimethylpropionic acid 2-[(R)-3-(2-amino-5-fluorophenylamino)piperidin-1-yl] ethyl ester (500 mg, 1.48 mmol), (S)-2-tert-butoxycarbonylaminopropionic acid (309 mg, 1.63 mmol) and HOAt (202 mg, 1.48 mmol) in DCM (30 mL) was added N-(3-dimethylaminopropyl)-n'-ethylcarbodiimide hydrochloride (341 mg, 1.78 mmol). The reaction mixture was stirred in the ice bath for 1.5 h, then diluted with DCM, washed with 2M $Na_2CO_3$ and then water. The organic fraction was dried ($Na_2SO_4$) and concentrated in vacuo. The resulting residue was purified by column chromatography (Si—PCC, gradient 50-100% EtOAc in cyclohexane) affording the title compound as a purple gum (quantitative). LCMS (Method B): $R_T$ 2.50 min $[M+H]^+$ 509.

2,2-Dimethylpropionic acid 2-{(R)-3-[2-((S)-2-aminopropionylamino)-5-fluorophenylamino]piperidin-1-yl}ethyl ester

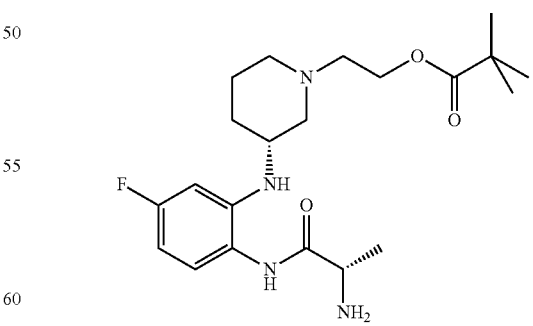

To an ice-cooled solution of 2,2-dimethylpropionic acid 2-{(R)-3-[2-((S)-2-tert-butoxycarbonylaminopropionylamino)-5-fluorophenylamino]-piperidin-1-yl}ethyl ester (0.74 mmol) in DCM (20 mL) was added TFA (5 mL) and the mixture stirred at RT for 1.5 h. Toluene was added and volatiles were removed in vacuo. The resulting residue was dissolved in MeOH and loaded onto an Isolute® SCX-2 cartridge. The cartridge was washed with MeOH and the product eluted with 0.5M NH₃/MeOH. The product containing fractions were combined and concentrated in vacuo affording the title compound as a purple oil (0.255 g, 84% over 2 steps). LCMS (Method J): R$_T$ 1.65 min [M+H]⁺ 409.

2,2-Dimethylpropionic acid 2-[(R)-3-(5-fluoro-2-{(S)-2-[9-(tetrahydropyran-2-yl)-9H-purin-6-ylamino]propionylamino}phenylamino)piperidin-1-yl]ethyl ester

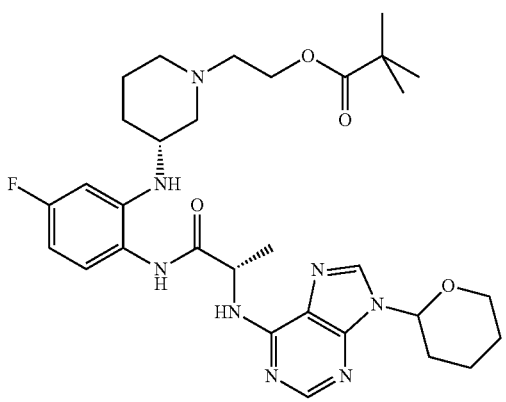 [SMILES: C[C@H](Nc1ncnc2c1ncn2C1CCCCO1)C(=O)Nc1ccc(F)cc1N[C@@H]1CCCN(CCOC(=O)C(C)(C)C)C1]

A mixture of 2,2-dimethylpropionic acid 2-{(R)-3-[2-((S)-2-aminopropionylamino)-5-fluorophenylamino]piperidin-1-yl}ethyl ester (0.255 g, 0.62 mmol), 6-chloro-9-(tetrahydropyran-2-yl)-9H-purine (0.149 g, 0.62 mmol), and DIPEA (0.32 mL, 1.87 mmol) in n-butanol (4 mL) was stirred in a sealed vial at 100° C. for 2 h, then at 90° C. for 16 h. After cooling to RT, volatiles were removed in vacuo and the resulting residue purified by column chromatography (Si—PCC, gradient 2-8% 2M NH₃/MeOH in DCM) affording the title compound as a colourless gum (0.301 g, 79%). LCMS (Method J): R$_T$ 2.29 min [M+H]⁺ 611.

2,2-Dimethylpropionic acid 2-{(R)-3-[2-((S)-2-tert-butoxycarbonylaminobutyrylamino)-5-fluorophenylamino]piperidin-1-yl}ethyl ester

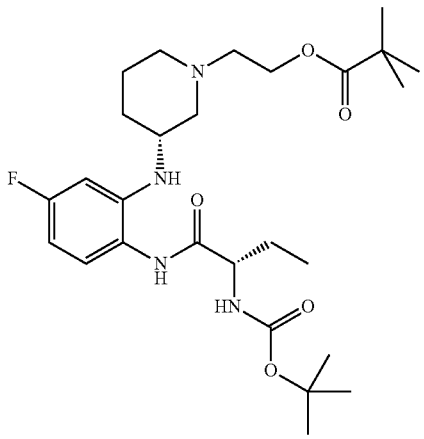 [SMILES: CC[C@H](NC(=O)OC(C)(C)C)C(=O)Nc1ccc(F)cc1N[C@@H]1CCCN(CCOC(=O)C(C)(C)C)C1]

To an ice-cooled mixture of 2,2-dimethylpropionic acid 2-[(R)-3-(2-amino-5-fluorophenylamino)piperidin-1-yl] ethyl ester (500 mg, 1.48 mmol), (S)-2-tert-butoxycarbonylaminobutyric acid (331 mg, 1.63 mmol) and HOAt (202 mg, 1.48 mmol) in DCM (30 mL) was added N-(3-dimethylaminopropyl)-N'-ethylcarbodiimide hydrochloride (341 mg, 1.78 mmol). The reaction mixture was stirred in the ice bath for 1 h, then diluted with DCM, washed with 2M Na₂CO₃, then water. The organic fraction was dried (Na₂SO₄) and concentrated in vacuo. The resulting residue was purified by column chromatography (Si—PCC, gradient 50-80% EtOAc in cyclohexane) affording the title compound as a pink gum (0.734 g, 95%). LCMS (Method B): R$_T$ 2.56 min [M+H]⁺ 523.

2,2-Dimethylpropionic acid 2-{(R)-3-[2-((S)-2-aminobutyrylamino)-5-fluorophenylamino]piperidin-1-yl}ethyl ester

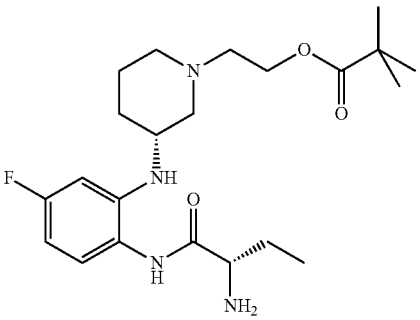 [SMILES: CC[C@H](N)C(=O)Nc1ccc(F)cc1N[C@@H]1CCCN(CCOC(=O)C(C)(C)C)C1]

To an ice-cooled solution of 2,2-dimethylpropionic acid 2-{(R)-3-[2-((S)-2-tert-butoxycarbonylaminobutyrylamino)-5-fluorophenylamino]piperidin-1-yl}ethyl ester (0.732 g, 1.4 mmol) in DCM (25 mL) was added TFA (6 mL) and the mixture stirred at RT for 1.5 h. Toluene was added and volatiles removed in vacuo, the resulting residue was dissolved in MeOH and loaded onto an Isolute® SCX-2 cartridge. The cartridge was washed with MeOH and the product eluted with 0.5M NH₃/MeOH. The product containing fractions were combined and concentrated in vacuo affording the title compound as a brown gum (0.59 g, 100%). LCMS (Method B): R_T 1.76 min [M+H]+ 423.

2,2-Dimethylpropionic acid 2-[(R)-3-(5-fluoro-2-{(S)-2-[9-(tetrahydropyran-2-yl)-9H-purin-6-ylamino]butyrylamino}phenylamino)piperidin-1-yl]ethyl ester

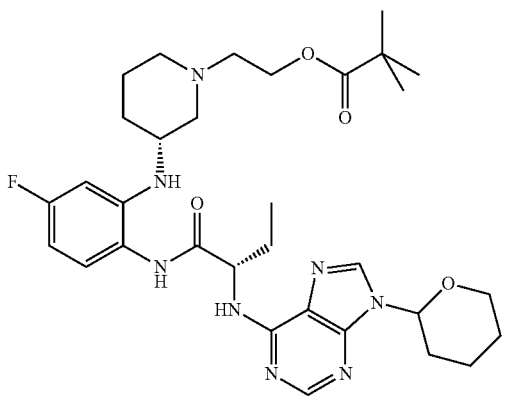 [SMILES: CC[C@H](Nc1ncnc2c1ncn2C1CCCCO1)C(=O)Nc1ccc(F)cc1N[C@@H]1CCCN(CCOC(=O)C(C)(C)C)C1]

A mixture of 2,2-dimethylpropionic acid 2-{(R)-3-[2-((S)-2-aminobutyrylamino)-5-fluorophenylamino]piperidin-1-yl}ethyl ester (0.588 g, 1.39 mmol), 6-chloro-9-(tetrahydropyran-2-yl)-9H-purine (0.333 g, 1.39 mmol), and DIPEA (0.71 mL, 4.15 mmol) in n-butanol (6 mL) was stirred in a sealed vial at 100° C. for 16 h. After cooling to RT, volatiles were removed in vacuo and the resulting residue purified by column chromatography (Si—PCC, gradient 2-10% 2M NH_3/MeOH in DCM) affording the title compound as a light brown gum (0.516 g, 59%). LCMS (Method B): R_T 2.47 min [M+H]+ 625.

2,2-Dimethylpropionic acid 2-((S)-3-tert-butoxycarbonylaminopiperidin-1-yl)ethyl ester

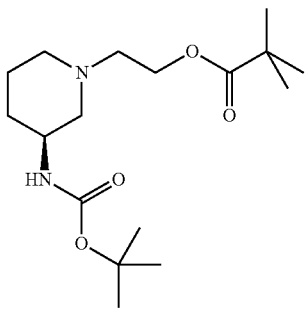 [SMILES: CC(C)(C)OC(=O)N[C@H]1CCCN(CCOC(=O)C(C)(C)C)C1]

A mixture of 2,2-dimethylpropionic acid 2-bromoethyl ester (2.3 g, 11 mmol), (S)-piperidin-3-ylcarbamic acid tert-butyl ester (2 g, 10.0 mmol), potassium carbonate (4.15 g, 30 mmol) and sodium iodide (0.15 g, 1 mmol) in DMF (20 mL) was stirred at RT for 3 days. The reaction mixture was partitioned between water and EtOAc. The aqueous phase was extracted with EtOAc and the combined organic fractions were washed with water, followed by brine, then dried (Na_2SO_4) and concentrated in vacuo. The resulting residue was purified by column chromatography (Si—PCC, eluant 10-40% EtOAc in cyclohexane) affording the title compound as a colourless oil (3.23 g, 98%). 1H NMR (CDCl_3, 300 MHz): 5.08 (1H, bs), 4.27-4.07 (2H, m), 3.73 (1H, bs), 2.65-2.50 (3H, m), 2.48 (1H, bs), 2.30-2.24 (1H, m), 1.74-1.61 (1H, m), 1.58-1.47 (3H, m), 1.44 (9H, s), 1.21 (9H, s).

2,2-Dimethylpropionic acid 2-((S)-3-amino-piperidin-1-yl)ethyl ester

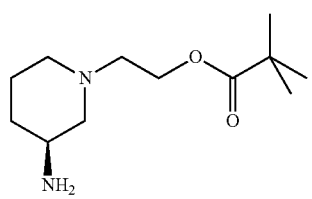 [SMILES: CC(C)(C)C(=O)OCCN1CCC[C@H](N)C1]

To an ice-cooled solution of 2,2-dimethylpropionic acid 2-((S)-3-tert-butoxycarbonylaminopiperidin-1-yl)ethyl ester (2.54 g, 7.73 mmol) in DCM (80 mL) was added TFA (20 mL) and the mixture was stirred at RT for 2 h. Toluene was added and volatiles removed in vacuo. The resulting residue was dissolved in MeOH and loaded onto an Isolute® SCX-2 cartridge. The cartridge was washed with MeOH and the product was eluted with 1M NH_3/MeOH. The product containing fractions were combined and concentrated in vacuo affording the title compound as a pale yellow oil (1.567 g, 89%). 1H NMR (CDCl_3, 300 MHz): 4.18 (2H, t, J=6.0 Hz), 2.89-2.77 (2H, m), 2.68-2.59 & 2.62 (3H, m & t, J=6.0 Hz), 2.20-2.12 (1H, m), 2.00-1.94 (1H, m), 1.82-1.65 (2H, m), 1.60-1.46 (1H, m), 1.28 (2H, bs), 1.20 (9H, s), 1.15-1.03 (1H, m).

2,2-Dimethylpropionic acid 2-[(S)-3-(5-fluoro-2-nitrophenylamino)piperidin-1-yl]ethyl ester

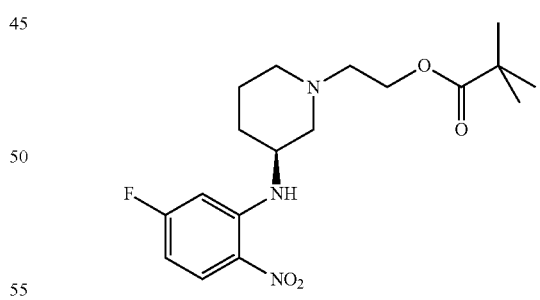

To an ice-cooled solution of 2,2-dimethylpropionic acid 2-((S)-3-aminopiperidin-1-yl)ethyl ester (1.565 g, 6.85 mmol) in DMF (30 mL) was added 2,4-difluoronitrobenzene (1.517 g, 8.92 mmol) and potassium carbonate (1.9 g, 13.8 mmol). The reaction mixture was stirred at RT for 16 h, then partitioned between water and EtOAc. The aqueous phase was extracted with EtOAc and the combined organic fractions washed with water, followed by brine, then dried (Na_2SO_4) and concentrated in vacuo. The resulting residue was purified by column chromatography (Si—PCC, eluant 10-40%

EtOAc in cyclohexane) affording the title compound as a yellow oil (2.307 g, 92%). LCMS (Method J): $R_T$ 2.34 min [M+H]$^+$ 368.

2,2-Dimethylpropionic acid 2-[(S)-3-(2-amino-5-fluorophenylamino)piperidin-1-yl]ethyl ester

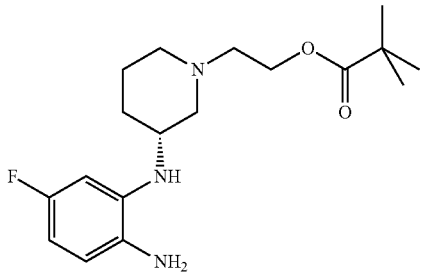

To a solution of 2,2-dimethylpropionic acid 2-[(S)-3-(5-fluoro-2-nitrophenylamino)piperidin-1-yl]ethyl ester (2.3 g, 6.26 mmol) in EtOAC (100 mL) was added a slurry of 10% Pd/C (200 mg) in IMS (20 mL) and the reaction mixture stirred at RT under a hydrogen atmosphere for 24 h. The suspension was filtered through a pad of Celite® and the filtrate concentrated in vacuo. The resulting residue was purified by column chromatography (Si—PCC, gradient 2-6% 2M NH$_3$/MeOH in DCM) affording the title compound as a colourless gum affording the title compound as a dark red oil (1.464 g, 69%). LCMS (Method J): $R_T$ 1.71 min [M+H]$^+$ 338.

2,2-Dimethylpropionic acid 2-{(S)-3-[2-((S)-2-tert-butoxycarbonylaminopropionylamino)-5-fluorophenylamino]piperidin-1-yl}ethyl ester

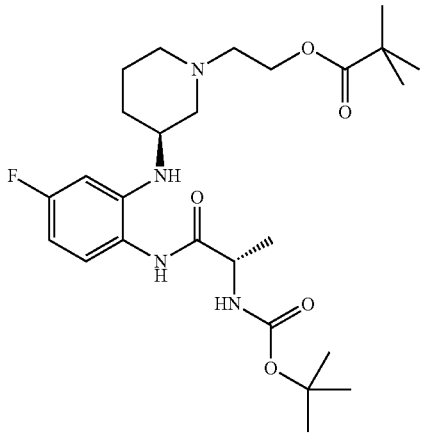 [SMILES: C[C@H](NC(=O)OC(C)(C)C)C(=O)Nc1ccc(F)cc1N[C@H]1CCCN(CCOC(=O)C(C)(C)C)C1]

To an ice-cooled mixture of 2,2-dimethylpropionic acid 2-[(S)-3-(2-amino-5-fluorophenylamino)piperidin-1-yl]ethyl ester (1.464 g, 4.34 mmol), (S)-2-tert-butoxycarbonylaminopropionic acid (0.904 g, 4.77 mmol) and HOAt (0.591 g, 4.34 mmol) in DCM (40 mL) was added N-(3-dimethylaminopropyl)-N'-ethylcarbodiimide hydrochloride (1.0 g, 5.21 mmol) portion wise over 10 min. The reaction mixture was stirred in the ice bath for 2 h, then diluted with DCM, washed with 2M Na$_2$CO$_3$ then water. The organic fractions were dried (Na$_2$SO$_4$) then concentrated in vacuo. The resulting residue was purified by column chromatography (Si—PCC, gradient 40-70% EtOAc in cyclohexane) affording the title compound as a dark red gum (2.054 g, 93%). LCMS (Method B): $R_T$ 2.46 min [M+H]$^+$ 509.

2,2-Dimethylpropionic acid 2-{(S)-3-[2-((S)-2-aminopropionylamino)-5-fluorophenylamino]piperidin-1-yl}ethyl ester

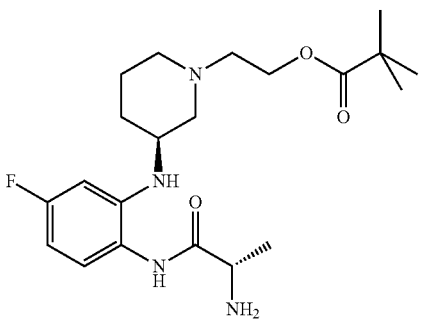

To an ice-cooled solution of 2,2-dimethylpropionic acid 2-{(S)-3-[2-((S)-2-tert-butoxycarbonylaminopropionylamino)-5-fluorophenylamino]piperidin-1-yl}ethyl ester (2.054 g, 4.04 mmol) in DCM (40 mL) was added TFA (14 mL) and the mixture stirred at RT for 1.5 h. Toluene was added and the volatiles removed in vacuo. The resulting residue was dissolved in MeOH and loaded onto an Isolute® SCX-2 cartridge. The cartridge was washed with MeOH and the product eluted with 0.5M NH$_3$/MeOH. The product containing fractions were combined and concentrated in vacuo. The resulting residue was purified by column chromatography (Si—PCC, gradient 2-10% 2M NH$_3$/MeOH in DCM) affording the title compound as a purple oil (1.443 g, 87%). LCMS (Method B): $R_T$ 1.60 min [M+H]$^+$ 409.

2,2-Dimethylpropionic acid 2-[(S)-3-(5-fluoro-2-{(S)-2-[9-(tetrahydropyran-2-yl)-9H-purin-6-ylamino]propionylamino}phenylamino)piperidin-1-yl]ethyl ester

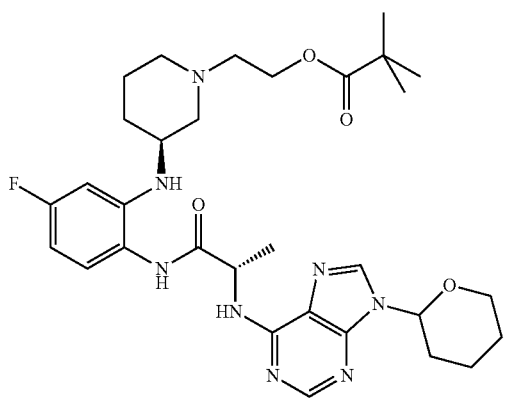 [SMILES: C[C@H](Nc1ncnc2c1ncn2C1CCCCO1)C(=O)Nc1ccc(F)cc1N[C@H]1CCCN(CCOC(=O)C(C)(C)C)C1]

A mixture of 2,2-dimethylpropionic acid 2-{(S)-3-[2-((S)-2-aminopropionylamino)-5-fluorophenylamino]piperidin-1-yl}ethyl ester, (0.591 g, 1.45 mmol), 6-chloro-9-(tetrahydropyran-2-yl)-9H-purine (0.346 g, 1.45 mmol), and DIPEA (0.74 mL, 4.32 mmol) in n-butanol (7 mL) was stirred in a sealed vial at 90° C. for 16 h. After cooling to RT the volatiles were removed in vacuo and the resulting residue purified by column chromatography (Si—PCC, gradient 2-8% 2M NH$_3$/MeOH in DCM) affording the title compound as a colourless gum (0.583 g, 66%). LCMS (Method J): R$_T$ 2.39 min [M+H]$^+$ 611.

2-{(S)-3-[2-((S)-1-Aminoethyl)-6-fluorobenzoimidazol-1-yl]piperidin-1-yl}ethanol

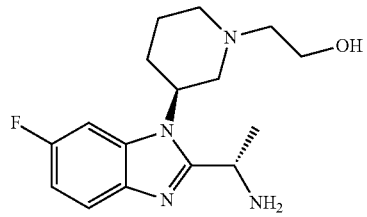 [SMILES: C[C@H](N)c1nc2ccc(F)cc2n1[C@H]1CCCN(CCO)C1]

A solution of 2,2-dimethylpropionic acid 2-{(S)-3-[2-((S)-2-aminopropionylamino)-5-fluorophenylamino]piperidin-1-yl}ethyl ester (200 mg, 0.49 mmol), in aqueous 6M HCl (8 mL) was refluxed for 30 min. After cooling to RT the volatiles were removed in vacuo and the resulting residue loaded in dioxane/water (1:1) onto an Isolute® SCX-2 cartridge. The cartridge was washed with dioxane/water (1:1), then dioxane and the product eluted with 10% 880 NH$_3$ in dioxane. The fractions containing product were purified by column chromatography (Si—PCC, gradient 3-18% 2M NH$_3$/MeOH in DCM) affording the title compound as a colourless gum (71.2 mg, 47%). LCMS (Method J): R$_T$ 0.39 min [M+H]$^+$ 307.

1-Phenyl-1H-imidazo[4,5-c]pyridine and 3-phenyl-3H-imidazo[4,5-c]pyridine

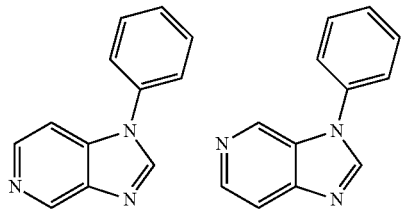 [SMILES: c1ccc(-n2cnc3cnccc32)cc1 ; c1ccc(-n2cnc3ccncc32)cc1]

1H-Imidazo[4,5-c]pyridine (2.01 g, 0.0169 mol), copper acetate (7.66 g, 42.2 mmol) and phenyl boronic acid (5.14 g, 042.2 mmol) in pyridine (60 mL) were stirred vigorously at 37° C. in a flask open to the atmosphere for 3 days. The mixture was allowed to cool to RT then partitioned between water and DCM (3×50 mL). The combined DCM extracts were washed with water, dried (Na$_2$SO$_4$) and concentrated in vacuo. The residue was purified by chromatography (SiO$_2$ 0-6% (2M ammonia in methanol) in DCM) to give 1-phenyl-1H-imidazo[4,5-c]pyridine (1.60 g) and 3-phenyl-3H-imidazo[4,5-c]pyridine (1.06 g) as white solids (combined 81%).

1-Phenyl-1H-imidazo[4,5-c]pyridine: LCMS (method H): R$_T$ 0.25 min, [M+H]$^+$ 196

3-Phenyl-3H-imidazo[4,5-c]pyridine: LCMS (method H): R$_T$ 0.28 min, [M+H]$^+$ 196

1-Phenyl-1H-imidazo[4,5-c]pyridine-2-carbaldehyde

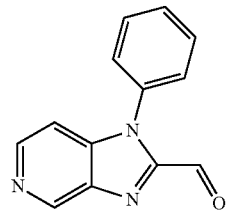 [SMILES: O=Cc1nc2cnccc2n1-c1ccccc1]

n-Butyl lithium (2.5M in hexanes, 6.8 mL, 17.1 mmol) was added to a solution of 1-phenyl-1H-imidazo[4,5-c]pyridine (1.85 g, 9.48 mmol) in THF (40 mL) at −78° C. under nitrogen. The mixture was kept at −78° C. for 15 minutes then at −10° C. for 10 minutes, and then re-cooled to −78° C. and DMF (1.5 mL, 0.190 mol) added. The reaction mixture was stirred at −78° C. for 15 minutes and −10° C. for 10 minutes. The mixture was poured into aqueous hydrochloric acid (1M, 80 mL) and the resultant mixture adjusted to pH 8 with saturated aqueous NaHCO$_3$ (50 mL), then extracted with EtOAc (3×50 mL). The combined EtOAc extracts were dried (Na$_2$SO$_4$) and concentrated in vacuo. The resulting residue was in purified by chromatography (SiO$_2$ 0-10% (2M ammonia in methanol) in DCM) to give the title compound as a yellow solid (0.72 g, 34%), containing methyl hemiacetal. LCMS (method H): R$_t$ 1.28 min, [M+H]$^+$ 224

1-(1-Phenyl-1H-imidazo[4,5-c]pyridin-2-yl)ethanol

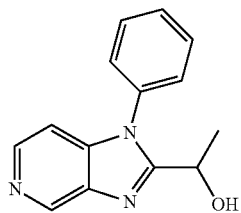 [SMILES: CC(O)c1nc2cnccc2n1-c1ccccc1]

Methylmagnesium bromide (3.0M in diethyl ether, 2.1 mL, 6.36 mmol) was added to a stirred solution of 1-phenyl-1H-imidazo[4,5-c]pyridine-2-carbaldehyde (0.71 g, 3.18 mmol) in THF (25 mL) at −78° C. under nitrogen. The resulting mixture was stirred at −78° C. for 2 h then at −10° C. for 20 minutes, then re-cooled to −78° C. and additional methyl magnesium bromide (3.0M in diethyl ether, 1 mL, 3.00 mmol) added. The resultant mixture was stirred at −10° C. for 30 minutes then poured into saturated aqueous ammonium chloride solution (25 mL) and extracted with EtOAc (3×50 mL). The combined EtOAc extracts were dried (Na$_2$SO$_4$) and concentrated in vacuo. The resulting residue was dissolved in THF (25 mL) and cooled to −78° C. and methyl magnesium bromide (3.0M in diethyl ether, 2.1 mL, 6.36 mmol) added, then stirred at −78° C. for 30 minutes followed by −10° C. for 1 h. The mixture was then poured into saturated aqueous ammonium chloride solution (25 mL) and extracted with EtOAc (3×50 mL). The combined EtOAc extracts were dried (Na$_2$SO$_4$) and concentrated in vacuo. The resulting residue was purified by chromatography (SiO$_2$ 0-10% (2M ammonia in methanol) in DCM) to give the title compound as a yellow oil (0.36 g, 47%). LCMS (method H): $R_t$ 1.42 min, [M+H]$^+$ 240.

2-(1-Azidoethyl)-1-phenyl-1H-imidazo[4,5-c]pyridine

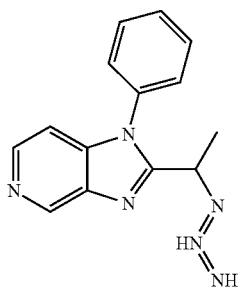

Diphenylphosphoryl azide (0.50 g, 1.81 mmol) and diisopropyl azadicarboxylate (0.61 g, 3.01 mmol) were added to a stirred solution of 1-(1-phenyl-1H-imidazo[4,5-c]pyridin-2-yl)ethanol (0.36 g, 1.50 mmol) and triphenylphosphine (0.79 g, 3.01 mmol) in dioxane (15 mL) at 0° C. under nitrogen. After addition the mixture was stirred at 20° C. for 16 h. Additional diphenyl phosphoryl azide (0.25 g, 0.91 mmol), triphenylphosphine (0.40 g, 1.53 mmol) and diisopropyl azadicarboxylate (0.30 g, 1.48 mmol) were added and the resultant mixture stirred at 20° C. for 30 minutes. The reaction mixture was concentrated in vacuo and the residue purified by chromatography (SiO$_2$ 0-10% (2M ammonia in methanol) in DCM) to give the title compound as an oil (0.60 g, contaminated with triphenylphosphine oxide). LCMS (method H): $R_t$ 1.86 min, [M+H]$^+$ 265

1-(1-Phenyl-1H-imidazo[4,5-c]pyridin-2-yl)ethylamine

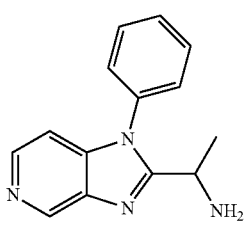 [SMILES: CC(N)c1nc2cnccc2n1-c1ccccc1]

A mixture of 2-(1-azidoethyl)-1-phenyl-1H-imidazo[4,5-c]pyridine (0.40 g, 1.50 mmol) and 10% palladium on carbon (0.10 g) in EtOAc (20 mL) was stirred under an atmosphere of hydrogen at atmospheric pressure and 20° C. for 16 h. The catalyst was removed by filtration, the filtrate concentrated in vacuo, and the resulting residue purified by chromatography (SiO$_2$ 0-10% (2M ammonia in methanol) in DCM) to give the title compound as a white solid (0.194 g, 54%). LCMS (method J): $R_t$ 0.26 min, [M+H]$^+$ 239.

1-(3-Phenyl-3H-imidazo[4,5-c]pyridin-2-yl)ethanone

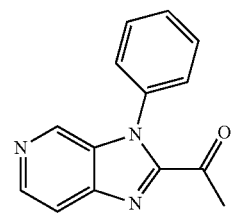 [SMILES: CC(=O)c1nc2ccncc2n1-c1ccccc1]

LiHMDS (2.0M in THF/heptane/ethyl benzene, 3.9 mL, 7.79 mmol) was added to a stirred solution of 3-phenyl-3H-imidazo[4,5-c]pyridine (0.95 g, 4.87 mol) in THF (20 mL) at −78° C. under nitrogen. The resultant mixture was stirred at −78° C. for 10 minutes then at −10° C. for 15 minutes. The reaction mixture was re-cooled to −78° C. and N,N-dimethylacetamide (0.72 mL, 7.79 mmol) added then stirred at −78° C. for 5 minutes then at −10° C. for 15 minutes. The reaction mixture was poured into saturated aqueous ammonium chloride solution (30 mL) and extracted with EtOAc (3×30 mL). The combined EtOAc extracts were dried (Na$_2$SO$_4$) and concentrated in vacuo. The residue was purified by chromatography (SiO$_2$ 0-4% (2M ammonia in methanol) in DCM) to give the title compound as an off white solid (0.96 g, 76%) LCMS (method H): $R_t$ 1.76 min, [M+H]$^+$ 238

1-(3-Phenyl-3H-imidazo[4,5-c]pyridin-2-yl)ethanol

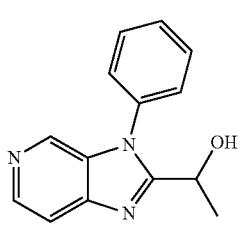 [SMILES: CC(O)c1nc2ccncc2n1-c1ccccc1]

Sodium borohydride (0.27 g, 7.17 mmol) was added to a stirred suspension of 1-(3-phenyl-3H-imidazo[4,5-c]pyridin-2-yl)ethanone (0.85 g, 3.58 mmol) in methanol (20 mL) at 0° C. under nitrogen. The reaction mixture was stirred for 15 minutes then poured into saturated aqueous ammonium chloride solution and extracted with EtOAc (3×50 mL). The combined EtOAc extracts were washed with water, dried (Na₂SO₄) and concentrated in vacuo to give the title compound as a white solid (0.74 g, 87%). LCMS (method H): R_t 1.76 min, [M+H]⁺ 240.

2-(1-Azidoethyl)-3-phenyl-3H-imidazo[4,5-c]pyridine

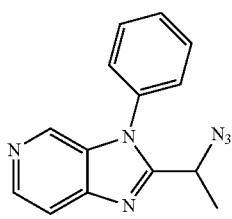 [SMILES: CC(N=[N+]=[N-])c1nc2ccncc2n1-c1ccccc1]

Diphenylphosphoryl azide (1.12 g, 4.06 mmol) and then diisopropyl azadicarboxylate (1.37 g, 6.77 mmol) were added to a stirred solution of 1-(3-phenyl-3H-imidazo[4,5-c]pyridin-2-yl)ethanol (0.81 g, 3.39 mmol) and triphenylphosphine (1.78 g, 6.77 mmol) in dioxane (50 mL) at 0° C. under nitrogen. The reaction mixture was stirred at 20° C. for 16 h then diluted with DCM to dissolve all the material. This was loaded onto an Isolute® SCX-2 cartridge and washed with methanol and the product eluted with 2M NH₃/MeOH then concentrated in vacuo. The residue was purified by chromatography (SiO₂ 0-4% (2M ammonia in methanol) in DCM) to give the title compound as a colourless oil (1.48 g, contaminated with triphenylphosphine oxide). LCMS (method H): R_t 1.79 min, [M+H]⁺ 265.

1-(3-Phenyl-3H-imidazo[4,5-c]pyridin-2-yl)ethylamine

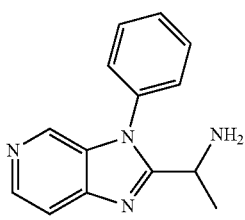 [SMILES: CC(N)c1nc2ccncc2n1-c1ccccc1]

A mixture of 2-(1-azidoethyl)-3-phenyl-3H-imidazo[4,5-c]pyridine (0.89 g, 3.39 mmol) and 10% palladium on carbon (0.20 g) in EtOAc (40 mL) was stirred under an atmosphere of hydrogen at atmospheric pressure and 20° C. for 3 h. The catalyst was removed by filtration and the filtrate concentrated in vacuo. The resulting residue was purified by chromatography (SiO₂ 0-10% (2M ammonia in methanol) in DCM) to give the title compound as a white solid (0.53 g, 65%). LCMS (method H): R_t 0.25 min, [M+H]⁺ 239.

[(S)-1-(3-Cyano-4-fluoro-2-phenylaminophenylcarbamoyl)propyl]carbamic acid tert-butyl ester

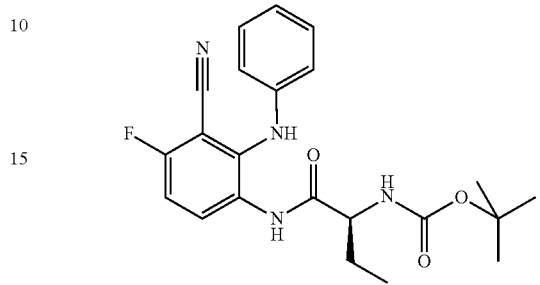

Triethylamine (0.55 mL, 3.96 mmol) was added to a stirred mixture of 3-amino-6-fluoro-2-phenylaminobenzonitrile (0.30 g, 1.32 mmol), (S)-(2-tert-butoxycarbonylamino)butyric acid (0.30 g, 1.45 mmol), N-(3-dimethylaminopropyl)-N'-ethylcarbodiimide hydrochloride (0.28 g, 1.45 mmol) and HOAt (0.20 g, 1.45 mmol) in DCM at 0° C. under nitrogen. The resultant mixture was stirred at 0° C. for 5 minutes then 20° C. for 16 h. The reaction mixture was re-cooled to 0° C. and (S)-2-tert-butoxycarbonylaminobutyric acid (0.30 g, 1.45 mmol), N-(3-dimethylaminopropyl)-N' ethylcarbodiimide hydrochloride (0.28 g, 1.45 mmol), HOAt (0.20 g, 1.45 mmol) and triethylamine (0.55 mL, 3.96 mmol) added sequentially, and the resultant mixture stirred at 20° C. for 24 h. The mixture was partitioned between saturated aqueous NaHCO₃ (20 mL) and DCM (3×20 mL). The combined DCM extracts were washed with water, dried (Na₂SO₄) and concentrated in vacuo to give the title compound as an off white foam (0.64 g). LCMS (method H): R_t 2.93 min, [M+H]⁺ 413.

2-((S)-1-Amino-propyl)-5-fluoro-3-phenyl-3H-benzoimidazole-4-carbonitrile

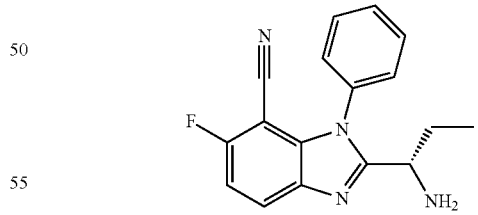

HCl in dioxane (4M, 10 mL, 0.04 mol) was added to a solution of [(S)-1-(3-cyano-4-fluoro-2-phenylaminophenylcarbamoyl)propyl]carbamic acid tert-butyl ester (0.54 g, 1.32 mmol) in dioxane (5 mL) at 20° C., and the resultant mixture stirred at 80° C. for 17 h. After cooling, the reaction mixture was partitioned between saturated aqueous NaHCO₃ (20 mL) and EtOAc (3×20 mL). The combined EtOAc extracts were dried (Na₂SO₄) and concentrated in vacuo. The resulting residue was purified by chromatography (SiO₂ 0-20% methanol in EtOAc) to give the title compound as an oil (0.27 g, 69%) LCMS (method H): $R_T$ 2.03 min, [M+H]⁺ 295.

(3-Nitro-pyridin-2-yl)-pyridin-2-yl-amine

2-Chloro-3-nitropyridine (3.42 g, 21.60 mmol) and pyridine-2-ylamine (6.09 g, 0.65 mol) in DMF (20 mL) were stirred together at 80° C. for 18 h. The reaction mixture was concentrated in vacuo and the residue purified by chromatography (SiO₂ 0-5% methanol in DCM) to give the title compound as an orange solid (1.68 g, 36%). LCMS (method H): $R_t$ 1.45 min, [M+H]⁺ 217.

N²-Pyridin-2-yl-pyridine-2,3-diamine

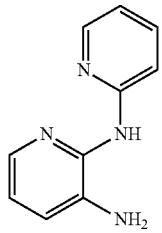 [SMILES: Nc1cccnc1Nc1ccccn1]

A mixture of (3-nitro-pyridin-2-yl)-pyridin-2-yl-amine (0.84 g, 3.89 mmol) and 10% palladium on carbon (0.30 g) in EtOAc (20 mL) was stirred under an atmosphere of hydrogen at atmospheric pressure and 20° C. for 16 h. The catalyst was removed by filtration and the filtrate concentrated in vacuo to give the title compound as a green solid (0.63 g, 88%). LCMS (method H): $R_t$ 1.87 min, [M+H]⁺ 187.

[(S)-1-(3-Pyridin-2-yl-3H-imidazo[4,5-b]pyridin-2-yl)ethyl]carbamic acid tert-butyl ester

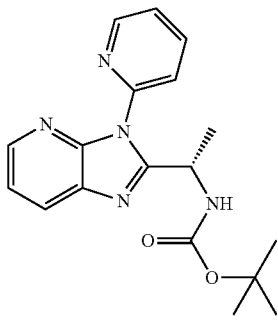 [SMILES: C[C@H](NC(=O)OC(C)(C)C)c1nc2cccnc2n1-c1ccccn1]

Triethyloxonium tetrafluoroborate (1.08 g, 5.66 mmol) was added to a solution of ((S)-1-carbamoylethyl)carbamic acid tert-butyl ester (1.00 g, 5.33 mmol) in THF (15 mL) at 20° C. under nitrogen and the resultant mixture stirred for 2 h then concentrated in vacuo. A solution of N²-pyridin-2-yl-pyridine-2,3-diamine (0.62 g, 3.33 mmol) in ethanol (15 mL) was added to the residue and the resultant solution stirred at 75° C. for 16 h. The reaction mixture was concentrated in vacuo and the residue partitioned between DCM (3×30 mL) and saturated aqueous NaHCO₃ (30 mL). The combined DCM extracts were dried (Na₂SO₄) and concentrated in vacuo. The resulting residue was purified by chromatography (SiO₂ 0-5% (2M ammonia in methanol) in DCM) to give the title compound as an oil (1.11 g, 98%). LCMS (method H): $R_t$ 2.73 min, [M+H]⁺ 340.

(S)-1-(3-Pyridin-2-yl-3H-imidazo[4,5-b]pyridin-2-yl)ethylamine

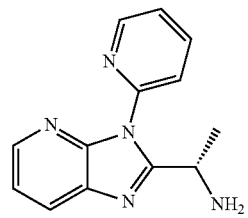 [SMILES: C[C@H](N)c1nc2cccnc2n1-c1ccccn1]

Trifluoroacetic acid (20 mL) was added to a solution of [(S)-1-(3-pyridin-2-yl-3H-imidazo[4,5-b]pyridin-2-yl)ethyl]carbamic acid tert-butyl ester (1.10 g, 3.24 mmol) in DCM (10 mL) and stirred for 30 min. The reaction mixture was concentrated in vacuo and the residue purified by chromatography (SiO₂ 0-10% (2M ammonia in methanol) in DCM) to give the title compound (0.145 g, 19%). LCMS (method H): $R_t$ 0.26 min, [M+H]⁺ 240.

(2-Bromo-3-fluoro-6-nitro-phenyl)-pyridin-2-yl-amine

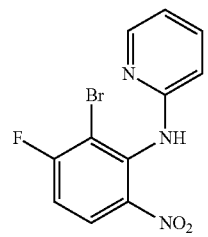 [SMILES: O=[N+]([O-])c1ccc(F)c(Br)c1Nc1ccccn1]

Potassium tert-butoxide (2.82 g, 25.2 mmol) was added to a solution of 2-aminopyridine (1.25 g, 13.2 mmol) in THF (40 mL) at 0° C. and the reaction mixture stirred at 0° C. for 30 min. 2-Bromo-1,3-difluoro-4-nitrobenzene (3 g, 12.6 mmol) was added as a solution in THF (10 mL) and the reaction mixture stirred at 0° C. for 2 h. The reaction mixture was diluted with water and the product extracted with EtOAc (3×40 mL). The combined organic extracts were washed with brine, dried (MgSO₄) and concentrated in vacuo. The resultant residue was subjected to flash chromatography (SiO₂, eluting with 0-100% EtOAc in cyclohexane) to yield the title compound as a yellow solid (2.38 g, 60%). ¹H NMR 400 MHz δ (CDCl$_3$): 8.16 (1H, ddd, J=5.1, 2.0, 1.0 Hz), 8.08 (1H, dd, J=9.3, 5.6 Hz), 7.82 (1H, br s), 7.62 (1H, ddd, J=8.1, 7.3, 1.8 Hz), 6.99 (1H, dd, J=9.2, 7.1 Hz), 6.91 (1H, ddd, J=7.3, 5.0, 1 Hz), 6.82 (1H, dt, J=8.3, 1.0 Hz).

3-Bromo-4-fluoro-N$^2$-pyridin-2-yl-benzene-1,2-diamine

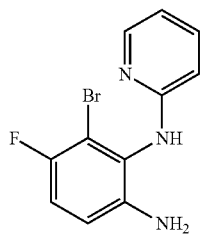

(2-Bromo-3-fluoro-6-nitro-phenyl)-pyridin-2-yl-amine (3.68 g, 11.8 mmol), iron powder (2.63 g, 47.2 mmol), and ammonium chloride (3.63 g, 70.7 mmol) in methanol (40 mL) and water (15 mL) were heated at 90° C. for 1.5 h. The reaction mixture was filtered and the filtrate concentrated in vacuo. The residue was dissolved in water and extracted with EtOAc (3×40 mL). The combined organic extracts were washed with brine, dried (MgSO$_4$) and concentrated in vacuo. The resultant residue was subjected to flash chromatography (SiO$_2$, eluting with 0-10% methanol in EtOAc) to yield the title compound as a white solid (2.5 g, 75%). $^1$H NMR 400 MHz δ (CDCl$_3$): 8.23-8.17 (1H, m), 7.48 (1H, ddd, J=8.4, 7.3, 1.9 Hz), 6.94 (1H, dd, J=8.8, 7.9 Hz), 6.77 (1H, ddd, J=7.2, 5.0, 1.0 Hz), 6.73 (1H, dd, J=8.8, 5.0 Hz), 6.31 (1H, dt, J=8.3, 1.0 Hz), 6.10 (1H, br s), 3.94 (2H, br s).

[(S)-1-(7-Bromo-6-fluoro-1-pyridin-2-yl-1H-benzoimidazol-2-yl)ethyl]carbamic acid tert-butyl ester

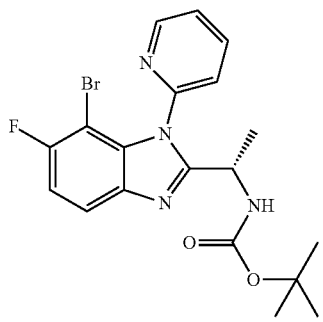 [SMILES: C[C@H](NC(=O)OC(C)(C)C)c1nc2ccc(F)c(Br)c2n1-c1ccccn1]

To a suspension of ((S)-1-carbamoylethyl)carbamic acid tert-butyl ester (1.0 g, 5.4 mmol) in DCM (10 mL) was added triethyloxonium tetrafluoroborate (1.1 g, 5.78 mmol) and the reaction mixture stirred at RT for 2 h, during which the solids dissolved. The reaction mixture was concentrated in vacuo and the residue dissolved in ethanol (10 mL). 3-Bromo-4-fluoro-N$^2$-pyridin-2-yl-benzene-1,2-diamine (0.96 g, 3.4 mmol) was added and the reaction heated at 75° C. for 16 h. The reaction mixture was concentrated in vacuo, the residue dissolved in water and the product extracted with EtOAc (3×20 mL). The combined organic extracts were washed with brine, dried (MgSO$_4$) and concentrated in vacuo. The resultant residue was subjected to flash chromatography (SiO$_2$, eluting with 0-100% EtOAc in cyclohexane) to yield the title compound as a white solid (832 mg, 56%). LCMS (Method C): R$_T$=3.39 min, [M+H]+=435+437.

[(S)-1-(7-Bromo-6-fluoro-1-pyridin-2-yl-1H-benzoimidazol-2-yl)ethyl]-[9-(tetrahydro-pyran-2-yl)-9H-purin-6-yl]-amine

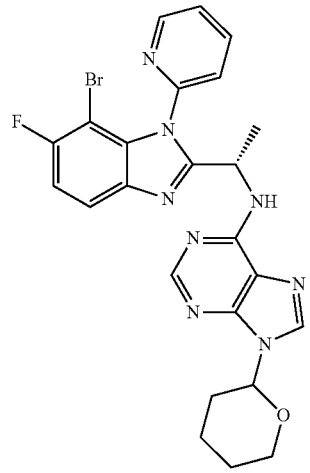 [SMILES: C[C@H](Nc1ncnc2c1ncn2C1CCCCO1)c1nc2ccc(F)c(Br)c2n1-c1ccccn1]

[(S)-1-(7-Bromo-6-fluoro-1-pyridin-2-yl-1H-benzoimidazol-2-yl)ethyl]carbamic acid tert-butyl ester (220 mg, 0.66 mmol) was dissolved in hydrochloric acid in dioxane (15 mL, 4M) and the reaction stirred at RT for 1 h. The reaction mixture was concentrated in vacuo then the residue dissolved in IPA and 6-chloro-9-(tetrahydro-pyran-2-yl)-9H-purine (203 mg, 0.85 mmol) and DIPEA (168 μL, 0.99 mmol) added. The reaction mixture was heated at 90° C. for 16 h then concentrated in vacuo. The resultant residue was subjected to flash chromatography (SiO$_2$, eluting with 0-100% methanol in EtOAc) to yield the title compound as a white solid (267 mg, 76%). LCMS (Method C): $R_T$=3.01 min, [M+H]+=537+538.

[(S)-1-(7-Cyclopropyl-6-fluoro-1-pyridin-2-yl-1H-benzoimidazol-2-yl)ethyl]-[9-(tetrahydro-pyran-2-yl)-9H-purin-6-yl]amine

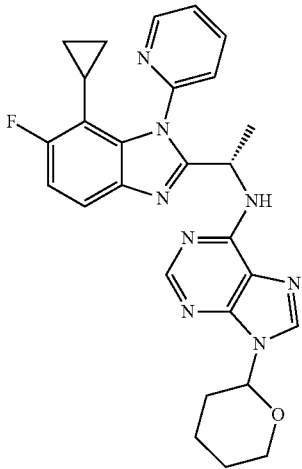 [SMILES: C[C@H](Nc1ncnc2c1ncn2C1CCCCO1)c1nc2ccc(F)c(C3CC3)c2n1-c1ccccn1]

To a solution of [(S)-1-(7-bromo-6-fluoro-1-pyridin-2-yl-1H-benzoimidazol-2-yl)ethyl]-[9-(tetrahydro-pyran-2-yl)-9H-purin-6-yl]amine (267 mg, 0.49 mmol) in dioxane (10 mL) and water (0.5 mL) was added cyclopropylboronic acid (64 mg, 0.75 mmol), cesium carbonate (242 mg, 0.75 mmol) and tetrakis(triphenylphosphine)palladium (0) (57 mg, 0.05 mmol) and the reaction mixture degassed by bubbling argon through the mixture whilst under sonication. The reaction mixture was heated at reflux for 16 h. The reaction mixture was diluted with water and extracted with EtOAc (3×20 mL). The combined organic extracts were washed with brine, dried (MgSO$_4$) and concentrated in vacuo. The resultant residue was subjected to preparative HPLC (C18 Phenomenex column, 10-90% MeCN in water 0.1% formic acid, 25 min gradient) to yield the title compound as a white solid (59 mg, 24%). LCMS (Method C): $R_T$=2.98 min, [M+H]+=499.

(3-Fluoro-2-methyl-6-nitro-phenyl)-pyridin-2-ylamine

Potassium tert-butoxide (2.59 g, 23.1 mmol) was added to a solution of 2-aminopyridine (1.14 g, 12.1 mmol) in THF (30 mL) at 0° C. and the reaction mixture stirred at 0° C. for 20 min. 1,3-Difluoro-2-methyl-4-nitrobenzene (2 g, 11.6 mmol) was added as a solution in THF (10 mL) and the reaction mixture stirred at 0° C. for 30 min. The reaction mixture was diluted with water and the product extracted with EtOAc (3×40 mL). The combined organic extracts were washed with brine, dried (MgSO$_4$) and concentrated in vacuo. The resultant residue was subjected to flash chromatography (SiO$_2$, eluting with 0-100% EtOAc in cyclohexane) to yield the title compound as a yellow solid (2 g, 70%). $^1$H NMR 400 MHz δ (CDCl$_3$): 8.53 (1H, br s), 8.19 (1H, ddd, J=5.1, 1.9, 0.8 Hz), 8.02 (1H, dd, J=9.2, 5.7 Hz), 7.57 (1H, ddd, J=8.2, 7.3, 1.9 Hz), 6.94 (1H, dd, J=9.1, 8.2 Hz), 6.86 (1H, ddd, J=7.3, 5.1, 1.0 Hz), 6.69 (1H, dt, J=8.3, 0.9 Hz), 2.06 (3H, d, J=2.8 Hz).

4-Fluoro-3-methyl-N$^2$-pyridin-2-yl-benzene-1,2-diamine

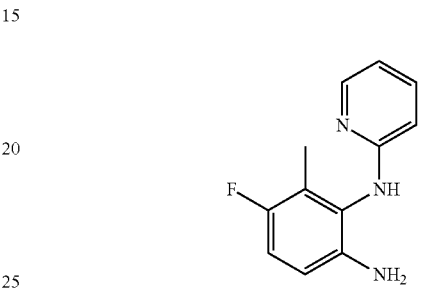

To a solution of (3-fluoro-2-methyl-6-nitro-phenyl)-pyridin-2-yl-amine (2 g, 8.1 mmol) in EtOAc (25 mL) was added palladium on carbon (200 mg, 10% by wt) and the reaction mixture stirred at RT under an atmosphere of hydrogen for 16 h. The reaction mixture was filtered and the filtrate concentrated in vacuo to give the title compound as a white solid (1.7 g, 100%). $^1$H NMR 400 MHz δ (CDCl$_3$): 8.19-8.11 (1H, m), 7.42 (1H, ddd, J=8.8, 7.1, 2.0 Hz), 6.86 (1H, t, J=8.9 Hz), 6.69 (1H, dd, J=6.9, 5.1 Hz), 6.61 (1H, dd, J=8.8, 5.4 Hz), 6.16 (1H, d, J=8.3 Hz), 6.07 (1H, br s), 3.76 (2H, br s), 2.10 (3H, d, J=1.9 Hz).

[(S)-1-(6-Fluoro-7-methyl-1-pyridin-2-yl-1H-benzoimidazol-2-yl)ethyl]-carbamic acid tert-butyl ester

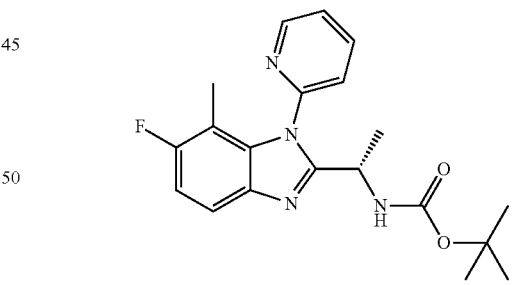

To a suspension of ((S)-1-carbamoylethyl)carbamic acid tert-butyl ester (1.52 g, 8.1 mmol) in DCM (15 mL) was added triethyloxonium tetrafluoroborate (1.63 g, 8.6 mmol) and the reaction mixture stirred at RT for 2 h, during which the solids dissolved. The reaction mixture was concentrated in vacuo and the residue dissolved in ethanol (15 mL). 4-fluoro-3-methyl-N$^2$-pyridin-2-yl-benzene-1,2-diamine (1.0 g, 5.1 mmol) was added and the reaction heated at 75° C. for 16 h. The reaction mixture was concentrated in vacuo, the residue dissolved in water and the product extracted with EtOAc (3×20 mL). The combined organic extracts were washed with brine, dried (MgSO$_4$) and concentrated in vacuo. The resultant residue was subjected to flash chromatography (SiO$_2$, eluting with 0-100% EtOAc in cyclohexane) to yield the title compound as a white solid (1.29 g, 76%). LCMS (Method C): R$_T$=3.22 min, [M+H]+=371.

(S)-1-(6-Fluoro-7-methyl-1-pyridin-2-yl-1H-benzoimidazol-2-yl)ethylamine dihydrochloride

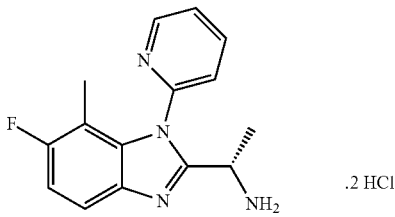 [SMILES: Cc1c(F)ccc2nc([C@H](C)N)n(-c3ccccn3)c12]

[(S)-1-(6-Fluoro-7-methyl-1-pyridin-2-yl-1H-benzoimidazol-2-yl)ethyl]carbamic acid tert-butyl ester (1.29 g, 3.5 mmol) was dissolved in hydrochloric acid in dioxane (15 mL, 4M) and the reaction stirred at RT for 1 h. The reaction mixture was concentrated in vacuo to yield the title compound as an off-white solid (1.17 g, 100%). LCMS (Method C): R$_T$=1.88 min, [M+H]+=271.

6-Fluoro-3-nitro-2-(pyridin-2-ylamino)benzonitrile

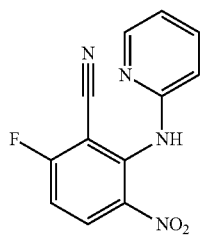

Potassium tert-butoxide (2.44 g, 21.6 mmol) was added to a solution of 2-aminopyridine (1.07 g, 11.4 mmol) in THF (40 mL) at 0° C. and the reaction mixture stirred at 0° C. for 20 min. The resultant mixture was added via cannula to a solution of 3-amino-2,6-difluorobenzonitrilee (2 g, 0.8 mmol) in THF (10 mL) at −78° C. and the reaction mixture stirred at −78° C. for 15 min. The reaction mixture was diluted with water and the product extracted with EtOAc (3×40 mL). The combined organic extracts were washed with brine, dried (MgSO$_4$) and concentrated in vacuo. The resultant residue was subjected to flash chromatography (SiO$_2$, eluting with 0-100% EtOAc in cyclohexane) to yield the title compound as a yellow solid (1.3 g, 46%). $^1$H NMR 400 MHz δ (CDCl$_3$): 9.28 (1H, d, J=16.6 Hz), 9.16-9.11 (1H, m), 7.92 (1H, dd, J=8.6, 5.3 Hz), 7.57 (1H, ddd, J=8.9, 6.5, 1.8 Hz), 7.34 (1H, ddd, J=9.0, 1.3, 0.8 Hz), 6.94 (1H, dd, J=11.8, 8.8 Hz), 6.84 (1H, dd, J=7.7, 6.5, 1.5 Hz).

3-Amino-6-fluoro-2-(pyridin-2-ylamino)benzonitrile

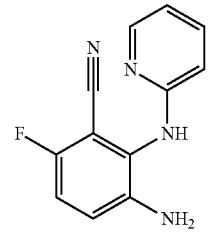 [SMILES: N#Cc1c(F)ccc([N+](=O)[O-])c1Nc1ccccn1]

6-Fluoro-3-nitro-2-(pyridin-2-ylamino)benzonitrile (1.3 g, 5.0 mmol), iron powder (1.12 g, 20.1 mmol), and ammonium chloride (1.55 g, 30.2 mmol) in methanol (20 mL) and water (7 mL) were heated at 90° C. for 3 h. The reaction mixture was filtered and the filtrate concentrated in vacuo. The residue was dissolved in water and extracted with EtOAc (3×40 mL). The combined organic extracts were washed with brine, dried (MgSO$_4$) and concentrated in vacuo to yield the title compound as a yellow solid (620 mg, 54%). $^1$H NMR 400 MHz δ (CDCl$_3$): 9.05 (1H, ddd, J=7.5, 1.1, 0.8 Hz), 9.00-8.89 (1H, m), 7.34 (1H, ddd, J=9.1, 6.2, 1.7 Hz), 7.23-7.19 (1H, m), 6.83 (1H, s), 6.80 (1H, d, J=2.8 Hz), 6.65 (1H, ddd, J=7.6, 6.4, 1.4 Hz), 4.53 (2H, br s).

[(S)-1-(7-Cyano-6-fluoro-1-pyridin-2-yl-1H-benzoimidazol-2-yl)ethyl]carbamic acid tert-butyl ester

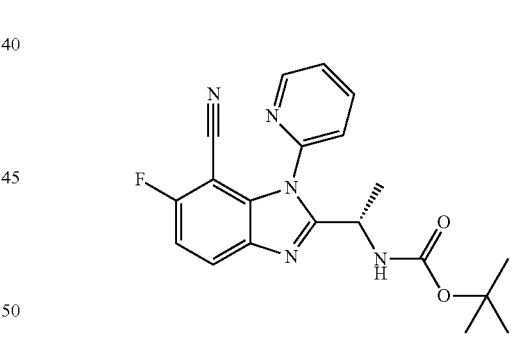

To a suspension of ((S)-1-carbamoylethyl)carbamic acid tert-butyl ester (820 mg, 4.4 mmol) in DCM (7 mL) was added triethyloxonium tetrafluoroborate (877 mg, 4.6 mmol) and the reaction mixture stirred at RT for 2 h, during which the solids dissolved. The reaction mixture was concentrated in vacuo and the residue dissolved in ethanol (7 mL). 3-Amino-6-fluoro-2-(pyridin-2-ylamino)benzonitrile (620 mg, 2.7 mmol) was added and the reaction heated at 75° C. for 16 h. The reaction mixture was concentrated in vacuo, the residue dissolved in water and the product extracted with EtOAc (3×20 mL). The combined organic extracts were washed with brine, dried (MgSO$_4$) and concentrated in vacuo. The resultant residue was subjected to flash chromatography (SiO$_2$, eluting with 0-100% EtOAc in cyclohexane) to yield the title compound as a white solid (563 mg, 54%). LCMS (Method C): $R_T$=3.20 min, [M+H]+=382.

2-((S)-1-Aminoethyl)-5-fluoro-3-pyridin-2-yl-3H-benzoimidazole-4-carbonitrile dihydrochloride

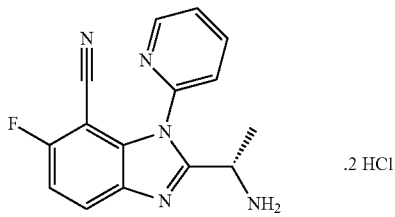 [SMILES: C[C@H](N)c1nc2ccc(F)c(C#N)c2n1-c1ccccn1]

[(S)-1-(7-Cyano-6-fluoro-1-pyridin-2-yl-1H-benzoimidazol-2-yl)ethyl]carbamic acid tert-butyl ester (563 mg, 1.47 mmol) was dissolved in hydrochloric acid in dioxane (10 mL, 4M) and the reaction stirred at RT for 1 h. The reaction mixture was concentrated in vacuo to yield the title compound as an off-white solid (523 mg, 100%). LCMS (Method C): $R_T$=1.75 min, [M+H]+=282.

2-((S)-1-Aminoethyl)-5-fluoro-3-phenyl-3H-benzoimidazole-4-carboxylic acid methyl ester dihydrochloride

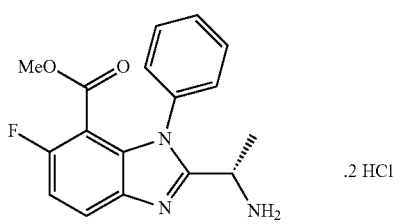 [SMILES: COC(=O)c1c(F)ccc2nc([C@H](C)N)n(-c3ccccc3)c12]

To a solution of 3-amino-6-fluoro-2-phenylaminobenzoic acid methyl ester (1 g, 3.8 mmol), Boc-ala-OH (727 mg, 3.8 mmol) and HOAT (522 mg, 3.8 mmol) in DCM (20 mL) at 0° C. was added N-(3-dimethylaminopropyl)-n'-ethylcarbodiimide hydrochloride (810 mg, 4.2 mmol) and the reaction mixture stirred at 0° C. for 2 h. The reaction mixture was diluted with water and extracted with DCM (3×10 mL). The combined organic fractions were washed with brine, dried (MgSO$_4$) and concentrated in vacuo. The residue was dissolved in HCl in dioxane (20 mL, 4 M) and the reaction mixture heated at 75° C. for 45 min. The reaction mixture was concentrated in vacuo to give the title product as a dark purple solid (1.48 g, 100%). LCMS (Method C): $R_T$=1.95 min, [M+H]+=314.

5-Fluoro-3-phenyl-2-{(S)-1-[9-(tetrahydro-pyran-2-yl)-9H-purin-6-ylamino]ethyl}-3H-benzoimidazole-4-carboxylic acid methyl ester

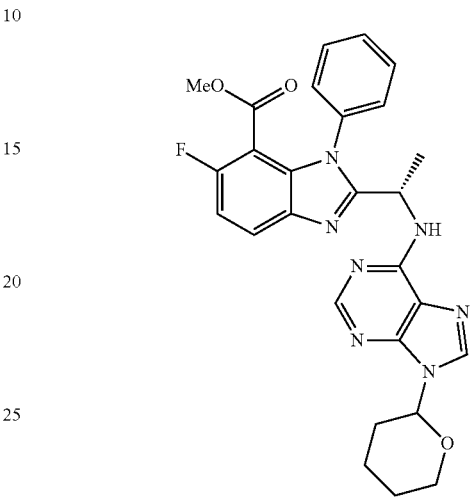

To a solution of 2-((S)-1-aminoethyl)-5-fluoro-3-phenyl-3H-benzoimidazole-4-carboxylic acid methyl ester dihydrochloride dihydrochloride (1.4 g, 3.8 mmol) in IPA (20 mL) was added 6-chloro-9-(tetrahydro-pyran-2-yl)-9H-purine (1.18 mg, 4.94 mmol) and DIPEA (2.6 mL, 15.2 mmol) and the reaction mixture heated at 90° C. for 16 h. The reaction mixture was concentrated in vacuo and the resultant residue subjected to flash chromatography (SiO$_2$, eluting with 0-10% methanol in EtOAc) to give the title compound as a white solid (1.34 g, 67%). LCMS (Method C): $R_T$=3.11 min, [M+H]+=516.

5-Fluoro-3-phenyl-2-{(S)-1-[9-(tetrahydro-pyran-2-yl)-9H-purin-6-ylamino]ethyl}-3H-benzoimidazole-4-carboxylic acid

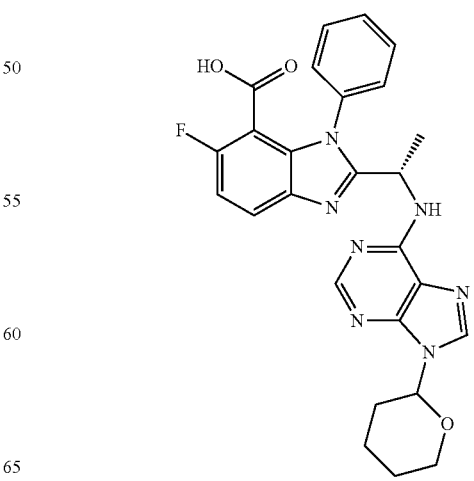

To a solution of 5-fluoro-3-phenyl-2-{(S)-1-[9-(tetrahydro-pyran-2-yl)-9H-purin-6-ylamino]ethyl}-3H-benzoimidazole-4-carboxylic acid methyl ester (1.34 g, 2.66 mmol) in methanol (40 mL) and water (4 mL) was added lithium hydroxide monohydrate (0.166 g, 15.9 mmol) and the reaction mixture heated at 80° C. for 16 h. The reaction mixture was concentrated in vacuo to remove methanol and the residual aqueous solution acidified to ph~4 by addition of HCl (1 M) causing a precipitate to form. The product was collected by filtration and dried in vacuo to give the title compound as an off white solid (564 mg, 43%). LCMS (Method C): $R_T$=2.44 min, [M+H]+=502.

(2,3-Difluoro-6-nitro-phenyl)-phenylamine

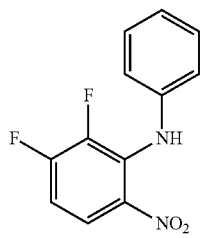

To a solution of aniline (1.6 g, 16.9 mmol) in THF (40 mL) at −78° C. was added LiHMDS (34 mL, 1M, 33.9 mmol) and the reaction mixture stirred at −78° C. for 10 min. This solution was added via cannula to a solution of 2,3,4-trifluoronitrobenzene (3 g, 16.9 mmol) in THF (10 mL) at −78° C. and the dark purple reaction mixture stirred at −78° C. for 30 min. The reaction mixture was diluted with water and extracted with EtOAc (3×30 mL). The combined organic fractions were washed with brine, dried (MgSO$_4$), concentrated in vacuo to give the title compound as a dark orange solid (4.2 g, 100%). $^1$H NMR 400 MHz δ (CDCl$_3$): 8.95 (1H, br s), 8.00 (1H, ddd, J=9.7, 5.4, 2.3 Hz), 7.31-7.25 (2H, m), 7.13-7.08 (1H, m), 7.04-6.99 (2H, m), 6.75-6.67 (1H, m).

3,4-Difluoro-N$^2$-phenylbenzene-1,2-diamine

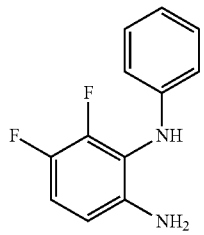

(2,3-Difluoro-6-nitro-phenyl)-phenylamine (4.2 g, 16.9 mmol), iron powder (3.8 g, 67.6 mmol), and ammonium chloride (5.2 g, 101.4 mmol) in methanol (60 mL) and water (15 mL) were heated at 90° C. for 3 h. The reaction mixture was filtered and the filtrate concentrated in vacuo. The residue was dissolved in water and extracted with EtOAc (3×40 mL). The combined organic extracts were washed with brine, dried (MgSO$_4$) and concentrated in vacuo to yield the title compound as a red solid (3.7 g, 100%). $^1$H NMR 400 MHz δ (CDCl$_3$): 7.25-7.16 (2H, m), 6.94-6.82 (2H, m), 6.70-6.64 (2H, m), 6.47 (1H, ddd, J=12.0, 6.1, 3.0 Hz), 5.23 (1H, br s), 3.71 (2H, br s).

(R)-1-(6,7-Difluoro-1-phenyl-1H-benzoimidazol-2-yl)-2-methoxyethylamine dihydrochloride

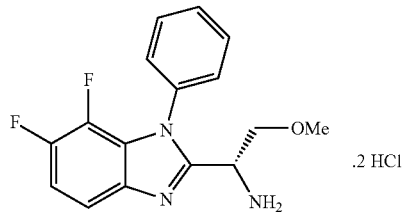 [SMILES: COC[C@H](N)c1nc2ccc(F)c(F)c2n1-c1ccccc1]

To a solution of 3,4-difluoro-N$^2$-phenylbenzene-1,2-diamine (400 mg, 1.8 mmol), Boc-ser(OMe)-OH (800 mg, 2.0 mmol), HOAT (340 mg, 2.0 mmol) and N-methylmorpholine (500 µL, 4.0 mmol) in DCM (5 mL) was added N-(3-dimethylaminopropyl)-n'-ethylcarbodiimide hydrochloride (480 mg, 2.0 mmol) and the reaction mixture stirred at RT for 16 h. The reaction mixture was diluted with water and extracted with DCM (3×10 mL). The combined organic fractions were washed with brine, dried (MgSO$_4$) and concentrated in vacuo. The residue was dissolved in HCl in dioxane (10 mL, 4 M) and the reaction mixture heated at 80° C. for 4 h. The reaction mixture was concentrated in vacuo and the resultant residue dissolved in EtOAc (10 mL). The solution was washed with sat. aq. NaHCO$_3$ and the product extracted with EtOAc (3×10 mL). The combined organic extracts were washed with brine, dried (MgSO$_4$), concentrated in vacuo and the resultant residue subjected to flash chromatography (SiO$_2$, eluting with 0-10% methanol in DCM) to give the title compound as an off white solid (207 mg, 38%). LCMS (Method C): $R_T$=2.27 min, [M+H]+=304.

[(R)-1-(6,7-Difluoro-1-phenyl-1H-benzoimidazol-2-yl)-2-methoxyethyl]-[9-(tetrahydro-pyran-2-yl)-9H-purin-6-yl]amine

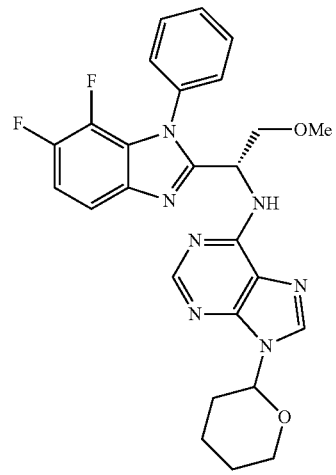 [SMILES: COC[C@H](Nc1ncnc2c1ncn2C1CCCCO1)c1nc2ccc(F)c(F)c2n1-c1ccccc1]

To a solution of (R)-1-(6,7-difluoro-1-phenyl-1H-benzoimidazol-2-yl)-2-methoxyethylamine dihydrochloride (0.20 g, 0.68 mmol) in 2-butanol (5 mL) was added 6-chloro-9-(tetrahydro-pyran-2-yl)-9H-purine (0.195 mg, 0.81 mmol) and DIPEA (233 μL, 1.36 mmol) and the reaction mixture heated at 90° C. for 16 h. The reaction mixture was concentrated in vacuo and the resultant residue was subjected to flash chromatography (SiO$_2$, eluting with 0-10% methanol in EtOAc) to give the title compound as an off white solid (290 mg, 84%). LCMS (Method C): R$_T$=3.48 min, [M+H]+=506.

2-Bromo-4-nitro-3-phenylaminophenol

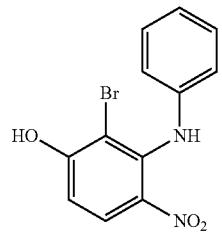 [SMILES: O=[N+]([O-])c1ccc(O)c(Br)c1Nc1ccccc1]

To a solution of (2-bromo-3-fluoro-6-nitrophenyl)phenylamine (1.5 g, 4.8 mmol) in dioxane (20 mL) and water (10 mL) was added tris(dibenzylideneacetone)dipalladium (0) (88 mg, 0.96 mmol), 2-di-tert-butylphosphino-2',4',6'-triisopropylbiphenyl (164 mg, 0.39 mmol) and potassium hydroxide (812 mg, 14.4 mmol). The reaction mixture was degassed by bubbling argon through the mixture whilst undergoing sonication. The reaction mixture was heated at 90° C. for 3 h before being diluted with water and acidified to ~pH 3 by addition of HCl (1N). The mixture was extracted with EtOAc (3×20 mL). The combined organic fractions were washed with brine, dried (MgSO$_4$), concentrated in vacuo and the resultant residue subjected to flash chromatography (SiO$_2$, eluting with 0-100% EtOAc in cyclohexane) to give the title compound as a yellow solid (879 mg, 59%). $^1$H NMR 400 MHz δ (CDCl$_3$): 8.85 (1H, br s), 8.18 (1H, d, J=12.6 Hz), 7.31-7.24 (2H, m), 7.10-7.03 (1H, m), 6.92-6.86 (2H, m), 6.80 (1H, d, J=12.6 Hz).

(2-Bromo-3-methoxy-6-nitro-phenyl)-phenylamine

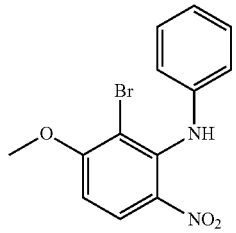

To a solution of 2-bromo-4-nitro-3-phenylaminophenol (450 mg, 1.45 mmol) in acetone was added methyl iodide (0.34 mL, 5.44 mmol) and potassium carbonate (751 mg, 5.44 mmol) and the reaction mixture heated at 40° C. for 16 h. The mixture was diluted with water and extracted with EtOAc (3×20 mL). The combined organic fractions were washed with brine, dried (MgSO$_4$), concentrated in vacuo to give the title compound as a yellow oil (470 mg, 100%). $^1$H NMR 400 MHz δ (CDCl$_3$): 8.36 (1H, br s), 8.19 (1H, d, J=9.6 Hz), 7.28-7.22 (2H, m), 7.05-7.00 (1H, m), 6.89-6.84 (2H, m), 6.69 (1H, d, J=9.7 Hz), 4.01 (3H, s).

3-Bromo-4-methoxy-N$^2$-phenylbenzene-1,2-diamine

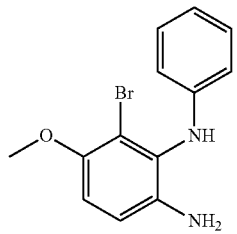 [SMILES: COc1ccc(N)c(Nc2ccccc2)c1Br]

To a solution of (2-bromo-3-methoxy-6-nitro-phenyl)-phenylamine (470 mg, 1.81 mmol) in EtOAc (15 mL) was added palladium on carbon (100 mg, 10% by wt) and the reaction mixture stirred at RT under an atmosphere of hydrogen for 16 h. The reaction mixture was filtered and the filtrate concentrated in vacuo to give the title compound as a yellow solid (426 mg, 100%). $^1$H NMR 400 MHz δ (CDCl$_3$): 7.24-7.17 (2H, m), 6.89-6.83 (1H, m), 6.74-6.72 (1H, m), 6.68-6.63 (2H, m), 5.48 (1H, br s), 3.85 (3H, s).

(S)-1-(7-Bromo-6-methoxy-1-phenyl-1H-benzoimidazol-2-yl)ethylamine dihydrochloride

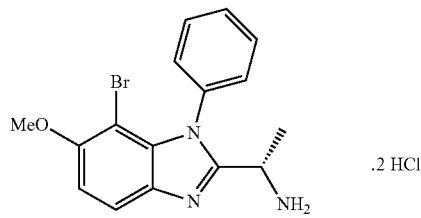 [SMILES: COc1ccc2nc([C@H](C)N)n(-c3ccccc3)c2c1Br]

To a solution of 3-bromo-4-methoxy-N$^2$-phenylbenzene-1,2-diamine (421 mg, 1.8 mmol), Boc-ala-OH (343 mg, 1.8 mmol) and HOAT (247 mg, 1.8 mmol) in DCM (10 mL) at 0° C. was added N-(3-dimethylaminopropyl)-n'-ethylcarbodiimide hydrochloride (383 mg, 1.99 mmol) and the reaction mixture stirred at 0° C. for 1 h. The reaction mixture was diluted with water and extracted with DCM (3×10 mL). The combined organic fractions were washed with brine, dried (MgSO$_4$) and concentrated in vacuo. The residue was dissolved in HCl in dioxane (10 mL, 4 M) and the reaction mixture heated at 75° C. for 1 h. The reaction mixture was

[(S)-1-(7-Bromo-6-methoxy-1-phenyl-1H-benzoimidazol-2-yl)ethyl]-[9-(tetrahydro-pyran-2-yl)-9H-purin-6-yl]amine

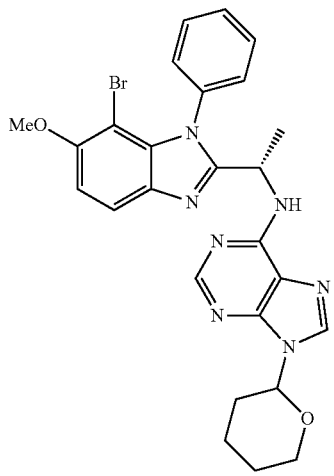 [SMILES: COc1ccc2nc([C@H](C)Nc3ncnc4c3ncn4C3CCCCO3)n(-c3ccccc3)c2c1Br]

To a solution of (S)-1-(7-bromo-6-methoxy-1H-benzoimidazol-2-yl)ethylamine dihydrochloride (0.75 g, 1.8 mmol) in IPA (10 mL) was added 6-chloro-9-(tetrahydro-pyran-2-yl)-9H-purine (0.56 mg, 2.34 mmol) and DIPEA (1.2 mL, 7.2 mmol) and the reaction mixture heated at 90° C. for 16 h. The reaction mixture was concentrated in vacuo and the resultant residue subjected to flash chromatography (SiO₂, eluting with 0-10% methanol in EtOAc) to give the title compound as a white solid (453 mg, 44%). LCMS (Method C): $R_T$=3.22 min, [M+H]+=548 & 550.

t-Butyl (3-oxocyclobutyl)carbamate

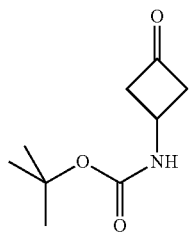

To a solution of the 3-oxocyclobutanecarboxylic acid (10 g, 87.64 mmol) in CH₂Cl₂ (60 mL) was added SOCl₂ (19 mL, 262.92 mmol) dropwise with vigorous stirring. The resulting mixture was refluxed for 1.5 h. After cooling, the solvent was evaporated under reduced pressure. The residue was dissolved in DCE (2×30 mL) and evaporated to remove HCl and SOCl₂. The crude product was dissolved in acetone (25 mL), and the resulting solution added dropwise to a precooled solution (at 0° C.) of NaN₃ (11.48 g, 177.03 mmol) in H₂O (30 mL) over 30 min. The mixture was stirred for 1 h at 0° C., then ice (80 g) was added, and the product extracted with Et₂O (4×75 mL), dried (MgSO₄), and concentrated to 120 mL under reduced pressure. The resulting solution was added to toluene (100 mL), and the mixture heated at 90° C. After the residual ether was distilled off, the mixture was stirred at 90° C. for 30 min until evolution of N₂ ceased. Then tert-butanol (27.68 mL) was added, and the mixture was heated at 90° C. for 16 h. The reaction mixture was allowed to cool to room temperature and the solvent removed in vacuo to afford the title compound as an pale red shiny solid (14.35 g, 88.5%). ¹H NMR (CDCl₃, 400 MHz): δ 4.9 (1H, br, NH), 4.35-4.17 (1H, m), 3.46-3.31 (2H, m), 3.11-2.96 (2H, m), 1.45 (9H, s). (NMR spectrum number: 328453)

tert-Butyl (cis-3-hydroxycyclobutyl)carbamate

t-Butyl-(3-oxocyclobutyl) carbamate (10 g, 54.05 mmol) was dissolved in dry THF (100 mL) under an argon atmosphere, and the solution cooled to −78° C. L-Selectride® (1 M in THF, 81.1 mL, 81.1 mmol) was added dropwise over 1 h period. The mixture was kept at −78° C. for 1 h, and a solution of NaOH (3.3 g) in H₂O (36 mL) added dropwise over 30 min followed by 30% aqueous H₂O₂ (30 mL) over 2 h. A dark yellow precipitate was observed. The resulting mixture was warmed to room temperature then diluted with EtOAc (250 mL), washed with 10% aqueous Na₂SO₃ (100 mL) and brine (50 mL), and dried (MgSO₄). The solvent was evaporated in vacuo resulting in a yellow oil, which solidified on standing. The product was triturated with cyclohexane (50 mL) afford the title compound as a yellow solid (7.2 g (72%). ¹H NMR (CDCl₃, 400 MHz): δ 4.62 (1H, br, NH), 4.08-3.95 (1H, m), 3.74-3.54 (1H, m), 2.83-2.69 (2H, m), 2.43 (1H, br, d, J=3.69 Hz), 1.86-1.72 (2H, m), 1.46 (9H, s).

(cis-3-Benzyloxycyclobutyl)carbamic acid tert-butyl ester

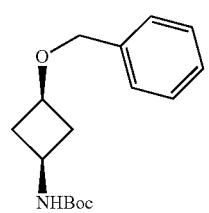 [SMILES: CC(C)(C)OC(=O)N[C@H]1C[C@@H](OCc2ccccc2)C1]

tert-Butyl(cis-3-hydroxycyclobutyl)carbamate (2.0 g, 10.7 mmol) was dissolved in dry THF (50 mL) under nitrogen atmosphere, and the solution cooled to 0° C. To this clear solution, sodium hydride (60% dispersion in oil, 0.428 g, 10.7 mmol) was added portion wise (evolution of H₂ observed). The mixture was stirred at rt for 30 min then benzyl bromide (1.91 mL, 16.04 mmol) added dropwise and the resulting yellow suspension stirred at rt for 16 h. The reaction was quenched with sat aq. NH₄Cl solution (20 mL) and partitioned between sat aq. NaHCO₃ (40 mL) and DCM (60 mL). The combined organic fractions were washed with brine (20 mL), dried (MgSO₄) and concentrated in vacuo. The resulting residue was purified by column chromatography (gradient 0-50% EtOAc in cyclohexane) to afford the title compound as a white solid (2.40 g, 81%). $^1$H NMR (CDCl$_3$, 400 MHz): δ 7.41-7.22 (5H, m), 4.66 (1H, br, NH), 4.42 (2H, s), 3.83-3.65 (2H, m), 2.79-2.61 (2H, m), 1.86-1.72 (2H, m), 1.46 (9H, s).

cis-3-Benzyloxycyclobutylamine

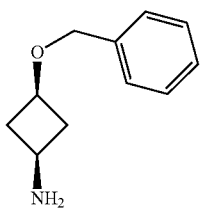 [SMILES: N[C@H]1C[C@@H](OCc2ccccc2)C1]

To a solution of (cis-3-benzyloxycyclobutyl)carbamic acid tert-butyl ester (2.40 g, 8.67 mmol) in DCM (20 mL) was added TFA (4 mL) and the mixture stirred at RT for 3 h. The volatiles were removed in vacuo and the resulting residue dissolved in DCM and loaded onto SCX-2 (20 g). The cartridge was washed with DCM then MeOH then 2M NH$_3$ in MeOH solution. The relevant fractions were concentrated in vacuo to afford the title compound as yellow oil (1.48 g, 95%). $^1$H NMR (CDCl$_3$, 400 MHz): δ 7.36-7.30 (5H, m), 4.40 (2H, s), 3.73-3.61 (1H, m), 3.06-2.93 (1H, m), 2.72-2.58 (2H, m), 1.74-1.61 (2H, m), 1.47 (2H, s, br).

N$^2$-(cis-3-Benzyloxycyclobutyl)-4-fluorobenzene-1,2-diamine

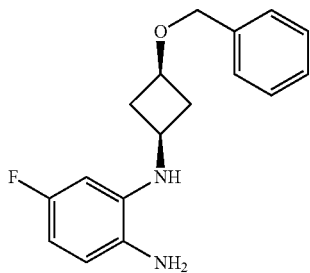

To a solution of 2,4-difluoro-1-nitrobenzene (0.92 mL, 8.36 mmol) in CH$_3$CN (60 mL) were added cis-3-benzyloxycyclobutylamine (1.48 g, 8.36 mmol) and DIPEA (1.46 mL, 8.36 mmol). The reaction mixture was stirred at RT for 18 h then concentrated in vacuo to afford the title compound as yellow oil (3.2 g, quantitative). To a solution of the product thus obtained (1.6 g, 5.03 mmol) in MeOH (20 mL) was added Iron powder (1.13 g, 20.12 mmol), NH$_4$Cl (1.56 g, 30.18 mmol) and H$_2$O (8 mL) and the reaction mixture stirred at 90° C. for 2 h under a nitrogen atmosphere. The resulting dark green mixture was filtered through a pad of Celite® and the filtrate concentrated in vacuo giving a dark brown solid. The crude material was partitioned between EtOAc (50 mL) and water (30 mL). Aqueous layer extracted with EtOAc (2×30 mL). The combined organic fractions were washed with brine (20 mL), dried (MgSO$_4$) and concentrated in vacuo to afford the title compound as a dark brown gum (1.13 g, 78%). $^1$H NMR (CDCl$_3$, 300 MHz): δ 7.25-7.30 (5H, m), 6.6 (1H, dd, J=14.0, 2.8 Hz), 6.35-6.26 (1H, m), 6.26-6.18 (1H, m), 4.43 (2H, s), 3.95-3.83 (1H, m), 3.50-3.37 (1H, m), 2.90-2.78 (2H, m), 1.92-1.79 (2H, m). NMR: 328138. LCMS (Method B): R$_T$ 2.87 min [M+H]$^+$ 287.

[(S)-1-[1-(cis-3-Benzyloxycyclobutyl)-6-fluoro-1H-benzoimidazol-2-yl]ethyl]carbamic acid tert-butyl ester

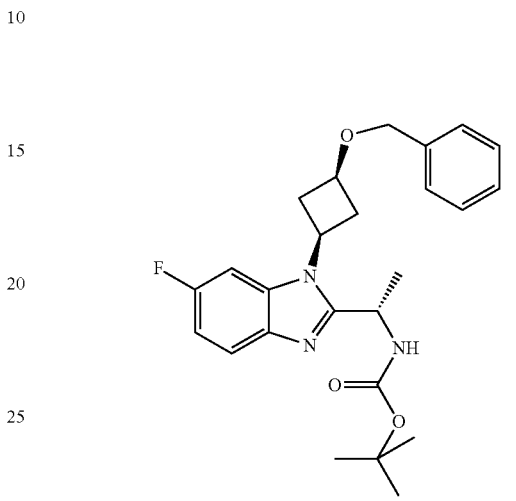

A mixture of N$^2$-(cis-3-benzyloxycyclobutyl)-4-fluorobenzene-1,2-diamine (1.13 g, 3.95 mmol), (S)-2-tertbutoxycarbonylaminopropionic acid (0.83 g, 4.35 mmol) and HOAt (0.59 g, 4.35 mmol) in DCM (20 mL) was cooled to 0° C. under nitrogen atmosphere. To this mixture N-(3-dimethylaminopropyl)-N-ethylcarbodiimide hydrochloride (0.83 g, 4.35 mmol) was added portion wise and the reaction mixture stirred at RT for 1 h. The reaction mixture allowed to warm to RT then partitioned between DCM and a 10% aq. citric acid. The organic fraction was washed with brine (20 mL), dried (MgSO$_4$), concentrated in vacuo and the resulting dark brown residue purified by column chromatography (Si—PCC, gradient 0-40% EtOAc in cyclohexane) to afford the title compound as a yellow gum, which solidified on standing (1.93 g, 93%). $^1$H NMR (CDCl$_3$, 400 MHz): δ 7.46 (1H, s, br), 7.36-7.30 (5H, m), 7.11 (1H, q, J=14.8 Hz, 2.5 Hz), 6.37 (1H, dt, J=19.5 Hz, 2.8 Hz), 6.25 (1H, dd, J=14 Hz, 2.82 Hz), 4.94 (1H, d, J=5.83 Hz), 4.43 (2H, s), 4.23-4.07 (1H, m), 3.93-3.81 (1H, m), 3.47-3.35 (1H, m), 2.88-2.75 (1H, m), 2.03-1.85 (1H, m), 1.45 (3H, d, J=2.46 Hz), 1.43 (9H, s). LCMS (Method B): R$_T$ 3.88 min [M+H]$^+$ 458. 110183151. The compound thus obtained (1 g, 2.19 mmol) was dissolved in AcOH (15 mL) and heated at 70° C. for 18 h. After cooling to RT, the volatiles were evaporated under reduced pressure and the residue partitioned between DCM (40 mL) and a saturated solution of NaHCO$_3$ (20 mL). The organic fraction was washed with brine (20 mL), dried (MgSO$_4$) and concentrated in vacuo. The resulting dark yellow residue was purified by column chromatography (Si—PCC, gradient 0-50% EtOAc in cyclohexane) to afford the title compound as pale red gum (570 mg, 60%). LCMS (Method B): R$_T$ 3.61 min [M+H]$^+$ 440.0. $^1$H NMR (CDCl$_3$, 400 MHz): δ 7.70-7.60 (2H, m), 7.44-7.37 (5H, m), 7.05-6.96 (1H, m), 5.38-5.26 (1H, m), 5.20-5.05 (1H, m), 4.82-4.68 (1H, m), 4.55 (2H, s), 4.10-3.97 (1H, m), 3.02-2.77 (4H, m), 1.47 (3H, d, J=2.44 Hz), 1.44 (9H, s).

(S)-1-[1-(cis-3-Benzyloxycyclobutyl)-6-fluoro-1H-benzoimidazol-2-yl]ethylamine

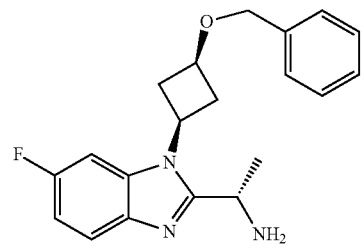

To a solution of [(S)-1-[1-(cis-3-benzyloxycyclobutyl)-6-fluoro-1H-benzoimidazol-2-yl]ethyl]carbamic acid tert-butyl ester (570 mg, 1.3 mmol) in DCM (10 mL) was added TFA (4 mL) and the mixture stirred at RT for 1 h. The volatiles were removed in vacuo and the resulting residue dissolved in DCM and loaded onto SCX-2 (20 g). The cartridge was washed with DCM then MeOH and then 2M NH$_3$ in MeOH solution. The relevant fractions were concentrated in vacuo to afford the title compound as yellow gum (320 mg, 73%). LCMS (Method J): R$_T$ 1.97 min [M+H]$^+$ 340. $^1$H NMR (CDCl$_3$, 400 MHz): δ 7.69-7.55 (2H, m), 7.44-7.24 (5H, m), 7.0 (1H, dt, J=11.8, 2.5 Hz), 4.81-4.66 (1H, m), 4.53 (2H, s), 4.32-4.21 (1H, m), 4.08-3.95 (1H, m), 3.02-2.75 (4H, m), 1.90 (2H, s, br), 1.50 (3H, d, J=7.0 Hz)-NMR: 328174

[(S)-1-[1-(cis-3-Benzyloxycyclobutyl)-6-fluoro-1H-benzoimidazol-2-yl]ethyl]-(9H-purin-6-yl)-amine

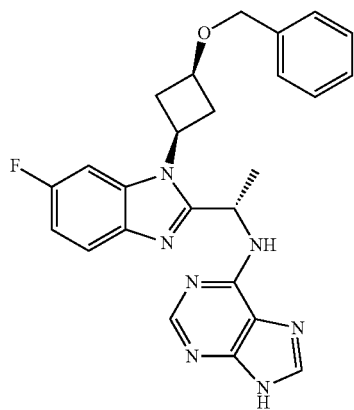 [SMILES: C[C@H](Nc1ncnc2[nH]cnc12)c1nc2ccc(F)cc2n1[C@H]1C[C@@H](OCc2ccccc2)C1]

A mixture of (S)-1-[1-(cis-3-benzyloxycyclobutyl)-6-fluoro-1H-benzoimidazol-2-yl]ethylamine (310 mg, 0.91 mmol), 6-chloro-9-(tetrahydropyran-2-yl)-9H-purine (219 mg, 0.91 mmol) and DIPEA (0.81 mL, 4.57 mmol) in IPA (5 mL) was heated at 90° C. in a sealed vial for 16 h. After cooling to RT, the reaction mixture was concentrated in vacuo, dissolved in DCM and loaded onto an Isolute® SCX-2 cartridge which was washed with DCM, MeOH followed by 2M NH$_3$/MeOH. The product containing fractions were combined and concentrated in vacuo. The resulting residue was purified by column chromatography (Si—PCC, gradient 0-10% 2M NH$_3$/MeOH in DCM) to afford the title compound as a glassy white solid (320 mg, 76%). LCMS (Method B): R$_T$ 2.76 min [M+H]$^+$ 458. $^1$H NMR (CDCl$_3$, 400 MHz): δ 8.48 (1H, s), 7.95 (1H, s), 7.71-7.58 (2H, m), 7.42-7.35 (5H, m), 7.07-6.90 (2H, m), 5.95 (1H, s, br), 4.97-4.80 (m, 1H), 4.52 (2H, s), 4.05-3.92 (1H, m), 3.01-2.86 (2H, m), 2.81-2.64 (1H, m), 1.75 (3H, d, J=6.85 Hz).

trans-4-Nitrobenzoic acid 3-tert-butoxycarbonylaminocyclobutyl ester

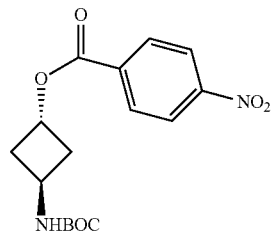

To a solution of tert-Butyl (cis-3-hydroxycyclobutyl) carbamate (2 g, 10.7 mmol) and p-nitrobenzoic acid (1.97 g, 11.8 mmol) in dry THF (40 mL) were added triphenylphosphine (4.20 g, 16.05 mol) and DEAD (3.17 mL, 20.0 mmol) consecutively at 0° C. The resulting mixture was stirred at rt (room temperature) overnight. The dark red solution formed was concentrated in vacuo, and the residue purified by column chromatography (Si—PCC, gradient 0-50% EtOAc in cyclohexane) to afford the title compound as a pale yellow solid (4.2 g, quantitative). $^1$H NMR (CDCl$_3$): δ 8.29 (2H, dd, J=8.9 Hz), δ 8.20 (2H, dd, J=8.9 Hz), 5.42-5.31 (1H, m), 4.7 (1H, s, br), 4.37-4.26 (1H, m), 2.71-2.57 (2H, m), 2.53-2.36 (2H, m), 1.45 (9H, s).

tert-Butyl (trans-3-hydroxycyclobutyl)carbamate

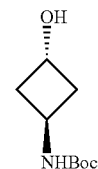

To a mixture of K$_2$CO$_3$ (1.26 g, 9.06 mmol), H$_2$O (8.5 mL), and methanol (40 mL) was added trans-4-nitrobenzoic acid 3-tert-(butoxycarbonylamino)cyclobutyl ester (2.0 g, 5.97 mmol). The resulting mixture was refluxed at 70° C. for 1 h. The reaction mixture was cooled to RT filtered, and the filtrate was concentrated in vacuo to give the title compound was obtained as a pale yellow solid (0.95 g, 82%). $^1$H NMR (CDCl₃) δ 4.67 (1H, s, br), 4.55-4.40 (1H, m), 2.38-2.14 (4H, m), 1.82 (1H, s, br), 1.43 (9H, s).

(trans-3-Benzyloxycyclobutyl)carbamic acid tert-butyl ester

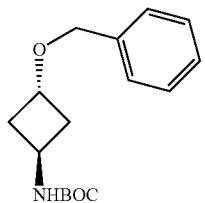

tert-Butyl(trans-3-hydroxycyclobutyl)carbamate (0.93 g, 4.97 mmol) was dissolved in dry THF (20 mL) under a nitrogen atmosphere, and the solution cooled to 0° C. To this clear solution, sodium hydride (60% dispersion in oil, 0.2 g, 4.97 mmol) was added portion wise (evolution of H₂ observed). The mixture was stirred at RT for 30 min then benzyl bromide (0.88 mL, 7.45 mmol) added dropwise and the resulting dark brown suspension stirred at rt for 16 h. The reaction mixture was quenched with saturated aqueous NH₄Cl (20 mL) and partitioned between saturated aqueous NaHCO₃ (40 mL) and DCM (60 mL). The combined organic fractions were washed with brine (20 mL), dried (MgSO₄) and concentrated in vacuo. The resulting residue was purified by column chromatography (gradient 0-50% EtOAc in cyclohexane) to afford the title compound as a off-white solid (0.99 g, 72%). ¹H NMR (CDCl₃, 400 MHz): δ 7.35-7.31 (5H, m), 4.65 (1H, br, NH), 4.40 (2H, s), 4.24-4.12 (2H, m), 2.50-2.35 (2H, m), 2.18-2.06 (2H, m), 1.43 (9H, s).

trans-3-Benzyloxycyclobutylamine

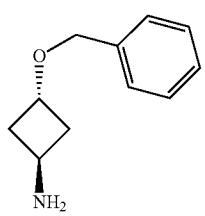 [SMILES: N[C@H]1C[C@H](OCc2ccccc2)C1]

To a solution of (trans-3-benzyloxycyclobutyl)carbamic acid tert-butyl ester (0.99 g, 3.56 mmol) in DCM (10 mL) was added TFA (2 mL) and the mixture stirred at RT for 3 h. The volatiles were removed in vacuo and the resulting residue dissolved in DCM and loaded onto an SCX-2 (20 g) cartridge. The cartridge was washed with DCM then MeOH and then 2M NH₃ in MeOH solution. The relevant fractions were concentrated in vacuo to afford the title compound as yellow oil (0.6 g, quantitative). ¹H NMR (CDCl₃, 400 MHz): δ 7.36-7.31 (5H, m), 4.40 (2H, s), 4.29-4.20 (1H, m), 3.75-3.65 (1H, m), 2.39-2.26 (2H, m), 2.02-1.90 (2H, m), 1.49 (2H, s, br).

N²-(trans-3-Benzyloxycyclobutyl)-4-fluorobenzene-1,2-diamine

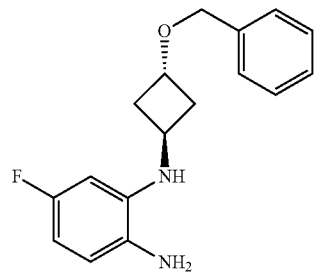 [SMILES: Nc1ccc(F)cc1N[C@H]1C[C@H](OCc2ccccc2)C1]

To a solution of 2,4-difluoro-1-nitrobenzene (0.37 mL, 3.39 mmol) in CH₃CN (10 mL) were added trans-3-benzyloxycyclobutylamine (0.6 g, 3.39 mmol) and DIPEA (0.6 mL, 3.39 mmol). The reaction mixture was stirred at RT for 18 h then concentrated in vacuo to afford the compound as yellow oil (1.2 g, quantitative). To a solution of the product thus obtained (1.2 g, 3.77 mmol) in MeOH (20 mL) was added iron powder (0.85 g, 15.08 mmol), NH₄Cl (1.17 g, 22.62 mmol) and H₂O (8 mL) and the reaction mixture stirred at 90° C. for 2 h under a nitrogen atmosphere. The resulting dark green mixture was filtered through a pad of Celite® and the filtrate concentrated in vacuo. The resulting residue was partitioned between EtOAc (50 mL) and water (30 mL). The aqueous layer was extracted with EtOAc (2×30 mL) and the combined organic fractions were washed with brine (20 mL), dried (MgSO₄) and concentrated in vacuo to afford the title compound as a dark yellow gum (0.73 g, 68%). ¹H NMR (CDCl₃, 300 MHz): δ 7.37-7.32 (5H, m), 6.63 (1H, q, J=14.0 Hz, 2.8 Hz), 6.40 (1H, dt, J=19.6 Hz, 2.7 Hz), 6.20 (1H, dd, J=13.6 Hz, 2.7 Hz), 4.44 (2H, s), 4.35-4.24 (1H, m), 4.01-3.92 (1H, m), 2.55-2.42 (2H, m), 2.25-2.13 (2H, m).

[(S)-1-[1-(trans-3-Benzyloxycyclobutyl)-6-fluoro-1H-benzoimidazol-2-yl]ethyl]carbamic acid tert-butyl ester

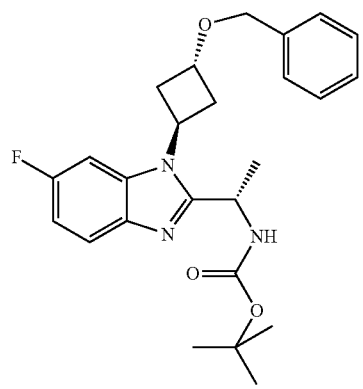 [SMILES: C[C@H](NC(=O)OC(C)(C)C)c1nc2ccc(F)cc2n1[C@H]1C[C@H](OCc2ccccc2)C1]

A mixture of N²-(trans-3-benzyloxycyclobutyl)-4-fluorobenzene-1,2-diamine (1.73 g, 2.55 mmol), (S)-2-tertbutoxycarbonylaminopropionic acid (0.54 g, 2.81 mmol) and HOAt (0.38 g, 2.81 mmol) in DCM (20 mL) were cooled to 0° C. under nitrogen atmosphere. To this mixture N-(3-dimethylaminopropyl)-N-ethylcarbodiimide hydrochloride (0.54 g, 2.81 mmol) was added portion wise and the reaction mixture was stirred at RT for 1 h. The reaction mixture allowed to warm to RT then partitioned between DCM (30 mL) and 10% aqueous citric acid (20 mL). The organic layer was washed with brine (20 mL), dried (MgSO$_4$) and concentrated in vacuo and the resulting residue purified by column chromatography (Si—PCC, gradient 0-50% EtOAc in cyclohexane) to afford the title compound as a off-white gum, which solidified on standing (0.88 g, 75%). NMR: 328289. LCMS (Method B): R$_T$ 3.85 min [M+H]$^+$ 458.

The compound thus obtained (0.88 g, 1.93 mmol) was dissolved in AcOH (10 mL) and heated at 70° C. for 18 h. After cooling to RT, the volatiles were evaporated in vacuo and the residue partitioned between DCM (40 mL) and a saturated aqueous solution of NaHCO$_3$ (20 mL). The organic fraction was washed with brine (20 mL), dried (MgSO$_4$) then concentrated in vacuo. The resulting dark brown residue was purified by column chromatography (Si—PCC, gradient 0-50% EtOAc in cyclohexane) to afford the title compound as dark yellow oil (0.46 g, 55%). LCMS (Method B): R$_T$ 3.63 min [M+H]$^+$ 440

(S)-1-[1-(trans-3-Benzyloxycyclobutyl)-6-fluoro-1H-benzoimidazol-2-yl]ethylamine

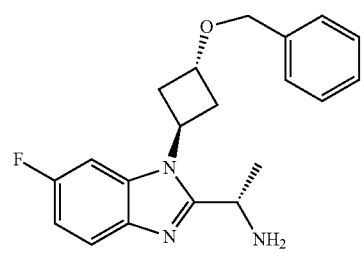 [SMILES: C[C@H](N)c1nc2ccc(F)cc2n1[C@H]1C[C@H](OCc2ccccc2)C1]

To a solution of [(S)-1-[1-(trans-3-benzyloxycyclobutyl)-6-fluoro-1H-benzoimidazol-2-yl]ethyl]carbamic acid tert-butyl ester (0.46 g, 1.05 mmol) in DCM (10 mL) was added TFA (4 mL) and the mixture stirred at RT for 1 h. The volatiles were removed in vacuo and the resulting pale red gummy residue dissolved in DCM and loaded onto an SCX-2 (20 g) cartridge. The cartridge washed with DCM then MeOH and then 2M NH$_3$ in MeOH solution. The relevant fractions were concentrated in vacuo to afford the title compound as yellow gum (0.28 g, 80%). LCMS (Method B): R$_T$ 2.17 min [M+H]$^+$ 340

[(S)-1-[1-(trans-3-Benzyloxycyclobutyl)-6-fluoro-1H-benzoimidazol-2-yl]ethyl]-(9H-purin-6-yl)amine

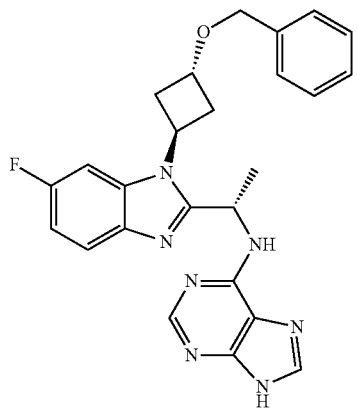 [SMILES: C[C@H](Nc1ncnc2[nH]cnc12)c1nc2ccc(F)cc2n1[C@H]1C[C@H](OCc2ccccc2)C1]

A mixture of (S)-1-[1-(trans-3-benzyloxycyclobutyl)-6-fluoro-1H-benzoimidazol-2-yl]ethylamine (210 mg, 0.62 mmol), 6-chloro-9-(tetrahydropyran-2-yl)-9H-purine (148 mg, 0.62 mmol) and DIPEA (0.55 mL, 3.09 mmol) in IPA (5 mL) was heated at 90° C. in a sealed vial for 16 h. After cooling to RT, the reaction mixture was concentrated in vacuo, dissolved in DCM and loaded onto an Isolute® SCX-2 cartridge which was washed with DCM, MeOH followed by 2M NH$_3$/MeOH. The product containing fractions were combined and concentrated in vacuo. The resulting residue was purified by column chromatography (Si—PCC, gradient 0-5% 2M NH$_3$/MeOH in DCM) to afford the title compound as a colourless glassy solid (120 mg, 43%). LCMS (Method J): R$_T$ 2.72 min [M+H]$^+$ 458

4-Amino-6-[(S)-1-[1-(trans-3-benzyloxycyclobutyl)-6-fluoro-1H-benzoimidazol-2-yl]ethylamino]-pyrimidine-5-carbonitrile

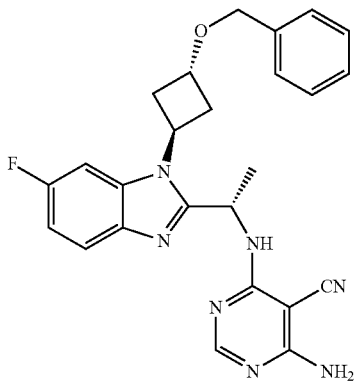 [SMILES: C[C@H](Nc1ncnc(N)c1C#N)c1nc2ccc(F)cc2n1[C@H]1C[C@H](OCc2ccccc2)C1]

A mixture of (S)-1-[1-(trans-3-benzyloxycyclobutyl)-6-fluoro-1H-benzoimidazol-2-yl]ethylamine (67 mg, 0.20 mmol), 4-amino-6-chloropyrimidine-5-carbonitrile (31 mg, 0.20 mmol) and DIPEA (0.18 mL, 0.99 mmol) in IPA (3 mL)

was heated at 90° C. in a sealed vial for 16 h. After cooling to RT, the reaction mixture was concentrated in vacuo, dissolved in DCM and loaded onto an Isolute® SCX-2 cartridge which was washed with DCM then MeOH and then 2M NH₃/MeOH. The product containing fractions were combined and concentrated in vacuo. The resulting residue was purified by column chromatography (Si—PCC, gradient 0-5% 2M NH₃/MeOH in DCM) to afford the title compound as a colourless glassy solid (60 mg, 67%). LCMS (Method B): $R_T$ 3.09 min [M+H]⁺ 458

(cis-3-Methoxycyclobutyl)carbamic acid tert-butyl ester

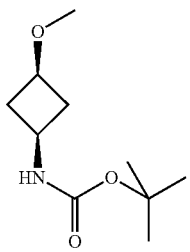

tert-Butyl (cis-3-hydroxycyclobutyl)carbamate (0.8 g, 4.3 mmol) was dissolved in dry THF (25 mL) under a nitrogen atmosphere, and the solution cooled to 0° C. To this clear solution, sodium hydride (60% dispersion in oil, 0.17 g, 4.3 mmol) was added portion wise (evolution of H₂ observed). The mixture was stirred at RT for 30 min. then iodomethane (0.40 mL, 1.5 mmol) added dropwise and the resulting yellow suspension stirred at rt for 16 h. The reaction mixture was quenched with saturated aqueous solution of NH₄Cl (20 mL) and partitioned between saturated aqueous solution of NaHCO₃ (40 mL) and DCM (60 mL). The combined organic fractions were washed with brine (20 mL), dried (MgSO₄) and concentrated in vacuo. The resulting residue was purified by column chromatography (gradient 0-70% EtOAc in cyclohexane) to afford the title compound as a white solid (0.58 g, 66%). ¹H NMR (CDCl₃, 300 MHz): δ 4.66 (1H, br, NH), 3.71-3.62 (1H, m), 3.61-3.50 (1H, m), 2.71 (3H, s), 2.76-1.62 (2H, m), 1.78-1.62 (2H, m), 1.41 (9H, s).

cis-3-Methoxycyclobutylamine

To a solution of (cis-3-methoxycyclobutyl)carbamic acid tert-butyl ester (580 mg, 2.8 mmol) in DCM (20 mL) was added TFA (10 mL) and the mixture stirred at RT for 2 h. The volatiles were removed in vacuo and the resulting residue loaded onto an Isolute® SCX-2 cartridge. The cartridge was washed with MeOH followed by 2M NH₃/MeOH. The basic fractions were combined and concentrated in vacuo to give the title compound as yellow oil (170 mg, 58%). ¹H NMR (CDCl₃, 300 MHz): δ 3.53-3.48 (1H, m), 3.06-2.93 (1H, m), 2.71-2.58 (2H, m), 1.64-1.52 (2H, m), 1.51 (2H, s, br).

4-Fluoro-N²-(cis-3-methoxycyclobutyl)benzene-1,2-diamine

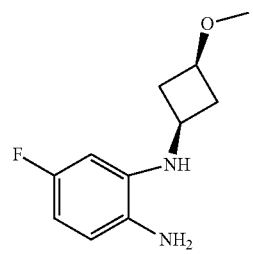

To a solution of 2,4-difluoro-1-nitrobenzene (0.18 mL, 1.6 mmol) in CH₃CN (3 mL) were added cis-3-methoxycyclobutylamine (0.17 g, 1.6 mmol) and DIPEA (0.28 mL, 1.6 mmol). The reaction mixture was stirred at RT for 18 h then concentrated in vacuo. The resulting residue was carried to the next step without any further purification (0.39 g, quantitative). To a solution of the product thus obtained (1.6 mmol) in EtOAc (15 mL) was added Pd/C (350 mg) and the reaction mixture stirred at RT for 18 h under a hydrogen atmosphere. The suspension was filtered through a pad of Celite® and the filtrate concentrated in vacuo to afford the title compound as a dark oil (0.453 g, quantitative). ¹H NMR (CDCl₃, 300 MHz): δ 6.67-6.06 (1H, m), 6.35-6.17 (2H, m), 3.75-3.63 (1H, m), 3.61-3.25 (3H, br s), 3.22 (3H, s), 3.12-2.93 (1H, m), 2.90-2.78 (2H, m), 1.85-1.60 (2H, m).

{(S)-1-[6-Fluoro-1-(cis-3-methoxycyclobutyl) 1Hbenzoimidazol-2-yl]ethyl}carbamic acid tert-butyl ester

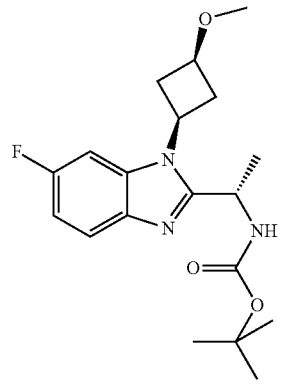 [SMILES: CO[C@H]1C[C@@H](n2c([C@H](C)NC(=O)OC(C)(C)C)nc3ccc(F)cc32)C1]

A mixture of 4-fluoro-N²-(cis-3-methoxycyclobutyl)benzene-1,2-diamine (0.34 g, 1.6 mmol), (S)-2-tertbutoxycarbonylaminopropionic acid (0.33 g, 1.8 mmol) and HOAt (0.24 g, 1.8 mmol) in DCM (8 mL) was cooled to 0° C. under a nitrogen atmosphere. To this mixture was added N-(3-dimethylaminopropyl)-N-ethylcarbodiimide hydrochloride (0.35 g, 1.8 mmol) portion wise and the mixture stirred at RT for 1 h. The reaction mixture allowed to warm to RT then partitioned between DCM (30 mL) and saturated aqueous solution of NaHCO₃ (20 mL). The organic fraction was washed with brine (20 mL), dried (MgSO₄) and concentrated in vacuo. The resulting residue was purified by column chromatography (Si—PCC, gradient 0-50% EtOAc in cyclohexane) to afford the compound as a pink oil (0.348 g, 57%). The compound thus obtained was dissolved in AcOH (8 mL) and heated at 70° C. for 18 h. After cooling to RT, the volatiles were evaporated in vacuo and the residue partitioned between DCM (40 mL) and a saturated aqueous solution of NaHCO$_3$ (20 mL). The organic fraction was washed with brine (20 mL), dried (MgSO$_4$) then concentrated in vacuo. The resulting dark brown residue was purified by column chromatography (Si—PCC, gradient 0-50% EtOAc in cyclohexane) to afford the title compound as yellow oil (0.222 g, 38%). LCMS (Method B): R$_T$ 2.86 min [M+H]$^+$ 364.03

(S)-1-[6-Fluoro-1-(cis-3-methoxycyclobutyl)-1Hbenzoimidazol-2-yl]ethylamine

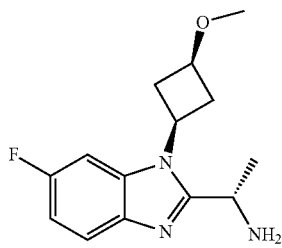 [SMILES: CO[C@H]1C[C@@H](n2c([C@H](C)N)nc3ccc(F)cc32)C1]

To a solution of {(S)-1-[6-fluoro-1-(cis-3-methoxycyclobutyl)1Hbenzoimidazol-2-yl]ethyl}carbamic acid tert-butyl ester (0.22 g, 0.61 mmol) in DCM (5 mL) was added TFA (3 mL) and the mixture was stirred at RT for 1.5 h. The volatiles were removed in vacuo and the resulting residue loaded onto an Isolute® SCX-2 cartridge. The cartridge was washed with MeOH followed by 2M NH$_3$/MeOH. The basic fractions were combined and concentrated in vacuo. The crude material was used in the following step without further purification. Yellow oil (quantitative). LCMS (Method B): R$_T$ 1.72 min [M+H]$^+$ 263.90.

(trans-3-Methoxycyclobutyl)carbamic acid tert-butyl ester

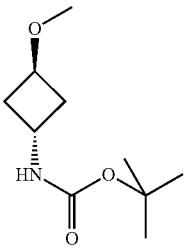

tert-Butyl(trans-3-hydroxycyclobutyl)carbamate (1.18 g, 6.3 mmol) was dissolved in dry THF (25 mL) under a nitrogen atmosphere, and the solution cooled to 0° C. To this clear solution was added, sodium hydride (60% dispersion in oil, 0.25 g, 6.3 mmol) portion wise (evolution of H$_2$ observed). The reaction mixture was stirred at RT for 30 min. then iodomethane (0.40 mL, 1.5 mmol) added dropwise and the resulting yellow suspension stirred at RT for 16 h. The reaction mixture was quenched with saturated aqueous solution of NH$_4$Cl (20 mL) and partitioned between saturated aqueous solution of NaHCO$_3$ (40 mL) and DCM (60 mL). The combined organic fractions were washed with brine (20 mL), dried (MgSO$_4$), filtered and concentrated in vacuo. The resulting residue was purified by column chromatography (gradient 0-70% EtOAc in cyclohexane) to afford the title compound as a yellow oil (1.05 g, 82%). $^1$H NMR (CDCl$_3$, 300 MHz): δ 4.65 (1H, br s), 4.22-4.10 (1H, m), 4.00-3.92 (1H, m), 2.40-2.28 (2H, m), 2.18-2.12 (2H, m), 1.43 (9H, s).

trans-3-Methoxycyclobutylamine

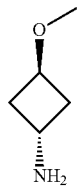

To a solution of (trans-3-methoxycyclobutyl)carbamic acid tert-butyl ester (1.05 g, 5.1 mmol) in DCM (30 mL) was added TFA (15 mL) and the mixture stirred at RT for 2 h. The volatiles were removed under in vacuo and the resulting residue loaded onto an Isolute® SCX-2 cartridge. The cartridge was washed with MeOH followed by 2M NH$_3$/MeOH. The basic fractions were combined and concentrated in vacuo to give the title compound as yellow oil (511 mg, 96%). $^1$H NMR (CDCl$_3$, 300 MHz): δ 7.42 (2H, br s), 4.30-4.09 (2H, m), 3.78 (1H, d, J=10.3 Hz), 3.12 (3H, s), 1.43-1.15 (3H, m).

4-FluoroN$^2$-(trans-3-methoxycyclobutyl)benzene-1,2-diamine

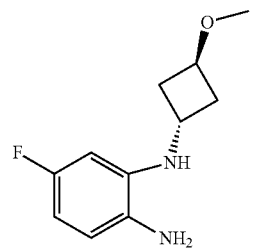

To a solution of 2,4-difluoro-1-nitrobenzene (0.2 mL, 1.7 mmol) in CH$_3$CN (3 mL) were added trans-3-methoxycyclobutylamine (0.18 g, 1.7 mmol) and DIPEA (0.3 mL, 1.7 mmol). The reaction mixture was stirred at RT for 18 h then concentrated in vacuo. The resulting residue was carried to the next step without further purification (0.41 g, quantitative). To a solution of the product thus obtained (1.7 mmol) in EtOAc (15 mL) was added Pd/C (350 mg) and the reaction mixture was stirred at RT for 18 h under a hydrogen atmosphere. The suspension was filtered through a pad of Celite® and the filtrate was concentrated in vacuo to afford the title compound as a dark oil (0.36 g, quantitative). $^1$H NMR (CDCl$_3$, 300 MHz): δ 6.68-6.59 (1H, m), 6.33 (1H, dt, J=19.6

Hz, 2.7 Hz), 6.18 (1H, dd, J=13.6 Hz, 2.7 Hz), 4.00-3.90 (1H, m), 3.76-3.63 (1H, m), 3.53 (3H, br s), 3.27 (3H, s), 2.49-2.37 (2H, m), 2.36-2.12 (2H, m).

{(S)-1-[6-Fluoro-1-(trans-3-methoxycyclobutyl)
1Hbenzoimidazol-2-yl]ethyl}carbamic acid tert-
butyl ester

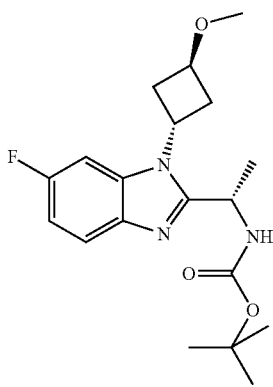 [SMILES: CO[C@H]1C[C@H](n2c([C@H](C)NC(=O)OC(C)(C)C)nc3ccc(F)cc32)C1]

A mixture of 4-fluoro-N²(trans-3-methoxycyclobutyl)benzene-1,2-diamine (0.36 g, 1.7 mmol), (S)-2-tertbutoxycarbonylaminopropionic acid (0.35 g, 1.9 mmol) and HOAt (0.26 g, 1.9 mmol) in DCM (8 mL) was cooled to 0° C. under a nitrogen atmosphere. To this mixture was added N-(3-dimethylaminopropyl)-N-ethylcarbodiimide hydrochloride (0.36 g, 1.9 mmol) portion wise and the mixture stirred at RT for 1 h. The reaction mixture was allowed to warm to RT then partitioned between DCM (30 mL) and a saturated aqueous solution of NaHCO₃ (20 mL). The organic fraction was washed with brine (20 mL), dried (MgSO₄) and concentrated in vacuo. The resulting residue was purified by column chromatography (Si—PCC, gradient 0-50% EtOAc in cyclohexane) to afford the compound as a pink solid (0.188 g, 29%). The compound thus obtained was dissolved in AcOH (8 mL) and heated at 70° C. for 18 h. After cooling to RT, the volatiles were evaporated in vacuo and the residue partitioned between DCM (40 mL) and a saturated aqueous solution of NaHCO₃ (20 mL). The organic fraction was washed with brine (20 mL), dried (MgSO₄) and concentrated in vacuo. The resulting dark brown residue was purified by column chromatography (Si—PCC, gradient 0-50% EtOAc in cyclohexane) to afford the title compound as yellow oil (0.125 g, 20%). LCMS (Method B): R$_T$ 2.84 min [M+H]⁺ 364.05

(S)-1-[6-Fluoro-1-(cis-3-methoxycyclobutyl)-
1Hbenzoimidazol-2-yl]ethylamine

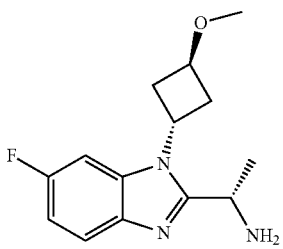 [SMILES: CO[C@H]1C[C@H](n2c([C@H](C)N)nc3ccc(F)cc32)C1]

To a solution of {(S)-1-[6-fluoro-1-(trans-3-methoxycyclobutyl)1Hbenzoimidazol-2-yl]ethyl}carbamic acid tert-butyl ester (0.125 g, 0.34 mmol) in DCM (3 mL) was added TFA (2 mL) and the mixture stirred at RT for 1.5 h. The volatiles were removed in vacuo and the resulting residue loaded onto an Isolute® SCX-2 cartridge. The cartridge was washed with MeOH followed by 2M NH₃/MeOH. The basic fractions were combined and concentrated in vacuo. The crude material was used in the following step without further purification. Yellow oil (85 mg, 95%). LCMS (Method J): R$_T$ 1.60 min [M+H]⁺ 264.23. 610116410

(5-Fluoro-2-nitrophenyl)-pyridin-4-yl-amine

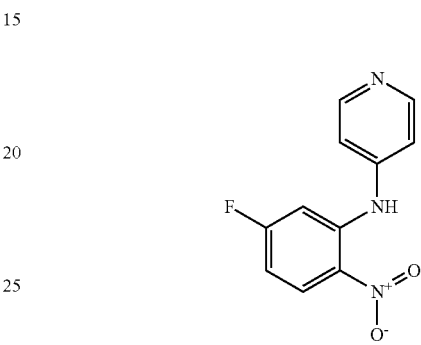

Potassium tert-butoxide (898 mg, 8.0 mmol) was added to a stirred solution of 4-aminopyridine (376 mg, 4.00 mmol) in anhydrous THF (5 mL) under a nitrogen atmosphere at 0° C. After 15 min stirring at 0° C., 2,4-difluoro-1-nitrobenzene (0.44 mL, 4.0 mmol) in anhydrous THF (5 mL) was added and stirring at 0° C. continued for 1 h. The reaction mixture was poured into a saturated aqueous solution of NH₄Cl (50 mL). The aqueous phase was extracted with EtOAc (×2) and the combined organic fractions washed with brine, dried (Na₂SO₄) and concentrated in vacuo. The resulting residue was purified by column chromatography (Si—PCC, gradient 0-10% MeOH in DCM) to afford the title compound as a yellow solid (557 mg, 60%). LCMS (Method C): R$_T$ 1.26 min [M+H]⁺ 234.12

4-Fluoro-N²-pyridin-4-yl-benzene-1,2-diamine

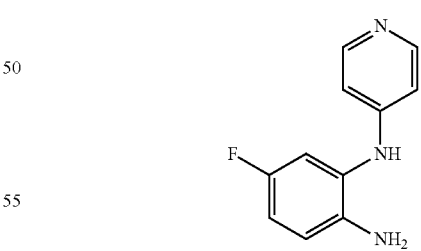

To a mixture of (5-fluoro-2-nitro-phenyl)-pyridin-4-yl-amine (375 mg, 1.61 mmol) in a 3:1 mixture of MeOH:water (40 mL) were added NH₄Cl (516 mg, 9.65 mmol) and iron powder (359 mg, 6.43 mmol) and the reaction mixture heated at 80° C. for 2 h. After cooling to RT, the solid was filtered through a pad of Celite® and washed with additional MeOH. The filtrate was concentrated in vacuo and the resulting residue partitioned between DCM and a saturated aqueous solution of NaHCO₃. The organic fraction was dried and concentrated in vacuo to afford the title compound as a dark beige solid (215 mg, 66%). LCMS (Method C): $R_T$ 1.32 min [M+H]+ 204.09

[1-(6-Fluoro-1-pyridin-4-yl-1H-benzoimidazol-2-yl)ethyl]carbamic acid tert-butyl ester

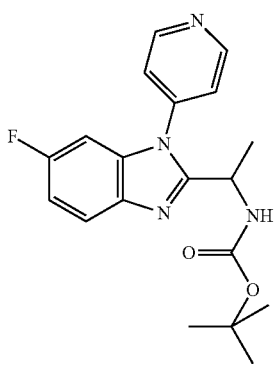 [SMILES: CC(NC(=O)OC(C)(C)C)c1nc2ccc(F)cc2n1-c1ccncc1]

To a suspension of (S)-Boc-alaninamide (385 mg, 2.05 mmol) in DCM (5 mL) was added triethyloxonium tetrafluoroborate (389 mg, 2.05 mmol) in one portion under a nitrogen atmosphere. The resulting mixture was left to stir at RT for 1 h. The volatiles were removed under reduced pressure and to the resulting residue was added 4-fluoro-$N^2$-pyridin-4-yl-benzene-1,2-diamine (208 mg, 1.02 mmol) in absolute EtOH (5 mL) and the mixture was stirred at 80° C. for 16 h. The volatiles were removed under reduced pressure and the resulting residue partitioned between DCM and a saturated aqueous solution of $NaHCO_3$. The organic fraction was dried, concentrated in vacuo and the resulting residue purified by column chromatography (Si—PCC, gradient 0-10% MeOH in EtOAc) to afford the title compound as a pale yellow oil (210 mg, 58%). LCMS (Method C): $R_T$ 2.84 min [M+H]+ 357.15

1-(6-Fluoro-1-pyridin-4-yl-1H-benzoimidazol-2-yl)ethylamine

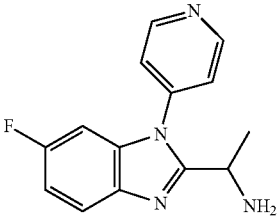 [SMILES: CC(N)c1nc2ccc(F)cc2n1-c1ccncc1]

A mixture of [1-(6-fluoro-1-pyridin-4-yl-1H-benzoimidazol-2-yl)ethyl]carbamic acid tert-butyl ester (210 mg, 0.59 mmol) in DCM (2 mL) and TFA (1 mL) was stirred at RT for 2 h. The reaction mixture was loaded onto an Isolute® SCX-2 cartridge which was washed with MeOH followed by 2M $NH_3$/MeOH. The basic fractions were combined and concentrated in vacuo to afford the title compound (120 mg, 79%) as a yellow solid. LCMS (Method C): $R_T$ 1.63 min [M+H]+ 257.15.

(5-Fluoro-2-nitrophenyl)-(5-fluoropyridin-3-yl)amine

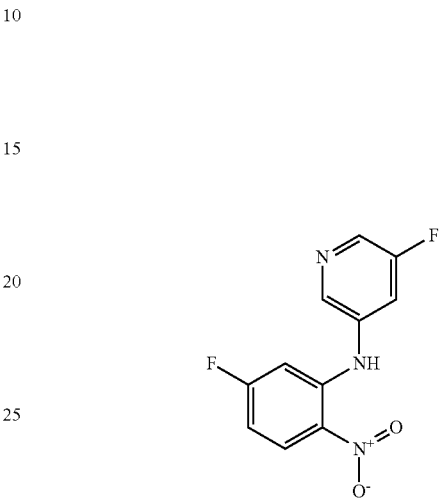

LiHMDS (1.0M in THF, 10.0 mL, 10.0 mmol) was added dropwise to a stirred solution of 3-amino-5-fluoropyridine (588 mg, 5.26 mmol) in anhydrous THF (10 mL) under a nitrogen atmosphere at −78° C. After 20 min 2,4-difluoro-1-nitrobenzene (0.55 mL, 5.0 mmol) was added and stirring at −78° C. was continued for 1 h. The reaction mixture was poured into a saturated aqueous solution of $NH_4Cl$ (50 mL). The aqueous phase was extracted with EtOAc (×2) and the combined organic fractions washed with brine, dried ($Na_2SO_4$) and concentrated in vacuo. The resulting residue was purified by column chromatography (Si—PCC, gradient 0-100% EtOAc in DCM) to afford the title compound as an orange solid (428 mg, 34%). LCMS (Method C): $R_T$ 3.27 min [M+H]+ 252.16

Alternative procedure: Potassium tert-butoxide (28.1 g, 0.25 mol) was added, in 2 portions, to a stirred solution of 3-amino-5-fluoropyridine (14.0 g, 0.125 mol) in anhydrous THF (400 mL) under a nitrogen atmosphere at 0° C. After 45 min stirring at 0° C., the resulting dark purple solution was transferred by cannula to a stirred solution of 2,4-difluoro-1-nitrobenzene (13.8 mL, 0.125 mol) in anhydrous THF (100 mL), at 0° C., over a period of 20 min. The resulting mixture was stirred for a further 45 min then poured onto a RT solution of $NH_4Cl$ (1:1 saturated solution:$H_2O$, 1 L). The resulting yellow precipitate was filtered, washed with water and dried under vacuum at 50° C. to afford the title compound as an orange solid (18.2 g). The filtrate was partially evaporated, to remove some of the reaction solvent, the resulting precipitate was filtered then triturated with EtOAc to give a further 3.5 g of the title compound (overall 21.7 g, 69%) LCMS (Method C): $R_T$ 3.18 min [M+H]$^+$ 252.13

4-Fluoro-N$^2$-(5-fluoropyridin-3-yl)benzene-1,2-diamine

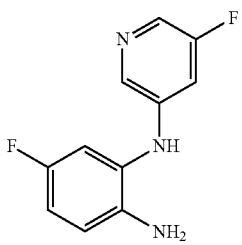

A mixture of (5-fluoro-2-nitro-phenyl)-(5-fluoropyridin-3-yl)amine (425 mg, 1.69 mmol) in EtOAc (30 mL) was degassed with a stream of nitrogen prior to addition of 10% Pd/C (50 mg) and was stirred at RT under a hydrogen atmosphere for 19 h. The mixture was filtered and the filtrate concentrated in vacuo to afford the title compound as a brown solid (395 mg, quantitative). LCMS (Method C): $R_T$ 2.24 min [M+H]$^+$ 222.07

(S)-1-[6-Fluoro-1-(5-fluoropyridin-3-yl)-1H-benzoimidazol-2-yl]ethylamine

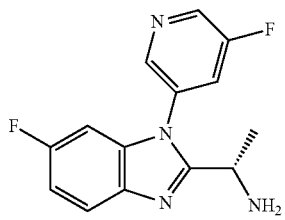 [SMILES: C[C@H](N)c1nc2ccc(F)cc2n1-c1cncc(F)c1]

To a suspension of (S)-Boc-alaninamide (337 mg, 1.79 mmol) in DCM (5 mL) was added triethyloxonium tetrafluoroborate (340 mg, 1.79 mmol) in one portion under a nitrogen atmosphere. The resulting mixture was left to stir at RT for 1 h. The volatiles were removed under reduced pressure and to the resulting residue was added 4-fluoro-N$^2$-(5-fluoropyridin-3-yl)-benzene-1,2-diamine (198 mg, 0.895 mmol) in absolute EtOH (5 mL) and the mixture stirred at 80° C. for 18 h. The volatiles were removed in vacuo and the resulting residue partitioned between DCM and a saturated aqueous solution of NaHCO$_3$. The organic fraction was dried, concentrated in vacuo and the resulting residue taken up in DCM (2 mL) and TFA (1 mL) added. After stirring at RT for 1 h, the reaction mixture was diluted with MeOH and loaded onto an Isolute® SCX-2 cartridge. The cartridge was washed with MeOH followed by 2M NH$_3$/MeOH. The basic fractions were combined and concentrated in vacuo and the resulting residue purified by column chromatography (Si—PCC, gradient 0-20% MeOH in DCM) to afford the title compound as a colourless oil (52 mg, 21% over 2 steps). LCMS (Method C): $R_T$ 1.76 min [M+H]$^+$ 275.20

{(S)-1-[6-Fluoro-1-(5-fluoropyridin-3-yl)-1H-benzoimidazol-2-yl]ethyl}carbamic acid tert-butyl ester

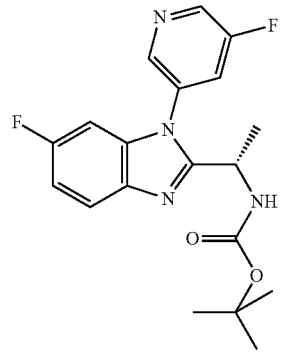 [SMILES: C[C@H](NC(=O)OC(C)(C)C)c1nc2ccc(F)cc2n1-c1cncc(F)c1]

To a suspension of (S)-Boc-alaninamide (17.4 g, 92.5 mmol) in DCM (180 mL, dried over molecular sieves) was added triethyloxonium tetrafluoroborate (16.0 g, 84.1 mmol) in one portion under a nitrogen atmosphere. The resulting mixture was stirred at RT for 2 h. The volatiles were removed in vacuo and the resulting residue taken up in absolute EtOH (200 mL) then 4-fluoro-N$^2$-(5-fluoropyridin-3-yl)-benzene-1,2-diamine (6.20 g, 28.0 mmol) added. After stirring the reaction mixture at 60° C. for 2 h, the solvent was removed in vacuo and the resulting residue partitioned between DCM and an aqueous solution of NaHCO$_3$. The layers were separated and the aqueous fraction extracted with DCM. The combined organic fractions were dried (Na$_2$SO$_4$) and concentrated in vacuo. The resulting residue was purified by column chromatography (120 g Si—PCC, gradient 0-70% EtOAc in DCM) to afford the title compound as a green solid (10.1 g, 96%). LCMS (Method C): $R_T$ 3.23 min [M+H]$^+$ 375.18.

2-Cyclopropylamino-6-fluoro-3-nitrobenzoic acid

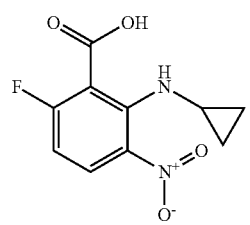 [SMILES: O=C(O)c1c(F)ccc([N+](=O)[O-])c1NC1CC1]

To a solution of 2,6-difluoro-3-nitrobenzoic acid (1.0 g, 4.92 mmol) in IMS (5 mL) and water (5 mL) were added Et$_3$N (1.23 mL, 8.86 mmol) and cyclopropylamine (360 µL, 5.17 mmol). The reaction mixture was stirred at RT for 28 h. The pH of the solution was adjusted to 1 by addition of 1M aqueous HCl. A precipitate formed and this solid was collected by filtration, washing with water to afford the title compound (841 mg, 71%) as a yellow solid. $^1$H NMR (CDCl₃, 400 MHz): δ 8.78 (1H, s), 8.28 (1H, dd, J=9.45, 5.85 Hz), 6.49 (1H, m), 2.84 (1H, m), 0.85 (2H, m), 0.68 (2H, m)

2-Cyclopropylamino-6-fluoro-3-nitrobenzoic acid methyl ester

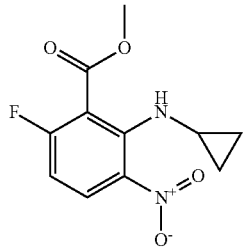

Trimethylsilyldiazomethane (2M in hexane, 2.6 mL, 5.21 mmol) was added dropwise to a solution of 2-cyclopropylamino-6-fluoro-3-nitrobenzoic acid (836 mg, 3.48 mmol) in MeOH (4 mL) and DCM (16 mL) at 0° C. The solution was stirred for 15 min then the volatiles were removed under reduced pressure to afford the title compound (867 mg, 98%). LCMS (Method C): $R_T$ 3.50 min [M+H]⁺ 255.10

3-Amino-2-cyclopropylamino-6-fluorobenzoic acid methyl ester

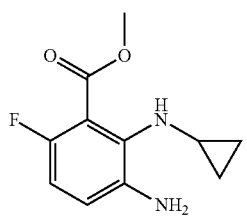

A mixture of 2-cyclopropylamino-6-fluoro-3-nitrobenzoic acid methyl ester (865 mg, 3.40 mmol) in EtOAc (25 mL) was degassed with a stream of nitrogen prior to addition of 10% Pd/C (116 mg) and was stirred at RT under a hydrogen atmosphere for 20 h. The suspension was filtered and the filtrate was concentrated in vacuo to afford the title compound as a dark yellow oil (756 mg, 99%). LCMS (Method C): $R_T$ 2.29 min [M+H]⁺ 225.18.

2-((S)-1-tert-Butoxycarbonylaminoethyl)-3-cyclopropyl-5-fluoro-3H-benzoimidazole-4-carboxylic acid methyl ester

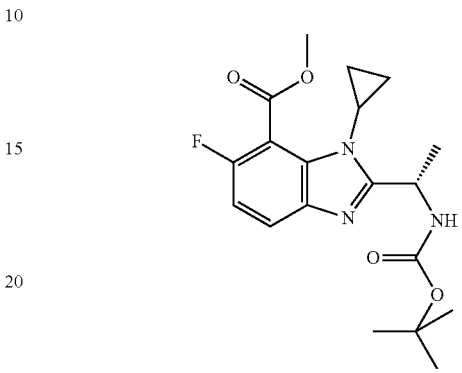

A mixture of 3-amino-2-cyclopropylamino-6-fluorobenzoic acid methyl ester (756 mg, 3.37 mmol), (S)-2-tertbutoxycarbonylaminopropionic acid (702 mg, 3.71 mmol), HOAt (505 mg, 3.71 mmol) and N-(3-dimethylaminopropyl)-N-ethylcarbodiimide hydrochloride (711 mg, 3.71 mmol) in DCM (20 mL) was stirred at 0° C. for 1 h. The reaction mixture was partitioned between DCM and a saturated aqueous solution of NaHCO₃. The organic fraction was dried and concentrated in vacuo. The resulting residue was taken up in AcOH (20 mL) and heated at 70° C. for 21 h. After cooling to RT, the volatiles were evaporated in vacuo and the residue partitioned between EtOAc and a saturated aqueous solution of NaHCO₃. The aqueous phase was extracted with EtOAc and the combined organic fractions washed with brine, dried (Na₂SO₄) and concentrated in vacuo. The resulting residue was purified by column chromatography (Si—PCC, gradient 0-50% EtOAc in DCM) to afford the title compound (700 mg, 55% over 2 steps). LCMS (Method C): $R_T$ 3.27 min [M+H]⁺ 378.18

3-Cyclopropyl-5-fluoro-2-{(S)-1-[9-(tetrahydropyran-2-yl)-9H-purin-6-ylamino]ethyl}-3H-benzoimidazole-4-carboxylic acid methyl ester

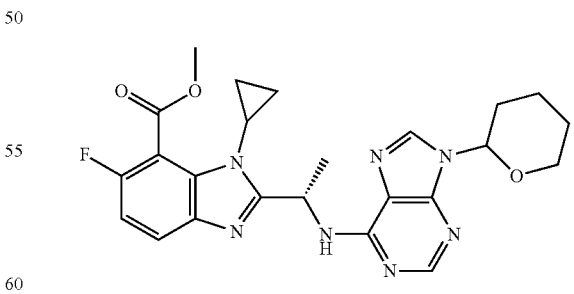

To a solution of 2-((S)-1-tert-butoxycarbonylaminoethyl)-3-cyclopropyl-5-fluoro-3H-benzoimidazole-4-carboxylic acid methyl ester (698 mg, 1.85 mmol) in DCM (3 mL) was added TFA (3 mL) and the reaction mixture stirred at RT for 2 h. The crude mixture was loaded onto an Isolute® SCX-2 cartridge which was washed with MeOH followed by 2M NH₃/MeOH. The basic fractions were combined and concentrated in vacuo to afford 2-((S)-1-aminoethyl)-3-cyclopropyl-5-fluoro-3H-benzoimidazole-4-carboxylic acid methyl ester as a yellow oil. The resulting residue was treated with 6-chloro-9-(tetrahydropyran-2-yl)-9H-purine (486 mg, 2.03 mmol) and DIPEA (970 µL, 5.55 mmol) in n-butanol (3 mL). The reaction mixture was heated in a sealed vial for 20 h at 100° C. After cooling to RT, the volatiles were removed under reduced pressure and the resulting residue purified by column chromatography (Si—PCC, gradient 0-10% MeOH in EtOAc) to afford the title compound (780 mg, 88% over 2 steps). LCMS (Method C): $R_T$ 2.91 min [M+H]⁺ 480.22.

3-Cyclopropyl-5-fluoro-2-{(S)-1-[9-(tetrahydropyran-2-yl)-9H-purin-6-ylamino]ethyl}-3H-benzoimidazole-4-carboxylic acid

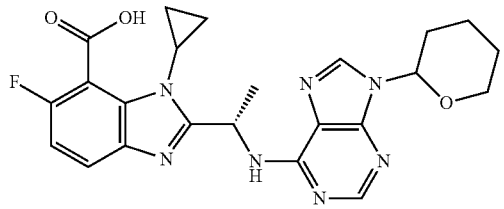 [SMILES: C[C@H](Nc1ncnc2c1ncn2C1CCCCO1)c1nc2ccc(F)c(C(=O)O)c2n1C1CC1]

A solution of 3-cyclopropyl-5-fluoro-2-{(S)-1-[9-(tetrahydropyran-2-yl)-9H-purin-6-ylamino]ethyl}-3H-benzoimidazole-4-carboxylic acid methyl ester (607 mg, 1.27 mmol) and LiOH.H₂O (266 mg, 6.33 mmol) in MeOH (20 mL) and water (2 mL) was heated at 80° C. for 22 h. Additional LiOH.H₂O (266 mg) was added and the mixture heated at 80° C. for 5 h. After cooling to RT, the pH of the mixture was adjusted to 4 by addition of 1M aqueous HCl. The organic solvent was removed under reduced pressure and the aqueous phase extracted with EtOAc. The organic fraction was washed with brine, dried (Na₂SO₄) and concentrated in vacuo. The resulting residue was purified by column chromatography (Si—PCC, gradient 0-20% 2M NH₃/MeOH in DCM) to afford the title compound (127 mg, 21% over 2 steps) as a white solid. LCMS (Method C): $R_T$ 2.17 min [M+H]⁺ 466.22.

(5-Fluoro-2-nitrophenyl)-(3-fluoropyridin-2-yl)amine

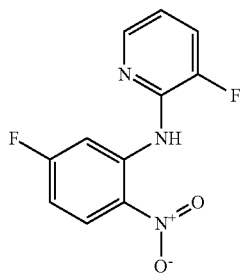 [SMILES: O=[N+]([O-])c1ccc(F)cc1Nc1ncccc1F]

LiHMDS (1.0M in THF, 4.0 mL, 4.0 mmol) was added dropwise to a stirred solution of 2-amino-3-fluoropyridine (224 mg, 2.0 mmol) in anhydrous THF (5 mL) under a nitrogen atmosphere at −78° C. After 15 min stirring at −78° C., a solution of 2,4-difluoro-1-nitrobenzene (0.22 mL, 2.0 mmol) in THF (5 mL) was added and stirring at −78° C. was continued for 1 h. The mixture was slowly warmed to 0° C. and stirring continued for 1 h. The crude solution was poured into a saturated aqueous solution of NH₄Cl (50 mL). The aqueous phase was extracted with EtOAc (×3) and the combined organic fractions were washed with water, followed by brine, dried (Na₂SO₄) and concentrated in vacuo. The resulting residue was purified by column chromatography (Si—PCC, gradient 0-100% DCM in cyclohexane) to afford the title compound as an orange solid (93 mg, 19%). LCMS (Method C): $R_T$ 3.97 min [M+H]⁺ 252.10.

4-Fluoro-N²-(3-fluoropyridin-2-yl)benzene-1,2-diamine

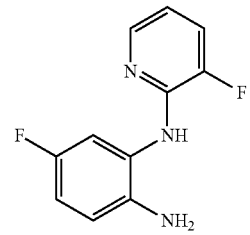 [SMILES: Nc1ccc(F)cc1Nc1ncccc1F]

A mixture of (5-fluoro-2-nitro-phenyl)-(3-fluoropyridin-2-yl)amine (93 mg, 0.370 mmol) in EtOAc (10 mL) was degassed with a stream of nitrogen prior to addition of 10% Pd/C (10 mg) and was stirred at RT under a hydrogen atmosphere for 3 h. The mixture was then filtered through a phase separator and the filtrate was concentrated in vacuo to afford the title compound as a brown solid (81 mg, 99%). LCMS (Method C): $R_T$ 1.70 min [M+H]⁺ 222.18.

{1-[6-Fluoro-1-(3-fluoropyridin-2-yl)-1H-benzoimidazol-2-yl]ethyl}carbamic acid tert-butyl ester

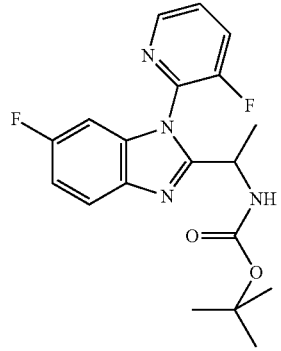 [SMILES: CC(NC(=O)OC(C)(C)C)c1nc2ccc(F)cc2n1-c1ncccc1F]

A mixture of 4-fluoro-N²-(3-fluoropyridin-2-yl)benzene-1,2-diamine (81 mg, 0.37 mmol), (S)-2-tertbutoxycarbonylaminopropionic acid (76 mg, 0.40 mmol), HOAt (55 mg, 0.40 mmol) and N-(3-dimethylaminopropyl)-N-ethylcarbodiimide hydrochloride (77 mg, 0.40 mmol) in DCM (5 mL) was stirred at 0° C. for 2 h. The reaction mixture was partitioned between DCM and a saturated aqueous solution of NaHCO₃. The organic layer was dried and concentrated in vacuo. The resulting residue was taken up in AcOH (5 mL) and heated at 70° C. for 24 h. After cooling to RT, the volatiles were removed in vacuo and the resulting residue partitioned between EtOAc and a saturated aqueous solution of NaHCO$_3$. The organic fraction was washed with water, followed by brine, then dried (Na$_2$SO$_4$) and concentrated in vacuo. The resulting oil was purified by column chromatography (Si—PCC, gradient 0-10% MeOH in EtOAc) to afford the title compound as an orange oil (84 mg, 61%). LCMS (Method C): R$_T$ 3.28 min [M+H]$^+$ 375.22

Benzyl-(5-fluoro-2-nitrophenyl)amine

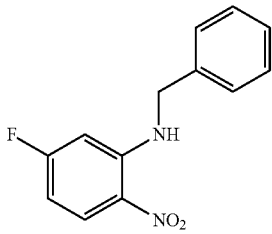 [SMILES: O=[N+]([O-])c1ccc(F)cc1NCc1ccccc1]

2,4-Difluoro-1-nitrobenzene (2.00 g, 12.57 mmol) was dissolved in acetonitrile (20 mL) and DIPEA (2.2 mL, 12.57 mmol) added, followed by the dropwise addition of benzylamine (1.35 g, 12.57 mmol). The reaction mixture was stirred at RT, under an atmosphere of nitrogen overnight. The mixture was concentrated in vacuo to afford the title compound as a yellow oil, which solidified on standing (3.8 g, 100%). The crude material was used without purification in the next step. $^1$H NMR (CDCl$_3$, 400 MHz): δ 8.55 (1H, s), 8.25 (1H, dd, J=9.46, 6.08 Hz), 7.43-7.29 (5H, m), 6.47 (1H, dd, J=11.35, 2.60 Hz), 6.39 (1H, ddd, J=9.46, 7.28, 2.61 Hz), 4.51 (2H, d, J=5.60 Hz)

N$^2$-Benzyl-4-fluoro-benzene-1,2-diamine

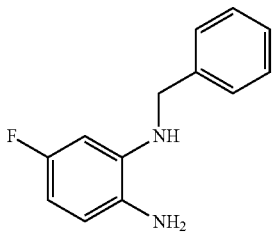

A mixture of benzyl-(5-fluoro-2-nitrophenyl)amine (3.8 g, 15.2 mmol), iron powder (3.42 g, 60.8 mmol) and ammonium chloride (4.7 g, 91.2 mmol) in methanol (40 mL) and water (10 mL) was heated to 90° C. for 2 h, under an atmosphere of nitrogen. The resultant mixture was diluted with methanol (20 mL) and filtered through Celite®. The Celite® was washed with DCM, methanol and EtOAc (4×) and the filtrate concentrated in vacuo. The residue was partitioned between water (25 mL) and EtOAc (40 mL) and the aqueous layer was extracted with EtOAc (2×30 mL). The combined organic fractions were washed with brine (25 mL), dried (MgSO$_4$), filtered and concentrated in vacuo to afford the title compound as a dark brown gum (2.17 g, 66%). The crude material was used without purification in the next step. $^1$H NMR (CDCl$_3$, 400 MHz): δ 7.41-7.25 (5H, m), 6.67-6.59 (1H, m), 6.40-6.28 (2H, m), 4.28 (2H, s)

[(S)-1-(2-Benzylamino-4-fluorophenylcarbamoyl) ethyl]carbamic acid tert-butyl ester

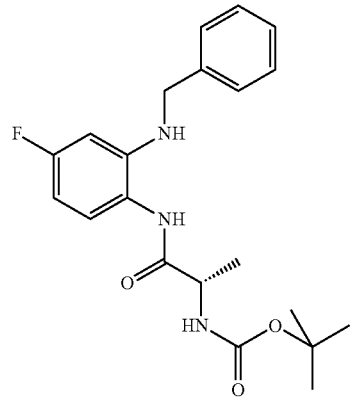 [SMILES: C[C@H](NC(=O)OC(C)(C)C)C(=O)Nc1ccc(F)cc1NCc1ccccc1]

N$^2$-Benzyl-4-fluoro-benzene-1,2-diamine (1.2 g, 5.55 mmol) was dissolved in DCM (20 mL) and (S)-2-tert-butoxycarbonylaminopropionic acid (1.14 g, 6.0 mmol) and HOAt (0.82 g, 6.0 mmol) added. The reaction mixture was cooled to 0° C. and N-(3-dimethylaminopropyl)-N' ethylcarbodiimide (1.15 g, 6.0 mmol) added. The resultant dark brown mixture was stirred at 0° C. for 1 h. The mixture was allowed to reach RT and was diluted with DCM (20 mL) and washed with 10% aqueous citric acid. The organic fraction was washed with brine (20 mL), dried (MgSO$_4$), filtered and concentrated in vacuo. The residue was purified by column chromatography (silica gel, gradient 0-50% EtOAc in cyclohexane) to afford the title compound as a dark yellow gum, which solidified on standing (1.7 g, 79%). LCMS (Method B): R$_T$ 3.67 min [M+H]$^+$ 388.1

[(S)-1-(1-Benzyl-6-fluoro-1H-benzoimidazol-2-yl) ethyl]carbamic acid tert-butyl ester

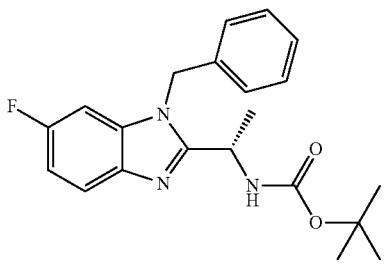 [SMILES: C[C@H](NC(=O)OC(C)(C)C)c1nc2ccc(F)cc2n1Cc1ccccc1]

[(S)-1-(2-Benzylamino-4-fluorophenylcarbamoyl)ethyl] carbamic acid tert-butyl ester (1.7 g, 4.39 mmol) was dissolved in acetic acid (15 mL) and heated at 70° C., overnight, under an atmosphere of nitrogen. The reaction mixture was then heated at 80° C. for 6 h. The resultant mixture was allowed to cool to RT and was concentrated in vacuo. The residue was purified by column chromatography (silica gel, gradient 0-50% EtOAc in cyclohexane) to afford the title compound as an off-white solid (0.88 g, 55%). $^1$H NMR (CDCl$_3$, 400 MHz): δ 7.68 (1H, dd, J=8.81, 4.79 Hz), 7.34-

7.26 (3H, m), 7.08-6.95 (3H, m), 6.90 (1H, dd, J=8.69, 2.43 Hz), 5.43 (2H, d, J=5.40 Hz), 5.18-5.06 (1H, m), 1.53 (3H, d, J=6.73 Hz), 1.37 (9H, s).

(S)-1-(1-Benzyl-6-fluoro-1H-benzoimidazol-2-yl)ethylamine

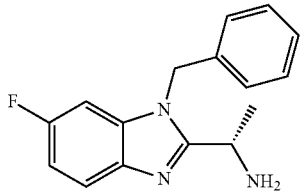 [SMILES: C[C@H](N)c1nc2ccc(F)cc2n1Cc1ccccc1]

[(S)-1-(1-Benzyl-6-fluoro-1H-benzoimidazol-2-yl)ethyl]carbamic acid tert-butyl ester (0.88 g, 2.39 mmol) was dissolved in DCM (10 mL) and TFA (4 mL) was added dropwise. The pale green mixture was stirred at RT for 1 h, under an atmosphere of nitrogen. The resultant mixture was concentrated in vacuo and the residue passed down an Isolute® SCX-2 cartridge, eluting with DCM, MeOH and then 2M NH₃ in MeOH solution to afford the title compound as a pale red gum (0.60 g, 93%). ¹H NMR (CDCl₃, 400 MHz): δ 7.69 (1H, dd, J=8.81, 4.80 Hz), 7.37-7.28 (3H, m), 7.09-7.95 (3H, m), 6.89 (1H, dd, J=8.75, 2.44 Hz), 5.54-5.34 (2H, m), 4.26 (1H, q, J=6.67 Hz), 1.54 (3H, d, J=6.61 Hz)

(5-Fluoro-2-nitrophenyl)isopropylamine

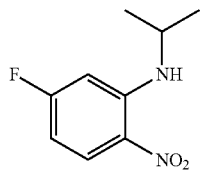

2,4-Difluoro-1-nitrobenzene (2.00 g, 12.57 mmol) was dissolved in acetonitrile (20 mL) and DIPEA (2.2 mL, 12.57 mmol) added, followed by isopropylamine (1.07 mL, 12.57 mmol). The bright yellow mixture was stirred at RT overnight. The resultant mixture was concentrated in vacuo and the residue purified by column chromatography (silica gel, gradient 0-5% EtOAc in cyclohexane) to afford the title compound as a yellow gum (2.1 g, 99%). Contaminated with some unreacted 2,4-difluoro-1-nitrobenzene, but used in the next step without any further purification. ¹H NMR (CDCl₃, 400 MHz): δ 8.20 (1H, dd, J=9.53, 6.21 Hz), 6.48 (1H, dd, J=11.71, 2.63 Hz), 6.33 (1H, m), 3.80-3.64 (1H, m), 1.33 (6H, d, J=6.36 Hz)

4-Fluoro-N²-isopropylbenzene-1,2-diamine

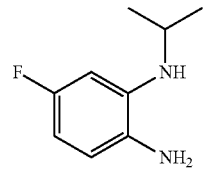

(5-Fluoro-2-nitrophenyl)isopropylamine (2.1 g, 12.6 mmol) was dissolved in EtOAc (60 mL) and the flask evacuated and flushed with nitrogen gas, prior to the addition of 10% Pd/C (0.21 g). The mixture was stirred under an atmosphere of hydrogen gas overnight. A further amount of 10% Pd/C (0.21 g) was added and the mixture was stirred under an atmosphere of hydrogen for a further 3 h. A further amount of 10% Pd/C (0.21 g) was added and the mixture stirred under an atmosphere of hydrogen for a further 2 h. The resultant mixture was filtered through Celite® under an atmosphere of nitrogen and the filtrate concentrated in vacuo to afford the title compound as a dark red oil (1.5 g, 88%). ¹H NMR (CDCl₃, 400 MHz): δ 6.62 (1H, dd, J=8.34, 5.72 Hz), 6.36 (1H, dd, J=11.17, 2.77 Hz), 6.28 (1H, td, J=8.43, 2.75 Hz), 3.61-3.47 (1H, m), 1.24 (6H, d, J=6.27 Hz)

[(S)-1-(6-Fluoro-1-isopropyl-1H-benzoimidazol-2-yl)ethyl]carbamic acid tert-butyl ester

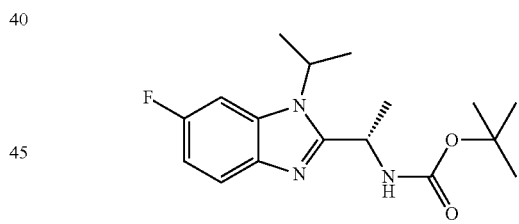

4-Fluoro-N²-isopropylbenzene-1,2-diamine (0.7 g, 5.07 mmol) was dissolved in DCM (10 mL) and (S)-2-tert-butoxycarbonylaminopropionic acid (1.06 g, 5.58 mmol) added. To the resultant dark red solution was added HOAt (0.76 g, 5.58 mmol), followed by N-methyl morpholine (1.23 mL, 11.15 mmol) and N-(3-dimethylaminopropyl)-N' ethylcarbodiimide (1.07 g, 5.58 mmol). The resultant blue/black solution was stirred at RT overnight, under an atmosphere of nitrogen. The mixture was diluted with DCM (40 mL) and washed with saturated aqueous NaHCO₃ (20 mL) and brine (20 mL). The organic fraction was dried (MgSO₄), filtered and concentrated in vacuo to afford a dark red oil. This was purified by column chromatography (silica gel, gradient 0-20% EtOAc in DCM) to afford a red oil which solidified on standing. This was dissolved in acetic acid (20 mL) and heated at 70° C. overnight. The resultant mixture was allowed to cool to RT and was concentrated in vacuo to afford the title compound as a dark red gum (1.0 g, 88%). This material was used in the next step without any purification. LCMS (Method B): $R_T$ 2.78 min [M+H]$^+$ 322.2

(S)-1-(6-Fluoro-1-isopropyl-1H-benzoimidazol-2-yl) ethylamine

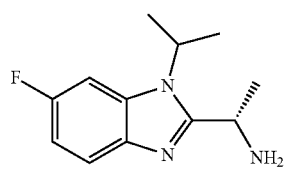 [SMILES: CC(C)n1c([C@H](C)N)nc2ccc(F)cc21]

[(S)-1-(6-Fluoro-1-isopropyl-1H-benzoimidazol-2-yl) ethyl]carbamic acid tert-butyl ester (1.0 g, 3.11 mmol) was dissolved in DCM (10 mL) and TFA (5 mL) added. The reaction mixture was stirred at RT for 30 minutes. The resultant mixture was concentrated in vacuo and the residue dissolved in DCM (40 mL) and stirred vigorously with saturated aqueous NaHCO$_3$ (20 mL), for 10 minutes. The layers were separated and the organic fraction washed with brine (20 mL), dried (MgSO$_4$), filtered and concentrated in vacuo to afford the title compound (0.5 g, 72%). $^1$H NMR (CDCl$_3$, 400 MHz): δ 7.65 (1H, dd, J=8.83, 5.01 Hz), 7.20 (1H, dd, J=9.40, 2.46 Hz), 6.97 (1H, ddd, J=9.58, 8.80, 2.43 Hz), 4.92-4.82 (1H, m), 4.37-4.28 (1H, q, J=6.68 Hz), 1.64 (6H, d, J=6.98 Hz), 1.58 (3H, d, J=6.65 Hz).

(5-Fluoro-2-nitrophenyl)-(4-fluorophenyl)amine

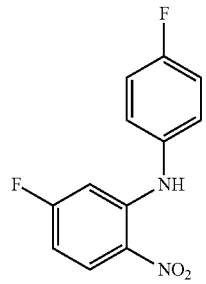 [SMILES: O=[N+]([O-])c1ccc(F)cc1Nc1ccc(F)cc1]

4-Fluorophenylamine (1.47 g, 13.19 mmol) was dissolved in THF (20 mL) and cooled to −70° C., under an atmosphere of nitrogen. A solution of 1M LiHMDS in THF (25.14 mL, 25.14 mmol) was added dropwise and the mixture stirred at −70° C., under an atmosphere of nitrogen for 15 minutes. A solution of 2,4-difluoronitrobenzene (2.0 g, 12.57 mmol) in THF (10 mL) was added dropwise to the mixture, at −70° C. and the resultant purple solution stirred at −70° C. for 30 min. The reaction mixture was quenched with saturated aqueous NH$_4$Cl solution and extracted into EtOAc (3×50 mL). The combined organic fractions were dried (MgSO$_4$), filtered and concentrated in vacuo. The residue was purified by column chromatography (silica gel, gradient 0-100% DCM in cyclohexane) to afford the title compound as an orange solid (2.94 g, 100%). $^1$H NMR (CDCl$_3$, 400 MHz): δ 9.53 (1H, s), 8.27 (1H, dd, J=9.48, 5.98 Hz), 7.29-7.22 (2H, m), 7.20-7.11 (2H, m), 6.64 (1H, dd, J=11.26, 2.65 Hz), 6.48 (1H, ddd, J=9.47, 7.12, 2.65 Hz)

4-Fluoro-N$^2$-(4-fluorophenyl)benzene-1,2-diamine

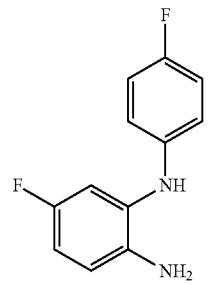

(5-Fluoro-2-nitrophenyl)-(4-fluorophenyl)amine (2.94 g, 11.76 mmol) was dissolved in EtOAc (120 mL) and the flask evacuated and flushed with nitrogen gas. 10% Pd/C (0.29 g) was added and the reaction mixture stirred at RT, under an atmosphere of hydrogen overnight. The resultant mixture was filtered through Celite® and the filtrate concentrated in vacuo to afford the title compound as an orange oil (2.67 g, 91%). $^1$H NMR (CDCl$_3$, 400 MHz): δ 7.01-6.92 (2H, m), 6.87-6.68 (4H, m), 6.61 (1H, td, J=8.35, 2.79 Hz), 5.24 (1H, s), 3.46 (2H, s)

{(S)-1-[6-Fluoro-1-(4-fluorophenyl)-1H-benzoimidazol-2-yl]ethyl}carbamic acid tert-butyl ester

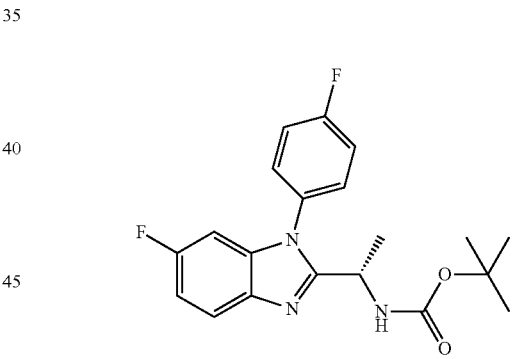

4-Fluoro-N$^2$-(4-fluorophenyl)benzene-1,2-diamine (0.7 g, 3.18 mmol) was dissolved in DCM (10 mL) and (S)-2-tert-butoxycarbonylaminopropionic acid (0.68 g, 3.55 mmol) added. To the resultant solution was added HOAt (0.49 g, 3.55 mmol), followed by N-methyl morpholine (0.85 mL, 7.69 mmol) then N-(3-dimethylaminopropyl)-N' ethylcarbodiimide (0.69 g, 3.55 mmol). The resultant dark yellow solution was stirred at RT overnight. Further quantities of (S)-2-tert-butoxycarbonylaminopropionic acid (0.38 g, 2.00 mmol), HOAt (0.24 g, 1.76 mmol), N-methyl morpholine (0.40 mL, 3.64 mmol) and N-(3-dimethylaminopropyl)-N' ethylcarbodiimide (0.34 g, 1.78 mmol) were added and the reaction mixture stirred at RT for 2 h. The mixture was diluted with DCM then washed with saturated aqueous NaHCO$_3$ (20 mL) and brine (20 mL). The organic fraction was dried (MgSO$_4$), filtered and concentrated in vacuo to afford a dark red oil. This was purified by column chromatography (SiO$_2$, gradient 0-10% EtOAc in DCM) to afford an off-white solid (1.25 g).

This was dissolved in acetic acid (20 mL) and heated to 70° C. for 48 h. The resultant mixture was allowed to cool to RT and concentrated in vacuo. The residue was dissolved in DCM (40 mL) and washed with saturated aqueous NaHCO$_3$ (20 mL) and brine (20 mL). The organic fraction was dried (MgSO$_4$), filtered and concentrated in vacuo. The resultant dark red oil was purified by column chromatography (SiO$_2$, gradient 0-20% EtOAc in DCM) to afford the title compound as a yellow gum (0.8 g, 68%). LCMS (Method J): R$_T$ 3.55 min [M+H]$^+$ 374.1

(S)-1-[6-Fluoro-1-(4-fluorophenyl)-1H-benzoimidazol-2-yl]ethylamine

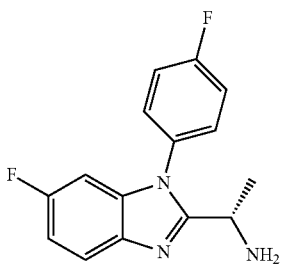 [SMILES: C[C@H](N)c1nc2ccc(F)cc2n1-c1ccc(F)cc1]

{(S)-1-[6-Fluoro-1-(4-fluorophenyl)-1H-benzoimidazol-2-yl]ethyl}carbamic acid tert-butyl ester (0.8 g, 2.14 mmol) was dissolved in DCM (10 mL) and TFA (5 mL) added. The reaction mixture was stirred at RT for 1 h. The resultant mixture was concentrated in vacuo to afford a dark green gum. This was dissolved in DCM (40 mL) and stirred vigorously with saturated aqueous NaHCO$_3$ (20 mL) for 10 minutes. The layers were separated and the organic fraction dried (MgSO$_4$), filtered and concentrated in vacuo. The residue was purified by column chromatography (silica gel, 10% MeOH in DCM) to afford the title compound (0.33 g, 57%). LCMS (Method C): R$_T$ 1.86 min [M+H]$^+$ 274.2

(5-Fluoro-2-nitrophenyl)-(3-fluorophenyl)amine

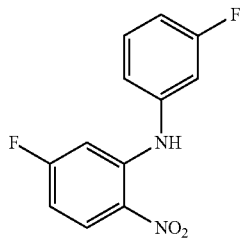

A solution of 3-fluorophenylamine (1.47 g, 13.19 mmol) in anhydrous THF (20 mL) was cooled to −70° C. To this was added dropwise, 1M LiHMDS in THF (25.14 mL, 25.14 mmol) over 10 minutes to afford a dark yellow solution. A solution of 2,4-difluoronitrobenzene (2.00 g, 12.57 mmol) in anhydrous THF (10 mL) was added dropwise to the yellow solution, to afford a purple solution. The reaction mixture was stirred at −70° C. for 15 minutes, before being allowed to reach RT. It was then quenched with saturated aqueous NH$_4$Cl solution (25 mL) and extracted into EtOAc (3×50 mL). The combined organic fractions were washed with brine (25 mL), dried (MgSO$_4$), filtered and concentrated in vacuo to afford a dark red solid. This was purified by column chromatography (SiO$_2$, gradient 0-100% DCM in cyclohexane) to afford the title compound as an orange solid (2.79 g, 89%). $^1$H NMR (CDCl$_3$, 400 MHz): δ 9.61 (1H, s), 8.28 (1H, dd, J=9.48, 5.96 Hz), 7.45-7.37 (1H, m), 7.11-6.94 (3H, m), 6.88 (1H, dd, J=11.16, 2.64 Hz), 6.58-6.49 (1H, m)

4-Fluoro-N$^2$-(3-fluorophenyl)benzene-1,2-diamine

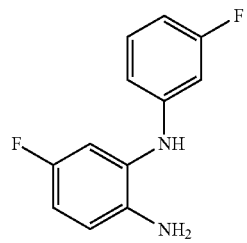 [SMILES: O=[N+]([O-])c1ccc(F)cc1Nc1cccc(F)c1]

(5-Fluoro-2-nitrophenyl)-(3-fluorophenyl)amine (2.79 g, 11.16 mmol) was dissolved in EtOAc (110 mL) and the flask evacuated and flushed with nitrogen gas. 10% Pd/C (0.3 g) was added and the reaction mixture stirred under an atmosphere of hydrogen gas, at RT overnight. A further amount of 10% Pd/C (0.3 g) was added and the reaction mixture stirred under an atmosphere of hydrogen gas for an further 2 h. The resultant mixture was filtered through Celite® and the filtrate concentrated in vacuo to afford the title compound as a brown oil, which solidified on standing (2.57 g, 100%). $^1$H NMR (CDCl$_3$, 400 MHz): δ 7.17 (1H, td, J=8.16, 6.58 Hz), 6.94-6.87 (1H, m), 6.76-6.70 (2H, m), 6.62-6.47 (3H, m), 5.35 (1H, s), 3.54 (2H, s)

{(S)-1-[4-Fluoro-2-(3-fluorophenylamino)phenylcarbamoyl]ethyl}carbamic acid tert-butyl ester and {(S)-1-[6-fluoro-1-(3-fluorophenyl)-1H-benzoimidazol-2-yl]ethyl}carbamic acid tert-butyl ester

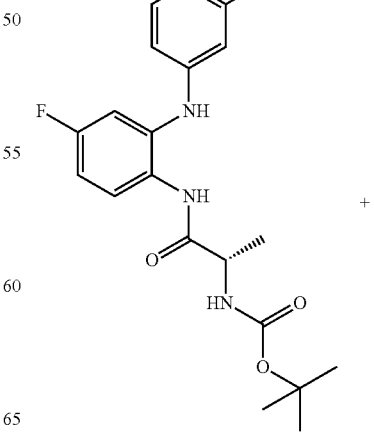

-continued

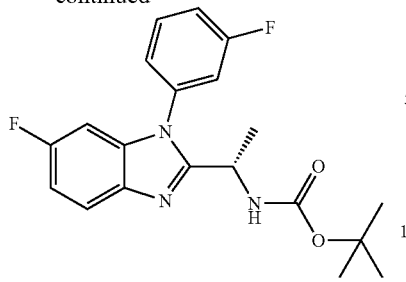

4-Fluoro-N²-(3-fluorophenyl)benzene-1,2-diamine (0.7 g, 3.18 mmol) was dissolved in DCM (10 mL), under an atmosphere of nitrogen and (S)-2-tert-butoxycarbonylaminopropionic acid (0.68 g, 3.55 mmol) added. To the resultant solution was added HOAt (0.49 g, 3.55 mmol), followed by N-methyl morpholine (0.85 mL, 7.69 mmol) and N-(3-dimethylaminopropyl)-N' ethylcarbodiimide (0.69 g, 3.55 mmol). The resultant dark yellow solution was stirred at RT (room temperature) overnight, under an atmosphere of nitrogen. The reaction mixture was diluted with DCM and washed with saturated aqueous NaHCO₃ (20 mL) and brine (20 mL). The organic fraction was dried (MgSO₄), filtered and concentrated in vacuo. The residue was purified by column chromatography (silica gel, gradient 0-10% EtOAc in DCM) to afford an off-white solid (1.2 g). This was dissolved in acetic acid (15 mL) and heated to 70° C. overnight. The resultant mixture was allowed to cool to RT and was concentrated in vacuo. The residue was dissolved in DCM and washed with saturated aqueous NaHCO₃ (20 mL) and brine (20 mL). The organic fraction was dried (MgSO₄), filtered and concentrated in vacuo. The residue was purified by column chromatography (SiO₂, gradient 0-20% EtOAc in DCM) to afford both title compounds as off-white solids (0.78 g and 0.15 g, respectively).

{(S)-1-[4-Fluoro-2-(3-fluorophenylamino)phenylcarbamoyl]ethyl}carbamic acid tert-butyl ester: ¹H NMR (CDCl₃, 400 MHz): δ 8.05 (1H, s), 7.45 (1H, dd, J=8.83, 5.91 Hz), 7.23-7.14 (1H, m), 7.04 (1H, dd, J=10.32, 2.82 Hz), 6.78-6.57 (4H, m), 6.38 (1H, s), 4.95-4.86 (1H, m), 4.27-4.17 (1H, m), 1.46-1.39 (12H, m)

{(S)-1-[6-Fluoro-1-(3-fluorophenyl)-1H-benzoimidazol-2-yl]ethyl}carbamic acid tert-butyl ester: ¹H NMR (CDCl₃, 400 MHz): δ 7.69 (1H, dd, J=8.83, 4.74 Hz), 7.62-7.53 (1H, m), 7.30-7.21 (2H, m), 7.17 (1H, d, J=8.97 Hz), 7.04 (1H, ddd, J=9.56, 8.82, 2.48 Hz), 6.81 (1H, dd, J=8.52, 2.48 Hz), 5.48-5.39 (1H, m), 5.03-4.89 (1H, m), 1.44 (3H, d, J=6.89 Hz), 1.40 (9H, s)

(S)-1-[6-Fluoro-1-(3-fluorophenyl)-1H-benzoimidazol-2-yl]ethylamine

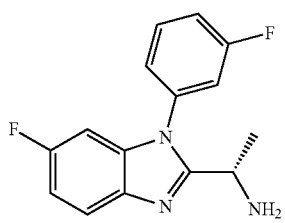 [SMILES: C[C@H](N)c1nc2ccc(F)cc2n1-c1cccc(F)c1]

Method 1: {(S)-1-[4-Fluoro-2-(3-fluorophenylamino)phenylcarbamoyl]ethyl}carbamic acid tert-butyl ester (0.5 g, 1.28 mmol) was dissolved in 4M HCl in dioxane solution (10 mL) and the reaction mixture heated to 70° C. for 2 h. The resultant mixture was allowed to cool to RT and was concentrated in vacuo. The residue was dissolved in DCM (40 mL) and washed with saturated aqueous NaHCO₃ (20 mL) and brine (20 mL). The organic layer was dried (MgSO₄), filtered and concentrated in vacuo to afford the title compound as a yellow gum (0.38 g, 100%).

Method 2: {(S)-1-[6-Fluoro-1-(3-fluorophenyl)-1H-benzoimidazol-2-yl]ethyl}carbamic acid tert-butyl ester (0.14 g, 0.38 mmol) was dissolved in DCM (6 mL) and TFA (3 mL) added dropwise. The reaction mixture was stirred at RT for 1 h. The resultant mixture was concentrated in vacuo. The residue was dissolved in DCM (40 mL) and stirred vigorously with saturated aqueous NaHCO₃ (20 mL) for 10 minutes. The organic fraction was separated, dried (MgSO₄), filtered and concentrated in vacuo to afford the title compound (80 mg, 80%). ¹H NMR (CDCl₃, 400 MHz): δ 7.72 (1H, dd, J=8.79, 4.74 Hz), 7.64-7.55 (1H, m), 7.33-7.16 (3H, m), 7.05 (1H, td, J=9.15, 2.48 Hz), 6.83 (1H, d, J=8.47 Hz), 4.16 (1H, s), 1.71 (2H, s), 1.50 (3H, d, J=6.52 Hz)

(5-Fluoro-2-nitrophenyl)-(2-fluorophenyl)amine

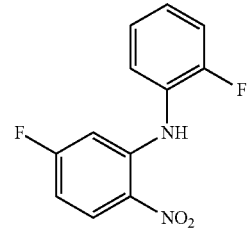 [SMILES: O=[N+]([O-])c1ccc(F)cc1Nc1ccccc1F]

A solution of 2-fluorophenylamine (1.47 g, 13.19 mmol) in anhydrous THF (20 mL) was cooled to −70° C. To this was added dropwise 1M LiHMDS in THF (25.14 mL, 25.14 mmol) over 10 minutes to afford a dark yellow solution. A solution of 2,4-difluoronitrobenzene (2.00 g, 12.57 mmol) in anhydrous THF (10 mL) was added dropwise to the yellow solution, to afford a purple solution. The was stirred at −70° C. for 15 minutes, before being allowed to reach RT. It was then quenched with saturated aqueous NH₄Cl solution (25 mL) and extracted into EtOAc (3×50 mL). The combined organic fractions were washed with brine (25 mL), dried (MgSO₄), filtered and concentrated in vacuo to afford an orange solid. This was purified by column chromatography (silica gel, gradient 0-100% DCM in cyclohexane) to afford the title compound as a yellow solid (3.04 g, 97%). ¹H NMR (CDCl₃, 400 MHz): δ 9.36 (1H, s), 8.20 (1H, dd, J=9.45, 5.94

Hz), 7.34-7.26 (1H, m), 7.24-7.10 (3H, m), 6.56 (1H, dt, J=11.09, 2.07 Hz), 6.45 (1H, ddd, J=9.44, 7.13, 2.63 Hz)

4-Fluoro-N²-(2-fluorophenyl)benzene-1,2-diamine

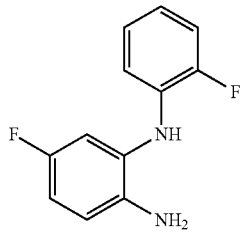

(5-Fluoro-2-nitrophenyl)-(2-fluorophenyl)amine (3.04 g, 12.16 mmol) was dissolved in EtOAc (120 mL) and the flask evacuated and flushed with nitrogen gas. 10% Pd/C (0.3 g) was added and the reaction mixture stirred under an atmosphere of hydrogen gas, at RT overnight. A further amount of 10% Pd/C (0.3 g) was added and the reaction mixture stirred under an atmosphere of hydrogen gas for an extra 2 h. The resultant mixture was filtered through Celite® and the filtrate concentrated in vacuo to afford the title compound as a dark yellow oil, which solidified on standing (2.89 g, 95%). ¹H NMR (CDCl₃, 400 MHz): δ 7.05-6.87 (2H, m), 6.83-6.68 (3H, m), 6.68-6.59 (2H, m), 5.36 (1H, s), 3.49 (2H, s)

{(S)-1-[4-Fluoro-2-(2-fluorophenylamino)phenylcarbamoyl]ethyl}carbamic acid tert-butyl ester

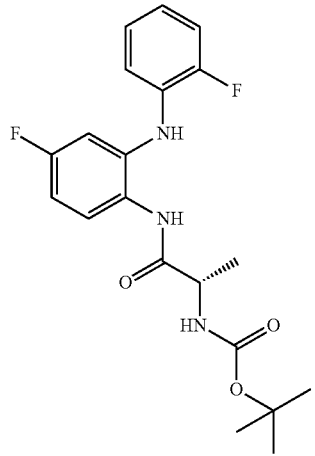 [SMILES: C[C@H](NC(=O)OC(C)(C)C)C(=O)Nc1ccc(F)cc1Nc1ccccc1F]

4-Fluoro-N²-(2-fluorophenyl)benzene-1,2-diamine (0.7 g, 3.18 mmol) was dissolved in DCM (10 mL), under an atmosphere of nitrogen and (S)-2-tert-butoxycarbonylaminopropionic acid (0.68 g, 3.55 mmol) added. To the resultant solution was added HOAt (0.49 g, 3.55 mmol), followed by N-methyl morpholine (0.85 mL, 7.69 mmol) and N-(3-dimethylaminopropyl)-N' ethylcarbodiimide (0.69 g, 3.55 mmol). The resultant dark yellow solution was stirred at RT overnight, under an atmosphere of nitrogen. Further amounts of (S)-2-tert-butoxycarbonylaminopropionic acid (0.34 g, 1.78 mmol), HOAt (0.24 g, 1.78 mmol), N-methyl morpholine (0.40 mL, 3.64 mmol) and N-(3-dimethylaminopropyl)-N'ethylcarbodiimide (0.34 g, 1.78 mmol) were added and the reaction stirred at RT for a further 2 h. The reaction mixture was diluted with DCM and washed with saturated aqueous NaHCO₃ (20 mL) and brine (20 mL). The organic fraction was dried (MgSO₄), filtered and concentrated in vacuo. The residual dark red oil was purified by column chromatography (SiO₂, gradient 0-10% EtOAc in DCM) to afford an off-white solid (1.04 g). This was dissolved in acetic acid (15 mL) and heated to 70° C. for 48 h. The resultant mixture was allowed to cool to RT and concentrated in vacuo. The residual pink oil was dissolved in DCM and washed with saturated aqueous NaHCO₃ (20 mL) and brine (20 mL). The organic fraction was dried (MgSO₄), filtered and concentrated in vacuo. The residue was purified by column chromatography (silica gel, gradient 0-20% EtOAc in DCM) to afford the title compound (0.7 g, 59%). LCMS (Method J): $R_T$ 3.62 min [M+H]⁺ 392.1

(S)-1-[6-Fluoro-1-(2-fluorophenyl)-1H-benzoimidazol-2-yl]ethylamine

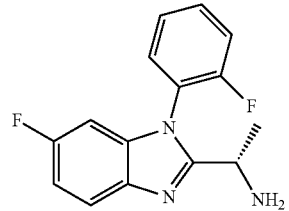 [SMILES: C[C@H](N)c1nc2ccc(F)cc2n1-c1ccccc1F]

{(S)-1-[4-Fluoro-2-(2-fluorophenylamino)phenylcarbamoyl]ethyl}carbamic acid tert-butyl ester (0.7 g, 1.80 mmol) was dissolved in 4M HCl in dioxane (10 mL) and the reaction mixture was heated to 70° C. for 5 h. The resultant mixture was concentrated in vacuo and the residue dissolved in DCM (40 mL) and washed with saturated aqueous NaHCO₃ (20 mL) and brine (20 mL). The organic fraction was dried (MgSO₄), filtered and concentrated in vacuo to afford a red gum. This was purified by column chromatography (silica gel, gradient 0-10% MeOH in DCM) to afford the title compound (0.22 g, 46%). LCMS (Method C): $R_T$ 1.74 min [M+H]⁺ 274.3

(5-Fluoro-2-nitrophenyl)-(3-methoxyphenyl)amine

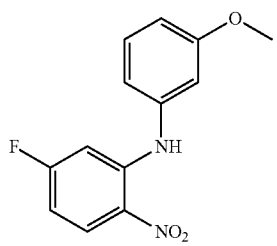 [SMILES: COc1cccc(Nc2cc(F)ccc2[N+](=O)[O-])c1]

A solution of 3-methoxyphenylamine (1.58 g, 12.82 mmol) in anhydrous THF (20 mL) was cooled to −70° C. To this was added dropwise 1M LiHMDS in THF (25.14 mL, 25.14 mmol), over 10 minutes. This was stirred at −70° C. for 15 minutes before a solution of 2,4-difluoronitrobenzene (2.00 g, 12.57 mmol) in anhydrous THF (10 mL) was added dropwise. The dark yellow solution was then allowed to reach RT and was quenched with saturated aqueous NH₄Cl solution. This was extracted into EtOAc (3×) and the combined organic fractions were washed with brine (20 mL), dried (MgSO$_4$), filtered and concentrated in vacuo to afford the title compound as a dark yellow gum, which solidified on standing (3.35 g, 100%). $^1$H NMR (CDCl$_3$, 400 MHz): δ 9.60 (1H, s), 8.25 (1H, dd, J=9.48, 5.99 Hz), 7.34 (1H, t, J=8.00 Hz), 6.90-6.77 (4H, m), 6.47 (1H, ddd, J=9.47, 7.11, 2.64 Hz), 3.83 (3H, s)

4-Fluoro-N$^2$-(3-methoxyphenyl)benzene-1,2-diamine

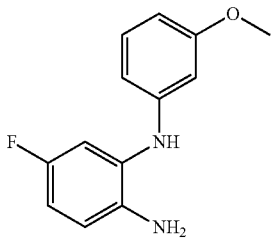 [SMILES: COc1cccc(Nc2cc(F)ccc2N)c1]

(5-Fluoro-2-nitrophenyl)-(3-methoxyphenyl)amine (3.35 g, 12.7 mmol) was dissolved in EtOAc (50 mL) and the flask evacuated and flushed with nitrogen gas. 10% Pd/C (0.35 g) was added and the reaction mixture stirred under an atmosphere of hydrogen gas, at RT overnight. A further amount of 10% Pd/C (0.35 g) was added and the reaction mixture stirred under an atmosphere of hydrogen gas for a further 1 h. The resultant mixture was filtered through Celite® and the filtrate concentrated in vacuo to afford the title compound as a red gum (2.97 g, 100%). $^1$H NMR (CDCl$_3$, 400 MHz): δ 7.15 (1H, t, J=8.08 Hz), 6.91 (1H, dd, J=9.89, 2.72 Hz), 6.76-6.62 (2H, m), 6.49-6.37 (3H, m), 5.29 (1H, s), 3.77 (3H, s), 3.52 (2H, s)

(S)-1-[6-Fluoro-1-(3-methoxyphenyl)-1H-benzoimidazol-2-yl]ethylamine

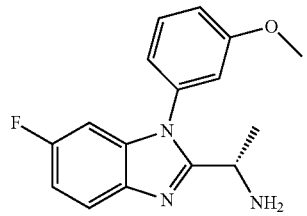 [SMILES: COc1cccc(-n2c([C@H](C)N)nc3ccc(F)cc32)c1]

4-Fluoro-N$^2$-(3-methoxyphenyl)benzene-1,2-diamine (0.7 g, 2.99 mmol) was dissolved in DCM (10 mL), under an atmosphere of nitrogen and (S)-2-tert-butoxycarbonylaminopropionic acid (0.63 g, 3.29 mmol) and HOAt (0.45 g, 3.29 mmol) added. The mixture was cooled to 0° C. before N-(3-dimethylaminopropyl)-N' ethylcarbodiimide (0.63 g, 3.29 mmol) was added portion wise. The reaction mixture was stirred at 0° C. for 1 h, before being allowed to reach RT. It was then diluted with DCM (40 mL) and washed with 10% citric acid and brine (20 mL). The organic fraction was dried (MgSO$_4$), filtered and concentrated in vacuo. The residue was dissolved in acetic acid (10 mL) and heated at 70° C. overnight. The resultant mixture was allowed to cool to RT and concentrated in vacuo to afford a dark brown gum. This was purified by column chromatography (SiO$_2$, gradient 0-5% MeOH in DCM) to afford boc protected title compound as a red gum, which solidified on standing (0.78 g, 68%). This was dissolved in DCM (10 mL) and TFA (3 mL) added. The reaction mixture was stirred at RT for 1 h. The resultant mixture was concentrated in vacuo and the residue dissolved in DCM (40 mL) and stirred vigorously with saturated aqueous NaHCO$_3$ for 10 minutes. The layers were separated and the organic fraction washed with brine (20 mL), dried (MgSO$_4$), filtered and concentrated in vacuo to afford the title compound as a red gum (0.4 g, 70%). LCMS (Method B): R$_T$ 1.90 min [M+H]$^+$ 286.0

{(S)-1-[6-Fluoro-1-(3-methoxyphenyl)-1H-benzoimidazol-2-yl]ethyl}-9H-purin-6-yl)amine

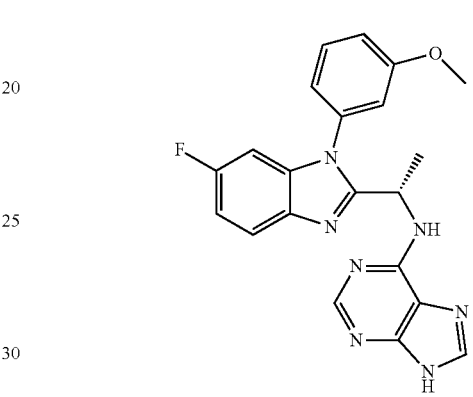

(S)-1-[6-Fluoro-1-(3-methoxyphenyl)-1H-benzoimidazol-2-yl]ethylamine (0.4 g, 1.4 mmol) was dissolved in n-butanol (5 mL) and 6-chloro-9-(tetrahydropyran-2-yl)-9H-purine (0.335 g, 1.4 mmol) and DIPEA (1.24 mL, 7.01 mmol) added. The reaction mixture was heated at 100° C. overnight. The resultant mixture was allowed to cool to RT and was concentrated in vacuo. The residue was passed down an Isolute® SCX-2 cartridge, eluting with DCM, MeOH and 2M NH$_3$ in MeOH to afford a pale red solid. This was purified by column chromatography (SiO$_2$, gradient 0-15% MeOH in DCM) to afford a mixture of the title compound plus (S)—N-[4-fluoro-2-(3-methoxyphenylamino)phenyl]-2-(9H-purin-6-ylamino)propionamide. This mixture was dissolved in acetic acid (3 mL) and heated at 100° C. for 5 h. The resultant mixture was allowed to cool to RT and was concentrated in vacuo. The residue was purified by column chromatography (silica gel, gradient 0-7% [2M NH$_3$ in MeOH] in DCM) to afford the title compound as an off-white solid (36%). LCMS (Method J): R$_T$ 2.55 min [M+H]$^+$ 404.2

Cyclohexyl-(5-fluoro-2-nitrophenyl)amine

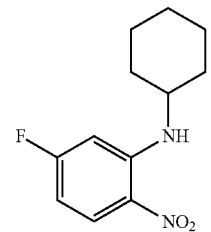 [SMILES: O=[N+]([O-])c1ccc(F)cc1NC1CCCCC1]

2,4-Difluoronitrobenzene (2.00 g, 12.57 mmol) was dissolved in acetonitrile (20 mL) and cyclohexylamine (1.25 g, 12.57 mmol) and DIPEA (2.2 mL, 12.57 mmol) added. The reaction mixture was stirred at RT overnight. The resultant mixture was concentrated in vacuo to afford a bright yellow gum. This was purified by column chromatography (silica gel, gradient 0-10% EtOAc in cyclohexane) to afford the title compound as a bright yellow oil (2.4 g, 92%). $^1$H NMR (CDCl$_3$, 400 MHz): δ 8.20 (1H, dd, J=9.50, 6.22 Hz), 6.49 (1H, dd, J=11.75, 2.62 Hz), 6.31 (1H, ddd, J=9.51, 7.26, 2.61 Hz), 3.47-3.33 (1H, m), 2.11-1.98 (2H, m), 1.85-1.77 (2H, m), 1.72-1.60 (1H, m), 1.48-1.26 (5H, m)

N$^2$-Cyclohexyl-4-fluorobenzene-1,2-diamine

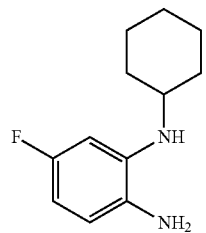

(Cyclohexyl-(5-fluoro-2-nitrophenyl)amine (2.4 g, 10.0 mmol) was dissolved in EtOAc (40 mL) and the flask evacuated and flushed with nitrogen gas. 10% Pd/C (0.24 g) was added and the reaction mixture stirred under an atmosphere of hydrogen gas, at RT overnight. The resultant mixture was filtered through Celite® and the filtrate was concentrated in vacuo to afford the title compound as a dark red oil (1.9 g, 92%). $^1$H NMR (CDCl$_3$, 400 MHz): δ 6.61 (1H, dd, J=8.35, 5.74 Hz), 6.35 (1H, dd, J=11.23, 2.77 Hz), 6.27 (1H, td, J=8.43, 2.76 Hz), 3.23-3.11 (1H, m), 2.11-2.00 (2H, m), 1.83-1.72 (2H, m), 1.70-1.60 (1H, m), 1.47-1.12 (5H, m)

[(S)-1-[1-Cyclohexyl-6-fluoro-1H-benzoimidazol-2-yl)ethyl]carbamic acid tert-butyl ester

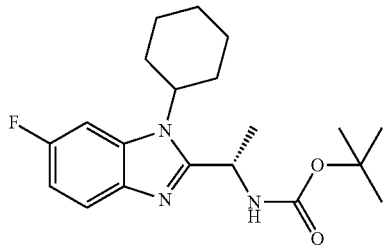 [SMILES: C[C@H](NC(=O)OC(C)(C)C)c1nc2ccc(F)cc2n1C1CCCCC1]

N$^2$-Cyclohexyl-4-fluorobenzene-1,2-diamine (0.7 g, 3.36 mmol) was dissolved in DCM (10 mL) and (S)-2-tert-butoxycarbonylaminopropionic acid (0.70 g, 3.70 mmol) and HOAt (0.51 g, 3.70 mmol) added. The dark green solution was cooled to 0° C. before N-(3-dimethylaminopropyl)-N' ethylcarbodiimide (0.71 g, 3.70 mmol) was added, portion wise over 5 minutes. The reaction mixture was stirred at 0° C. for 1 h. The resultant mixture was allowed to reach RT before being diluted with DCM (20 mL) and washed with citric acid (20 mL) and brine (20 mL). The organic fraction was dried (MgSO$_4$), filtered and concentrated in vacuo to afford a pale red gum (1.36 g). This was dissolved in acetic acid (10 mL) and heated at 80° C. overnight. The resultant mixture was allowed to cool to RT and was concentrated in vacuo. The residue was dissolved in DCM (40 mL) and washed with saturated aqueous NaHCO$_3$ (20 mL) and brine (20 mL). The organic fraction was dried (MgSO$_4$), filtered and concentrated in vacuo to afford a dark red gum. This was purified by column chromatography (silica gel, gradient 0-50% EtOAc in cyclohexane) to afford the title compound as a yellow gum (0.55 g, 43%). LCMS (Method B): R$_T$ 3.22 min [M+H]$^+$ 362.1

(S)-1-(1-Cyclohexyl-6-fluoro-1H-benzoimidazol-2-yl)ethylamine

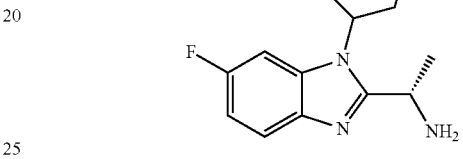

[(S)-1-[1-Cyclohexyl-6-fluoro-1H-benzoimidazol-2-yl)ethyl]carbamic acid tert-butyl ester (0.55 g, 1.52 mmol) was dissolved in DCM (10 mL) and TFA (4 mL) added. The reaction mixture was stirred at RT for 30 minutes. The resultant mixture was concentrated in vacuo and the residue was dissolved in DCM (40 mL) and stirred vigorously with saturated aqueous NaHCO$_3$ for 10 minutes. The layers were separated and the organic fraction was washed with brine (20 mL), dried (MgSO$_4$), filtered and concentrated in vacuo to afford the title compound as a dark yellow gum which solidified on standing (0.41 g, 100%). $^1$H NMR (CDCl$_3$, 400 MHz): δ 7.63 (1H, s), 7.22 (1H, s), 7.01-6.89 (1H, m), 4.43-4.21 (2H, m), 2.29-2.09 (2H, m), 2.06-1.66 (5H, m), 1.57 (3H, s), 1.51-1.23 (3H, m)

3-Bromo-N$^2$-cyclopropyl-4-fluorobenzene-1,2-diamine

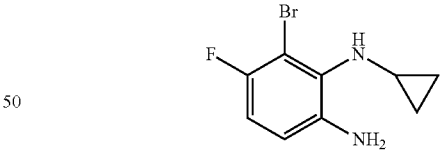

To a solution of 2-bromo-1,3-difluoro-4-nitrobenzene (1.19 g, 5.0 mmol) in MeCN (10 mL) were added DIPEA (1.74 mL, 10.0 mmol) and cyclopropylamine (360 mL, 5.17 mmol). The reaction mixture was stirred at RT for 4 h. The volatiles were removed under reduced pressure and the resulting residue was partitioned between DCM and water. The organic fraction was dried, concentrated in vacuo and the resulting residue taken up in a 3:1 mixture of MeOH:water (40 mL). NH$_4$Cl (1.53 g, 28.6 mmol) and iron powder (1.06 g, 4.76 mmol) were added and the reaction mixture heated at 80° C. for 3 h. After cooling to RT, the mixture was filtered through a pad of Celite® and washed with additional MeOH. The filtrate was concentrated in vacuo and the resulting residue partitioned between DCM and an aqueous solution of NaHCO$_3$. The organic fraction was dried and concentrated in vacuo and the resulting residue purified by column chromatography (Si—PCC, gradient 0-5% MeOH in EtOAc) to afford the title compound as a brown oil (759 mg, 62% over 2 steps). LCMS (Method C): R$_T$ 2.97 min [M+H]$^+$ 245.02

[(S)-1-(3-Bromo-2-cyclopropylamino-4-fluorophenylcarbamoyl)ethyl]carbamic acid tert-butyl ester

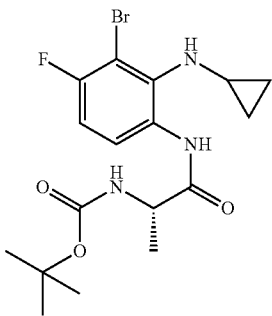 [SMILES: C[C@H](NC(=O)OC(C)(C)C)C(=O)Nc1ccc(F)c(Br)c1NC1CC1]

A mixture of 3-bromo-N$^2$-cyclopropyl-4-fluorobenzene-1,2-diamine (759 mg, 3.10 mmol), (S)-2-tertbutoxycarbonylaminopropionic acid (644 mg, 3.41 mmol), HOAt (464 mg, 3.41 mmol) and N-(3-dimethylaminopropyl)-N-ethylcarbodiimide hydrochloride (654 mg, 3.41 mmol) in DCM (20 mL) was stirred at 0° C. for 1 h. The reaction mixture was then partitioned between DCM and a saturated solution of NaHCO$_3$. The organic fraction was dried and concentrated in vacuo. The resulting residue was purified by column chromatography (Si—PCC, gradient 0-50% EtOAc in cyclohexane) to afford the title compound (1.05 g, 81%) as a pale beige solid. LCMS (Method C): R$_T$ 3.66 min [M+H]$^+$ 416.05

[(S)-1-(7-Bromo-1-cyclopropyl-6-fluoro-1H-benzoimidazol-2-yl)ethyl]carbamic acid tert-butyl ester

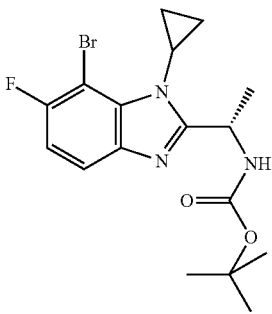 [SMILES: C[C@H](NC(=O)OC(C)(C)C)c1nc2ccc(F)c(Br)c2n1C1CC1]

[(S)-1-(3-Bromo-2-cyclopropylamino-4-fluoro-phenylcarbamoyl)ethyl]carbamic acid tert-butyl ester (1.05 g, 2.52 mmol) was taken up in AcOH (12 mL) and heated at 70° C. for 16 h. After cooling to RT, the volatiles were evaporated in vacuo and the residue was partitioned between EtOAc and a saturated solution of NaHCO$_3$. The aqueous phase was further extracted with EtOAc and the combined organic fractions were washed with brine, dried (Na$_2$SO$_4$) and concentrated in vacuo. The resulting residue was purified by column chromatography (Si—PCC, gradient 0-50% EtOAc in cyclohexane) to afford the title compound (771 mg, 77%) as a yellow oil. LCMS (Method C): R$_T$ 3.65 min [M+H]$^+$ 398.09.

(S)-1-(7-Bromo-1-cyclopropyl-6-fluoro-1H-benzoimidazol-2-yl)ethylamine

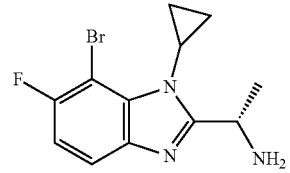 [SMILES: C[C@H](N)c1nc2ccc(F)c(Br)c2n1C1CC1]

TFA (1 mL) was added to a solution of [(S)-1-(7-bromo-1-cyclopropyl-6-fluoro-1H-benzoimidazol-2-yl)ethyl]carbamic acid tert-butyl ester (133 mg, 0.33 mmol) in DCM (3 mL). After stirring at RT for 2 h, the reaction mixture was diluted with MeOH and loaded onto an Isolute® SCX-2 cartridge. The cartridge was washed with MeOH followed by 2M NH$_3$/MeOH. The basic fractions were combined and concentrated in vacuo to afford the title compound as a colourless oil (87 mg, 87%). LCMS (Method C): R$_T$ 1.99 min [M+H]$^+$ 298.10

{(S)-1-[1-Cyclopropyl-6-fluoro-7-(morpholine-4-carbonyl)-1H-benzoimidazol-2-yl]ethyl}carbamic acid tert-butyl ester

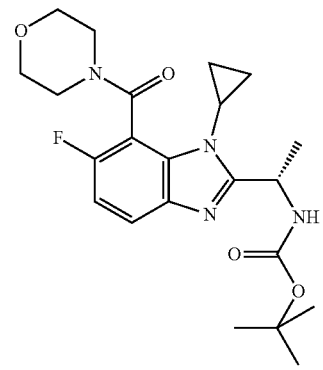 [SMILES: C[C@H](NC(=O)OC(C)(C)C)c1nc2ccc(F)c(C(=O)N3CCOCC3)c2n1C1CC1]

A solution of 2-((S)-1-tert-butoxycarbonylaminoethyl)-3-cyclopropyl-5-fluoro-3H-benzoimidazole-4-carboxylic acid methyl ester (441 mg, 1.17 mmol) and LiOH.H$_2$O (196 mg, 4.67 mmol) in MeOH (20 mL) and water (2 mL) was heated at 90° C. for 4 h. Additional LiOH.H$_2$O (196 mg) was added and the mixture heated at 90° C. for 48 h. After cooling to RT, the organic solvent was removed in vacuo and the pH of the mixture adjusted to 3 by addition of 1M HCl$_{(aq)}$. The aqueous phase was extracted with EtOAc (×3) and the combined organic fractions were washed with brine, dried (Na$_2$SO$_4$) and concentrated in vacuo. A mixture of this residue (349 mg), HATU (401 mg, 1.06 mmol), morpholine (125 µL, 1.44 mmol) and DIPEA (335 µL, 1.92 mmol) in DCM (10 mL) was stirred at RT for 1 h. The reaction mixture was partitioned between DCM and a saturated solution of NaHCO$_3$. The organic layer was dried and concentrated in vacuo. The resulting residue was purified by column chromatography (Si—PCC, gradient 0-100% EtOAc in cyclohexane) to afford the title compound (380 mg, 75% over 2 steps) as a pale yellow oil. LCMS (Method C): $R_T$ 2.64 min [M+H]$^+$ 433.25

[2-((S)-1-Aminoethyl)-3-cyclopropyl-5-fluoro-3H-benzoimidazol-4-yl]-morpholin-4-yl-methanone

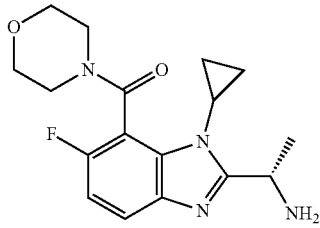 [SMILES: C[C@H](N)c1nc2ccc(F)c(C(=O)N3CCOCC3)c2n1C1CC1]

TFA (1 mL) was added to a stirring solution of {(S)-1-[1-cyclopropyl-6-fluoro-7-(morpholine-4-carbonyl)-1H-benzoimidazol-2-yl]ethyl}carbamic acid tert-butyl ester (380 mg, 0.88 mmol) in DCM (3 mL). After stirring at RT for 2 h, the reaction mixture was diluted with MeOH and loaded onto an Isolute® SCX-2 cartridge. The cartridge was washed with MeOH followed by 2M NH$_3$/MeOH. The basic fractions were combined and concentrated in vacuo to afford the title compound as a pale yellow oil (214 mg, 73%). LCMS (Method B): $R_T$ 1.62 and 1.70 min [M+H]$^+$ 333.12

(5-Fluoro-2-nitro-phenyl)(1-methyl-1H-pyrazol-3-yl)amine

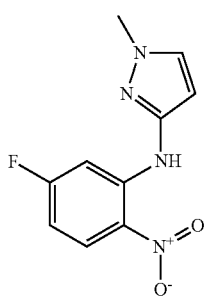

Potassium tert-butoxide (898 mg, 8.0 mmol) was added to a stirred solution of 1-methyl-1H-pyrazol-3-ylamine (0.35 mL 4.00 mmol) in anhydrous THF (5 mL) under a nitrogen atmosphere at 0° C. After 15 min 2,4-difluoro-1-nitrobenzene (0.44 mL, 4.0 mmol) in anhydrous THF (5 mL) was added and stirring at 0° C. continued for 1 h. The reaction mixture was poured into a solution of NH$_4$Cl (50 mL). The aqueous phase was extracted with EtOAc (×2) and the combined organic fractions washed with brine, dried (Na$_2$SO$_4$) and concentrated in vacuo. The resulting residue was purified by column chromatography (Si—PCC, gradient 0-100% EtOAc in cyclohexane) to afford the title compound as a dark red solid (386 mg, 41%). LCMS (Method C): $R_T$ 3.29 min [M+H]$^+$ 237.08

4-Fluoro-N$^2$-(1-methyl-1H-pyrazol-3-yl)-benzene-1,2-diamine

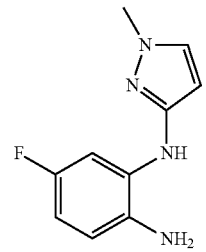

A mixture of (5-fluoro-2-nitro-phenyl)-(1-methyl-1H-pyrazol-3-yl)amine (386 mg, 1.63 mmol) in EtOAc (10 mL) was degassed with a stream of nitrogen prior to the addition of 10% Pd/C (50 mg) and was stirred at RT under a hydrogen atmosphere for 24 h. The mixture was filtered and the filtrate was concentrated in vacuo to afford the title compound as a grey oil (350 mg, quant.). LCMS (Method C): $R_T$ 1.63 min [M+H]$^+$ 207.17

{(S)-1-[6-Fluoro-1-(1-methyl-1H-pyrazol-3-yl)-1H-benzoimidazol-2-yl]ethyl}carbamic acid tert-butyl ester

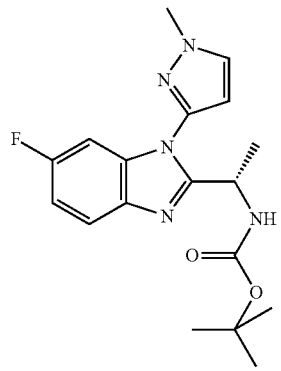 [SMILES: C[C@H](NC(=O)OC(C)(C)C)c1nc2ccc(F)cc2n1-c1ccn(C)n1]

To a suspension of (S)-Boc-alaninamide (614 mg, 3.27 mmol) in DCM (5 mL) was added triethyloxonium tetrafluoroborate (621 mg, 3.27 mmol) in one portion under a nitrogen atmosphere. The resulting mixture stirred at RT for 1 h. The volatiles were removed in vacuo and to the resulting residue was added 4-fluoro-N$^2$-(1-methyl-1H-pyrazol-3-yl)-benzene-1,2-diamine (350 mg, 1.70 mmol) in absolute EtOH (5 mL) and the mixture stirred at 80° C. for 2 h. The volatiles were removed in vacuo and the resulting residue partitioned between DCM and an aqueous solution of NaHCO$_3$. The organic fraction was dried, concentrated in vacuo and the resulting residue purified by column chromatography (Si—

PCC, gradient 0-50% EtOAc in DCM) to afford the title compound as a purple oil (187 mg, 31%). LCMS (Method B): $R_T$ 3.18 min [M+H]$^+$ 360.05

(2-Bromo-6-nitrophenyl)phenylamine

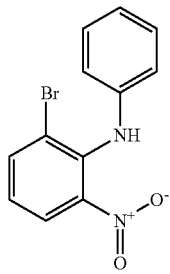 [SMILES: O=[N+]([O-])c1cccc(Br)c1Nc1ccccc1]

A solution of 1-bromo-2-fluoro-3-nitrobenzene (5 g, 22.7 mmol) and aniline (4.2 mL, 45 mmol) in DMSO (10 mL, 2M) in a sealed flask was evacuated and purged with argon. The mixture was heated at 100° C. for 12 h. The cooled mixture was diluted with KHSO$_4$ (aq. satd. solution, 100 mL) and brine, dried (Na$_2$SO$_4$) and concentrated to give the product (2-bromo-6-nitrophenyl)phenylamine as a bright orange solid (6.5 g, quant.). $^1$H NMR (400 MHz, CDCl$_3$): δ 7.96 (1H, dd, J=8.5, 1.7 Hz), 7.86 (1H, br s), 7.75 (1H, dd, J=8.2, 1.5 Hz), 7.16-7.22 (2H, m), 6.90-6.99 (2H, m), 6.77 (2H, m).

3-Bromo-N$^2$-phenylbenzene-1,2-diamine

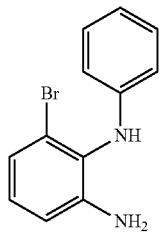

(2-Bromo-6-nitrophenyl)phenylamine (6.5 g, 22.7 mmol) was dissolved in EtOAc (100 mL) and SnCl$_2$.H$_2$O (25 g) added under a nitrogen atmosphere. The resulting mixture was heated at reflux for 5 h. The cooled reaction mixture was diluted with NaHCO$_3$ (aq. satd. solution, 100 mL) and additional NaHCO$_3$ added until all effervescence had ceased. The mixture was filtered through Celite® to remove insoluble inorganic material. The EtOAc layer was separated, washed with brine, dried (Na$_2$SO$_4$) and concentrated in vacuo. The residue was purified by chromatography (Si—PCC, 0-50% EtOAc in cyclohexane) to give the product as a yellow crystalline solid (4.41 g, 77%). $^1$H NMR (300 MHz, CDCl$_3$): δ 7.24-7.17 (2H, m), 7.01 (1H, dd, J=8.0, 1.5 Hz), 6.94 (1H, d, J=7.9 Hz), 6.85 (1H, dt, J=7.4, 1.0 Hz), 6.72 (1H, dd, J=7.9, 1.5 Hz), 6.67-6.61 (2H, m), 5.36 (1H, br s), 3.97 (2H, br s)

[(S)-1-(3-Bromo-2-phenylamino(phenylcarbamoyl))ethyl]carbamic acid tert-butyl ester

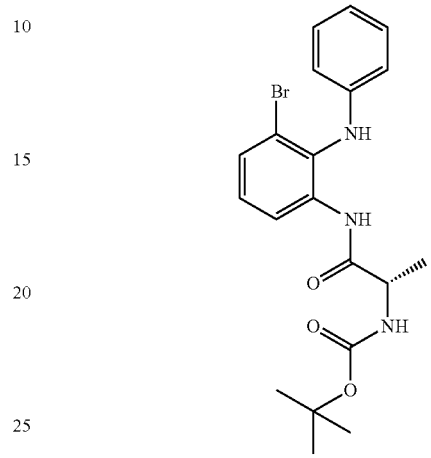

3-Bromo-N$^2$-phenylbenzene-1,2-diamine (2.46 g, 9 mmol), (S)-(2-tert-butoxycarbonylamino)propionic acid (1.7 g, 9 mmol) and HOAt (1.43 g, 10.8 mmol) were suspended in DCM (50 mL) and the resulting mixture cooled at 0° C. The reaction mixture was stirred under nitrogen for 1 h whereupon all solid material dissolved. N-(3-dimethylaminopropyl)-N-ethylcarbodiimide hydrochloride (2.57 g, 13.3 mmol) was added to the solution and stirring continued for 1 h. Citric acid (aq. satd. solution, 50 mL) was added to the reaction mixture resulting in the precipitation of a white solid. The mixture was diluted with water until the solid dissolved. The resulting solution was extracted with additional DCM. The DCM extract was washed with brine, dried (Na$_2$SO$_4$) and was concentrated in vacuo to give the product as white foam (3.9 g, quant.). LCMS (Method B): $R_T$ 3.90 min; m/z [M+H]$^+$ 434/436

(S)-1-(7-Bromo-1-phenyl-1H-benzoimidazol-2-yl)ethylamine dihydrochloride

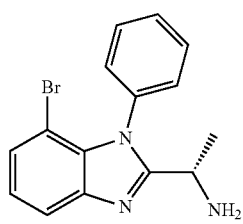 [SMILES: C[C@H](N)c1nc2cccc(Br)c2n1-c1ccccc1]

[(S)-1-(3-Bromo-2-phenylamino(phenylcarbamoyl))ethyl]carbamic acid tert-butyl ester (3.9 g, 9 mmol) was dissolved in HCl (25 mL, 2M in dioxane). The resulting brown solution was heated to 60° C. for 6 h; during this time effervescence was observed and a white solid was deposited. The white solid was isolated by filtration and washed with EtOAc and ether to give the product as a white solid (2.7 g, 77%). LCMS (Method B): $R_T$ 2.22 min; m/z [M+H]$^+$ 316/318

[(S)-1-(7-Bromo-1-phenyl-1H-benzoimidazol-2-yl) ethyl][9-(tetrahydropyran-2-yl)-9H-purin-6-yl]amine

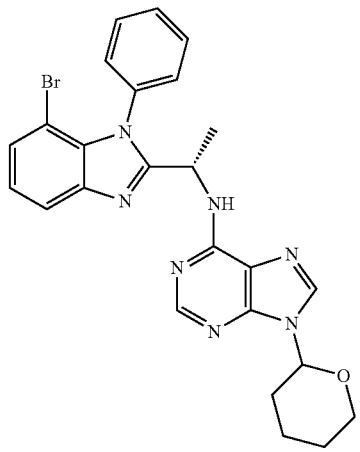 [SMILES: C[C@H](Nc1ncnc2c1ncn2C1CCCCO1)c1nc2cccc(Br)c2n1-c1ccccc1]

(S)-1-(7-Bromo-1-phenyl-1H-benzoimidazol-2-yl)ethylamine dihydrochloride (1 g, 2.5 mmol), 6-chloro-9-(tetrahydropyran-2-yl)-9H-purine (0.736 g, 3.1 mmol) and DIPEA (2.26 mL, 13 mmol) in IPA (4 mL) were heated in a sealed tube for 4 h. The cooled reaction mixture was concentrated in vacuo; the residue dissolved in EtOAc and the resulting solution washed with water, brine, dried (Na$_2$SO$_4$) and concentrated in vacuo. The residue was purified on silica (Si—PCC, 0-10% MeOH in DCM) to give the product as a white solid (870 mg, 67%). LCMS (Method B): $R_T$ 3.48 min; m/z [M+H]$^+$ 518/520

2-Amino-4-chloro-6-methylpyrimidine-5-carbonitrile step i)
4-Chloro-5-iodo-6-methylpyrimidin-2-ylamine

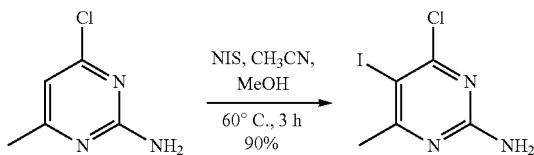

4-Chloro-6-methylpyrimidin-2-ylamine (5 g, 0.04 mol) was suspended in acetonitrile (50 mL) and methanol (50 mL) and N-iodosuccinimide (12 g, 0.05 mol, 1.5 equiv.) added to the resulting mixture. The mixture was heated to 60° C. under a nitrogen atmosphere for 3 h. A solid precipitated in the resulting brown mixture and was isolated by filtration and washed with cyclohexane to give a white crystalline solid 6 g, 65%. Additional product (~2.5 g) was present in the mother liquors. LCMS m/e 270 $^{35}$Cl/272 $^{37}$Cl (M$^+$+1);

step ii)
2-Amino-4-chloro-6-methylpyrimidine-5-carbonitrile

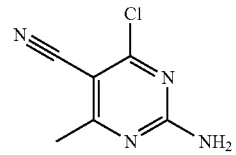

A mixture of 4-chloro-5-iodo-6-methylpyrimidin-2-ylamine (1.35 g, 5.0 mmol), zinc cyanide (288 mg, 2.45 mmol) and tetrakis(triphenylphosphine)palladium (290 mg, 5 mol %) in DMF (20 mL) was purged with argon gas and heated at 140° C., for 15 min, by microwave irradiation. After cooling to RT, the residue was partitioned between EtOAc and water. The aqueous phase was further extracted with EtOAc and the combined organic fractions washed with brine, dried (Na$_2$SO$_4$) and concentrated in vacuo. The resulting residue was purified by column chromatography (Si—PCC, gradient 0-30% EtOAc in DCM) followed by further column chromatography (Si—PCC, gradient 0-7% MeOH in DCM) to afford the title compound (40 mg, 5%) as a pale yellow solid. LCMS (Method C): $R_T$ 2.23 min [M+H]$^+$ 169.00. $^1$H NMR (DMSO-d$_6$, 400 MHz): δ 8.11 (2H, br s), 2.42 (3H, s)

(5-Fluoro-2-nitrophenyl)pyrimidin-4-ylamine

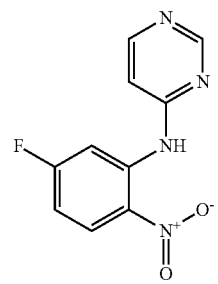 [SMILES: O=[N+]([O-])c1ccc(F)cc1Nc1ccncn1]

To 4-aminopyrimidine (1.0 g, 10.52 mmol) in THF (40 ml) at 0° C. under nitrogen was added potassium tert-butoxide (2.46 g, 22 mmol). After stirring for 5 min 2,4-difluoronitrobenzene (1.672 g, 10.52 mmol) was added dropwise. The reaction was stirred for 1 h at 0° C. then at 20° C. for 1 h, then quenched with 5% citric acid to give a pH of 5. The mixture was extracted with EtOAc (150 mL), dried (Na$_2$SO$_4$) and evaporated to an orange gum. This was purified by column chromatography (Si—PCC, gradient 0-5% MeOH in DCM to give the title compound as a yellow solid, (0.31 g, 12%). LCMS (Method B): $R_T$=2.16 min, $[M+H]^+$=234.91

4-Fluoro-$N^2$-pyrimidin-4-ylbenzene-1,2-diamine

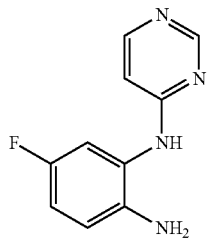 [SMILES: Nc1ccc(F)cc1Nc1ccncn1]

(5-Fluoro-2-nitrophenyl)pyrimidin-4-ylamine (0.31 g, 1.32 mmol) in IMS was hydrogenated at RT and pressure for 3.5 h using Pd—C (30 mg) as a catalyst. The catalyst was removed by filtration through Celite. The filtrate was concentrated in vacuo to give the title compound as an orange solid, (0.249 g, 92%). LCMS (Method J): $R_T$=0.56 min, $[M+H]^+$=205.16

{(S)-1-[4-Fluoro-2-(pyrimidin-4-ylamino)phenylcarbamoyl]ethyl}carbamic acid tert-butyl ester

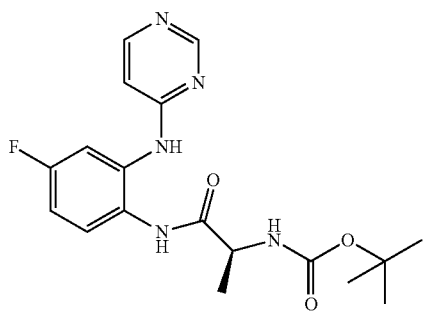 [SMILES: C[C@H](NC(=O)OC(C)(C)C)C(=O)Nc1ccc(F)cc1Nc1ccncn1]

To 4-fluoro-$N^2$-pyrimidin-4-ylbenzene-1,2-diamine (0.247 g, 1.21 mmol), Boc-alanine (0.24 g, 1.27 mmol), and HOAT (0.165 g, 1.21 mmol) in DCM at 0° C. under nitrogen was added N-(3-dimethylaminopropyl)-n'-ethylcarbodiimide hydrochloride (0.244 g, 1.27 mmol). The reaction was stirred and allowed to warm to RT overnight. The mixture was diluted with DCM (20 mL) and washed with 0.5M NaHCO₃ (20 mL). The organic extract was dried (Na₂SO₄), concentrated in vacuo and purified by column chromatography (Si—PCC, gradient 0-8% (9:1 MeOH/0.880 NH₃) in DCM). Product containing fractions were evaporated to give the title compound, (0.272 g, 60%) LCMS (Method J): $R_T$=1.93 min, $[M+H]^+$=376.20

(S)—N-[4-Fluoro-2-(pyrimidin-4-ylamino)phenyl]-2-[9-(tetrahydropyran-2-yl)-9H-purin-6-ylamino]propionamide

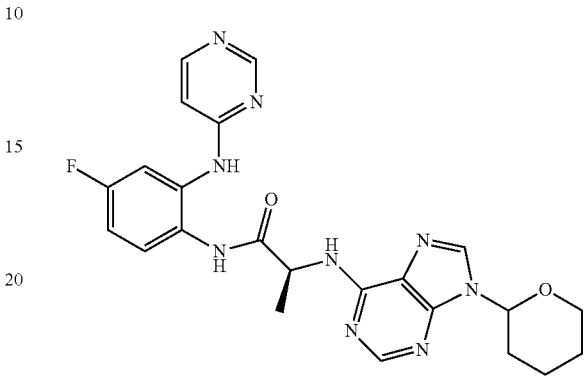

{(S)-1-[4-Fluoro-2-(pyrimidin-4-ylamino)phenylcarbamoyl]ethyl}carbamic acid tert-butyl ester (0.27 g, 0.72 mmol) was treated with 4M HCl in dioxane (10 mL) for 45 min at 20° C. The solvent was removed by evaporation under reduced pressure to give a solid, (0.29 g). 0.145 g of this solid was treated in a sealed tube with 6-chloro-9-(tetrahydropyran-2-yl)-9H-purine (103 mg, 0.43 mmol) and DIPEA (0.25 mL), 1.44 mmol) in IPA (1.5 mL) at 80° C. under argon for 16 h. The reaction mixture was diluted with EtOAc (20 mL) and washed with water (5 mL). The aqueous layer was extracted with EtOAc (10 mL). The combined organic extracts were dried (Na₂SO₄), concentrated in vacuo and purified by column chromatography (Si—PCC, gradient 0-10% (9:1 MeOH/0.880 NH₃) in DCM) to give the title compound as an orange gum, (88 mg, 51%). LCMS (Method B): $R_T$ 1.99 min $[M+H]^+$ 478.13

(S)—N-[4-Fluoro-2-(pyrimidin-4-ylamino)phenyl]-2-(9H-purin-6-ylamino)thiopropionamide

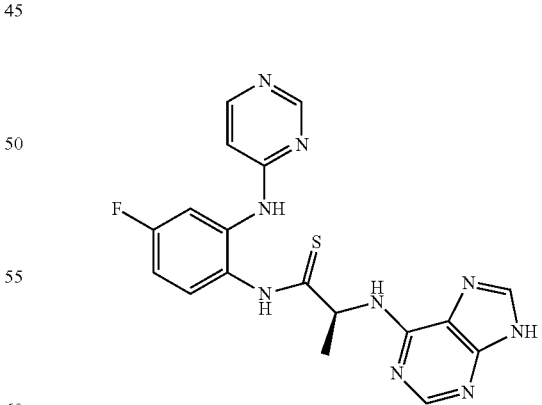

(S)—N-[4-Fluoro-2-(pyrimidin-4-ylamino)phenyl]-2-[9-(tetrahydro-pyran-2-yl)-9H-purin-6-ylamino]propionamide (88 mg, 0.18 mmol) and Lawesson's reagent (298 mg, 0.74 mmol) were heated at reflux in THF (4 mL) under nitrogen for 16 h. Further Lawesson's reagent (150 mg, 0.37 mmol) was added and the reaction refluxed for a further 24 h. The reaction mixture was cooled, diluted with EtOAc (30 mL) and extracted with 1M HCl (2×5 mL). The aqueous extracts were basified with Na₂CO₃ and extracted with EtOAc (2×20 mL). The combined organic extracts were dried (Na₂SO₄), concentrated in vacuo and purified by column chromatography (Si—PCC, gradient 0-10% (9:1 MeOH/0.880 NH₃) in DCM to give the title compound as a colourless gum, (9 mg, 12%). LCMS (Method B): $R_T$ 1.88 min [M+H]⁺ 410.09

5-Fluoro-2-nitro-phenyl)-pyrazin-2-yl-amine

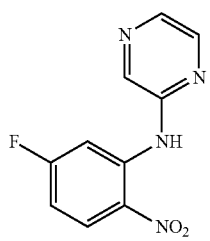 [SMILES: O=[N+]([O-])c1ccc(F)cc1Nc1cnccn1]

LiHMDS (1.0 M in tetrahydrofuran, 27.4 ml, 27.4 mmol) was added to a solution of aminopyrazine (1.43 g, 15.0 mmol) in tetrahydrofuran (50.0 ml) at −5° C. The reaction was stirred for 15 minutes then 2,4-difluoronitrobenzene (1.50 ml, 13.7 mmol) was added and the reaction stirred for a further 45 minutes. The reaction was quenched with water then poured into sodium bicarbonate (dilute aqueous) and the aqueous layer extracted with EtOAc (×3). The combined organic fractions were washed with brine, dried (Na₂SO₄) and concentrated in vacuo. The product was purified by chromatography (SiO₂, 0-70% EtOAc/cyclohexane) to yield the title compound (918 mg, 29%). ¹H NMR (CDCl₃, 400 MHz): δ 10.7 (1H, br s), 8.84 (1H, dd, J 12.3, 2.8 Hz), 8.37 (1H, d, J=1.7 Hz), 8.34 (1H, dd, J 9.4, 5.7 Hz), 8.29 (1H, dd, J 2.8, 1.6 Hz), 8.23 (1H, d, J=2.7 Hz), 6.75 (1H, ddd, J 9.6, 6.8, 2.7 Hz).

4-Fluoro-N²-pyrazin-2-yl-benzene-1,2-diamine

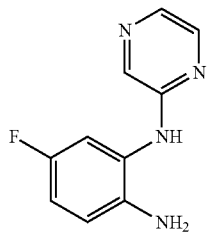 [SMILES: Nc1ccc(F)cc1Nc1cnccn1]

(5-Fluoro-2-nitrophenyl)pyrazin-2-yl-amine (415 mg, 1.77 mmol) in IMS (15.0 ml) was added to palladium on charcoal (10 wt %, 45.0 mg) and stirred under a hydrogen atmosphere overnight. The reaction mixture was filtered through Celite® and the filtrate concentrated in vacuo. The product was purified by chromatography (SiO₂, 0-10% 2M ammonia methanol/DCM) to yield the title compound (160 mg, 0.78 mmol, 44%). ¹H NMR (MeOD, 400 MHz): δ 8.04 (2H, m), 7.83 (1H, m), 7.21 (1H, dd, J 9.9, 2.8 Hz), 6.84 (1H, dd, J 8.7, 5.6 Hz), 6.74 (1H, ddd, J 8.9, 8.2, 2.9 Hz).

{(S)-1-[4-Fluoro-2-(pyrazin-2-ylamino)-phenylcarbamoyl]-ethyl}-carbamic acid tert-butyl ester

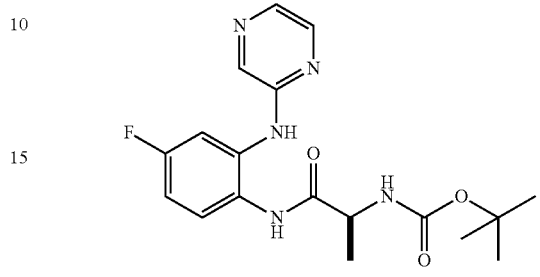

N-(tert-Butoxycarbonyl)-L-alanine (150 mg, 0.78 mmol), N-(3-dimethylaminopropyl)-N'-ethylcarbodiimide hydrochloride (165 mg, 0.86 mmol) and HOAt (106 mg, 0.78 mmol) were added to 4-fluoro-N²-pyrazin-2-yl-benzene-1,2-diamine (160 mg, 0.78 mmol) in DCM (10.0 ml) and DMF (1.00 ml) at 0° C. The reaction was stirred for 3 h then poured into water and the aqueous layer extracted with DCM (×3). The combined organic fractions were washed with brine, dried (Na₂SO₄) and concentrated in vacuo. The product was purified by chromatography (SiO₂, 0-10% methanol/DCM) to yield the title compound (144 mg, 0.38 mmol, 50%). LCMS: $R_T$ 3.02 min [M+H]⁺ 376.2. ¹H NMR (CDCl₃, 400 MHz): δ 8.36 (1H, s), 8.12 (1H, dd, J2.8, 1.5 Hz), 8.03 (1H, br s), 8.02 (1H, d, J=2.7 Hz), 7.92 (1H, br s), 7.62 (1H, br s), 7.28 (1H, m), 6.77 (1H, td, J 8.4, 2.9 Hz), 4.97 (1H, br s), 4.20 (1H, m), 1.49 (3H, d, J 7.2 Hz), 1.45 (9H, s).

(S)-2-Amino-N-[4-fluoro-2-(pyrazin-2-ylamino)-phenyl]-propionamide hydrochloride

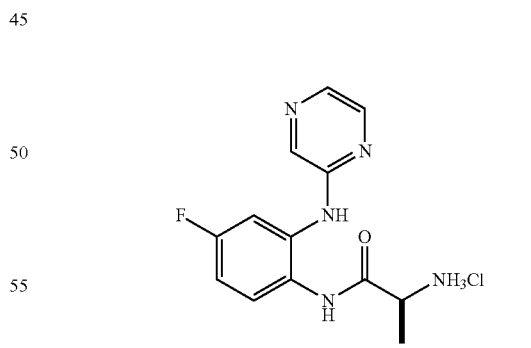

{(S)-1-[4-Fluoro-2-(pyrazin-2-ylamino)phenylcarbamoyl]ethyl}carbamic acid tert-butyl ester (144 mg, 0.38 mmol) was suspended in hydrochloric acid (4.0 M in 1,4-dioxane, 5.0 ml) and heated at 60° C. for 20 minutes, then concentrated in vacuo to yield the title compound (118 mg, 0.38 mmol, 99%). ¹H NMR (MeOD, 400 MHz): δ 8.20 (2H, m), 7.96 (1H, d, J=2.7 Hz), 7.59 (1H, dd, J 10.1, 2.7 Hz), 7.53 (1H, dd, J 9.2, 5.9 Hz), 6.96 (1H, td, J 8.3, 2.9 Hz), 4.10 (3H, m), 1.49 (3H, d, J=7.0 Hz).

(S)—N-[4-Fluoro-2-(pyrazin-2-ylamino)-phenyl]-2-[9-(tetrahydropyran-2-yl)-9H-purin-6-ylamino]propionamide

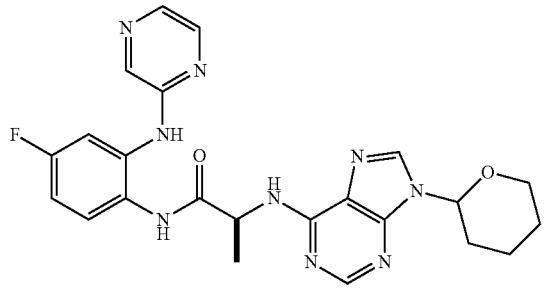 [SMILES: C[C@H](Nc1ncnc2c1ncn2C1CCCCO1)C(=O)Nc1ccc(F)cc1Nc1cnccn1]

Triethylamine (211 μl, 1.52 mol) was added to (S)-2-amino-N-[4-fluoro-2-(pyrazin-2-ylamino)phenyl]propionamide hydrochloride (118 mg, 0.38 mmol) and 6-chloro-9-(tetrahydro-2-pyranyl)purine (109 mg, 0.45 mol) in IPA (5.0 ml) and heated at 80° C. overnight. The reaction was poured into water and the aqueous layer extracted into EtOAc (×3). The combined organic fractions were washed with brine, dried (Na₂SO₄) and concentrated in vacuo. The product was purified by chromatography (SiO₂, 0-10% 2M ammonia methanol/DCM) to yield the title compound as a 1:1 mixture of diastereomers (100 mg, 0.21 mmol, 55%). LCMS (Method C): R$_T$ 2.55 min [M+H]⁺ 478.2. ¹H NMR (MeOD, 400 MHz): δ 8.26 (2H, m), 7.84 (2H, m), 7.58 (2H, m), 7.32 (1H, ddd, J 11.9, 10.1, 2.8 Hz), 6.92 (1H, ddd, J 8.9, 8.1, 2.9 Hz), 5.70 (1H, m), 4.16 (1H, m), 4.80 (1H, m), 3.80 (1H, m), 2.18 (3H, m), 1.80 (2H, m), 1.61 (4H, m).

(5-Fluoro-2-nitrophenyl)-pyrimidin-2-yl-amine

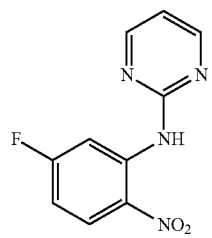

LiHMDS (1.0 M in tetrahydrofuran, 27.4 ml, 27.4 mmol) was added to 2-aminopyrimidine (1.43 g, 15.0 mmol) in tetrahydrofuran (50.0 ml) and stirred for 10 min. 2,4-Difluoronitrobenzene (1.50 ml, 13.7 mmol) was added and the reaction stirred for a further 15 min. The reaction mixture was quenched with water then poured into sodium bicarbonate (dilute aqueous) and the aqueous layer extracted with EtOAc (×3). The combined organic fractions were washed with brine, dried (Na₂SO₄) and concentrated in vacuo. The product was purified by chromatography (SiO₂, 0-100% EtOAc/cyclohexane) to yield the title compound (800 mg, 3.42 mmol, 25%). ¹H NMR (CDCl₃, 400 MHz): δ 8.94 (1H, dd, J 12.3, 2.4 Hz), 8.62 (2H, d, J=4.8 Hz), 8.36 (1H, dd, J 9.4, 6.1 Hz), 7.08 (1H, t, J=4.8 Hz), 6.88 (1H, ddd, J 9.6, 7.2, 2.8 Hz).

4-Fluoro-N²-pyrimidin-2-yl-benzene-1,2-diamine

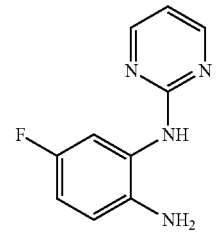 [SMILES: O=[N+]([O-])c1ccc(F)cc1Nc1ncccn1]

(5-Fluoro-2-nitrophenyl)pyrimidin-2-yl-amine (336 mg, 1.43 mmol) in IMS (25.0 ml) was added to palladium on charcoal (10 wt %, 35.0 mg) and stirred under a hydrogen atmosphere overnight. The mixture was filtered through Celite® and the filtrate concentrated in vacuo. The product was purified by chromatography (SiO₂, 0-10% methanol/DCM) to yield the title compound (215 mg, 1.05 mmol, 74%). ¹H NMR (MeOD, 400 MHz): δ 8.37 (2H, d, J=4.9 Hz), 7.29 (1H, dd, J 10.4, 2.9 Hz), 6.84 (1H, dd, J 8.8, 5.6 Hz), 6.77 (1H, t, J=4.9 Hz), 6.72 (1H, ddd, J 8.6, 8.1, 2.9 Hz).

{(S)-1-[4-Fluoro-2-(pyrimidin-2-ylamino)phenylcarbamoyl]ethyl}carbamic acid tert-butyl ester

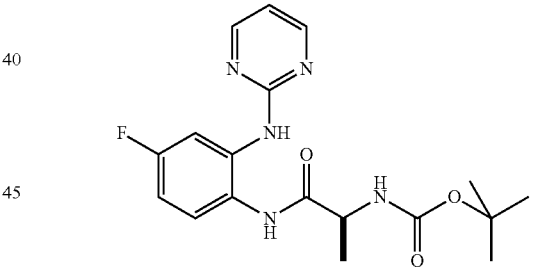

N-(tert-Butoxycarbonyl)-L-alanine (199 mg, 1.05 mmol), N-(3-dimethylaminopropyl)-N'-ethylcarbodiimide hydrochloride (222 mg, 1.15 mmol) and HOAt (143 mg, 1.05 mmol) were added to 4-fluoro-N²-pyrimidin-2-yl-benzene-1,2-diamine (215 mg, 1.05 mmol) in DCM (8.0 ml) and DMF (800 μl) at 0° C. The reaction was stirred for 2 h then poured into water and the aqueous layer extracted with DCM (×3). The combined organic fractions were washed with brine, dried (Na₂SO₄) and concentrated in vacuo. The product was purified by chromatography (SiO₂, 0-10% methanol/DCM) to yield the title compound (350 mg, 0.93 mmol, 89%). LCMS: R$_T$ 2.98 min [M+H]⁺ 376.1. ¹H NMR (CDCl₃, 300 MHz): δ 8.48 (1H, br s), 8.42 (2H, d, J=4.9 Hz), 7.69 (1H, br s), 7.50 (2H, m), 6.84 (1H, td, J 8.5, 2.9 Hz), 6.76 (1H, t, J=4.9 Hz), 5.01 (1H, br s), 4.28 (1H, qn, J=7.6 Hz), 1.44 (9H, s), 1.43 (3H, d, J=7.4 Hz).

(S)-2-Amino-N-[4-fluoro-2-(pyrimidin-2-ylamino) phenyl]propionamide hydrochloride salt

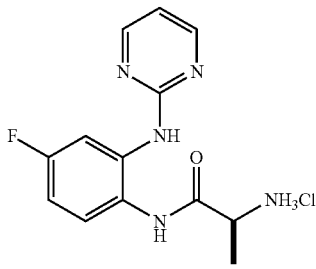

{(S)-1-[4-Fluoro-2-(pyrimidin-2-ylamino)phenylcarbamoyl]ethyl}carbamic acid tert-butyl ester (350 mg, 0.93 mmol) was dissolved in hydrochloric acid (4.0M in 1,4-dioxane) and stirred for 1 h. The reaction was concentrated in vacuo to yield the title compound (289 mg, 0.93 mmol, 99%). $^1$H NMR (MeOD, 400 MHz): δ 8.69 (2H, d, J=5.3 Hz), 7.62 (1H, d, J=9.3 Hz), 7.60 (1H, dd, J 8.7, 2.7 Hz), 7.19 (1H, 9.0, 7.9, 2.9 Hz), 7.19 (1H, t, J=5.3 Hz), 4.21 (1H, q, J=7.2 Hz), 1.58 (3H, d, J=7.2 Hz).

(S)—N-[4-Fluoro-2-(pyrimidin-2-ylamino)phenyl]-2-[9-(tetrahydropyran-2-yl)-9H-purin-6-ylamino] propionamide

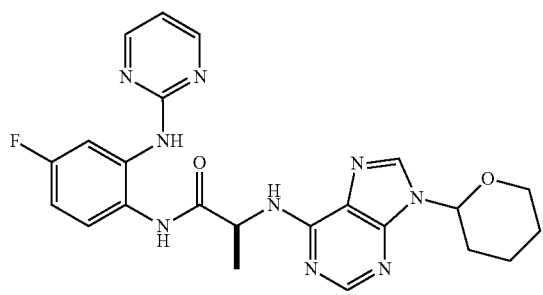 [SMILES: C[C@H](Nc1ncnc2c1ncn2C1CCCCO1)C(=O)Nc1ccc(F)cc1Nc1ncccn1]

Triethylamine (518 µl, 3.72 mol) was added to (S)-2-amino-N-[4-fluoro-2-(pyrimidin-2-ylamino)phenyl]propionamide hydrochloride salt 161b (289 mg, 0.93 mmol) and 6-chloro-9-(tetrahydropyran-2-yl)purine (265 mg, 1.10 mol) in IPA (5.0 ml) and heated to 80° C. overnight. The reaction was poured into water and the aqueous layer extracted into EtOAc (×3). The combined organic fractions were washed with brine, dried (Na$_2$SO$_4$) and concentrated in vacuo. The product was purified by chromatography (SiO$_2$, 0-10% 2M ammonia methanol/DCM) to yield the title compound as a 1:1 mixture of diastereomers (236 mg, 0.50 mmol, 53%). LCMS R$_T$ 2.63 min [M+H]$^+$ 478.2.

(5-Fluoro-2-nitrophenyl)pyridin-3-ylamine

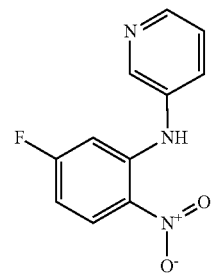 [SMILES: O=[N+]([O-])c1ccc(F)cc1Nc1cccnc1]

Potassium tert-butoxide (4.48 g, 40 mmol), was slowly added to a solution of 3-aminopyridine (1.88 g, 20 mmol) in anhydrous THF (40 mL) at 0° C. 2-4-difluoronitrobenzene (2.2 mL, 20 mmol) in anhydrous THF (40 mL) was added dropwise to the purple solution and stirred for 1 h at 0° C. The reaction mixture was poured onto sat. ammonium chloride (200 mL) and extracted with EtOAc (2×200 mL). The combined organic fractions were washed with brine (200 mL), dried (Na$_2$SO$_4$) and concentrated in vacuo. The dark orange solid was purified by column chromatography (Si—PPC, gradient 0-50% EtOAc/DCM) to afford the title compound as a bright orange solid (2.21 g, 47%). LCMS (Method C): R$_T$ 2.39 min [M+H]$^+$ 234. $^1$H NMR (CDCl$_3$, 400 MHz): δ 9.58 (1H, bs), 8.61 (1H, d, J=2.5 Hz), 8.54 (1H, dd, J=5.0, 1.5 Hz), 8.29 (1H, dd, J=9.5, 6.0 Hz), 7.65-7.62 (1H, m), 7.40 (1H, ddd, J=8.0, 5.0, 1.0 Hz), 6.73 (1H, dd, J=11.0, 2.5 Hz), 6.55 (1H, ddd, J=9.5, 7.0, 2.5 Hz).

4-Fluoro-N$^2$-pyridin-3-yl-benzene-1,2-diamine

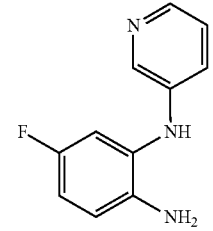 [SMILES: Nc1ccc(F)cc1Nc1cccnc1]

A solution of (5-fluoro-2-nitrophenyl)pyridin-3-ylamine (2.21 g, 9.5 mmol) in EtOAc (65 mL) was added to a slurry of palladium on carbon (10% by wt, 220 mg) in EtOAc (10 mL) under N$_2$. The reaction mixture was stirred at RT under an atmosphere of hydrogen for 16 h. The mixture was filtered through Celite® and the filtrate concentrated in vacuo to give the title compound as a white solid that turned red upon standing (1.83 mg, 95%). LCMS (Method B): R$_T$ 0.81 min [M+H]$^+$ 204. $^1$H NMR (CDCl$_3$, 400 MHz): δ 8.23 (1H, dd, J=3.0, 1.0 Hz), 8.13 (1H, dd, J=4.5 1.5 Hz), 7.15 (1H, ddd, J=8.0, 4.5, 0.5 Hz), 7.10 (1H, ddd, J=8.5, 2.5, 1.5 Hz), 6.85 (1H, dd, J=9.5, 2.5 Hz), 6.76-6.68 (2H, m), 5.50 (1H, bs), 3.56 (2H, bs).

[(S)-1-(6-Fluoro-1-pyridin-3-yl-1H-benzoimidazol-2-yl)ethyl]carbamic acid tert-butyl ester

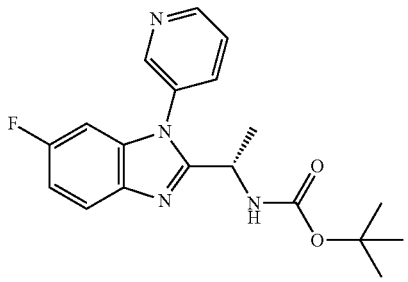 [SMILES: C[C@H](NC(=O)OC(C)(C)C)c1nc2ccc(F)cc2n1-c1cccnc1]

A solution of triethyloxonium tetrafluoroborate (561 mg, 3.0 mmol) in DCM (4 mL) was added to a slurry of (S)-2-methylaminopropionamide (561, mg, 3.15 mmol) in DCM (6 mL) and stirred for 1.5 h at RT. The reaction mixture was concentrated in vacuo and 4-fluoro-N²-pyridin-3-yl-benzene-1,2-diamine (200 mg, 0.98 mmol) in EtOH (6 mL) added and heated for 2.5 h at 60° C. The reaction mixture was cooled to RT and concentrated in vacuo. The resulting residue was taken up in DCM (25 mL) and washed with sat. NaHCO₃ (25 mL). The aqueous was further extracted with DCM (2×25 mL). The combined organic fractions were dried (Na₂SO₄) and concentrated in vacuo. The resulting residue was purified by column chromatography (Si—PPC, gradient 10-50% EtOAc/DCM) to afford the title compound as an orange oil (292 mg, 83%). LCMS (Method C): R$_T$ 2.96 min [M+H]⁺ 357. ¹H NMR (CDCl₃, 400 MHz): δ 8.80 (1H, dd, J=5.0, 1.5 Hz), 8.72 (1H, d, J=2.5 Hz), 7.84-7.83 (1H, m), 7.70 (1H, dd, J=9.0, 4.5 Hz), 7.57 (1H, ddd, 8.0, 5.0, 1.0 Hz), 7.05 (1H, ddd, J=9.5, 9.0, 2.5 Hz), 6.76 (1H, dd, J=8.5, 2.5 Hz), 5.43 (1H, d, 7.0 Hz), 4.89 (1H, dq, J=7.0, 7.0 Hz), 1.46 (3H, d, J=7.0 Hz), 1.38 (9H, s).

(S)-1-(6-Fluoro-1-pyridin-3-yl-1H-benzoimidazol-2-yl)ethylamine

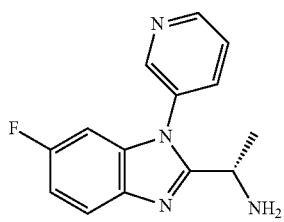 [SMILES: C[C@H](N)c1nc2ccc(F)cc2n1-c1cccnc1]

A solution of [(S)-1-(6-fluoro-1-pyridin-3-yl-1H-benzoimidazol-2-yl)ethyl]carbamic acid tert-butyl ester (292 mg, 0.82 mmol) in TFA (4 mL) and DCM (12 mL) was stirred for 1 h at RT. The reaction mixture was loaded onto an Isolute® SCX-2 cartridge. The cartridge was washed with MeOH, followed by 2M NH₃/MeOH. The basic fractions were combined and concentrated in vacuo. The resulting residue was purified by column chromatography (Si—PPC, gradient 0-10% 2M NH₃ in MeOH/DCM) to afford the title compound as a pale yellow oil (141 mg, 67%). Marfey's test: 76% de. LCMS (Method C): R$_T$ 1.34 min [M+H]⁺ 257. ¹H NMR (CDCl₃, 400 MHz): δ 8.80 (1H, dd, J=5.0, 1.5 Hz), 8.73-8.72 (1H, m), 7.81 (1H, ddd, J=8.0, 2.5, 1.5 Hz), 7.71 (1H, ddd, J=9.0, 4.5, 0.5 Hz), 7.56 (1H, ddd, J=8.0, 5.0, 1.0 Hz), 7.04 (1H, ddd, J=9.5, 9.0, 2.5 Hz), 6.75 (1H, ddd, J=8.5, 2.5, 0.5 Hz), 4.08 (1H, q, 6.5 Hz), 1.87 (2H, bs), 1.48 (3H, d, J=6.5 Hz).

(3,5-Difluorophenyl)-(5-fluoro-2-nitrophenyl)amine

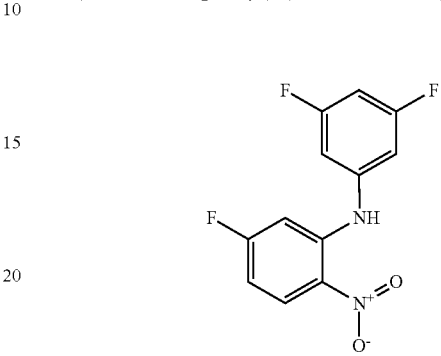

Potassium tert-butoxide (4.45 g, 40 mmol), was slowly added to a solution of 3,5-difluoroaniline (2.56 g, 20 mmol) in anhydrous THF (40 mL) at 0° C. 2-4-difluoronitrobenzene (2.2 mL, 20 mmol) in anhydrous THF (40 mL) was added dropwise to the purple solution and stirred for 1 h at 0° C. The reaction mixture was poured onto sat ammonium chloride (150 mL) and extracted with EtOAc (2×100 mL). The combined organic fractions were washed with brine (200 mL), dried (Na₂SO₄) and concentrated in vacuo. The dark orange solid was purified by column chromatography (Si—PPC, gradient 0-10% EtOAc/cyclohexane) to afford the title compound as a brown solid (4.1, 61%). LCMS (Method B): R$_T$ 4.04 min [M−H]⁺ 267. ¹H NMR (CDCl₃, 400 MHz): δ 9.56 (1H, bs), 8.28 (1H, dd, J=9.5, 6.0 Hz), 6.96 (1H, dd, J=11.0, 2.5 Hz), 6.86-6.79 (2H, m), 6.73-6.67 (1H, m), 6.60 (1H, ddd, J=9.5, 7.0, 2.5 Hz).

N²-(3,5-Difluorophenyl)-4-fluorobenzene-1,2-diamine

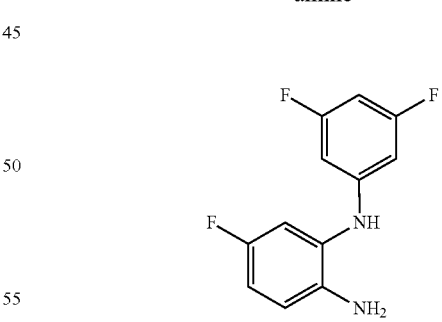

A solution of (3,5-difluorophenyl)-(5-fluoro-2-nitrophenyl)amine (2.0 g, 7.5 mmol) in EtOAc (65 mL) was added to a slurry of palladium on carbon (10% by wt, 200 mg) in EtOAc (10 mL) under nitrogen. The reaction mixture was stirred at RT under an atmosphere of hydrogen for 4 h. The mixture was filtered through Celite® and the filtrate concentrated in vacuo. The resulting residue was purified by column chromatography (Si—PPC, gradient 0-30% EtOAc/cyclohexane) to afford the title compound as a white solid that turned red upon standing (1.07 g, 60%). LCMS (Method C):

R$_T$ 3.40 min [M+H]$^+$ 239. $^1$H NMR (CDCl$_3$, 400 MHz): δ 6.90-6.87 (1H, m), 6.81-6.73 (2H, m), 6.31-6.23 (3H, m), 5.42 (1H, bs), 3.58 (2H, bs).

{(S)-1-[1-(3,5-Difluorophenyl)-6-fluoro-1H-benzoimidazol-2-yl]ethyl}carbamic acid tert-butyl ester

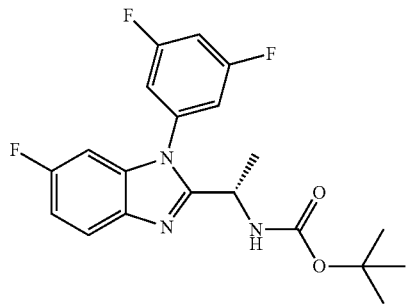 [SMILES: C[C@H](NC(=O)OC(C)(C)C)c1nc2ccc(F)cc2n1-c1cc(F)cc(F)c1]

A solution of triethyloxonium tetrafluoroborate (1.2 g, 6.3 mmol) in DCM (10 mL) was added to a slurry of (S)-2-methylaminopropionamide (1.26 g, 6.7 mmol) in DCM (10 mL) and stirred for 1.5 h at RT. The reaction solution was concentrated in vacuo and N$^2$-(3,5-difluorophenyl)-4-fluorobenzene-1,2-diamine (500 mg, 2.1 mmol) in EtOH (12 mL) added and heated for 4.5 h at 60° C. The reaction mixture was cooled to RT and concentrated in vacuo. The resulting residue was taken up in DCM (25 mL) and washed with sat. NaHCO$_3$ (25 mL). The aqueous was further extracted with DCM (2×25 mL). The combined organic fractions were dried (Na$_2$SO$_4$) and concentrated in vacuo. The resulting residue was purified by column chromatography (Si—PPC, gradient 0-50% EtOAc/cyclohexane) to afford the title compound as a pale yellow oil (668 mg, 81%). LCMS (Method C): R$_T$ 3.70 min [M+H]$^+$ 392. $^1$H NMR (CDCl$_3$, 400 MHz): δ 7.70 (1H, dd, J=9.0, 5.0 Hz), 7.08-7.00 (4H, m), 6.84 (1H, dd, J=8.5, 2.5 Hz), 5.36 (1H, d, J=7.0 Hz), 4.98 (1H, dq, J=7.0, 7.0 Hz), 1.48 (3H, d, J=7.0 Hz), 1.40 (9H, s).

(S)-1-[1-(3,5-Difluorophenyl)-6-fluoro-1H-benzoimidazol-2-yl]ethylamine

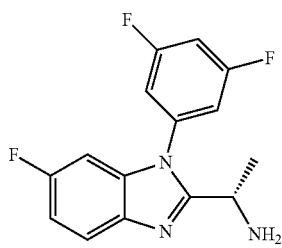 [SMILES: C[C@H](N)c1nc2ccc(F)cc2n1-c1cc(F)cc(F)c1]

A solution of {(S)-1-[1-(3,5-difluorophenyl)-6-fluoro-1H-benzoimidazol-2-yl]ethyl}carbamic acid tert-butyl ester (668 mg, 1.7 mmol) in TFA (4 mL) and DCM (12 mL) was stirred for 1 h at RT. The reaction solution was loaded onto an Isolute® SCX-2 cartridge. The cartridge was washed with MeOH, followed by 2M NH$_3$/MeOH. The basic fractions were combined and concentrated in vacuo to afford the title compound as a pale yellow oil (497 mg, 99%). Marfey's test: 97% de. LCMS (Method C): R$_T$ 1.96 min [M+H]$^+$ 292. $^1$H NMR (CDCl$_3$, 400 MHz): δ 7.70 (1H, dd, J=9.0, 5.0 Hz), 7.08-7.00 (2H, m), 6.97-6.93 (2H, m), 6.80 (1H, dd, J=8.0, 2.5 Hz), 6.19 (2H, bs), 4.51 (1H, q, 7.0 Hz), 1.55 (3H, d, J=7.0 Hz).

{(S)-1-[1-(3,5-Difluorophenyl)-6-fluoro-1H-benzoimidazol-2-yl]-ethyl}-[9-(tetrahydropyran-2-yl)-9H-purin-6-yl]amine

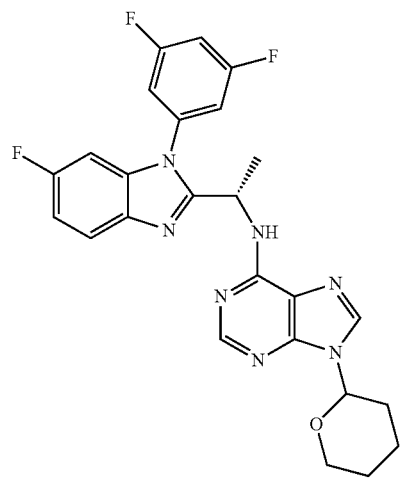 [SMILES: C[C@H](Nc1ncnc2c1ncn2C1CCCCO1)c1nc2ccc(F)cc2n1-c1cc(F)cc(F)c1]

A mixture of (S)-1-[1-(3,5-difluorophenyl)-6-fluoro-1H-benzoimidazol-2-yl]ethylamine (206 mg, 0.71 mmol), 6-chloro-9-(tetrahydropyran-2-yl)-9H-purine (169 mg, 0.71 mmol) and DIPEA (0.37 mL, 2.1 mmol) in IPA (1.4 mL) was heated in a sealed tube for 20 h at 90° C. After cooling to RT, the volatiles were removed in vacuo and the resulting residue purified by column chromatography (Si—PPC, gradient 0-10% 2M NH$_3$ in MeOH/DCM) to afford the title compound as a colourless glass (141 mg, 40%). LCMS (Method C): R$_T$ 3.38 min [M+H]$^+$ 494. $^1$H NMR (CDCl$_3$, 400 MHz): δ 8.29-8.28 (1H, m), 7.97-7.96 (1H, m), 7.72-7.68 (1H, m), 7.10-7.01 (3H, m), 6.97-6.91 (1H, m), 6.86-6.82 (1H, m), 6.37 (1H, bs), 5.79-5.67 (2H, m), 4.18-4.13 (1H, m), 3.80-3.73 (1H, m), 2.11-1.97 (3H, m), 1.80-1.63 (6H, m).

(3-Fluoro-6-nitro-2-pyridin-2-yl-phenyl)-(2-methoxyethyl)amine

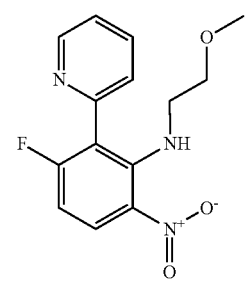 [SMILES: COCCNc1c([N+](=O)[O-])ccc(F)c1-c1ccccn1]

A mixture of 2-(2-chloro-6-fluoro-3-nitrophenyl)pyridine* (618 mg, 2.6 mmol), 2-methoxyethylamine (0.23 mL, 2.6 mmol) and DIPEA (0.48 mL, 2.7 mmol) in MeCN (5 mL) was stirred for 1.5 h at 0° C. After warming to RT, the volatiles were removed in vacuo. The resulting residue was purified by column chromatography (Si—PPC, gradient 0-70% EtOAc/ cyclohexane) to afford the title compound as a yellow oil (414 mg, 54%). LCMS (Method C): $R_T$ 2.95 min [M+H]$^+$ 292. $^1$H NMR (CDCl$_3$, 400 MHz): δ 8.73 (1H, ddd, J=5.0, 2.0, 1.0 Hz), 8.47 (1H, bs), 8.26 (1H, dd, J=9.5, 6.0 Hz), 7.79 (1H, ddd, 8.0, 8.0, 2.0 Hz), 7.45-7.43 (1H, m), 7.32 (1H, ddd, J=7.5, 5.0, 1.0 Hz), 6.52 (1H, dd, 9.5, 8.0 Hz), 3.29-3.26 (2H, m), 3.28 (3H, s), 2.63-2.60 (2H, m)

4-Fluoro-N$^2$-(2-methoxyethyl)-3-pyridin-2-yl-benzene-1,2-diamine

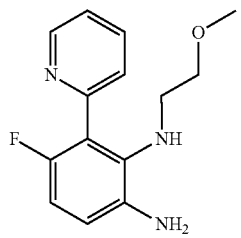 [SMILES: COCCNc1c(N)ccc(F)c1-c1ccccn1]

A solution of (3-fluoro-6-nitro-2-pyridin-2-yl-phenyl)-(2-methoxyethyl)amine (414 mg, 1.4 mmol) in EtOAc (5 mL) was added to a slurry of palladium on carbon (10% by wt, 41 mg) in EtOAc (5 mL) under nitrogen. The reaction mixture was stirred at RT under an atmosphere of hydrogen for 4 h. The mixture was filtered through Celite® and the filtrate concentrated in vacuo to give the title compound as a yellow oil (382 mg, 99%). LCMS (Method C): $R_T$ 1.92 min [M+H]$^+$ 262. $^1$H NMR (CDCl$_3$, 400 MHz): δ 8.72 (1H, ddd, J=5.0, 2.0, 1.0 Hz), 7.77, (1H, ddd, J=8.0, 8.0, 2.0 Hz), 7.60-7.56 (1H, m), 7.26 (1H, ddd, J=7.5, 5.0, 1.0 Hz), 6.73-6.66 (2H, m), 5.67 (1H, bs), 3.86 (2H, bs), 3.18-3.16 (2H, m), 3.01 (3H, s), 2.96-2.93 (2H, m)

{(S)-1-[4-Fluoro-2-(2-methoxyethylamino)-3-pyridin-2-yl-phenylcarbamoyl]-ethyl}-carbamic acid tert-butyl ester

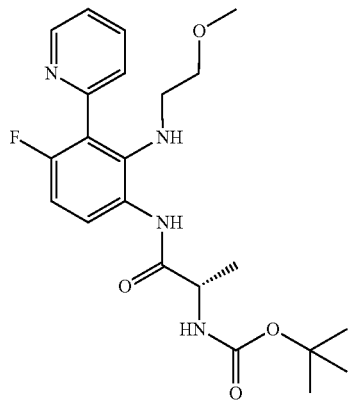 [SMILES: COCCNc1c(NC(=O)[C@H](C)NC(=O)OC(C)(C)C)ccc(F)c1-c1ccccn1]

To a solution of 4-fluoro-N$^2$-(2-methoxyethyl)-3-pyridin-2-yl-benzene-1,2-diamine (371 mg, 4.42 mmol), L-Boc-ala-OH (296 mg, 1.56 mmol) and HOAt (213 mg, 1.56 mmol) in DCM (5 mL) at 0° C. was added piecewise N-(3-dimethylaminopropyl)-n'-ethylcarbodiimide hydrochloride (299 mg, 1.56 mmol) and the reaction mixture stirred at 0° C. for 1 h. The reaction mixture was diluted with DCM (20 mL) and washed with citric acid solution (10% by wt, 20 mL). The aqueous was further extracted with DCM (3×20 mL). The combined organic fractions were dried (Na$_2$SO$_4$) and concentrated in vacuo. The resulting residue was purified by column chromatography (Si—PPC, gradient 25-75% EtOAc/cyclohexane) to afford the title compound as a white solid (373 mg, 61%). LCMS (Method C): $R_T$ 2.80 min [M+H]$^+$ 433. $^1$H NMR (CDCl$_3$, 400 MHz): δ 8.89 (1H, bs), 8.71 (1H, ddd, J=5.0, 2.0, 1.0 Hz), 8.29 (1H, dd, J=9.0, 6.0 Hz), 7.80 (1H, ddd, J=8.0, 8.0, 2.0 Hz), 7.63-7.60 (1H, m), 7.29 (1H, ddd, J=7.5, 5.0, 1.5 Hz), 6.88 (1H, dd, 10.0, 10.0 Hz), 5.74 (1H, bs), 5.32 (1H, bs), 4.44-4.34 (1H, m), 3.27 (2H, t, 5.0 Hz), 3.24 (3H, s), 2.85-2.79 (2H, m), 1.47 (3H, d, J=7.0 Hz), 1.46 (9H, s).

{(S)-1-[6-Fluoro-1-(2-methoxyethyl)-7-pyridin-2-yl-1H-benzoimidazol-2-yl]ethyl}carbamic acid tert-butyl ester

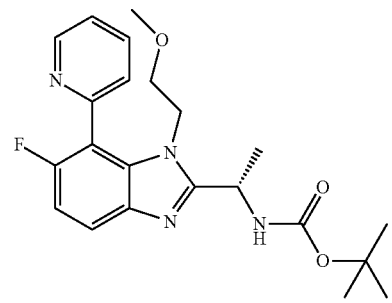 [SMILES: COCCn1c([C@H](C)NC(=O)OC(C)(C)C)nc2ccc(F)c(-c3ccccn3)c21]

A solution of {(S)-1-[4-fluoro-2-(2-methoxyethylamino)-3-pyridin-2-yl-phenylcarbamoyl]ethyl}carbamic acid tert-butyl ester (368 mg, 0.85 mmol) in AcOH (5 mL) was heated for 16 h at 70° C. in a sealed tube. After cooling to RT, the volatiles were removed in vacuo and the resulting residue taken up in DCM (15 mL) and washed with sat. NaHCO$_3$ (30 mL). The aqueous was further extracted with DCM (2×15 mL). The combined organic fractions were washed with brine (15 mL), dried (Na$_2$SO$_4$) and concentrated in vacuo. The resulting residue was purified by column chromatography (Si—PPC, gradient 20-75% EtOAc/cyclohexane) to afford the title compound as a white solid (239 mg, 68%). LCMS (Method C): $R_T$ 2.92 min [M+H]$^+$ 415. $^1$H NMR (CDCl$_3$, 400 MHz): δ 7.84 (1H, ddd, J=7.5, 7.5, 2.0 Hz), 7.71 (1H, dd, J=9.0, 5.0 Hz), 7.59-7.56 (1H, m), 7.38 (1H, ddd, J=7.5, 5.0, 1.5 Hz), 7.09 (1H, dd, J=10.5, 9.0 Hz), 5.29-5.19 (2H, m), 4.33-4.26 (1H, m), 3.91 (1H, ddd, J=15.0, 4.0, 4.0 Hz), 3.14-3.08 (2H, m), 3.07 (1H, s), 1.60 (3H, d, J=6.5 Hz), 1.41 (9H, s)

(S)-1-[6-Fluoro-1-(2-methoxyethyl)-7-pyridin-2-yl-1H-benzoimidazol-2-yl]ethylamine

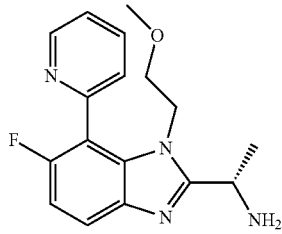 [SMILES: COCCn1c([C@H](C)N)nc2ccc(F)c(-c3ccccn3)c21]

A solution of {(S)-1-[6-fluoro-1-(2-methoxyethyl)-7-pyridin-2-yl-1H-benzoimidazol-2-yl]ethyl}carbamic acid tert-butyl ester (231 mg, 0.56 mmol) in TFA (2 mL) and DCM (6 mL) was stirred for 45 min at RT. The reaction mixture was loaded onto an Isolute® SCX-2 cartridge. The cartridge was washed with MeOH, followed by 2M NH$_3$/MeOH. The basic fractions were combined and concentrated in vacuo to afford the title compound as a pale yellow oil (179 mg, 99%). Marfey's test: >99% de. LCMS (Method C): R$_T$ 1.76 min [M+H]$^+$ 315. $^1$H NMR (CDCl$_3$, 400 MHz): δ 8.75 (1H, ddd, J=5.0, 2.0, 1.0 Hz), 7.84 (1H, ddd, J=7.5, 7.5, 2.0 Hz), 7.73 (1H, dd, J=9.0, 5.0 Hz), 7.60-7.57 (1H, m), 7.38 (1H, ddd, J=7.5, 5.0, 1.0 Hz), 7.09 (1H, dd, J=10.0, 9.0 Hz), 4.33 (1H, q, J=6.5 Hz), 4.12 (1H, ddd, J=15.5, 5.5, 4.5 Hz), 4.02 (1H, ddd, J=15.5, 7.0, 5.0 Hz), 3.12-3.01 (2H, m), 3.06 (3H, m), 2.00 (2H, bs), 1.59 (3H, d, J=6.5 Hz).

(2-Bromo-6-nitrophenyl)methylamine

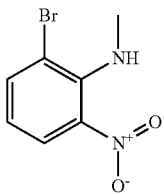

A mixture of 1-bromo-2-fluoro-3-nitrobenzene (3.96 g, 18 mmol), 2M methylamine in MeOH (18 mL, 36 mmol) and DIPEA (3.3 mL, 19 mmol) was stirred for 3 h at RT. The reaction mixture was concentrated in vacuo. The resulting residue was taken up in DCM (100 mL) and washed with sat. NaHCO$_3$ (100 mL). The aqueous layer was further extracted with DCM (100 mL). The combined organic fractions were washed with brine (50 mL), dried over Na$_2$SO$_4$ and concentrated in vacuo to afford the title compound as bright orange oil (4.16 g, 99%). LCMS (Method C): R$_T$ 3.39 min [M+H]$^+$ 231 (for $^{79}$Br). $^1$H NMR (CDCl$_3$, 400 MHz): δ 7.86 (1H, dd, J=8.5, 1.5 Hz), 7.67 (1H, dd, J=8.0, 1.5 Hz), 6.67 (1H, dd, J=8.5, 8.0 Hz), 3.13 (1H, bs), 3.01 (3H, d, J=5.5 Hz).

3-Bromo-N$^2$-methylbenzene-1,2-diamine

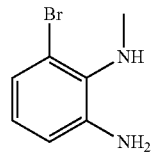

A mixture of (2-bromo-6-nitrophenyl)methylamine (4.16 g, 18 mmol), ammonium chloride (5.6 g, 108 mmol) and iron powder (4.09 g, 72 mmol) in H$_2$O (32 mL) and MeOH (80 mL) was stirred vigorously for 5 h at 90° C. After cooling to RT, the reaction mixture was filtered through Celite®, washed with MeOH/DCM and the filtrate concentrated in vacuo. The resulting residue was taken up in EtOAc (75 mL) and washed with H$_2$O (75 mL). The aqueous was further extracted with EtOAc (2×75 mL). The combined organic fractions were washed with brine (50 mL), dried (Na$_2$SO$_4$) and concentrated in vacuo. The resulting residue was purified by column chromatography (Si—PPC, gradient 10-75% EtOAc/cyclohexane) to afford the title compound as a red oil (1.46 g, 40%). LCMS (Method C): R$_T$ 1.79 min [M+H]$^+$ 211 (for $^{79}$Br). $^1$H NMR (CDCl$_3$, 400 MHz): δ 6.92 (1H, dd, J=8.0, 1.5 Hz), 6.75 (1H, dd, 8.0, 8.0 Hz), 6.64 (1H, dd, J=8.0, 1.5 Hz), 4.02 (2H, bs), 3.25 (1H, bs), 2.68 (3H, s).

[(S)-1-(7-Bromo-1-methyl-1H-benzoimidazol-2-yl)ethyl]carbamic acid tert-butyl ester

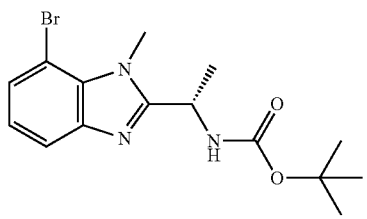 [SMILES: C[C@H](NC(=O)OC(C)(C)C)c1nc2cccc(Br)c2n1C]

To a solution of 3-bromo-N$^2$-methylbenzene-1,2-diamine (1.46 g, 7.3 mmol), L-Boc-ala-OH (1.51 g, 8.0 mmol) and HOAt (1.09 g, 8.0 mmol) in DCM (25 mL) at 0° C. was added piecewise N-(3-dimethylaminopropyl)-n'-ethylcarbodiimide hydrochloride (1.53 g, 8.0 mmol), the reaction mixture was stirred at 0° C. for 1 h. The reaction mixture was diluted with DCM (20 mL) and washed with citric acid solution (10% by wt, 20 mL). The aqueous was further extracted with DCM (3×20 mL). The combined organic fractions were dried (Na$_2$SO$_4$) and concentrated in vacuo. The resulting residue was purified by column chromatography (Si—PPC, gradient 25-75% EtOAc/cyclohexane) to afford a mixture of two amide regioisomers and cyclised adduct. The mixture was dissolved in AcOH (20 mL) and heated for 16 h at 70° C. in a sealed tube. After cooling to RT, the volatiles were removed in vacuo and the resulting residue taken up in DCM (30 mL) and washed with sat. NaHCO$_3$ (60 mL). The aqueous was further extracted with DCM (2×30 mL). The combined organic fractions were washed with brine (30 mL), dried (Na$_2$SO$_4$) and concentrated in vacuo to afford the title compound as a red oil (1.8 g, 70%). LCMS (Method C): $R_T$ 3.14 min [M+H]$^+$ 354 (for $^{79}$Br). $^1$H NMR (CDCl$_3$, 400 MHz): δ 7.64 (1H, d, J=8.0 Hz), 7.38 (1H, d, J=7.5 Hz), 7.08 (1H, dd, J=8.0 Hz), 5.48 (1H, d, J=8.5 Hz, 5.16 (1H, dq, J=8.5, 7.0 Hz), 4.12 (3H, m), 1.61 (3H, d, J=7.0 Hz), 1.45 (9H, s).

(S)-1-(7-Bromo-1-methyl-1H-benzoimidazol-2-yl)ethylamine

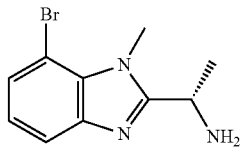

A solution of [(S)-1-(7-bromo-1-methyl-1H-benzoimidazol-2-yl)ethyl]carbamic acid tert-butyl ester (1.8 g, 5.1 mmol) in TFA (7.5 mL) and DCM (22.5 mL) was stirred for 45 min at RT. The reaction solution was loaded onto an Isolute® SCX-2 cartridge. The cartridge was washed with MeOH, followed by 2M NH$_3$/MeOH. The basic fractions were combined and concentrated in vacuo to afford the title compound as a pale red solid (1.3 g, 99%). Marfey's test: 98% de. LCMS (Method C): $R_T$ 1.49 min [M+H]$^+$ 415 (for $^{79}$Br).

{(S)-1-[6-Fluoro-1-(5-fluoropyridin-3-yl)-1H-benzoimidazol-2-yl]propyl}carbamic acid tert-butyl ester

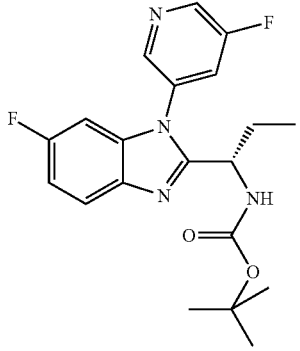 [SMILES: CC[C@H](NC(=O)OC(C)(C)C)c1nc2ccc(F)cc2n1-c1cncc(F)c1]

To a suspension of ((S)-1-carbamoylpropyl)carbamic acid tert-butyl ester (250 mg, 1.24 mmol) in DCM (5 mL) was added triethyloxonium tetrafluoroborate (228 mg, 1.20 mmol) and the reaction mixture stirred at RT for 1.5 h under argon. The reaction mixture was concentrated in vacuo and the residue dissolved in ethanol (3 mL). 4-Fluoro-N$^2$-(5-fluoropyridin-3-yl)benzene-1,2-diamine (88 mg, 0.40 mmol) was added and the reaction mixture heated at 60° C. for 20 min. The reaction mixture was concentrated in vacuo, and the residue partitioned between DCM and sat. NaHCO$_3$. The organic fraction was washed with brine, dried (Na$_2$SO$_4$) and concentrated in vacuo. The resultant residue was subjected to flash chromatography (Si—PPC, gradient 0-50% EtOAc in cyclohexane) to afford the title compound as a white foam (128 mg, 82%). LCMS (Method J): $R_T$=3.42 min, [M+H]$^+$= 389.

(S)-1-[6-Fluoro-1-(5-fluoropyridin-3-yl)-1H-benzoimidazol-2-yl]propylamine

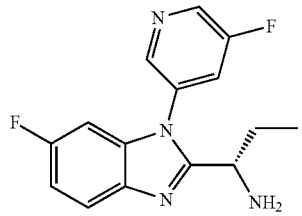 [SMILES: CC[C@H](N)c1nc2ccc(F)cc2n1-c1cncc(F)c1]

TFA (0.12 mL, 1.58 mmol) was added to a solution of {(S)-1-[6-fluoro-1-(5-fluoropyridin-3-yl)-1H-benzoimidazol-2-yl]propyl}carbamic acid tert-butyl ester (123 mg, 0.33 mmol) in DCM (2 mL) and the reaction stirred at RT for 18 h. The reaction mixture was concentrated in vacuo and passed through a 2 g Isolute® SCX-2 cartridge, eluting with 2M NH$_3$/MeOH. The basic fraction was concentrated in vacuo to give the title compound (92 mg, quant.) as brown oil. LCMS (Method J): $R_T$=1.86 min, [M+H]$^+$=289.

{(S)-1-[6-Fluoro-1-(5-fluoropyridin-3-yl)-1H-benzoimidazol-2-yl]propyl}-[9-(tetrahydropyran-2-yl)-9H-purin-6-yl]amine

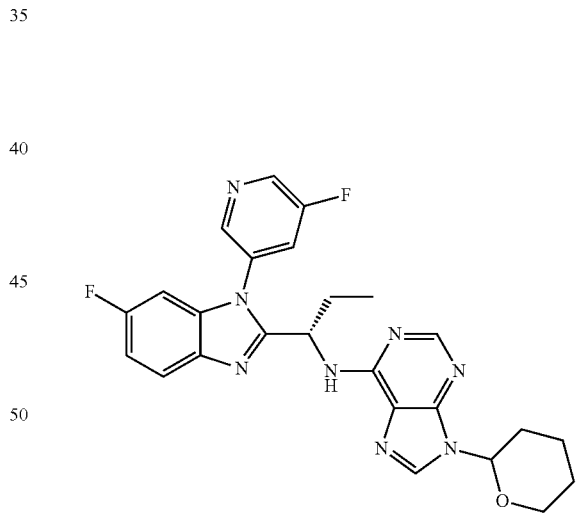

A mixture of (S)-1-[6-fluoro-1-(5-fluoropyridin-3-yl)-1H-benzoimidazol-2-yl]propylamine (70 mg, 0.24 mmol), 6-chloro-9-(tetrahydropyran-2-yl)-9H-purine (57 mg, 0.24 mmol) and DIPEA (84 µL, 0.48 mmol) in IPA (3 mL) was heated for 24 h at 90° C. After cooling to RT, the volatiles were removed in vacuo and the resulting residue purified by column chromatography (Si—PPC, gradient 0-7% MeOH in DCM) to afford the title compound as a pale brown oil (96 mg, 82%). LCMS (Method J): $R_T$=3.03 min, [M+H]$^+$=491.

[(S)-1-(6-Fluoro-1-phenyl-1H-benzoimidazol-2-yl) propyl]carbamic acid tert-butyl ester

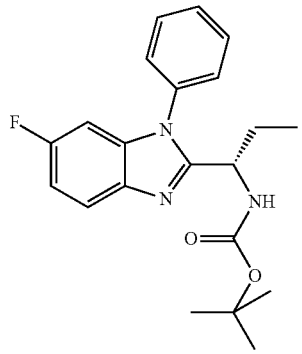 [SMILES: CC[C@H](NC(=O)OC(C)(C)C)c1nc2ccc(F)cc2n1-c1ccccc1]

To a suspension of ((S)-1-carbamoylpropyl)carbamic acid tert-butyl ester (300 mg, 1.48 mmol) in DCM (5 mL) was added triethyloxonium tetrafluoroborate (273 mg, 1.43 mmol) and the reaction mixture stirred at RT for 1.5 h under argon. The reaction mixture was concentrated in vacuo and the resulting residue dissolved in ethanol (3 mL). 4-Fluoro-N$^2$-phenylbenzene-1,2-diamine (97 mg, 0.48 mmol) was added and the reaction heated at 70° C. for 1 h. The reaction mixture was concentrated in vacuo, and the resulting residue partitioned between DCM and sat. NaHCO$_3$. The organic fraction was washed with brine, dried (Na$_2$SO$_4$) and concentrated in vacuo. The resultant residue was subjected to flash chromatography (Si—PPC, gradient 0-20% EtOAc in cyclohexane) to afford the title compound as a pink foam (96 mg, 54%). LCMS (Method J): $R_T$=3.70 min, [M+H]$^+$=370.

(S)-1-(6-Fluoro-1-phenyl-1H-benzoimidazol-2-yl) propylamine

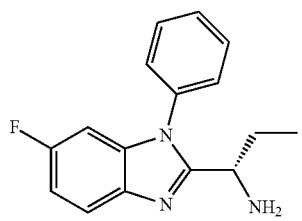

TFA (0.50 mL, 6.73 mmol) was added to a solution of [(S)-1-(6-fluoro-1-phenyl-1H-benzoimidazol-2-yl)propyl] carbamic acid tert-butyl ester (92 mg, 0.25 mmol) in DCM (2 mL) and the reaction stirred at RT for 1.5 h. The reaction mixture was concentrated in vacuo and passed through a 2 g Isolute® SCX-2 cartridge, eluting with 2M NH$_3$/MeOH. The basic fraction was concentrated in vacuo to give the title compound (57 mg, 85%) as a red oil. LCMS (Method J): $R_T$=2.08 min, [M+H]$^+$=270.

[(S)-1-(6-Fluoro-1-phenyl-1H-benzoimidazol-2-yl) propyl]-[9-(tetrahydropyran-2-yl)-9H-purin-6-yl] amine

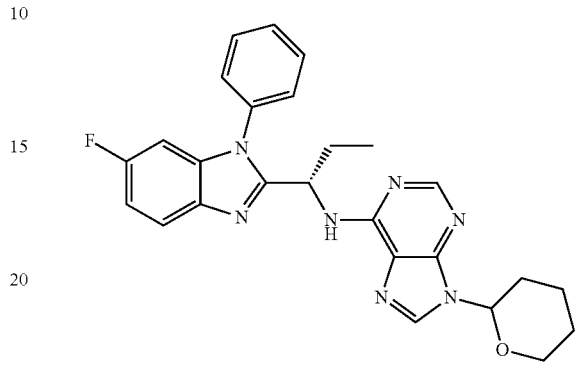

A mixture of (S)-1-(6-fluoro-1-phenyl-1H-benzoimidazol-2-yl)propylamine (55 mg, 0.20 mmol), 6-chloro-9-(tetrahydropyran-2-yl)-9H-purine (49 mg, 0.20 mmol) and DIPEA (105 µL, 0.60 mmol) in IPA (0.5 mL) was heated for 24 h at 90° C. After cooling to RT, the volatiles were removed in vacuo and the resulting residue purified by column chromatography (Si—PPC, gradient 0-5% MeOH in DCM) to afford the title compound as a pale brown oil (84 mg, 89%). LCMS (Method J): $R_T$=3.30 min, [M+H]$^+$=471.

2-Amino-4-chloropyrimidine-5-carbonitrile

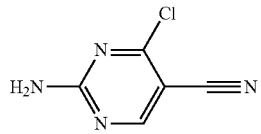

To a stirred solution of 2,4-dichloropyrimidine-5-carbonitrile (500 mg, 2.87 mmol) in MeOH (5 mL) was added 2M NH$_3$/MeOH (5 mL). After stirring for 20 min the resulting precipitate was filtered and washed with MeOH to afford the title compound as a white solid (173 mg, 39%). LCMS (Method C): $R_T$ 1.91 min [M+H]$^+$ 155.1. $^1$H NMR (DMSO-d$_6$, 400 MHz): δ 8.68 (1H, s), 8.23 (2H, br s)

(2-Bromo-3-fluoro-6-nitrophenyl)methylamine

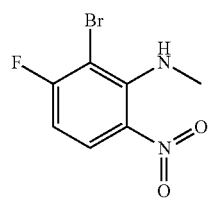

Methylamine (2M in THF, 19 mL, 38.1 mmol) was added to a solution of 2-bromo-1,3-difluoro-4-nitrobenzene (4.53 g, 19 mmol) and DIPEA (6.8 mL, 38.1 mmol) in THF (70 mL) and the resultant mixture stirred at 60° C. for 3 h. The reaction mixture was concentrated in vacuo and the residue purified by chromatography eluting with (SiO₂ 0-80% DCM in cyclohexane) to give title compound as an orange/yellow solid (4.32 g, 91%). LCMS (Method C): R$_T$ 3.46 min [M+H]⁺ 249.0, 251.0.

3-Bromo-4-fluoro-N²-methylbenzene-1,2-diamine

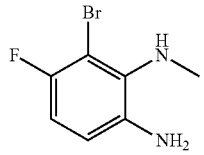

Ammonium chloride (6.24 g, 117 mmol) and iron powder (4.34 g, 77.7 mmol) were added to a stirred mixture of (2-bromo-3-fluoro-6-nitrophenyl)methylamine (4.84 g, 19.4 mmol) in 3:1 methanol/water (320 mL) and the resultant mixture heated at reflux for 24 h. The solid material was removed by filtration and the filtrate concentrated to approximately ⅓ volume. This mixture was partitioned between DCM (3×) and water then the combined DCM extracts were dried (Na₂SO₄) and concentrated in vacuo. The resulting residue was purified by chromatography (SiO₂, eluting with 0-5% methanol in DCM) to give title compound as an oil (1.99 g, 47%). LCMS (Method C): R$_T$ 2.37 min [M+H]⁺ 219.0, 221.0

[(S)-1-(3-Bromo-2,4-difluorophenylcarbamoyl)ethyl]carbamic acid tert-butyl ester

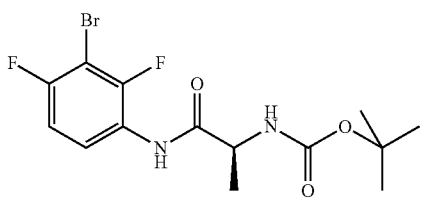 [SMILES: C[C@H](NC(=O)OC(C)(C)C)C(=O)Nc1ccc(F)c(Br)c1F]

N-(3-dimethylaminopropyl)-n'-ethylcarbodiimide hydrochloride (1.54 g, 8.13 mmol) was added to a stirred mixture of 3-bromo-4-fluoro-N²-methylbenzene-1,2-diamine (1.78 g, 8.13 mmol), (S)-2-tert-(butoxycarbonylamino)propionic acid (1.54 g, 8.13 mmol) and HOAt (1.11 g, 8.13 mmol) in DCM at 0° C. under nitrogen and stirring continued for 16 h. The reaction mixture was partitioned between DCM and saturated aqueous NaHCO₃. The combined DCM extracts were dried (Na₂SO₄) and concentrated in vacuo. The residue was purified by chromatography (SiO₂ 0-3% (2M ammonia in methanol) in DCM) to give title compound as an off white solid (2.91 g, 92%). LCMS (Method C): R$_T$ 3.33 min [M+H]⁺ 390.1, 392.1

[(S)-1-(7-Bromo-6-fluoro-1-methyl-1H-benzoimidazol-2-yl)ethyl]carbamic acid tert-butyl ester

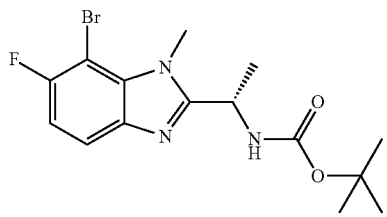 [SMILES: C[C@H](NC(=O)OC(C)(C)C)c1nc2ccc(F)c(Br)c2n1C]

A solution of [(S)-1-(3-bromo-2,4-difluorophenylcarbamoyl)ethyl]carbamic acid tert-butyl ester (2.91 g, 7.46 mmol) in acetic acid (50 mL) was stirred at 75° C. under nitrogen for 1 h. A separate solution of [(S)-1-(3-bromo-2,4-difluorophenylcarbamoyl)ethyl]carbamic acid tert-butyl ester (0.36 g, 0.91 mmol) in acetic acid (10 mL) was stirred at 75° C. under nitrogen for 2 h. The reactions were combined then concentrated in vacuo and the residue partitioned between DCM and saturated aqueous NaHCO₃. The combined DCM extracts were dried (Na₂SO₄) and concentrated in vacuo to give title compound as a white solid (3.03 g, 97%). LCMS (Method C): R$_T$ 3.41 min [M+H]⁺ 372.1, 374.1.

(S)-1-(7-Bromo-6-fluoro-1-methyl-1H-benzoimidazol-2-yl)ethylamine

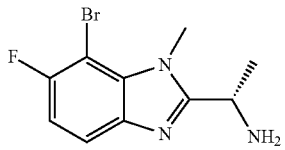

TFA (40 mL) was added to a solution of [(S)-1-(7-bromo-6-fluoro-1-methyl-1H-benzoimidazol-2-yl)ethyl]carbamic acid tert-butyl ester (3.02 g, 8.11 mmol) in DCM (20 mL) and stirred for 15 minutes. The reaction mixture was concentrated in vacuo and the residue partitioned between DCM and saturated aqueous NaHCO₃. The combined DCM extracts were dried (Na₂SO₄) and concentrated in vacuo to give the title compound as a white solid (2.04 g, 92%). LCMS (Method C): $R_T$ 1.83 min [M+H]$^+$ 271.9, 273.9

4-Amino-6-[(S)-1-(7-bromo-6-fluoro-1-methyl-1H-benzoimidazol-2-yl)ethylamino]pyrimidine-5-carbonitrile

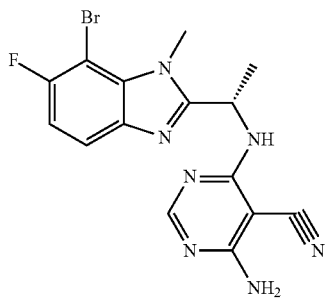 [SMILES: C[C@H](Nc1ncnc(N)c1CN)c1nc2ccc(F)c(Br)c2n1C]

4-Amino-6-chloropyrimidine-5-carbonitrile (0.88 g, 5.71 mmol) was added to a solution of (S)-1-(7-bromo-6-fluoro-1-methyl-1H-benzoimidazol-2-yl)ethylamine (1.11 g, 4.08 mmol) and DIPEA (2.6 mL, 14.7 mmol) in IPA (30 mL) and the resultant mixture stirred at 85° C. for 16 h. The reaction mixture was poured into water and the precipitated solid removed by filtration. The solid was washed with water and dried to give the title compound as an off white solid (1.61 g, 100%). LCMS (Method C): $R_T$ 2.68 min [M+H]$^+$ 390.1, 392.1

(5-Fluoro-2-nitro-phenyl)-(1-methyl-1H-pyrazol-4-yl)-amine

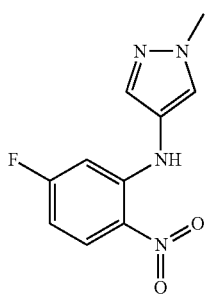 [SMILES: Cn1cc(Nc2cc(F)ccc2[N+](=O)[O-])cn1]

Potassium tert-butoxide (1.16 g, 10.3 mmol) was added to a solution of 1-methyl-1H-pyrazol-4-ylamine (0.50 g, 5.15 mmol) in THF (10 mL) at 0° C. under nitrogen and resultant mixture stirred for 15 min. 2,4-difluoro-1-nitrobenzene (0.98 g, 6.18 mmol) in THF (5 mL) was added and stirring continued for 1 h. The reaction mixture was poured into saturated aqueous ammonium chloride solution and extracted with EtOAc (×3). The combined EtOAc extracts were dried (Na$_2$SO$_4$) and concentrated in vacuo. The resulting residue was purified by chromatography (SiO$_2$, 0-2% methanol in DCM) to give the title compound as a red gummy solid (0.19 g, 16%). LCMS (Method B): $R_T$ 3.12 min [M+H]$^+$ 236.9

4-Fluoro-N$^2$-(1-methyl-1H-pyrazol-4-yl)-benzene-1,2-diamine

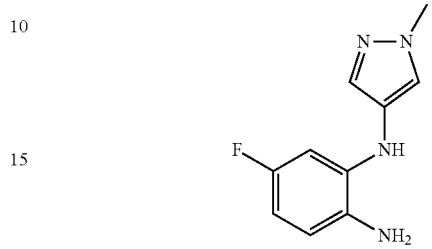

A mixture of (5-fluoro-2-nitrophenyl)-(1-methyl-1H-pyrazol-4-yl)amine (102 mg, 0.43 mmol) and 10% palladium on carbon (25 mg) in EtOAc (10 mL) was stirred under an atmosphere of hydrogen at atmospheric pressure and 20° C. for 6 h. A separate mixture of (5-fluoro-2-nitrophenyl)-(1-methyl-1H-pyrazol-4-yl)amine (0.19 g, 0.80 mmol) and 10% palladium on carbon (50 mg) in EtOAc (10 mL) was stirred under an atmosphere of hydrogen at atmospheric pressure and 20° C. for 5 h. The catalyst was removed by filtration and the filtrates combined and concentrated in vacuo. The resulting residue was purified by chromatography (SiO$_2$, 0-8% (2M ammonia in methanol) in DCM) to give the title compound as a brown oil (0.188 g, 74%). LCMS (Method C): $R_T$ 1.61 min [M+H]$^+$ 207.1

{(S)-1-[6-Fluoro-1-(1-methyl-1H-pyrazol-4-yl)-1H-benzoimidazol-2-yl]-ethyl}-carbamic acid tert-butyl ester

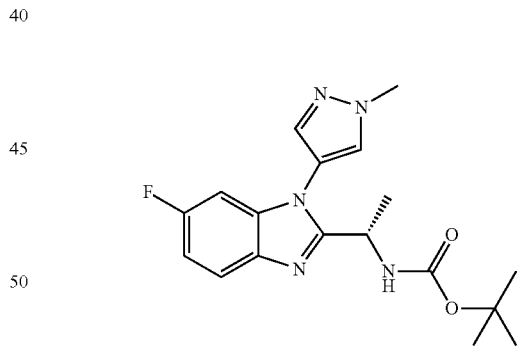

Triethyloxonium tetrafluoroborate (0.35 g, 1.86 mmol) was added to a solution of ((S)-1-carbamoylethyl)carbamic acid tert-butyl ester (0.41 g, 2.22 mmol) in DCM (10 mL) at 20° C. under nitrogen and the resultant mixture stirred for 3 h then was concentrated in vacuo. The residue was dissolved in ethanol (10 mL) and 4-fluoro-N$^2$-(1-methyl-1H-pyrazol-4-yl)-benzene-1,2-diamine (0.183 g, 0.89 mmol) added. The resultant solution was stirred at reflux for 16 h under nitrogen. The reaction mixture was concentrated in vacuo and the residue partitioned between DCM (×3) and saturated aqueous NaHCO$_3$. The combined DCM extracts were dried (Na$_2$SO$_4$) and concentrated in vacuo. The resultant residue was purified by chromatography (SiO$_2$, 0-5% (2M ammonia in methanol)

in DCM) to give the title compound as a brown oil (0.274 g, 86%). LCMS (Method C): $R_T$ 2.77 min [M+H]$^+$ 360.2.

(S)-1-[6-Fluoro-1-(1-methyl-1H-pyrazol-4-yl)-1H-benzoimidazol-2-yl]ethylamine

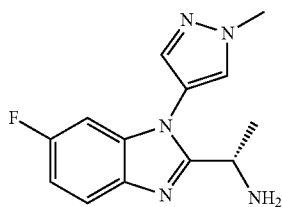

TFA (10 mL) was added to a solution of {(S)-1-[6-fluoro-1-(1-methyl-1H-pyrazol-4-yl)-1H-benzoimidazol-2-yl]ethyl}carbamic acid tert-butyl ester (0.268 g, 0.75 mmol) in DCM (5 mL) and stirred for 15 minutes. The reaction mixture was concentrated in vacuo and the residue partitioned between DCM (×3) and saturated aqueous NaHCO$_3$. The combined DCM extracts were dried (Na$_2$SO$_4$) and concentrated in vacuo. The resultant residue was purified by chromatography (SiO$_2$, 0-10% (2M ammonia in methanol) in DCM) to give the title compound as an oil (0.113 g, 59%). LCMS (Method C): $R_T$ 1.72 min [M+H]$^+$ 260.1

(5-Fluoro-2-nitrophenyl)-(2-methyl-2H-pyrazol-3-yl)amine

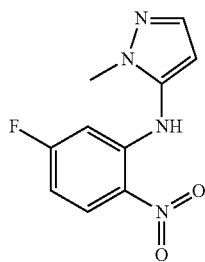

Potassium tert-butoxide (1.16 g, 10.3 mmol) was added to a solution of 2-methyl-2H-pyrazol-3-ylamine (0.50 g, 5.15 mmol) in THF (10 mL) at 0° C. under nitrogen and the resultant mixture stirred for 15 min. 2,4-difluoro-1-nitrobenzene (0.98 g, 6.18 mmol) in THF (5 mL) was added and stirring continued for 2 h. The reaction mixture was poured into saturated aqueous ammonium chloride solution and extracted with EtOAc (×3). The combined EtOAc extracts were dried (Na$_2$SO$_4$) and concentrated in vacuo. The resultant residue was purified by chromatography (SiO$_2$, 0-2% methanol in DCM) to give the title compound as a yellow/brown crystalline solid (0.98 g, 80%). LCMS (Method C): $R_T$ 2.98 min [M+H]$^+$ 237.0

4-Fluoro-N$^2$-(2-methyl-2H-pyrazol-3-yl)benzene-1,2-diamine

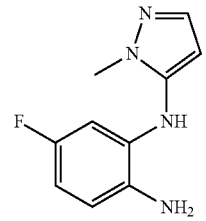

A mixture of (5-fluoro-2-nitrophenyl)-(2-methyl-2H-pyrazol-3-yl)-amine (0.96 g, 4.06 mmol) and 10% palladium on carbon (0.20 g) in EtOAc (40 mL) was stirred under an atmosphere of hydrogen at atmospheric pressure and 20° C. for 5 h. The catalyst was removed by filtration and the filtrate concentrated in vacuo to give the title compound as a white solid (0.63 g, 88%). LCMS (Method C): $R_T$ 1.88 min [M+H]$^+$ 207.0

{(S)-1-[6-Fluoro-1-(2-methyl-2H-pyrazol-3-yl)-1H-benzoimidazol-2-yl]-ethyl}-carbamic acid tert-butyl ester

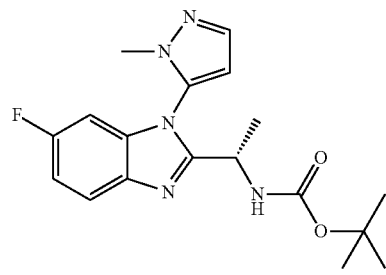 [SMILES: C[C@H](NC(=O)OC(C)(C)C)c1nc2ccc(F)cc2n1-c1ccnn1C]

Triethyloxonium tetrafluoroborate (1.06 g, 5.60 mmol) was added to a solution of ((S)-1-carbamoylethyl)carbamic acid tert-butyl ester (1.26 g, 6.67 mmol) in DCM (20 mL) at 20° C. under nitrogen and the resultant mixture stirred for 3 h then concentrated in vacuo. The resultant residue was dissolved in ethanol (20 mL) and 4-fluoro-N$^2$-(2-methyl-2H-pyrazol-3-yl)-benzene-1,2-diamine (0.55 g, 2.67 mmol) added, and the reaction mixture stirred at reflux for 16 h under nitrogen. The reaction mixture was concentrated in vacuo and residue partitioned between DCM (×3) and saturated aqueous NaHCO$_3$. The combined DCM extracts were dried (Na$_2$SO$_4$) and concentrated in vacuo. The resultant residue was purified by chromatography (SiO$_2$, 0-5% (2M ammonia in methanol)

in DCM) to give the title compound as a yellow oil (1.25 g, 100%). LCMS (Method C): $R_T$ 3.08 min [M+H]$^+$ 360.2. 310091751

(S)-1-[6-Fluoro-1-(2-methyl-2H-pyrazol-3-yl)-1H-benzoimidazol-2-yl]-ethylamine

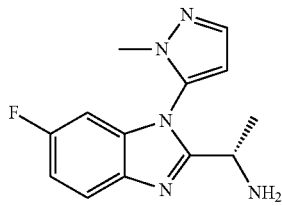 [SMILES: C[C@H](N)c1nc2ccc(F)cc2n1-c1ccnn1C]

TFA (20 mL) was added to a solution of {(S)-1-[6-fluoro-1-(2-methyl-2H-pyrazol-3-yl)-1H-benzoimidazol-2-yl]-ethyl}carbamic acid tert-butyl ester (0.96 g, 2.67 mmol) in DCM (10 mL) and stirred for 15 min. The reaction mixture was concentrated in vacuo and the residue partitioned between DCM (×3) and saturated aqueous NaHCO$_3$. The combined DCM extracts were dried (Na$_2$SO$_4$) and concentrated in vacuo. The resultant residue was purified by chromatography (SiO$_2$, 0-10% (2M ammonia in methanol) in DCM) to give the title compound as a colourless oil (0.69 g, 51%). LCMS (Method C): $R_T$ 1.55, 1.72 min [M+H]$^+$ 260.1.

[2-((S)-1-Aminoethyl)-5-fluoro-3-phenyl-3H-benzoimidazol-4-yl]morpholin-4-yl-methanone dihydrochloride

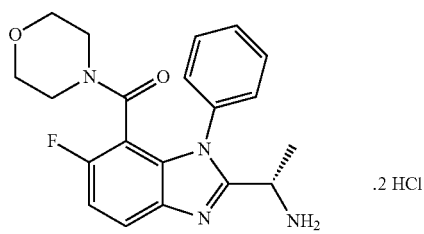 [SMILES: C[C@H](N)c1nc2ccc(F)c(C(=O)N3CCOCC3)c2n1-c1ccccc1]

To a solution of 2-((S)-1-tert-butoxycarbonylaminoethyl)-5-fluoro-3-phenyl-3H-benzoimidazole-4-carboxylic acid (279 mg, 0.69 mmol) and morpholine (244 µL, 2.80 mmol) in DCM (5 mL) was added HATU (398 mg, 1.05 mmol) and the reaction stirred at RT for 1 h. The reaction mixture was diluted with sat. aq. NaHCO$_3$ and extracted with DCM (3×10 mL). The combined organic fractions were washed with brine, dried (MgSO$_4$), and concentrated in vacuo to give the product as yellow oil. LCMS (Method C): $R_T$=3.01 min, [M+H]$^+$= 469. The product was dissolved in HCl in dioxane (4N, 10 mL) and the reaction mixture stirred at RT for 30 min. The reaction mixture was concentrated in vacuo to give the product as an off white solid. LCMS (Method C): $R_T$=0.27 min, [M+H]$^+$=369.

1,3-Difluoro-4-nitro-2-vinylbenzene

A solution of 2-bromo-1,3-difluoro-4-nitrobenzene (0.20 g, 0.84 mmol), tributylvinylstannane (0.27 mL, 0.924 mmol) and Pd(PPh$_3$)$_4$ (48.6 mg, 0.042 mmol) in dioxane (4 mL) was heated at 150° C. for 1 h using microwave irradiation. The cooled reaction mixture was concentrated in vacuo, the resulting residue was purified by column chromatography (Si—PCC, eluant 2-10% EtOAc in cyclohexane) affording the title compound as a pale orange oil (0.119 g, 77%). $^1$H NMR (CDCl$_3$, 300 MHz): 8.01-7.93 (1H, m), 7.03 (1H, dt, J=9.2, 1.9 Hz), 6.71 (1H, dd, J=18.0, 12.0 Hz), 6.15 (1H, d, J=18.0 Hz), 5.77 (1H, d, J=12.0 Hz)

Allyl-(3-fluoro-6-nitro-2-vinylphenyl)amine

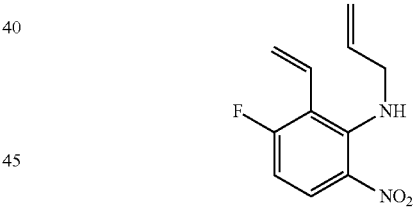

To a solution of 1,3-difluoro-4-nitro-2-vinylbenzene (115 mg, 0.621 mmol) in DMF (3 mL) was added allylamine (0.0513 mL, 0.683 mmol) and potassium carbonate (0.173 g, 1.24 mmol). The reaction mixture was stirred at RT for 2 h, and then partitioned between water and EtOAc. The aqueous phase was extracted with EtOAc and the combined organic layers were washed with water, followed by brine, then dried (Na$_2$SO$_4$) and concentrated in vacuo. The resulting residue was purified by column chromatography (Si—PCC, eluant 1-5% EtOAc in cyclohexane) affording the title compound as a yellow oil (109.6 mg, 79%). $^1$H NMR (CDCl$_3$, 300 MHz): 8.08 (1H, dd J=9.4, 5.8 Hz), 7.64 (1H, bs), 6.57 (1H, t, J=9.3 Hz), 6.51 (1H, dd, J=18.0, 11.6 Hz), 5.81 (1H, tdd, J=17.1, 10.2, 5.5 Hz), 5.72 (1H, ddd, J=18.0, 2.5, 1.6 Hz), 5.65 (1H, ddd, J=11.6, 1.5, 0.9 Hz), 5.26 (1H, dq, J=17.1, 1.5 Hz), 5.17 (1H, dq, J=10.2, 1.4 Hz), 3.98 (2H, ddt, J=6.3, 5.5, 1.6 Hz)

5-Fluoro-8-nitro-1,2-dihydroquinoline

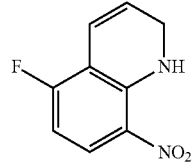

To a solution of allyl-(3-fluoro-6-nitro-2-vinylphenyl) amine (109 mg, 0.49 mmol) in DCM (10 mL) was added Grubbs catalyst (2$^{nd}$ generation, benzylidene[1,3-bis(2,4,6-trimethylphenyl)-2-imidazolidinylidene]dichloro(tricyclohexylphosphine)ruthenium) (8.5 mg, 0.01 mmol). The reaction mixture was stirred at RT for 16 h, and then purified by column chromatography (Si—PCC, eluant DCM) affording the title compound as a red solid (83.6 mg, 88%). $^1$H NMR (CDCl$_3$, 300 MHz): 8.17 (1H, bs), 7.88 (1H, dd, J=9.6, 6.0 Hz), 6.52 (1H, dt, J=10.3, 2.2 Hz), 6.22 (1H, dd, J=9.7, 8.3 Hz), 5.77-5.71 (1H, m), 4.55-4.52 (2H, m)

5-Fluoro-1,2,3,4-tetrahydroquinolin-8-ylamine

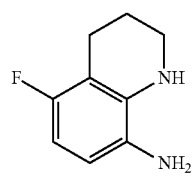

To a solution of 5-fluoro-8-nitro-1,2-dihydroquinoline (83.6 mg, 0.43 mmol) in EtOAc (10 mL) was added a slurry of 10% Pd/C (28 mg) in IMS (3 mL) and the reaction mixture was stirred at RT under a hydrogen atmosphere for 22 h. The suspension was then filtered through a pad of Celite® and the filtrate was concentrated in vacuo affording a mixture of the title compound and 5-fluoroquinolin-8-ylamine as a purple oil (70.4 mg, 99%). $^1$H NMR (CDCl$_3$, 300 MHz) (signals due to title compound): 6.46 (1H, dd, J=8.5, 5.5 Hz), 6.28 (1H, dd, J=9.2, 8.5 Hz), 3.31-3.28 (2H, m), 3.24 (3H, bs), 2.72 (2H, t, J=6.5 Hz), 1.94-1.86 (2H, m)

[(S)-1-(5-Fluoro-1,2,3,4-tetrahydroquinolin-8-ylcarbamoyl)ethyl]carbamic acid tert-butyl ester

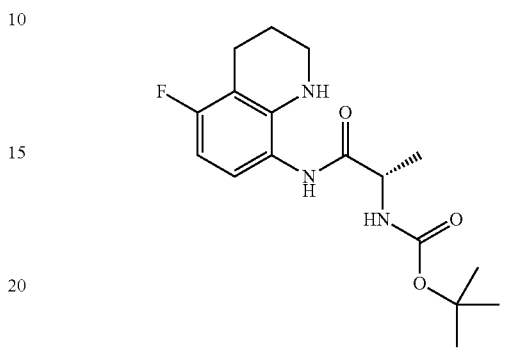

To an ice-cooled mixture of the 5-fluoro-1,2,3,4-tetrahydroquinolin-8-ylamine and 5-fluoroquinolin-8-ylamine from the previous step (70.4 mg, 0.424 mmol), (S)-2-tert-butoxycarbonylaminopropionic acid (88.3 mg, 0.466 mmol) and HOAt (57.7 mg, 0.424 mmol) in DCM (6 mL) was added EDCI HCl (97.7 mg, 0.51 mmol). The reaction mixture was stirred in the ice bath for 2 h, then diluted with DCM, washed with aqueous Na$_2$CO$_3$ and then water. The organic layer was dried (Na$_2$SO$_4$) and then concentrated in vacuo. The resulting residue was purified by column chromatography (Si—PCC, gradient 20-50% EtOAc in cyclohexane) affording the title compound as a purple gum (105 mg, 73%). LCMS (Method B): R$_T$ 3.35 min [M+H]$^+$ 338.

[(S)-1-(7-Fluoro-5,6-dihydro-4H-imidazo[4,5,1-ij]quinolin-2-yl)ethyl]carbamic acid tert-butyl ester

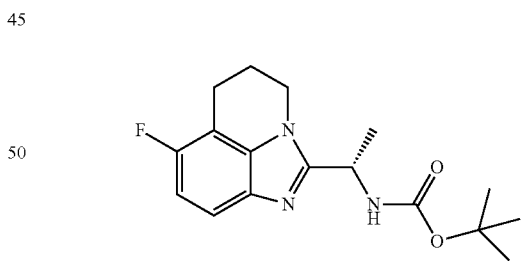

A solution of [(S)-1-(5-fluoro-1,2,3,4-tetrahydroquinolin-8-ylcarbamoyl)ethyl]carbamic acid tert-butyl ester (15 mg, 0.044 mmol) in AcOH (1 mL) was stirred at 100° C. for 2 h, then concentrated in vacuo. A further portion of [(S)-1-(5-fluoro-1,2,3,4-tetrahydroquinolin-8-ylcarbamoyl)ethyl]carbamic acid tert-butyl ester (90 mg, 0.267 mmol) in AcOH (5 mL) was stirred at 100° C. for 1 h, then concentrated in vacuo. The combined residues were purified by column chromatography (Si—PCC, gradient 30-60% EtOAc in cyclohexane)

affording the title compound as a colourless gum (78 mg, 79%). LCMS (Method J): $R_T$ 2.19 min [M+H]$^+$ 320

(S)-1-(7-Fluoro-5,6-dihydro-4H-imidazo[4,5,1-ij]quinolin-2-yl)ethylamine

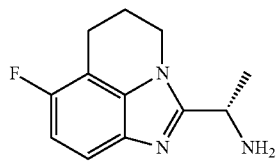 [SMILES: C[C@H](N)c1nc2ccc(F)c3c2n1CCC3]

To an ice-cooled solution of [(S)-1-(7-fluoro-5,6-dihydro-4H-imidazo[4,5,1-ij]quinolin-2-yl)ethyl]carbamic acid tert-butyl ester (78 mg, 0.244 mmol) in DCM (4 mL) was added TFA (1.3 mL) and the mixture was stirred at RT for 1.5 h. Toluene was added and volatiles were removed under reduced pressure, the resulting residue was dissolved in MeOH and loaded onto an Isolute® SCX-2 cartridge. The cartridge was washed with MeOH and the product was eluted with 0.5M NH$_3$/MeOH. The product containing fractions were combined and concentrated in vacuo affording the title compound as a colourless gum (49.5 mg, 93%). LCMS (Method B): $R_T$ 1.78 min [M+H]$^+$ 220

But-3-enyl-(3-fluoro-6-nitro-2-vinylphenyl)amine

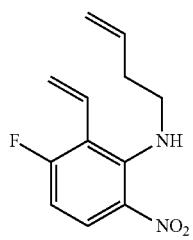 [SMILES: C=CCCNc1c([N+](=O)[O-])ccc(F)c1C=C]

To an ice-cooled solution of 1,3-difluoro-4-nitro-2-vinylbenzene (389 mg, 2.1 mmol) in DMF (8 mL) was added 3-butenylamine hydrochloride (248 mg, 2.31 mmol) and potassium carbonate (0.87 g, 6.3 mmol). The reaction mixture was stirred at RT for 2 h, and then partitioned between water and EtOAc. The aqueous phase was extracted with EtOAc and the combined organic layers were washed with water, followed by brine, then dried (Na$_2$SO$_4$) and concentrated in vacuo. The resulting residue was purified by column chromatography (Si—PCC, eluant 2-4% EtOAc in cyclohexane) affording the title compound as an orange oil (327.6 mg, 66%). LCMS (Method B): $R_T$ 4.27 min [M+H]$^+$ 237

6-Fluoro-9-nitro-2,3-dihydro-1H-benzo[b]azepine

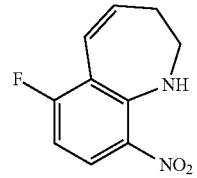

To a solution of but-3-enyl-(3-fluoro-6-nitro-2-vinylphenyl)amine (327.6 mg, 1.386 mmol) in DCM (30 mL) was added Grubbs catalyst (2$^{nd}$ generation, benzylidene[1,3-bis(2,4,6-trimethylphenyl)-2-imidazolidinylidene]dichloro(tricyclohexylphosphine)ruthenium) (47 mg, 0.055 mmol). The reaction mixture was stirred at RT for 16 h, and then a further portion of the Grubbs catalyst (47 mg, 0.055 mmol) was added and stirring continued for a further 64 h. The reaction mixture was concentrated in vacuo and then purified by column chromatography (Si—PCC, eluant 2-6% EtOAc in cyclohexane). The recovered starting material (145 mg) was dissolved in DCM (20 mL) and Grubbs 2$^{nd}$ generation catalyst (30 mg, 0.035 mmol) was added. The reaction mixture was heated under reflux for 6 h, then left at RT for 16 h. The reaction mixture was concentrated in vacuo, combined with the product from the initial purification and purified by column chromatography (Si—PCC, eluant 2-8% EtOAc in cyclohexane) affording the title compound as a red solid (225.4 mg, 78%). $^1$H NMR (CDCl$_3$, 300 MHz): 8.90 (1H, bs), 8.09 (1H, dd, J=9.4, 6.0 Hz), 6.67 (1H, dt, J=12.3, 1.8 Hz), 6.47 (1H, t, J=9.6 Hz), 6.16 (1H, dt, J=12.3, 4.7 Hz), 3.52 (2H, q, J=4.9 Hz), 2.65 (2H, dq, J=4.8, 1.8 Hz)

6-Fluoro-2,3,4,5-tetrahydro-1H-benzo[b]azepin-9-ylamine

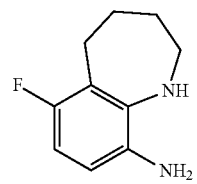

To a solution of 6-fluoro-9-nitro-2,3-dihydro-1H-benzo[b]azepine (225.4 mg, 1.0826 mmol) in EtOAc (15 mL) was added a slurry of 10% Pd/C (50 mg) in IMS (4 mL) and the reaction mixture was stirred at RT under a hydrogen atmosphere for 20 h. The suspension was then filtered through a pad of Celite® and the filtrate was concentrated in vacuo affording the title compound as a purple oil (197 mg, quantitative). LCMS (Method J): $R_T$ 1.69 min [M+H]$^+$ 181\

[(S)-1-(6-Fluoro-2,3,4,5-tetrahydro-1H-benzo[b]azepin-9-ylcarbamoyl)ethyl]carbamic acid tert-butyl ester=

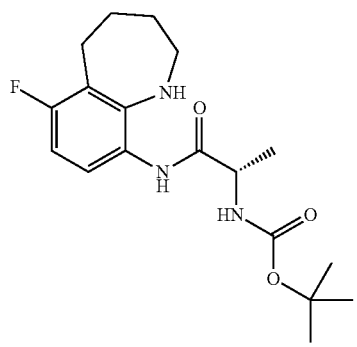 [SMILES: C[C@H](NC(=O)OC(C)(C)C)C(=O)Nc1ccc(F)c2c1NCCCC2]

To an ice-cooled mixture of 6-fluoro-2,3,4,5-tetrahydro-1H-benzo[b]azepin-9-ylamine=(195 mg, 1.0826 mmol), (S)-2-tert-butoxycarbonylaminopropionic acid (225 mg, 1.19 mmol) and HOAt (147 mg, 1.083 mmol) in DCM (10 mL) was added EDCI HCl (249 mg, 1.3 mmol). The reaction mixture was stirred in the ice bath for 2 h, then diluted with DCM, washed with aqueous Na$_2$CO$_3$ and then water. The organic layer was dried (Na$_2$SO$_4$) and then concentrated in vacuo. The resulting residue was purified by column chromatography (Si—PCC, gradient 20-50% EtOAc in cyclohexane) affording the title compound as a pink gum (270.6 mg, 71%). LCMS (Method J): $R_T$ 3.26 min [M+H]$^+$ 352

[(S)-1-(5-Fluoro-6,7,8,9-tetrahydro-2,9a-diazabenzo[cd]azulen-1-yl)ethyl]carbamic acid tert-butyl ester

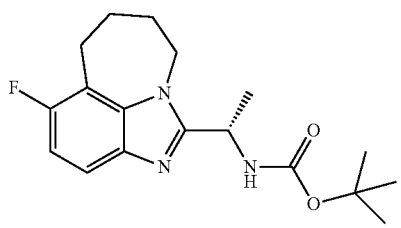 [SMILES: C[C@H](NC(=O)OC(C)(C)C)c1nc2ccc(F)c3c2n1CCCC3]

A solution of [(S)-1-(6-fluoro-2,3,4,5-tetrahydro-1H-benzo[b]azepin-9-ylcarbamoyl)ethyl]carbamic acid tert-butyl ester (270 mg, 0.768 mmol) in AcOH (4 mL) was stirred at 80° C. for 1 h, then concentrated in vacuo. The residue was purified by column chromatography (Si—PCC, gradient 30-60% EtOAc in cyclohexane) affording the title compound as a pale pink gum (252.6 mg, 99%). LCMS (Method B): $R_T$ 2.63 min [M+H]$^+$ 334

(S)-1-(5-Fluoro-6,7,8,9-tetrahydro-2,9a-diazabenzo[cd]azulen-1-yl)ethylamine

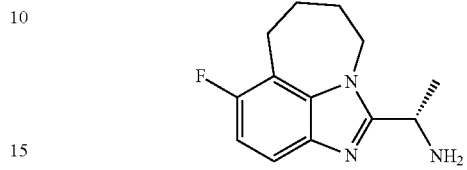

To an ice-cooled solution of [(S)-1-(5-fluoro-6,7,8,9-tetrahydro-2,9a-diazabenzo[cd]azulen-1-yl)ethyl]carbamic acid tert-butyl ester (252.6 mg, 0.7576 mmol) in DCM (8 mL) was added TFA (2 mL) and the mixture was stirred at RT for 1.5 h. Toluene was added and volatiles were removed under reduced pressure, the resulting residue was dissolved in MeOH and loaded onto an Isolute® SCX-2 cartridge. The cartridge was washed with MeOH and the product was eluted with 0.5M NH$_3$/MeOH. The product containing fractions were combined and concentrated in vacuo affording the title compound as a light pink solid (144.5 mg, 82%). LCMS (Method J): $R_T$ 1.93 min [M+H]$^+$ 234

2-(1-Methylallyl)isoindole-1,3-dione

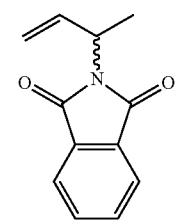

To a suspension of potassium phthalimide (7.08 g, 38.2 mmol) in DMF (60 mL) was added potassium carbonate (1.06 g, 7.6 mmol) and 3-chloro-1-butene (5.0 mL, 49.7 mmol). The mixture was heated under reflux in a bath at 135° C. for 4 h. The cooled reaction mixture was concentrated in vacuo and water (65 mL) was added over 5 minutes with rapid stirring at 40° C. The resulting suspension was cooled in an ice bath and then the solid was collected by filtration, washed with water (2×7 mL), then ethanol/water (45:55, 14 mL) and dried in vacuo at 50° C. for 16 h to give the title compound as a buff solid (5.0 g, 65%). $^1$H NMR ((CD$_3$)$_2$SO, 300 MHz): 7.87-7.83 (4H, m), 6.12 (1H, ddd, J=17.3, 10.5, 5.7 Hz), 5.17 (1H, dt, J=17.3, 1.4 Hz), 5.13 (1H, dt, J=10.4, 1.4 Hz), 4.88-4.78 (1H, m), 1.51 (3H, d, J=7.1 Hz)

1-Methylallylamine solution in ethanol

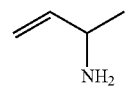

2-Aminoethanol (3.2 mL) was added to a solution of 2-(1-methylallyl)isoindole-1,3-dione (2.5 g, 12.4 mmol) in EtOH (5.2 mL). The mixture was stirred at 35° C. for 3 h and then set up for a short path distillation. A mixture of 1-methylallylamine and EtOH was collected by distillation (bp 65-70° C.) and used directly in the next step. $^1$H NMR (CDCl$_3$, 300 MHz) (signals due to title compound): 5.86 (1H, ddd, J=17.2, 10.3, 6.1 Hz), 5.10 (1H, dt, J=17.2, 1.4 Hz), 4.97 (1H, dt, J=10.3, 1.4 Hz), 3.52-3.43 (1H, m), 1.17 (3H, d, J=6.6 Hz)

(3-Fluoro-6-nitro-2-vinylphenyl)-(1-methylallyl)amine

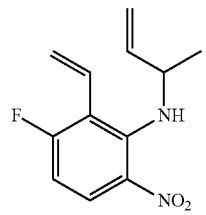

To a solution of 1,3-difluoro-4-nitro-2-vinylbenzene (150 mg, 0.81 mmol) in DMF (3 mL) was added a mixture of 1-methylallylamine in ethanol (0.4 mL). Potassium carbonate (0.224 g, 1.62 mmol) was added and the mixture stirred at RT for 1 h. A further portion of 1-methylallylamine in ethanol (0.3 mL) was added and stirring was continued for 1 h, and then the reaction mixture was partitioned between water and EtOAc. The aqueous phase was extracted with EtOAc and the combined organic layers were washed with water, followed by brine, then dried (Na$_2$SO$_4$) and concentrated in vacuo. The resulting residue was purified by column chromatography (Si—PCC, eluant 2-6% EtOAc in cyclohexane) affording the title compound as a yellow oil (134 mg, 70%). $^1$H NMR (CDCl$_3$, 300 MHz): 8.06 (1H, dd J=9.4, 5.7 Hz), 7.23 (1H, bs), 6.62 (1H, t, J=9.3 Hz), 6.48 (1H, dd, J=18.0, 11.6 Hz), 5.81-5.62 (2H, m), 5.64 (1H, dt, J=11.6, 1.3 Hz), 5.12-5.00 (2H, m), 4.38-4.25 (1H, m), 1.27 (3H, d, J=6.6 Hz)

5-Fluoro-2-methyl-8-nitro-1,2-dihydroquinoline

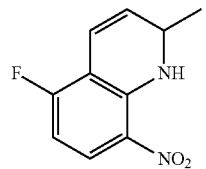

To a solution of (3-fluoro-6-nitro-2-vinylphenyl)-(1-methylallyl)amine (134 mg, 0.567 mmol) in DCM (10 mL) was added Grubbs catalyst (2$^{nd}$ generation, benzylidene[1,3-bis(2,4,6-trimethylphenyl)-2-imidazolidinylidene]dichloro(tricyclohexylphosphine)ruthenium) (9.6 mg, 0.011 mmol). The reaction mixture was stirred at RT for 64 h, and then purified by column chromatography (Si—PCC, eluant 1-4% EtOAc in cyclohexane) affording recovered starting material (56 mg) and the title compound (62.8 mg). The recovered starting material was dissolved in DCM (10 mL) and Grubbs catalyst (2$^{nd}$ generation, benzylidene[1,3-bis(2,4,6-trimethylphenyl)-2-imidazolidinylidene]dichloro(tricyclohexylphosphine)ruthenium) (12 mg) was added. The reaction mixture was stirred at 45° C. for 16 h, and then purified by column chromatography (Si—PCC, DCM). The combined products were further purified by column chromatography (Si—PCC, eluant 1.5-4% EtOAc in cyclohexane) affording the title compound as a red solid (76.8 mg, 65%). $^1$H NMR (CDCl$_3$, 300 MHz): 8.26 (1H, bs), 7.92 (1H, dd, J=9.6, 6.0 Hz), 6.53 (1H, dd, J=10.2, 1.7 Hz), 6.24 (1H, dd, J=9.7, 8.4 Hz), 5.70-5.65 (1H, m), 4.72-4.63 (1H, m), 1.43 (3H, J=6.6 Hz)

5-Fluoro-2-methyl-1,2,3,4-tetrahydroquinolin-8-ylamine

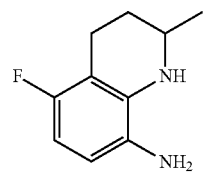

A suspension of 10% Pd/C (30 mg) in a mixture of IMS (3 mL) and EtOAc (5 mL) was stirred under an atmosphere of hydrogen for 15 min before a solution of 5-fluoro-2-methyl-8-nitro-1,2-dihydroquinoline (76.8 mg, 0.369 mmol) in EtOAc (15 mL) was added. The reaction mixture was stirred at RT under a hydrogen atmosphere for 20 h. The suspension was then filtered through a pad of Celite® and the filtrate was concentrated in vacuo affording a mixture of the title compound and 5-fluoro-2-methylquinolin-8-ylamine as a purple oil. LCMS (Method J): R$_T$ 1.90 min (28%) [M+H]$^+$ 181 and 2.26 min (42%) [M+H]$^+$ 177

[(S)-1-(5-Fluoro-2-methyl-1,2,3,4-tetrahydroquinolin-8-ylcarbamoyl)ethyl]carbamic acid tert-butyl ester

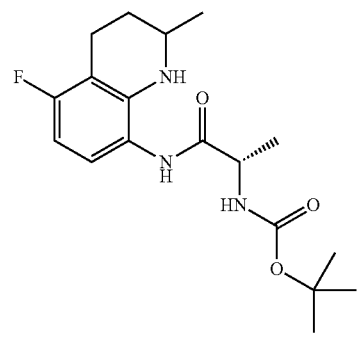 [SMILES: CC1CCc2c(F)ccc(NC(=O)[C@H](C)NC(=O)OC(C)(C)C)c2N1]

To the mixture of 5-fluoro-2-methyl-1,2,3,4-tetrahydroquinolin-8-ylamine and 5-fluoro-2-methylquinolin-8-ylamine from the previous step (0.369 mmol) in DCM (10 mL) was added (S)-2-tert-butoxycarbonylaminopropionic acid (76.8 mg, 0.405 mmol) and HOAt (56 mg, 0.41 mmol). The mixture was cooled in an ice bath, then EDCI HCl (85 mg, 0.44 mmol) was added. The reaction mixture was stirred in the ice bath for 2 h, then diluted with DCM, washed with aqueous Na$_2$CO$_3$ and then water. The organic layer was dried (Na$_2$SO$_4$) and then concentrated in vacuo. The resulting residue was purified by column chromatography (Si—PCC, gradient 20-50% EtOAc in cyclohexane) affording the title compound as a colourless solid (63.6 mg, 49%, 2 steps). LCMS (Method J): R$_T$ 3.40 min [M+H]$^+$ 352

[(S)-1-(7-Fluoro-4-methyl-5,6-dihydro-4H-imidazo [4,5,1-ij]quinolin-2-yl)ethyl]carbamic acid tert-butyl ester

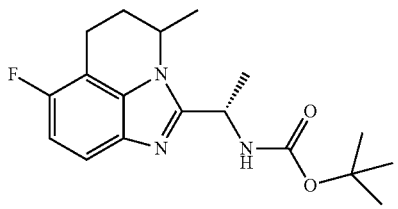 [SMILES: CC1CCc2c(F)ccc3nc([C@H](C)NC(=O)OC(C)(C)C)n1c23]

A solution of [(S)-1-(5-fluoro-2-methyl-1,2,3,4-tetrahydroquinolin-8-ylcarbamoyl)ethyl]carbamic acid tert-butyl ester (63.6 mg, 0.181 mmol) in AcOH (5 mL) was stirred at 80° C. for 2.5 h, then concentrated in vacuo. The residue was purified by column chromatography (Si—PCC, gradient 20-50% EtOAc in cyclohexane) affording the title compound as a colourless gum (24.2 mg, 40%) LCMS (Method B): R$_T$ 2.45 min [M+H]$^+$ 334

(S)-1-(7-Fluoro-4-methyl-5,6-dihydro-4H-imidazo [4,5,1-ij]quinolin-2-yl)ethylamine

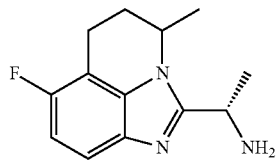 [SMILES: CC1CCc2c(F)ccc3nc([C@H](C)N)n1c23]

To an ice-cooled solution of [(S)-1-(7-fluoro-4-methyl-5, 6-dihydro-4H-imidazo[4,5,1-ij]quinolin-2-yl)ethyl]carbamic acid tert-butyl ester (24.2 mg, 0.0726 mmol) in DCM (4 mL) was added TFA (0.8 mL) and the mixture was stirred at RT for 16 h. Toluene was added and volatiles were removed under reduced pressure, the resulting residue was dissolved in MeOH and loaded onto an Isolute® SCX-2 cartridge. The cartridge was washed with MeOH and the product was eluted with 0.5M NH$_3$/MeOH. The product containing fractions were combined and concentrated in vacuo affording the title compound as a colourless gum (15.8 mg, 93%). LCMS (Method B): R$_T$ 1.98 min [M+H]$^+$ 234

2,6-Difluoro-3-nitrophenol

A solution of 1,3-difluoro-2-methoxy-4-nitrobenzene (0.50 g, 2.644 mmol) in 33% HBr in AcOH (4 mL) was heated at 100° C. for 1 h using microwave irradiation. The cooled reaction mixture was diluted with toluene and concentrated in vacuo. The resulting residue was partitioned between aqueous NaHCO$_3$ and EtOAc. The aqueous phase was acidified with 1M HCl and extracted twice with DCM. The combined DCM extracts were washed with water, dried (Na$_2$SO$_4$) and concentrated in vacuo affording the title compound as a buff solid (0.29 g, 63%). $^1$H NMR (CDCl$_3$, 300 MHz): 7.70 (1H, ddd, J=9.5, 7.8, 5.4 Hz), 7.06 (1H, ddd, J=9.4, 9.0, 2.2 Hz), 5.61 (1H, bs)

[2-(2,6-Difluoro-3-nitrophenoxy)ethyl]carbamic acid tert-butyl ester

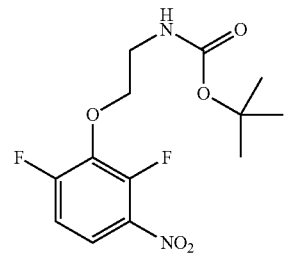 [SMILES: CC(C)(C)OC(=O)NCCOc1c(F)ccc([N+](=O)[O-])c1F]

To a solution of 2,6-difluoro-3-nitrophenol (248 mg, 1.416 mmol) and triphenylphosphine (558 mg, 2.127 mmol) in THF (10 mL) was added a solution of (2-hydroxyethyl)carbamic acid tert-butyl ester (274 mg, 1.70 mmol) in THF (2 mL). The mixture was cooled in an ice bath and a solution of diethyl azodicarboxylate (372 mg, 2.127 mmol) in THF (2 mL) was added over 5 min. The reaction was removed from the ice bath after 5 min and stirred at RT for 2 h, then concentrated in vacuo. The resulting residue was purified by column chromatography (Si—PCC, eluant 30-40% EtOAc in cyclohexane) affording the title compound as a colourless gum (483 mg, quantitative). $^1$H NMR (CDCl$_3$, 300 MHz): 7.84 (1H, ddd, J=9.5, 7.8, 5.3 Hz), 7.05 (1H, dt, J=9.9, 2.2 Hz), 5.05 (1H, bs), 4.26 (2H, t, J=5.0 Hz), 3.52 (2H, q, J=5.4 Hz), 1.45 (9H, s)

8-Fluoro-5-nitro-3,4-dihydro-2H-benzo[1,4]oxazine

To an ice-cold solution of [2-(2,6-difluoro-3-nitrophenoxy)ethyl]carbamic acid tert-butyl ester (450 mg, 1.416 mmol) in DCM (20 mL) was added TFA (4 mL). The reaction mixture was stirred at RT for 2.5 h, then toluene was added and volatiles were removed under reduced pressure. The resulting residue was dissolved in acetonitrile (10 mL), 2M Na$_2$CO$_3$ (10 mL) was added and the mixture stirred at RT for 1 h. The reaction mixture was partitioned between EtOAc and brine, the organic phase was dried (Na$_2$SO$_4$) and concentrated in vacuo. The residue was purified by column chromatography (Si—PCC, eluant 10-30% EtOAc in cyclohexane) affording the title compound as an orange solid (250 mg, 89%). ¹H NMR (CDCl₃, 300 MHz): 7.94 (1H, bs), 7.78 (1H, dd, J=9.7, 5.4 Hz), 6.45 (1H, t, J=9.5 Hz), 4.31 (2H, t, J=4.6 Hz), 3.70-3.66 (2H, m)

8-Fluoro-3,4-dihydro-2H-benzo[1,4]oxazin-5-ylamine

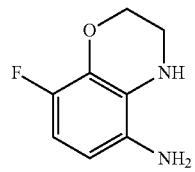

To a solution of 8-fluoro-5-nitro-3,4-dihydro-2H-benzo[1,4]oxazine (290 mg, 1.463 mmol) in EtOAc (15 mL) was added a slurry of 10% Pd/C (50 mg) in IMS (2 mL) and the reaction mixture was stirred at RT under a hydrogen atmosphere for 18 h. The suspension was then filtered through a pad of Celite® and the filtrate was concentrated in vacuo affording the title compound as purple oil (243 mg, 99%).

[(S)-1-(8-Fluoro-3,4-dihydro-2H-benzo[1,4]oxazin-5-ylcarbamoyl)ethyl]carbamic acid tert-butyl ester

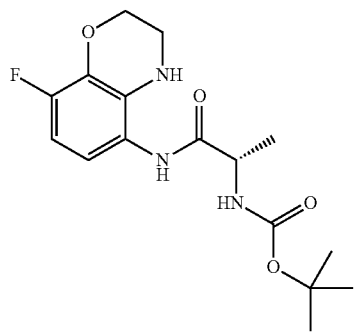 [SMILES: C[C@H](NC(=O)OC(C)(C)C)C(=O)Nc1ccc(F)c2c1NCCO2]

To an ice-cooled mixture of 8-fluoro-3,4-dihydro-2H-benzo[1,4]oxazin-5-ylamine (243 mg, 1.445 mmol), (S)-2-tert-butoxycarbonylaminopropionic acid (305 mg, 1.61 mmol) and HOAt (200 mg, 1.463 mmol) in DCM (15 mL) was added EDCI HCl (337 mg, 1.76 mmol). The reaction mixture was stirred in the ice bath for 90 min, then diluted with DCM, washed with aqueous Na₂CO₃ and then water. The organic layer was dried (Na₂SO₄) and then concentrated in vacuo. The resulting residue was purified by column chromatography (Si—PCC, gradient 50-70% EtOAc in cyclohex-ane) affording the title compound as a pale yellow foam (440 mg, 89%). LCMS (Method B): R_T 3.02 min [M+H]⁺ 340

[1-(6-Fluoro-3,4-dihydro-5-oxa-1,2a-diaza-acenaphthylen-2-yl)ethyl]carbamic acid tert-butyl ester

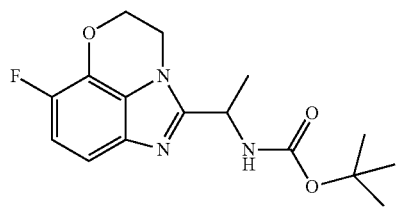 [SMILES: CC(NC(=O)OC(C)(C)C)c1nc2ccc(F)c3c2n1CCO3]

A solution of [(S)-1-(8-fluoro-3,4-dihydro-2H-benzo[1,4]oxazin-5-ylcarbamoyl)ethyl]carbamic acid tert-butyl ester (440 mg, 1.297 mmol) in AcOH (15 mL) was stirred successively at 80° C. for 1 h, 100° C. for 5 h and then 85° C. for 16 h. Toluene was added and the reaction mixture concentrated in vacuo to give a mixture of the title compound and N-[1-(6-fluoro-3,4-dihydro-5-oxa-1,2a-diaza-acenaphthylen-2-yl)ethyl]acetamide. LCMS (Method B): R_T 1.72 min [M+H]⁺ 264 & 2.51 min [M+H]⁺ 322

1-(6-Fluoro-3,4-dihydro-5-oxa-1,2a-diaza-acenaphthylen-2-yl)ethylamine

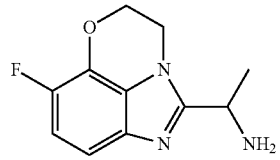 [SMILES: CC(N)c1nc2ccc(F)c3c2n1CCO3]

To an ice-cooled solution of the mixture of [1-(6-fluoro-3,4-dihydro-5-oxa-1,2a-diaza-acenaphthylen-2-yl)ethyl]carbamic acid tert-butyl ester and N-[1-(6-fluoro-3,4-dihydro-5-oxa-1,2a-diaza-acenaphthylen-2-yl)ethyl]acetamide from the previous step in DCM (15 mL) was added TFA (3 mL) and the mixture was stirred at RT for 2 h. Toluene was added and volatiles were removed under reduced pressure, the resulting residue was dissolved in MeOH and loaded onto an Isolute® SCX-2 cartridge. The cartridge was washed with MeOH and the product was eluted with 0.5M NH₃/MeOH. The product containing fractions were combined and concentrated in vacuo. Purification by column chromatography (Si—PCC, gradient 2-8% 2M NH₃/MeOH in DCM) afforded the title compound as a light brown gum (185.6 mg, 65%, 2 steps). LCMS (Method B): $R_T$ 1.54 min [M+H]$^+$ 222

[1-(6-Fluoro-3,4-dihydro-5-oxa-1,2a-diazaacenaphthylen-2-yl)ethyl]-[9-(tetrahydropyran-2-yl)-9H-purin-6-yl]amine

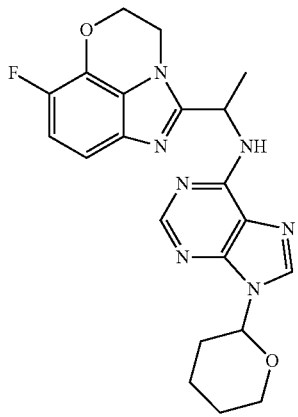 [SMILES: CC(Nc1ncnc2c1ncn2C1CCCCO1)c1nc2ccc(F)c3c2n1CCO3]

A mixture of 1-(6-fluoro-3,4-dihydro-5-oxa-1,2a-diazaacenaphthylen-2-yl)ethylamine (85 mg, 0.38 mmol), 6-chloro-9-(tetrahydropyran-2-yl)-9H-purine (92 mg, 0.38 mmol) and DIPEA (132 µL, 0.76 mmol) in IPA (1 mL) was heated for 18 h at 100° C. After cooling to RT, the volatiles were removed in vacuo and the resulting residue was purified by column chromatography (Si—PPC, gradient 0-5% MeOH in DCM) to afford the title compound as a pale yellow oil (132 mg, 82%). LCMS (Method J): $R_T$=2.22 min, [M+H]$^+$=424

[3-(2,6-Difluoro-3-nitrophenoxy)propyl]carbamic acid tert-butyl ester

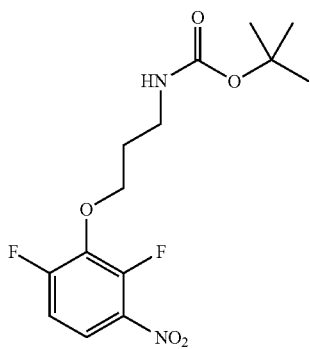 [SMILES: CC(C)(C)OC(=O)NCCCOc1c(F)ccc([N+](=O)[O-])c1F]

To a solution of 2,6-difluoro-3-nitrophenol (170 mg, 0.971 mmol) and triphenylphosphine (383 mg, 1.46 mmol) in THF (8 mL) was added a solution of (3-hydroxypropyl)carbamic acid tert-butyl ester (204 mg, 1.165 mmol) in THF (1 mL). The mixture was cooled in an ice bath and a solution of diethyl azodicarboxylate (255 mg, 1.46 mmol) in THF (1 mL) was added. The reaction was stirred at RT for 30 min, then concentrated in vacuo. The resulting residue was purified by column chromatography (Si—PCC, eluant 25-40% EtOAc in cyclohexane) affording the title compound as a colourless gum (296 mg, 92%). $^1$H NMR (CDCl$_3$, 300 MHz): 7.81 (1H, ddd, J=9.4, 7.8, 5.3 Hz), 7.04 (1H, dt, J=9.4, 2.2 Hz), 4.77 (1H, bs), 4.27 (2H, t, J=6.0 Hz), 3.37 (2H, q, J=6.4 Hz), 2.00 (2H, quintet, J=6.3 Hz), 1.45 (9H, s)

4-Fluoro-1-nitro-6,7,8,9-tetrahydro-5-oxa-9-azabenzocycloheptene

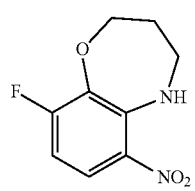 [SMILES: O=[N+]([O-])c1ccc(F)c2c1NCCCO2]

To an ice-cold solution of [3-(2,6-difluoro-3-nitrophenoxy)propyl]carbamic acid tert-butyl ester (296 mg, 0.8907 mmol) in DCM (15 mL) was added TFA (3 mL). The reaction mixture was stirred at RT for 2 h, then toluene was added and volatiles were removed under reduced pressure. The resulting residue was dissolved in acetonitrile (6 mL), 2M Na$_2$CO$_3$ (6 mL) was added and the mixture stirred at RT for 1.5 h. The reaction mixture was partitioned between EtOAc and brine, the organic phase was dried (Na$_2$SO$_4$) and concentrated in vacuo. The residue was purified by column chromatography (Si—PCC, eluant 10-20% EtOAc in cyclohexane) affording the title compound as a red solid (158.4 mg, 84%). $^1$H NMR (CDCl$_3$, 300 MHz): 8.08 (1H, bs), 7.87 (1H, dd, J=9.6, 5.6 Hz), 6.44 (1H, dd, J=9.8, 8.7 Hz), 4.40 (2H, t, J=6.6 Hz), 3.78-3.73 (2H, m), 2.29-2.20 (2H, m)

4-Fluoro-6,7,8,9-tetrahydro-5-oxa-9-azabenzocyclohepten-1-ylamine

To a solution of 4-fluoro-1-nitro-6,7,8,9-tetrahydro-5-oxa-9-azabenzocycloheptene (158 mg, 0.746 mmol) in EtOAc (10 mL) was added a slurry of 10% Pd/C (30 mg) in IMS (1 mL) and the reaction mixture was stirred at RT under a hydrogen atmosphere for 18 h. The suspension was then filtered through a pad of Celite® and the filtrate was concentrated in vacuo affording the title compound as a brown solid (131.5 mg, 97%). $^1$H NMR (CDCl$_3$, 300 MHz): 6.46 (1H, dd, J=10.2, 8.6 Hz), 6.35 (1H, dd, J=8.7, 5.1 Hz), 4.25 (2H, t, J=5.8 Hz), 3.36-3.32 (5H, bs & m), 2.06 (2H, quintet, J=5.8 Hz)

[(S)-1-(5-Fluoro-8,9-dihydro-7H-6-oxa-2,9a-diazabenzo[c,d]azulen-1-yl)ethyl]carbamic acid tert-butyl ester

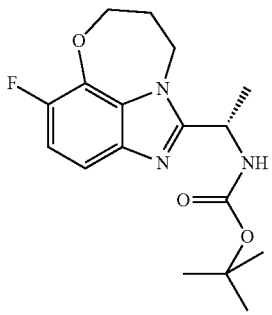 [SMILES: C[C@H](NC(=O)OC(C)(C)C)c1nc2ccc(F)c3c2n1CCCO3]

To a suspension of ((S)-1-carbamoylethyl)carbamic acid tert-butyl ester (413 mg, 2.19 mmol) in DCM (5 mL) was added triethyloxonium tetrafluoroborate (405 mg, 2.13 mmol) and the reaction mixture was stirred at RT for 1.5 hours under argon. The reaction mixture was concentrated in vacuo and the residue dissolved in ethanol (3 mL). 4-Fluoro-6,7,8,9-tetrahydro-5-oxa-9-azabenzocyclohepten-1-ylamine (129 mg, 0.71 mmol) was added and the reaction was heated at 70° C. for 45 min. The reaction mixture was concentrated in vacuo, and the residue was partitioned between DCM and sat. NaHCO$_3$. The organic phase was washed with brine, dried (Na$_2$SO$_4$) and concentrated in vacuo. The resultant residue was subjected to flash chromatography (Si—PPC, gradient 0-30% DCM in cyclohexane) to afford the title compound as a white foam (154 mg, 65%). $^1$H NMR (CDCl$_3$, 300 MHz): δ 7.25 (1H, dd, J=8.7, 3.9 Hz), 7.05 (1H, dd, J=11.6, 8.7 Hz), 5.34-5.29 (1H, m), 5.18-5.08 (1H, m), 4.48-4.44 (2H, m), 4.38-4.20 (2H, m), 2.50-2.43 (2H, m), 1.63 (3H, d, J=6.7 Hz), 1.44 (9H, s). $^1$H NMR (DMSO, 400 MHz): δ 8.03 (1H, s), 7.66 (1H, d, J=7.2 Hz), 7.26 (2H, br s), 7.14 (1H, dd, J=8.6, 4.0 Hz), 7.02 (1H, dd, J=11.9, 8.6 Hz), 5.62 (1H, dq, J=7.2, 6.7 Hz), 4.41 (1H, ddd, J=12.1, 4.6, 3.7 Hz), 4.33 (1H, ddd, J=12.1, 9.2, 4.4 Hz), 4.24-4.12 (2H, m), 2.34-2.28 (2H, m), 1.55 (3H, d, J=6.7 Hz)

(S)-1-(5-Fluoro-8,9-dihydro-7H-6-oxa-2,9a-diazabenzo[c,d]azulen-1-yl)ethylamine

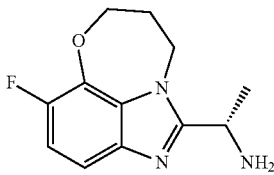 [SMILES: C[C@H](N)c1nc2ccc(F)c3c2n1CCCO3]

TFA (0.50 mL, 6.73 mmol) was added to a solution of [(S)-1-(5-fluoro-8,9-dihydro-7H-6-oxa-2,9a-diazabenzo[c,d]azulen-1-yl)ethyl]carbamic acid tert-butyl ester (151 mg, 0.45 mmol) in DCM (2 mL) and the reaction was stirred at RT for 30 min. The crude reaction mixture was passed through a 2 g Isolute® SCX-2 cartridge, eluting with 2M NH$_3$/MeOH. The basic fraction was concentrated in vacuo to give the title compound (104 mg, 98%) as a beige solid. LCMS (Method B): R$_T$=1.74 min, [M+H]$^+$=236

(S,R)— and (S,S)—O-methylmandelic acid amides of have dr 1.3:98.7 and 98.8:1.2 respectively, as determined by LCMS (Method K): R$_T$ 3.68 and 3.64 min [M+H]$^+$ 384.2

[(S)-1-(5-fluoro-8,9-dihydro-7H-6-oxa-2,9a-diazabenzo[c,d]azulen-1-yl)ethyl]-[9-(tetrahydropyran-2-yl)-9H-purin-6-yl]amine

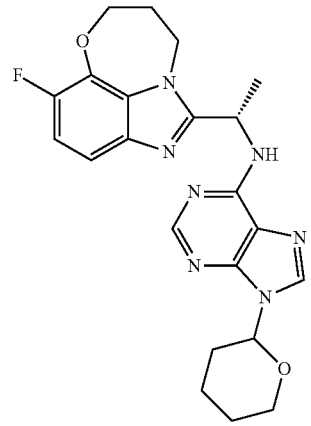 [SMILES: C[C@H](Nc1ncnc2c1ncn2C1CCCCO1)c1nc2ccc(F)c3c2n1CCCO3]

A mixture of (S)-1-(5-fluoro-8,9-dihydro-7H-6-oxa-2,9a-diazabenzo[c,d]azulen-1-yl)ethylamine (64 mg, 0.27 mmol), 6-chloro-9-(tetrahydropyran-2-yl)-9H-purine (65 mg, 0.27 mmol) and DIPEA (94 μL, 0.54 mmol) in IPA (0.5 mL) was heated for 24 h at 100° C. After cooling to RT, the volatiles were removed in vacuo and the resulting residue was purified by column chromatography (Si—PPC, gradient 0-5% MeOH in DCM) to afford the title compound as a pale yellow oil (86 mg, 73%). LCMS (Method J): R$_T$=2.33 min, [M+H]$^+$=438.

[(S)-2-(2,6-Difluoro-3-nitrophenoxy)-1-methylethyl] carbamic acid tert-butyl ester

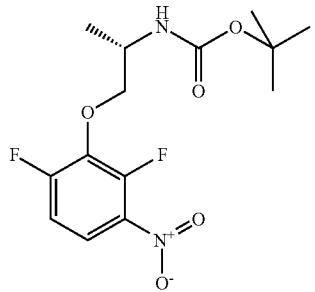 [SMILES: C[C@@H](COc1c(F)ccc([N+](=O)[O-])c1F)NC(=O)OC(C)(C)C]

Diethylazodicarboxylate (349 μL, 2.22 mmol) in THF (1 mL) was added slowly to a solution of 2,6-difluoro-3-nitrophenol (260 mg, 1.48 mmol), ((S)-2-hydroxy-1-methylethyl) carbamic acid tert-butyl ester (312 mg, 1.78 mmol) and triphenylphosphine (582 mg, 2.22 mmol) in THF (10 mL) at 0° C. The solution was stirred for 30 min at 0° C., and then concentrated in vacuo. The residue was purified by flash chromatography (Si—PPC, gradient 0-30% EtOAc in cyclohexane) to afford the title compound as a pale yellow oil (340 mg, 69%). $^1$H NMR (CDCl$_3$, 300 MHz): δ 7.82 (1H, ddd, J=13.0, 9.5, 5.3 Hz), 7.04 (1H, app. td, J=9.4, 2.1 Hz), 4.75 (1H, br s), 4.24-4.12 (2H, m), 4.00 (1H, br s), 1.44 (9H, s), 1.34 (3H, d, J=6.9 Hz)

(S)-8-Fluoro-3-methyl-5-nitro-3,4-dihydro-2H-benzo[1,4]oxazine

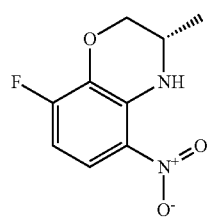

TFA (3 mL) was added to a solution of [(S)-2-(2,6-difluoro-3-nitrophenoxy)-1-methylethyl]carbamic acid tert-butyl ester (340 mg, 1.02 mmol) in DCM (15 mL) and the mixture was stirred for 90 min at rt. PhMe (25 mL) was added and the solution was concentrated in vacuo. The resultant residue was taken up in MeCN (7 mL); aqueous 2M $Na_2CO_3$ (7 mL) was added and the mixture was stirred vigorously for a further 90 min at rt. EtOAc (25 mL) and brine (25 mL) were added and the phases were separated. The aqueous was extracted with EtOAc (2×25 mL), and the combined organics were dried ($Na_2SO_4$) and concentrated in vacuo. The crude reaction mixture was purified by flash chromatography (Si—PPC, gradient 0-20% EtOAc in cyclohexane) to afford the title compound as a bright yellow solid (183 mg, 84%). $^1$H NMR ($CDCl_3$, 300 MHz): δ 7.85 (1H, br s), 7.78 (1H, dd, J=9.8, 5.5 Hz), 6.45 (1H, app. t, J=9.8 Hz), 4.36-4.28 (1H, m), 3.84-3.77 (2H, m), 1.35 (3H, d, J=6.2 Hz)

(S)-8-Fluoro-3-methyl-3,4-dihydro-2H-benzo[1,4]oxazin-5-ylamine

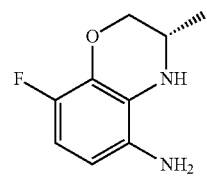

A suspension of (S)-8-fluoro-3-methyl-5-nitro-3,4-dihydro-2H-benzo[1,4]oxazine (183 mg, 0.86 mmol) and 10% Pd/C (37 mg) in EtOAc (12 mL) and IMS (1.2 mL) was stirred under a $H_2$ balloon for 16 h. The reaction mixture was filtered through celite and the filtrate was concentrated in vacuo to give the title compound as a pale yellow oil (160 mg, quant.). $^1$H NMR ($CDCl_3$, 300 MHz): δ 6.35 (1H, dd, J=10.8, 8.6 Hz), 6.14 (1H, dd, J=8.6, 4.6 Hz), 4.19 (1H, dd, J=10.5, 2.9 Hz), 3.64 (1H, dd, J=10.5, 8.4 Hz), 3.43 (1H, dqd, J=8.4, 6.5, 2.9 Hz), 3.10 (3H, br s), 1.17 (3H, d, J=6.5 Hz)

[(S)-1-((S)-6-Fluoro-3-methyl-3,4-dihydro-5-oxa-1,2a-diazaacenaphthylen-2-yl)ethyl]carbamic acid tert-butyl ester

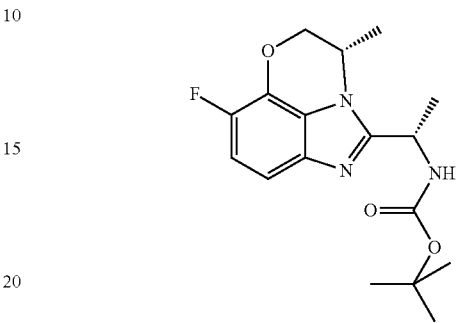

(S)-8-Fluoro-3-methyl-3,4-dihydro-2H-benzo[1,4]oxazin-5-ylamine (160 mg, 0.86 mmol) was added to a solution of (S)-2-tert-butoxycarbonylaminopropionimidic acid ethyl ester (570 mg, 2.64 mmol) in EtOH (10 mL) and the reaction was heated at 75° C. for 60 min. The reaction mixture was concentrated in vacuo, and the residue was partitioned between DCM and sat. $NaHCO_3$. The organic phase was washed with brine, dried ($Na_2SO_4$) and concentrated in vacuo. The resultant residue was subjected to flash chromatography (Si—PPC, gradient 0-40% DCM in cyclohexane) to afford the title compound as an off-white foam (220 mg, 76%). LCMS (Method J): $R_T$=2.50 min, [M+H]$^+$=336.

(S)-1-(S)-6-Fluoro-3-methyl-3,4-dihydro-5-oxa-1,2a-diazaacenaphthylen-2-yl)ethylamine

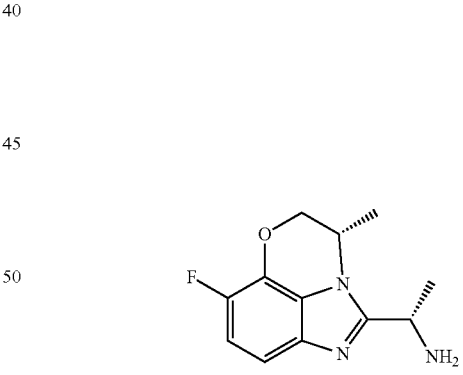

TFA (1.00 mL) was added to a solution of [(S)-1-(S)-6-fluoro-3-methyl-3,4-dihydro-5-oxa-1,2a-diazaacenaphthylen-2-yl)ethyl]carbamic acid tert-butyl ester (220 mg, 0.66 mmol) in DCM (4 mL) and the reaction was stirred at RT for 60 min. The crude reaction mixture was passed through a 2 g Isolute® SCX-2 cartridge, eluting with 2M $NH_3$/MeOH. The basic fraction was concentrated in vacuo to give the title compound (149 mg, 96%) as a pale brown oil. LCMS (Method J): $R_T$=0.32 min, [M+H]$^+$=236.

[(S)-1-((S)-6-Fluoro-3-methyl-3,4-dihydro-5-oxa-1,2a-diazaacenaphthylen-2-yl)ethyl][9-(tetrahydropyran-2-yl)-9H-purin-6-yl]amine

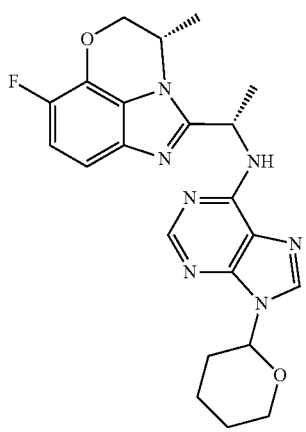 [SMILES: C[C@H](Nc1ncnc2c1ncn2C1CCCCO1)c1nc2ccc(F)c3c2n1[C@@H](C)CO3]

A mixture of (S)-1-(S)-6-fluoro-3-methyl-3,4-dihydro-5-oxa-1,2a-diazaacenaphthylen-2-yl)ethylamine (69 mg, 0.29 mmol), 6-chloro-9-(tetrahydropyran-2-yl)-9H-purine (70 mg, 0.29 mmol) and DIPEA (101 μL, 0.58 mmol) in IPA (1 mL) was heated for 18 h at 100° C. After cooling to RT, the volatiles were removed in vacuo and the resulting residue was purified by column chromatography (Si—PPC, gradient 0-6% 2M NH$_3$/MeOH in DCM) to afford the title compound as a pale brown oil (117 mg, 92%). LCMS (Method J): $R_T$=2.50 min, [M+H]$^+$=438

[(R)-2-(2,6-Difluoro-3-nitrophenoxy)-1-methylethyl]carbamic acid tert-butyl ester

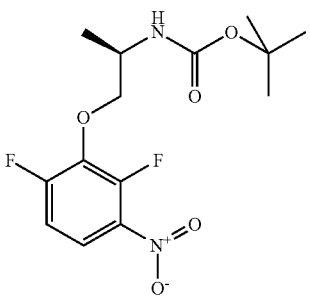 [SMILES: C[C@H](COc1c(F)ccc([N+](=O)[O-])c1F)NC(=O)OC(C)(C)C]

Diethylazodicarboxylate (328 μL, 2.09 mmol) in THF (1 mL) was added slowly to a solution of 2,6-difluoro-3-nitrophenol (243 mg, 1.39 mmol), ((R)-2-hydroxy-1-methylethyl)carbamic acid tert-butyl ester (292 mg, 1.67 mmol) and triphenylphosphine (547 mg, 2.09 mmol) in THF (10 mL) at 0° C. The solution was stirred for 30 min at 0° C., then concentrated in vacuo. The residue was purified by flash chromatography (Si—PPC, gradient 0-30% EtOAc in cyclohexane) to afford the title compound as a pale yellow oil (333 mg, 72%). $^1$H NMR (CDCl$_3$, 300 MHz): δ 7.82 (1H, ddd, J=13.0, 9.4, 5.3 Hz), 7.04 (1H, app. td, J=9.4, 2.2 Hz), 4.76 (1H, br s), 4.23-4.12 (2H, m), 4.07-3.95 (1H, m), 1.44 (9H, s), 1.34 (3H, d, J=6.8 Hz)

(R)-8-Fluoro-3-methyl-5-nitro-3,4-dihydro-2H-benzo[1,4]oxazine

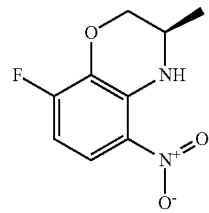

TFA (3 mL) was added to a solution of [(R)-2-(2,6-difluoro-3-nitrophenoxy)-1-methylethyl]carbamic acid tert-butyl ester (333 mg, 1.00 mmol) in DCM (15 mL) and the mixture was stirred for 90 min at rt. PhMe (25 mL) was added and the solution was concentrated in vacuo. The resultant residue was taken up in MeCN (7 mL); aqueous 2M Na$_2$CO$_3$ (7 mL) was added and the mixture was stirred vigorously for a further 90 min at rt. EtOAc (25 mL) and brine (25 mL) were added and the phases were separated. The aqueous was extracted with EtOAc (2×25 mL), and the combined organics were dried (Na$_2$SO$_4$) and concentrated in vacuo. The crude reaction mixture was purified by flash chromatography (Si—PPC, gradient 0-20% EtOAc in cyclohexane) to afford the title compound as a bright yellow solid (184 mg, 87%). $^1$H NMR (CDCl$_3$, 300 MHz): δ 7.84 (1H, br s), 7.79 (1H, dd, J=9.8, 5.6 Hz), 6.45 (1H, app. t, J=9.8 Hz), 4.36-4.28 (1H, m), 3.84-3.76 (2H, m), 1.35 (3H, d, J=6.3 Hz)

(R)-8-Fluoro-3-methyl-3,4-dihydro-2H-benzo[1,4]oxazin-5-ylamine

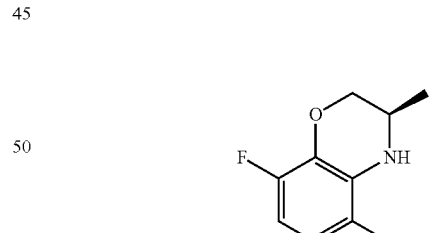

A suspension of (R)-8-fluoro-3-methyl-5-nitro-3,4-dihydro-2H-benzo[1,4]oxazine (183 mg, 0.86 mmol) and 10% Pd/C (37 mg) in EtOAc (12 mL) and IMS (1.2 mL) was stirred under a H$_2$ balloon for 16 h. The reaction mixture was filtered through celite and the filtrate was concentrated in vacuo to give the title compound as a pale yellow oil (162 mg, quant.). $^1$H NMR (CDCl$_3$, 300 MHz): δ 6.36 (1H, dd, J=10.6, 8.6 Hz), 6.14 (1H, dd, J=8.6, 4.6 Hz), 4.19 (1H, dd, J=10.4, 2.7 Hz), 3.65 (1H, dd, J=10.4, 8.0 Hz), 3.44 (1H, dqd, J=8.0, 6.5, 2.7 Hz), 3.13 (3H, br s), 1.17 (3H, d, J=6.5 Hz)

[(S)-1-(R)-6-Fluoro-3-methyl-3,4-dihydro-5-oxa-1,2a-diazaacenaphthylen-2-yl)ethyl]carbamic acid tert-butyl ester

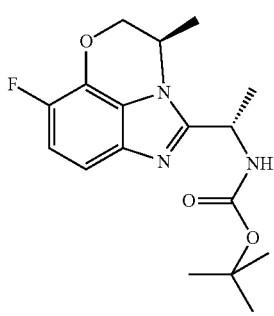 [SMILES: C[C@H](NC(=O)OC(C)(C)C)c1nc2ccc(F)c3c2n1[C@H](C)CO3]

(R)-8-Fluoro-3-methyl-3,4-dihydro-2H-benzo[1,4]oxazin-5-ylamine (162 mg, 0.86 mmol) was added to a solution of (S)-2-tert-butoxycarbonylaminopropionimidic acid ethyl ester (570 mg, 2.64 mmol) in EtOH (10 mL) and the reaction was heated at 75° C. for 60 min. The reaction mixture was concentrated in vacuo, and the residue was partitioned between DCM and sat. NaHCO$_3$. The organic phase was washed with brine, dried (Na$_2$SO$_4$) and concentrated in vacuo. The resultant residue was subjected to flash chromatography (Si—PPC, gradient 0-40% DCM in cyclohexane) to afford the title compound as an off-white foam (188 mg, 65%). LCMS (Method J): R$_T$=2.42 min, [M+H]$^+$=336.

(S)-1-((R)-6-Fluoro-3-methyl-3,4-dihydro-5-oxa-1,2a-diazaacenaphthylen-2-yl)ethylamine

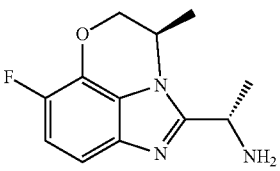

TFA (1.00 mL) was added to a solution of [(S)-1-(R)-6-fluoro-3-methyl-3,4-dihydro-5-oxa-1,2a-diazaacenaphthylen-2-yl)ethyl]carbamic acid tert-butyl ester (188 mg, 0.56 mmol) in DCM (4 mL) and the reaction was stirred at RT for 60 min. The crude reaction mixture was passed through a 2 g Isolute® SCX-2 cartridge, eluting with 2M NH$_3$/MeOH. The basic fraction was concentrated in vacuo to give the title compound (130 mg, 99%) as a pale brown oil. LCMS (Method B): R$_T$=1.82 min, [M+H]$^+$=236.

[(S)-1-((R)-6-Fluoro-3-methyl-3,4-dihydro-5-oxa-1,2a-diazaacenaphthylen-2-yl)ethyl][9-(tetrahydropyran-2-yl)-9H-purin-6-yl]amine

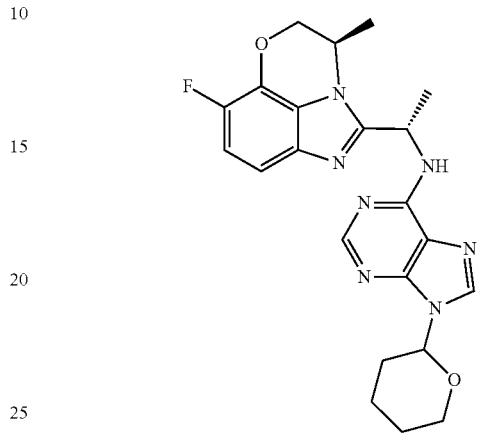

A mixture of (S)-1-(R)-6-fluoro-3-methyl-3,4-dihydro-5-oxa-1,2a-diazaacenaphthylen-2-yl)ethylamine (68 mg, 0.29 mmol), 6-chloro-9-(tetrahydropyran-2-yl)-9H-purine (70 mg, 0.29 mmol) and DIPEA (101 μL, 0.58 mmol) in IPA (1 mL) was heated for 18 h at 100° C. After cooling to RT, the volatiles were removed in vacuo and the resulting residue was purified by column chromatography (Si—PPC, gradient 0-6% 2M NH$_3$/MeOH in DCM) to afford the title compound as a pale brown oil (93 mg, 73%). LCMS (Method J): R$_T$=2.39 min, [M+H]$^+$=438.

1,3-Difluoro-2-methoxy-4-nitrobenzene

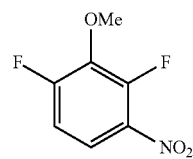

To a solution of trifluoroacetic anhydride (26.2 mL, 0.19 mol) in DCM (100 mL) at 0° C. was added, dropwise, hydrogen peroxide (50% in water, 12.9 mL, 0.17 mol) and the reaction mixture was stirred at 0° C. for 1.5 h. 2,4-Difluoro-3-methoxyphenylamine (3 g, 18.9 mmol) was added as a solution in DCM (20 mL) and the reaction mixture stirred at RT for 3 h. The reaction mixture was diluted with brine and extracted with DCM (3×30 mL). The combined organic fractions were washed with sat. aq. NaHCO$_3$ solution, dried (MgSO$_4$) and concentrated in vacuo. The resultant residue was subjected to flash chromatography (SiO$_2$, eluting with 0-100% Et$_2$O in cyclohexane) to give the title compound as a colourless solid (2.03 g, 57%). ¹H NMR 400 MHz δ (CDCl₃): 7.83-7.76 (1H, m), 7.03 (1H, td, J=9.4, 2.5 Hz), 4.08 (3H, t, J=1.1 Hz).

(3-Fluoro-2-methoxy-6-nitrophenyl)phenylamine

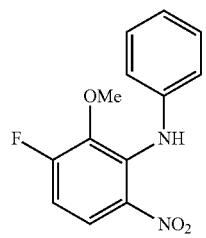

A solution of 1,3-difluoro-2-methoxy-4-nitrobenzene (1 g, 5.29 mmol) and aniline (0.53 mL, 5.82 mmol) in DMSO (10 mL) was heated at 100° C. for 4 h. The reaction mixture was diluted with water and the product extracted with EtOAc (3×15 mL). The combined organic extracts were washed with brine, dried (MgSO₄) and concentrated in vacuo. The resultant residue was subjected to flash chromatography (SiO₂, eluting with 0-50% Et₂O in cyclohexane) to yield the title compound as an off white solid (1.05 g, 76%). ¹H NMR 400 MHz δ (CDCl₃): 8.82 (1H, br s), 7.96 (1H, dd, J=9.5, 5.3 Hz), 7.32-7.26 (2H, m), 7.12-7.07 (1H, m), 7.02-6.98 (2H, m), 6.74 (1H, t, J=9.5 Hz), 3.53 (3H, d, J=1.1 Hz).

4-Fluoro-3-methoxy-N²-phenylbenzene-1,2-diamine

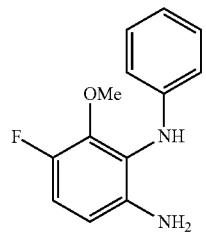 [SMILES: COc1c(F)ccc(N)c1Nc1ccccc1]

To a solution of (3-fluoro-2-methoxy-6-nitrophenyl)phenylamine (322 mg, 1.2 mmol) in EtOAc (5 mL) was added palladium on carbon (30 mg, 10% by wt) and the reaction mixture stirred at RT under an atmosphere of hydrogen for 4 hours. The reaction mixture was filtered and the filtrate concentrated in vacuo to give the title compound as a white solid which darkened to red on standing (284 mg, 100%). ¹H NMR 400 MHz δ (CDCl₃): 7.24-7.18 (2H, m), 6.88-6.78 (2H, m), 6.71-6.66 (2H, m), 6.43 (1H, dd, J=9.0, 4.5 Hz), 5.50 (1H, br s), 3.77 (3H, d, J=1.7 Hz), 3.64 (2H, br s).

[(S)-1-(6-Fluoro-7-methoxy-1-phenyl-1H-benzoimidazol-2-yl)ethyl]-carbamic acid tert-butyl ester

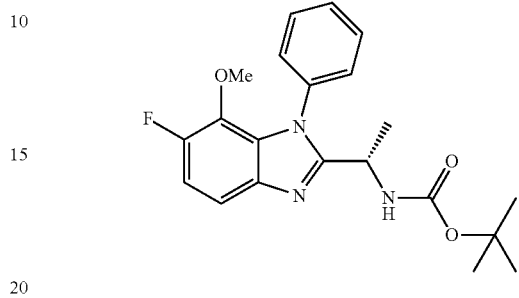

To a suspension of ((S)-1-carbamoylethyl)carbamic acid tert-butyl ester (779 mg, 4.1 mmol) in DCM (5 mL) was added triethyloxonium tetrafluoroborate (671 mg, 3.5 mmol) and the reaction mixture stirred at RT for 2 hours, during which the solids dissolved. The reaction mixture was concentrated in vacuo and the residue dissolved in ethanol (5 mL). 4-Fluoro-3-methoxy-N²-phenylbenzene-1,2-diamine (283 mg, 1.2 mmol) was added and the reaction heated at 70° C. for 1.5 hours. The reaction mixture was concentrated in vacuo, the residue dissolved in water and the product extracted with EtOAc (3×20 mL). The combined organic extracts were washed with brine, dried (MgSO₄) and concentrated in vacuo. The resultant residue was subjected to flash chromatography (SiO₂, eluting with 0-100% EtOAc in cyclohexane) to yield the title compound as a white solid (349 mg, 74%). LCMS (Method C): R_T=3.52 min, [M+H]+=386.

(S)-1-(6-Fluoro-7-methoxy-1-phenyl-1H-benzoimidazol-2-yl)ethylamine dihydrochloride

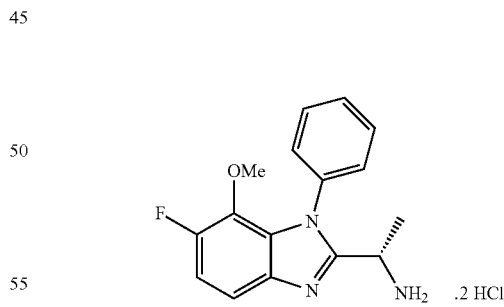

[(S)-1-(6-Fluoro-7-methoxy-1-phenyl-1H-benzoimidazol-2-yl)ethyl]carbamic acid tert-butyl ester (349 mg, 0.91 mmol) was dissolved in methanol (1 mL) and hydrochloric acid in dioxane (3 mL, 4M) and the reaction stirred at RT for 1 hour. The reaction mixture was concentrated in vacuo to yield the title compound as an off-white solid (321 mg, 100%). LCMS (Method C): $R_T$=2.02 min, [M+H]$^+$=286.

(2,6-Difluoro-3-nitrophenyl)acetonitrile

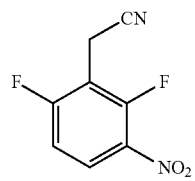 [SMILES: N#CCc1c(F)ccc([N+](=O)[O-])c1F]

To a solution of (2,6-difluorophenyl)acetonitrile (5 g, 32.7 mmol) in conc. Sulphuric acid (15 mL) at −78° C. was added dropwise a solution of nitric acid (65%, 2.25 mL, 32.7 mmol) in conc. sulphuric acid (5 mL). On completion of addition the reaction mixture was poured onto ice and the precipitate that formed collected by filtration, washed with water and dried in vacuo to give the title product as a white solid (6.4 g, 100%). $^1$H NMR 400 MHz δ (CDCl$_3$): 8.24-8.16 (1H, m), 7.17 (1H, ddd, J=9.6, 7.8, 1.9 Hz), 3.84 (2H, t, J=1.2 Hz).

(6-Fluoro-3-nitro-2-phenylaminophenyl)acetonitrile

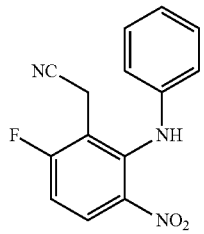

A solution of (2,6-difluoro-3-nitrophenyl)acetonitrile (4 g, 20.1 mmol) and aniline (1.83 mL, 20.1 mmol) in DMSO (20 mL) was heated at 100° C. for 16 h. The reaction mixture was diluted with water (100 mL) and extracted with EtOAc (3×20 mL). The combined organic extracts were washed with brine, dried (MgSO$_4$) and concentrated in vacuo. The resultant residue was subjected to flash chromatography (SiO$_2$, eluting with 0-100% EtOAc in cyclohexane) to yield the title compound as brown oil (959 mg, 18%). $^1$H NMR 400 MHz δ (CDCl$_3$): 8.27 (1H, dd, J=9.4, 5.9 Hz), 7.38-7.32 (2H, m), 7.17-7.12 (1H, m), 6.98-6.90 (3H, m), 3.44 (2H, d, J=1.7 Hz).

(3-Amino-6-fluoro-2-phenylaminophenyl)acetonitrile

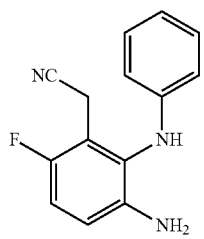 [SMILES: N#CCc1c(F)ccc([N+](=O)[O-])c1Nc1ccccc1]

(6-Fluoro-3-nitro-2-phenylaminophenyl)acetonitrile (463 mg, 1.70 mmol), iron powder (194 mg, 3.41 mmol), and ammonium chloride (263 mg, 5.12 mmol) in methanol (10 mL) and water (3 mL) were heated at 90° C. for 1 h. The reaction mixture was filtered and the filtrate concentrated in vacuo. The residue was dissolved in water and extracted with EtOAc (3×20 mL). The combined organic extracts were washed with brine, dried (MgSO$_4$) and concentrated in vacuo. The resultant residue was subjected to flash chromatography (SiO$_2$, eluting with 0-100% EtOAc in cyclohexane) to yield the title compound as brown solid (228 mg, 55%). $^1$H NMR 400 MHz δ (CDCl$_3$): 7.23-7.17 (2H, m), 6.95 (1H, t, J=8.9 Hz), 6.83 (1H, tt, J=7.4, 1.0 Hz), 6.77 (1H, dd, J=8.9, 5.5 Hz), 6.61-6.56 (2H, m), 5.12 (1H, br s), 3.79 (2H, br s), 3.59 (2H, d, J=1.2 Hz).

[2-((S)-1-Aminoethyl)-5-fluoro-3-phenyl-3H-benzoimidazol-4-yl]acetonitrile dihydrochloride

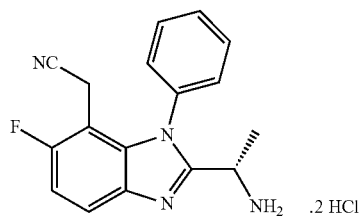 [SMILES: C[C@H](N)c1nc2ccc(F)c(CC#N)c2n1-c1ccccc1]

To a suspension of ((S)-1-carbamoylethyl)carbamic acid tert-butyl ester (435 mg, 2.31 mmol) in DCM (5 mL) was added triethyloxonium tetrafluoroborate (369 mg, 1.94 mmol) and the reaction mixture stirred at RT for 2 hours, during which the solids dissolved. The reaction mixture was concentrated in vacuo and the residue dissolved in ethanol (5 mL). (3-Amino-6-fluoro-2-phenylaminophenyl)acetonitrile (223 mg, 0.92 mmol) was added and the reaction heated at 70° C. for 1 h. The reaction mixture was concentrated in vacuo, the residue dissolved in water and the product extracted with EtOAc (3×20 mL). The combined organic extracts were washed with brine, dried (MgSO$_4$) and concentrated in vacuo. The resultant residue was subjected to flash chromatography (SiO$_2$, eluting with 0-100% EtOAc in cyclohexane) LCMS (Method C): $R_T$=3.36 min, [M+H]+=395. The product was dissolved in HCl in dioxane (4N, 10 mL) and the reaction stirred at RT for 1 h. The reaction mixture was concentrated in vacuo to give the title product as an off white solid (227 mg, 67%). LCMS (Method C): $R_T$=1.88 min, [M+H]+=295.

6-Fluoro-2-(5-fluoropyridin-3-ylamino)-3-nitrobenzonitrile

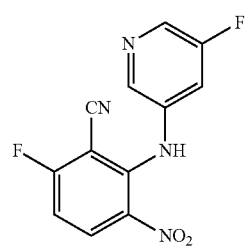 [SMILES: N#Cc1c(F)ccc([N+](=O)[O-])c1Nc1cncc(F)c1]

To a solution of 5-Fluoropyridin-3-ylamine (1.22 g, 10.9 mmol) in THF (30 mL) at −0° C. was added potassium tert-butoxide (2.43 g, 21.7 mmol) and the reaction mixture stirred at 0° C. for 10 min. This solution was added via cannula to a solution of 2,6-difluoro-3-nitrobenzonitrile (2 g, 10.9 mmol) in THF (20 mL) at −78° C. and the dark purple reaction mixture stirred at −78° C. for 10 min. The reaction mixture was diluted with water and extracted with EtOAc (3×30 mL). The combined organic fractions were washed with brine, dried (MgSO$_4$), concentrated in vacuo. The resultant residue was subjected to flash chromatography (SiO$_2$, eluting with 0-100% EtOAc in cyclohexane). The solid obtained was triturated with pentane to give the title compound as an orange solid (1.73 g, 58%). $^1$H NMR 400 MHz δ (CDCl$_3$): 9.73 (1H, br s), 8.53 (1H, dd, J=9.5, 5.7 Hz), 8.47 (1H, d, J=2.5 Hz), 8.43-8.40 (1H, m), 7.33 (1H, dt, J=8.8, 2.2 Hz), 6.83 (1H, dd, J=9.5, 7.3 Hz).

3-Amino-6-fluoro-2-(5-fluoropyridin-3-ylamino) benzonitrile

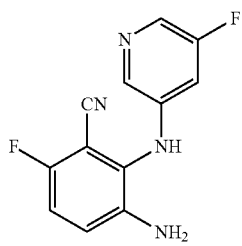

(6-Fluoro-2-(5-fluoropyridin-3-ylamino)-3-nitrobenzonitrile (1.73 g, 6.26 mmol), iron powder (712 mg, 12.5 mmol), and ammonium chloride (966 mg, 18.8 mmol) in methanol (40 mL) and water (12 mL) were heated at 90° C. for 1 h. The reaction mixture was filtered and the filtrate concentrated in vacuo. The residue was dissolved in water and extracted with EtOAc (3×20 mL). The combined organic extracts were washed with brine, dried (MgSO$_4$) and concentrated in vacuo. The resultant residue was subjected to flash chromatography (SiO$_2$, eluting with 0-100% EtOAc in cyclohexane) to yield the title compound as brown solid (948 mg, 61%). $^1$H NMR 400 MHz δ (CDCl$_3$): 8.05 (1H, d, J=2.4 Hz), 8.03-7.99 (1H, m), 7.01 (1H, d, J=2.1 Hz), 6.99 (1H, s), 6.59 (1H, dt, J=10.2, 2.4 Hz), 5.78 (1H, br s), 3.84 (2H, br s).

{(S)-1-[7-Cyano-6-fluoro-1-(5-fluoropyridin-3-yl)-1H-benzoimidazol-2-yl]-ethyl}carbamic acid tert-butyl ester

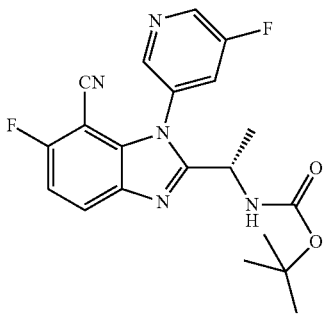 [SMILES: C[C@H](NC(=O)OC(C)(C)C)c1nc2ccc(F)c(C#N)c2n1-c1cncc(F)c1]

To a suspension of ((S)-1-carbamoyl-ethyl)carbamic acid tert-butyl ester (1.81 g, 9.63 mmol) in DCM (20 mL) was added triethyloxonium tetrafluoroborate (1.54 g, 8.08 mmol) and the reaction mixture stirred at RT for 2 hours, during which the solids dissolved. The reaction mixture was concentrated in vacuo and the residue dissolved in ethanol (20 mL). 3-Amino-6-fluoro-2-(5-fluoropyridin-3-ylamino)benzonitrile (948 mg, 3.86 mmol) was added and the reaction heated at 70° C. for 1 h. The reaction mixture was concentrated in vacuo, the residue dissolved in water and the product extracted with EtOAc (3×20 mL). The combined organic extracts were washed with brine, dried (MgSO$_4$) and concentrated in vacuo. The resultant residue was subjected to flash chromatography (SiO$_2$, eluting with 0-100% EtOAc in cyclohexane) to give the title compound as an off white solid. LCMS (Method C): R$_T$=3.20 min, [M+H-$^t$Bu]+=344, 100%, [M+H]+=400, 10%.

Acetic acid 2,6-difluorobenzyl ester

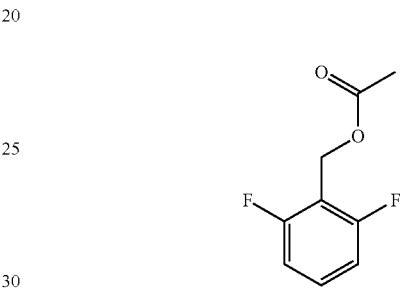

Acetyl chloride (1.13 mL, 15.8 mmol) was added dropwise to a solution of 2,6-difluorobenzyl alcohol (1.76 g, 12.2 mmol) and triethylamine (3.43 mL, 24.4 mmol) in DCM (20 mL) at 0° C. The reaction mixture was stirred at 0° C. for 30 min. The reaction mixture was diluted with water and extracted with DCM (3×20 mL). The combined organic fractions were washed with brine, dried (MgSO$_4$) and concentrated in vacuo. The resultant residue was subjected to flash chromatography (SiO$_2$, eluting with 0-100% EtOAc in cyclohexane) to yield the title compound as a colourless oil (1.72 g, 76%). $^1$H NMR 400 MHz δ (CDCl$_3$): 7.37-7.28 (1H, m), 6.96-6.88 (2H, m), 5.20 (2H, s), 2.08 (3H, s).

Acetic acid 2,6-difluoro-3-nitrobenzyl ester

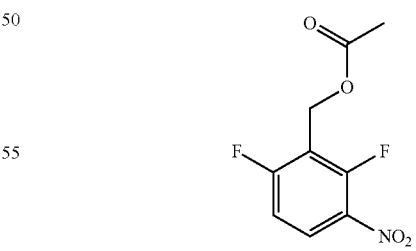

Acetic acid 2,6-difluorobenzyl ester (8 g, 42.9 mmol) was added dropwise to fuming nitric acid (50 mL) at 0° C. and the reaction mixture stirred at 0° C. for 30 min. The reaction mixture was poured onto ice and the product extracted with DCM (3×30 mL). The combined organic fractions were washed with sat, aq, NaHCO$_3$ then brine, dried (MgSO$_4$) and concentrated in vacuo to give the title compound as a yellow oil (8.69 g, 87%). ¹H NMR 300 MHz δ (CDCl₃): 8.21-8.12 (1H, m), 7.09 (1H, ddd, J=9.6, 7.9, 1.9 Hz), 5.24 (2H, t, J=1.5 Hz), 2.10 (3H, s).

Acetic acid 6-fluoro-3-nitro-2-phenylaminobenzyl ester

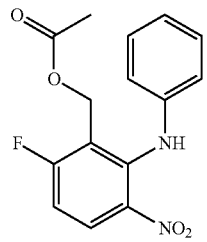 [SMILES: CC(=O)OCc1c(F)ccc([N+](=O)[O-])c1Nc1ccccc1]

A solution of acetic acid 2,6-difluoro-3-nitrobenzyl ester (3 g, 12.9 mmol) and aniline (1.5 mL, 16.9 mmol) in DMSO (10 mL) was heated at 100° C. for 16 h. The reaction mixture was diluted with water and extracted with EtOAc (3×15 mL). The combined organic fractions were washed with brine, dried (MgSO₄) and concentrated in vacuo. The resultant residue was subjected to flash chromatography (SiO₂, eluting with 0-100% EtOAc in cyclohexane) to give the title compound as a brown oil (3.2 g, 81%). ¹H NMR 400 MHz δ (CDCl₃): 8.21 (1H, dd, J=9.4, 5.9 Hz), 7.30-7.24 (2H, m), 7.10-7.04 (1H, m), 6.97-6.92 (2H, m), 6.83 (1H, dd, J=9.3, 8.4), 4.93 (2H, d, J=2.0 Hz), 1.94 (3H, s)

Acetic acid 3-amino-6-fluoro-2-phenylaminobenzyl ester

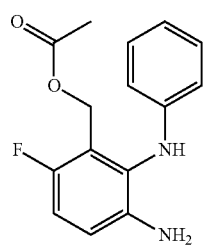 [SMILES: CC(=O)OCc1c(F)ccc(N)c1Nc1ccccc1]

To a solution of acetic acid 6-fluoro-3-nitro-2-phenylaminobenzyl ester (3.2 g, 10.5 mmol) in EtOAc (50 mL) was added palladium on carbon (600 mg, 10% by wt) and the reaction mixture stirred at RT under an atmosphere of hydrogen for 16 h. The reaction mixture was filtered and the filtrate concentrated in vacuo. The resultant residue was subjected to flash chromatography (SiO₂, eluting with 0-100% DCM in cyclohexane) to give the title compound as a brown solid (2.3 mg, 80%). ¹H NMR 400 MHz δ (CDCl₃): 7.22-7.15 (2H, m), 6.86 (1H, t, J=8.9 Hz), 6.81 (1H, tt, J=7.4, 1.0 Hz), 6.78-6.71 (1H, m), 6.63-6.58 (2H, m), 6.43 (1H, br s), 5.10 (2H, d, J=1.9 Hz), 3.72 (2H, br s), 1.99 (3H, s).

Acetic acid 2-((S)-1-tert-butoxycarbonylaminoethyl)-5-fluoro-3-phenyl-3H-benzoimidazol-4-ylmethyl ester

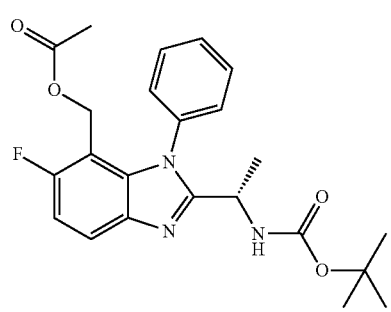 [SMILES: CC(=O)OCc1c(F)ccc2nc([C@H](C)NC(=O)OC(C)(C)C)n(-c3ccccc3)c12]

To a suspension of ((S)-1-carbamoylethyl)carbamic acid tert-butyl ester 3.94 g, 20.9 mmol) in DCM (20 mL) was added triethyloxonium tetrafluoroborate (3.35 g, 17.6 mmol) and the reaction mixture stirred at RT for 2 hours, during which the solids dissolved. The reaction mixture was concentrated in vacuo and the residue dissolved in ethanol (20 mL). Acetic acid 3-amino-6-fluoro-2-phenylaminobenzyl ester (2.3 g, 8.38 mmol) was added and the reaction heated at 75° C. for 1 h. The reaction mixture was concentrated in vacuo, the residue dissolved in water and the product extracted with EtOAc (3×20 mL). The combined organic extracts were washed with brine, dried (MgSO₄) and concentrated in vacuo. The resultant residue was subjected to flash chromatography (SiO₂, eluting with 0-100% EtOAc in cyclohexane) to give the title compound as an off white solid. LCMS (Method C): R$_T$=3.37 min, [M+H-$^t$Bu]+=372, 100%, [M+H]+=428, 40%.

[2-((S)-1-Aminoethyl)-5-fluoro-3-phenyl-3H-benzoimidazol-4-yl]-methanol dihydrochloride

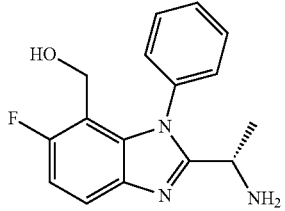 [SMILES: C[C@H](N)c1nc2ccc(F)c(CO)c2n1-c1ccccc1]

To a solution of acetic acid 2-((S)-1-tert-butoxycarbonylaminoethyl)-5-fluoro-3-phenyl-3H-benzoimidazol-4-ylmethyl ester (190 mg, 0.44 mmol) in methanol (2 mL) was added HCl in dioxane (4N, 5 mL) and the reaction stirred at RT for 2 h. The reaction mixture was concentrated in vacuo to

4-Amino-6-[(S)-1-[1-(cis-3-benzyloxycyclobutyl)-6-fluoro-1H-benzoimidazol-2-yl]ethylamino]-pyrimidine-5-carbonitrile

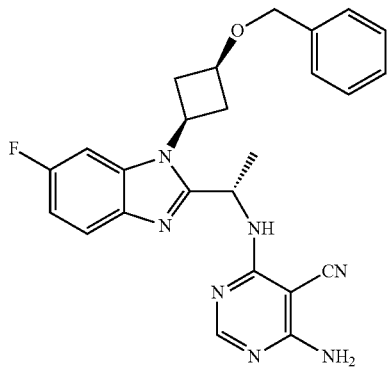 [SMILES: C[C@H](Nc1ncnc(N)c1C#N)c1nc2ccc(F)cc2n1[C@H]1C[C@@H](OCc2ccccc2)C1]

A mixture of (S)-1-[1-(cis-3-benzyloxycyclobutyl)-6-fluoro-1H-benzoimidazol-2-yl]ethylamine (50 mg, 0.15 mmol), 4-amino-6-chloropyrimidine-5-carbonitrile (23 mg, 0.15 mmol) and DIPEA (0.13 mL, 0.74 mmol) in IPA (3 mL) was heated at 90° C. in a sealed vial for 16 h. After cooling to RT, the reaction mixture was concentrated in vacuo, dissolved in DCM and loaded onto an Isolute® SCX-2 cartridge which was washed with DCM then MeOH and then 2M $NH_3$/MeOH. The product containing fractions were combined and concentrated in vacuo. The resulting residue was purified by column chromatography (Si—PCC, gradient 0-5% 2M $NH_3$/MeOH in DCM) to afford the title compound as a colourless glassy solid (50 mg, 75%). LCMS (Method B): $R_T$ 3.11 min [M+H]$^+$ 458. 110185004

2-(2,6-Difluoro-3-nitrophenyl)pyridine

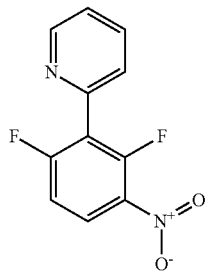 [SMILES: O=[N+]([O-])c1ccc(F)c(-c2ccccn2)c1F]

2-Tributylstannanylpyridine (4.24 g, 12 mmol), 2-bromo-1,3-difluoro-4-nitrobenzene (2.5 g, 10 mmol) and Pd(PPh$_3$)$_4$ (605 mg, 0.5 mmol) in dioxane (20 mL) were placed in a microwave vial. The sealed vial was evacuated and purged with argon (×3). The resulting mixture was heated, under microwave irradiation, at 150° C. for 1.5 h. The cooled mixture was evaporated, and the residue was suspended in DCM and the resulting mixture filtered to remove insoluble material. The filtrate was concentrated in vacuo and the resulting residue was purified by chromatography (Si—PCC, gradient 0-50% EtOAc/cyclohexane) to afford the title compound as a bright orange solid (0.8 g, 33%). $^1$H NMR (CDCl$_3$, 400 MHz): δ 8.79 (1H, ddd, J=6.5, 2.4, 1.3 Hz), 8.18 (1H, ddd, J=12.4, 10.8, 7.4 Hz), 7.86 (1H, td, J=10.4, 2.4 Hz), 7.51 (1H, dquin, J=10.5, 1.6 Hz), 7.41 (1H, ddd, J=10.2, 6.5, 1.5 Hz), 7.16 (1H, ddd, J=13.3, 10.8, 2.5 Hz)

(3-Fluoro-6-nitro-2-pyridin-2-yl-phenyl)isopropylamine

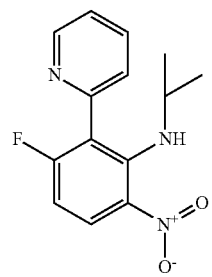 [SMILES: CC(C)Nc1c([N+](=O)[O-])ccc(F)c1-c1ccccn1]

A mixture of 2-(2,6-difluoro-3-nitrophenyl)pyridine (0.85 g, 3.6 mmol), isopropylamine (0.31 mL, 3.6 mmol) and DIPEA (0.63 mL, 3.6 mmol) in acetonitrile (10 mL) was stirred overnight at RT. The mixture was concentrated in vacuo and the resulting residue was purified by chromatography (Si—PPC, gradient 0-50% EtOAc/cyclohexane) to afford the title compound as a yellow oil (0.49 g, 50%). $^1$H NMR (CDCl$_3$, 400 MHz): δ 8.76 (1H, ddd, J=6.5, 3.7, 2.4 Hz), 8.26 (1H, dd, J=12.7, 8.1 Hz), 7.86 (1H, br s), 7.81 (1H, td, J=10.4, 2.5 Hz), 7.46 (1H, dq, J=10.5, 1.5 Hz), 7.34 (1H, ddd, J=10.2, 6.5, 1.6 Hz), 6.57 (1H, dd, J=12.7, 10.8 Hz), 2.70-2.54 (1H, m), 0.93 (6H, d, J=8.4 Hz)

4-Fluoro-N$^2$-isopropyl-3-pyridin-2-yl-benzene-1,2-diamine

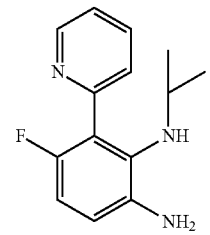

(3-Fluoro-6-nitro-2-pyridin-2-yl-phenyl)isopropylamine (0.49 g, 1.79 mmol) was dissolved in EtOAc (10 mL). The flask was evacuated and purged with N$_2$. Pd/C (10%) was added and the mixture was hydrogenated at atmospheric pressure under a H$_2$ atmosphere. The mixture was stirred overnight. The flask was evacuated and purged with N$_2$. The catalyst was removed by filtration and the filtrate was concentrated in vacuo and the resulting residue was purified by chromatography (Si—PPC, gradient 0-50% EtOAc/cyclohexane) to afford the title compound as a yellow oil (0.47 g, 99%). $^1$H NMR (CDCl$_3$, 400 MHz): δ 8.71 (1H, ddd, J=6.6, 2.4, 1.3 Hz), 7.78 (1H, ddd, J=10.6, 10.2, 2.5 Hz), 7.57 (1H, ddt, J=10.6, 5.2, 1.4 Hz), 7.26 (1H, ddd, J=10.0, 6.6, 1.6 Hz), 6.76-6.66 (2H, m), 5.34 (1H, br s), 3.80 (2H, br s), 3.19 (1H, sept, J=8.5 Hz), 7.63 (6H, d, J=8.5 Hz)

(S)-1-(4-Fluoro-2-isopropylamino-3-pyridin-2-yl-phenylcarbamoyl)ethyl]carbamic acid tert-butyl ester

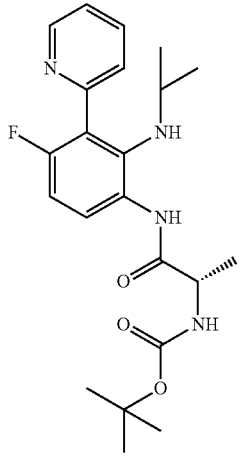 [SMILES: CC(C)Nc1c(NC(=O)[C@H](C)NC(=O)OC(C)(C)C)ccc(F)c1-c1ccccn1]

A solution of 4-fluoro-N²-isopropyl-3-pyridin-2-yl-benzene-1,2-diamine (0.47 g, 1.91 mmol), Boc-Alanine (0.4 g, 2.1 mmol), HOAt (0.29 g, 2.1 mmol) in DCM (15 mL) was cooled to 0° C. EDC (0.40 g, 2.1 mmol) was added portion wise and the resulting mixture was stirred for 1 h. The mixture was diluted with DCM (20 mL) and the organic layer was washed with citric acid, brine, dried (MgSO₄) and evaporated. The resulting residue was purified by chromatography (Si—PPC, gradient 0-50% EtOAc/cyclohexane) to afford the title compound as a colourless oil (0.7 g, 88%). LCMS (Method K): $R_T$ 3.10 min [M+H]⁺ 417

[(S)-1-(6-Fluoro-1-isopropyl-7-pyridin-2-yl-1H-benzoimidazol-2-yl)ethyl]carbamic acid tert-butyl ester

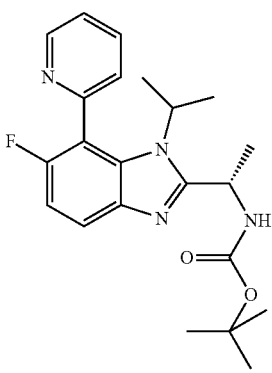 [SMILES: CC(C)n1c([C@H](C)NC(=O)OC(C)(C)C)nc2ccc(F)c(-c3ccccn3)c21]

(S)-1-(4-Fluoro-2-isopropylamino-3-pyridin-2-yl-phenylcarbamoyl)ethyl]carbamic acid tert-butyl ester (0.7 g) was dissolved in AcOH (10 mL) and the resultant solution was heated at 70° C. overnight. The cooled mixture was evaporated and the residue was dissolved in DCM and the organic layer was washed with NaHCO₃, brine, dried (MgSO₄) and evaporated to afford the title compound as a yellow solid (0.6 g, 89%). ¹H NMR (CDCl₃, 400 MHz): δ 8.78 (1H, ddd, J=6.5, 2.4, 1.2 Hz), 7.87 (1H, td, J=10.3, 2.4 Hz), 7.70 (1H, dd J=11.8, 6.4 Hz), 7.56 (1H, dq, J=10.4, 1.5 Hz), 7.41 (1H, ddd, J=10.2, 6.6, 1.6 Hz), 7.09 (1H, dd, J=13.4, 11.8 Hz), 6.45 (1H, d, J=12.6 Hz), 5.38-5.26 (1H, m), 4.02 (1H, sept, J=9.2 Hz), 1.59 (3H, d, J=9.1 Hz), 1.48-1.35 (15H, m)

(S)-1-(6-Fluoro-1-isopropyl-7-pyridin-2-yl-1H-benzoimidazol-2-yl)ethylamine

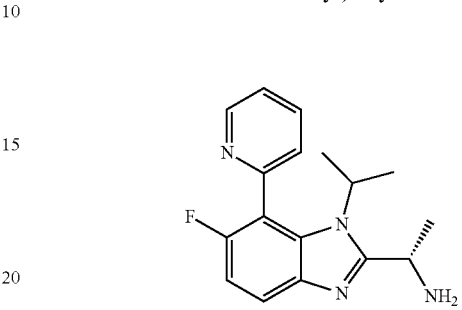

[(S)-1-(6-Fluoro-1-isopropyl-7-pyridin-2-yl-1H-benzoimidazol-2-yl)ethyl]carbamic acid tert-butyl ester (0.6 g, 1.5 mmol) was dissolved in 20% TFA in DCM (10 mL). The resulting solution was stirred for 1 h then the mixture was passed through an SCX column. The column was washed with DCM and MeOH to remove non-basic impurities and the product was then eluted with 2M NH₃ in MeOH. The product fractions were concentrated to give a yellow solid (0.34 g, 76%). ¹H NMR (CDCl₃, 400 MHz): δ 8.77 (1H, d, J=6.1 Hz), 7.85 (1H, td, J=10.5, 2.4 Hz), 7.69 (1H, dd, J=11.4, 6.4 Hz), 7.57 (1H, d, J=10.8 Hz), 7.38 (1H, dd, J=9.8, 6.9 Hz), 7.07 (1H, dd, J=13.7, 11.6 Hz), 4.35 (1H, q, J=8.7 Hz), 4.03 (1H, sept, J=9.3 Hz), 1.60 (3H, d, J=8.8 Hz), 1.40-1.29 (6H, m)

(3-Fluoro-6-nitro-2-pyridin-2-yl-phenyl)methylamine

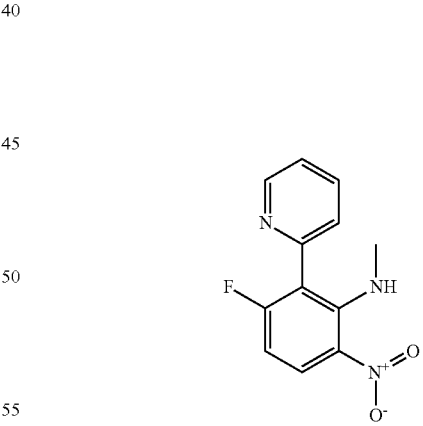

A mixture of 2-(2,6-difluoro-3-nitrophenyl)pyridine (1.0 g, 4.2 mmol), methylamine (2.24 mL, 4.24 mmol, 2M in THF) and DIPEA (0.75 mL, 4.2 mmol) in acetonitrile (10 mL) was stirred overnight at RT. The mixture was concentrated in vacuo and the resulting residue was purified by chromatography (Si—PPC, gradient 0-40% EtOAc/cyclohexane) to afford the title compound as a yellow solid (0.89 g, 84%). ¹H NMR (CDCl₃, 400 MHz): δ 8.74 (1H, ddd, 5.0, 2.1, 1.0 Hz) 8.46 (1H, br s) 8.27 (1H, dd, 9.5, 6.2 Hz), 7.80 (1H, td, 7.8, 2.1 Hz), 7.47 (1H, dq, 4.0, 1.2 Hz), 7.34 (1H, dd, 9.5, 8.2 Hz), 2.36 (3H, d, 5.3 Hz)

4-Fluoro-$N^2$-methyl-3-pyridin-2-yl-benzene-1,2-diamine

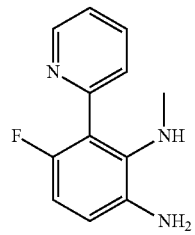

(3-Fluoro-6-nitro-2-pyridin-2-yl-phenyl)methylamine (0.89 g, 3.59 mmol) was dissolved in EtOAc (15 mL). The flask was evacuated and purged with $N_2$. Pd/C (180 mg, 10%) was added and the mixture was hydrogenated at atmospheric pressure with $H_2$. The mixture was stirred overnight. The flask was evacuated and purged with $N_2$. The catalyst was removed by filtration and the filtrate was concentrated in vacuo and the resulting residue was purified by chromatography (Si—PPC, gradient 0-50% EtOAc/cyclohexane) to afford the title compound as a yellow oil (0.75 g, 96%). $^1$H NMR (CDCl$_3$, 400 MHz): δ 8.70 (1H, ddd, 5.0, 1.9, 1.0 Hz), 7.78 (1H, td, 7.8, 1.9 Hz), 7.59 (1H, ddt, 7.9, 3.6, 1.1 Hz), 7.27 (1H, ddd, 7.6, 4.9, 1.2 Hz), 6.72 (1H, d, 1.1), 6.70 (1H, s), 5.10 (1H, s), 3.82 (2H, s), 2.44 (3H, s)

[(S)-1-(6-Fluoro-1-methyl-7-pyridin-2-yl-1H-benzoimidazol-2-yl)ethyl]carbamic acid tert-butyl ester

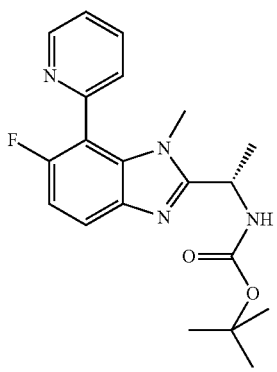 [SMILES: C[C@H](NC(=O)OC(C)(C)C)c1nc2ccc(F)c(-c3ccccn3)c2n1C]

A solution of 4-fluoro-$N^2$-methyl-3-pyridin-2-yl-benzene-1,2-diamine (0.75 g, 3.44 mmol), Boc-Ala (0.72 g, 3.78 mmol), HOAt (0.52 g, 3.78 mmol) in DCM (10 mL) was cooled to 0° C. EDC (0.73 g, 3.78 mmol) was added portion wise and the resulting mixture was stirred for 1 h. The mixture was diluted with DCM (20 mL) and the organic layer was washed with citric acid, brine, dried (MgSO$_4$) and evaporated. The resulting residue was purified by chromatography (Si—PPC, gradient 0-50% EtOAc/cyclohexane) to afford the title compound as a white solid (0.3 g, 24%). LCMS (Method J): R$_T$ 2.42 min [M+H]$^+$ 371

(S)-1-(6-Fluoro-1-methyl-7-pyridin-2-yl-1H-benzoimidazol-2-yl)ethylamine

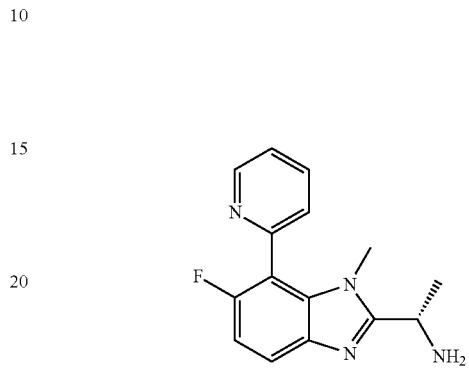

[(S)-1-(6-Fluoro-1-methyl-7-pyridin-2-yl-1H-benzoimidazol-2-yl)ethyl]carbamic acid tert-butyl ester (0.3 g, 0.81 mmol) was dissolved in 20% TFA in DCM (10 mL). The resulting solution was stirred for 1 h then the mixture was passed through an SCX column. The column was washed with DCM, MeOH and the product was eluted with 2M NH$_3$ in MeOH. The product fractions were concentrated to give a yellow solid (0.2 g, 92%). LCMS (Method J): R$_T$ 1.39 min [M+H]$^+$ 271

Ethyl-(3-fluoro-6-nitro-2-pyridin-2-yl-phenyl)amine

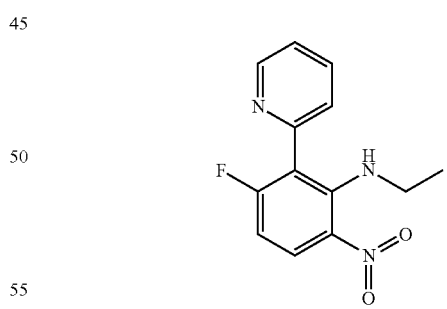

2-(2,6-Difluoro-3-nitrophenyl)pyridine (1.00 g, 4.29 mmol), ethylamine (2.24 mL, 4.29 mmol) and then DIPEA (0.75 mL, 4.29 mmol) were added to acetonitrile (10 mL) and the resultant mixture stirred at 20° C. for 40 hours under a nitrogen atmosphere. The mixture was concentrated in vacuo and the residue was purified by silica gel chromatography (Si—PPC, gradient 0-50% EtOAc/cyclohexane) to give the title compound as yellow oil (1.00 g, 90%). $^1$H NMR (CDCl$_3$) δ: 8.73 (1H, ddd, J=6.6, 2.4, 1.3 Hz), 8.28 (1H, dd, J=12.6, 8.1 Hz), 7.80 (1H, td, J=10.3, 2.4 Hz), 7.45 (1H, dq, J=10.4, 1.6

Hz), 7.33 (1H, ddd, J=10.1, 6.5, 1.6 Hz), 6.51 (1H, dd, J=12.7, 10.9 Hz), 2.54-2.44 (2H, m), 1.03 (3H, t, J=9.6 Hz)

N²-Ethyl-4-fluoro-3-pyridin-2-yl-benzene-1,2-diamine

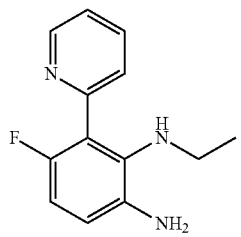 [SMILES: CCNc1c(N)ccc(F)c1-c1ccccn1]

A mixture of ethyl-(3-fluoro-6-nitro-2-pyridin-2-yl-phenyl)amine (1.00 g, 3.82 mmol) and 10% palladium on carbon (0.10 g) in ethyl acetate (15 mL) was stirred under an atmosphere of hydrogen at atmospheric pressure and 20° C. for 3 days. The catalyst was removed by filtration and the resultant solution was concentrated in vacuo. The residue was purified by silica gel chromatography eluting (Si—PPC, gradient 0-100% EtOAc/cyclohexane) to give the title compound as yellow oil (0.61 g, 69%). $^{1}$H NMR (CDCl$_{3}$) δ: 8.71 (1H, ddd, J=6.6, 2.5, 1.3 Hz), 7.78 (1H, ddd, J=10.5, 10.1, 2.5 Hz), 7.58 (1H, ddt, J=10.6, 5.0, 1.4 Hz), 7.27 (1H, ddd, J=10.0, 6.5, 1.6 Hz), 6.76-6.66 (2H, m), 5.24 (1H, br s), 3.82 (2H, br s), 2.76 (2H, t, J=9.5 Hz), 0.82 (3H, t, J=9.5 Hz)

[(S)-1-(1-Ethyl-6-fluoro-7-pyridin-2-yl-1H-benzoimidazol-2-yl)ethyl]carbamic acid tert-butyl ester

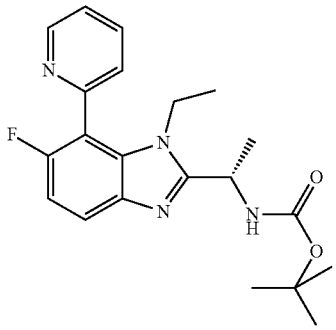 [SMILES: CCn1c([C@H](C)NC(=O)OC(C)(C)C)nc2ccc(F)c(-c3ccccn3)c21]

N²-Ethyl-4-fluoro-3-pyridin-2-yl-benzene-1,2-diamine (0.61 g, 2.63 mmol) was dissolved in DCM (10 mL) and then (S)-(2-tert-butoxycarbonylamino)propionic acid (0.55 g, 2.89 mmol) and 1-hydroxy-7-azabenzotriazole (0.40 g, 2.89 mmol) were added. The mixture was cooled to 0° C. and EDCI (1.54 g, 8.13 mmol) was added, and the resultant mixture stirred at 0° C. under a nitrogen atmosphere for 1 hour. The mixture was diluted with DCM (40 mL) and washed with 10% aqueous citric acid solution and then brine. The organic solution was dried (MgSO$_{4}$) and concentrated in vacuo. The residue was purified by silica gel chromatography (Si—PPC, gradient 0-50% EtOAc/cyclohexane) to give the title compound as yellow oil (0.65 g, 65%). LCMS (Method J): R$_{T}$ 1.88 min [M+H]$^{+}$ 385.3

(S)-1-(1-Ethyl-6-fluoro-7-pyridin-2-yl-1H-benzoimidazol-2-yl)ethylamine

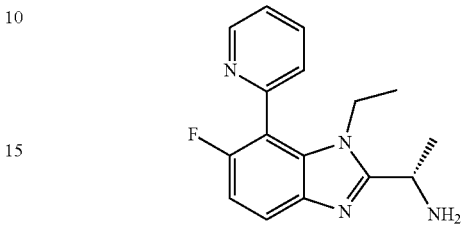

[(S)-1-(1-Ethyl-6-fluoro-7-pyridin-2-yl-1H-benzoimidazol-2-yl)ethyl]-carbamic acid tert-butyl ester (0.65 g, 1.7 mmol) was added to 20% TFA in DCM (10 mL) and the resultant solution stirred at 20° C. for 1 hour. The reaction mixture was concentrated in vacuo and the residue loaded onto an Isolute® SCX-2 cartridge which was washed with MeOH and the product eluted with 2M NH$_{3}$/MeOH then concentrated in vacuo to give title compound as a light yellow gum (0.42 g, 88%). LCMS (Method B): R$_{T}$ 1.65 min [M+H]$^{+}$ 285.1

(3-Cyanocyclobutyl)carbamic acid tert-butyl ester

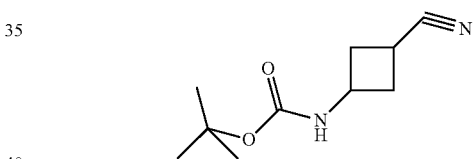

Sodium cyanide (0.29 g, 5.9 mmol) was added to a solution of methanesulfonic acid (3-tert-butoxycarbonylamino)cyclobutyl ester (1.05 g, 3.9 mmol) in DMF (5 mL) and resultant mixture stirred at 85° C. under nitrogen for 24 hours. Additional sodium cyanide (0.38 g, 7.8 mmol) was added and the mixture was stirred at 85° C. under nitrogen for 24 hours. The cooled reaction mixture was poured into water and extracted with ethyl acetate. The organic layer was washed with water (2×) and brine, and then concentrated in vacuo. The residue was purified by silica gel chromatography (Si—PPC; eluting with ethyl acetate in cyclohexane 0-50%) to give the title compound as white solid (0.45 g, 72%)

3-Aminocyclobutanecarbonitrile

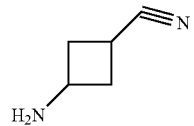

(3-Cyanocyclobutyl)carbamic acid tert-butyl ester (0.45 g, 2.3 mmol) was added to 20% TFA in DCM (5 mL) and the resultant solution stirred at 20° C. for 1 hour. The reaction mixture was concentrated in vacuo and the residue loaded onto an Isolute® SCX-2 cartridge which was washed with DCM and MeOH, then the product eluted with 2M NH$_3$/MeOH then concentrated in vacuo to give title compound as a light yellow oil (0.238 g, 100%). $^1$H NMR (CDCl$_3$) δ: 3.79-3.93 (1H, m), 2.94-3.07 (1H, m), 2.55-2.69 (2H, m), 2.04-2.18 (2H, m), 1.42-1.57 (2H, br s)

3-(5-Fluoro-2-nitrophenylamino)cyclobutanecarbonitrile

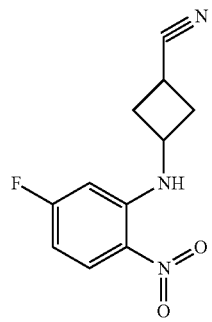 [SMILES: N#CC1CC(Nc2cc(F)ccc2[N+](=O)[O-])C1]

2,4-Difluoro-1-nitrobenzene (0.38 g, 2.4 mmol), 3-aminocyclobutanecarbonitrile (0.23 g, 2.4 mmol) and then DIPEA (0.425 mL, 2.4 mmol) were added to acetonitrile (10 mL) and the resultant mixture stirred at 20° C. for 16 hours under a nitrogen atmosphere. The mixture was concentrated in vacuo and the residue was purified by silica gel chromatography (Si—PPC; eluting with ethyl acetate in cyclohexane 0-50%) to give the title compound as a yellow solid (0.38 g, 68%). $^1$H NMR (CDCl$_3$) δ: 8.23 (1H, dd, J=9.2, 5.8 Hz), 8.20 (1H, br s), 6.41-6.49 (1H, m), 6.29 (1H, dd, J=11.0, 2.7 Hz), 4.30-4.43 (1H, m), 3.20-3.31 (1H, m), 2.87-2.98 (2H, m), 2.42-2.55 (2H, m)

3-(2-Amino-5-fluorophenylamino)cyclobutanecarbonitrile

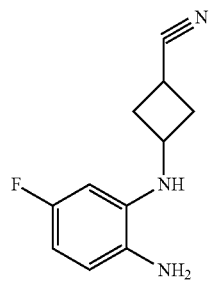 [SMILES: N#CC1CC(Nc2cc(F)ccc2N)C1]

A mixture of 3-(5-fluoro-2-nitrophenylamino)cyclobutanecarbonitrile (0.38 g, 1.61 mmol), iron powder (0.36 g, 6.44 mmol) and ammonium chloride (0.50 g, 9.66 mmol) in methanol (10 mL) and water (4 mL) was stirred at 90° C. for 2 hours. After cooling the solid material was filtered off and the solution was concentrated in vacuo. The residue was partitioned between ethyl acetate (3×) and water, then the combined organic layers were washed with brine, dried (Na$_2$SO$_4$) and concentrated in vacuo to give the title compound as a dark green gum (0.26 g, 79%). LCMS (Method B): R$_T$ 1.75 min [M+H]$^+$ 206.0

{(S)-1-[2-(3-Cyanocyclobutylamino)-4-fluorophenylcarbamoyl]ethyl}carbamic acid tert-butyl ester

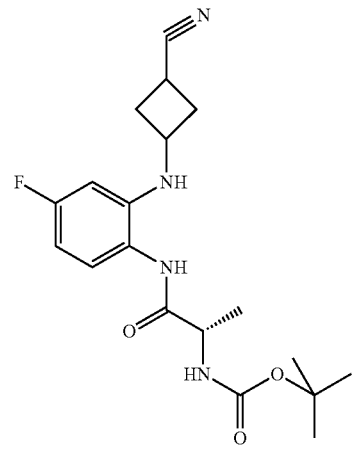 [SMILES: C[C@H](NC(=O)OC(C)(C)C)C(=O)Nc1ccc(F)cc1NC1CC(C#N)C1]

3-(2-Amino-5-fluorophenylamino)cyclobutanecarbonitrile (0.0.26 g, 1.27 mmol) was dissolved in DCM (10 mL) and then (S)-(2-tert-butoxycarbonylamino)propionic acid (0.265 g, 1.39 mmol) and 1-hydroxy-7-azabenzotriazole (0.19 g, 1.39 mmol) were added. The mixture was cooled to 0° C. and EDCI (0.267 g, 1.39 mmol) was added, and the resultant mixture stirred at 0° C. under a nitrogen atmosphere for 1 hour. The mixture was diluted with DCM (20 mL) and washed with 10% aqueous citric acid solution and then brine. The organic solution was dried (MgSO$_4$) and concentrated in vacuo. The residue was purified by silica gel chromatography (Si—PPC; eluting with ethyl acetate in cyclohexane 0-60%) to give the title compound as yellow gum (0.31 g, 66%). $^1$H NMR (CDCl$_3$) δ: 7.46 (1H, br s), 7.05 (1H, dd, J=8.8, 6.0 Hz), 6.36-6.45 (1H, m), 6.20 (1H, dd, J=11.0, 2.7 Hz), 4.89-5.01 (1H, m), 4.14-4.25 (1H, m), 3.10-3.24 (1H, m), 2.71-2.86 (2H, m), 2.32-2.48 (2H, m), 1.46 (9H, s)

{(S)-1-[1-(3-Cyanocyclobutyl)-6-fluoro-1H-benzoimidazol-2-yl]ethyl}carbamic acid tert-butyl ester

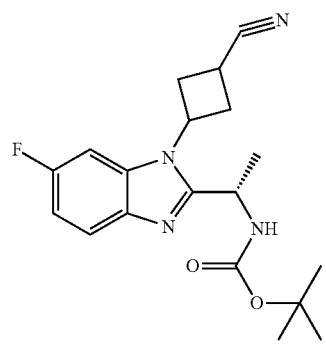 [SMILES: C[C@H](NC(=O)OC(C)(C)C)c1nc2ccc(F)cc2n1C1CC(C#N)C1]

A solution of {(S)-1-[2-(3-cyanocyclobutylamino)-4-fluorophenylcarbamoyl]-ethyl}carbamic acid tert-butyl ester (0.31 g, 0.83 mmol) in acetic acid (5 mL) was stirred at 70° C.

for 16 hours and then at 80° C. for 8 hours. The mixture was concentrated in vacuo and the residue dissolved in DCM then washed with saturated aqueous NaHCO$_3$ and brine, dried (Na$_2$SO$_4$) and concentrated in vacuo. The residue was purified by chromatography (Si—PPC; eluting with ethyl acetate in cyclohexane 0-100%) to give the title compound as colourless gum (0.21 g, 73%). LCMS (Method J): R$_T$ 2.87 min [M+H]$^+$ 358.0

3-[2-((S)-1-Aminoethyl)-6-fluorobenzoimidazol-1-yl]cyclobutanecarbonitrile

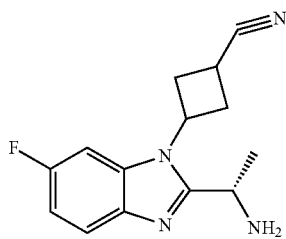 [SMILES: C[C@H](N)c1nc2ccc(F)cc2n1C1CC(C#N)C1]

{(S)-1-[1-(3-Cyanocyclobutyl)-6-fluoro-1H-benzoimidazol-2-yl]ethyl}carbamic acid tert-butyl ester (0.21 g, 0.586 mmol) was added to 20% TFA in DCM (7 mL) and the resultant solution stirred at 20° C. for 1 hour. The reaction mixture was concentrated in vacuo and the residue loaded onto an Isolute® SCX-2 cartridge which was washed with DCM and MeOH, then the product was eluted with 2M NH$_3$/MeOH and concentrated in vacuo to give title compound as a colourless solid (0.076 g, 51%). LCMS (Method J): R$_T$ 1.52 min [M+H]$^+$ 259

[(4-Fluoro-2-phenylaminophenylcarbamoyl)methyl]carbamic acid tert-butyl ester

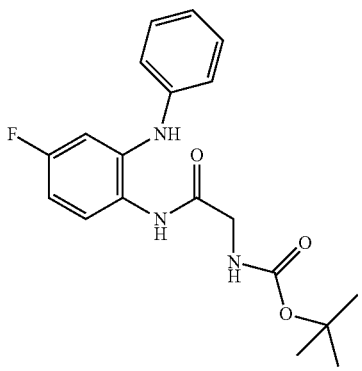 [SMILES: CC(C)(C)OC(=O)NCC(=O)Nc1ccc(F)cc1Nc1ccccc1]

To a mixture of 4-fluoro-2-phenylaminoaniline (3.0 g, 14.85 mmol), tert-butoxycarbonyl glycine (2.4 g, 15 mmol) and HOAt (0.68 g, 5 mmol) in DCM (20 mL) and DMF (1 mL) at 0° C. was added EDCI (2.88 g, 15 mmol). The mixture was stirred at 0° C. for 1 h. To the reaction mixture was added a saturated aqueous solution of NaHCO$_3$ (20 mL), saturated aqueous solution of Na$_2$CO$_3$ (10 mL) and water (10 mL). The mixture was extracted with DCM (2×20 mL) and the combined organic layers were dried (Na$_2$SO$_4$) and concentrated in vacuo. The resulting residue was purified by column chromatography (Si—PCC, gradient 0-8% MeOH in DCM) to afford the title compound as a brown gum, (4.79 g, 89%). $^1$H NMR δ (ppm) (CHCl$_3$-d): 7.95 (1H, s), 7.50 (1H, dd, J=8.83, 5.91 Hz), 7.32-7.22 (2H, m), 6.98-6.97 (4H, m), 6.68 (1H, dt, J=8.6, 2.7 Hz), 6.05 (1H, s), 5.06 (1H, s), 3.89 (2H, d, J=5.92 Hz), 1.42 (9H, s)

(6-Fluoro-1-phenyl-1H-benzoimidazol-2-ylmethyl)-carbamic acid tert-butyl ester

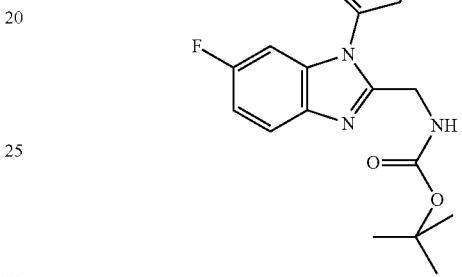

[(4-Fluoro-2-phenylaminophenylcarbamoyl)methyl]carbamic acid tert-butyl ester (0.37 g, 1.03 mmol) was taken up in AcOH (10 mL) and heated at 70° C. for 16 h. After cooling to RT, the volatiles were removed under reduced pressure, the resulting residue was partitioned between EtOAc and water and the mixture basified with Na$_2$CO$_3$. The organic layer was dried (Na$_2$SO$_4$) and concentrated in vacuo. The resulting oil was purified by column chromatography (Si—PCC, gradient 0-60% EtOAc in cyclohexane) to afford the title compound as a white foam (0.265 g, 75%). LCMS (Method B): R$_T$ 3.35 min [M+H]$^+$ 342.03

(6-Fluoro-1-phenyl-1H-benzoimidazol-2-yl)methylamine hydrochloride

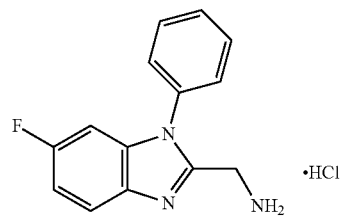 [SMILES: NCc1nc2ccc(F)cc2n1-c1ccccc1 ; Cl]

(6-Fluoro-1-phenyl-1H-benzoimidazol-2-ylmethyl)carbamic acid tert-butyl ester (0.265 g, 0.77 mmol) was treated with 4M HCl in dioxan (5 mL) for 45 min at room temperature. The reaction was evaporated to dryness and the residue triturated with diethyl ether to give the title product as a white solid, (226 mg, approx 100%). LCMS (Method B): R$_T$ 2.06 min [M+H]$^+$ 241.98

(6-Fluoro-1-phenyl-1H-benzoimidazol-2-ylmethyl)[9-(tetrahydropyran-2-yl)-9H-purin-6-yl]amine

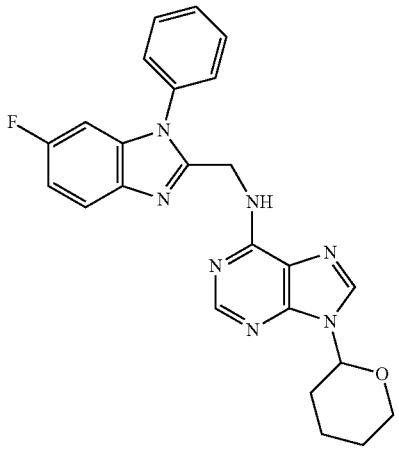 [SMILES: Fc1ccc2nc(CNc3ncnc4c3ncn4C3CCCCO3)n(-c3ccccc3)c2c1]

(6-Fluoro-1-phenyl-1H-benzoimidazol-2-yl)methylamine hydrochloride (0.113 g, 0.4 mmol), 6-chloro-9-(tetrahydropyran-2-yl)-9H-purine (0.19 g, 0.8 mmol), triethylamine (0.28 mL, 2 mmol) in isopropanol (2 mL) was heated to 80° C. in a sealed tube for 6 h. The reaction mixture was partitioned between DCM and water and the organic layer was dried (Na$_2$SO$_4$) and concentrated in vacuo. The resulting residue was purified by column chromatography (Si—PCC, gradient 0-3.5% MeOH in DCM) to afford the title compound as a colourless gum, (0.125 g, 70%). LCMS (Method B): R$_T$ 2.99 min [M+H]$^+$ 444.19.

4-Chloro-2-methylnicotinonitrile

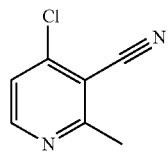

To 4-methoxy-2-methylnicotinonitrile (Tet 6222, 2006) (100 mg, 0.67 mmol) in phosphoryl chloride (2 mL) was added phosphorus pentachloride (156 mg, 0.75 mmol). The mixture was heated to reflux under nitrogen for 15 h. The reaction was quenched with ice, stirred for 10 min, then neutralised with NaHCO$_3$ and extracted with EtOAc. The combined organic extracts were dried (Na$_2$SO$_4$), evaporated to dryness and purified by column chromatography (Si—PCC, gradient 0-50% EtOAc in cyclohexane). Product containing fractions were evaporated to give the title compound as a pale pink solid, (35 mg, 34%). $^1$H NMR δ (ppm) (CDCl$_3$-d): 8.56 (1H, d, J=5.46 Hz), 7.32 (2H, d, J=5.46 Hz), 2.81 (3H, s).

Formula I Compounds

Example 101

N-(1-(3-phenylbenzo[b]thiophen-2-yl)ethyl)-9H-purin-6-amine

A mixture of 1-(3-phenylbenzo[b]thiophen-2-yl)ethylamine from Example 23 (160 mg, 0.63 mmol), 6-chloro-9H-purine (98 mg, 0.63 mmol) and DIPEA (0.16 mL, 0.95 mmol) in n-butanol (1.3 mL) was stirred in a sealed vial for 3 days at 120° C. After cooling to RT, the crude reaction mixture was loaded into an Isolute® SCX-2 which was washed with MeOH and the product eluted with 2M NH$_3$/MeOH. The product containing fractions were combined and concentrated in vacuo and the resulting residue was purified by column chromatography (Si—PCC, gradient 0-6% MeOH in DCM) and then triturated with EtOAc affording 101 (105 mg, 45%). LCMS: R$_T$ 4.33 min [M+H]$^+$ 372.1. $^1$H NMR (DMSO, 400 MHz): δ 8.21 (1H, s), 8.16-8.10 (2H, m), 7.92-7.86 (1H, m), 7.66-7.54 (4H, m), 7.50-7.44 (1H, m), 7.37-7.26 (3H, m), 5.76 (1H, s), 1.50 (3H, d, J=6.94 Hz)

Example 102

N-(1-(1-phenyl-1H-benzo[d]imidazol-2-yl)ethyl)-9H-purin-6-amine 102

1-(1-Phenyl-1H-benzoimidazol-2-yl)ethylamine from Example 4 (211 mg, 0.89 mmol) and 6-chloro-9H-purine (137 mg, 0.89 mmol) was placed in a sealed tube with n-butanol (1.7 mL) and the solution was heated to 120° C. for 48 h. The cooled suspension was diluted with MeOH/CHCl$_3$ and the resulting solution was loaded onto an Isolute® SCX-2 cartridge. The cartridge was washed with MeOH and the product eluted with 2M NH$_3$/MeOH. The product was further purified by column chromatography (Si—PCC, gradient 0-6% MeOH in DCM) and then triturated with EtOAc to afford racemic 102 as a cream solid (190 mg, 60%). LCMS: R$_T$ 2.99 min [M+H]$^+$ 356.2. $^1$H NMR (DMSO, 400 MHz): δ 8.18-8.07 (2H, m), 7.94-7.85 (1H, m), 7.71-7.45 (7H, m), 7.27-7.17 (2H, m), 7.11-7.06 (1H, m), 5.52 (1H, br), 1.57 (3H, d, J=6.83 Hz)

Example 103

N-(1-(3-phenylbenzofuran-2-yl)ethyl)-9H-purin-6-amine 103

A mixture of 1-(3-phenylbenzofuran-2-yl)ethylamine Example 24 (0.706 mmol), 6-chloro-9H-purine (213 mg, 1.38 mmol) and DIPEA (0.24 mL, 1.38 mmol) in n-butanol (5 mL) was heated at 100° C. for 18 h. After cooling to RT, volatiles were removed under reduced pressure and the resulting residue was purified by column chromatography (Si—PCC, gradient 0-5% MeOH in DCM) and then triturated from MeOH with water affording 103 as an off-white solid (107 mg, 43% over two steps). LCMS: R$_T$ 4.15 min [M+H]$^+$ 356.1. $^1$H NMR (DMSO, 400 MHz): δ 8.21-7.95 (3H, m), 7.73-7.60 (3H, m), 7.58-7.49 (3H, m), 7.46-7.23 (3H, m), 5.84 (1H, s), 1.67 (3H, d, J=6.99 Hz)

Example 104

(S)—N-(1-(1-phenyl-1H-benzo[d]imidazol-2-yl)ethyl)-9H-purin-6-amine 104

Racemic N-(1-(1-phenyl-1H-benzo[d]imidazol-2-yl)ethyl)-9H-purin-6-amine 102 was subjected to chiral HPLC separation to isolate 104.

Example 105

(R)—N-(1-(1-phenyl-1H-benzo[d]imidazol-2-yl)ethyl)-9H-purin-6-amine 105

Racemic N-(1-(1-phenyl-1H-benzo[d]imidazol-2-yl)ethyl)-9H-purin-6-amine 102 was subjected to chiral HPLC separation to isolate 105.

Example 106

9-((1-phenyl-1H-benzo[d]imidazol-2-yl)methyl)-9H-purin-6-amine 106

To a mixture of 9H-purin-6-ylamine (61 mg, 0.454 mmol) in DMF (1 mL) was added NaH (60% in mineral oil, 18 mg, 0.454 mmol) and the suspension was stirred at RT for 10 min under a nitrogen atmosphere. 2-Bromomethyl-1-phenyl-1H-benzoimidazole from Example 5 (0.454 mmol) in DMF (3 mL) was subsequently added and the reaction mixture was stirred at RT for 1 h. The crude reaction mixture was loaded onto an Isolute® SCX-2 cartridge which was washed with MeOH and the product eluted with 2M $NH_3$/MeOH. The product containing fractions were combined and concentrated under reduced pressure. The resulting residue was purified by column chromatography (Si—PCC, gradient 0-10% MeOH in DCM), then triturated with diethyl ether and purified by preparative HPLC (Phenomenex Gemini 5 μm C18 on a gradient 20-98% 0.1% $HCO_2H$ in acetonitrile/water). Crystallization from EtOAc/MeOH afforded 106 as a white solid (10 mg, 6%). LCMS: $R_T$ 3.47 min $[M+H]^+$ 342.1. $^1H$ NMR ($CDCl_3$, 400 MHz): δ 8.21 (1H, s), 7.87 (1H, s), 7.84 (1H, d, J=8.01 Hz), 7.48-7.43 (3H, m), 7.36-7.20 (4H, m), 7.12 (1H, d, J=8.03 Hz), 5.57 (2H, s), 5.50 (2H, br).

Alternatively, a mixture of 2-chloromethyl-1-phenyl-1H-benzoimidazole (140 mg, 0.57 mmol), 9H-purin-6-ylamine (78 mg, 0.57 mmol), $Cs_2CO_3$ (200 mg, 0.57 mmol) and sodium iodide (85 mg, 0.25 mmol) in DMF (1 mL) was heated for 18 h in a sealed tube at 80° C. under microwave irradiation. The mixture was diluted with water (80 mL) and extracted with EtOAc followed by $CHCl_3$. The combined organic layers were dried ($Na_2SO_4$) and concentrated in vacuo. The resulting residue was purified by column chromatography (Si—PCC, ISCO column, gradient 0-8% MeOH in DCM) and then crystallised from EtOAc:MeOH affording 106 (60 mg, 31%). LCMS: $R_T$ 2.99 min $[M+H]^+$ 342.0. $^1H$ NMR ($CDCl_3$, 400 MHz): δ 8.21 (1H, s), 7.87 (1H, s), 7.84 (1H, d, J=8.01 Hz), 7.48-7.43 (3H, m), 7.36-7.20 (4H, m), 7.12 (1H, d, J=8.03 Hz), 5.57 (2H, s), 5.50 (2H, br)

Example 107

N-(1-(1-ethyl-1H-benzo[d]imidazol-2-yl)ethyl)-9H-purin-6-amine 107

A mixture of 1-(1-ethyl-1H-1,3-benzodiazol-2-yl)ethan-1-amine dihydrochloride (346 mg, 1.32 mmol), 6-chloro-9H-purine (204 mg, 1.32 mmol) and DIPEA (904 μL, 5.28 mmol) in n-butanol (2.5 mL) was stirred in a sealed tube for 3 h at 120° C. After cooling to RT, the crude reaction mixture was loaded onto an Isolute® SCX-2 cartridge which was washed with MeOH and the product eluted with 2M $NH_3$/MeOH. The product containing fractions were combined and concentrated under reduced pressure. The resulting residue was purified by column chromatography (Si—PCC, gradient 0-10% 2M $NH_3$/MeOH in DCM) and triturated with a mixture EtOAc/diethyl ether, filtered and further washed with additional diethyl ether affording racemic 107 as a pale pink solid (182 mg, 45%). LCMS: $R_T$ 2.18 min $[M+H]^+$ 308.1. $^1H$ NMR ($CDCl_3$, 400 MHz): δ 8.51 (1H, s), 7.95 (1H, s), 7.76 (1H, d, J=7.17 Hz), 7.39-7.34 (1H, m), 7.31-7.15 (3H, m), 6.03 (1H, br), 4.51-4.39 (1H, m), 4.37-4.26 (1H, m), 1.97-1.80 (4H, m), 1.43 (3H, t, J=7.21 Hz)

Example 108

(S)—N-(1-(4-methyl-1-phenyl-1H-benzo[d]imidazol-2-yl)ethyl)-9H-purin-6-amine 108

A mixture of (S)-1-(4-methyl-1-phenyl-1H-benzoimidazol-2-yl)ethylamine from Example 3 (100 mg, 0.398 mmol), 6-chloro-9H-purine (68 mg, 0.438 mmol) and DIPEA (83 μL, 0.478 mmol) in n-butanol (1 mL) was stirred in a sealed vial at 100° C. for 20 h. After cooling to RT, the mixture was partitioned between DCM and water. The organic layer was then separated, dried and concentrated in vacuo. The resulting residue was purified by column chromatography (Si—PCC, gradient 0-10% 2M $NH_3$/MeOH in DCM) and then sonicated in cyclohexane affording 108 as an off-white solid (56 mg, 38%) LCMS: $R_T$ 3.17 min $[M+H]^+$ 370.1. $^1H$ NMR (DMSO, 400 MHz): δ 8.13 (1H, bs), 8.08 (1H, s), 7.96-7.85 (1H, m), 7.67-7.44 (5H, m), 7.12-6.99 (2H, m), 6.86 (1H, d, J=7.80 Hz), 5.49 (1H, br), 2.56 (3H, s), 1.57 (3H, d, J=6.86 Hz)

Example 109

(R)—N-(1-(4-methyl-1-phenyl-1H-benzo[d]imidazol-2-yl)ethyl)-9H-purin-6-amine 109

A mixture of (R)-1-(4-methyl-1-phenyl-1H-benzoimidazol-2-yl)ethylamine from Example 2 (100 mg, 0.398 mmol), 6-chloro-9H-purine (68 mg, 0.438 mmol) and DIPEA (83 μL, 0.478 mmol) in n-butanol (1 mL) was stirred in a sealed vial at 100° C. for 20 h. After cooling to RT, the mixture was partitioned between DCM and water. The organic layer was then separated, dried and concentrated in vacuo. The resulting residue was purified by column chromatography (Si—PCC, gradient 0-10% 2M $NH_3$/MeOH in DCM) and then sonicated in cyclohexane affording 109 as a brown solid (62 mg, 42%) LCMS: $R_T$ 3.17 min $[M+H]^+$ 370.1. $^1H$ NMR (DMSO, 400 MHz): δ 8.18-8.06 (2H, m), 7.95-7.86 (1H, m), 7.66-7.45 (5H, m), 7.11-7.00 (2H, m), 6.86 (1H, d, J=7.81 Hz), 5.49 (1H, br), 2.56 (3H, s), 1.57 (3H, d, J=6.84 Hz)

Example 110

(S)—N-(1-(7-methyl-1-phenyl-1H-benzo[d]imidazol-2-yl)ethyl)-9H-purin-6-amine 110

A mixture of (S)-1-(7-methyl-1-phenyl-1H-benzoimidazol-2-yl)ethylamine from Example 1 (100 mg, 0.398 mmol), 6-chloro-9H-purine (65 mg, 0.418 mmol) and DIPEA (77 μL, 0.438 mmol) in n-butanol (2 mL) was stirred at 140° C. for 1 h under microwave irradiation. Volatiles were removed under reduced pressure and the residue was partitioned between DCM and water. The organic phase was then separated, dried and concentrated in vacuo. The resulting crude material was purified by column chromatography (Si—PCC, gradient 0-10% 2M NH$_3$/MeOH in DCM) and then triturated with IMS affording 110 as a white solid (6.2 mg, 4%) LCMS: R$_T$ 3.08 min [M+H]$^+$ 370.1. $^1$H NMR (DMSO, 400 MHz): δ 8.12 (1H, bs), 8.07 (1H, s), 7.83-7.75 (1H, m), 7.64-7.37 (7H, m), 7.09 (1H, t, J=7.67 Hz), 6.92 (1H, d, J=7.29 Hz), 5.25 (1H, br), 1.81 (3H, s), 1.54 (3H, d, J=6.84 Hz)

Example 111

4-amino-8-((1-phenyl-1H-benzo[d]imidazol-2-yl) methyl)pyrido[2,3-d]pyrimidin-5(8H)-one 111

A mixture of 4-amino-8H-pyrido[2,3-d]pyrimidin-5-one (35 mg, 0.214 mmol), 2-chloromethyl-1-phenyl-1H-benzoimidazole (52 mg, 0.214 mmol), Cs$_2$CO$_3$ (105 mg, 0.321 mmol) and potassium iodide (4 mg, 0.021 mmol) in DMF (1 mL) was stirred for 3 h in a sealed tube at 130° C. Volatiles were then removed under reduced pressure and the residue suspended in DCM and filtered. The filtrate was purified by column chromatography (Si—PCC, gradient 0-10% 2M NH$_3$/MeOH in DCM) and the resulting material was triturated with diethyl ether affording 111 as a pale yellow solid (28 mg, 36%). LCMS: R$_T$ 3.47 min [M+H]$^+$ 369.1. $^1$H NMR (CDCl$_3$, 400 MHz): δ 9.76 (1H, bs), 8.07 (1H, s), 7.82-7.77 (1H, m), 7.65 (1H, d, J=7.97 Hz), 7.50-7.44 (3H, m), 7.34-7.23 (4H, m), 7.14-7.09 (1H, m), 6.28 (1H, d, J=7.97), 5.86-5.78 (1H, m), 5.63 (2H, s)

Example 112

(S)-tert-butyl 4-(2-(1-(9H-purin-6-ylamino)ethyl)-1H-benzo[d]imidazol-1-yl)piperidine-1-carboxylate 112

A mixture of 4-[2-((S)-1-aminoethyl)benzoimidazol-1-yl] piperidine-1-carboxylic acid tertbutyl ester from Example 6 (202 mg), 6-chloro-9H-purine (91 mg, 0.586 mmol) and DIPEA (0.2 mL, 1.17 mmol) in n-butanol (1 mL) was stirred in a sealed tube for 3 h at 120° C. After cooling to RT, the crude reaction mixture was partitioned between EtOAc and water. The organic layer was washed with brine, then dried (Na$_2$SO$_4$) and concentrated in vacuo. The resulting residue was purified by column chromatography (Si—PCC, gradient 0-10% 2M NH$_3$/MeOH in DCM) and then triturated with diethyl ether affording 112 as a pale brown solid (113 mg, 38% over two steps). LCMS: R$_T$ 3.24 min [M+H]$^+$ 463.2. $^1$H NMR (CDCl$_3$, 400 MHz): δ 8.54 (1H, s), 7.98 (1H, s), 7.78 (1H, d, J=7.55 Hz), 7.49 (1H, d, J=7.36 Hz), 7.28-7.07 (3H, m), 6.13 (1H, br), 4.89-4.78 (1H, m), 4.47-4.04 (2H, m), 2.97-2.78 (1H, m), 2.60-2.26 (3H, m), 1.99-1.62 (6H, m), 1.49 (9H, s)

Example 113

(S)—N-(1-(1-(piperidin-4-yl)-1H-benzo[d]imidazol-2-yl)ethyl)-9H-purin-6-amine 113

To a solution of 4-{2-[(S)-1-(9H-purin-6-ylamino)ethyl] benzoimidazol-1-yl}piperidine-1-carboxylic acid tertbutyl ester 112 (101 mg, 0.218 mmol) in DCM (3 mL) was added TFA (1 mL) and the mixture was stirred at RT for 2 h. The reaction mixture was loaded onto an Isolute® SCX-2 cartridge which was washed with MeOH and the product eluted with 2M NH$_3$/MeOH. The product containing fractions were combined and concentrated under reduced pressure. The resulting residue was purified by column chromatography (Si—PCC, gradient 0-20% 2M NH$_3$/MeOH in DCM) affording 113 as a white solid (68 mg, 86%). LCMS: R$_T$ 1.65 min [M+H]$^+$ 363.1. $^1$H NMR (CDCl$_3$, 400 MHz): δ 8.34 (1H, s), 7.88 (1H, s), 7.75-7.65 (3H, m), 7.27-7.19 (3H, m), 6.01 (1H, br), 4.80-4.70 (1H, m), 3.39-3.38 (1H, m), 3.37-3.30 (1H, m), 3.19-3.09 (1H, m), 2.89-2.38 (3H, m) 1.99-1.70 (6H, m)

Example 114

(S)—N-(1-(3-phenyl-3H-imidazo[4,5-b]pyridin-2-yl) ethyl)-9H-purin-6-amine 114

A mixture of (S)-1-(3-phenyl-3H-imidazo[4,5-b]pyridin-2-yl)ethylamine from Example 10 (270 mg, 1.13 mmol), 6-chloro-9H-purine (250 mg, 1.59 mmol) and DIPEA (0.36 mL, 2.04 mmol) in n-butanol (1.5 mL) was stirred in a sealed tube for 48 h at 120° C. After cooling to RT, the crude reaction mixture was partitioned between DCM and a saturated solution of NaHCO$_3$. The aqueous phase was further extracted with DCM (×3) and the combined organic layers were washed with brine, then dried (Na$_2$SO$_4$) and concentrated in vacuo. The resulting residue was purified by column chromatography (Si—PCC, gradient 0-10% 2M NH$_3$/MeOH in DCM), then triturated with diethyl ether and then submitted to preparative HPLC (Phenomenex Gemini 5 μm C18 on a 60 min gradient 20-98% 0.1% HCO$_2$H in acetonitrile/water) affording 114 as an off-white solid (32 mg, 8%). LCMS: R$_T$ 2.64 min [M+H]$^+$ 357.0. $^1$H NMR (DMSO, 400 MHz): δ 8.23 (1H, dd, J=4.76, 1.48 Hz), 8.18-7.97 (4H, m), 7.67-7.41 (5H, m), 7.29 (1H, dd, J=7.99, 4.76 Hz), 1.57 (3H, d, J=6.83 Hz)

Example 115

(S)-1-(4-(2-(1-(9H-purin-6-ylamino)ethyl)-1H-benzo [d]imidazol-1-yl)piperidin-1-yl)ethanone 115

To a stirred suspension of [(S)-1-(1-piperidin-4-yl-1H-benzoimidazol-2-yl)ethyl]-(9H-purin-6-yl)amine 113 (46 mg, 0.127 mmol) and DIPEA (26 μL, 0.152 mmol) in anhydrous THF (3 mL) and anhydrous DCM (1 mL) was added acetyl chloride (9 μL, 0.127 mmol). Stirring at RT was continued for 3 h then volatiles were removed under reduced pressure and the resulting residue was partitioned between EtOAc and water. The aqueous layer was further washed with DCM and the organic layers were then washed with brine, dried (Na$_2$SO$_4$) and concentrated in vacuo. The resulting residues were combined, purified by preparative HPLC (Phenomenex Gemini 5 μm C18 on a 20 min gradient 5-70% 0.1% HCO$_2$H in acetonitrile/water) and then loaded onto an Isolute® SCX-2 cartridge. The cartridge was washed with MeOH and the product eluted with 2M NH$_3$/MeOH. The product containing fractions were combined and concentrated under reduced pressure affording 115 as a white solid (10 mg, 19%). LCMS: R$_T$ 2.13 min [M+H]$^+$ 405.1. $^1$H NMR (CDCl$_3$, 400 MHz): δ 8.35 (1H, s), 7.88 (1H, s), 7.78-7.70 (1H, m), 7.49-7.42 (1H, m), 7.28-7.20 (3H, m), 6.05 (1H, s), 4.98-4.82 (1.5H, m), 4.71-4.61 (0.5H, m), 4.09-3.99 (0.5H, m), 3.90-3.78 (0.5H, m), 3.42-3.37 (0.5H, m), 3.32-3.18 (0.5H, m), 2.88-2.37 (1H, m), 2.20-2.10 (4H, m), 2.06-1.96 (1H, m), 1.90-1.69 (5H, m). Signals split due to presence of rotamers Example 116

N-(1-(3-phenyl-1H-indol-2-yl)ethyl)-9H-purin-6-amine 116

A mixture of {1-[3-phenyl-1-(toluene-4-sulfonyl)-1H-indol-2-yl]ethyl}-(9H-purin-6-yl)amine from Example 21

(200 mg, 0.393 mmol) and 2M KOH (0.8 mL) in MeOH (4 mL) was stirred at 70° C. for 72 h. Volatiles were removed under reduced pressure and the resulting residue was diluted with water. The pH of the solution was adjusted to 1 by addition of 1M HCl and then to 8 by addition of a saturated solution of NaHCO$_3$. The aqueous layer was extracted with EtOAc (×3) and the combined organic layers were dried (Na$_2$SO$_4$) and concentrated in vacuo. The resulting residue was purified by preparative HPLC (Phenomenex Gemini 5 μm C18 on a gradient 10-98% 0.1% HCO$_2$H in acetonitrile/water) and then by column chromatography (Si—PCC, gradient 0-10% 2M NH$_3$/MeOH in DCM) affording 116 as a white solid (83 mg, 60%). LCMS: R$_T$ 3.98 min [M+H]$^+$ 355.0. $^1$H NMR (DMSO, 400 MHz): δ 11.29 (1H, s), 8.21-8.09 (2H, m), 7.71-7.55 (3H, m), 7.52-7.42 (5H, m), 7.32 (1H, t, J=7.39 Hz), 7.13 (1H, t, J=7.93 Hz), 7.02 (1H, t, J=7.93 Hz), 5.96 (1H, s), 1.62 (3H, d, J=6.93 Hz)

Example 117

(S)—N-(1-(5-methyl-1-phenyl-1H-benzo[d]imidazol-2-yl)ethyl)-9H-purin-6-amine 117

A mixture of (S)-1-(5-methyl-1-phenyl-1H-benzoimidazol-2-yl)ethylamine from Example 14 (100 mg, 0.398 mmol), 6-chloro-9H-purine (74 mg, 0.478 mmol) and DIPEA (0.347 mL, 1.99 mmol) in n-butanol (2 mL) was stirred in a sealed vial for 20 h at 120° C. After cooling to RT, volatiles were removed under reduced pressure and the resulting residue was purified by column chromatography (Si—PCC, gradient 0-20% MeOH in EtOAc) and then triturated with acetonitrile affording 117 as an off-white solid (54 mg, 37%). LCMS: R$_T$ 3.11 min [M+H]$^+$ 370.1. $^1$H NMR (DMSO, 400 MHz): δ 12.90 (1H, bs), 8.20-8.00 (2H, m), 7.84 (1H, s), 7.69-7.39 (6H, m), 7.07-6.89 (2H, m), 5.49 (1H, bs), 2.39 (3H, s), 1.53 (3H, d, J=6.79 Hz)

Example 118

(S)—N-(1-(6-methyl-1-phenyl-1H-benzo[d]imidazol-2-yl)ethyl)-9H-purin-6-amine 118

A mixture of (S)-1-(6-methyl-1-phenyl-1H-benzoimidazol-2-yl)ethylamine from Example 13 (100 mg, 0.398 mmol), 6-chloro-9H-purine (65 mg, 0.418 mmol) and DIPEA (0.347 mL, 1.99 mmol) in dioxane (3 mL) was stirred in a sealed vial for 20 h at 100° C. After cooling to RT, volatiles were removed under reduced pressure and the resulting residue was purified by column chromatography (Si—PCC, gradient 0-20% MeOH in EtOAc) and then crystallised from acetonitrile affording 118 as a white solid (35 mg, 24%). LCMS: R$_T$ 3.15 min [M+H]$^+$ 370.1. $^1$H NMR (DMSO, 400 MHz): δ 8.17-8.07 (2H, m), 7.88-7.78 (1H, m), 7.64-7.45 (6H, m), 7.06 (1H, d, J=8.26 Hz), 6.86 (1H, s), 5.50 (1H, br), 2.35 (3H, s), 1.54 (3H, d, J=6.82 Hz)

Example 119

(S)—N-(1-(1-phenyl-1H-benzo[d]imidazol-2-yl)propyl)-9H-purin-6-amine 119

A mixture of (S)-1-(1-phenyl-1H-benzoimidazol-2-yl)propylamine from Example 12 (100 mg, 0.398 mmol), 6-chloro-9H-purine (65 mg, 0.418 mmol) and DIPEA (0.348 mL, 2.0 mmol) in dioxane (3 mL) was stirred for 24 h at 100° C. After cooling to RT, volatiles were removed under reduced pressure and the resulting residue was purified by column chromatography (Si—PCC, gradient 0-20% MeOH in EtOAc) and then crystallised from acetonitrile affording 119 as a white solid (50 mg, 34%). LCMS: R$_T$ 3.23 min [M+H]$^+$ 370.0. $^1$H NMR (DMSO, 400 MHz): δ 8.21-8.07 (2H, m), 7.86-7.49 (7H, m), 7.28-7.17 (2H, m), 7.08 (1H, d, J=7.68 Hz), 5.42 (1H, br), 2.08-1.90 (2H, m), 0.83 (3H, t, J=7.32 Hz)

Example 120

(S)—N-(1-(4-chloro-1-phenyl-1H-benzo[d]imidazol-2-yl)ethyl)-9H-purin-6-amine 120

A mixture of (S)-1-(4-chloro-1-phenyl-1H-benzoimidazol-2-yl)ethylamine from Example 9 (250 mg, 0.92 mmol), 6-chloro-9H-purine (200 mg, 1.29 mmol) and DIPEA (0.29 mL, 1.66 mmol) in n-butanol (2 mL) was stirred in a sealed tube for 16 h at 120° C. Additional amounts of 6-chloro-9H-purine (100 mg, 0.64 mmol) and DIPEA (0.14 mL, 0.802 mmol) were added and the stirring was continued at 120° C. for 24 h. After cooling to RT, the crude reaction mixture was partitioned between DCM and water. The aqueous phase was further extracted with DCM (×3) and then the combined organic layers were washed with brine, dried (Na$_2$SO$_4$) and concentrated in vacuo. The resulting residue was purified by column chromatography (Si—PCC, gradient 0-8% 2M NH$_3$/MeOH in DCM) and then by preparative HPLC (Phenomenex Gemini 5 μm C18 on a 60 min gradient 20-98% 0.1% HCO$_2$H in acetonitrile/water) affording 120 (66 mg, 42%). LCMS: R$_T$ 3.69 min [M+H]$^+$ 390.0. $^1$H NMR (CDCl$_3$, 400 MHz): δ 12.90 (1H, bs), 8.28-7.90 (3H, m), 7.71-7.41 (5H, m), 7.32 (1H, d, J=7.75 Hz), 7.19 (1H, t, J=7.90 Hz), 7.03 (1H, d, J=8.10 Hz), 5.46 (1H, br), 1.67-1.53 (3H, m)

Example 121

(S)-1-(4-(2-(1-(9H-purin-6-ylamino)ethyl)-1H-benzo[d]imidazol-1-yl)piperidin-1-yl)-2-hydroxy-2-methylpropan-1-one 121

To a stirred solution of [(S)-1-(1-piperidin-4-yl-1H-benzoimidazol-2-yl)ethyl]-(9H-purin-6-yl)amine 113 (97 mg, 0.268 mmol) in DMF (5 mL) were added 2-hydroxy-2-methylpropionic acid (31 mg, 0.294 mmol), DIPEA (230 μL, 1.34 mmol) and HATU (153 mg, 0.401 mmol). Stirring at RT was continued for 18 h then the crude reaction mixture was partitioned between EtOAc and a saturated solution of NaHCO$_3$. The organic layer was washed with brine, then dried (Na$_2$SO$_4$) and concentrated in vacuo. The resulting residue was purified column chromatography (Si—PCC, gradient 0-10% 2M NH$_3$/MeOH in DCM) affording 121 as a pale beige solid (33 mg, 31%). LCMS: R$_T$ 2.28 min [M+H]$^+$ 449.1. $^1$H NMR (CDCl$_3$, 400 MHz): δ 8.51 (1H, s), 7.98 (1H, s), 7.79 (1H, d, J=7.80 Hz), 7.36-6.99 (4H, m), 5.32 (1H, bs), 5.02-4.88 (2H, m), 4.78 (1H, bs), 4.59-4.49 (1H, br), 2.64-2.44 (2H, m), 2.37-2.22 (1H, m), 2.05 (1H, d, J=12.70 Hz), 2.95-1.49 (11H, m)

Example 122

(S)-2-(1-(9H-purin-6-ylamino)ethyl)-1-phenyl-1H-benzo[d]imidazole-6-carbonitrile 122

A mixture of 2-((S)-1-aminoethyl)-3-phenyl-3H-benzoimidazole-5-carbonitrile from Example 11 (370 mg, 1.4 mmol), 6-chloro-9H-purine (217 mg, 1.4 mmol) and DIPEA (0.36 mL, 2.1 mmol) in n-butanol (2.8 mL) was stirred in a sealed tube for 6 h at 120° C. After cooling to RT, the crude reaction mixture was loaded onto an Isolute® SCX-2 cartridge which was washed with MeOH and the product eluted with 2M NH₃/MeOH. The product containing fractions were combined and concentrated under reduced pressure. The resulting residue was purified by column chromatography (Si—PCC, gradient 0-10% 2M NH₃/MeOH in EtOAc followed by gradient 0-10% 2M NH₃/MeOH in DCM) affording 122 as a white solid (200 mg, 37%). LCMS: $R_T$ 3.29 min [M+H]⁺ 381.1. ¹H NMR (DMSO, 400 MHz): δ 8.21-7.97 (3H, m), 7.84 (1H, d, J=8.35 Hz), 7.72-7.46 (7H, m), 5.49 (1H, br), 1.59 (3H, d, J=6.87 Hz)

Example 123

(S)—N-(1-(6-fluoro-1-phenyl-1H-benzo[d]imidazol-2-yl)ethyl)-9H-purin-6-amine 123

A mixture of (S)-1-(6-fluoro-1-phenyl-1H-benzoimidazol-2-yl)ethylamine from Example 8 (861 mg, 3.37 mmol), 6-chloro-9H-purine (521 mg, 3.37 mmol) and DIPEA (1.73 mL, 10.12 mmol) in n-butanol (3.5 mL) was stirred in a sealed tube for 18 h at 100° C. After cooling to RT, volatiles were removed under reduced pressure and the resulting residue was loaded onto an Isolute® SCX-2 cartridge which was washed with MeOH and the product eluted with 2M NH₃/MeOH. The product containing fractions were combined and concentrated under reduced pressure. The product thus obtained was further purified by column chromatography (Si—PCC, gradient 0-20% 2M NH₃/MeOH in EtOAc) and then sonicated in EtOAc. The suspension was concentrated in vacuo and the solid was triturated with diethyl ether affording 123 as a white/pink solid (136 mg, 11%). LCMS: $R_T$ 3.38 min [M+H]⁺ 374.0. ¹H NMR (DMSO, 400 MHz): δ 8.20-8.03 (2H, m), 7.91 (1H, bs), 7.73-7.44 (6H, m), 7.09 (1H, t, J=9.72 Hz), 6.85 (1H, d, J=8.92 Hz), 5.50 (1H, bs), 1.55 (3H, d, J=6.82 Hz)

Alternatively, [(S)-1-(6-Fluoro-1-phenyl-1H-benzoimidazol-2-yl)ethyl]-[9-(tetrahydropyran-2-yl)-9H-purin-6-yl]amine (30 g, 65.6 mmol) was dissolved in EtOAc (200 mL) and HCl (1 M in MeOH, 210 mL) was added dropwise and the resulting solution was stirred for 2 h. The solvents were removed in vacuo and the resulting solid was recrystallised from hot EtOAc/EtOH to give 123 as a white crystalline solid (11 g, 45%). Further product crystallised from the mother liquors. ¹H NMR (MeOD-d₄, 400 MHz): δ 8.60 (1H, s), 8.53 (1H, s), 7.8 (1H, dd, J 9.8, 4.2 Hz), 7.67 (5H, br s), 7.42 (1H, td, J 9.2, 2.3 Hz), 7.14 (1H, dd, J 7.1, 2.4 Hz), 5.67 (1H, m), 1.87 (3H, d, J=6.9 Hz)

Example 124

(S)—N-(1-(7-fluoro-1-phenyl-1H-benzo[d]imidazol-2-yl)ethyl)-9H-purin-6-amine 124

A mixture of (S)-1-(7-fluoro-1-phenyl-1H-benzoimidazol-2-yl)ethylamine from Example 7 (367 mg, 1.44 mmol), 6-chloro-9H-purine (222 mg, 1.44 mmol) and DIPEA (0.74 mL, 4.31 mmol) in n-butanol (3.5 mL) was stirred in a sealed tube for 48 h at 100° C. After cooling to RT, volatiles were removed under reduced pressure and the resulting residue was loaded onto an Isolute® SCX-2 cartridge which was washed with MeOH and the product eluted with 2M NH₃/MeOH. The product containing fractions were combined and concentrated under reduced pressure. The product thus obtained was further purified by column chromatography (Si—PCC, gradient 0-20% 2M NH₃/MeOH in EtOAc) followed by (Si—PCC, gradient 0-10% 2M NH₃/MeOH in DCM) and then sonicated in MeOH. The suspension was then diluted with diethyl ether and the solid collected by filtration affording 124 as a white solid (103 mg, 19%). LCMS: $R_T$ 3.40 min [M+H]⁺ 374.0. ¹H NMR (DMSO, 400 MHz): δ 8.17-8.04 (2H, m), 7.98-7.86 (1H, br), 7.75-7.35 (6H, m), 7.19 (1H, td, J=8.09, 4.87 Hz), 7.02 (1H, dd, J=11.60, 8.02 Hz), 5.37 (1H, bs), 1.56 (3H, d, J=6.86 Hz)

Example 125

(S)-1-(4-(2-(1-(9H-purin-6-ylamino)ethyl)-1H-benzo[d]imidazol-1-yl)piperidin-1-yl)-2-(dimethylamino)ethanone 125

To a solution of [(S)-1-(1-piperidin-4-yl-1H-benzoimidazol-2-yl)ethyl]-(9H-purin-6-yl)amine 113 (97 mg, 0.268 mmol), dimethylaminoacetic acid (30 mg, 0.294 mmol) and DIPEA (230 μL, 1.34 mmol) in DMF (5 mL) was added HATU (153 mg, 0.401 mmol) and the mixture was stirred at RT for 1 h. The crude reaction mixture was loaded onto an Isolute® SCX-2 cartridge which was washed with MeOH and the product eluted with 2M NH₃/MeOH. The product containing fractions were combined, then concentrated in vacuo, purified by column chromatography (Si—PCC, gradient 0-20% 2M NH₃/MeOH in DCM) and triturated with diethyl ether. The product thus obtained was further purified by preparative HPLC (Phenomenex Gemini 5 μm C18 on a 20 min gradient 5-60% 0.1% NH₄OH in acetonitrile/water) and loaded into an Isolute® SCX-2. The cartridge was washed with MeOH and the product eluted with 2M NH₃/MeOH. The basic fractions were then combined and concentrated in vacuo affording 125 as a white solid (40 mg, 33%). LCMS: $R_T$ 1.67 min [M+H]⁺ 448.1. ¹H NMR (CDCl₃ plus MeOD, 400 MHz): δ 8.45 (1H, s), 7.94 (1H, s), 7.77 (1H, d, J=7.62 Hz), 7.41 (1H, d, J=7.73 Hz), 7.26-7.17 (3H, m), 6.10 (1H, s), 4.99-4.81 (1.5H, m), 4.64-4.53 (0.5H, m), 4.38-4.27 (0.5H, m), 4.21-4.08 (0.5H, m), 3.32-3.01 (2H, m), 2.87-2.16 (10H, m), 2.05-1.27 (6H, m). Signals split due to presence of rotamers Example 126

(S)-3-(4-(2-(1-(9H-purin-6-ylamino)ethyl)-1H-benzo[d]imidazol-1-yl)piperidin-1-yl)propanenitrile 126

A mixture of [(S)-1-(1-piperidin-4-yl-1H-benzoimidazol-2-yl)ethyl]-(9H-purin-6-yl)amine 113 (75 mg, 0.207 mmol) and acrylonitrile (75 μL, 1.14 mmol) in IMS (3 mL) was stirred in a sealed tube at 70° C. for 3 h. After cooling to RT, the crude reaction mixture was loaded onto an Isolute® SCX-2 cartridge which was washed with MeOH and the product eluted with 2M NH₃/MeOH. The product containing fractions were combined, concentrated in vacuo and purified by column chromatography (Si—PCC, gradient 0-10% 2M NH₃/MeOH in DCM), followed by preparative HPLC (Phenomenex Gemini 5 μm C18 on a 20 min gradient 5-60% 0.1% NH₄OH in acetonitrile/water) and finally loaded into an Isolute® SCX-2 which was washed with MeOH and the product eluted with 2M NH₃/MeOH. The ammonia fractions were combined and concentrated in vacuo affording 126 as a white solid (28 mg, 33%). LCMS: $R_T$ 1.67 min [M+H]⁺ 416.1. ¹H NMR (CDCl₃, 400 MHz): δ 8.52 (1H, s), 7.96 (1H, s), 7.80-7.73 (1H, m), 7.65-7.59 (1H, m), 7.26-7.08 (3H, m), 5.29 (1H, bs), 4.69-4.57 (1H, m), 3.09 (1H, bd, J=11.28 Hz), 2.90 (1H, d, J=11.11 Hz), 2.76-2.60 (3H, m), 2.37-2.25 (3H, m), 2.30-2.30 (1H, m), 1.98-1.66 (7H, m)

Example 127

(S)—N-(1-(1-(tetrahydro-2H-pyran-4-yl)-1H-benzo[d]imidazol-2-yl)ethyl)-9H-purin-6-amine 127

A mixture of (S)-1-[1-(tetrahydropyran-4-yl)-1H-benzoimidazol-2-yl]ethylamine from Example 17 (195 mg, 0.796 mmol), 6-chloro-9-(tetrahydropyran-2-yl)-9H-purine (266 mg, 1.11 mmol) and DIPEA (0.25 mL, 1.43 mmol) in n-butanol (2 mL) was stirred in a sealed vial for 3 days at 120° C. After cooling to RT, volatiles were removed under reduced pressure and the resulting residue was loaded into an Isolute® SCX-2 which was washed with MeOH and the product eluted with 2M NH$_3$/MeOH. The product containing fractions were combined and concentrated in vacuo and the resulting residue was purified by column chromatography (Si—PCC, gradient 0-10% 2M NH$_3$/MeOH in DCM) and then triturated with a mixture EtOAc and MeOH affording 127 as an off-white solid (148 mg, 51%). LCMS: R$_T$ 2.29 min [M+H]$^+$ 364.0. $^1$H NMR (DMSO, 400 MHz): δ 12.93 (1H, bs), 8.30-7.81 (3H, m), 7.61-7.59 (2H, m), 7.17-7.03 (2H, m), 5.96 (1H, bs), 4.81-4.63 (1H, m), 3.94 (1H, d, J=11.07 Hz), 3.74 (1H, d, J=11.25 Hz), 3.35 (1H, bs), 2.84 (1H, bs), 2.47-2.35 (1H, m), 2.30-2.17 (1H, m), 1.75 (1H, bd), 1.64 (3H, d, J=6.71 Hz), 1.50 (1H, bs)

Example 128

N-((1S)-1-(1-(tetrahydro-2H-pyran-3-yl)-1H-benzo[d]imidazol-2-yl)ethyl)-9H-purin-6-amine 128

A mixture of (S)-1-[1-(tetrahydropyran-3-yl)-1H-benzoimidazol-2-yl]ethylamine from Example 18 (295 mg, 1.20 mmol), 6-chloro-9-(tetrahydropyran-2-yl)-9H-purine (400 mg, 1.68 mmol) and DIPEA (0.38 mL, 2.16 mmol) in n-butanol (2 mL) was stirred in a sealed vial for 16 h at 100° C. After cooling to RT, volatiles were removed under reduced pressure and the resulting residue was loaded into an Isolute® SCX-2 which was washed with MeOH and the product eluted with 2M NH$_3$/MeOH. The product containing fractions were combined and concentrated in vacuo. Purification by Isolute® SCX-2 was repeated a second time and then the resulting residue was purified by column chromatography (Si—PCC, gradient 0-10% 2M NH$_3$/MeOH in DCM) affording 128 as a white solid (310 mg, 71%). LCMS: R$_T$ 2.42 and 2.46 min [M+H]$^+$ 364.0. $^1$H NMR (DMSO, 400 MHz): δ 8.38-7.88 (3H, m), 7.80 (1H, t, J=8.38 Hz), 7.65-7.54 (1H, m), 7.21-7.09 (2H, m), 5.95 (1H, br), 4.71-4.57 (1H, m), 4.14-4.04 (1H, m), 4.00-3.86 (1H, m), 3.83-3.71 (1H, m), 3.55-3.43 (1H, m), 3.16 (0.5H, d, J=4.68 Hz), 2.56-2.43 (0.5H, m), 2.36-2.23 (0.5H, m), 2.02 (0.5H, br), 1.83-1.72 (4H, m), 1.56 (0.5H, bd, J=13.68 Hz), 1.24-1.08 (0.5H, m). Signals split due to presence of rotamers/tautomers

Example 129

(S)—N-(1-(1-(1-(oxetan-3-yl)piperidin-4-yl)-1H-benzo[d]imidazol-2-yl)ethyl)-9H-purin-6-amine 129

To a mixture of (S)—N-(1-(1-(piperidin-4-yl)-1H-benzo[d]imidazol-2-yl)ethyl)-9H-purin-6-amine from Example 113 (99 mg, 0.273 mmol) in anhydrous DCE (10 mL) was added oxetan-3-one (32 μL, 0.546 mmol) followed by AcOH (16 μL, 0.273 mmol) and 4 Å (angstrom) powdered molecular sieves (0.1 g). After stirring for 4 h, sodium triacetoxyborohydride (116 mg, 0.546 mmol) was added and stirring was continued for 48 h. The crude reaction mixture was loaded into an Isolute® SCX-2 which was washed with MeOH and the product eluted with 2M NH$_3$/MeOH. The product containing fractions were combined and concentrated in vacuo and the resulting residue was purified by column chromatography (Si—PCC, gradient 0-10% 2M NH$_3$/MeOH in DCM) and then triturated with diethyl ether and MeOH affording 129 as a white solid (50 mg, 44%). LCMS: R$_T$ 1.61 min [M+H]$^+$ 419.1. $^1$H NMR (DMSO, 400 MHz, 80° C.): δ 8.25 (1H, s), 8.05 (1H, s), 7.65-7.59 (2H, m), 7.44 (1H, bs), 7.20-7.13 (2H, m), 6.16-6.04 (1H, m), 4.63-4.39 (6H, m), 3.50-3.42 (1H, m), 2.93-2.85 (1H, bd, J=10.45 Hz), 2.76-2.69 (1H, bd, J=10.45 Hz), 2.40-2.28 (1H, m), 2.04-1.93 (1H, t, J=11.60 Hz), 1.90-1.81 (1H, m), 1.76-1.53 (6H, m)

Example 130

(S)-4-(2-(1-(9H-purin-6-ylamino)ethyl)-1H-benzo[d]imidazol-1-yl)-N-isopropylpiperidine-1-carboxamide 130

To a mixture of [(S)-1-((R)-1-piperidin-3-yl-1H-benzoimidazol-2-yl)ethyl]-(9H-purin-6-yl)amine from Example 16 (88 mg, 0.243 mmol) in anhydrous DCM (5 mL) was added 2-isocyanatopropane (31 μL, 0.316 mmol) and the reaction mixture was stirred at RT for 3 h. The crude reaction mixture was partitioned between DCM and water and the organic layer was then washed with brine, dried (Na$_2$SO$_4$) and concentrated in vacuo. The resulting residue was purified by preparative HPLC (Phenomenex Gemini 5 μm C18 on a 20 min gradient 5-70% 0.1% HCO$_2$H in acetonitrile/water) followed by Isolute® SCX-2 purification. The cartridge was washed with MeOH and the product eluted with 2M NH$_3$/MeOH. The product containing fractions were combined and concentrated in vacuo affording 130 as a white solid (26 mg, 24%). LCMS: R$_T$ 2.48 min [M+H]$^+$ 448.1. $^1$H NMR (DMSO plus TFA, 400 MHz): δ 8.72 (1H, s), 8.56 (1H, s), 7.98-7.91 (1H, m), 7.79-7.73 (1H, m), 7.58-7.52 (2H, m), 6.11 (1H, bs), 5.13-5.02 (1H, m), 4.19 (2H, t, J=14.33 Hz), 3.87-3.76 (1H, m), 2.88 (1H, t, J=12.16 Hz), 2.74-2.64 (1H, m), 2.44-2.23 (4H, m), 2.08-1.91 (3H, m), 1.86 (3H, d, J=6.95 Hz), 1.09 (6H, d, J=7.82 Hz)

Example 131

(S)—N-(1-(1-(1-isopropylpiperidin-4-yl)-1H-benzo[d]imidazol-2-yl)ethyl)-9H-purin-6-amine 131

To a mixture of (S)—N-(1-(1-(piperidin-4-yl)-1H-benzo[d]imidazol-2-yl)ethyl)-9H-Aurin-6-amine from Example 113 (81 mg, 0.223 mmol) in anhydrous DCM (2 mL) was added acetone (49 μL, 0.67 mmol) followed by AcOH (1 drop). After stirring for 5 min, sodium triacetoxyborohydride (71 mg, 0.335 mmol) was added and stirring was continued for 19 h. The crude reaction mixture was loaded into an Isolute® SCX-2 which was washed with MeOH and the product eluted with 2M NH$_3$/MeOH. The product containing fractions were combined and concentrated in vacuo and the resulting residue was purified by preparative HPLC (Phenomenex Gemini 5 μm C18 on a 20 min gradient 5-40% 0.1% NH$_4$OH in acetonitrile/water) followed by Isolute® SCX-2 purification. The cartridge was washed with MeOH and the product eluted with 2M NH$_3$/MeOH. The product containing fractions were combined and concentrated in vacuo affording 131 as a pale yellow solid (22 mg, 24%). LCMS: R$_T$ 1.68 min [M+H]$^+$ 405.1. $^1$H NMR (DMSO plus TFA, 400 MHz): δ 8.82 (1H, bs), 8.57 (1H, s), 8.22 (1H, d, J=8.16 Hz), 7.77 (1H, d, J=7.78 Hz), 7.64-7.52 (2H, m), 5.97 (1H, bs), 5.49-5.35 (1H, br), 3.79-3.58 (3H, m), 3.43-3.24 (2H, m), 3.00-2.78 (2H, m), 2.68-2.48 (3H, m), 2.38 (1H, bd, J=16.58 Hz), 1.89 (3H, d, J=6.93 Hz), 1.36 (6H, dd, J=6.61, 2.47 Hz)

Example 132

N—((S)-1-(1-((R)-1-isopropylpiperidin-3-yl)-1H-benzo[d]imidazol-2-yl)ethyl)-9H-purin-6-amine 132

To a mixture of [(S)-1-((R)-1-piperidin-3-yl-1H-benzoimidazol-2-yl)ethyl]-(9H-purin-6-yl)amine from Example 16 (150 mg, 0.414 mmol) in anhydrous DCM (3 mL) was added acetone (90 µL, 1.24 mmol) followed by AcOH (1 drop). After stirring for 5 min, sodium triacetoxyborohydride (132 mg, 0.621 mmol) was added and stirring was continued for 22 h. The mixture was then treated with NaOH (1N, 2 mL) and then vigorously stirred for 10 min. Volatiles were removed in vacuo and the resulting residue was purified by column chromatography (Si—PCC, gradient 0-15% 2M NH$_3$/MeOH in DCM) affording 132 (58 mg, 35%). LCMS: R$_T$ 1.91 min [M+H]$^+$ 405.1. $^1$H NMR (DMSO, 400 MHz): δ 12.97 (1H, s), 8.33-8.06 (2H, m), 7.96 (1H, br), 7.72 (1H, d, J=7.33 Hz), 7.62 (1H, d, J=7.14 Hz), 7.24-7.07 (2H, m), 5.93 (1H, s), 4.66-4.52 (1H, m), 3.00-2.83 (2H, m), 2.81-2.65 (2H, m), 2.23 (1H, t, J=11.59 Hz), 2.15-2.01 (1H, m), 1.84-1.57 (5H, m), 1.26-1.07 (1H, m), 0.96 (6H, d, J=6.51 Hz)

Example 133

2-((R)-3-(2-((S)-1-(9H-purin-6-ylamino)ethyl)-1H-benzo[d]imidazol-1-yl)piperidin-1-yl)acetamide 133

A mixture of [(S)-1-((R)-1-piperidin-3-yl-1H-benzoimidazol-2-yl)ethyl]-(9H-purin-6-yl)amine from Example 16 (150 mg, 0.414 mmol), 2-bromo-acetamide (57 mg, 0.414 mmol) and DIPEA (215 mL, 1.24 mmol) in IMS (2 mL) was stirred in a sealed vial at 70° C. for 20 h. After cooling to RT, volatiles were removed under reduced pressure and the resulting residue was purified by column chromatography (Si—PCC, gradient 0-15% 2M NH$_3$/MeOH in DCM). The product containing fractions were concentrated in vacuo and the resulting residue was triturated with MeOH affording 133 (59 mg, 34%). LCMS: R$_T$ 1.80 min [M+H]$^+$ 420.1. $^1$H NMR (DMSO, 400 MHz): δ 8.25 (1H, s), 8.14 (1H, s), 8.01-7.90 (1H, m), 7.74-7.66 (1H, m), 7.63-7.55 (1H, m), 7.28-7.03 (4H, m), 5.95 (1H, bs), 4.75 (1H, br), 3.04-2.86 (4H, m), 2.74 (1H, bd, J=11.16 Hz), 2.24 (1H, bt, J=11.70 Hz), 1.80-1.55 (5H, m), 1.35-1.19 (1H, m)

Example 134

1-((R)-3-(2-((S)-1-(9H-purin-6-ylamino)ethyl)-1H-benzo[d]imidazol-1-yl)piperidin-1-yl)-2-(dimethylamino)ethanone 134

A mixture of [(S)-1-((R)-1-piperidin-3-yl-1H-benzoimidazol-2-yl)ethyl]-(9H-purin-6-yl)amine from Example 16 (150 mg, 0.414 mmol), dimethylaminoacetic acid (47 mg, 0.455 mmol), HOAt (62 mg, 0.455 mmol), N-(3-dimethylaminopropyl)-N'-ethylcarbodiimide hydrochloride (87 mL, 0.455 mmol) and 4-methylmorpholine (0.10 mL, 0.911 mmol) in anhydrous DCM (4 mL) was stirred at RT for 20 h. Volatiles were removed in vacuo and the resulting residue was purified by column chromatography (Si—PCC, gradient 0-15% 2M NH$_3$/MeOH in DCM) then triturated with diethyl ether affording 134 (55 mg, 30%). LCMS: R$_T$ 1.79 min [M+H]$^+$ 448.1. $^1$H NMR (DMSO, 400 MHz): δ 8.23-7.93 (3H, m), 7.90-7.78 (1H, m), 7.68-7.58 (1H, m), 7.21-7.12 (2H, m), 4.80-4.69 (1H, br), 4.53-4.30 (1H, m), 4.22 (0.6H, bd, J=12.25 Hz), 4.03 (0.4H, bd, J=12.25 Hz), 3.85 (0.6H, t, J=12.08 Hz), 3.44-3.26 (1.4H, t, J=12.08 Hz), 3.21-3.10 (1H, m), 2.99 (0.4H, bd, J=13.04 Hz), 2.90-2.64 (1.6H, m), 2.44-2.26 (1H, m), 2.25-2.11 (6H, m), 1.85-1.58 (5H, m), 1.13-0.97 (1H, m). Signals split due to presence of rotamers Example 135

1-((R)-3-(2-((S)-1-(9H-purin-6-ylamino)ethyl)-1H-benzo[d]imidazol-1-yl)piperidin-1-yl)-2-hydroxy-2-methylpropan-1-one 135

A mixture of [(S)-1-((R)-1-piperidin-3-yl-1H-benzoimidazol-2-yl)ethyl]-(9H-purin-6-yl)amine from Example 16 (150 mg, 0.414 mmol), 2-hydroxy-2-methylpropionic acid (47 mg, 0.455 mmol), HOAt (62 mg, 0.455 mmol), N-(3-dimethylaminopropyl)-N'-ethylcarbodiimide hydrochloride (87 µL, 0.455 mmol) and 4-methylmorpholine (0.10 mL, 0.911 mmol) in anhydrous DCM (4 mL) was stirred at RT for 20 h. Volatiles were removed in vacuo and the resulting residue was purified by column chromatography (Si—PCC, gradient 0-15% 2M NH$_3$/MeOH in DCM) then triturated with diethyl ether affording 135 (65 mg, 35%). LCMS: R$_T$ 2.44 min [M+H]$^+$ 449.1. $^1$H NMR (DMSO, 400 MHz): δ 8.24-7.90 (3H, m), 7.88-7.81 (1H, m), 7.67-7.56 (1H, m), 7.23-7.07 (2H, m), 5.90 (1H, s), 5.51 (1H, s), 5.30-3.76 (4H, br), 2.45-2.28 (1H, m), 1.93-1.61 (5H, m), 1.48-1.27 (6H, m), 1.20-1.08 (1H, m)

Example 136

(S)—N-(1-(4-fluoro-1-phenyl-1H-benzo[d]imidazol-2-yl)ethyl)-9H-purin-6-amine 136

A mixture of (S)-1-(4-fluoro-1-phenyl-1H-benzoimidazol-2-yl)ethylamine from Example 15 (0.407 mmol), 6-chloro-9-(tetrahydropyran-2-yl)-9H-purine (122 mg, 0.509 mmol) and DIPEA (0.444 mL, 2.55 mmol) in n-butanol (3 mL) was stirred in a sealed vial for 20 h at 100° C. After cooling to RT, volatiles were removed under reduced pressure and the resulting residue was purified by column chromatography (Si—PCC, gradient 0-10% MeOH in EtOAc). The product containing fractions were concentrated in vacuo and the resulting residue was dissolved in EtOAc (10 mL) and stirred with 2N HCl (10 mL) for 15 min. Volatiles were removed under reduced pressure and the residue was dissolved in MeOH (2 mL) and triturated with diethyl ether affording 136 as a beige powder (126 mg, 78%). LCMS: R$_T$ 3.47 min [M+H]$^+$ 374.0. $^1$H NMR (DMSO, 400 MHz): δ 10.03 (1H, s), 8.66 (1H, s), 8.55 (1H, s), 7.68-7.38 (5H, m), 7.28-7.21 (1H, m), 7.13 (1H, dd, J=10.91, 7.98 Hz), 6.94 (1H, dd, J=8.11, 0.82 Hz), 5.68-5.59 (1H, m), 1.72 (3H, d, J=6.85 Hz)

Example 137

(S)-2-(1-(9H-purin-6-ylamino)ethyl)-1-phenyl-1H-benzo[d]imidazole-6-carboxamide 137

To a solution of (S)-2-(1-(9H-purin-6-ylamino)ethyl)-1-phenyl-1H-benzo[d]imidazole-6-carbonitrile 122 (70 mg, 0.18 mmol) in DMSO (2 mL) was added potassium carbonate (10 mg, 0.07 mmol) followed by hydrogen peroxide (30%, 0.2 mL). After 1 h stirring, additional potassium carbonate (10 mg, 0.07 mmol) in water and hydrogen peroxide 90.2 mL)

were added and stirring was continued for 1 h. The solution was then diluted with water (30 mL) and EtOAc was added. A precipitate formed and was filtered off affording 137 as a white solid (47 mg, 64%). LCMS: $R_T$ 2.41 min [M+H]$^+$ 399.1. $^1$H NMR (DMSO, 400 MHz): δ 8.20-8.07 (2H, m), 8.03-7.92 (2H, m), 7.81 (1H, d, J=9.19 Hz), 7.76-7.50 (6H, m), 7.24 (1H, s), 5.51 (1H, bs), 1.58 (3H, d, J=6.84 Hz)

Example 138

(S)—N-(1-(7-chloro-1-phenyl-1H-benzo[d]imidazol-2-yl)ethyl)-9H-purin-6-amine 138

A mixture of (S)-1-(7-chloro-1-phenyl-1H-benzoimidazol-2-yl)ethylamine from Example 19 (482 mg, 1.77 mmol), 6-chloro-9-(tetrahydropyran-2-yl)-9H-purine (466 mg, 1.95 mmol) and DIPEA (0.91 mL, 5.32 mmol) in IMS (3.5 mL) was stirred in a sealed vial for 48 h at 90° C. After cooling to RT, volatiles were removed under reduced pressure and the resulting residue was loaded into an Isolute® SCX-2 which was washed with MeOH followed by 2M NH$_3$/MeOH. The product containing fractions (basic and methanolic) were combined and concentrated in vacuo. Purification by Isolute® SCX-2 was repeated a second time and the resulting residue was purified by column chromatography (Si—PCC, gradient 0-10% 2M NH$_3$/MeOH in DCM). The basic fractions were combined and concentrated in vacuo and the residue was refluxed in MeOH. After cooling to RT the solid was filtered off and washed with EtOAc affording 138 as a white solid (379 mg, 55%). LCMS: $R_T$ 3.65 min [M+H]$^+$ 390.0. $^1$H NMR (DMSO, 400 MHz): δ 8.20-8.06 (2H, m), 7.94 (1H, s), 7.69-7.36 (6H, m), 7.24-7.19 (2H, m), 5.26 (1H, bs), 1.10 (3H, d, J=7.00 Hz)

Example 139

7-((1-phenyl-1H-benzo[d]imidazol-2-yl)methyl)-7H-pyrrolo[2,3-d]pyrimidin-4-amine 139

Step 1: 4-chloro-7-(1-phenyl-1H-benzoimidazol-2-ylmethyl)-7H-pyrrolo[2,3-d]pyrimidine

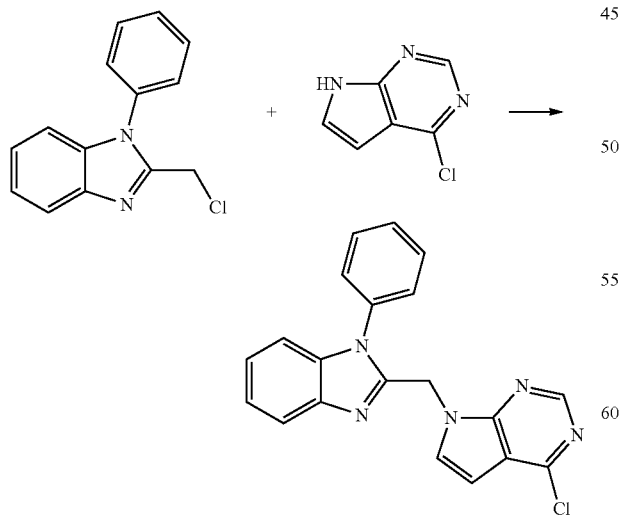

A mixture of 4-chloro-7H-pyrrolo[2,3-d]pyrimidine (0.62 g, 4.1 mmol), 2-(chloromethyl)-1-phenyl-1H-benzo[d]imidazole (1.0 g, 4.1 mmol) and K$_2$CO$_3$ (0.6 g, 4.3 mmol) in DMSO (20 mL) was stirred at room temperature overnight. Then the mixture was added H$_2$O (50 mL) and extracted with EtOAc (20 mL×3). The combine organic layers were concentrated in vacuo to give 4-chloro-7-(1-phenyl-1H-benzoimidazol-2-ylmethyl)-7H-pyrrolo[2,3-d]pyrimidine (1.2 g, yield 80%) as brown solid.

Step 2

A solution of 4-chloro-7-(1-phenyl-1H-benzoimidazol-2-ylmethyl)-7H-pyrrolo[2,3-d]-pyrimidine (1.0 g, 2.7 mmol) in NH$_4$OH (5 mL) and MeOH (10 mL) was stirred at 90° C. in a sealed tube overnight. Then the mixture was concentrated in vacuo. The residue was purified by P-TLC to give 139 (0.2 g, yield 22%) as a white solid. LCMS (ESI), M+H$^+$=339.14. 1HNMR (400 MHz, CDCl$_3$) δ 5.505 (s, 1H), 6.503 (s, 1H), 6.936 (s, 2H), 7.031 (s, 1H), 7.205-7.209 (q, J=1.6 Hz, 1H), 7.219-7.228 (m, 2H), 7.490-7.540 (m, 5H), 7.555-7.559 (d, J=1.6 Hz, 1H), 7.910 (s, 1H)

Example 140

5-iodo-7-((1-phenyl-1H-benzo[d]imidazol-2-yl)methyl)-7H-pyrrolo[2,3-d]pyrimidin-4-amine 140

Step 1: 4-chloro-5-iodo-7H-pyrrolo[2,3-d]pyrimidine

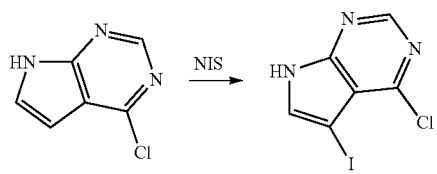

A mixture of 4-chloro-7H-pyrrolo[2,3-d]pyrimidine (3.0 g, 20 mmol) and NIS (4.9 g, 20.1 mmol) in DMF (100 mL) was stirred in darkness at room temperature overnight. Then the mixture was concentrated in vacuo. The residue was treated with 10% Na$_2$SO$_3$ and filtered to give 4-chloro-5-iodo-7H-pyrrolo[2,3-d]pyrimidine (4.0 g, yield 72%) as a yellow solid.

Step 2: 4-chloro-5-iodo-7-(1-phenyl-1H-benzoimidazol-2-ylmethyl)-7H-pyrrolo[2,3-d]pyrimidine

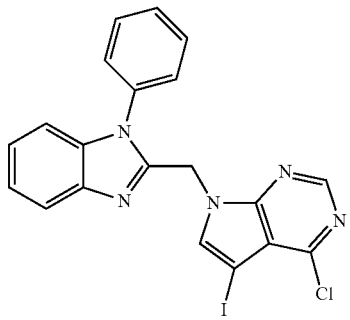 [SMILES: Clc1ncnc2c1c(I)cn2Cc1nc2ccccc2n1-c1ccccc1]

A mixture of 4-chloro-5-iodo-7H-pyrrolo[2,3-d]pyrimidine (1.15 g, 4.1 mmol), 1-(1-phenyl-1H-benzo[d]imidazol-2-yl)ethanamine from Example 4 (1.0 g, 4.1 mol) and K$_2$CO$_3$ (0.6 g, 4.3 mmol) in DMSO (20 mL) was stirred at room temperature overnight. Then the mixture was added H₂O (50 mL) and extracted with CH₂Cl₂ (20 mL×3). The combined organic layers were concentrated in vacuo to give 4-chloro-5-iodo-7-(1-phenyl-1H-benzoimidazol-2-ylmethyl)-7H-pyrrolo[2,3-d]pyrimidine (1.7 g, yield 85%) as brown solid.

Step 3

A solution of 4-chloro-5-iodo-7-(1-phenyl-1H-benzoimidazol-2-ylmethyl)-7H-pyrrolo[2,3-d]pyrimidine (1.0 g, 2 mmol) in NH₄OH (5 mL) and MeOH (10 mL) was stirred at 90° C. in a sealed tube overnight. Then the mixture was filtered. The precipitate was purified by P-TLC to give 140 (0.4 g, yield 42%) as a white solid. LCMS (ESI), M+H⁺= 465.04 1HNMR (400 MHz, DMSO) δ 5.518 (s, 2H), 6.574 (s, 2H), 7.128 (s, 2H), 7.210-7.232 (m, 2H), 7.343 (s, 1H), 7.521-7.622 (m, 6H), 7.968 (s, 1H)

Example 141

3-iodo-1-((1-phenyl-1H-benzo[d]imidazol-2-yl)methyl)-1H-pyrazolo[3,4-d]pyrimidin-4-amine 141

Step 1:
3-iodo-1H-pyrazolo[3,4-d]pyrimidin-4-ylamine

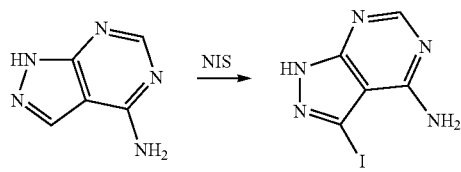

A mixture of 1H-pyrazolo[3,4-d]pyrimidin-4-ylamine (5.0 g, 37 mmol) and NIS (10.7 g, 45 mmol) in DMF (100 mL) was stirred at 70° C. overnight. Then the mixture was cooled to room temperature and filtered to give 3-iodo-1H-pyrazolo[3,4-d]pyrimidin-4-ylamine (4.1 g) as a white solid. The filtrate was concentrated and the residue was treated with 10% Na₂SO₃ and filtered to give another batch. (5.1 g, 96% of total yield)

Step 2

A mixture of 3-iodo-1H-pyrazolo[3,4-d]pyrimidin-4-ylamine (11.0 g, 41.1 mmol), 2-(chloromethyl)-1-phenyl-1H-benzo[d]imidazole (10.0 g, 41.4 mmol) and K₂CO₃ (6.0 g, 43.4 mmol) in DMSO (60 mL) was stirred at room temperature overnight. Then the mixture was added H₂O (100 mL) and extracted with EtOAc (100 mL×3). The combined organic layers were concentrated in vacuo, and the residue was purified by column chromatography on silica gel (PE: EtOAc=2:1) to give 141 (10.0 g, yield 52%) as a yellow solid. LCMS (ESI), M+H⁺=466.04. 1HNMR (400 MHz, CDCl₃) δ 5.783 (s, 2H), 5.785 (s, 2H), 7.068-7.090 (q, J=0.8 Hz, 1H), 7.088-7.307 (m, 3H), 7.362-7.422 (m, 4H), 7.800-7.822 (d, J=0.8 Hz, 1H), 8.219-8.221 (d, J=1.2 Hz, 2H)

Example 142

3-methyl-1-((1-phenyl-1H-benzo[d]imidazol-2-yl)methyl)-1H-pyrazolo[3,4-d]pyrimidin-4-amine 142

Step 1: 2-(1-ethoxy-ethylidene)-malononitrile

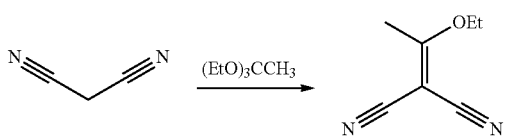

A mixture of malononitrile (5.0 g, 76 mmol), (EtO)₃CCH₃ (14.8 g, 91 mmol) and CH₃COOH (1 mL) was stirred at 80° C. for 45 min. Then the mixture was cooled to room temperature and filtered to give 2-(1-ethoxy-ethylidene)-malononitrile (8.9 g, yield 86%) as a yellow solid.

Step 2:
5-amino-3-methyl-1H-pyrazole-4-carbonitrile

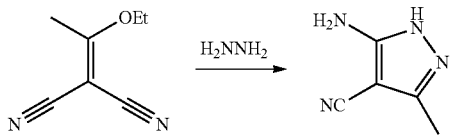

To a solution of hydrazine H₂NNH₂ (3.7 g, 74 mmol) in EtOH (5 mL), 2-(1-ethoxy-ethylidene)-malononitrile (5.0 g, 37 mmol) was added in portion at 0° C. Then the mixture was heated to 80° C. for 1.5 hrs. Then the mixture was cooled to room temperature, added H₂O, cooled with ice/water bath and filtered to give 5-amino-3-methyl-1H-pyrazole-4-carbonitrile (2.3 g, yield 51%) as a yellow solid.

Step 3:
3-methyl-1H-pyrazolo[3,4-d]pyrimidin-4-ylamine

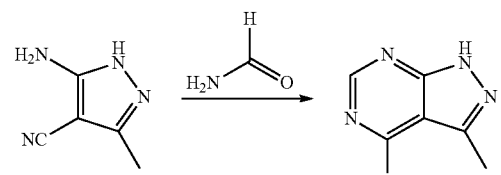

A solution of 5-amino-3-methyl-1H-pyrazole-4-carbonitrile (1.5 g, 12.3 mmol) in formamide (6 mL) was stirred at 210° C. for 45 min. After cooled to room temperature, the mixture was poured into water (5 mL), filtered and washed with water to give 3-methyl-1H-pyrazolo[3,4-d]pyrimidin-4-ylamine (1.2 g, yield 65%) as a grey solid.

Step 4

A mixture of 3-methyl-1H-pyrazolo[3,4-d]pyrimidin-4-ylamine (1.2 g, 8 mmol), (2.0 g, 8 mmol) and K₂CO₃ (1.16 g, 8.4 mmol) in DMSO (40 mL) was stirred at 50° C. for 3 hrs. Then the mixture was cooled to room temperature, added H₂O (50 ml) and extracted with EtOAc (40 mL×3). The combined organic layers were concentrated in vacuo. The residue was purified by P-TLC to give 142 (0.8 g, yield 28%) as a yellow solid. LCMS (ESI), M+H⁺=354.15. 1HNMR (400 MHz, CDCl₃) δ 2.443 (s, 3H), 5.532 (s, 2H), 5.646 (s, 2H), 7.017-7.037 (d, J=8 Hz, 1H), 7.153-7.205 (m, 4H), 7.239-7.258 (m, 3H), 7.720-7.739 (d, J=7.6 Hz, 1H), 8.129 (s, 1H)

Example 143

(S)—N-(1-(1-phenyl-1H-benzo[d]imidazol-2-yl)ethyl)thieno[2,3-d]pyrimidin-4-amine 143

Into a 10-mL sealed tube was placed (1S)-1-(1-phenyl-1H-1,3-benzodiazol-2-yl)ethan-1-amine from Example 4 (300 mg, 1.26 mmol, 1.00 equiv), 4-chlorothieno[2,3-d]pyrimidine (250 mg, 1.47 mmol, 1.16 equiv), N-ethyl-N-isopropylpropan-2-amine (322 mg) and BuOH (5 mL). The resulting solution was stirred for 1 overnight at 120° C. and concentrated under vacuum. The residue was applied onto a silica gel column eluted with ethyl acetate/petroleum ether (0:100-80:20) to afford 260 mg (55%) of 143 as a light yellow solid. LC-MS (ES, m/z): 372 [M+H]⁺. 1H-NMR (300 MHz, CD₃OD, ppm): δ 8.19 (s, 1H), 7.70 (d, 1H), 7.68-7.08 (m, 10H), 5.74-5.67 (m, 1H), 1.73 (d, 3H)

Example 144

(S)-5-methyl-N-(1-(1-phenyl-1H-benzo[d]imidazol-2-yl)ethyl)-7H-pyrrolo[2,3-d]pyrimidin-4-amine 144

Into a 10-mL sealed tube was placed (S)-1-(1-phenyl-1H-benzo[d]imidazol-2-yl)ethanamine from Example 4 (300 mg, 1.26 mmol, 1.00 equiv), 4-chloro-5-methyl-7H-pyrrolo[2,3-d]pyrimidine (250 mg, 1.49 mmol, 1.18 equiv), N-ethyl-N-isopropylpropan-2-amine (322 mg, 2.50 mmol, 1.97 equiv) and BuOH (5 mL). The resulting solution was stirred for overnight at 120° C. and concentrated under vacuum. The residue was applied onto a silica gel column eluted with ethyl acetate/hexane (0:100-80:20) to afford 270 mg (58%) of 144 as a white solid. LC-MS (ES, m/z): 369 [M+H]⁺. H-NMR (300 MHz, CD₃OD, ppm): δ 7.98 (s, 1H), 7.70-7.53 (m, 6H), 7.33-7.23 (m, 2H), 7.14-7.11 (m, 1H), 6.83 (d, 1H), 5.68-5.61 (m, 1H), 2.49 (d, 3H), 1.67 (d, 3H)

Example 145

(S)—N4-(1-(1-phenyl-1H-benzo[d]imidazol-2-yl)ethyl)pyrimidine-2,4-diamine 145

Into a 25-mL round-bottom flask was placed a solution of (S)-1-(1-phenyl-1H-benzo[d]imidazol-2-yl)ethanamine from Example 4 (238 mg, 1.00 mmol, 1.00 equiv) in ethanol (8 mL) and 4-chloropyrimidin-2-amine (130 mg, 0.99 mmol, 0.98 equiv, 98%). The resulting solution was stirred overnight at 100° C. and concentrated under vacuum. The crude product was applied onto a C18 Column (water/acetonitrile) to afford 150 mg (44%) of 145 as a white solid. LC-MS (ES, m/z): 331 [M+H]+ H-NMR (300 MHz, CD3OD, ppm): δ 7.83 (d, 1H), 7.57 (m, 8H), 6.11 (q, 1H), 5.61 (q, 1H), 1.67 (d, 3H)

Example 146

(S)—N4-(1-(1-phenyl-1H-benzo[d]imidazol-2-yl)ethyl)pyrimidine-4,6-diamine 146

A solution of (S)-1-(1-phenyl-1H-benzo[d]imidazol-2-yl)ethanamine from Example 4 (321.6 mg, 1.36 mmol, 1.00 equiv) in dioxane (10 mL) and 6-chloropyrimidin-4-amine hydrochloride (456.3 mg, 2.71 mmol, 2.00 equiv, 98%) was stirred overnight at 130° C. in an oil bath. The resulting mixture was concentrated under vacuum. The residue was applied onto a C18 column with acetonitrile/water (0-40%) to afford 298.6 mg (60%) of 146 hydrochloride as yellow crystals. LC-MS (ES, m/z): 331 [M+H]+H-NMR: (400 MHz, CD3OD, ppm) δ: 8.15 (s, 1H), 7.87-7.58 (m, 8H), 7.38-7.36 (m, 1H), 5.88 (br s, 1H), 5.41-5.36 (q, 1H), 1.747-1.73 (d, 3H)

Example 147

(S)—N-(1-(1-phenyl-1H-benzo[d]imidazol-2-yl)ethyl)-5H-pyrrolo[3,2-d]pyrimidin-4-amine 147

Into a 25-mL round-bottom flask was placed a solution of (S)-1-(1-phenyl-1H-benzo[d]imidazol-2-yl)ethanamine from Example 4 (238 mg, 1.00 mmol, 1.00 equiv) in n-BuOH (8 mL), 4-chloro-5H-pyrrolo[3,2-d]pyrimidine from Example 20 (155 mg, 0.99 mmol, 0.99 equiv, 98%) and N-ethyl-N-isopropylpropan-2-amine (400 mg, 3.03 mmol, 3.02 equiv, 98%). The resulting solution was stirred overnight at 130° C. and concentrated under vacuum. The residue was purified by applying onto a C18 column eluted with water/acetonitrile (95:5-20:80) to afford 150 mg (41%) of 147 as a light-yellow solid. LC-MS (ES, m/z): 355 [M+H]⁺. 1H-NMR (300 MHz, CD₃OD, ppm): δ 8.49 (s, 1H), 7.85-7.48 (m, 9H), 7.32-7.30 (m, 1H), 6.63 (d, 1H), 5.81-5.74 (m, 1H), 1.89 (d, 3H)

Example 148

(S)—N-(1-(1-phenyl-1H-benzo[d]imidazol-2-yl)ethyl)-7H-pyrrolo[2,3-d]pyrimidin-4-amine 148

Into a 25-mL round-bottom flask was placed a solution of (S)-1-(1-phenyl-1H-benzo[d]imidazol-2-yl)ethanamine from Example 4 (238 mg, 1.00 mmol, 1.00 equiv) in n-BuOH (5 mL), 4-chloro-7H-pyrrolo[2,3-d]pyrimidine (153 mg, 1.00 mmol, 1.00 equiv) and N-ethyl-N-isopropylpropan-2-amine (0.5 mL). The resulting solution was stirred overnight at 130° C. and concentrated under vacuum. The crude product was purified by applying onto a C18 Column (water/acetonitrile) to afford 150 mg (41%) of 148 as a white solid. LC-MS (ES, m/z): 355 [M+H]⁺. H-NMR (300 MHz, CD₃OD, ppm): δ 7.97 (s, 1H), 7.69 (d, 1H), 7.48 (m, 5H), 7.25 (m, 2H), 7.11 (m, 2H), 6.58 (d, 1H), 5.65 (q, 1H), 1.71 (d, 3H)

Example 149

(S)—N6-(1-(1-phenyl-1H-benzo[d]imidazol-2-yl)ethyl)-9H-purine-2,6-diamine 149

Into a 25-mL round-bottom flask was placed a solution of (S)-1-(1-phenyl-1H-benzo[d]imidazol-2-yl)ethanamine from Example 4 (238 mg, 1.00 mmol, 1.00 equiv) in n-BuOH (8 mL), 6-chloro-9H-purin-2-amine (155 mg, 0.91 mmol, 0.91 equiv, 98%) and N-ethyl-N-isopropylpropan-2-amine (390 mg, 2.96 mmol, 2.95 equiv, 98%). The resulting solution was stirred overnight at 130° C. and concentrated under vacuum. The residue was eluted onto a C18 column (water/acetonitrile) to afford 0.150 g (40%) of 149 as a white solid. LC-MS (ES, m/z): 371 [M+H]⁺. H-NMR (300 MHz, CD₃OD, ppm): δ 7.71 (d, 2H), 7.51 (s, 5H), 7.29 (m, 2H), 7.10 (d, 1H), 5.67 (s, 1H), 1.69 (d, 3H)

Example 150

2-((R)-3-(2-((S)-1-(9H-purin-6-ylamino)ethyl)-1H-benzo[d]imidazol-1-yl)piperidin-1-yl)ethanol 150

A mixture of [(S)-1-((R)-1-piperidin-3-yl-1H-benzoimidazol-2-yl)ethyl]-(9H-purin-6-yl)amine from Example 16 (150 mg, 0.414 mmol), 2-bromoethanol (30 µL, 0.414 mmol) and DIPEA (215 µL, 1.24 mmol) in IMS (2 mL) was stirred in a sealed vial at 70° C. for 20 h. After cooling to RT, volatiles were removed under reduced pressure and the resulting residue was purified by column chromatography (Si—PCC, gradient 0-15% 2M NH$_3$/MeOH in DCM) followed by sonication in cyclohexane and HPLC purification (Phenomenex Gemini 5 µm C18 on a 20 min gradient 5-50% 0.1% NH$_4$OH in acetonitrile/water). The product containing fractions were concentrated in vacuo affording 150 as a white solid (8 mg, 5%). LCMS: $R_T$ 1.72 min [M+H]$^+$ 407.1. $^1$H NMR (DMSO, 400 MHz): 8.30-8.07 (2H, m), 7.95 (1H, bs), 7.73-7.68 (1H, m), 7.63-7.58 (1H, m), 7.20-7.11 (2H, m), 5.93 (1H, bs), 4.68-4.57 (1H, m), 4.36 (1H, bs), 3.48 (2H, bs), 3.03-2.97 (1H, m), 2.89-2.77 (2H, m), 2.52-2.39 (3H, m), 2.14-2.98 (2H, m), 1.74-1.66 (4H, m), 1.61-1.53 (1H, m), 1.24-1.10 (1H, m)

Example 151

2-((R)-3-(2-((S)-1-(9H-purin-6-ylamino)ethyl)-1H-benzo[d]imidazol-1-yl)piperidin-1-yl)-N,N-dimethylacetamide 151

A mixture of [(S)-1-((R)-1-piperidin-3-yl-1H-benzoimidazol-2-yl)ethyl]-(9H-purin-6-yl)amine from Example 16 (150 mg, 0.414 mmol), 2-chloro-N,N-dimethylacetamide (43 µL, 0.414 mmol) and DIPEA (215 µL, 1.24 mmol) in IMS (2 mL) was stirred in a sealed vial at 70° C. for 20 h. After cooling to RT, volatiles were removed under reduced pressure and the resulting residue was purified by column chromatography (Si—PCC, gradient 0-15% 2M NH$_3$/MeOH in DCM) followed by HPLC purification (Phenomenex Gemini 5 µm C18 on a 20 min gradient 5-50% 0.1% NH$_4$OH in acetonitrile/water). The product containing fractions were concentrated in vacuo affording 151 as a white solid (8 mg, 4%). LCMS: $R_T$ 1.87 min [M+H]$^+$ 448.1. $^1$H NMR (DMSO, 400 MHz): δ 8.24 (1H, s), 8.10 (1H, s), 7.95 (1H, bs), 7.73-7.68 (1H, m), 7.65-7.58 (1H, m), 7.21-7.12 (2H, m), 4.66-4.55 (1H, m), 3.22 (2H, s), 3.06-2.88 (6H, m), 2.80 (3H, s), 2.75-2.68 (1H, m), 2.21 (1H, t, J=11.73 Hz), 2.10-1.96 (1H, m), 1.77-1.64 9 4 H, m), 1.55 (1H, bd, J=13.18 Hz), 1.13-0.98 (1H, m)

Example 152

3-(4-amino-1-((1-phenyl-1H-benzo[d]imidazol-2-yl)methyl)-1H-pyrazolo[3,4-d]pyrimidin-3-yl)prop-2-yn-1-ol 152

A mixture of 3-iodo-1-((1-phenyl-1H-benzo[d]imidazol-2-yl)methyl)-1H-pyrazolo[3,4-d]pyrimidin-4-amine 141 (1.5 g, 3.2 mmol), prop-2-yn-1-ol (0.4 g, 6.4 mmol), CuI (0.2 g, 0.64 mmol) and Pd(PPh$_3$)$_2$Cl$_2$ (0.25 g, 0.32 mmol) in Et$_2$NH (30 mL) was stirred at 25 for 2 hrs. Then the mixture was added H$_2$O (50 mL) and extracted with CH$_2$Cl$_2$ (30 mL×3). The combined organic layers were concentrated in vacuo. The residue was treated with CH$_2$Cl$_2$ and filtered to give 152 (400 mg, yield 32%) as a yellow solid. LCMS (ESI), M+H$^+$=394.15. 1HNMR (400 MHz, DMSO) δ 4.322-4.337 (d, J=6 Hz, 2H), 5.395-5.425 (t, J=6 Hz, 1H), 5.710 (s, 2H), 5.735 (s, 2H), 7.090-7.107 (d, J=6.8 Hz, 1H), 7.223-7.249 (m, 2H), 7.414-7.491 (s, 5H), 7.643-7.663 (d, J=8 Hz, 1H), 8.092 (s, 1H)

Example 153

3-(4-amino-1-((1-phenyl-1H-benzo[d]imidazol-2-yl)methyl)-1H-pyrazolo[3,4-d]pyrimidin-3-yl)-5-fluorophenol 153

A mixture of 3-iodo-1-((1-phenyl-1H-benzo[d]imidazol-2-yl)methyl)-1H-pyrazolo[3,4-d]pyrimidin-4-amine 141 (1.0 g, 2.14 mmol), 3-fluoro-5-hydroxyphenylboronic acid (0.4 g, 2.56 mmol), Pd(dppf)Cl$_2$ (0.2 g) and CsF (0.65 g, 4.3 mmol) in DME (20 mL) and H$_2$O (2 mL) was refluxed overnight. Then the mixture was cooled to room temperature, added H$_2$O (50 mL) and extracted with EtOAc (20 mL×3). The combined organic layers were washed with brine, dried over Na$_2$SO$_4$ and then concentrated in vacuo. The residue was treated with CH$_2$Cl$_2$ and filtered to give 153 (300 mg, yield 31%) as a grey solid. LCMS (ESI), M+H$^+$=450.16. 1HNMR (400 MHz, DMSO) δ 5.795 (s, 2H), 6.606-6.633 (d, J=10.8 Hz, 1H), 6.720-6.724 (d, J=8.8 Hz, 1H), 6.800 (s, 2H), 7.065-7.083 (d, J=7.2 Hz, 1H), 7.213-7.260 (m, 2H), 7.400 (s, 5H), 7.657-7.676 (d, J=7.6 Hz, 1H), 8.119 (s, 1H), 10.139 (s, 1H)

Example 154

3-(1H-indol-3-yl)-1-((1-phenyl-1H-benzo[d]imidazol-2-yl)methyl)-1H-pyrazolo[3,4-d]pyrimidin-4-amine 154

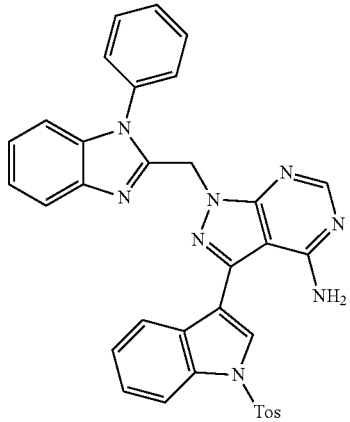

A solution of 1-(1-phenyl-1H-benzoimidazol-2-ylmethyl)-3-[1-(toluene-4-sulfonyl)-1H-indol-3-yl]-1H-pyrazolo[3,4-d]pyrimidin-4-ylamine in EtOH (20 mL) was added NaOH (2 M, 20 mL). After stirred at room temperature overnight, the mixture was concentrated in vacuo. The residue was added H$_2$O and extracted with CH$_2$Cl$_2$. The combined organic layers were evaporated and the residue was purified by P—HPLC to give 154 (500 mg, yield 51%) as a white solid. LCMS (ESI), M+H$^+$=455.18. 1HNMR (400 MHz, DMSO) δ 5.891 (s, 2H), 7.033-7.068 (t, J=7 Hz, 1H), 7.111-7.186 (m, 2H), 7.233-7.284 (m, 2H), 7.458-7.513 (m, 6H), 7.622-7.642 (d, J=8 Hz, 1H), 7.682-7.703 (d, J=1.8 Hz, 1H), 7.724-7.731 (d, J=2.8 Hz, 1H), 8.367 (s, 1H), 11.639-11.644 (d, J=2 Hz, 1H)

Example 155

4-(4-amino-1-((1-phenyl-1H-benzo[d]imidazol-2-yl)methyl)-1H-pyrazolo[3,4-d]pyrimidin-3-yl)-2-fluorophenol 155

A mixture of 3-iodo-1-((1-phenyl-1H-benzo[d]imidazol-2-yl)methyl)-1H-pyrazolo[3,4-d]pyrimidin-4-amine 141 (1.5 g, 3.2 mmol), 3-fluoro-4-hydroxyphenylboronic acid (0.6 g, 3.8 mmol), Pd(dppf)Cl₂ (0.3 g) and CsF (1.0 g, 6.4 mmol) in DME (30 mL) and H₂O (3 mL) was refluxed overnight. Then the mixture was cooled to room temperature, added H₂O (50 mL) and extracted with EtOAc (30 mL×3). The combined organic layers were washed with brine and concentrated in vacuo. The residue was treated with CH₂Cl₂ and filtered to give 155 (500 mg, yield 34%) as a white solid. LCMS (ESI), M+H⁺=450.16. 1HNMR (400 MHz, DMSO) δ 5.875 (s, 2H), 7.046-7.120 (m, 2H), 7.175-7.200 (d, J=1.6 Hz, 1H), 7.242-7.307 (m, 3H), 7.432-7.472 (m, 5H), 7.687-7.708 (d, J=1.2 Hz, 1H), 8.335 (s, 1H)

Example 156

N-(6-(4-amino-1-((1-phenyl-1H-benzo[d]imidazol-2-yl)methyl)-1H-pyrazolo[3,4-d]pyrimidin-3-yl)benzo[d]thiazol-2-yl)acetamide 156

Step 1: Preparation of n-(6-Bromo-benzothiazol-2-yl)-acetamide

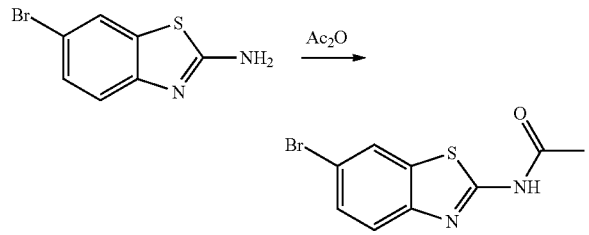

A mixture of 6-bromo-benzothiazol-2-ylamine (3.0 g, 13 mmol), Ac₂O (1.6 g, 16.5 mmol) and DMAP (2.4 g, 19.5 mmol) in CH₂Cl₂ (50 mL) was stirred at room temperature for 1 hr. Then the mixture was washed with HCl (2M), saturated Na₂CO₃, then brine and dried over Na₂SO₄. The CH₂Cl₂ phase was evaporated to give n-(6-Bromo-benzothiazol-2-yl)-acetamide (2.5 g, yield 71%) as a white solid.

Step 2: n-[6-(4,4,5,5-tetramethyl-[1,3,2]dioxaborolan-2-yl)-benzothiazol-2-yl]-acetamide

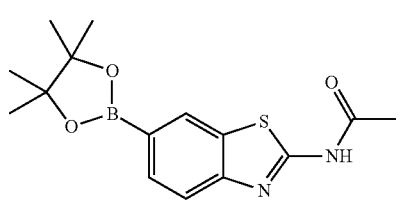 [SMILES: CC(=O)Nc1nc2ccc(B3OC(C)(C)C(C)(C)O3)cc2s1]

A mixture of n-(6-bromo-benzothiazol-2-yl)-acetamide (1.35 g, 5 mmol), 4,4,4',4',5,5,5',5'-octamethyl-2,2'-bi(1,3,2-dioxaborolane) (2.51 g, 10 mmol), Pd(dppf)Cl₂ (0.25 g, 0.3 mmol) and potassium acetate CH₃COOK (2.45 g, 25 mmol) in DMSO (20 mL) was stirred at 80 for 2 hrs under N₂. Then the mixture was cooled to room temperature, added H₂O (100 mL) and extracted with EtOAc (40 mL×3). The combined organic layers were concentrated in vacuo. The residue was purified by column chromatography on silica gel (PE: EtOAc=3:1) to give n-[6-(4,4,5,5-tetramethyl-[1,3,2]dioxaborolan-2-yl)-benzothiazol-2-yl]-acetamide (1.2 g, yield 75%) as a yellow solid.

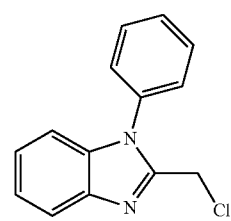 [SMILES: ClCc1nc2ccccc2n1-c1ccccc1]

Step 3

A mixture of n-[6-(4,4,5,5-Tetramethyl-[1,3,2]dioxaborolan-2-yl)-benzothiazol-2-yl]-acetamide (1.0 g, 3.3 mmol), 2-(chloromethyl)-1-phenyl-1H-benzo[d]imidazole (1.4 g, 3.0 mmol), Pd(dppf)Cl₂ (0.5 g) and CsF (0.91 g, 6.0 mmol) in DME (20 mL) and H₂O (2 mL) was refluxed overnight under N₂. Then the mixture was cooled to room temperature, added H₂O (50 mL) and extracted with EtOAc (20 mL×3). The combined organic layers were washed with brine, dried over Na₂SO₄, and concentrated in vacuo. The residue was purified by P-TLC to give 156 (400 mg, yield 25%) as a brown solid.

Example 157

1-((1-phenyl-1H-benzo[d]imidazol-2-yl)methyl)-1H-pyrazolo[3,4-d]pyrimidin-6-amine 157

Step 1: 4-chloro-1H-pyrazolo[3,4-d]pyrimidin-6-ylamine

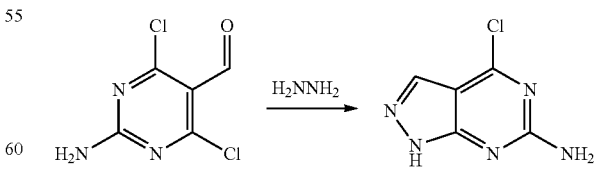

To a mixture of 2-amino-4,6-dichloro-pyrimidine-5-carbaldehyde (1.0 g, 5.2 mmol) and Et₃N (0.63 g, 6.2 mmol) in THF (20 mL) and H₂O (2 mL) was added hydrazine H₂NNH₂ (10 g, 0.2 mol). Then the mixture was stirred at room temperature for 1.5 hrs. Then the mixture was concentrated in vacuo. The residue was added H₂O and filtered to give 4-chloro-1H-pyrazolo[3,4-d]-pyrimidin-6-ylamine (0.8 g, yield 91%) as a yellow solid.

Step 2: 4-chloro-1-(1-phenyl-1H-benzoimidazol-2-ylmethyl)-1H-pyrazolo[3,4-d]pyrimidin-6-ylamine

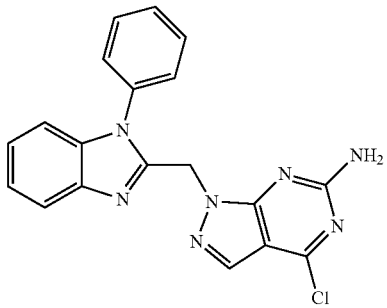 [SMILES: Nc1nc(Cl)c2cnn(Cc3nc4ccccc4n3-c3ccccc3)c2n1]

A mixture of 4-chloro-1H-pyrazolo[3,4-d]pyrimidin-6-ylamine (1.0 g, 5.9 mmol), 2-(chloromethyl)-1-phenyl-1H-benzo[d]imidazole (1.4 g, 5.9 mmol) and K₂CO₃ (0.86 g, 6.2 mmol) in DMSO (20 mL) was stirred at room temperature overnight. Then the mixture was added H₂O (50 mL) and extracted with CH₂Cl₂ (20 mL×3). The combined organic layers were concentrated in vacuo to give 4-chloro-1-(1-phenyl-1H-benzoimidazol-2-ylmethyl)-1H-Pyrazolo[3,4-d]pyrimidin-6-ylamine (1.5 g, yield 68%) as orange solid.

Step 3

A solution of 4-chloro-1-(1-phenyl-1H-benzoimidazol-2-ylmethyl)-1H-Pyrazolo[3,4-d]pyrimidin-6-ylamine (1.5 g, 4 mmol) and Pd/C (0.3 g) in MeOH was stirred with H₂ 40 psi at 50° C. overnight. The mixture was filtered, and the filtrate was concentrated in vacuo. The residue was purified by P-TLC to give 157 (200 mg, yield 15%) as white solid. LCMS (ESI), M+H⁺=340.14. 1HNMR (400 MHz, DMSO) δ 5.0374 (s, 2H), 5.597 (s, 2H), 7.015 (s, 1H), 7.152-7.211 (m, 5H), 7.309-7.327 (m, 3H), 7.746 (s, 2H), 8.567 (s, 1H)

Example 158

(S)-8-methyl-N-(1-(1-phenyl-1H-benzo[d]imidazol-2-yl)ethyl)-9H-purin-6-amine 158

Step 1: 6-chloro-8-methyl-9H-purine

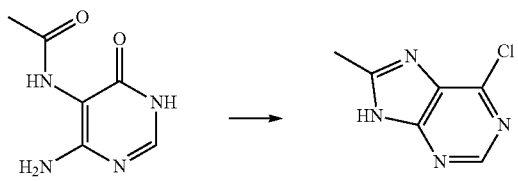

A solution of N-(4-amino-6-oxo-1,6-dihydropyrimidin-5-yl)acetamide (330 mg, 1.92 mmol, 1.00 equiv, 98%) in phosphorus oxychloride (5 mL) was refluxed overnight. The resulting mixture was concentrated under vacuum. The residue was redissolved in 10 mL of ethyl acetate, washed with 10 mL of saturated aqueous sodium bicarbonate solution, 1×10 mL of water and 1×10 mL of brine. The organic layer was dried over anhydrous sodium sulfate and concentrated under vacuum to give 20 mg (6%) of 6-chloro-8-methyl-9H-purine as a yellow solid.

Step 2

A solution of (1S)-1-(1-phenyl-1H-1,3-benzodiazol-2-yl)ethan-1-amine from Example 4 (150 mg, 0.62 mmol, 1.00 equiv, 98%), 6-chloro-8-methyl-9H-purine (150 mg, 0.87 mmol, 1.41 equiv) and ethylbis(propan-2-yl)amine (0.3 mL, 98%) in butan-1-ol (6 mL) was stirred overnight at 130° C. The resulting mixture was concentrated under vacuum. The residue was purified on a C18 column eluted with water/acetonitrile to give 75 mg (30%) of 158 as a white solid. LC-MS (ES, m/z) 370 [M+H]+. H-NMR (300 MHz CD3OD, ppm) δ 8.04 (s, 1H), 7.69 (d, 1H), 7.55 (m, 5H), 7.30 (m, 2H), 7.11 (d, 1H), 5.63 (s, 1H), 2.55 (s, 3H), 1.71 (d, 3H)

Example 159

(S)-1-methyl-N-(1-(1-phenyl-1H-benzo[d]imidazol-2-yl)ethyl)-1H-pyrazolo[4,3-d]pyrimidin-5-amine 159

Step 1: N-(2-chloro-4-methylpyrimidin-5-yl)acetamide

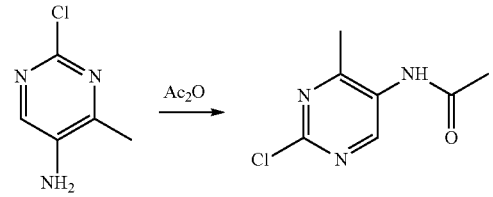

A solution of 2-chloro-4-methylpyrimidin-5-amine (10 g, 68.26 mmol, 1.00 equiv, 98%) and acetic anhydride (14.3 g, 137.27 mmol, 2.01 equiv, 98%) in acetic acid (50 mL) was stirred at room temperature for 2 h. The resulting mixture was concentrated under vacuum to give 11 g (82%) of N-(2-chloro-4-methylpyrimidin-5-yl)acetamide as an off-white solid Step 2: 1-[5-chloro-1H-pyrazolo[4,3-d]pyrimidin-1-yl]ethan-1-one

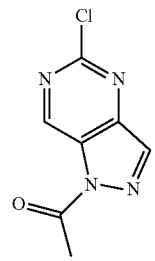

A solution of N-(2-chloro-4-methylpyrimidin-5-yl)acetamide (9 g, 46.06 mmol, 1.00 equiv, 95%), potassium acetate (3.3 g, 32.95 mmol, 0.72 equiv, 98%), acetic anhydride (17.27 g, 165.78 mmol, 3.60 equiv) and isoamyl nitrite (13.6 g, 116.24 mmol, 2.52 equiv, 98%) in chloroform (180 mL) was reflux overnight. The resulting mixture was washed with water, dried over anhydrous sodium sulfate and concentrated under vacuum to give 7 g (73%) of 1-[5-chloro-1H-pyrazolo[4,3-d]pyrimidin-1-yl]ethan-1-one as a white solid.

Step 3: 5-chloro-1H-pyrazolo[4,3-d]pyrimidine

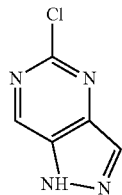

Hydrochloric acid (70 mL, 8%) was added dropwise to a solution of 1-[5-chloro-1H-pyrazolo[4,3-d]pyrimidin-1-yl]ethan-1-one (7 g, 33.83 mmol, 1.00 equiv, 95%) in tetrahydrofuran (70 mL) at 50° C. The resulting solution was refluxed for 30 min and then extracted with 2×100 mL of ethyl acetate. The organic layers were combined, dried over anhydrous sodium sulfate and concentrated under vacuum to give 2.5 g (45%) of 5-chloro-1H-pyrazolo[4,3-d]pyrimidine as a white solid.

Step 4:
5-chloro-1-methyl-1H-pyrazolo[4,3-d]pyrimidine

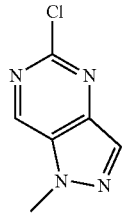

Potassium t-butoxide (1.68 g, 14.67 mmol, 1.14 equiv) was added to a solution of 5-chloro-1H-pyrazolo[4,3-d]pyrimidine (2.1 g, 12.91 mmol, 1.00 equiv, 95%) in tetrahydrofuran (50 mL) at 0° C. After the reaction mixture was stirred at 0° C. for 30 min, iodomethane (3 g, 20.71 mmol, 1.60 equiv, 98%) was added dropwise at 0° C. The resulting solution was stirred for 4.5 h at room temperature and then concentrated under vacuum. The residue was loaded onto a silica gel column and eluted with dichloromethane/ethyl acetate (10/1) to give 300 mg (14%) of 5-chloro-1-methyl-1H-pyrazolo[4,3-d]pyrimidine as a white solid.

Step 5

A solution of (S)-1-(1-phenyl-1H-benzo[d]imidazol-2-yl)ethanamine from Example 4 (200 mg, 0.83 mmol, 1.00 equiv, 98%), 5-chloro-1-methyl-1H-pyrazolo[4,3-d]pyrimidine (180 mg, 1.07 mmol, 1.29 equiv) and methylbis(propan-2-yl)amine (0.3 mL, 98%) in n-butanol (8 mL) was stirred at 130° C. for 96 h. The resulting mixture was concentrated under vacuum and the residue was purified on a C18 column eluted with water/acetonitrile to give 110 mg (31%) of 159 as a light yellow solid. LC-MS: (ES, m/z) 370 [M+H]$^+$, 221, 115.

H-NMR: (CD$_3$OD, 300 Hz, ppm) δ 8.86 (s, 1H), 7.70 (s, 1H), 7.65-7.54 (m, 6H), 7.61 (d, 2H), 7.09 (s, 1H), 5.30 (m, 1H), 4.04 (s, 3H), 1.64 (d, 3H)

Example 160

(S)—N-(1-(6-fluoro-1-phenyl-1H-benzo[d]imidazol-2-yl)propyl)-7H-purin-6-amine 160

A mixture of (S)-1-(6-fluoro-1-phenyl-1H-benzoimidazol-2-yl)propylamine from Example 28 (42 mg, 0.16 mmol), 6-chloro-9-(tetrahydropyran-2-yl)-9H-purine (37 mg, 0.16 mmol) and DIPEA (0.14 mL, 0.8 mmol) in n-butanol (1 mL) was stirred in a sealed vial for 16 h at 90° C. After cooling to RT, the crude reaction mixture was loaded into an Isolute® SCX-2 which was washed with MeOH followed by 2M NH$_3$/MeOH. The basic fractions were combined and concentrated in vacuo. The resulting residue was purified by column chromatography (Si—PCC, gradient 0-10% 2M NH$_3$/MeOH in DCM) affording 160 as a white solid (13 mg, 21%). LCMS: R$_T$ 3.61 min [M+H]$^+$ 388.1. $^1$H NMR (DMSO, 400 MHz): δ 8.22-8.03 (2H, m), 7.80 (1H, s), 7.71-7.43 (6H, m), 7.09 (1H, t, J=9.42 Hz), 6.85 (1H, d, J=8.93 Hz), 5.38 (1H, s), 2.08-1.88 (2H, m), 0.83 (3H, t, J=7.34 Hz)

Example 161

(S)—N-(1-(5-fluoro-1-phenyl-1H-benzo[d]imidazol-2-yl)ethyl)-7H-purin-6-amine 161

A mixture of (S)-1-(5-fluoro-1-phenyl-1H-benzoimidazol-2-yl)ethylamine from Example 29 (379 mg, 1.4 mmol), 6-chloro-9-(tetrahydropyran-2-yl)-9H-purine (340 mg, 1.4 mmol) and DIPEA (1.2 mL, 7.0 mmol) in n-butanol (7 mL) was stirred in a sealed vial for 18 h at 90° C. After cooling to RT, volatiles were removed under reduced pressure and the resulting residue was loaded into an Isolute® SCX-2 which was washed with MeOH followed by 2M NH$_3$/MeOH. The basic fractions were combined and concentrated in vacuo. The resulting residue was purified by column chromatography (Si—PCC, gradient 0-10% 2M NH$_3$/MeOH in DCM) affording 161 (65 mg, 12%). LCMS: R$_T$ 3.34 min [M+H]$^+$ 374.1. $^1$H NMR (DMSO, 400 MHz): δ 8.19-8.00 (2H, m), 7.92 (1H, s), 7.67-7.41 (6H, m), 7.06 (2H, d, J=7.13 Hz), 5.47 (1H, s), 1.56 (3H, d, J=6.83 Hz)

Example 162

9-((3-phenyl-1H-indol-2-yl)methyl)-9H-purin-6-amine 162

A mixture of 9-[3-phenyl-1-(toluene-4-sulfonyl)-1H-indol-2-ylmethyl]-9H-purin-6-ylamine from Example 22 (330 mg, 0.667 mmol) and 2M KOH (1.3 mL) in MeOH (20 mL) was stirred at 70° C. for 5 h. Volatiles were removed under reduced pressure and the resulting residue was diluted with water. The pH of the solution was adjusted to 1 by addition of 1M HCl and then to 8 by addition of a saturated solution of NaHCO$_3$. The aqueous layer was extracted with EtOAc (×3) and the combined organic layers were dried (Na$_2$SO$_4$) and concentrated in vacuo. The resulting residue was purified by column chromatography (Si—PCC, gradient 0-9% MeOH in DCM) affording 162 as a white solid (102 mg, 45%). LCMS: R$_T$ 3.79 min [M+H]$^+$ 341.2. $^1$H NMR (DMSO, 400 MHz): δ 11.31 (1H, s), 8.16 (1H, s), 8.02 (1H, s), 7.64-7.59 (2H, m), 7.57 (1H, d, J=7.96 Hz), 7.50 (2H, t, J=7.96 Hz), 7.43-7.33 (2H, m), 7.24 (2H, s), 7.16 (1H, t, J=7.50 Hz), 7.07 (1H, t, J=7.50 Hz), 5.59 (2H, s)

Example 163

9-((3-phenylbenzofuran-2-yl)methyl)-9H-purin-6-amine 163

To a mixture of NaH (60% in mineral oil, 18 mg, 0.43 mmol) in DMF (5 mL) at 0° C. was added 9H-purin-6-ylamine (54 mg, 0.397 mmol). After 5 min stirring at 0° C., a solution of methanesulfonic acid 3-phenylbenzofuran-2-ylmethyl ester from Example 25 (100 mg, 0.331 mmol) in DMF (1 mL) was added dropwise and the mixture was slowly warmed to RT and stirred at RT for 2.5 h. The reaction mixture was then quenched by addition of water and diluted with DCM. The organic layer was dried ($Na_2SO_4$) and concentrated in vacuo. The resulting residue was purified by column chromatography (Si—PCC, gradient 0-10% MeOH in EtOAc) and triturated form EtOAc with cyclohexane affording 163 as an off-white solid (33 mg, 29%). LCMS: $R_T$ 3.85 min $[M+H]^+$ 342.1. $^1$H NMR (DMSO, 400 MHz): δ 8.21 (1H, s), 8.11 (1H, s), 7.79-7.74 (2H, m), 7.63-7.53 (4H, m), 7.50-7.44 (1H, m), 7.38-7.27 (2H, m), 7.23 (2H, s), 5.65 (2H, s)

Example 164

1-((3-phenylbenzo[b]thiophen-2-yl)methyl)-1H-pyrazolo[3,4-d]pyrimidin-4-amine 164

NaH (60% in mineral oil, 13 mg, 0.314 mmol) was added in one portion to a mixture of 1H-pyrazolo[3,4-d]pyrimidin-4-ylamine (42 mg, 0.314 mmol) in DMF (5 mL) at RT. After 5 min stirring a solution of methanesulfonic acid 3-phenylbenzo[b]thiophen-2-ylmethyl ester from Example 26 (100 mg, 0.314 mmol) in DMF (1 mL) was added dropwise and stirring at RT was continued for 30 min. The reaction mixture was then quenched by addition of water and diluted with EtOAc. The aqueous phase was further extracted with EtOAc (2×100 mL) and the combined organic layers were washed with brine, then dried ($Na_2SO_4$) and concentrated in vacuo. The resulting residue was purified by column chromatography (Si—PCC, gradient 0-10% MeOH in EtOAc) and triturated from MeOH with water affording 164 as an off-white solid (17 mg, 15%). LCMS: $R_T$ 4.13 min $[M+H]^+$ 358.1. $^1$H NMR (DMSO, 400 MHz): δ 8.23 (1H, s), 8.16 (1H, s), 7.95-7.90 (1H, m), 7.70-7.59 (4H, m), 7.56-7.49 (2H, m), 7.42-7.35 (2H, m), 5.72 (2H, s)

Example 165

N-((3-phenylbenzo[b]thiophen-2-yl)methyl)-9H-purin-6-amine 165

A mixture of C-(3-phenylbenzo[b]thiophen-2-yl)methylamine from Example 26 (230 mg, 0.961 mmol), 6-chloro-9H-purine (278 mg, 1.80 mmol) and DIPEA (0.34 mL, 1.92 mmol) in n-butanol (10 mL) was heated at 100° C. for 20 h. After cooling to RT, volatiles were removed under reduced pressure and the resulting residue was purified by column chromatography (Si—PCC, gradient 0-10% MeOH in DCM) and then sonicated in diethyl ether. Further purification by column chromatography (Si—PCC, gradient 0-5% MeOH in DCM) afforded 165 as a white solid (132 mg, 38%). LCMS: $R_T$ 4.22 min $[M+H]^+$ 358.1. $^1$H NMR (DMSO, 400 MHz): δ 12.96 (1H, s), 8.40 (1H, s), 8.23 (1H, s), 8.14 (1H, s), 7.94-7.85 (1H, m), 7.63-7.54 (4H, m), 7.51-7.43 (2H, m), 7.38-7.29 (2H, m), 4.94 (2H, s)

Example 166

9-((3-phenylbenzo[b]thiophen-2-yl)methyl)-9H-purin-6-amine 166

NaH (60% in mineral oil, 15 mg, 0.377 mmol) was added in one portion to a mixture of 9H-purin-6-ylamine (47 mg, 0.345 mmol) in DMF (3 mL) at RT. After 5 min stirring, a solution of methanesulfonic acid 3-phenylbenzo[b]thiophen-2-ylmethyl ester from Example 26 (100 mg, 0.314 mmol) in DMF (2 mL) was added dropwise and stirring at RT was continued for 30 min. The reaction mixture was then quenched by addition of water and a solid formed. The precipitated was collected by filtration and was purified by column chromatography (Si—PCC, gradient 0-10% MeOH in EtOAc) and triturated from diethyl ether affording 166 as a white solid (52 mg, 46%). LCMS: $R_T$ 3.99 min $[M+H]^+$ 358.1. $^1$H NMR (DMSO, 400 MHz): δ 8.15 (1H, s), 8.06 (1H, s), 7.98-7.92 (1H, m), 7.64-7.59 (4H, m), 7.57-7.46 (2H, m), 7.42-7.37 (2H, m), 7.27 (2H, s), 5.63 (2H, s)

Example 167

9-((3-o-tolylbenzo[b]thiophen-2-yl)methyl)-9H-purin-6-amine 167

NaH (60% in mineral oil, 16 mg, 0.39 mmol) was added in one portion to a mixture of 9H-purin-6-ylamine (49 mg, 0.36 mmol) in DMF (5 mL) at RT. After 5 min stirring, a solution of methanesulfonic acid 3-o-tolylbenzo[b]thiophen-2-ylmethyl ester from Example 27 (100 mg, 0.30 mmol) in DMF (1 mL) was added dropwise and stirring at RT was continued for 19 h. The reaction mixture was then quenched by addition of water and a solid formed. The precipitated was collected by filtration and was purified by column chromatography (Si—PCC, gradient 0-10% MeOH in EtOAc) affording 167 as a white solid (75 mg, 67%). LCMS: $R_T$ 4.13 min $[M+H]^+$ 372.1. $^1$H NMR (DMSO, 400 MHz): δ 8.11 (1H, s), 7.96-7.88 (2H, m), 7.45-7.30 (6H, m), 7.23 (2H, s), 7.12-7.07 (1H, m), 5.46 (1H, d, J=16.2 Hz), 5.38 (1H, d, J=16.2 Hz), 1.99 (3H, s)

Example 168

(9H-Purin-6-yl)-[1-(3-o-tolyl-3H-imidazo[4,5-b]pyridin-2-yl)-ethyl]-amine 168

A mixture of (S)-1-(3-o-tolyl-3H-imidazo[4,5-b]pyridin-2-yl)ethylamine (330 mg, 1.31 mmol), 6-chloro-9-(tetrahydropyran-2-yl)-9H-purine (430 mg, 1.83 mmol) and DIPEA (0.41 mL, 2.35 mmol) in n-butanol (2 mL) was heated at 90° C. in a sealed vial for 16 h. After cooling to RT, the crude reaction mixture was loaded onto an Isolute® SCX-2 cartridge and washed with MeOH followed by 2M $NH_3$/MeOH. The product containing fractions were combined and concentrated in vacuo. The resulting residue was purified by column chromatography (Si—PCC, gradient 0-10% 2M $NH_3$/MeOH in DCM) to afford 168 as a white solid (155 mg, 32%). LCMS (Method K): $R_T$ 2.70 and 2.83 min $[M+H]^+$ 371.1. $^1$H NMR (DMSO-$d_6$, 400 MHz): δ 12.89 (1H, s), 8.30-7.86 (4H, m), 7.69-7.08 (5H, m), 5.47 (1H, s), 1.96 (3H, s), 1.68 (1.5H, d, J=6.77 Hz), 1.50 (1.5H, d, J=6.84 Hz). Signals split due to presence of rotamers/tautomers.

Example 169

[(S)-1-(3-Phenyl-3H-imidazo [4,5-b]pyridin-2-yl)-propyl]-(9H-purin-6-yl)-amine 169

A mixture of (S)-1-(3-phenyl-3H-imidazo[4,5-b]pyridin-2-yl)propylamine (430 mg, 1.70 mmol), 6-chloro-9-(tetrahydropyran-2-yl)-9H-purine (560 mg, 2.39 mmol) and DIPEA (0.54 mL, 3.07 mmol) in n-butanol (3 mL) was heated at 90° C. in a sealed vial for 16 h. After cooling to RT, the crude reaction mixture was loaded onto an Isolute® SCX-2 cartridge and washed with MeOH followed by 2M NH$_3$/MeOH. The basic fractions were combined and concentrated in vacuo. The resulting residue was purified by column chromatography (Si—PCC, gradient 0-8% 2M NH$_3$/MeOH in DCM) to afford 169 as a white solid (136 mg, 22%). LCMS (Method K): R$_T$ 2.89 min [M+H]$^+$ 371.1. $^1$H NMR (DMSO-d$_6$, 400 MHz): δ 12.91 (1H, s), 8.30-7.70 (5H, m), 7.68-7.21 (6H, m), 5.42 (1H, s), 2.01 (2H, bs), 1.01-0.71 (3H, m).

Example 170

3-{2-[(S)-1-(9H-Purin-6-ylamino)-ethyl]-benzoimidazol-1-yl}-benzonitrile 170

A mixture of 3-[2-((S)-1-aminoethyl)benzoimidazol-1-yl] benzonitrile (54 mg, 0.21 mmol), 6-chloro-9-(tetrahydropyran-2-yl)-9H-purine (69 mg, 0.29 mmol) and DIPEA (65 mL, 0.37 mmol) in n-butanol (0.5 mL) was heated at 90° C. in a sealed vial for 16 h. After cooling to RT, the crude reaction mixture was loaded onto an Isolute® SCX-2 cartridge and washed with MeOH followed by 2M NH$_3$/MeOH. The basic fractions were combined and concentrated in vacuo. The resulting residue was purified by column chromatography (Si—PCC, gradient 0-10% 2M NH$_3$/MeOH in DCM) then by preparative HPLC (Phenomenex Gemini 5 μm C18 on a gradient 20-98%, 0.1% HCO$_2$H in acetonitrile/water) to afford 170 as a white solid (29 mg, 37%). LCMS (Method K): R$_T$ 3.03 min [M+H]$^+$ 381.0. $^1$H NMR (DMSO-d$_6$, 400 MHz): δ 12.90 (1H, s), 8.25-7.49 (8H, m), 7.32-7.17 (2H, m), 7.09 (1H, d, J=7.84 Hz), 5.60 (1H, s), 1.64 (3H, d, J=6.81 Hz)

Example 171

[1-(6-Fluoro-1-phenyl-1H-benzoimidazol-2-yl)-2-methoxy-ethyl]-(7H-purin-6-yl)-amine 171

A mixture of (R)-1-(6-fluoro-1-phenyl-1H-benzoimidazol-2-yl)-2-methoxyethylamine (110 mg, 0.39 mmol), 6-chloro-9-(tetrahydropyran-2-yl)-9H-purine (93 mg, 0.39 mmol) and DIPEA (340 mL, 1.9 mmol) in n-butanol (2.5 mL) was heated at 90° C. in a sealed vial for 18 h. After cooling to RT, the volatiles were removed under reduced pressure and the resulting residue was loaded onto an Isolute® SCX-2 cartridge and washed with MeOH followed by 2M NH$_3$/MeOH. The product containing fractions were combined and concentrated in vacuo. The resulting residue was purified by column chromatography (Si—PCC, gradient 0-10% 2M NH$_3$/MeOH in DCM) to afford 171 as a white solid (51 mg, 32%). LCMS (Method B): R$_T$ 3.52 min [M+H]$^+$ 404.0. $^1$H NMR (DMSO-d$_6$, 400 MHz): δ 8.25-8.01 (2H, m), 7.87 (1H, s), 7.77-7.47 (6H, m), 7.15-7.05 (1H, m), 6.87 (1H, dd, J=8.93, 2.37 Hz), 5.64 (1H, s), 3.84 (2H, d, J=6.60 Hz), 3.14 (3H, s). Signals split due to presence of rotamers/tautomers

Example 172

2-(6-Fluoro-1-phenyl-1H-benzoimidazol-2-yl)-2-(7H-purin-6-ylamino)-ethanol 172

To a solution of [(R)-2-benzyloxy-1-(6-fluoro-1-phenyl-1H-benzoimidazol-2-yl)ethyl]-(7H-purin-6-yl)amine (124 mg, 0.26 mmol) in anhydrous DCM (3 mL) at 0° C. under a nitrogen atmosphere was added boron tribromide (1.0M in DCM, 0.3 mL, 0.26 mmol) dropwise. The reaction mixture was slowly warmed to RT and stirred at RT for 1 h. Additional BBr$_3$ (0.3 mL) was added and stirring continued for 1 h. MeOH was added then the volatiles removed under reduced pressure. The resulting residue was purified by column chromatography (Si—PCC, gradient 0-10% 2M NH$_3$/MeOH in DCM) to afford 172 (60 mg, 59%). LCMS (Method K): R$_T$ 3.11 min [M+H]$^+$ 390.0. $^1$H NMR (DMSO-d$_6$, 400 MHz): δ 12.93 (0.8H, s), 12.17 (0.2H, s), 8.27-8.01 (2H, m), 7.74-7.43 (6H, m), 7.16-7.01 (1H, m), 6.93-6.79 (1H, m), 5.56-5.31 (1H, m), 5.21-5.02 (1H, m), 3.95-3.74 (2H, m). Signals split due to presence of rotamers/tautomers

Example 173

[(S)-1-(6-Chloro-1-phenyl-1H-benzoimidazol-2-yl)-ethyl]-(9H-Aurin-6-yl)-amine 173

A mixture of (S)-1-(6-chloro-1-phenyl-1H-benzoimidazol-2-yl)ethylamine (796 mg, 2.93 mmol), 6-chloro-9-(tetrahydropyran-2-yl)-9H-purine (769 mg, 3.22 mmol) and DIPEA (1.50 mL, 8.79 mmol) in n-butanol (6 mL) was heated at 100° C. in a sealed vial for 17 h. After cooling to RT, the volatiles were removed under reduced pressure and the resulting residue was loaded onto an Isolute® SCX-2 cartridge and washed with MeOH followed by 2M NH$_3$/MeOH. The basic fractions were combined and concentrated in vacuo. The resulting residue was triturated from hot MeOH to afford 173 as an off-white solid (334 mg, 29%). LCMS (Method K): R$_T$ 3.73 min [M+H]$^+$ 390.0. $^1$H NMR (DMSO-d$_6$, 400 MHz): δ 12.85 (1H, s), 8.18-8.04 (2H, m), 7.94 (1H, s), 7.71-7.45 (6H, m), 7.26 (1H, dd, J=8.57, 2.01 Hz), 7.05 (1H, d, J=1.97 Hz), 5.48 (1H, s), 1.56 (3H, d, J=6.84 Hz)

Example 174

4-{6-Fluoro-2-[(S)-1-(9H-purin-6-ylamino)-ethyl]-benzoimidazol-1-yl}-cyclohexanecarbonitrile 174

A mixture of 4-[2-((S)-1-aminoethyl)-6-fluorobenzoimidazol-1-yl]cyclohexanecarbonitrile (100 mg, 0.35 mmol), 6-chloro-9-(tetrahydropyran-2-yl)-9H-purine (91 mg, 0.38 mmol) and DIPEA (0.10 mL, 0.72 mmol) in n-butanol (0.7 mL) was heated for 48 h at 105° C. After cooling to RT, the crude reaction mixture was treated with 4N HCl in dioxane (0.5 mL) and stirred for 1 h at RT. The crude mixture was loaded onto an Isolute® SCX-2 cartridge and washed with MeOH followed by 2M NH$_3$/MeOH. The basic fractions were combined, concentrated in vacuo and the resulting residue purified by column chromatography (Si—PCC, gradient 0-8% MeOH in DCM), then triturated with hot EtOAc and purified by preparative HPLC (Phenomenex Gemini 5 μm C18 on a gradient 0-40%, 0.1% HCO$_2$H in acetonitrile/water) to afford 174 as a white solid (26 mg, 18%). LCMS (Method K): R$_T$ 2.93 min [M+H]$^+$ 405.1. $^1$H NMR (DMSO-d$_6$, 400 MHz): δ 12.45 (1H, s), 8.34-7.94 (3H, m), 7.71-7.56 (2H, m), 7.05-6.96 (1H, m), 5.96 (1H, bs), 4.62-4.59 (1H, m), 3.09-2.95 (1H, m), 2.38-2.25 (1H, m), 2.21-2.07 (2H, m), 1.93 (1H, bd, J=12.75 Hz), 1.84 (1H, bd, J=12.00 Hz), 1.73-1.65 (5H, m), 1.02 (1H, bs). Broad signals due to presence of rotamers/tautomers Example 175

(1R,2R)-1-(6-Fluoro-1-phenyl-1H-benzoimidazol-2-yl)-1-(7H-Aurin-6-ylamino)-propan-2-ol 175

To a solution of [(1R,2R)-2-benzyloxy-1-(6-fluoro-1-phenyl-1H-benzoimidazol-2-yl)propyl]-(7H-purin-6-yl)amine (128 mg, 0.26 mmol) in anhydrous DCM (3 mL) at 0° C. under a nitrogen atmosphere was added boron tribromide (1.0M in DCM, 0.5 mL, 0.5 mmol) dropwise. The reaction mixture was slowly warmed to RT and stirred at RT was 1.5 h. MeOH was added and the volatiles were removed under reduced pressure. The resulting residue was purified by column chromatography (Si—PCC, gradient 0-10% 2M $NH_3$/MeOH in DCM) to afford 175 (25 mg, 24%). LCMS (Method K): $R_T$ 3.30 min [M+H]$^+$ 404.1. $^1$H NMR (DMSO-$d_6$, 400 MHz): δ 12.99 (1H, s), 8.32-8.06 (2H, m), 7.83-7.48 (6H, m), 7.28-7.03 (2H, m), 6.88 (1H, dd, J=8.94, 2.49 Hz), 5.18 (1H, s), 4.20-4.02 (2H, m), 1.08-0.93 (3H, m). Signals split due to presence of rotamers/tautomers Example 176

[1-(6-Fluoro-1-pyridin-3-yl-1H-benzoimidazol-2-yl)-ethyl]-(9H-purin-6-yl)-amine 176

A mixture of (S)-1-(6-fluoro-1-pyridin-3-yl-1H-benzoimidazol-2-yl)ethylamine (81 mg, 0.32 mmol), 6-chloro-9-(tetrahydropyran-2-yl)-9H-purine (83 mg, 0.35 mmol) and DIPEA (162 μL, 0.95 mmol) in n-butanol (1 mL) was heated at 90° C. in a sealed vial for 65 h. After cooling to RT, the volatiles were removed under reduced pressure and the resulting residue was loaded onto an Isolute® SCX-2 cartridge which and with MeOH followed by 2M $NH_3$/MeOH (purification by SCX cartridge repeated three times). The product containing fractions were combined and concentrated in vacuo. The resulting residue was purified by column chromatography (Si—PCC, gradient 0-10% MeOH in DCM) and then triturated with MeOH to afford 176 as an off-white solid (47 mg, 40%). LCMS (Method K): $R_T$ 2.75 min [M+H]$^+$ 375.0. $^1$H NMR (DMSO-$d_6$, 400 MHz): δ 12.65 (1H, s), 8.79 (1H, d, J=2.46 Hz), 8.61 (1H, s), 8.15-7.91 (4H, m), 7.71 (1H, dd, J=8.80, 4.84 Hz), 7.55-7.46 (1H, m), 7.11 (1H, td, J=9.33, 2.43 Hz), 6.93 (1H, dd, J=8.91, 2.44 Hz), 5.49 (1H, s), 1.62 (3H, d, J=6.83 Hz)

Example 177

(9H-Purin-6-yl)-[(S)-1-(3-m-tolyl-3H-imidazo[4,5-b]pyridin-2-yl)-ethyl]-amine 177

A mixture of (S)-1-(3-m-tolyl-3H-imidazo[4,5-b]pyridin-2-yl)ethylamine (420 mg, 1.66 mmol), 6-chloro-9-(tetrahydropyran-2-yl)-9H-purine (550 mg, 2.33 mmol) and DIPEA (0.52 mL, 3.00 mmol) in n-butanol (3 mL) was heated at 90° C. in a sealed vial for 16 h. After cooling to RT, the crude reaction mixture was loaded onto an Isolute® SCX-2 cartridge and washed with MeOH followed by 2M $NH_3$/MeOH. The basic fractions were combined and concentrated in vacuo. The resulting residue was purified by column chromatography (Si—PCC, gradient 0-10% 2M $NH_3$/MeOH in DCM) to afford 177 as a white solid (190 mg, 31%). LCMS (Method K): $R_T$ 2.84 min [M+H]$^+$ 371.0. $^1$H NMR (DMSO-$d_6$, 400 MHz): δ 12.90 (1H, s), 8.33-7.77 (5H, m), 7.45-7.14 (5H, m), 5.56 (1H, br), 2.25 (3H, s), 1.58 (3H, d, J=6.81 Hz). Broad signals due to presence of rotamers/tautomers Example 178

[(S)-1-(7-Bromo-6-fluoro-1-phenyl-1H-benzoimidazol-2-yl)-ethyl]-(9H-purin-6-yl)-amine 178

4N HCl in dioxane (0.5 mL) was added to a solution of [(S)-1-(7-bromo-6-fluoro-1-phenyl-1H-benzoimidazol-2-yl)ethyl]-[9-(tetrahydropyran-2-yl)-9H-purin-6-yl]amine (128 mg, 0.24 mmol) in MeOH (3 mL) and the mixture stirred at RT for 30 min. The volatiles were removed in vacuo and the resulting residue purified by HPLC (Phenomenex Gemini 5 μm C18 on a 25 min gradient 10-90% 0.1% $HCO_2H$ in acetonitrile/water) to afford 178 (88 mg, 81%). LCMS (Method K): $R_T$ 3.82 min [M+H]$^+$ 451.9/453.8. $^1$H NMR (DMSO-$d_6$, 400 MHz): δ 8.19-7.86 (3H, m), 7.70 (1H, dd, J=8.75, 4.59 Hz), 7.64-7.33 (5H, m), 7.26 (1H, t, J=9.22 Hz), 5.22 (1H, s), 1.56 (3H, d, J=6.87 Hz)

Example 179

[1-(7-Chloro-6-fluoro-1-phenyl-1H-benzoimidazol-2-yl)-ethyl]-(9H-purin-6-yl)-amine 179

4N HCl in dioxane (0.5 mL) was added to a solution of [(S)-1-(7-chloro-6-fluoro-1-phenyl-1H-benzoimidazol-2-yl)ethyl]-[9-(tetrahydropyran-2-yl)-9H-purin-6-yl]amine (166 mg, 0.34 mmol) in MeOH (5 mL) and the mixture was stirred at RT for 1 h. The volatiles were removed in vacuo and the resulting residue was purified by HPLC (Phenomenex Gemini 5 μm C18 on a 25 min gradient 10-90%, 0.1% $HCO_2H$ in acetonitrile/water) to afford 179 (96 mg, 69%). LCMS (Method K): $R_T$ 3.80 min [M+H]$^+$ 408.0/409.9/411.08. $^1$H NMR (DMSO-$d_6$, 400 MHz): δ 8.22-7.83 (3H, m), 7.69-7.34 (6H, m), 7.33-7.24 (1H, t, J=9.50 Hz), 5.25 (1H, s), 1.56 (3H, d, J=6.88 Hz)

Example 181

[(S)-1-(6-Fluoro-1-phenyl-1H-benzoimidazol-2-yl)-ethyl]-methyl-(9H-purin-6-yl)-amine 181

A mixture of [(S)-1-(6-fluoro-1-phenyl-1H-benzoimidazol-2-yl)ethyl]methylamine (102 mg, 0.38 mmol), 6-chloro-9-(tetrahydropyran-2-yl)-9H-purine (91 mg, 0.38 mmol) and DIPEA (0.33 mL, 1.9 mmol) in n-butanol (2 mL) was heated at 90° C. for 18 h in a sealed vial. After cooling to RT, the volatiles were removed under reduced pressure and the resulting residue loaded onto an Isolute® SCX-2 cartridge. The cartridge was washed with MeOH followed by 2M $NH_3$/MeOH. The basic fractions were combined, concentrated in vacuo and the resulting residue purified by column chromatography (Si—PCC, gradient 0-10% 2M $NH_3$/MeOH in DCM) to afford 181 (123 mg, 84%). LCMS (Method K): $R_T$ 3.39 min [M+H]$^+$ 388.1. $^1$H NMR (DMSO-$d_6$, 400 MHz, 80° C.): δ 7.99 (1H, s), 7.90 (1H, s), 7.75 (1H, dd, J=8.81, 4.87 Hz), 7.30-7.22 (2H, m), 7.17-6.95 (5H, m), 6.73 (1H, dd, J=8.93, 2.53 Hz), 3.12 (3H, br s), 1.71 (3H, d, J=6.76 Hz)

Example 182

[1-(6-Fluoro-1-pyridin-2-yl-1H-benzoimidazol-2-yl)-ethyl]-(9H-purin-6-yl)-amine 182

A mixture of (S)—N-[4-fluoro-2-(pyridin-2-ylamino)phenyl]-2-(9H-purin-6-ylamino)propionamide (130 mg, 0.332 mmol) in AcOH (1 mL) was heated for 2 h at 80° C. A second portion of (S)—N-[4-fluoro-2-(pyridin-2-ylamino)phenyl]-2-(9H-purin-6-ylamino)propionamide (136 mg, 0.347 mmol) in AcOH (5 mL) was heated for 2 h at 100° C. The two crude reaction mixtures were combined and the volatiles removed in vacuo. The resulting residue was partitioned between EtOAc and a saturated aqueous solution of NaHCO$_3$. The organic layer was washed with water, followed by brine, then dried (Na$_2$SO$_4$) and concentrated in vacuo. The resulting residue was purified by column chromatography (Si—PCC, gradient 0-10% MeOH in DCM) then triturated in MeOH/diethyl ether to afford 182 as an off-white solid (66 mg, 26%). LCMS (Method K): R$_T$ 2.94 min [M+H]$^+$ 375.0. $^1$H NMR (DMSO-d$_6$, 400 MHz): δ 12.89 (1H, br s), 8.61 (1H, br s), 8.20-7.80 (4H, m), 7.79-7.67 (2H, m), 7.52-7.43 (1H, m), 7.20-7.08 (2H, m), 5.86 (1H, br s), 1.63 (3H, d, J=6.82 Hz)

Example 183

[(S)-1-(6-Fluoro-7-methyl-1-phenyl-1H-benzoimidazol-2-yl)-ethyl]-(9H-purin-6-yl)-amine 183

A mixture of (S)-1-(6-fluoro-7-methyl-1-phenyl-1H-benzoimidazol-2-yl)ethylamine dihydrochloride (330 mg, 1.23 mmol), 6-chloro-9-(tetrahydropyran-2-yl)-9H-purine (351 mg, 1.47 mmol) and DIPEA (320 µL, 2.45 mmol) in n-butanol (6 mL) was heated at 90° C. in a sealed vial for 18 h. After cooling to RT, the volatiles were removed under reduced pressure and the resulting residue purified by column chromatography (Si—PCC, gradient 0-10% MeOH in EtOAc). A solution of the compound thus obtained in MeOH (5 mL) and 4N HCl in dioxane (1 ml) was stirred at RT for 1 h then the volatiles were removed under reduced pressure. The resulting residue was partitioned between EtOAc and a saturated solution of NaHCO$_3$. A white solid precipitated and was collected by filtration to afford 183 (333 mg, 70%). LCMS (Method K): R$_T$ 3.46 min [M+H]$^+$ 388.1. $^1$H NMR (DMSO-d$_6$, 400 MHz): δ 12.55 (1H, s), 8.06-8.00 (2H, m), 7.71-7.39 (7H, m), 7.05 (1H, dd, J=10.58, 8.77 Hz), 5.30 (1H, br s), 1.70 (3H, d, J=1.84 Hz), 1.53 (3H, d, J=6.84 Hz)

Example 185

{(S)-1-[6-Fluoro-1-(3-fluoro-phenyl)-1H-benzoimidazol-2-yl]-ethyl}-(9H-purin-6-yl)-amine 185

(S)-1-[6-Fluoro-1-(3-fluorophenyl)-1H-benzoimidazol-2-yl]ethylamine (0.45 g, 1.64 mmol) was dissolved in n-butanol (10 mL) and 6-chloro-9-(tetrahydropyran-2-yl)-9H-purine (0.39 g, 1.64 mmol) and DIPEA (1.45 mL, 8.24 mmol) were added. The reaction mixture was heated at 90° C. overnight. The resultant mixture was allowed to cool to RT and was concentrated in vacuo. The residue was passed down an Isolute® SCX-2 cartridge, eluting with DCM, MeOH and 2M NH$_3$ in MeOH to afford crude product. This material was purified by column chromatography (silica gel, gradient 0-7.5% MeOH in DCM) to afford 185 as an off-white solid (100 mg, 20%). LCMS (Method K): R$_T$ 3.52 min [M+H]$^+$ 392.0 $^1$H NMR (DMSO-d$_6$, 400 MHz): δ 8.09 (1H, s), 8.05 (1H, s), 7.91 (1H, s), 7.68 (1H, dd, J=8.80, 4.85 Hz), 7.58-7.47 (2H, m), 7.42 (1H, d, J=7.91 Hz), 7.32-7.23 (1H, m), 7.09 (1H, td, J=9.32, 2.48 Hz), 6.92 (1H, dd, J=8.93, 2.50 Hz), 5.63-5.47 (1H, m), 1.58 (3H, d, J=6.82 Hz)

Example 186

{1-[6-Fluoro-1-(4-fluoro-phenyl)-1H-benzoimidazol-2-yl]-ethyl}-(9H-purin-6-yl)-amine 186

(S)-1-[6-Fluoro-1-(4-fluorophenyl)-1H-benzoimidazol-2-yl]ethylamine (0.33 g, 1.21 mmol) was dissolved in n-butanol (10 mL) and 6-chloro-9-(tetrahydropyran-2-yl)-9H-purine (0.29 g, 1.21 mmol) and DIPEA (1.05 mL, 6.04 mmol) were added. The reaction mixture was heated to 100° C. overnight. A further quantity of DIPEA (0.53 mL, 3.02 mmol) was added and the reaction mixture heated at 100° C. for 2 h. The resultant mixture was allowed to cool to RT then concentrated in vacuo. The residue was passed down an Isolute® SCX-2 cartridge, eluting with DCM, MeOH and then 2M NH$_3$ in MeOH solution to afford a yellow gum. This was purified by column chromatography (silica gel, gradient 0-10% MeOH in DCM) to afford 186 as an off-white solid (0.13 g, 32%). LCMS (Method K): R$_T$ 3.50 min [M+H]$^+$ 392.1 $^1$H NMR (DMSO-d$_6$, 400 MHz): δ 8.11 (1H, s), 8.07 (1H, s), 7.92 (1H, s), 7.71-7.62 (3H, m), 7.38-7.28 (2H, m), 7.13-7.06 (1H, m), 6.87 (1H, dd, J=8.92, 2.50 Hz), 5.49 (1H, s), 1.58 (3H, d, J=6.85 Hz)

Example 187

(S)-3-(6-Fluoro-1-phenyl-1H-benzoimidazol-2-yl)-3-(9H-purin-6-ylamino)-propan-1-ol 187

To a solution of [(S)-3-benzyloxy-1-(6-fluoro-1-phenyl-1H-benzoimidazol-2-yl)propyl]-(9H-purin-6-yl)amine (296 mg, 0.6 mmol) in anhydrous DCM (6 mL) at 0° C. under a nitrogen atmosphere was added dropwise boron tribromide (1.0 M in DCM, 1.2 mL, 1.2 mmol). The reaction mixture was stirred at 0° C. for 1 h. MeOH was then added and the volatiles were removed under reduced pressure. The resulting residue was purified by column chromatography (Si—PCC, gradient 0-10% 2M NH$_3$/MeOH in DCM) to afford 187 (160 mg, 66%). LCMS (Method K): R$_T$ 3.10 min [M+H]$^+$ 404.1 $^1$H NMR (DMSO-d$_6$, 400 MHz): δ 12.55 (1H, s), 8.28-7.83 (3H, m), 7.81-7.44 (6H, m), 7.16-7.01 (1 m), 6.91-6.79 (1H, m), 5.56 (1H, br s), 4.60 (1H, br s), 3.57-3.38 (2H, m), 2.23-2.00 (2H, m). Signals split due to presence of rotamers/tautomers Example 188

[(R)-1-(6-Fluoro-7-methyl-1-phenyl-1H-benzoimidazol-2-yl)-2-methoxy-ethyl]-(9H-purin-6-yl)-amine 188

A mixture of (R)-1-(6-fluoro-7-methyl-1-phenyl-1H-benzoimidazol-2-yl)-2-methoxyethylamine (270 mg, 0.9 mmol), 6-chloro-9-(tetrahydropyran-2-yl)-9H-purine (258 mg, 1.08 mmol) and DIPEA (308 µL, 1.8 mmol) in n-butanol (5 mL) was heated at 90° C. in a sealed vial for 18 h. After cooling to RT, the volatiles were removed under reduced pressure and the resulting residue purified by column chromatography (Si—PCC, gradient 0-10% MeOH in EtOAc) to afford [(R)-1-(6-fluoro-7-methyl-1-phenyl-1H-benzoimidazol-2-yl)-2-methoxyethyl]-[9-(tetrahydropyran-2-yl)-9H-purin-6-yl]amine: LCMS (Method C): R$_T$ 3.38 min [M+H]$^+$ 502.2.

A solution of the compound thus obtained in MeOH (5 mL) and 4N HCl in dioxane (2 ml) was stirred at RT for 30 min and then the volatiles were removed under reduced pressure. The resulting residue was partitioned between EtOAc and a saturated solution of NaHCO$_3$. The aqueous phase was further extracted with EtOAc and the combined organic fractions were washed with brine, dried (MgSO$_4$) and concentrated in vacuo. The resulting residue was purified by column chromatography (Si—PCC, gradient 0-10% MeOH in EtOAc) then triturated with hot EtOAc to afford 188 (183 mg, 49% over two steps). LCMS (Method K): R$_T$ 3.64 min [M+H]$^+$ 418.1. $^1$H NMR (DMSO-d$_6$, 400 MHz): δ 12.50 (1H, s), 8.27-8.01 (2H, m), 7.92-7.36 (7H, m), 7.07 (1H, dd, J=10.56, 8.79 Hz), 5.44 (1H, br s), 3.83 (2H, d, J=6.49 Hz), 3.16 (3H, s), 1.71 (3H, s)

Example 189

5-Fluoro-3-phenyl-2-[1-(9H-purin-6-ylamino)-ethyl]-3H-benzoimidazole-4-carbonitrile 189

A mixture of 3-amino-6-fluoro-2-phenylaminobenzonitrile (960 mg, 4.22 mmol), (S)-2-tertbutoxycarbonylaminopropionic acid (879 mg, 4.6 mmol), HOAt (633 mg, 4.6 mmol), 4-methylmorpholine (1.02 mL, 9.29 mmol) and N-(3-dimethylaminopropyl)-N'-ethylcarbodiimide hydrochloride (892 mg, 4.6 mmol) in DCM (5 mL) was stirred at RT for 1 h. The reaction mixture was diluted with water and extracted with DCM (×3). The combined organic fractions were washed with brine, then dried (MgSO$_4$) and concentrated in vacuo. A solution of the resulting residue in AcOH (5 mL) was heated at 70° C. for 18 h and then concentrated under reduced pressure. The resulting residue was partitioned between EtOAc and a saturated aqueous solution of NaHCO$_3$. The aqueous phase was extracted with EtOAc (×3) and the combined organic fractions were washed with brine, dried (MgSO$_4$) and concentrated in vacuo. The resulting residue was dissolved in 4N HCl in dioxane (5 mL) and stirred at RT for 1 h. The volatiles were removed under reduced pressure to afford 2-((S)-1-aminoethyl)-5-fluoro-3-phenyl-3H-benzoimidazole-4-carbonitrile hydrochloride as a brown solid which was used in the following step without further purification.

A portion of the compound thus obtained (250 mg, 0.89 mmol) was treated with 6-chloro-9-(tetrahydropyran-2-yl)-9H-purine (255 mg, 1.07 mmol) and DIPEA (609 μL, 3.57 mmol) in n-butanol (5 mL) and heated at 90° C. in a sealed vial for 18 h. After cooling to RT, the volatiles were removed under reduced pressure and the resulting residue purified by column chromatography (Si—PCC, gradient 0-10% MeOH in EtOAc). The relevant fractions were combined and concentrated under reduced pressure. The resulting residue was dissolved in MeOH (5 mL) and treated with 4N HCl in dioxane (1 mL). The reaction mixture was stirred at RT for 1 h then the volatiles were removed under reduced pressure. The resulting residue was purified by reverse phase HPLC (Phenomenex Gemini 5 μm C18 on a 20 min gradient 10-90%, 0.1% HCO$_2$H in acetonitrile/water) to afford 189 (58 mg, 16%). LCMS (Method K): R$_T$ 3.30 min [M+H]$^+$ 399.0. $^1$H NMR (DMSO-d$_6$, 400 MHz): δ 12.88 (1H, br s), 8.18-7.80 (4H, m), 7.72-7.39 (5H, m), 7.36 (1H, t, J=9.62 Hz), 5.31 (1H, br s), 1.58 (3H, d, J=6.89 Hz)

Example 190

[1-(6,7-Difluoro-1-phenyl-1H-benzoimidazol-2-yl)-2-methoxy-ethyl]-(9H-purin-6-yl)-amine 190

To a solution of [(R)-1-(6,7-difluoro-1-phenyl-1H-benzoimidazol-2-yl)-2-methoxyethyl]-[9-(tetrahydro-pyran-2-yl)-9H-purin-6-yl]amine (290 mg, 0.57 mmol) in methanol (5 mL) was added HCl in dioxane (0.5 mL, 4M) and the reaction stirred at RT for 30 min. The reaction mixture was concentrated in vacuo and the resultant residue dissolved in EtOAc (10 mL). The solution was washed with sat. aq. NaHCO$_3$ and the product extracted with EtOAc (3×10 mL). The combined organic extracts were washed with brine, dried (MgSO$_4$) and concentrated in vacuo. The resultant residue was triturated with diethyl ether, collected by filtration and dried in vacuo to yield 190 as a white solid (111 mg, 46%). $^1$H NMR 400 MHz (DMSO-d$_6$): δ 8.13-7.98 (2H, m), 7.89 (1H, br s), 7.74-7.58 (2H, m), 7.59-7.39 (4H, m), 7.29-7.14 (1H, m), 5.47 (1H, br s), 3.87-3.77 (2H, m), 3.11 (3H, s). LCMS (Method K): R$_T$=3.72 min, [M+H]+=422

Example 191

{(S)-1-[3-(3-Chloro-phenyl)-3H-imidazo[4,5-b]pyridin-2-yl]-ethyl}-(9H-purin-6-yl)-amine 191

To a solution of {(S)-1-[3-(3-chlorophenyl)-3H-imidazo[4,5-b]pyridin-2-yl]ethyl}carbamic acid tert-butyl ester (35 mg, 0.09 mmol) in DCM (1 mL) was added TFA (1 mL) and the mixture was stirred at RT for 3 h. The crude mixture was loaded onto an Isolute® SCX-2 cartridge and washed with MeOH followed by 2M NH$_3$/MeOH. The basic fractions were combined and concentrated in vacuo to afford (S)-1-[3-(3-chlorophenyl)-3H-imidazo[4,5-b]pyridin-2-yl]ethylamine as an orange oil (23 mg).

A mixture of the compound thus obtained (23 mg), 6-chloro-9-(tetrahydropyran-2-yl)-9H-purine (21 mg, 0.09 mmol) and DIPEA (45 μL, 0.25 mmol) in n-butanol (0.5 mL) was heated at 100° C. in a sealed vial for 18 h. After cooling to RT, the crude mixture was loaded onto an Isolute® SCX-2 cartridge and washed with MeOH followed by 2M NH$_3$/MeOH. The basic fractions were combined, concentrated in vacuo and the resulting residue purified by column chromatography (Si—PCC, gradient 0-10% MeOH in DCM) to afford 191 as a pink/red solid (18 mg, 49% over two steps). LCMS (Method K): R$_T$ 2.97 min [M+H]$^+$ 391.0. $^1$H NMR (DMSO-d$_6$, 400 MHz): δ 8.26 (1H, dd, J=4.77, 1.47 Hz), 8.14-7.95 (4H, m), 7.71 (1H, br s), 7.58-7.53 (1H, m), 7.49-7.41 (2H, m), 7.33 (1H, dd, J=7.99, 4.78 Hz), 5.62 (1H, br s), 1.63 (3H, d, J=6.82 Hz)

Example 192

{(S)-1-[3-(4-Chloro-phenyl)-3H-imidazo[4,5-b]pyridin-2-yl]-ethyl}-(9H-purin-6-yl)-amine 192

To a mixture of {(S)-1-[3-(4-chlorophenyl)-3H-imidazo[4,5-b]pyridin-2-yl]ethyl}carbamic acid tert-butyl ester (99 mg, 0.27 mmol) in DCM (1 mL) was added TFA (1 mL) and the reaction mixture was stirred at RT for 3 h. The crude mixture was loaded onto an Isolute® SCX-2 cartridge and washed with MeOH followed by 2M NH$_3$/MeOH. The basic fractions were combined and concentrated in vacuo to afford (S)-1-[3-(4-chlorophenyl)-3H-imidazo[4,5-b]pyridin-2-yl]ethylamine as an orange oil (71 mg).

A mixture of the compound thus obtained (71 mg), 6-chloro-9-(tetrahydropyran-2-yl)-9H-purine (65 mg, 0.27 mmol) and DIPEA (135 μL, 0.78 mmol) in n-butanol (1 mL) was heated at 100° C. in a sealed vial for 18 h. After cooling to RT, the crude mixture was loaded onto an Isolute® SCX-2 cartridge and washed with MeOH followed by 2M NH$_3$/MeOH. The basic fractions were combined and concentrated in vacuo and the resulting residue was purified by column chromatography (Si—PCC, gradient 0-10% MeOH in DCM) to afford 192 as a pink/red solid (29 mg, 28% over two steps). LCMS (Method K): $R_T$ 3.03 min [M+H]$^+$ 391.0. $^1$H NMR (DMSO-d$_6$, 400 MHz): δ 8.25 (1H, dd, J=4.77, 1.47 Hz), 8.16-7.94 (4H, m), 7.67-7.60 (2H, m), 7.58-7.49 (2H, m), 7.31 (1H, dd, J=7.99, 4.77 Hz), 5.55 (1H, br s), 1.61 (3H, d, J=6.85 Hz)

Example 195

{1-[6-Fluoro-1-(2-fluoro-phenyl)-1H-benzoimidazol-2-yl]-ethyl}-(9H-purin-6-yl)-amine 195

(S)-1-[6-Fluoro-1-(2-fluorophenyl)-1H-benzoimidazol-2-yl]ethylamine (0.22 g, 0.81 mmol) was dissolved in n-butanol (5 mL) and 6-chloro-9-(tetrahydropyran-2-yl)-9H-purine (0.193 g, 0.81 mmol) and DIPEA (0.70 mL, 4.03 mmol) added. The reaction mixture was heated at 100° C. overnight. The resultant mixture was allowed to cool to RT and then concentrated in vacuo. The residue was passed down an Isolute® SCX-2 cartridge, eluting with DCM, MeOH and 2M NH$_3$ in MeOH to afford a light yellow gum. This was purified by column chromatography (silica gel, gradient 0-5% MeOH in DCM) to afford 195 as an off-white solid (209 mg, 67%). LCMS (Method K): $R_T$ 3.34/3.52 min [M+H]$^+$ 392.0 $^1$H NMR (DMSO-d$_6$, 400 MHz): δ 8.16-7.79 (3H, m), 7.77-7.64 (2H, m), 7.58-7.21 (3H, m), 7.16-7.09 (1H, m), 6.92-6.83 (1H, m), 5.63-5.38 (1H, m), 1.69 (1.5H, d, J=6.85 Hz), 1.58 (1.5H, d, J=6.86 Hz). NMR signals represent a mixture of rotamers Example 196

[2-Methyl-1-(3-phenyl-3H-imidazo [4,5-b]pyridin-2-yl)-propyl]-(9H-purin-6-yl)-amine 196

A solution of (S)-3-methyl-N-(2-phenylaminopyridin-3-yl)-2-(9H-purin-6-ylamino)butyramide (821 mg, 2.0 mmol) in AcOH (10 mL) was heated at 100° C. for 2 h. After cooling to RT, the volatiles were removed under reduced pressure and the resulting residue partitioned between DCM and a saturated aqueous solution of NaHCO$_3$. The aqueous phase was extracted with DCM and the combined organic fractions dried (MgSO$_4$) and concentrated in vacuo. The resulting residue was purified by column chromatography (Si—PCC, gradient 0-10% 2M NH$_3$/MeOH in DCM) to afford 196 as a light brown solid (365 mg, 46%). LCMS (Method K): $R_T$ 3.18 min [M+H]$^+$ 385.1. $^1$H NMR (DMSO-d$_6$, 400 MHz): δ 8.29-7.99 (4H, m), 7.78-7.42 (6H, m), 7.31 (1H, dd, J=8.01, 4.75 Hz), 5.40 (1H, br s), 2.45-2.34 (1H, m), 0.95 (3H, d, J=6.69 Hz), 0.81 (3H, br d, J=6.59 Hz). Signals split due to presence of rotamers/tautomers Example 197

5-Fluoro-3-phenyl-2-[1-(9H-purin-6-ylamino)-ethyl]-3H-benzoimidazole-4-carboxylic acid methyl ester 197

A solution of 5-fluoro-3-phenyl-2-{(S)-1-[9-(tetrahydropyran-2-yl)-9H-purin-6-ylamino]ethyl}-3H-benzoimidazole-4-carboxylic acid methyl ester (50 mg, 0.097 mmol) in MeOH (2 mL) and 4N HCl in dioxane (0.5 ml) was stirred at RT for 30 min then the volatiles were removed under reduced pressure. The resulting residue was dissolved in a minimum amount of MeOH and EtOAc. A solid precipitated on standing and was collected by filtration to afford 197 (21 mg, 46%). LCMS (Method K): $R_T$ 3.28 min [M+H]$^+$ 432.1. $^1$H NMR (DMSO-d$_6$, 400 MHz): δ 12.65 (1H, s), 9.92 (1H, br s), 8.61 (1H, s), 8.50 (1H, s), 7.89 (1H, dd, J=8.90, 4.75 Hz), 7.59-7.48 (2H, m), 7.45-7.30 (3H, m), 7.25 (1H, dd, J=10.49, 8.90 Hz), 5.51-5.40 (1H, m), 3.09 (3H, s), 1.65 (3H, d, J=6.84 Hz)

Example 198

[1-(7-Cyclopropyl-6-fluoro-1-phenyl-1H-benzoimidazol-2-yl)-ethyl]-(9H-purin-6-yl)-amine 198

To a mixture of [(S)-1-(7-cyclopropyl-6-fluoro-1-phenyl-1H-benzoimidazol-2-yl)ethyl]-[9-(tetrahydropyran-2-yl)-9H-purin-6-yl]amine (20 mg, 0.04 mmol) in MeOH (2 mL) was added 4N HCl in dioxane (0.25 mL) and the reaction mixture stirred at RT for 30 min. The volatiles were removed under reduced pressure and the resulting residue purified by reverse phase HPLC (Phenomenex Gemini 5 µm C18 on a 20 min gradient 10-90%, 0.1% HCO$_2$H in acetonitrile/water) to afford 198 (8 mg, 48%). LCMS (Method K): $R_T$ 3.74 and 3.81 min [M+H]$^+$ 414.1. $^1$H NMR (DMSO-d$_6$, 400 MHz): δ 12.89 (1H, br s), 8.19-7.97 (2H, m), 7.90-7.30 (7H, m), 7.04-6.95 (1H, dd, J=11.67, 8.76 Hz), 5.29 (1H, br s), 1.52 (3H, d, J=6.81 Hz), 1.28-1.18 (1H, m), 0.43-0.29 (2H, m), 0.25-0.08 (2H, m)

Example 199

[1-(1-Phenyl-1H-imidazo[4,5-b]pyridin-2-yl)-ethyl]-(9H-purin-6-yl)-amine 199

A mixture of (S)-1-(1-phenyl-1H-imidazo[4,5-b]pyridin-2-yl)ethylamine (330 mg, 1.38 mmol), 6-chloro-9-(tetrahydropyran-2-yl)-9H-purine (460 mg, 1.94 mmol) and DIPEA (440 µL, 2.49 mmol) in n-butanol (2 mL) was heated at 90° C. in a sealed vial for 16 h. After cooling to RT, the volatiles were removed under reduced pressure and the resulting residue loaded onto an Isolute® SCX-2 cartridge and washed with MeOH followed by 2M NH$_3$/MeOH. The product containing fractions were combined and concentrated in vacuo. The resulting residue was purified by column chromatography (Si—PCC, gradient 0-15% 2M NH$_3$/MeOH in DCM) and then crystallised from EtOAc and MeOH to afford 199 as a white solid (178 mg, 36%). LCMS (Method K): $R_T$ 2.72 min [M+H]$^+$ 357.0. $^1$H NMR (DMSO-d$_6$, 400 MHz): δ 8.42 (1H, dd, J=4.73, 1.53 Hz), 8.20-7.94 (3H, m), 7.68 (2H, d, J=7.55 Hz), 7.63-7.48 (4H, m), 7.23 (1H, dd, J=8.06, 4.74 Hz), 5.51 (1H, br s), 1.60 (3H, d, J=6.85 Hz)

Example 200

[2-Ethoxy-1-(6-fluoro-1-phenyl-1H-benzoimidazol-2-yl)-ethyl]-(9H-purin-6-yl)-amine 200

A mixture of (R)-2-ethoxy-1-(6-fluoro-1-phenyl-1H-benzoimidazol-2-yl)ethylamine (510 mg, 1.7 mmol), 6-chloro-9-(tetrahydropyran-2-yl)-9H-purine (410 mg, 1.7 mmol) and DIPEA (1.5 mL, 8.5 mmol) in n-butanol (6 mL) was heated at 90° C. for 18 h in a sealed vial. After cooling to RT, the volatiles were removed under reduced pressure and the resulting residue loaded onto an Isolute® SCX-2 cartridge. The cartridge was washed with MeOH followed by 2M NH$_3$/MeOH. The basic fractions were combined, concentrated in vacuo and the resulting residue purified by column chromatography (Si—PCC, gradient 0-10% 2M NH$_3$/MeOH in DCM) to afford 200 as a white solid (158 mg, 22%). LCMS (Method K): $R_T$ 3.80 min [M+H]$^+$ 418.1. $^1$H NMR (DMSO-d$_6$, 400 MHz): δ 12.60 (1H, s), δ 8.22-8.05 (2H, m), 7.87 (1H, br s), 7.75-7.49 (6H, m), 7.11 (1H, td, J=9.32, 2.48 Hz), 6.89 (1H, dd, J=8.92, 2.50 Hz), 5.63 (1H, br s), 3.88 (2H, br d, J=6.76 Hz), 3.40-3.33 (2H, m), 1.01-0.91 (3H, m)

Example 201

[(S)-1-(1-Cyclohexyl-6-fluoro-1H-benzoimidazol-2-yl)-ethyl]-(9H-purin-6-yl)-amine 201

(S)-1-(1-Cyclohexyl-6-fluoro-1H-benzoimidazol-2-yl) ethylamine (0.41 g, 1.56 mmol) was dissolved in n-butanol (5 mL) and 6-chloro-9-(tetrahydropyran-2-yl)-9H-purine (0.374 g, 1.56 mmol) and DIPEA (1.38 mL, 7.82 mmol) added. The reaction mixture was heated to 100° C. overnight. The resultant mixture was allowed to cool to RT and was concentrated in vacuo. The residue was passed down an Isolute® SCX-2 cartridge, eluting with DCM, MeOH and 2M NH$_3$ in MeOH to afford crude product. This was purified by column chromatography (silica gel, gradient 0-10% MeOH in DCM) to afford 201 as a pale yellow gum, which solidified on standing (204 mg, 35%). LCMS (Method K): R$_T$ 3.31 min [M+H]$^+$ 380.1 $^1$H NMR (DMSO-d$_6$, 400 MHz): δ 8.30 (1H, s), 8.15 (1H, s), 8.04 (1H, s), 7.66-7.54 (2H, m), 7.02 (1H, td, J=9.29, 2.34 Hz), 6.00 (1H, s), 4.51-4.37 (1H, m), 2.27-2.13 (1H, m), 2.07-1.95 (1H, m), 1.88-1.75 (2H, m), 1.70 (3H, d, J=6.70 Hz), 1.64-1.44 (3H, m), 1.39-1.26 (2H, m), 0.75-0.57 (1H, m)

Example 202

{5-Fluoro-3-phenyl-2-[1-(9H-purin-6-ylamino)-ethyl]-3H-benzoimidazol-4-yl}-(4-methyl-piperazin-1-yl)-methanone 202

A mixture of 5-fluoro-3-phenyl-2-{(S)-1-[9-(tetrahydro-pyran-2-yl)-9H-purin-6-ylamino]ethyl}-3H-benzoimidazole-4-carboxylic acid (100 mg, 0.2 mmol), HATU (91 mg, 0.24 mmol), 1-methylpiperazine (33 μL, 0.3 mmol) and DIPEA (69 μL, 0.4 mmol) in DCM (2 mL) was stirred at RT for 1 h. The crude mixture was diluted with water and extracted with DCM. The aqueous phase was further extracted with DCM and the combined organic fractions were dried (MgSO$_4$) and concentrated in vacuo. The resulting residue was dissolved in MeOH (1 mL) and 4N HCl in dioxane (0.25 mL) and the mixture stirred at RT for 30 min. The volatiles were removed under reduced pressure and the resulting residue purified by HPLC (Waters C18 XBridge, on a 20 min gradient 10-90%, 0.1% NH$_4$OH in acetonitrile/water) to afford 202 (59 mg, 59%). LCMS (Method K): R$_T$ 2.02 min [M+H]$^+$ 500.1. $^1$H NMR (DMSO-d$_6$+TFA-D, 400 MHz, 80° C.): δ 12.45 (1H, s), 8.52 (1H, br s), 8.44 (1H, d, J=6.07 Hz), 7.85-7.80 (1H, m), 7.56-7.27 (5H, m), 7.24-7.17 (1H, m), 5.67 (1H, br s), 3.76-3.52 (1H, m), 3.49-3.37 (1H, m), 3.34-2.87 (7H, m), 2.81 (3H, s), 1.71-1.64 (3H, m)

Example 203

{5-Fluoro-3-phenyl-2-[1-(9H-purin-6-ylamino)-ethyl]-3H-benzoimidazol-4-yl}-morpholin-4-yl-methanone 203

A mixture of 5-fluoro-3-phenyl-2-{(S)-1-[9-(tetrahydro-pyran-2-yl)-9H-purin-6-ylamino]ethyl}-3H-benzoimidazole-4-carboxylic acid (100 mg, 0.2 mmol), HATU (91 mg, 0.24 mmol), morpholine (26 μL, 0.3 mmol) and DIPEA (69 μL, 0.4 mmol) in DCM (2 mL) was stirred at RT for 1 h. The crude mixture was diluted with water and extracted with DCM. The aqueous phase was further extracted with DCM and the combined organic fractions were dried (MgSO$_4$) and concentrated in vacuo. The resulting residue was dissolved in MeOH (2 mL) and 4N HCl in dioxane (0.25 mL) and the mixture was stirred at RT for 30 min. The volatiles were removed under reduced pressure and the resulting residue purified by HPLC (Waters C18 XBridge, on a 20 min gradient 10-90%, 0.1% NH$_4$OH in acetonitrile/water) to afford 203 (69 mg, 71%). LCMS (Method K): R$_T$ 2.64 and 2.67 min [M+H]$^+$ 487.1. $^1$H NMR (DMSO-d$_6$+TFA-D, 400 MHz, 80° C.): δ 8.52 (1H, br s), 8.46 (1H, d, J=6.25 Hz), 7.83-7.75 (1H, m), 7.57-7.43 (5H, m), 7.32-7.15 (2H, m), 5.66 (1H, br s), 3.50-3.24 (5H, m), 3.15-3.05 (1H, m), 3.04-2.95 (1H, m), 2.70-2.58 (1H, m), 1.74-1.65 (3H, m)

Example 204

5-Fluoro-3-phenyl-2-[1-(9H-purin-6-ylamino)-ethyl]-3H-benzoimidazole-4-carboxylic acid dimethylamide 204

A mixture of 5-fluoro-3-phenyl-2-{(S)-1-[9-(tetrahydro-pyran-2-yl)-9H-purin-6-ylamino]ethyl}-3H-benzoimidazole-4-carboxylic acid (100 mg, 0.2 mmol), HATU (91 mg, 0.24 mmol), dimethylamine (2M in THF, 0.2 mL, 0.4 mmol) and DIPEA (69 μL, 0.4 mmol) in DCM (2 mL) was stirred at RT for 1 h. The crude mixture was diluted with water and extracted with DCM. The aqueous phase was further extracted with DCM and the combined organic fractions were dried (MgSO$_4$) and concentrated in vacuo. The resulting residue was dissolved in MeOH (2 mL) and 4N HCl in dioxane (0.25 mL) and the mixture was stirred at RT for 30 min. The volatiles were removed under reduced pressure and the resulting residue purified by HPLC (Waters C18 XBridge, on a 20 min gradient 10-90%, 0.1% NH$_4$OH in acetonitrile/water) to afford 204 (60 mg, 68%). LCMS (Method K): R$_T$ 2.58 and 2.71 min [M+H]$^+$ 445.1. $^1$H NMR (DMSO-d$_6$, 400 MHz, 80° C.): δ 12.45 (1H, s), 8.04 (1H, d, J=4.86), 8.00 (1H, s), 7.69 (1H, dd, J=8.83, 4.88 Hz), 7.52-7.25 (6H, m), 7.12-7.05 (1H, m), 5.58-5.39 (1H, m), 2.64 (1.5H, s), 2.58 (1.5H, s), 2.34 (3H, d, J=4.31 Hz), 1.56 (3H, t, J=6.63 Hz)

Example 205

[1-(6-Fluoro-1-pyridin-3-yl-1H-benzoimidazol-2-yl)-propyl]-(9H-purin-6-yl)-amine 205

A mixture of (S)-1-(6-fluoro-1-pyridin-3-yl-1H-benzoimidazol-2-yl)propylamine (243 mg, 0.90 mmol), 6-chloro-9-(tetrahydropyran-2-yl)-9H-purine (210 mg, 0.90 mmol) and DIPEA (780 μL, 4.5 mmol) in n-butanol (3 mL) was heated at 100° C. in a sealed vial for 18 h. After cooling to RT, the volatiles were removed under reduced pressure and the resulting residue loaded onto an Isolute® SCX-2 cartridge and washed with MeOH followed by 2M NH$_3$/MeOH. The product containing fractions were combined and concentrated in vacuo. The resulting residue was purified by column chromatography (Si—PCC, gradient 0-10% 2M NH$_3$/MeOH in DCM) to afford 205 (145 mg, 42%). LCMS (Method K): R$_T$ 2.96 min [M+H]$^+$ 389.1. $^1$H NMR (DMSO-d$_6$, 400 MHz): δ 12.65 (1H, s), 8.81 (1H, d, J=2.47 Hz), 8.67 (1H, br s), 8.21-8.01 (3H, m), 7.91 (1H, br s), 7.73 (1H, dd, J=8.81, 4.84 Hz), 7.56 (1H, br s), 7.18-7.08 (1H, m), 6.95 (1H, dd, J=8.88, 2.48 Hz), 5.35 (1H, br s), 2.19-2.01 (2H, m), 0.90 (3H, t, J=7.32 Hz)

Example 206

[1-(6-Fluoro-1-pyridin-3-yl-1H-benzoimidazol-2-yl)-2-methyl-propyl]-(9H-purin-6-yl)-amine 206

A mixture of (S)-1-(6-fluoro-1-pyridin-3-yl-1H-benzoimidazol-2-yl)-2-methylpropylamine (135 mg, 0.48 mmol), 6-chloro-9-(tetrahydropyran-2-yl)-9H-purine (110 mg, 0.48 mmol) and DIPEA (0.4 mL, 2.4 mmol) in n-butanol (2 mL) was heated for 18 h at 100° C. in a sealed vial. After cooling to RT, the volatiles were removed under reduced pressure and the resulting residue loaded onto an Isolute® SCX-2 cartridge. The cartridge was washed with MeOH followed by 2M NH$_3$/MeOH. The basic fractions were combined, concentrated in vacuo and the resulting residue was purified by column chromatography (Si—PCC, gradient 0-10% 2M NH$_3$/MeOH in DCM) to afford 206 (75 mg, 39%). LCMS (Method K): R$_T$ 3.19 min [M+H]$^+$ 403.0. $^1$H NMR (DMSO-d$_6$, 400 MHz): δ 12.85 (1H, s), 8.86-8.59 (2H, m), 8.18-7.88 (3H, m), 7.79-7.47 (3H, m), 7.11 (1H, td, J=9.31, 2.48 Hz), 6.93 (1H, br d, J=8.83 Hz), 5.21 (1H, br s), 0.99-0.90 (4H, m), 0.85 (3H, br s)

Example 207

{1-[6-Fluoro-1-(6-methoxy-pyridin-3-yl)-1H-benzoimidazol-2-yl]-ethyl}-(9H-purin-6-yl)-amine 207

A mixture of {(S)-1-[6-fluoro-1-(6-methoxypyridin-3-yl)-1H-benzoimidazol-2-yl]ethyl}carbamic acid tert-butyl ester (52 mg, 0.14 mmol) in DCM (3 mL) and TFA (1 mL) was stirred at RT for 2 h. The crude reaction mixture was loaded onto an Isolute® SCX-2 cartridge and washed with MeOH followed by 2M NH$_3$/MeOH. The basic fractions were combined and concentrated in vacuo to afford (S)-1-[6-fluoro-1-(6-methoxypyridin-3-yl)-1H-benzoimidazol-2-yl]ethylamine as a pink oil (37 mg, 96%). LCMS (Method C): R$_T$ 1.98 min [M+H]$^+$ 287.2.

A mixture of the compound thus obtained (37 mg, 0.13 mmol), 6-chloro-9-(tetrahydropyran-2-yl)-9H-purine (32 mg, 0.14 mmol) and DIPEA (66 μL, 0.39 mmol) in n-butanol (0.5 mL) was heated at 100° C. in a sealed vial for 18 h. After cooling to RT, the crude mixture was diluted with MeOH and loaded onto an Isolute® SCX-2 cartridge. The cartridge was washed with MeOH followed by 2M NH$_3$/MeOH. The basic fractions were combined, concentrated in vacuo and the resulting residue subjected to a second SCX-2 cartridge purification. The basic fractions were combined, concentrated in vacuo and the resulting residue purified by column chromatography (Si—PCC, gradient 0-10% MeOH in DCM) to afford 207 as a pale yellow solid (29 mg, 55%). LCMS (Method K): R$_T$ 3.24 min [M+H]$^+$ 405.0. $^1$H NMR (DMSO-d$_6$, 400 MHz): δ 12.88 (1H, br s), 8.33 (1H, s), 8.20-7.78 (4H, m), 7.72-7.63 (1H, m), 7.09 (1H, t, J=9.41 Hz), 6.98-6.72 (2H, m), 5.50 (1H, br s), 3.86 (3H, s), 1.62 (3H, d, J=6.85 Hz)

Example 208

{1-[6-Fluoro-1-(5-fluoro-pyridin-2-yl)-1H-benzoimidazol-2-yl]-ethyl}-(9H-purin-6-yl)-amine 208

A mixture of {(S)-1-[6-fluoro-1-(5-fluoropyridin-2-yl)-1H-benzoimidazol-2-yl]ethyl}carbamic acid tert-butyl ester (33 mg, 0.09 mmol) in DCM (1 mL) and TFA (0.5 mL) was stirred at RT for 2 h. The crude reaction mixture was loaded onto an Isolute® SCX-2 cartridge and washed with MeOH followed by 2M NH$_3$/MeOH. The basic fractions were combined and concentrated in vacuo to afford (S)-1-[6-fluoro-1-(5-fluoropyridin-2-yl)-1H-benzoimidazol-2-yl]ethylamine as a yellow oil (19 mg, 79%). LCMS (Method C): R$_T$ 0.27 and 1.84 min [M+H]$^+$ 275.2.

A mixture of the compound thus obtained (19 mg, 0.07 mmol), 6-chloro-9-(tetrahydropyran-2-yl)-9H-purine (17 mg, 0.07 mmol) and DIPEA (36 μL, 0.21 mmol) in n-butanol (0.5 mL) was heated at 100° C. in a sealed vial for 18 h. After cooling to RT, the crude mixture was diluted with MeOH and loaded onto an Isolute® SCX-2 cartridge. The cartridge was washed with MeOH followed by 2M NH$_3$/MeOH. The basic fractions were combined, concentrated in vacuo and the resulting residue was subjected to a second SCX-2 cartridge purification. The basic fractions were combined, concentrated in vacuo and the resulting residue purified by column chromatography (Si—PCC, gradient 0-10% MeOH in DCM) to afford 208 as a pale yellow solid (24 mg, 88%). LCMS (Method K): R$_T$ 3.22 min [M+H]$^+$ 393.0. $^1$H NMR (DMSO-d$_6$, 400 MHz): δ 12.35 (1H, s), 8.55 (1H, br s), 8.07 (1H, br s), 8.00 (1H, s), 7.95-7.75 (3H, m), 7.73-7.65 (1H, m), 7.15-7.10 (2H, m), 5.79 (1H, br s), 1.63 (3H, d, J=6.84 Hz)

Example 210

[1-(6-Fluoro-1-pyridin-2-yl-1H-benzoimidazol-2-yl)-ethyl]-(9H-purin-6-yl)-amine 210

A mixture of (S)-1-(6-fluoro-1-pyridin-2-yl-1H-benzoimidazol-2-yl)ethylamine (764 mg, 3.0 mmol), 6-chloro-9-(tetrahydropyran-2-yl)-9H-purine (710 mg, 3.0 mmol) and DIPEA (2.6 mL, 15 mmol) in IPA (8 mL) was heated for 16 h at 90° C. After cooling to RT, the volatiles were removed under reduced pressure and the resulting residue loaded onto an Isolute® SCX-2 cartridge. The cartridge was washed with MeOH followed by 2M NH$_3$/MeOH. The basic fractions were combined, concentrated in vacuo and the resulting residue purified by column chromatography (Si—PCC, gradient 0-10% 2M NH$_3$/MeOH in EtOAc) to afford 210 as a white solid (700 mg, 63%). LCMS (Method K): R$_T$ 2.94 min [M+H]$^+$ 375.0. $^1$H NMR (DMSO-d$_6$, 400 MHz): δ 12.89 (1H, br s), 8.61 (1H, br s), 8.20-7.80 (4H, m), 7.79-7.67 (2H, m), 7.52-7.43 (1H, m), 7.20-7.08 (2H, m), 5.86 (1H, br s), 1.63 (3H, d, J=6.82 Hz)

Example 228

3-{6-Fluoro-2-[1-(9H-purin-6-ylamino)-ethyl]-benzoimidazol-1-yl}-phenol 228

{(S)-1-[6-Fluoro-1-(3-methoxyphenyl)-1H-benzoimidazol-2-yl]ethyl}-9H-purin-6-yl)amine (0.215 g, 0.53 mmol) was suspended in DCM (8 mL) and cooled to 0° C., under an atmosphere of nitrogen. Boron tribromide (1M in DCM) (1.06 mL, 1.06 mmol) was added dropwise and the reaction mixture allowed to reach RT then stirred for 1 h. The mixture was re-cooled to 0° C. and a further quantity of boron tribromide solution (1.06 mL, 1.06 mmol) added and the reaction mixture stirred at RT for 3 h. The reaction mixture was again re-cooled to 0° C. and a further quantity of boron tribromide solution (1.06 mL, 1.06 mmol) added. The reaction mixture was stirred at RT overnight. The off-white suspension was quenched with MeOH (5 mL) to afford a clear solution. This was concentrated in vacuo and the residue was purified by column chromatography (silica gel, gradient 0-15% [2M NH$_3$ in MeOH] in DCM) to afford an insoluble off-white solid. This was suspended in water and filtered through a nylon membrane. The solid obtained was dried, in vacuo, at 50° C. overnight to afford 228 (153 mg, 79%). LCMS (Method K): $R_T$ 2.95 min [M+H]$^+$ 390.0 $^1$H NMR (DMSO-d$_6$, 400 MHz): δ 8.17-8.05 (2H, m), 7.86 (1H, s), 7.65 (1H, dd, J=8.79, 4.84 Hz), 7.39-7.29 (1H, m), 7.12-6.84 (5H, m), 5.51 (1H, s), 1.53 (3H, d, J=6.84 Hz)

Example 236

[1-(1-Phenyl-1H-imidazo[4,5-c]pyridin-2-yl)-ethyl]-(9H-purin-6-yl)-amine 236

A mixture of 1-(1-phenyl-1H-imidazo[4,5-c]pyridin-2-yl) ethylamine (184 mg, 0.77 mmol), 6-chloro-9-(tetrahydropyran-2-yl)-9H-purine (256 mg, 1.08 mmol) and DIPEA (0.25 mL, 1.39 mmol) in 1-butanol (2 mL) was stirred at 90° C. in a sealed microwave tube for 16 h. The resulting mixture was loaded onto an Isolute® SCX-2 cartridge and washed with MeOH. The product was eluted with 2M NH$_3$/MeOH then concentrated in vacuo. The resulting residue was purified by chromatography (SiO$_2$ 0-10% (2M ammonia in methanol) in DCM), then by preparative HPLC (Phenomenex Gemini 5 μm C18 on a 60 min gradient 20-98% 0.1% HCO$_2$H in acetonitrile/water) to give 236 as a white solid (0.017 g, 6%). LCMS (method K): R$_t$ 2.04 min, [M+H]$^+$ 357. $^1$H NMR (DMSO-d$_6$): δ 12.89 (1H, s), 8.94 (1H, s), 8.30 (1H, d, J=5.54 Hz), 8.09-8.00 (2H, m), 7.65-7.50 (5H, m), 7.12 (1H, d, J=5.57 Hz), 5.53 (1H, s), 1.58 (4H, d, J=7.36 Hz)

Example 237

[1-(3-Phenyl-3H-imidazo[4,5-c]pyridin-2-yl)-ethyl]-(9H-purin-6-yl)-amine 237

A mixture of 1-(3-phenyl-3H-imidazo[4,5-c]pyridin-2-yl) ethylamine (254 mg, 1.07 mmol), 6-chloro-9-(tetrahydropyran-2-yl)-9H-purine (0.35 g, 1.49 mmol) and DIPEA (0.34 mL, 1.92 mmol) in 1-butanol (3 mL) was stirred at 90° C. in a sealed tube for 16 h. The resulting mixture was concentrated in vacuo and residue was purified by chromatography (SiO$_2$ 0-10% (2M ammonia in methanol) in DCM). The product was dissolved in methanol and treated with HCl/dioxane (4M, 1.3 mL, 5.35 mmol) and stirred for 20 minutes. The mixture was loaded onto an Isolute® SCX-2 cartridge, washed with MeOH and the product eluted with 2M NH$_3$/MeOH then concentrated in vacuo. The resulting residue was purified by chromatography (SiO$_2$, 0-15% (2M ammonia in methanol) in DCM) to give a waxy solid which was triturated with EtOAc/diethyl ether to give 237 as a brown solid (0.056 g, 15%). LCMS (method K): R$_t$ 1.98 min, [M+H]$^+$ 357. $^1$H NMR (DMSO-d$_6$): δ 13.10-12.60 (1H, bs), 8.43 (1H, s), 8.37 (1H, d, J=5.53 Hz), 8.13 (1H, s), 8.07 (1H, s), 7.70-7.68 (3H, m), 7.61-7.50 (3H, m), 5.49 (1H, m), 1.59 (3H, d, J=6.87 Hz)

Example 238

{1-[6-Fluoro-1-(3-fluoro-pyridin-2-yl)-1H-benzoimidazol-2-yl]-ethyl}-(9H-purin-6-yl)-amine 238

A mixture of {1-[6-fluoro-1-(3-fluoropyridin-2-yl)-1H-benzoimidazol-2-yl]ethyl}-carbamic acid tert-butyl ester (84 mg, 0.22 mmol) in DCM (1 mL) and TFA (1 mL) was stirred at RT for 2 h. The reaction mixture was loaded onto an Isolute® SCX-2 cartridge and washed with MeOH followed by 2M NH$_3$/MeOH. The basic fractions were combined and concentrated in vacuo to afford a dark orange oil. A mixture of this residue, 6-chloro-9-(tetrahydropyran-2-yl)-9H-purine (53 mg, 0.22 mmol) and DIPEA (110 μL, 0.63 mmol) in n-butanol (0.5 mL) was heated at 100° C. in a sealed vial for 16 h. After cooling to RT, the reaction mixture was diluted with MeOH and loaded onto an Isolute® SCX-2 cartridge. The cartridge was washed with MeOH followed by 2M NH$_3$/MeOH. The basic fractions were combined, concentrated in vacuo and the resulting residue purified by column chromatography (Si—PCC, gradient 0-10% MeOH in DCM) followed by reverse phase HPLC (Phenomenex Gemini 5 μm C18 on a gradient 5-60%, 0.1% NH$_4$OH in acetonitrile/water) to afford 238 as a white solid (14 mg, 16%). LCMS (Method K): R$_T$ 3.09 min [M+H]$^+$ 393.01. $^1$H NMR (DMSO-d$_6$, 400 MHz): δ 8.40 (1H, s), 8.07-7.81 (4H, m), 7.73 (1H, dd, J=8.86, 4.85 Hz), 7.56 (1H, s), 7.18-7.04 (2H, m), 5.68 (1H, s), 1.70 (3H, d, J=6.75 Hz)

Example 243

[1-(6-Fluoro-1-pyrazin-2-yl-1H-benzoimidazol-2-yl)-ethyl]-(7H-purin-6-yl)-amine 243

(S)—N-[4-Fluoro-2-(pyrazin-2-ylamino)phenyl]-2-[9-(tetrahydropyran-2-yl)-9H-purin-6-ylamino]propionamide (100 mg, 0.21 mmol) was dissolved in acetic acid (6.0 ml) and heated to 80° C. overnight. The reaction was cooled and neutralized with sodium hydroxide (1.0M aqueous) and the aqueous layer extracted with EtOAc (×3). The combined organic fractions were washed with brine, dried over sodium sulfate and concentrated in vacuo. The product was purified by chromatography (SiO$_2$, 0-10% methanol in DCM) to yield 243 (30.0 mg, 39%). LCMS (Method C): R$_T$ 2.85 min [M+H]$^+$ 376.0. $^1$H NMR (MeOD, 400 MHz): δ 8.94 (1H, s), 8.60 (2H, m), 7.98 (2H, s), 7.67 (1H, dd, J=8.7, 4.6 Hz), 7.10 (2H, m), 5.83 (1H, br s), 1.81 (3H, d, J=7.0 Hz)

Example 244

5-Fluoro-3-phenyl-2-[(S)-1-(9H-purin-6-ylamino)-propyl]-3H-benzoimidazole-4-carbonitrile 244

A mixture of 2-((S)-1-amino-propyl)-5-fluoro-3-phenyl-3H-benzoimidazole-4-carbonitrile (0.260 g, 0.88 mmol), 6-chloro-9-(tetrahydropyran-2-yl)-9H-purine (0.290 g, 1.24 mmol) and DIPEA (0.28 mL, 1.59 m mol) in IPA (2 mL) was stirred at 90° C. in a sealed tube for 16 h. The resulting mixture was concentrated in vacuo and the residue purified by chromatography (SiO$_2$ 0-10% (2M ammonia in methanol) in DCM). The product was dissolved in methanol and treated with HCl/dioxane (4M, 1.1 mL, 0.00450 mol) and stirred for 20 minutes. The mixture was loaded onto an Isolute® SCX-2 cartridge, washed with MeOH and the product eluted with 2M NH$_3$/MeOH then concentrated in vacuo. The resulting residue was purified by chromatography (SiO$_2$, 0-10% (2M ammonia in methanol) in DCM) to give 244 as a white solid (0.205 g, 57%). LCMS (method K): R$_t$ 3.51 min, [M+H]$^+$ 413. $^1$H NMR (DMSO-d$_6$): δ 13.20-12.50 (1H, bs), 9.60 (1H, s), 8.00 (1H, s), 7.71 (1H, m), 7.60 (2H, s), 7.51-7.49 (3H, m), 7.11-7.08 (1H, m), 6.86 (1H, m), 5.64 (1H, m), 2.10 (3H, s), 1.50 (3H, d, J=6.81 Hz)

Example 246

4-Amino-6-[(S)-1-(6-fluoro-1-phenyl-1H-benzoimidazol-2-yl)-ethylamino]-pyrimidine-5-carbonitrile 246

(S)-1-(6-Fluoro-1-phenyl-1H-benzoimidazol-2-yl)ethylamine dihydrochloride (328 mg, 1.00 mmol) was placed in a sealed tube with 4-amino-6-chloropyrimidine-5-carbonitrile (154.5 mg, 1.00 mol), DIPEA (0.7 mL, 4.00 mol) and IPA (1 mL). The tube was flushed with argon, sealed and the contents heated at 90° C. for 16 h. The cooled mixture was evaporated then diluted with EtOAc and water. The organic layer was washed with brine, dried (MgSO$_4$) and evaporated. The crude residue was purified by chromatography on silica (Si—PCC, 1-80% EtOAc in DCM). The product containing fractions were pooled and evaporated almost to dryness. The residue was triturated in ether to afford 246 as a cream solid (240 mg, 65%). $^1$H NMR (CDCl$_3$, 400 MHz): δ 8.01 (1H, s), 7.69 (1H, dd, J=8.8, 4.7 Hz), 7.59-7.49 (3H, m), 7.43-7.36 (2H, m), 7.02 (1H, td, J=9.2, 1.1 Hz), 6.77 (1H, dd, J=8.6, 2.4 Hz), 6.18 (1H, d, J=7.5 Hz), 5.52 (1H, quin, J=7.2 Hz), 5.30 (2H, br s), 1.54 (3H, d, J=6.9 Hz). LCMS (Method K): R$_T$ 3.80 min [M+H]$^+$ 374

Example 247

[(S)-1-(6-Fluoro-1-pyridin-2-yl-1H-benzoimidazol-2-yl)-propyl]-(9H-purin-6-yl)-amine 247

A mixture of (S)-1-(6-fluoro-1-pyridin-2-yl-1H-benzoimidazol-2-yl)propylamine (348 mg, 1.3 mmol), 6-chloro-9-(tetrahydropyran-2-yl)-9H-purine (310 mg, 1.3 mmol) and DIPEA (1.1 mL, 6.4 mmol) in IPA (4 mL) was heated for 72 h at 90° C. After cooling to RT, the volatiles were removed under reduced pressure and the resulting residue loaded onto an Isolute® SCX-2 cartridge. The cartridge was washed with MeOH followed by 2M NH$_3$/MeOH. The basic fractions were combined, concentrated in vacuo and the resulting residue was purified by column chromatography (Si—PCC, gradient 0-5% 2M NH$_3$/MeOH in DCM) to afford 247 as a white solid (320 mg, 63%). LCMS (Method K): R$_T$ 3.17 min [M+H]$^+$ 389.1. $^1$H NMR (DMSO-d$_6$, 400 MHz): δ 12.85 (1H, br s), 8.65 (1H, s), 8.15-8.03 (2H, m), 7.99 (1H, s), 7.84-7.76 (2H, m), 7.71 (1H, dd, J=8.75, 4.90 Hz), 7.55-7.48 (1H, m), 7.20-7.08 (2H, m), 5.73 (1H, s), 2.15-2.06 (1H, m), 2.05-1.95 (1H, m), 0.90 (3H, t, J=7.30 Hz)

Example 256

2-((R)-3-{6-Fluoro-2-[(S)-1-(9H-purin-6-ylamino)-ethyl]-benzoimidazol-1-yl}-piperidin-1-yl)-ethanol 256

A solution of 2,2-dimethylpropionic acid 2-[(R)-3-(5-fluoro-2-{(S)-2-[9-(tetrahydropyran-2-yl)-9H-purin-6-ylamino]propionylamino}phenylamino)piperidin-1-yl]ethyl ester (213 mg, 0.35 mmol), in aqueous 6M HCl (10 mL) was refluxed for 40 min. After cooling to RT, volatiles were removed under reduced pressure and the resulting residue was purified by column chromatography (C$_{18}$, gradient 2-35% MeOH in 0.5% TFA/H$_2$O) then loaded in dioxane/water (1:1) onto an Isolute® SCX-2 cartridge. The cartridge was washed with dioxane/water (1:1), then dioxane and the product eluted with 10% 880 NH$_3$ in dioxane, then 2M NH$_3$/MeOH. Further purification by column chromatography (Si—PCC, gradient 3-21% 2M NH$_3$/MeOH in DCM) afforded 256 as a pale yellow solid (40 mg, 27%). LCMS (Method K): R$_T$ 1.94 min [M+H]$^+$ 425.1. $^1$H NMR (CD$_3$OD, 400 MHz): δ 8.30 (1H, s), 8.08 (1H, s), 7.59 (1H, dd, J=8.9, 5.0 Hz), 7.49 (1H, dd, J=9.5, 2.3 Hz), 7.01 (1H, dt, J=9.2, 2.4 Hz), 6.03 (1H, bs), 3.67 (2H, t, J=5.8 Hz), 3.13-3.09 (1H, m), 2.98-2.92 (2H, m), 2.69-2.55 (2H, m), 2.28-2.14 (2H, m), 1.93-1.88 (1H, m), 1.82 (3H, d, J=7.0 Hz), 1.77-1.74 (1H, m), 1.51-1.41 (1H, m)

Example 258

N—[(S)-1-(6-Fluoro-1-phenyl-1H-benzoimidazol-2-yl)-ethyl]-6-methyl-[1,3,5]triazine-2,4-diamine 258

A mixture of (S)-1-(6-fluoro-1-phenyl-1H-benzoimidazol-2-yl)ethylamine dihydrochloride (100 mg, 0.31 mmol), 4-chloro-6-methyl-[1,3,5]triazin-2-ylamine (48.4 mg, 0.34 mmol) and DIPEA (0.26 mL, 1.52 mmol) in n-butanol (2 mL) was stirred at 90° C. in a sealed vial for 16 h. After cooling to RT, volatiles were removed under reduced pressure and the resulting residue purified by column chromatography (C$_{18}$, gradient 20-45% MeOH in 0.5% TFA/H$_2$O) then loaded onto an Isolute® SCX-2 cartridge. The cartridge was washed with MeOH and the product eluted with 0.5M NH$_3$/MeOH affording 258 as a white solid (94.2 mg, 85%). LCMS (Method K): R$_T$ 3.04 min [M+H]$^+$ 364.1. $^1$H NMR (DMSO-d$_6$, 400 MHz, 80° C.): δ 7.65 (1H, dd, J=8.7, 4.8 Hz), 7.61-7.57 (2H, m), 7.55-7.51 (3H, m), 7.04 (1H, ddd, J=9.8, 8.7, 2.5 Hz), 6.91 (1H, bs), 6.77 (1H, dd, J=9.0, 2.5 Hz), 6.13 (2H, bs), 5.26 (1H, quintet, J=7.3 Hz), 2.02 (3H, s), 1.44 (3H, d, J=6.9 Hz)

Example 259

2-((R)-3-{6-Fluoro-2-[(S)-1-(9H-purin-6-ylamino)-propyl]-benzoimidazol-1-yl}-piperidin-1-yl)-ethanol 259

A solution of 2,2-dimethylpropionic acid 2-[(R)-3-(5-fluoro-2-{(S)-2-[9-(tetrahydropyran-2-yl)-9H-purin-6-ylamino]butyrylamino}phenylamino)piperidin-1-yl]ethyl ester (258 mg, 0.41 mmol), in aqueous 6M HCl (3 mL) was refluxed for 40 min. After cooling to RT, volatiles were removed under reduced pressure and the resulting residue purified by column chromatography (C$_{18}$, gradient 2-30% MeOH in 0.5% TFA/H$_2$O) then loaded in dioxane/water (1:1) onto an Isolute® SCX-2 cartridge. The cartridge was washed with dioxane/water (1:1), then dioxane and the product eluted with 10% 880 NH$_3$ in dioxane, then 2M NH$_3$/MeOH. Further purification by column chromatography (Si—PCC, gradient 3-21% 2M NH$_3$/MeOH in DCM) afforded a colourless solid. The preparation was repeated on the same scale to give a combined yield of 44.4 mg of 259 (12%). LCMS (Method K): R$_T$ 2.07 min [M+H]$^+$ 439.1. $^1$H NMR (CD$_3$OD, 400 MHz): δ 8.28 (1H, s), 8.09 (1H, s), 7.59 (1H, dd, J=8.9, 5.0 Hz), 7.50 (1H, dd, J=9.6, 2.3 Hz), 7.00 (1H, dt, J=9.2, 2.3 Hz), 5.84 (1H, bs), 5.04-4.94 (1H, m), 3.68 (2H, t, J=5.8 Hz), 3.12-3.08 (1H, m), 3.00-2.93 (2H, m), 2.71-2.57 (2H, m), 2.33-2.16 (4H, m), 1.89-1.86 (1H, m), 1.82-1.77 (1H, m), 1.62-1.51 (1H, m), 1.09 (3H, t, J=7.4 Hz)

Example 260

{(S)-1-[6-Fluoro-1-(5-fluoro-pyridin-3-yl)-1H-benzoimidazol-2-yl]-ethyl}-(9H-purin-6-yl)-amine 260

A mixture of (S)-1-[6-fluoro-1-(5-fluoropyridin-3-yl)-1H-benzoimidazol-2-yl]ethylamine (46 mg, 0.17 mmol), 6-chloro-9-(tetrahydropyran-2-yl)-9H-purine (44 mg, 0.18 mmol) and DIPEA (86 µL, 0.50 mmol) in n-butanol (1 mL) was heated at 90° C. in a sealed vial for 60 h. After cooling to RT, the resulting mixture was diluted with MeOH and loaded onto an Isolute® SCX-2 cartridge. The cartridge was washed with MeOH followed by 2M NH$_3$/MeOH. The basic fractions were combined, concentrated in vacuo and the resulting residue purified by column chromatography (Si—PCC, gradient 0-10% MeOH in DCM) to afford 260 as a pale yellow solid (48 mg, 73%). LCMS (Method K): $R_T$ 3.04 min [M+H]$^+$ 393.02. $^1$H NMR (DMSO-d$_6$, 400 MHz): δ 8.63 (1H, s), 8.56 (1H, s), 8.14-8.05 (2H, m), 8.03-7.93 (2H, m), 7.72 (1H, dd, J=8.80, 4.85 Hz), 7.12 (1H, ddd, J=9.86, 8.79, 2.51 Hz), 7.05 (1H, dd, J=8.96, 2.48 Hz), 5.60 (1H, s), 1.65 (3H, d, J=6.80 Hz)

Example 261

[(S)-1-(6-Fluoro-1-pyrimidin-2-yl-1H-benzoimidazol-2-yl)-ethyl]-(7H-purin-6-yl)-amine 261

2,4-Bis(4-methoxyphenyl)-2,4-dithioxo-1,3,2,4-dithiadiphosphetane (369 mg, 0.91 mmol) was added to (S)—N-[4-fluoro-2-(pyrimidin-2-ylamino)phenyl]-2-[9-(tetrahydropyran-2-yl)-9H-purin-6-ylamino]propionamide (109 mg, 0.23 mmol) in tetrahydrofuran (5.0 ml) and heated to 80° C. overnight. The reaction mixture was cooled and concentrated in vacuo. The residue was taken up in EtOAc/1M hydrochloric acid (aqueous), and the aqueous layer extracted with EtOAc three times. The aqueous layer was neutralised with sodium hydroxide (1M aqueous) and extracted with EtOAc (×3). The neutral organic fractions were washed with brine, dried (Na$_2$SO$_4$) and concentrated in vacuo. The product was purified by chromatography (SiO$_2$, 0-20% methanol in DCM) to yield 261 (35 mg, 41%). LCMS: $R_T$ 3.08 min [M+H]$^+$ 376.0. $^1$H NMR (CDCl$_3$, 400 MHz): δ 8.90 (2H, d, J=4.9 Hz), 8.02 (2H, s), 7.97 (1H, dd, J=9.8, 2.7 Hz), 7.60 (1H, dd, J=8.7, 5.0 Hz), 7.42 (1H, t, J=4.8 Hz), 7.08 (1H, td, J 9.0, 2.6 Hz), 6.52 (1H, br s), 1.83 (3H, d, J=6.8 Hz)

Example 262

N-{6-[(S)-1-(6-Fluoro-1-phenyl-1H-benzoimidazol-2-yl)-ethylamino]-9H-purin-2-yl}-acetamide 262

A mixture of (S)-1-(6-fluoro-1-phenyl-1H-benzoimidazol-2-yl)ethylamine dihydrochloride (0.22 g, 0.68 mmol), N-(6-chloro-9H-purin-2-yl)acetamide (0.20 g, 0.95 mmol) and DIPEA (0.60 mL, 3.38 mmol) in IPA (2 mL) was stirred at 85° C. in a sealed tube for 16 h. The resulting mixture was diluted with DCM/methanol then concentrated in vacuo onto silica gel and this residue was purified by chromatography (SiO$_2$, 0-15% (2M ammonia in methanol) in DCM), and then by preparative HPLC (Phenomenex Gemini 5 μm C18 on a 60 min gradient 20-98% 0.1% HCO$_2$H in acetonitrile/water) to give 262 as a white solid (0.067 g, 23%). LCMS (method K): $R_t$ 3.14 min, [M+H]$^+$ 431. $^1$H NMR (DMSO-d$_6$): δ 13.20-12.50 (1H, bs), 9.60 (1H, s), 8.00 (1H, s), 7.71 (1H, m), 7.60 (2H, s), 7.51-7.49 (3H, m), 7.11-7.08 (1H, m), 6.86 (1H, m), 5.64 (1H, m), 2.10 (3H, s), 1.50 (3H, d, J=6.81 Hz)

Example 267

N—[(S)-1-(6-Fluoro-1-phenyl-1H-benzoimidazol-2-yl)-ethyl]-[1,3,5]triazine-2,4-diamine 267

To a solution of 6-chloro-N—[(S)-1-(6-fluoro-1-phenyl-1H-benzoimidazol-2-yl)ethyl]-[1,3,5]triazine-2,4-diamine (100 mg, 0.26 mmol) in EtOAc (10 mL) was added a slurry of 10% Pd/C (40 mg) in IMS (5 mL) and the reaction mixture stirred at RT under a hydrogen atmosphere for 18 h. The suspension was then filtered through a pad of Celite® and the filtrate was concentrated in vacuo. The residue was purified by column chromatography (C$_{18}$, gradient 20-55% MeOH in 0.5% TFA/H$_2$O) then loaded onto an Isolute® SCX-2 cartridge. The cartridge was washed with MeOH and the product eluted with 0.5M NH$_3$/MeOH affording 267 as a colourless foam (42.3 g, 46%). LCMS (Method K): $R_T$ 3.14 min [M+H]$^+$ 350.0. $^1$H NMR (DMSO-d$_6$, 400 MHz, 80° C.): δ 7.87 (1H, s), 7.66 (1H, dd, J=8.8, 4.9 Hz), 7.60-7.56 (2H, m), 7.54-7.49 (3H, m), 7.08 (1H, bs), 7.04 (1H, ddd, J=9.8, 8.7, 2.5 Hz), 6.77 (1H, dd, J=9.0, 2.5 Hz), 6.28 (2H, bs), 5.23 (1H, quintet, J=7.1 Hz), 1.45 (3H, d, J=6.9 Hz)

Example 269

6-Chloro-N—[(S)-1-(6-fluoro-1-phenyl-1H-benzoimidazol-2-yl)-ethyl]-[1,3,5]triazine-2,4-diamine 269

To an ice-cooled mixture of (5)-1-(6-fluoro-1-phenyl-1H-benzoimidazol-2-yl)ethylamine dihydrochloride (226 mg, 0.69 mmol), 4,6-dichloro-[1,3,5]triazin-2-ylamine (125 mg, 0.76 mmol) and IPA (5 mL) was added DIPEA (0.59 mL, 3.45 mmol). The reaction mixture was stirred at RT (room temperature) for 64 h. The solvent was removed under reduced pressure and the resulting residue was partitioned between EtOAc and aqueous Na$_2$CO$_3$. The aqueous phase was extracted with EtOAc and the combined organic fractions washed with water, followed by brine, then dried (Na$_2$SO$_4$) and concentrated in vacuo. The resulting residue was purified by column chromatography (Si—PCC, eluant EtOAc) affording the title compound as a colourless foam (quantitative). A portion (50 mg) was further purified by column chromatography (Si—PCC, eluant EtOAc) affording 269 after evaporation from acetone as a colourless foam (31.8 mg). LCMS (Method K): $R_T$ 4.06 min [M+H]$^+$ 384.0/385.9. $^1$H NMR (DMSO-d$_6$, 400 MHz, 80° C.): δ 7.69 (1H, bs), 7.66 (1H, dd, J=8.8, 4.9 Hz), 7.60-7.50 (5H, m), 7.07-7.02 (1H, m), 6.78 (2H, bs), 6.77 (1H, dd, J=8.9, 2.4 Hz), 5.21 (1H, quintet, J=7.1 Hz), 1.46 (3H, d, J=6.9 Hz)

Example 270

[(R)-1-(6-Fluoro-1-pyridin-2-yl-1H-benzoimidazol-2-yl)-2-methoxy-ethyl]-(9H-purin-6-yl)-amine 270

A mixture of (R)-1-(6-fluoro-1-pyridin-2-yl-1H-benzoimidazol-2-yl)-2-methoxyethylamine (69 mg, 0.24 mmol), 6-chloro-9-(tetrahydropyran-2-yl)-9H-purine (56 mg, 0.24 mmol) and DIPEA (0.21 mL, 1.2 mmol) in IPA (1 mL) was heated for 16 h at 90° C. After cooling to RT, the volatiles were removed under reduced pressure and the resulting residue loaded onto an Isolute® SCX-2 cartridge. The cartridge was washed with MeOH followed by 2M NH$_3$/MeOH. The basic fractions were combined, concentrated in vacuo and the resulting residue was purified by column chromatography (Si—PCC, gradient 0-7.5% 2M NH$_3$/MeOH in DCM) to afford 270 as a white solid (48 mg, 49%). LCMS (Method K): $R_T$ 3.07 min [M+H]$^+$ 405.0. $^1$H NMR (DMSO-d$_6$, 400 MHz): δ 12.80 (1H, br s), 8.65 (1H, s), 8.16-8.04 (2H, m), 7.98 (1H, s), 7.87-7.81 (1H, m), 7.79 (1H, d, J=8.01 Hz), 7.72 (1H, dd, J=8.82, 4.90 Hz), 7.56-7.49 (1H, m), 7.21-7.10 (2H, m), 6.05 (1H, s), 3.90 (2H, d, J=6.25 Hz), 3.20 (3H, s)

Example 271

4-Amino-6-[(R)-1-(6-fluoro-1-pyridin-2-yl-1H-benzoimidazol-2-yl)-2-methoxy-ethylamino]-pyrimidine-5-carbonitrile 271

A mixture of (R)-1-(6-fluoro-1-pyridin-2-yl-1H-benzoimidazol-2-yl)-2-methoxyethylamine (69 mg, 0.24 mmol), 4-amino-6-chloropyrimidine-5-carbonitrile (37 mg, 0.24 mmol) and DIPEA (0.21 mL, 1.2 mmol) in IPA (1 mL) was heated for 16 h at 90° C. After cooling to RT, the volatiles were removed under reduced pressure and the resulting residue was loaded onto an Isolute® SCX-2 cartridge. The cartridge was washed with MeOH followed by 2M $NH_3$/MeOH. The basic fractions were combined, concentrated in vacuo and the resulting residue purified by column chromatography (Si—PCC, gradient 0-20% DCM in EtOAc) to afford 271 as a yellow solid (78 mg, 80%). LCMS (Method K): $R_T$ 3.52 min [M+H]$^+$ 405.0. $^1$H NMR (DMSO-$d_6$, 400 MHz): δ 8.68-8.64 (1H, m), 8.11 (1H, td, J=7.76, 1.94 Hz), 7.84 (1H, s), 7.79-7.73 (2H, m), 7.66 (1H, d, J=7.94 Hz), 7.56 (1H, ddd, J=7.52, 4.87, 0.98 Hz), 7.30-7.13 (4H, m), 6.03-5.95 (1H, m), 3.83 (2H, d, J=6.59 Hz), 3.19 (3H, s)

Example 272

[1-(7-Bromo-6-methoxy-1-phenyl-1H-benzoimidazol-2-yl)-ethyl]-(9H-purin-6-yl)-amine 272

[(S)-1-(7-Bromo-6-methoxy-1-phenyl-1H-benzoimidazol-2-yl)ethyl]-[9-(tetrahydro-pyran-2-yl)-9H-purin-6-yl]amine (453 mg, 0.83 mmol) was dissolved in HCl in methanol (5 mL, 2.5M) and the reaction stirred at RT for 2 h. The reaction mixture was concentrated in vacuo and the resultant residue was subjected to preparative HPLC (C18 Phenomenex column, 10-90% MeCN in water 0.1% formic acid, 20 min gradient) to yield 272 as a white solid (70 mg, 18%). $^1$H NMR 400 MHz 6 (DMSO-$d_6$): 8.08 (1H, br s), 8.02 (1H, s), 7.84 (1H, br s), 7.59 (1H, d, J=8.6 Hz), 7.55-7.26 (5H, m), 7.05 (1H, d, J=9.0 Hz), 5.15 (1H, br s), 3.79 (3H, s), 1.49 (3H, d, J=6.6 Hz). LCMS (Method K): $R_T$=3.53 min, [M+H]$^+$=464+466

Example 273

{5-Fluoro-3-phenyl-2-[(S)-1-(9H-purin-6-ylamino)-ethyl]-3H-benzoimidazol-4-yl}-morpholin-4-yl-methanone 273

To a solution of 5-fluoro-3-phenyl-2-{(S)-1-[9-(tetrahydro-pyran-2-yl)-9H-purin-6-ylamino]ethyl}-3H-benzoimidazole-4-carboxylic acid (200 mg, 0.39 mmol) and morpholine (42 µL, 0.48 mmol) in DCM (10 mL) was added HATU (197 mg, 0.52 mmol) and the reaction stirred at RT for 1 h. The reaction mixture was diluted with water and extracted with DCM (3×10 mL). The combined organic fractions were washed with brine, dried (MgSO$_4$), concentrated in vacuo and the resultant residue subjected to flash chromatography (SiO$_2$, eluting with 0-10% methanol in EtOAc) LCMS (Method C): $R_T$=2.60 min, [M+H]$^+$=571. The product was dissolved HCl in methanol (5 mL, 2.5M) and the reaction stirred at RT for 2 h. The reaction mixture was concentrated in vacuo and the resultant residue loaded onto an SCX 2 cartridge, washed with methanol then eluted with ammonia in methanol (2M). The eluent was concentrated in vacuo and the residue subjected to HPLC purification (C18, 10-90% MeCN in H$_2$O, 0.1% formic acid, 20 min gradient) to give 273 as a white solid (107 mg, 55%) $^1$H NMR (DMSO-$d_6$+TFA-D, 400 MHz, 80° C.): δ 8.52 (1H, br s), 8.46 (1H, d, J=6.25 Hz), 7.83-7.75 (1H, m), 7.57-7.43 (5H, m), 7.32-7.15 (2H, m), 5.66 (1H, br s), 3.50-3.24 (5H, m), 3.15-3.05 (1H, m), 3.04-2.95 (1H, m), 2.70-2.58 (1H, m), 1.74-1.65 (3H, m). LCMS (Method K): $R_T$=2.63 min, [M+H]$^+$=487, $R_T$=2.66 min, [M+H]$^+$=487

Example 274

[(S)-1-(7-Cyclopropyl-6-fluoro-1-pyridin-2-yl-1H-benzoimidazol-2-yl)-ethyl]-(9H-purin-6-yl)-amine 274

[(S)-1-(7-Cyclopropyl-6-fluoro-1-pyridin-2-yl-1H-benzoimidazol-2-yl)ethyl]-[9-(tetrahydro-pyran-2-yl)-9H-purin-6-yl]amine (59 mg, 0.12 mmol) was dissolved in HCl in methanol (5 mL, 2.5M) and the reaction stirred at RT for 30 min. The reaction mixture was concentrated in vacuo and the resultant residue subjected to preparative HPLC (C18 Phenomenex column, 5-80% MeCN in water 0.1% formic acid, 20 min gradient) to yield 274 as a white solid (28 mg, 57%). $^1$H NMR 400 MHz (DMSO-$d_6$): δ 12.83 (1H, br s), 8.50 (1H, br s), 8.22-7.58 (7H, m), 7.00 (1H, dd, J=11.3, 9.4 Hz), 5.66-5.20 (1H, m), 1.52 (3H, d, J=6.6 Hz), 1.32-1.21 (1H, m), 0.37-0.20 (2H, m), 1.89-0.07 (1H, m), 0.03-0.00 (1H, m), LCMS (Method K): $R_T$=3.27 min, [M+H]$^+$=415

Example 275

4-Amino-6-[(S)-1-(6-fluoro-1-pyridin-2-yl-1H-benzoimidazol-2-yl)-ethylamino]-pyrimidine-5-carbonitrile 275

A mixture of (S)-1-(6-fluoro-1-pyridin-2-yl-1H-benzoimidazol-2-yl)ethylamine (281 mg, 1.1 mmol), 4-amino-6-chloropyrimidine-5-carbonitrile (170 mg, 1.1 mmol) and DIPEA (1 mL, 5.5 mmol) in IPA (2 mL) was heated for 16 h at 90° C. After cooling to RT, the volatiles were removed under reduced pressure and the resulting residue loaded onto an Isolute® SCX-2 cartridge. The cartridge was washed with MeOH followed by 2M $NH_3$/MeOH. The basic fractions were combined, concentrated in vacuo and the resulting residue purified by column chromatography (Si—PCC, gradient 0-20% DCM in EtOAc) to afford 275 as a white solid (295 mg, 72%). LCMS (Method K): $R_T$ 3.37 min [M+H]$^+$ 375.0. $^1$H NMR (DMSO-$d_6$, 400 MHz): δ 8.60 (1H, ddd, J=4.88, 1.91, 0.81 Hz), 8.06 (1H, td, J=7.75, 1.94 Hz), 7.86 (1H, s), 7.78-7.68 (3H, m), 7.50 (1H, ddd, J=7.52, 4.87, 0.98 Hz), 7.21-7.11 (4H, m), 5.87-5.78 (1H, m), 1.53 (3H, d, J=6.83 Hz)

Example 277

4-Amino-6-{(S)-1-[6-fluoro-1-(5-fluoro-pyridin-3-yl)-1H-benzoimidazol-2-yl]-ethylamino}-pyrimidine-5-carbonitrile 277

A mixture of {(S)-1-[6-fluoro-1-(5-fluoropyridin-3-yl)-1H-benzoimidazol-2-yl]ethyl}carbamic acid tert-butyl ester (165 mg, 0.44 mmol) in DCM (3 mL) and TFA (1 mL) was stirred at RT for 2 h. The reaction mixture was loaded onto an Isolute® SCX-2 cartridge and washed with MeOH followed by 2M $NH_3$/MeOH. The basic fractions were combined and concentrated in vacuo to afford a yellow oil. A mixture of this residue, 4-amino-6-chloropyrimidine-5-carbonitrile (68 mg, 0.44 mmol) and DIPEA (230 mL, 1.32 mmol) in IPA (1 mL) was heated at 90° C. in a sealed vial for 16 h. After cooling to RT, the crude mixture was diluted with MeOH and loaded onto an Isolute® SCX-2 cartridge. The cartridge was washed with MeOH followed by 2M $NH_3$/MeOH. The basic fractions were combined, concentrated in vacuo and the resulting residue purified by column chromatography (Si—PCC, gradient 0-100% EtOAc in cyclohexane) followed by trituration from EtOAc/cyclohexane/Et$_2$O to afford 277 as an off white solid (73 mg, 42% over 2 steps). $^1$H NMR (DMSO-d$_6$, 400 MHz): δ 8.66 (1H, d, J=2.64 Hz), 8.62 (1H, s), 8.11-8.03 (1H, m), 7.83 (1H, s), 7.78-7.73 (2H, m), 7.26-7.04 (4H, m), 5.64-5.54 (1H, m), 1.58 (3H, d, J=6.77 Hz). LCMS (Method K): R$_T$ 3.40 min [M+H]$^+$ 393

Alternatively, to a suspension of {(S)-1-[6-fluoro-1-(5-fluoropyridin-3-yl)-1H-benzoimidazol-2-yl]ethyl}carbamic acid tert-butyl ester (10.1 g, 27.0 mmol) in MeOH (40 mL) was added 4M HCl in dioxane (100 mL). After stirring the resulting solution at RT for 1 h, the mixture was evaporated to dryness to give a dark green solid (13.7 g). To a suspension of this solid was added 4-amino-6-chloropyrimidine-5-carbonitrile (4.17 g, 27.0 mmol) and DIPEA (23 mL, 134.9 mmol) and the resulting mixture heated at 90° C. for 17 h. After cooling to RT, the crude mixture was concentrated in vacuo to remove the majority of the solvents. The resulting residue was partitioned between EtOAc and H$_2$O. The layers were separated and the ageous layer extracted with additional EtOAc. The combined organic fractions were washed with water, brine, dried (Na$_2$SO$_4$) and concentrated in vacuo. The resulting residue was taken up in DCM/EtOAc and purified by column chromatography (120 g Si—PCC, gradient 50-100% EtOAc in cyclohexane) to afford the title compound as a yellow solid (3.3 g). Purification of the impure fractions by chromatography (Si—PCC, gradient 50-100% EtOAc in cyclohexane) gave a further 2.4 g material (overall 5.0 g, 47%). The product (4 g) was taken up in MeOH (~30 mL) and stirred at reflux. To this suspension was added portions of EtOAc until no solid remained (~30 mL added). The hot solution was filtered and the resulting solution allowed to cool to ambient temperature depositing a crystalline substance. After standing overnight, the crystalline material was filtered, washed with a small volume of MeOH and dried under vacuum at 45° C. for 3 days to give 277 as a pale champagne solid (1.65 g). $^1$H NMR (DMSO-d$_6$, 400 MHz): δ 8.66 (1H, d, J=2.64 Hz), 8.62 (1H, s), 8.11-8.03 (1H, m), 7.83 (1H, s), 7.78-7.73 (2H, m), 7.26-7.04 (4H, m), 5.64-5.54 (1H, m), 1.58 (3H, d, J=6.77 Hz). LCMS (Method K): R$_T$ 3.39 min [M+H]$^+$ 393.1

Example 278

2-((S)-3-{6-Fluoro-2-[(S)-1-(9H-purin-6-ylamino)-ethyl]-benzoimidazol-1-yl}-piperidin-1-yl)-ethanol 278

A solution of 2,2-dimethylpropionic acid 2-[(S)-3-(5-fluoro-2-{(S)-2-[9-(tetrahydropyran-2-yl)-9H-purin-6-ylamino]propionylamino}phenylamino)piperidin-1-yl]ethyl ester (583 mg, 0.95 mmol), in aqueous 6M HCl (20 mL) was refluxed for 30 min. After cooling to RT, volatiles were removed under reduced pressure and the resulting residue loaded in dioxane/water (1:1) onto an Isolute® SCX-2 cartridge. The cartridge was washed with dioxane/water (1:1), then dioxane and the product eluted with 10% 880 NH$_3$ in dioxane. The fractions containing product were purified by column chromatography (C$_{18}$, gradient 2-40% MeOH in 0.5% TFA/H$_2$O) then loaded in dioxane onto an Isolute® SCX-2 cartridge. The cartridge was washed with dioxane then the product eluted with 10% 880 NH$_3$ in dioxane. Further purification by column chromatography (Si—PCC, gradient 3-21% 2M NH$_3$/MeOH in DCM) afforded 278 as a colourless solid (85.8 mg, 21%). LCMS (Method K): R$_T$ 2.05 min [M+H]$^+$ 425.1. $^1$H NMR (CD$_3$OD, 400 MHz): δ 8.29 (1H, s), 8.09 (1H, s), 7.58 (1H, dd, J=9.0, 5.0 Hz), 7.50 (1H, dd, J=9.6, 2.3 Hz), 7.00 (1H, dt, J=9.3, 2.3 Hz), 5.97 (1H, bs), 4.80-4.71 (1H, m), 3.41-3.39 (2H, m), 3.15-3.10 (1H, m), 2.92 (1H, bd, J=11.3 Hz), 2.81 (1H, t, J=11.0 Hz), 2.53-2.21 (4H, m), 2.01-1.97 (1H, m), 1.92-1.86 (1H, m), 1.80 (3H, d, J=6.9 Hz), 1.78-1.70 (1H, m)

Example 279

3-Phenyl-2-[(S)-1-(9H-purin-6-ylamino)-ethyl]-3H-benzoimidazole-4-carbonitrile 279

[(S)-1-(7-Bromo-1-phenyl-1H-benzoimidazol-2-yl)ethyl][9-(tetrahydropyran-2-yl)-9H-purin-6-yl]amine (300 mg, 0.58 mmol) was dissolved in DMF (1 mL) in a microwave vial and zinc cyanide (68 mg, 0.58 mmol) and Pd(PPh$_3$)$_4$ (67 mg, 0.058 mmol) added. The vial was sealed and evacuated and purged with argon (×3). The vial was heated at 150° C. by microwave irradiation for 15 min. The resulting colourless solution was poured onto a mixture of EtOAc and water. A white solid precipitated and was dispersed between the 2 phases. The solid was isolated by filtration and dissolved in DCM and the resulting solution washed with NaHCO$_3$ (satd. aq. soln.). The DCM fraction was passed through a PTFE cartridge. The DCM was removed in vacuo and the residue purified by passage through an SCX cartridge. The cartridge was washed with MeOH and the product eluted with 2M NH$_3$ in MeOH. The product fractions were combined and evaporated and the residue purified by chromatography (Si—PCC) eluting with 0-8% MeOH in DCM. The product fractions were concentrated in vacuo to give white solid. This was triturated in ether, filtered and dried in vacuo to give 279 as a white solid (160 mg, 73%). $^1$H NMR (DMSO-d$_6$, 400 MHz) δ: 8.09 (1H, br s), 8.03 (1H, s), 7.98 (2H, d, J=8.2 Hz), 7.66-7.59 (3H, m), 7.56-7.37 (4H, m), 7.33 (1H, t, J=7.9 Hz), 5.35-5.21 (1H, m), 1.54 (3H, d, J=6.9 Hz). LCMS (Method K): R$_T$ 3.07 min; m/z 381 [M+H]$^+$ Example 280

(R)-2-(6-Fluoro-1-pyridin-2-yl-1H-benzoimidazol-2-yl)-2-(9H-purin-6-ylamino)-ethanol 280

To a solution of [(R)-2-benzyloxy-1-(6-fluoro-1-pyridin-2-yl-1H-benzoimidazol-2-yl)ethyl](7H-purin-6-yl)amine (336 mg, 0.7 mmol) in anhydrous DCM (8 mL) at 0° C. under a nitrogen atmosphere was added dropwise boron tribromide (1.0M in DCM, 2.6 mL, 2.6 mmol). The reaction mixture was stirred at 0° C. for 1 h. MeOH was added and the volatiles removed under reduced pressure. The resulting residue was purified by column chromatography (Si—PCC, gradient 0-10% MeOH in DCM) to afford 280 as a white solid (225 mg, 82%). LCMS (Method K): R$_T$ 2.72 min [M+H]$^+$ 391.0. $^1$H NMR (DMSO-d$_6$, 400 MHz): δ 12.90 (1H, br s), 8.68 (1H, s), 8.20-8.08 (2H, m), 8.03 (1H, s), 7.85 (1H, d, J=7.87 Hz), 7.71 (1H, dd, J=8.80, 4.89 Hz), 7.57 (1H, t, J=6.07 Hz), 7.30-7.06 (3H, m), 5.84 (1H, s), 5.11 (1H, s), 4.01-3.82 (2H, m)

Example 285

4-Amino-6-((S)-1-{6-fluoro-1-[(S)-1-(2-hydroxy-ethyl)-piperidin-3-yl]-1H-benzoimidazol-2-yl}-ethylamino)-pyrimidine-5-carbonitrile 285

A mixture of 2-{(S)-3-[2-((S)-1-aminoethyl)-6-fluorobenzoimidazol-1-yl]piperidin-1-yl}ethanol (35.6 mg, 0.12 mmol), 4-amino-6-chloropyrimidine-5-carbonitrile (18 mg, 0.12 mmol), and DIPEA (40 μL, 0.23 mmol) in IPA (1 mL) was stirred at 90° C. for 3 h. After cooling to RT, volatiles were removed under reduced pressure and the resulting residue purified by column chromatography (Si—PCC, gradient 2-10% 2M NH$_3$/MeOH in DCM) affording 285 as a colourless solid (17 mg, 35%). LCMS (Method K): R$_T$ 2.24 min [M+H]$^+$ 425.1. $^1$H NMR (CD$_3$OD, 400 MHz): δ 8.06 (1H, s), 7.58 (1H, dd, J=8.9, 5.0 Hz), 7.49 (1H, dd, J=9.6, 2.4 Hz), 7.01 (1H, dt, J=9.2, 2.4 Hz), 5.84 (1H, q, J=6.9 Hz), 4.70-4.61 (1H, m), 3.63 (2H, t, J=6.0 Hz), 3.17-3.12 (1H, m), 3.01-2.96 (1H, m), 2.83 (1H, t, J=11.0 Hz), 2.66-2.54 (2H, m), 2.39-2.24 (2H, m), 1.99-1.88 (2H, m), 1.86-1.77 (1H, m), 1.70 (3H, d, J=6.9 Hz)

Example 286

N—[(S)-1-(6-Fluoro-1-phenyl-1H-benzoimidazol-2-yl)-ethyl]-[1,3,5]triazine-2,4,6-triamine 286

To a solution of 6-chloro-N—[(S)-1-(6-fluoro-1-phenyl-1H-benzoimidazol-2-yl)ethyl]-[1,3,5]triazine-2,4-diamine (100 mg, 0.26 mmol) in dioxane (1 mL) was added 880 NH$_3$ (4 mL). The reaction mixture was heated at 100° C. for 1 h using microwave irradiation. After cooling to RT, the reaction mixture was evaporated and purified by column chromatography (Si—PCC, gradient 2-12% 2M NH$_3$/MeOH in DCM) affording 286 as a pink foam (72.9 mg, 77%). LCMS (Method K): R$_T$ 2.89 min [M+H]$^+$ 365.0. $^1$H NMR (DMSO-d$_6$, 400 MHz, 80° C.): δ 7.67-7.60 (3H, m), 7.57-7.51 (3H, m), 7.05 (1H, ddd, J=10.1, 8.8, 2.6 Hz), 6.78 (1H, dd, J=9.0, 2.5 Hz), 6.31 (1H, bd, J=7.5 Hz), 5.61 (4H, bs), 5.22 (1H, quintet, J=7.1 Hz), 1.40 (3H, d, J=6.9 Hz)

Example 288

[(S)-1-(6-Fluoro-7-methyl-1-pyridin-2-yl-1H-benzoimidazol-2-yl)-ethyl]-(9H-purin-6-yl)-amine 288

To a solution of (S)-1-(6-fluoro-7-methyl-1-pyridin-2-yl-1H-benzoimidazol-2-yl)ethylamine dihydrochloride (300 mg, 0.87 mmol) in IPA (10 mL) was added 6-chloro-9-(tetrahydropyran-2-yl)-9H-purine (271 mg, 1.14 mmol) and DIPEA (448 μL, 2.62 mmol) and the reaction mixture heated at 90° C. for 16 h. The reaction mixture was concentrated in vacuo and the resultant residue subjected to flash chromatography (SiO$_2$, eluting with 0-10% methanol in EtOAc). LCMS (Method C): R$_T$=2.81 min, [M+H]$^+$=473. The product was dissolved HCl in methanol (5 mL, 2.5M) and the reaction stirred at RT for 30 min. The reaction mixture was concentrated in vacuo and the resultant residue loaded onto an SCX 2 cartridge, washed with methanol then eluted with ammonia in methanol (2M). The eluent was concentrated in vacuo and the residue triturated with diethyl ether to give 288 as a white solid (174 mg, 51%) $^1$H NMR 400 MHz δ (DMSO-d$_6$ 80° C.): 8.55-8.49 (1H, m), 8.01 (1H, s), 7.89 (1H, td, J=7.7, 1.9 Hz), 7.65 (1H, d, J=7.6 Hz), 7.49 (1H, dd, J=8.7, 4.7 Hz), 7.46 (1H, ddd, J=7.6, 4.9, 0.9 Hz), 7.17 (1H, br s), 7.02 (1H, dd, J=10.6, 9.0 Hz), 5.57 (1H, br s), 1.66 (3H, s), 1.55 (3H, d, J=6.8 Hz). LCMS (Method K): R$_T$=3.01 min, [M+H]+=389

Example 289

4-Amino-6-[(S)-1-(6-fluoro-7-methyl-1-pyridin-2-yl-1H-benzoimidazol-2-yl)-ethylamino]-pyrimidine-5-carbonitrile 289

To a solution of (S)-1-(6-fluoro-7-methyl-1-pyridin-2-yl-1H-benzoimidazol-2-yl)ethylamine dihydrochloride (300 mg, 0.87 mmol) in IPA (10 mL) was added 4-amino-6-chloropyrimidine-5-carbonitrile (135 mg, 0.87 mmol) and DIPEA (448 μL, 2.62 mmol) and the reaction mixture heated at 90° C. for 16 h. The reaction mixture was concentrated in vacuo and the resultant residue subjected to flash chromatography (SiO$_2$, eluting with 0-10% methanol in EtOAc). The product was triturated with diethyl ether then subjected to HPLC purification (C18, 10-90% MeCN in H$_2$O, 0.1% formic acid, 20 min gradient) to give 289 as a white solid (164 mg, 48%). $^1$H NMR 400 MHz 6 (DMSO-d$_6$): 8.55 (1H, br s), 8.00-7.91 (1H, m), 7.81-7.73 (1H, m), 7.70-7.60 (1H, m), 7.53 (1H, dd, J=8.7, 4.6 Hz), 7.55-7.45 (1H, m), 7.21-7.09 (1H, m), 7.06 (1H, dd, J=10.3, 8.7 Hz), 5.65-5.13 (1H, m), 1.63 (3H, s), 1.46 (3H, d, J=6.7 Hz). LCMS (Method K): R$_T$=3.40 min, [M+H]+=389

Example 290

5-Fluoro-2-[(S)-1-(9H-purin-6-ylamino)-ethyl]-3-pyridin-2-yl-3H-benzoimidazole-4-carbonitrile 290

To a solution of 2-((S)-1-aminoethyl)-5-fluoro-3-pyridin-2-yl-3H-benzoimidazole-4-carbonitrile dihydrochloride (250 mg, 0.71 mmol) in IPA (7 mL) was added 6-chloro-9-(tetrahydro-pyran-2-yl)-9H-purine (220 mg, 0.92 mmol) and DIPEA (361 μL, 2.1 mmol) and the reaction mixture heated at 90° C. for 16 h. The reaction mixture was concentrated in vacuo and the resultant residue subjected to flash chromatography (SiO$_2$, eluting with 0-10% methanol in EtOAc). LCMS (Method C): R$_T$=2.86 min, [M+H]+=484. The product was dissolved HCl in methanol (5 mL, 2.5M) and the reaction stirred at RT for 2 h. The reaction mixture was concentrated in vacuo and the resultant residue loaded onto an SCX 2 cartridge, washed with methanol then eluted with ammonia in methanol (2M). The eluent was concentrated in vacuo and the residue triturated with diethyl ether to give 290 as a white solid (174 mg, 51%) $^1$H NMR 400 MHz (DMSO-d$_6$): δ 12.57 (1H, br s), 8.53-8.50 (1H, m), 8.04 (1H, dd, J=9.0, 4.72 Hz), 8.00 (1H, s), 7.96-7.88 (1H, m), 7.74 (1H, d, J=8.0 Hz), 7.47 (1H, dd, J=7.2, 4.9 Hz), 7.43-7.34 (1H, m), 7.30 (1H, dd, J=10.3, 9.2 Hz), 5.71 (1H, br s), 1.62 (3H, d, J=7.0 Hz). LCMS (Method K): R$_T$=2.88 min, [M+H]+=400

Example 292

[(S)-1-(7-Bromo-1-phenyl-1H-benzoimidazol-2-yl)-ethyl]-(9H-purin-6-yl)-amine 292

[(S)-1-(7-Bromo-1-phenyl-1H-benzoimidazol-2-yl)ethyl][9-(tetrahydropyran-2-yl)-9H-purin-6-yl]amine (60 mg, 0.12 mmol) was dissolved in HCl (1 mL, 1M in MeOH) and the resulting solution was stirred for 15 min. The solvent was removed in vacuo and the residue was crystallised from hot IPA to give 292 as white crystals (53 mg, 98%). $^1$H NMR (DMSO-d$_6$, 400 MHz): δ 8.64-8.47 (2H, m), 7.82-7.76 (2H, m), 7.74-7.50 (5H, m), 7.44 (1H, t, J=8.1 Hz), 5.53-5.41 (1H, m), 1.84 (3H, d, J=7.0 Hz). LCMS (Method K): R$_T$ 3.69 min; m/z [M+H]$^+$ 434/436

Example 293

(9H-Purin-6-yl)-[(S)-1-(3-pyridin-2-yl-3H-imidazo[4,5-b]pyridin-2-yl)-ethyl]-amine 293

A mixture of (S)-1-(3-pyridin-2-yl-3H-imidazo[4,5-b]pyridin-2-yl)ethylamine (0.134 g, 0.56 mmol), 6-chloro-9-(tetrahydropyran-2-yl)-9H-purine (0.186 g, 0.78 mmol) and DIPEA (0.18 mL, 1.01 mmol) in IPA (2 mL) was stirred at 90°

C. in a sealed tube for 16 h. The resulting mixture was concentrated in vacuo and residue was purified by chromatography (SiO$_2$, 0-10% (2M ammonia in methanol) in DCM). The product was dissolved in methanol and treated with HCl/dioxane (4M, 1.0 mL, 4.00 mol) and stirred for 30 min. The resulting mixture was loaded onto an Isolute® SCX-2 cartridge, washed with MeOH and the product eluted with 2M NH$_3$/MeOH then concentrated in vacuo to give 293 as a white solid (0.160 g, 80%). LCMS (method K): R$_t$ 2.28 min, [M+H]$^+$ 358. $^1$H NMR (DMSO-d$_6$): δ 13.20-12.70 (1H, bs), 8.59 (1H, s), 8.31 (1H, m), 8.13 (2H, m), 8.03 (2H, tm), 7.81-7.81 (1H, m), 7.47 (1H, s), 7.36 (1H, m), 5.99 (1H, m), 1.67 (3H, d, J=6.82 Hz)

Example 296

4-Amino-6-[1-(6-fluoro-1-pyridin-4-yl-1H-benzoimidazol-2-yl)-ethylamino]-pyrimidine-5-carbonitrile 296

A mixture of 1-(6-fluoro-1-pyridin-4-yl-1H-benzoimidazol-2-yl)ethylamine (55 mg, 0.22 mmol), 4-amino-6-chloropyrimidine-5-carbonitrile (33 mg, 0.22 mmol) and DIPEA (115 μL, 0.64 mmol) in IPA (1 mL) was heated at 90° C. in a sealed vial for 16 h. After cooling to RT, the crude mixture was diluted with MeOH and loaded onto an Isolute® SCX-2 cartridge. The cartridge was washed with MeOH followed by 2M NH$_3$/MeOH. The basic fractions were combined, concentrated in vacuo and the resulting residue purified by column chromatography (Si—PCC, gradient 0-10% MeOH in EtOAc) followed by reverse phase HPLC (Phenomenex Gemini 5 μm C18 on a gradient 5-60%, 0.1% NH$_4$OH in acetonitrile/water) to afford 296 as a pale beige solid (21 mg, 26%). LCMS (Method K): R$_T$ 3.00 min [M+H]$^+$ 375.06. $^1$H NMR (DMSO-d$_6$, 400 MHz): δ 8.75-8.71 (2H, m), 7.88 (1H, s), 7.79-7.72 (2H, m), 7.65-7.60 (2H, m), 7.24-7.12 (3H, m), 7.06 (1H, dd, J=8.98, 2.49 Hz), 5.65-7.56 (1H, m), 1.57 (3H, d, J=6.77 Hz)

Example 302

4-Amino-6-[1-(3-phenyl-3H-imidazo[4,5-b]pyridin-2-yl)-ethylamino]-pyrimidine-5-carbonitrile 302

A mixture of (S)-1-(3-phenyl-3H-imidazo[4,5-b]pyridin-2-yl)ethylamine (0.194 g, 0.81 mmol), 4-amino-6-chloropyrimidine-5-carbonitrile (0.176 g, 1.14 mmol) and DIPEA (0.26 mL, 1.47 mol) in IPA (2 mL) was stirred at 90° C. in a sealed tube for 16 h. The resulting mixture was concentrated in vacuo and the residue purified by chromatography (SiO$_2$, 0-10% MeOH in EtOAc) to give 302 as a white solid (0.190 g, 66%). LCMS (method K): R$_t$ 3.01 min, [M+H]$^+$ 357. $^1$H NMR (DMSO-d$_6$): δ 8.25 (1H, dd, J=4.76, 1.48 Hz), 8.12 (1H, dd, J=7.98, 1.48 Hz), 7.87 (1H, s), 7.72 (1H, d, J=7.21 Hz), 7.53-7.52 (4H, m), 7.32 (1H, dd, J=7.99, 4.77 Hz), 7.19 (2H, s), 5.51 (1H, m, J=6.98 Hz), 1.52 (3H, d, J=6.84 Hz)

Example 303

[1-(6-Fluoro-1-pyridin-4-yl-1H-benzoimidazol-2-yl)-ethyl]-(9H-purin-6-yl)-amine 303

A mixture of 1-(6-fluoro-1-pyridin-4-yl-1H-benzoimidazol-2-yl)ethylamine (60 mg, 0.23 mmol), 6-chloro-9-(tetrahydropyran-2-yl)-9H-purine (59 mg, 0.25 mmol) and DIPEA (125 μL, 0.70 mmol) in n-butanol (0.5 mL) was heated at 100° C. in a sealed vial for 23 h. After cooling to RT, the resulting mixture was diluted with MeOH and loaded onto an Isolute® SCX-2 cartridge. The cartridge was washed with MeOH followed by 2M NH$_3$/MeOH. The basic fractions were combined, concentrated in vacuo and the resulting residue purified by column chromatography (Si—PCC, gradient 0-10% 2M NH$_3$/MeOH in DCM) followed by reverse phase HPLC (Phenomenex Gemini 5 μm C18 on a gradient 5-60%, 0.1% NH$_4$OH in acetonitrile/water) to afford 303 as a pale orange solid (12 mg, 14%). LCMS (Method K): R$_T$ 2.70 min [M+H]$^+$ 375.05. $^1$H NMR (DMSO-d$_6$, 400 MHz): δ 12.90 (1H, s), 8.72-8.66 (2H, m), 8.09-8.01 (2H, m), 7.73-7.67 (3H, m), 7.19-7.01 (2H, m), 5.68-5.11 (1H, m), 1.62 (3H, d, J=7.26 Hz)

Example 304

(S)-3-(6-Fluoro-1-pyridin-2-yl-1H-benzoimidazol-2-yl)-3-(9H-purin-6-ylamino)-propan-1-ol 304

To a solution of [(S)-3-benzyloxy-1-(6-fluoro-1-pyridin-2-yl-1H-benzoimidazol-2-yl)propyl](7H-purin-6-yl)amine (465 mg, 0.8 mmol) in anhydrous DCM (8 mL) at 0° C. under a nitrogen atmosphere was added dropwise boron tribromide (1.0 M in DCM, 2.4 mL, 2.4 mmol). The reaction mixture was stirred at 0° C. for 1 h. MeOH was added and the volatiles removed under reduced pressure. The resulting residue was purified by column chromatography (Si—PCC, gradient 0-15% MeOH in DCM) to afford 304 as a white solid (143 mg, 44%). LCMS (Method K): R$_T$ 2.73 min [M+H]$^+$ 404.9. $^1$H NMR (DMSO-d$_6$, 400 MHz): δ 9.56-9.48 (1H, m), 8.65-8.57 (2H, m), 8.49 (1H, s), 8.11 (1H, td, J=7.74, 1.90 Hz), 7.83-7.74 (2H, m), 7.56 (1H, t, J=6.09 Hz), 7.28-7.16 (2H, m), 6.07-5.97 (1H, m), 3.59-3.45 (2H, m), 2.39-2.29 (1H, m), 2.24-2.12 (1H, m)

Example 305

5-Fluoro-3-phenyl-2-[(S)-1-(9H-purin-6-ylamino)-ethyl]-3H-benzoimidazole-4-carboxylic acid (2-methoxy-ethyl)-amide 305

To a solution of 5-fluoro-3-phenyl-2-{(S)-1-[9-(tetrahydropyran-2-yl)-9H-purin-6-ylamino]ethyl}-3H-benzoimidazole-4-carboxylic acid (180 mg, 0.36 mmol) and 2-methoxyethanolamine (40 mg, 0.54 mmol) in DCM (10 mL) was added HATU (177 mg, 0.47 mmol) and the reaction stirred at RT for 2 h. The reaction mixture was diluted with water and extracted with DCM (3×10 mL). The combined organic fractions were washed with brine, dried (MgSO$_4$), concentrated in vacuo and the resultant residue subjected to flash chromatography (SiO$_2$, eluting with 0-10% methanol in EtOAc) LCMS (Method C): R$_T$=2.51 min, [M+H]+=559. The product was dissolved HCl in methanol (5 mL, 2.5M) and the reaction stirred at RT for 10 min. The reaction mixture was concentrated in vacuo and the resultant residue subjected to HPLC purification (C18, 10-90% MeCN in H$_2$O, 0.1% formic acid, 20 min gradient) to give 305 as a white solid (65 mg, 38%). $^1$H NMR 400 MHz (DMSO-d$_6$): δ 8.29 (1H, t, J=5.3 Hz), 8.08 (1H, br s), 8.02 (1H, s), 84 (1H, br s), 7.64 (1H, dd, J=8.8, 4.9 Hz), 7.50-7.29 (5H, m), 7.07 (1H, t, J=9.4 Hz), 5.22 (1H, s), 3.13 (3H, s), 3.03 (2H, t, J=6.2 Hz), 2.63 (2H, q, J=8.8 Hz), 1.47 (3H, d, J=6.9 Hz). LCMS (Method K): R$_T$=2.50 min, [M+H]+=475

Example 310

(S)—N6-(1-(6-fluoro-1-phenyl-1H-benzo[d]imidazol-2-yl)ethyl)-9H-purine-2,6-diamine 310

A mixture of (S)-1-(6-fluoro-1-phenyl-1H-benzoimidazol-2-yl)ethylamine.2HCl (195 mg, 0.59 mmol), 6-chloro- 9H-purin-2-ylamine (106 mg, 0.62 mmol) and DIPEA (415 μL, 2.38 mmol) in n-butanol (1 mL) was heated at 100° C. in a sealed vial for 24 h. After cooling to RT, the reaction mixture was diluted with MeOH and loaded onto an Isolute® SCX-2 cartridge. The cartridge was washed with MeOH followed by 2M NH$_3$/MeOH. The basic fractions were combined, concentrated in vacuo and the resulting residue purified by column chromatography (Si—PCC, gradient 0-10% 2M NH$_3$/MeOH in DCM) followed by reverse phase HPLC (Phenomenex Gemini 5 μm C18 on a gradient 5-60%, 0.1% NH$_4$OH in acetonitrile/water) to afford 310 as a white solid (52 mg, 23%). LCMS (Method K): R$_T$ 2.89 min [M+H]$^+$ 389.02. $^1$H NMR (CDCl$_3$, 400 MHz): δ 7.67 (1H, dd, J=8.67, 4.59 Hz), 7.62-7.38 (5H, m), 7.20 (1H, s), 7.00 (1H, td, J=9.19, 2.45 Hz), 6.79 (1H, dd, J=8.61, 2.46 Hz), 5.65 (1H, s), 4.92 (1H, s), 1.64 (3H, d, J=6.94 Hz)

Example 311

3-Phenyl-2-[(S)-1-(9H-purin-6-ylamino)-ethyl]-3H-benzoimidazole-4-carboxylic acid amide 311

3-Phenyl-2-[(S)-1-(9H-purin-6-ylamino)ethyl]-3H-benzoimidazole-4-carbonitrile (70 mg, 0.18 mmol) was dissolved in DMSO (2 mL) and to this solution was added a solution of K$_2$CO$_3$ (10 mg) in water (0.1 mL). H$_2$O$_2$ (0.2 mL, 30% in water) was added dropwise and the resulting solution stirred for 2 h. Very slow hydrolysis occurred as observed by LCMS. The solution was heated at 60° C. over 2 days with additional aliquots of H$_2$O$_2$ (2×0.2 mL). The cooled mixture was poured onto water. The resulting aqueous solution was passed through an SCX cartridge, the cartridge was washed with water and MeOH and the product eluted with 2M NH$_3$ in MeOH. The product fractions were combined and evaporated and the residue purified by chromatography (Si—PCC, 0-10% 2M methanolic NH$_3$ in DCM). The product fractions were concentrated in vacuo to give white solid. This was triturated in ether, filtered and dried in vacuo to give 311 as a white solid (35 mg, 50%). $^1$H NMR (DMSO-d$_6$, 400 MHz): δ 8.18-8.00 (2H, m), 7.87-7.77 (1H, m), 7.66 (1H, d, J=7.4 Hz), 7.55-7.27 (6H, m), 7.23-7.13 (2H, m), 6.95 (1H, s), 5.38-5.18 (1H, m), 1.46 (3H, d, J=6.7 Hz). LCMS (Method K): R$_T$ 1.99 min; m/z 399 [M+H]$^+$ Example 313

[(S)-1-(6-Fluoro-1-pyridin-2-yl-1H-benzoimidazol-2-yl)-ethyl]-(2-trifluoromethyl-9H-purin-6-yl)-amine 313

A mixture of (S)-1-(6-fluoro-1-pyridin-2-yl-1H-benzoimidazol-2-yl)ethylamine (0.055 g, 0.22 mmol), 6-chloro-2-trifluoromethyl-9H-purine (0.040 g, 0.18 mmol) and DIPEA (0.096 mL, 5.39 mol) in IPA (1 mL) was stirred at 80° C. in a sealed tube for 16 h. The resulting mixture was concentrated in vacuo and the residue purified by chromatography (SiO$_2$, O-15% (2M ammonia in methanol) in DCM) then by preparative HPLC (Phenomenex Gemini 5 μm C18 on a 60 min gradient 20-98% 0.1% HCO$_2$H in acetonitrile/water) to give 313 as a white solid (0.042 g, 23%). LCMS (method K): R$_T$ 4.11 min, [M+H]$^+$ 443. $^1$H NMR (DMSO-d$_6$) δ: 13.20-12.70 (1H, bs), 8.59 (2H, m), 8.32 (1H, s), 7.97 (1H, m), 7.74-7.67 (2H, m), 7.43 (1H, s), 7.16-7.13 (2H, m), 5.86 (1H, m), 1.69 (3H, d, J=6.82 Hz)

Example 315

4-[(S)-1-(6-Fluoro-1-pyridin-2-yl-1H-benzoimidazol-2-yl)-ethylamino]-pyrimidine-5-carbonitrile 315

(S)-1-(6-Fluoro-1-pyridin-2-yl-1H-benzoimidazol-2-yl)ethylamine (256 mg, 0.54 mmol), 4-chloropyrimidine-5-carbonitrile (139 mg, 0.51 mmol), DIPEA (0.2 mL, 1.14 mmol) and IPA (1 mL) were placed in a sealed tube and the mixture heated at 60° C. for 1 h. The cooled brown mixture was concentrated in vacuo. The residue was dispersed between DCM and water and the DCM extract isolated by passage through a PTFE cartridge. The DCM extract was concentrated in vacuo and the residue purified on silica (Si—PPC, 1-100% EtOAc in DCM). The product fractions were concentrated in vacuo to give 315 as a yellow foam: (100 mg, 52%). 1H NMR (CDCl$_3$, 400 MHz): δ 8.76 (1H, dd, J=4.6, 1.8 Hz), 8.57 (1H, s), 8.41 (1H, s), 8.02 (1H, td, J=7.8, 1.9 Hz), 7.79-7.69 (2H, m), 7.55 (1H, d, J=8.0 Hz), 7.47 (1H, ddd, J=7.5, 4.9, 0.8 Hz), 7.09-7.02 (2H, m), 6.11-6.03 (1H, m), 1.49 (3H, d, J=7.0 Hz). LCMS (Method K): R$_T$ 3.74 min [M+H]$^+$ 360

Example 316

4-[(S)-1-(6-Fluoro-1-phenyl-1H-benzoimidazol-2-yl)-ethylamino]-pyrimidine-5-carbonitrile 316

(S)-1-(6-Fluoro-1-phenyl-1H-benzoimidazol-2-yl)ethylamine dihydrochloride (366 mg, 1.10 mmol), 4-chloropyrimidine-5-carbonitrile (155 mg, 1.10 mmol), DIPEA (0.77 mL, 4.4 mmol) and IPA (1 mL) were placed in a sealed tube and the reaction mixture heated at 90° C. for 2 h. The cooled brown mixture was concentrated in vacuo. The residue was dispersed between DCM and water and the DCM extract isolated by passage through a PTFE cartridge. The DCM extract was concentrated in vacuo and the residue was purified on silica (Si—PPC, 1-8% MeOH in DCM). The product fractions were concentrated in vacuo to give a tan foam. The foam was further purified by chromatography (Si—PCC, 1-100% EtOAc in DCM) to give 316 as a yellow solid (274 mg, 70%). $^1$H NMR (CDCl$_3$, 400 MHz): δ 8.40 (1H, s), 8.19 (1H, d, J=6.2 Hz), 7.72 (1H, dd, J=8.8, 4.8 Hz), 7.60-7.54 (3H, m), 7.27 (1H, br s), 7.04 (1H, td, J=9.2, 2.5 Hz), 6.73 (1H, dd, J=8.5, 2.4 Hz), 6.35 (1H, d, J=6.1 Hz), 5.52 (1H, d, J=7.4 Hz), 4.91 (1H, quin, J=6.9 Hz), 1.62 (3H, d, J=6.8 Hz). LCMS (Method K): R$_T$ 4.20 min [M+H]$^+$ 359

Example 317

[(S)-1-(6-Fluoro-1-phenyl-1H-benzoimidazol-2-yl)-ethyl]-pyrido[3,2-d]pyrimidin-4-yl-amine 317

(S)-1-(6-Fluoro-1-phenyl-1H-benzoimidazol-2-yl)ethylamine dihydrochloride (0.082 g, 0.25 mmol), 4-chloropyrido [3,2-d]pyrimidine (J. Med Chem, 1833, 1996) (0.035 g, 0.21 mmol) and DIPEA (0.174 mL, 1.0 mmol) in IPA (1 mL) was heated to 70° C. in a sealed tube under argon for 1 h. The reaction mixture was cooled, diluted with EtOAc (20 mL) and washed with water (2 mL). The aqueous was extracted with EtOAc (10 mL). The combined organic extracts were dried (Na$_2$SO$_4$), evaporated to dryness and purified by column chromatography (Si—PCC, gradient 0-8% (9:1 MeOH/0.880 NH$_3$) in DCM). Product containing fractions were evaporated and freeze dried to give 317 as an off white solid, (15 mg, 18%). LCMS (Method C): R$_T$ 3.55 min [M+H]$^+$ 385.05. $^1$H NMR δ (ppm) (DMSO-d$_6$): 8.83 (1H, dd, J=4.24, 1.57 Hz), 8.63 (1H, d, J=7.55 Hz), 8.40 (1H, s), 8.11 (1H, dd, J=8.46, 1.57 Hz), 7.84 (1H, dd, J=8.47, 4.24 Hz), 7.74 (1H, dd, J=8.81, 4.85 Hz), 7.59 (2H, d, J=7.53 Hz), 7.50-7.50 (3H, m), 7.12 (1H, ddd, J=9.87, 8.81, 2.53 Hz), 6.86 (1H, dd, J=8.92, 2.51 Hz), 5.59 (1H, dq, J=7.09 Hz), 1.59 (3H, d, J=6.81 Hz)

Example 318

4-Amino-6-{(S)-1-[6-fluoro-7-(morpholine-4-carbonyl)-1-phenyl-1H-benzoimidazol-2-yl]-ethylamino}-pyrimidine-5-carbonitrile 318

To a solution of [2-((S)-1-aminoethyl)-5-fluoro-3-phenyl-3H-benzoimidazol-4-yl]-morpholin-4-ylmethanone dihydrochloride (300 mg, 0.69 mmol) in IPA (5 mL) was added 4-amino-6-chloropyrimidine-5-carbonitrile (108 mg, 0.69 mmol) and DIPEA (353 mL, 2.07 mmol) and the reaction mixture heated at 90° C. for 16 h. The reaction mixture was concentrated in vacuo and the resultant residue subjected to flash chromatography (SiO$_2$, eluting with 0-4% methanol in EtOAc). The product was triturated with diethyl ether. The solid obtained was purified by prep HPLC (C18 Phenomenex column, 10-90% MeCN in water 0.1% formic acid, 20 min gradient) to give the title compound as a white solid (140 mg, 42%). $^1$H NMR 400 MHz δ (DMSO-d$_6$) (mixture of rotamers): 7.80 (0.5H, s), 7.76 (0.5H, s), 7.73 (1H, dd, J=8.8, 4.8 Hz), 7.67 (0.5H, d, J=7.5 Hz), 7.54 (0.5H, d, J=7.2 Hz), 7.50-7.31 (5H, m), 7.19-7.07 (3H, m), 5.28 (0.5H, quin, J=7.1 Hz), 5.21 (0.5H, quin, J=7.0 Hz), 3.48-3.35 (1H, m), 3.34-3.18 (4H, m), 3.10-2.87 (2H, m), 2.56-2.47 (1H, m), 1.47-1.40 (3H, m), LCMS (Method K): R$_T$=2.96 min, [M+H]+= 487, R$_T$=3.00 min, [M+H]+=487 (mixture of rotamers)

Example 321

[(S)-1-(6-Fluoro-1-phenyl-1H-benzoimidazol-2-yl)-ethyl]-imidazo[2,1-f][1,2,4]triazin-4-yl-amine 321

(S)-1-(6-Fluoro-1-phenyl-1H-benzoimidazol-2-yl)ethylamine dihydrochloride (0.106 g, 0.32 mmol), 4-chloroimidazo[2,1-f][1,2,4]triazine (WO2010/014930) (0.050 g, 0.32 mmol) and diisopropylethylamine (0.222 mL, 1.28 mmol) in isopropanol (2 mL) was heated to 60° C. in a sealed tube for 0.5 h. The reaction mixture was cooled and diluted with EtOAc (20 mL) and washed with water (2 mL) The organic extracts were dried (Na$_2$SO$_4$), evaporated to dryness and purified by column chromatography (Si—PCC, gradient 0-10% (9:1 MeOH/0.880 NH$_3$) in DCM). Product containing fractions were evaporated and freeze dried to give 321 as a pale pink solid, (94 mg, 78%). LCMS (Method C): R$_T$ 4.31 min [M+H]$^+$ 374.01. $^1$H NMR δ (ppm) (DMSO-d): 9.15 (1H, d, J=7.24 Hz), 8.02 (1H, d, J=1.09 Hz), 7.95 (1H, s), 7.71 (1H, dd, J=8.81, 4.85 Hz), 7.57-7.54 (3H, m), 7.48-7.39 (3H, m), 7.10 (1H, td, J=9.33, 2.51 Hz), 6.83 (1H, dd, J=8.91, 2.52 Hz), 5.57 (1H, dq, J=7.00 Hz), 1.61 (3H, d, J=6.88 Hz)

Example 322

[(S)-1-(6-Fluoro-1-pyridin-2-yl-1H-benzoimidazol-2-yl)-ethyl]-imidazo[2,1-f][1,2,4]triazin-4-yl-amine 322

(S)-1-(6-Fluoro-1-pyrid-2-yl-1H-benzoimidazol-2-yl)ethylamine (0.066 g, 0.26 mmol), 4-chloroimidazo[2,1-f][1,2,4]triazine (WO2010/014930) (0.040 g, 0.26 mmol) and diisopropylethylamine (0.090 mL, 0.52 mmol) in isopropanol (2 mL) was heated to 60° C. in a sealed tube for 0.5 h. The reaction mixture was cooled and diluted with EtOAc (20 mL) and washed with water (2 mL) The organic extracts were dried (Na$_2$SO$_4$), evaporated to dryness and purified by column chromatography (Si—PCC, gradient 0-10% (9:1 MeOH/0.880 NH$_3$) in DCM). Product containing fractions were evaporated and freeze dried to give 322 as a white solid, (62 mg, 63%). LCMS (Method C): R$_T$ 3.78 min [M+H]$^+$ 375.04. $^1$H NMR δ (ppm) (DMSO-d): 9.13 (1H, d, J=7.61 Hz), 8.57 (1H, dd, J=4.90, 1.81 Hz), 8.01-7.98 (2H, m), 7.93 (1H, s), 7.74-7.73 (2H, m), 7.55 (1H, d, J=1.12 Hz), 7.44-7.44 (1H, m), 7.15-7.15 (2H, m), 5.92 (1H, dq, J=7.11 Hz), 1.65 (3H, d, J=6.87 Hz)

Example 323

5-Chloro-4-[(S)-1-(6-fluoro-1-phenyl-1H-benzoimidazol-2-yl)-ethylamino]-2-methyl-2H-pyridazin-3-one 323

(S)-1-(6-Fluoro-1-phenyl-1H-benzoimidazol-2-yl)ethylamine dihydrochloride (1.0 g, 3.05 mmol), 4,5-dichloro-2-methyl-2H-pyridazin-3-one (J. Org. Chem. 2473-76, 46, 1981) (0.546 g, 3.05 mmol) and diisopropylethylamine (2.1 mL, 12.8 mmol) in isopropanol (5 mL) was heated to reflux for 4.25 h then at 75° C. for 20 h. The reaction mixture was cooled, diluted with EtOAc (20 mL) and washed with 1M sodium carbonate (10 mL). The organic extracts were dried (Na$_2$SO$_4$), evaporated to dryness and purified by column chromatography (Si—PCC, gradient 0-10% MeOH in DCM then gradient 20-100% EtOAc in DCM). Fractions containing the less polar product were evaporated and freeze dried to give 323 as a yellow solid, (78 mg, 6.4%). LCMS (Method C): R$_T$ 4.80 min [M+H]$^+$ 398.00. $^1$H NMR δ (ppm) (DMSO-d): 7.77 (1H, dd, J=8.82, 4.85 Hz), 7.56-7.55 (6H, m), 7.14 (1H, ddd, J=9.9, 8.9, 2.50 Hz), 6.89 (1H, dd, J=8.91, 2.51 Hz), 6.61 (1H, d, J=9.09 Hz), 5.94 (1H, t, J=7.66 Hz), 3.56 (3H, s), 1.51 (3H, d, J=6.65 Hz)

Example 326

4-[(S)-1-(6-Fluoro-1-phenyl-1H-benzoimidazol-2-yl)-ethylamino]-2-methyl-2H-pyridazin-3-one 326

5-Chloro-4-[(S)-1-(6-fluoro-1-phenyl-1H-benzoimidazol-2-yl)ethylamino]-2-methyl-2H-pyridazin-3-one (0.06 g, 0.15 mmol) in ethyl acetate (5 mL) and sat. aq sodium hydrogen carbonate (1 mL) was hydrogenated over 10% palladium on carbon (20 mg) at room temperature and pressure for 3 h. The reaction mix was filtered, evaporated to dryness and purified by column chromatography (Si—PCC, gradient 50-100% EtOAc in DCM). Fractions containing the product were evaporated and freeze dried to give 326 as a white solid, (30 mg, 55%). LCMS (Method C): R$_T$ 4.0 min [M+H]$^+$ 364.09. $^1$H NMR δ (ppm) (DMSO-d): 7.76 (1H, dd, J=8.83, 4.84 Hz), 7.58-7.56 (5H, m), 7.44 (1H, d, J=4.98 Hz), 7.13 (1H, ddd, J=9.9, 8.9, 2.5 Hz), 6.85 (1H, dd, J=8.90, 2.47 Hz), 6.74 (1H, d, J=7.91 Hz), 5.90 (1H, d, J=5.04 Hz), 4.81 (1H, dq, J=7.12 Hz), 3.59 (3H, s), 1.49 (3H, d, J=6.65 Hz)

Example 327

5-Fluoro-3-phenyl-2-[1-(9H-purin-6-ylamino)-ethyl]-3H-benzoimidazol-4-ol 327

A solution of [(S)-1-(7-bromo-6-fluoro-1-phenyl-1H-benzoimidazol-2-yl)ethyl]-[9-(tetrahydropyran-2-yl)-9H-purin-6-yl]amine (300 mg, 0.56 mmol), tris(dibenzylideneacetone)dipalladium (0) (10 mg, 11 µmol), 2-di-tert-butylphosphino-2',4',6'-triisopropylbiphenyl (19 mg, 45 µmol), potassium hydroxide (94 mg, 1.6 mmol) in dioxane (3 mL), and water (2 mL) in a sealed tube were degassed by bubbling argon through the solution then heated by microwave at 150° C. for 30 min. Further portions of tris(dibenzylideneacetone)dipalladium (0) (30 mg, 33 µmol), 2-di-tert-butylphosphino-2',4',6'-triisopropylbiphenyl (57 mg, 135 µmol) were added and the mixture heated by microwave at 180° C. for 1 hour. The reaction mixture was diluted with water and extracted with EtOAc (3×10 mL). The combined organic fractions were washed with brine, dried (MgSO$_4$), concentrated in vacuo. The product was purified by prep HPLC (C18 phenomonix column, 10-90% MeCN in water 0.1% formic acid, 20 min gradient). The product was dissolved in HCl in methanol (1.25 M, 3 mL) and the reaction mixture stirred at RT for 10 min before being concentrated in vacuo. The product was purified by prep HPLC (C18 phenomonix column, 10-90% MeCN in water 0.1% formic acid, 20 min gradient) to give 327 as a white solid (15 mg, 7%). $^1$H NMR 400 MHz δ (d$_6$-DMSO): 9.53-9.38 (1H, m), 8.10-7.99 (2H, m), 7.82-7.69 (1H, m), 7.62-7.27 (5H, m), 7.10-6.93 (2H, m), 5.37-5.17 (1H, m), 1.43 (3H, d, J=7.0 Hz), LCMS (Method K): R$_T$=2.55 min, [M+H]+=390

Example 328

2-Amino-4-[(S)-1-(6-fluoro-1-phenyl-1H-benzoimidazol-2-yl)-ethylamino]-6-methyl-pyrimidine-5-carbonitrile 328

(S)-1-(6-Fluoro-1-phenyl-1H-benzoimidazol-2-yl)ethylamine dihydrochloride (200 mg, 0.6 mmol), 2-amino-4-chloro-6-methylpyrimidine-5-carbonitrile (102 mg, 0.6 mmol), DIPEA (0.4 mL, 2.29 mmol) and IPA (1 mL) were placed in a sealed tube and the mixture was heated at 90° C. for 12 h. The cooled brown mixture was concentrated in vacuo. The residue was dispersed between DCM and water and the DCM extract isolated by passage through a PTFE cartridge. The DCM extract was concentrated in vacuo and the residue purified on silica (Si—PPC 1-5% MeOH in DCM). The product fractions were concentrated in vacuo to give a yellow foam. The foam was crystallised from EtOAc in cyclohexane to give 328 as a pale yellow solid (25 mg, 11%). 1H NMR (CDCl$_3$, 400 MHz): δ 7.70 (1H, dd, J=8.8, 4.8 Hz), 7.59-7.49 (3H, m), 7.38-7.33 (2H, m), 7.02 (1H, td, J=9.2, 2.6 Hz), 6.77 (1H, dd, J=8.5, 2.4 Hz), 6.00 (1H, d, J=8.0 Hz), 5.49 (1H, quin, J=7.3 Hz), 4.89 (2H, br s), 2.33 (3H, s), 1.57 (3H, d, J=6.9 Hz). LCMS (Method K): R$_T$ 3.43 min [M+H]+ 388

Example 330

2-[(S)-1-(6-Amino-5-cyano-pyrimidin-4-ylamino)-ethyl]-5-fluoro-3-phenyl-3H-benzoimidazole-4-carbonitrile 330

To a solution of 2-((S)-1-aminoethyl)-5-fluoro-3-phenyl-3H-benzoimidazole-4-carbonitrile dihydrochloride (110 mg, 0.29 mmol) in IPA (3 mL) was added 4-amino-6-chloropyrimidine-5-carbonitrile (45 mg, 0.29 mmol) and DIPEA (148 µL, 0.87 mmol) and the reaction mixture heated at 90° C. for 16 hours. The reaction mixture was concentrated in vacuo and the resultant residue purified by prep HPLC (C18 phenomenex column, 10-90% MeCN in water 0.1% formic acid, 20 min gradient) to give 330 as a white solid (65 mg, 56%). $^1$H NMR 400 MHz δ (d$_6$-DMSO): 8.08 (1H, dd, J=8.9, 4.9 Hz), 7.78 (1H, s), 7.70 (1H, d, J=7.2 Hz), 7.62-7.56 (1H, m), 7.55-7.43 (4H, m), 7.33 (1H, dd, J=10.4, 9.0 Hz), 7.15 (2H, br s), 5.28 (1H, quin, J=6.9 Hz), 1.48 (3H, d, J=6.9 Hz), LCMS (Method K): R$_T$=3.73 min, [M+H]+=399

Example 332

[(S)-1-(6-Fluoro-1-pyrimidin-4-yl-1H-benzoimidazol-2-yl)-ethyl]-(9H-purin-6-yl)-amine 332

(S)—N-[4-Fluoro-2-(pyrimidin-4-ylamino)phenyl]-2-(9H-purin-6-ylamino)thiopropionamide (9 mg, 0.02 mmol) was heated in toluene at reflux under nitrogen for 15 h. The reaction mixture was purified by column chromatography (Si—PCC, gradient 0-10% (9:1 MeOH/0.880 NH$_3$) in DCM). Product containing fractions were evaporated and freeze dried to give 332 as a colourless solid, (7 mg, 85%). LCMS (Method C): R$_T$ 2.82 min [M+H]+ 376.02 $^1$H NMR (DMSO-d$_6$) δ: 12.8 (1H, bs), 9.20 (1H, s), 8.95 (1H, d, J=5.41 Hz), 8.01-7.89 (4H, m), 7.73 (1H, dd, J=8.81, 4.94 Hz), 7.46 (1H, dd, J=9.30, 2.50 Hz), 7.18 (1H, td, J=9.27, 2.48 Hz), 6.03 (1H, bs), 1.71 (3H, d, J=6.78 Hz)

Example 333

2-Amino-4-[(S)-1-(6-fluoro-1-pyridin-2-yl-1H-benzoimidazol-2-yl)-ethylamino]-6-methyl-pyrimidine-5-carbonitrile 333

(S)-1-(6-Fluoro-1-pyridin-2-yl-1H-benzoimidazol-2-yl)ethylamine (217 mg, 0.85 mmol), 2-amino-4-chloro-6-methylpyrimidine-5-carbonitrile (142 mg, 0.85 mmol), DIPEA (0.6 mL, 3.4 mmol) and IPA (1 mL) were placed in a sealed tube and the mixture heated at 70° C. for 12 h. The cooled brown mixture was concentrated in vacuo. The residue was dispersed between DCM and water and the DCM extract isolated by passage through a PTFE cartridge. The DCM extract was concentrated in vacuo and the residue purified on silica (Si—PPC, 50-100% EtOAc in cyclohexane). The product fractions were concentrated in vacuo to give a red solid. The solid was crystallised from EtOAc in cyclohexane to give 333 as a pale orange solid (40 mg, 12%). $^1$H NMR (CDCl$_3$, 400 MHz): δ 8.79-8.75 (1H, m), 7.99 (1H, td, J=7.7, 1.8 Hz), 7.70 (1H, dd, J=9.4, 4.8 Hz), 7.51-7.43 (2H, m), 7.11 (1H, d, J=8.2 Hz), 7.07-7.00 (2H, m), 5.94-5.85 (1H, m), 5.03 (2H, br s), 2.32 (3H, s), 1.49 (3H, d, J=7.0 Hz). LCMS (Method K): R$_T$ 3.09 min [M+H]+ 389.1

Example 338

[(S)-1-(6-Fluoro-7-methoxy-1-phenyl-1H-benzoimidazol-2-yl)-ethyl]-(9H-purin-6-yl)-amine 338

To a solution of (S)-1-(6-fluoro-7-methoxy-1-phenyl-1H-benzoimidazol-2-yl)ethylamine dihydrochloride (0.16 g, 0.44 mmol) in IPA (3 mL) was added 6-chloro-9-(tetrahydropyran-2-yl)-9H-purine (139 mg, 0.58 mmol) and DIPEA (229 µL, 1.34 mmol) and the reaction mixture heated at 90° C. for 72 hours. The reaction mixture was concentrated in vacuo and the resultant residue was subjected to flash chromatography (SiO$_2$, eluting with 0-10% methanol in EtOAc) to give a white solid: LCMS (Method C): R$_T$=3.13 min, [M+H]+=488. The solid was dissolved in HCl in methanol (1.25 M, 5 mL) and the reaction mixture stirred at RT for 10 min. The reaction mixture was concentrated in vacuo and the resultant residue subjected to prep. HPLC (C18 phenomonix column, 10-90% MeCN in water 0.1% formic acid, 20 min gradient) to give 338 as a white solid (113 mg, 63%). $^1$H NMR 400 MHz δ (d$_6$-DMSO): 8.10-8.00 (2H, m), 7.89-7.75 (1H, m), 7.66-7.29

(7H, m), 7.13-7.02 (1H, m), 5.38-5.17 (1H, m), 3.33 (3H, s), 1.48 (3H, d, J=6.8 Hz), LCMS (Method K): $R_T$=3.40 min, [M+H]$^+$=404

Example 339

4-Amino-6-[(S)-1-(6-fluoro-7-methoxy-1-phenyl-1H-benzoimidazol-2-yl)-ethylamino]-pyrimidine-5-carbonitrile 339

To a solution of (S)-1-(6-fluoro-7-methoxy-1-phenyl-1H-benzoimidazol-2-yl)ethylamine dihydrochloride (160 mg, 0.44 mmol) in IPA (3 mL) was added 4-amino-6-chloropyrimidine-5-carbonitrile (72 mg, 0.47 mmol) and DIPEA (229 µL, 1.34 mmol) and the reaction mixture heated at 90° C. for 72 hours. The reaction mixture was concentrated in vacuo and the resultant residue purified by prep HPLC (C18 phenomenex column, 10-90% MeCN in water 0.1% formic acid, 20 min gradient) to give 339 as a white solid (119 mg, 66%). $^1$H NMR 400 MHz δ (d$_6$-DMSO): 7.80 (1H, s), 7.58 (1H, d, J=7.3 Hz), 7.55-7.47 (2H, m), 7.47-7.40 (3H, m), 7.39 (1H, dd, J=8.8, 4.0 Hz), 7.14 (2H, br s), 7.10 (1H, dd, J=12.2, 8.8 Hz), 5.24 (1H, quin, J=6.9 Hz), 3.32 (3H, d, J=0.7 Hz), 1.43 (3H, d, J=6.8 Hz), LCMS (Method K): $R_T$=3.86 min, [M+H]+= 404

Example 340

4-[(S)-1-(6-Fluoro-1-phenyl-1H-benzoimidazol-2-yl)-ethylamino]-2-methyl-nicotinonitrile 340

(S)-1-(6-Fluoro-1-phenyl-1H-benzoimidazol-2-yl)ethylamine dihydrochloride (0.083 g, 0.25 mmol), 4-chloro-2-methylnicotinonitrile (0.035 g, 0.23 mmol) and diisopropylethylamine (0.160 mL, 0.92 mmol) in isopropanol (1 mL) was heated to 80° C. in a sealed tube under argon for 2 h then at 75° C. for 86 h. The reaction mixture was cooled, diluted with EtOAc (20 mL) and washed with water (10 mL). The organic extracts were dried (Na$_2$SO$_4$), evaporated to dryness and purified by column chromatography (Si—PCC, gradient 0-8% (9:1 MeOH/0.880 NH$_3$) in DCM). Product containing fractions were evaporated and freeze dried to give 340 as a pale brown solid, (21 mg, 24%). LCMS (Method C): $R_T$ 3.11 min [M+H]$^+$ 372.08. $^1$H NMR δ (ppm DMSO-d6): 7.98 (1H, d, J=6.15 Hz), 7.77 (1H, dd, J=8.82, 4.86 Hz), 7.52-7.50 (5H, m), 7.12-7.11 (2H, m), 6.85 (1H, dd, J=8.91, 2.51 Hz), 6.40 (1H, d, J=6.24 Hz), 5.11 (1H, dq, J=7.04 Hz), 2.41 (3H, s), 1.56 (3H, d, J=6.64 Hz)

Example 341

6-Amino-5-chloro-4-[(S)-1-(6-fluoro-1-phenyl-1H-benzoimidazol-2-yl)-ethylamino]-2-methyl-2H-pyridazin-3-one 341

(S)-1-(6-Fluoro-1-phenyl-1H-benzoimidazol-2-yl)ethylamine dihydrochloride (1.0 g, 3.05 mmol), 6-amino-4,5-dichloro-2-methyl-2H-pyridazin-3-one (J. Het Chem, 5-10 37, 2000) (0.59 g, 3.05 mmol) and diisopropylethylamine (2.1 mL, 12.8 mmol) in butanol (5 mL) was heated to 115° C. in a sealed tube under argon for 19 h. The reaction mixture was cooled and diluted with EtOAc (50 mL) and washed with water (20 mL). The organic extracts were dried (Na$_2$SO$_4$), evaporated to dryness and purified by column chromatography (Si—PCC, gradient 1-8% (9:1 MeOH/0.880 NH$_3$) in DCM then gradient 20-100% EtOAc in cyclohexane). Fractions containing the less polar product were evaporated and freeze dried to give 341 as a yellow solid, (167 mg, 13%). LCMS (Method C): $R_T$ 4.01 min [M+H]$^+$ 313.02. $^1$H NMR δ (ppm DMSO-d6): 7.76 (1H, dd, J=8.81, 4.85 Hz), 7.56-7.40 (5H, m), 7.13 (1H, ddd, J=9.85, 8.80, 2.53 Hz), 6.88 (1H, dd, J=8.91, 2.51 Hz), 5.70 (1H, d, J=9.37 Hz), 5.61-5.60 (1H, m), 5.52 (2H, s), 3.37 (3H, s), 1.59 (3H, d, J=6.56 Hz)

Example 344

6-Amino-4-[(S)-1-(6-fluoro-1-phenyl-1H-benzoimidazol-2-yl)-ethylamino]-2-methyl-2H-pyridazin-3-one 344

6-Amino-5-chloro-4-[(S)-1-(6-fluoro-1-phenyl-1H-benzoimidazol-2-yl)ethylamino]-2-methyl-2H-pyridazin-3-one (0.13 g, 0.315 mmol) in ethyl acetate (10 mL) and sat. aq sodium hydrogen carbonate (1 mL) was hydrogenated over 10% palladium on carbon (40 mg) at room temperature and pressure for 24 h. The reaction mix was filtered, evaporated to dryness and purified by column chromatography (Si—PCC, gradient 0-5% (9:1 MeOH/0.880 NH$_3$) in DCM). Fractions containing the product were evaporated and freeze dried to give 344 as a white solid, (77 mg, 64%). LCMS (Method C): $R_T$ 3.57 min [M+H]$^+$ 379.05. $^1$H NMR δ (ppm DMSO-d6): 7.76 (1H, dd, J=8.82, 4.84 Hz), 7.63-7.62 (5H, m), 7.14 (1H, ddd, J=9.9, 8.9, 2.5 Hz), 6.87 (1H, dd, J=8.88, 2.51 Hz), 6.47 (1H, d, J=7.48 Hz), 5.44 (1H, s), 5.18 (2H, s), 4.62 (1H, dq, J=6.95 Hz), 3.40 (3H, s), 1.41 (3H, d, J=6.63 Hz)

Example 345

4-Amino-6-[(S)-1-(7-cyanomethyl-6-fluoro-1-phenyl-1H-benzoimidazol-2-yl)-ethylamino]-pyrimidine-5-carbonitrile 345

To a solution of [2-((S)-1-aminoethyl)-5-fluoro-3-phenyl-3H-benzoimidazol-4-yl]acetonitrile dihydrochloride (100 mg, 0.27 mmol) in IPA (2 mL) was added 4-amino-6-chloropyrimidine-5-carbonitrile (44 mg, 0.28 mmol) and DIPEA (139 µL, 0.82 mmol) and the reaction mixture heated at 90° C. for 16 h. The reaction mixture was concentrated in vacuo and the resultant residue purified by prep HPLC (C18 phenomenex column, 10-90% MeCN in water 0.1% formic acid, 20 min gradient) to give 345 as a white solid (119 mg, 66%). $^1$H NMR 400 MHz δ (d$_6$-DMSO): 7.73 (1H, dd, J=8.8, 4.8 Hz), 7.67 (1H, d, J=7.2 Hz), 7.63-7.58 (1H, m), 7.56-7.45 (4H, m), 7.18 (1H, dd, J=10.6, 8.8 Hz), 7.14 (2H, br s), 5.22 (1H, quin, J=5.2 Hz), 3.38-3.21 (2H, m), 1.47 (3H, d, J=6.8 Hz), LCMS (Method K): $R_T$=3.56 min, [M+H]+=413

Example 346

5-Fluoro-3-(5-fluoro-pyridin-3-yl)-2-[(S)-1-(9H-purin-6-ylamino)-ethyl]-3H-benzoimidazole-4-carbonitrile 346

{(S)-1-[7-Cyano-6-fluoro-1-(5-fluoropyridin-3-yl)-1H-benzoimidazol-2-yl]-ethyl}carbamic acid tert-butyl ester (215 mg, 0.54 mmol) was dissolved in HCl in dioxane (4N, 5 mL) and the reaction mixture stirred at RT for 1 hour. The mixture was concentrated in vacuo and the residue dissolved in IPA (5 mL). 6-Chloro-9-(tetrahydropyran-2-yl)-9H-purine (167 mg, 0.70 mmol) and DIPEA (275 µL, 1.61 mmol) were added and the reaction mixture heated at 90° C. for 16 hours. The reaction mixture was concentrated in vacuo and the resultant residue was subjected to flash chromatography (SiO$_2$, eluting with 0-10% methanol in EtOAc) to give an off white solid LCMS (Method C): $R_T$=2.89 min, [M+H]+=502. The solid was dissolved in HCl in methanol (1.25 M, 5 mL) and the reaction mixture stirred at RT for 10 min. The reaction mixture was concentrated in vacuo and the resultant residue subjected to prep. HPLC (C18 phenomenex column, 10-90% MeCN in water 0.1% formic acid, 20 min gradient) to give 346 as a white solid (66 mg, 29%). $^1$H NMR 300 MHz δ ($d_6$-DMSO): 12.91 (1H, br s), 8.89-8.46 (2H, m), 8.44-7.85 (5H, m), 7.42 (1H, t, J=9.6 Hz), 5.65-5.37 (1H, m), 1.67 (3H, t, J=6.8 Hz), LCMS (Method K): $R_T$=3.03 min, [M+H]+=418

Example 347

2-[(S)-1-(6-Amino-5-cyano-pyrimidin-4-ylamino)-ethyl]-5-fluoro-3-(5-fluoro-pyridin-3-yl)-3H-benzoimidazole-4-carbonitrile 347

{(S)-1-[7-Cyano-6-fluoro-1-(5-fluoropyridin-3-yl)-1H-benzoimidazol-2-yl]-ethyl}carbamic acid tert-butyl ester (215 mg, 0.54 mmol) was dissolved in HCl in dioxane (4N, 5 mL) and the reaction mixture stirred at RT for 1 hour. The mixture was concentrated in vacuo and the residue dissolved in IPA (5 mL) 4-amino-6-chloropyrimidine-5-carbonitrile (87 mg, 0.56 mmol) and DIPEA (275 μL, 1.61 mmol) were added and the reaction mixture heated at 90° C. for 16 h. The reaction mixture was concentrated in vacuo and the resultant residue purified by prep HPLC (C18 phenomenex column, 10-90% MeCN in water 0.1% formic acid, 20 min gradient) to give 347 as a white solid (76 mg, 34%). $^1$H NMR 300 MHz δ ($d_6$-DMSO): 8.83-8.63 (2H, m), 8.38-8.00 (2H, m), 7.87-7.74 (2H, m), 7.43 (1H, t, J=9.6 Hz), 7.25 (2H, br s), 5.58-5.43 (1H, m), 1.65-1.54 (3H, m). LCMS (Method K): $R_T$=3.35 min, [M+H]+=418

Example 348

4-Amino-6-[(S)-1-(6-fluoro-1-pyridin-3-yl-1H-benzoimidazol-2-yl)-ethylamino]-pyrimidine-5-carbonitrile 348

A mixture of (S)-1-(6-fluoro-1-pyridin-3-yl-1H-benzoimidazol-2-yl)ethylamine (80 mg, 0.31 mmol), 4-amino-6-chloropyrimidine-5-carbonitrile (51 mg, 0.33 mmol) and DIPEA (0.16 mL, 0.93 mmol) in IPA (0.7 mL) was heated in a sealed tube for 16 h at 90° C. After cooling to RT, the volatiles were removed under reduced pressure and the resulting residue loaded onto an Isolute® SCX-2 cartridge. The cartridge was washed with MeOH, followed by 2M $NH_3$/MeOH. The basic fractions were combined, concentrated in vacuo and the resulting residue purified by column chromatography (Si—PPC, gradient 0-10% 2M $NH_3$ in MeOH/DCM) to give a pale yellow oil. The residue was taken up in EtOAc and product triturated with cyclohexane. The solid was filtered to afford 348 as an off white solid (31 mg, 26%). LCMS (Method K): $R_T$ 3.04 min [M+H]$^+$ 3.75. $^1$H NMR (DMSO-$d_6$, 400 MHz): δ 8.73 (1H, d, J=2.5 Hz), 8.64 (1H, dd, J=5.0, 1.5 Hz), 8.01-7.98, (1H, m), 7.81 (1H, s), 7.76-7.73 (2H, m), 7.55 (1H, ddd, J=8.0, 5.0, 1.0 Hz), 7.18 (2H, bs), 7.12 (1H, ddd, J=10.0, 9.0, 2.5 Hz), 6.93 (1H, dd, J=7.0, 2.5 Hz), 7.48 (1H, dq, 7.0, 7.0 Hz), 1.55 (3H, d, J=7.0 Hz)

Example 349

4-Amino-6-{(S)-1-[1-(3,5-difluoro-phenyl)-6-fluoro-1H-benzoimidazol-2-yl]-ethylamino}-pyrimidine-5-carbonitrile 349

A mixture of (S)-1-[1-(3,5-difluorophenyl)-6-fluoro-1H-benzoimidazol-2-yl]ethylamine (245 mg, 0.84 mmol), 4-amino-6-chloropyrimidine-5-carbonitrile (137 mg, 0.88 mmol) and DIPEA (0.44 mL, 2.5 mmol) in IPA (1.7 mL) was heated in a sealed tube for 16 h at 90° C. After cooling to RT, the volatiles were removed under reduced pressure and the resulting residue loaded onto an Isolute® SCX-2 cartridge. The cartridge was washed with MeOH, followed by 2M $NH_3$/MeOH. The basic fractions were combined, concentrated in vacuo and the resulting residue purified by column chromatography (Si—PPC, gradient 25-75% EtOAc/cyclohexane) to give colourless oil. The residue was taken up in EtOAc and the product triturated with cyclohexane. The solid was filtered to afford 349 as a white solid (134 mg, 39%). LCMS (Method K): $R_T$ 4.10 min [M+H]$^+$ 410. $^1$H NMR (DMSO-$d_6$, 400 MHz): δ 7.87 (1H, s), 7.76-7.7 (2H, m), 7.36-7.31 (3H, m), 7.18 (2H, bs), 7.13 (1H, ddd, J=10.0, 8.5, 2.5 Hz), 7.05 (1H, dd, J=9.0, 2.5 Hz), 5.64 (1H, dq, J=7.0, 7.0 Hz), 1.56 (3H, d, J=7.0 Hz)

Example 350

4-Amino-6-{(S)-1-[6-fluoro-1-(5-fluoro-pyridin-3-yl)-1H-benzoimidazol-2-yl]-propylamino}-pyrimidine-5-carbonitrile 350

A mixture of (S)-1-[6-fluoro-1-(5-fluoropyridin-3-yl)-1H-benzoimidazol-2-yl]propylamine (88 mg, 0.32 mmol), 4-amino-6-chloro-5-cyanopyrimidine (49 mg, 0.32 mmol) and DIPEA (0.11 mL, 0.64 mmol) in IPA (1 mL) was heated for 5.5 h at 90° C. After cooling to RT, the volatiles were removed in vacuo and the resulting residue was purified by column chromatography (Si—PPC, gradient 0-5% 2M $NH_3$/MeOH in EtOAc) to afford 350 as a pale yellow solid (83 mg, 64%). LCMS (Method K): $R_T$ 3.67 min [M+H]$^+$ 407.0. $^1$H NMR (CDCl$_3$, 400 MHz): δ 8.68 (1H, d, J=2.7 Hz), 8.60 (1H, br s), 8.01 (1H, s), 7.70 (1H, dd, J=9.0, 4.9 Hz), 7.67 (1H, br s), 7.06 (1H, app. td, J=9.2, 2.4 Hz), 6.79 (1H, dd, J=8.3, 2.4 Hz), 6.00 (1H, d, J=8.0 Hz), 5.40 (2H, s), 5.31 (1H, dt, J=8.0, 7.3 Hz), 2.05 (1H, dqd, J=14.7, 7.4, 7.3 Hz), 1.97 (1H, dqd, J=14.7, 7.4, 7.3 Hz), 0.86 (3H, t, J=7.4 Hz)

Example 353

4-Amino-6-[(S)-1-(6-fluoro-7-hydroxymethyl-1-phenyl-1H-benzoimidazol-2-yl)-ethylamino]-pyrimidine-5-carbonitrile 353

To a solution of [2-((S)-1-aminoethyl)-5-fluoro-3-phenyl-3H-benzoimidazol-4-yl]methanol dihydrochloride (159 mg, 0.45 mmol) in IPA (5 mL) was added 4-amino-6-chloropyrimidine-5-carbonitrile (69 mg, 0.45 mmol) and DIPEA (228 μL, 1.33 mmol) and the reaction mixture heated at 80° C. for 16 h. The reaction mixture was concentrated in vacuo and the resultant residue purified by prep HPLC (C18 phenomenex column, 10-90% MeCN in water 0.1% formic acid, 20 min gradient) to give 353 as a white solid (87 mg, 49%). $^1$H NMR 400 MHz δ ($d_6$-DMSO): 7.78 (1H, s), 7.65-7.56 (2H, m), 7.55-7.38 (5H, m), 7.16 (2H, br s), 7.05 (1H, dd, J=10.6, 8.8 Hz), 5.15 (1H, quin, J=6.9 Hz), 4.51 (1H, t, J=5.0 Hz), 3.97 (2H, d, J=5.0 Hz), 1.43 (3H, d, J=6.9 Hz)

Example 358

4-Amino-6-[(S)-1-(6-fluoro-1-phenyl-1H-benzoimidazol-2-yl)-propylamino]-pyrimidine-5-carbonitrile 358

A mixture of (S)-1-(6-fluoro-1-phenyl-1H-benzoimidazol-2-yl)propylamine (62 mg, 0.23 mmol), 4-amino-6- chloro-5-cyanopyrimidine (36 mg, 0.23 mmol) and DIPEA (0.08 mL, 0.46 mmol) in IPA (2 mL) was heated for 6 h at 90° C. After cooling to RT, the volatiles were removed in vacuo and the resulting residue was purified by column chromatography (Si—PPC, gradient 0-5% 2M $NH_3$/MeOH in EtOAc) to afford 358 as a white solid (70 mg, 79%). LCMS (Method K): $R_T$ 4.10 min $[M+H]^+$ 388.1. $^1$H NMR (DMSO-$d_6$, 400 MHz): δ 7.81 (1H, s), 7.68 (1H, dd, J=8.8, 4.9 Hz), 7.56-7.44 (6H, m), 7.16 (2H, br s), 7.07 (1H, ddd, J=9.8, 8.8, 2.5), 6.79 (1H, dd, J=8.9, 2.5), 5.29 (1H, dt, J=7.7, 6.2), 1.97 (1H, dqd, J=14.9, 7.5, 6.2), 1.87 (1H, dqd, J=14.9, 7.5, 6.2), 0.75 (3H, t, J=7.5)

Example 359

{(S)-1-[6-Fluoro-1-(5-fluoro-pyridin-3-yl)-1H-benzoimidazol-2-yl]-propyl}-(9H-purin-6-yl)-amine 359

HCl (0.25 mL of a 4M solution in dioxane) was added to a solution of {(S)-1-[6-fluoro-1-(5-fluoropyridin-3-yl)-1H-benzoimidazol-2-yl]propyl}-[9-(tetrahydropyran-2-yl)-9H-purin-6-yl]amine (96 mg, 0.20 mmol) in MeOH (1 mL) and the reaction mixture stirred at RT for 10 min. The crude reaction mixture was passed through a 2 g Isolute® SCX-2 cartridge, eluting with 2M $NH_3$/MeOH. The basic fraction was concentrated in vacuo to give 359 (76 mg, 94%) as a white solid. LCMS (Method K): $R_T$ 3.23 min $[M+H]^+$ 407.1. $^1$H NMR (CD$_3$OD, 400 MHz): δ 8.59 (1H, s), 8.51 (1H, s), 8.05 (1H, s), 8.03 (1H, br s), 7.95 (1H, d, J=8.4 Hz), 7.65 (1H, dd, J=8.8, 4.6 Hz), 7.07 (1H, ddd, J=9.7, 8.8, 2.6 Hz), 6.88 (1H, dd, J=8.6, 2.6 Hz), 5.54-5.42 (1H, m), 2.26 (1H, dqd, J=14.9, 7.5, 6.4 Hz), 2.12 (1H, dqd, J=14.9, 7.5, 6.4 Hz), 1.01 (3H, t, J=7.5 Hz)

Example 360

[(S)-1-(6-Fluoro-1-phenyl-1H-benzoimidazol-2-yl)-propyl]-(7H-purin-6-yl)-amine 360

HCl (0.22 mL of a 4M solution in dioxane) was added to a solution of [(S)-1-(6-fluoro-1-phenyl-1H-benzoimidazol-2-yl)propyl]-[9-(tetrahydropyran-2-yl)-9H-purin-6-yl]amine (82 mg, 0.17 mmol) in MeOH (2 mL) and the reaction was stirred at RT for 10 min. The reaction mixture was passed through a 2 g Isolute® SCX-2 cartridge, eluting with 2M $NH_3$/MeOH. The basic fraction was concentrated in vacuo to give 360 (65 mg, quant.) as a white solid. LCMS (Method K): $R_T$ 3.58 min $[M+H]^+$ 388.1. $^1$H NMR (CD$_3$OD, 400 MHz): δ 8.06 (1H, s), 8.04 (1H, br s), 7.61 (1H, dd, J=8.8, 4.6 Hz), 7.57-7.43 (5H, m), 7.02 (1H, ddd, J=9.6, 8.8, 2.7 Hz), 6.76 (1H, dd, J=8.7, 2.7 Hz), 5.44 (1H, br s), 2.14 (1H, dqd, J=14.8, 7.4, 6.5 Hz), 2.05 (1H, dqd, J=14.8, 7.4, 6.5 Hz), 0.95 (3H, t, J=7.4 Hz)

Example 361

{(S)-1-[1-(3,5-Difluoro-phenyl)-6-fluoro-1H-benzoimidazol-2-yl]-ethyl}-(9H-purin-6-yl)-amine 361

A solution of {(S)-1-[1-(3,5-difluorophenyl)-6-fluoro-1H-benzoimidazol-2-yl]ethyl}-[9-(tetrahydropyran-2-yl)-9H-purin-6-yl]amine (137 mg, 0.28 mmol) in 4M HCL in dioxane (10 mL) was stirred for 1 h at RT. The reaction mixture was concentrated in vacuo, diluted with MeOH and loaded onto an Isolute® SCX-2 cartridge. The cartridge was washed with MeOH, followed by 2M $NH_3$/MeOH. The basic fractions were combined and concentrated in vacuo. The resulting residue was purified by column chromatography (Si—PPC, gradient 2.5-10% 2M $NH_3$ in MeOH/DCM) to afford 361 as a white solid (48 mg, 42%). LCMS (Method K): $R_T$ 3.65 min $[M+H]^+$ 410. $^1$H NMR (CDCl$_3$, 400 MHz): δ 12.87 (1H, bs), 8.09-7.94 (3H, m), 7.70 (1H, dd, J=9.0, 5.0 Hz), 7.40-7.38 (2H, m), 7.27-7.23 (1H, m), 7.11 (1H, ddd, J=10.0, 10.0, 2.5 Hz), 7.05-7.02 (1H, m), 5.71-5.61 (1H, m), 1.63 (3H, d, J=7.0 Hz)

Example 362

2-Amino-4-[(S)-1-(6-fluoro-1-phenyl-1H-benzoimidazol-2-yl)-ethylamino]-pyrimidine-5-carbonitrile 362

A mixture of (S)-1-(6-fluoro-1-phenyl-1H-benzoimidazol-2-yl)ethylamine.2HCl (85 mg, 0.259 mmol), 2-amino-4-chloropyrimidine-5-carbonitrile (40 mg, 0.26 mmol) and DIPEA (222 µL, 1.29 mmol) in IPA (0.75 mL) was heated at 90° C. in a sealed vial for 21 h. After cooling to RT, the crude mixture was diluted with MeOH and loaded into an Isolute®SCX-2 cartridge. The cartridge was washed with MeOH followed by 2M $NH_3$/MeOH. The basic fractions were combined, concentrated in vacuo and the resulting residue purified by column chromatography (Si—PCC, gradient 0-100% EtOAc in DCM) followed by trituration from EtOAc/Et$_2$O/cyclohexane to afford 362 as a white solid (61 mg, 63%). LCMS (Method K): $R_T$ 3.47 min $[M+H]^+$ 374.02. $^1$H NMR (DMSO-$d_6$, 400 MHz): δ 8.08 (1H, s), 7.74 (1H, dd, J=8.80, 4.85 Hz), 7.68 (1H, d, J=7.49 Hz), 7.58-7.52 (5H, m), 7.16-6.70 (4H, m), 5.51 (1H, m), 1.47 (3H, d, J=6.80 Hz)

Example 363

2-Amino-4-{(S)-1-[6-fluoro-1-(5-fluoro-pyridin-3-yl)-1H-benzoimidazol-2-yl]-ethylamino}-pyrimidine-5-carbonitrile 363

A mixture of (S)-1-[6-fluoro-1-(5-fluoropyridin-3-yl)-1H-benzoimidazol-2-yl]-ethylamine.2HCl (118 mg, 0.34 mmol), 2-amino-4-chloropyrimidine-5-carbonitrile (40 mg, 0.26 mmol) and DIPEA (222 µL, 1.29 mmol) in IPA (0.75 mL) was heated at 90° C. in a sealed vial for 18 h. After cooling to RT, the reaction mixture was diluted with MeOH and loaded into an Isolute® SCX-2 cartridge. The cartridge was washed with MeOH followed by 2M $NH_3$/MeOH. The basic fractions were combined, concentrated in vacuo and the resulting residue purified by column chromatography (Si—PCC, gradient 0-100% EtOAc in DCM) followed by reverse phase HPLC (Phenomenex Gemini 5 µm C18 on a gradient 5-75%, 0.1% $NH_4OH$ in acetonitrile/water) to afford 363 as a white solid (58 mg, 57%). LCMS (Method K): $R_T$ 3.10 min $[M+H]^+$ 392.97. $^1$H NMR (DMSO-$d_6$, 400 MHz): δ 8.66 (1H, d, J=2.64 Hz), 8.62 (1H, s), 8.06 (1H, s), 8.03 (1H, d, J=9.27 Hz), 7.76-7.75 (2H, m), 7.15 (1H, ddd, J=9.85, 8.79, 2.51 Hz), 7.08 (1H, dd, J=8.96, 2.50 Hz), 7.05-6.60 (2H, m), 5.56 (1H, m), 1.55 (3H, d, J=6.75 Hz)

Example 364

2-Amino-4-{(S)-1-[6-fluoro-1-(5-fluoro-pyridin-3-yl)-1H-benzoimidazol-2-yl]-ethylamino}-6-methyl-pyrimidine-5-carbonitrile 364

A mixture of (S)-1-[6-fluoro-1-(5-fluoropyridin-3-yl)-1H-benzoimidazol-2-yl]-ethylamine.2HCl (165 mg, 0.48 mmol), 2-amino-4-chloro-6-methylpyrimidine-5-carbonitrile (60 mg, 0.36 mmol) and DIPEA (315 µL, 1.82 mmol) in IPA (1 mL) was heated at 90° C. in a sealed vial for 18 h. After cooling to RT, the reaction mixture was diluted with MeOH and loaded onto an Isolute® SCX-2 cartridge. The cartridge was washed with MeOH followed by 2M NH$_3$/MeOH. The basic fractions were combined, concentrated in vacuo and the resulting residue purified by column chromatography (Si—PCC, gradient 0-100% EtOAc in cyclohexane) followed by reverse phase HPLC (Phenomenex Gemini 5 µm C18 on a gradient 5-75%, 0.1% NH$_4$OH in acetonitrile/water) to afford 364 as a white solid (21 mg, 15%). LCMS (Method K): R$_T$ 3.04 min [M+H]$^+$ 407.04. $^1$H NMR (DMSO-d$_6$, 400 MHz): δ 8.66 (1H, d, J=2.64 Hz), 8.61 (1H, d, J=1.63 Hz), 8.02 (1H, d, J=9.22 Hz), 7.77 (1H, dd, J=8.80, 4.84 Hz), 7.55 (1H, d, J=7.75 Hz), 7.15 (1H, ddd, J=9.84, 8.79, 2.50 Hz), 7.07 (1H, dd, J=8.96, 2.48 Hz), 7.05-6.58 (2H, m), 5.53 (1H, m), 2.18 (3H, s), 1.54 (3H, d, J=6.75 Hz)

Example 365

2-Amino-4-[1-(3-phenyl-3H-imidazo[4,5-b]pyridin-2-yl)-ethylamino]-pyrimidine-5-carbonitrile 365

A mixture of 1-(3-phenyl-3H-imidazo[4,5-b]pyridin-2-yl)ethylamine (68 mg, 0.29 mmol), 2-amino-4-chloropyrimidine-5-carbonitrile (44 mg, 0.29 mmol) and DIPEA (147 µL, 0.86 mmol) in IPA (1 mL) was heated at 90° C. in a sealed vial for 18 h. After cooling to RT, the reaction mixture was diluted with MeOH and loaded onto an Isolute® SCX-2 cartridge. The cartridge was washed with MeOH followed by 2M NH$_3$/MeOH. The basic fractions were combined, concentrated in vacuo and the resulting residue purified by column chromatography (Si—PCC, gradient 50-100% EtOAc in cyclohexane) followed by trituration from EtOAc to afford 365 as an off-white solid (47 mg, 46%). LCMS (Method K): R$_T$ 2.58 min [M+H]$^+$ 357.09. $^1$H NMR (DMSO-d$_6$, 400 MHz): δ 8.25 (1H, dd, J=4.76, 1.48 Hz), 8.14 (1H, dd, J=7.98, 1.47 Hz), 8.09 (1H, s), 7.72 (1H, d, J=7.41 Hz), 7.55-7.43 (5H, m), 7.32 (1H, dd, J=7.99, 4.77 Hz), 7.16-6.68 (2H, m), 5.55 (1H, m), 1.49 (3H, d, J=6.81 Hz)

Example 366

2-Amino-4-methyl-6-[1-(3-phenyl-3H-imidazo[4,5-b]pyridin-2-yl)-ethylamino]-pyrimidine-5-carbonitrile 366

A mixture of 1-(3-phenyl-3H-imidazo[4,5-b]pyridin-2-yl)ethylamine (66 mg, 0.28 mmol), 2-amino-4-chloro-6-methylpyrimidine-5-carbonitrile (38 mg, 0.23 mmol) and DIPEA (142 µL, 0.831 mmol) in IPA (1 mL) was heated at 90° C. in a sealed vial for 18 h. After cooling to RT, the reaction mixture was diluted with MeOH and loaded into an Isolute® SCX-2 cartridge. The cartridge was washed with MeOH followed by 2M NH$_3$/MeOH. The basic fractions were combined, concentrated in vacuo and the resulting residue purified by column chromatography (Si—PCC, gradient 50-100% EtOAc in cyclohexane) followed by trituration from EtOAc to afford 366 as an off-white solid (41 mg, 40%). LCMS (Method K): R$_T$ 2.54 min [M+H]$^+$ 371.10. $^1$H NMR (DMSO-d$_6$, 400 MHz): δ 8.25 (1H, dd, J=4.77, 1.47 Hz), 8.14 (1H, dd, J=7.98, 1.47 Hz), 7.55-7.44 (6H, m), 7.33 (1H, m), 7.12-6.61 (2H, m), 5.52 (1H, m), 2.21 (3H, s), 1.47 (3H, d, J=6.81 Hz)

Example 367

2-Amino-4-[(S)-1-(6-fluoro-1-pyridin-2-yl-1H-benzoimidazol-2-yl)-ethylamino]-pyrimidine-5-carbonitrile 367

A mixture of (S)-1-(6-fluoro-1-pyridin-2-yl-1H-benzoimidazol-2-yl)ethylamine.2HCl (164 mg, 0.50 mmol), 2-amino-4-chloropyrimidine-5-carbonitrile (77 mg, 0.50 mmol) and DIPEA (427 µL, 2.49 mmol) in IPA (1 mL) was heated at 90° C. in a sealed vial for 17 h. After cooling to RT, the reaction mixture was diluted with MeOH and loaded onto an Isolute® SCX-2 cartridge. The cartridge was washed with MeOH followed by 2M NH$_3$/MeOH. The basic fractions were combined, concentrated in vacuo and the resulting residue purified by column chromatography (Si—PCC, gradient 0-100% EtOAc in cyclohexane) followed by trituration from Et$_2$O to afford 367 as a white solid (72 mg, 39%). LCMS (Method K): R$_T$ 3.06 min [M+H]$^+$ 375.00. $^1$H NMR (DMSO-d$_6$, 400 MHz): δ 8.59 (1H, m), 8.06 (2H, m), 7.77 (2H, m), 7.68 (1H, d, J=7.41 Hz), 7.48 (1H, m), 7.19-6.80 (4H, m), 5.85 (1H, m), 1.52 (3H, d, J=6.81 Hz)

Example 368

2-[(S)-1-(2-Amino-5-cyano-6-methyl-pyrimidin-4-ylamino)-ethyl]-5-fluoro-3-pyridin-2-yl-3H-benzoimidazole-4-carbonitrile 368

A mixture of 2-((S)-1-aminoethyl)-5-fluoro-3-pyridin-2-yl-3H-benzoimidazole-4-carbonitrile (0.085 g, 0.240 mmol), 2-amino-4-chloro-6-methylpyrimidine-5-carbonitrile (0.057 g, 0.335 mmol) and DIPEA (0.17 mL, 0.960 mmol) in IPA (1.5 mL) was stirred at 80° C. in a sealed microwave tube for 16 hours. After cooling, the mixture was concentrated in vacuo and the residue was purified by chromatography (Si—PPC, gradient 0-8% 2M NH$_3$/MeOH in DCM) to give 368 as an off white solid (0.064 g, 64%). LCMS (Method K): R$_T$ 2.87 min [M+H]$^+$ 414.1. $^1$H NMR (DMSO, 400 MHz): δ 8.76-8.74 (1H, d), 8.02-7.97 (1H, t), 7.96-7.92 (1H, m), 7.58-7.54 (1H, m), 7.47-7.44 (1H, d), 7.15-7.10 (1H, t), 6.06-6.02 (1H, d), 5.42-5.35 (1H, m), 5.15-5.11 (2H, s), 2.32 (3H, s), 1.61-1.59 (3H, d)

Example 371

4-amino-6-((6-fluoro-1-phenyl-1H-benzo[d]imidazol-2-yl)methylamino)pyrimidine-5-carbonitrile 371

(6-Fluoro-1-phenyl-1H-benzoimidazol-2-yl)methylamine hydrochloride (0.113 g, 0.4 mmol), 4-amino-6-chloropyrimidine-5-carbonitrile (0.123 g, 0.8 mmol), triethylamine (0.28 mL, 2 mmol) in isopropanol (2 mL) was heated to 80° C. in a sealed tube for 2 h. After cooling the pink solid was removed by filtration and washed with isopropanol (0.5 mL). This material was purified by column chromatography (Si—PCC, gradient 0-4% MeOH in DCM). Product containing fractions were evaporated to a white solid. This was triturated with diethyl ether and dried to give 371 as a white solid, (70 mg, 69%). LCMS (Method C): R$_T$ 3.54 min [M+H]$^+$ 360.02. $^1$H NMR δ (ppm) (DMSO-d): 7.87 (1H, s), 7.69 (1H, t, J=5.2 Hz), 7.65 (1H, dd, J=8.80, 4.87 Hz), 7.64-7.46 (5H, m), 7.22 (2H, s), 7.06 (1H, ddd, J=9.86, 8.79, 2.53 Hz), 6.87 (1H, dd, J=8.97, 2.51 Hz), 4.62 (2H, d, J=5.37 Hz)

Example 372

9-[(6-fluoro-1-phenyl-benzimidazol-2-yl)methyl]purin-2-amine 372

To a stirred mixture of 9H-purin-2-ylamine (93 mg, 0.69 mmol) in DMF (1 mL) at RT and under a nitrogen atmosphere was added NaH (60% in mineral oil, 23 mg, 0.69 mmol). After 5 min, 2-chloromethyl-6-fluoro-1-phenyl-1H-benzoimidazole (150 mg, 0.575 mmol) in DMF (1 mL) was added. Stirring was continued for 18 h at RT. The crude reaction mixture was loaded onto an Isolute® SCX-2 cartridge and washed with MeOH followed by 2M NH$_3$/MeOH. The basic fractions were combined, concentrated in vacuo and the resulting residue purified by column chromatography (Si—PCC, gradient 0-10% 2M NH$_3$/MeOH in DCM) to afford 372 as a white solid (96 mg, 47%). LCMS (Method K): R$_T$ 3.17 min [M+H]$^+$ 360.0. $^1$H NMR (DMSO-d$_6$, 400 MHz): δ 8.56 (1H, s), 8.00 (1H, s), 7.70-7.57 (6H, m), 7.16-7.07 (1H, m), 6.97 (1H, dd, J=8.93, 2.50 Hz), 6.43 (2H, s), 5.48 (2H, s)

Example 373

N-[(1S)-1-(1-cyclobutyl-6-fluoro-benzimidazol-2-yl)ethyl]-9H-purin-6-amine 373

A mixture of (S)-1-(1-cyclobutyl-6-fluoro-1H-benzoimidazol-2-yl)ethylamine (251 mg, 1.1 mmol), 6-chloro-9-(tetrahydropyran-2-yl)-9H-purine (260 mg, 1.1 mmol) and DIPEA (1.0 mL, 5.5 mmol) in n-butanol (4 mL) was heated at 100° C. for 18 h. After cooling to RT, the volatiles were removed under reduced pressure and the resulting residue was loaded onto an Isolute® SCX-2 cartridge. The cartridge was washed with MeOH followed by 2M NH$_3$/MeOH. The basic fractions were combined, concentrated in vacuo and the resulting residue purified by column chromatography (Si—PCC, gradient 0-10% 2M NH$_3$/MeOH in DCM) to afford 373 as a white solid (140 mg, 36%). LCMS (Method K): R$_T$ 2.93 min [M+H]$^+$ 352.1 $^1$H NMR (DMSO-d$_6$, 400 MHz): δ 12.97 (1H, br), 8.33-7.76 (3H, m), 7.69-7.53 (2H, m), 7.09-6.98 (1H, m), 5.87 (1H, br s), 5.27-5.14 (1H, m), 2.93-2.72 (2H, m), 2.44 (1H, br s), 2.23 (1H, br s), 2.02-1.89 (1H, m), 1.82-1.61 (4H, m)

Example 374

N-[(1S)-1-(1-cyclopropyl-6-fluoro-benzimidazol-2-yl)ethyl]-9H-purin-6-amine 374

A mixture of (S)-1-(1-cyclopropyl-6-fluoro-1H-benzoimidazol-2-yl)ethylamine (166 mg, 0.76 mmol), 6-chloro-9-(tetrahydropyran-2-yl)-9H-purine (180 mg, 0.76 mmol) and DIPEA (0.7 mL, 3.8 mmol) in n-butanol (3 mL) was heated at 100° C. for 18 h. After cooling to RT, the volatiles were removed under reduced pressure and the resulting residue loaded onto an Isolute® SCX-2 cartridge. The cartridge was washed with MeOH followed by 2M NH$_3$/MeOH. The basic fractions were combined, concentrated in vacuo and the resulting residue purified by column chromatography (Si—PCC, gradient 0-10% 2M NH$_3$/MeOH in DCM) to afford 374 as a white solid (125 mg, 49%). LCMS (Method K): R$_T$ 2.72 min [M+H]$^+$ 338.1. $^1$H NMR (DMSO-d$_6$, 400 MHz): δ 8.23-8.09 (2H, m), 7.90 (1H, br s), 7.56 (1H, dd, J=8.77, 4.94 Hz), 7.37 (1H, dd, J=9.27, 2.53 Hz), 7.05-6.97 (1H, m), 5.94 (1H, br s), 3.43-3.36 (1H, m), 1.69 (3H, d, J=6.80 Hz), 1.33-1.00 (4H, m)

Example 376

9-[(6-fluoro-1-phenyl-benzimidazol-2-yl)methyl]purin-6-amine 376

Sodium hydride, NaH (60% in mineral oil, 23 mg, 0.69 mmol) was added to a suspension of 9H-purin-6-ylamine (93 mg, 0.69 mmol) in DMF (1 mL) under a nitrogen atmosphere. The reaction mixture was stirred for 15 min then 2-chloromethyl-6-fluoro-1-phenyl-1H-benzoimidazole (148 mg, 0.57 mmol) in DMF (1 mL) added. After 30 min stirring at RT, the temperature was increased to 70° C. and stirring continued for 3 h. The volatiles were removed under reduced pressure and the resulting residue partitioned between DCM and water. The aqueous phase was extracted with DCM (×3) and the combined organic fractions dried (Na$_2$SO$_4$) and concentrated in vacuo. The resulting residue was purified by column chromatography (Si—PCC, gradient 0-10% 2N NH$_3$/MeOH in DCM) to afford still impure 9-(6-fluoro-1-phenyl-1H-benzoimidazol-2-ylmethyl)-9H-purin-6-ylamine. Impure 9-(6-fluoro-1-phenyl-1H-benzoimidazol-2-ylmethyl)-9H-purin-6-ylamine was purified by reverse phase HPLC (Phenomenex Gemini 5 µm C18 on a gradient 20-98%, 0.1% HCO$_2$H in acetonitrile/water) to afford pure 376 as a white solid (45 mg, 22%). LCMS (Method K): R$_T$ 3.18 min [M+H]$^+$ 360.0. $^1$H NMR (DMSO-d$_6$, 400 MHz): δ 8.06 (1H, s), 8.04 (1H, s), 7.68-7.55 (6H, m), 7.21 (2H, br s), 7.15-7.08 (1H, m), 6.97 (1H, dd, J=8.98, 2.55 Hz), 5.58 (2H, s)

Example 377 tert-butyl 3-[6-fluoro-2-[1-(9H-purin-6-ylamino)ethyl]benzimidazol-1-yl]azetidine-1-carboxylate 377

A mixture of 3-[2-((S)-1-aminoethyl)-6-fluorobenzoimidazol-1-yl]azetidine-1-carboxylic acid tert-butyl ester (354 mg, 1.05 mmol), 6-chloro-9-(tetrahydropyran-2-yl)-9H-purine (278 mg, 1.16 mmol) and DIPEA (0.41 mL, 3.18 mmol) in n-butanol (1.4 mL) was heated at 90° C. in a sealed vial for 16 h. After cooling to RT, the volatiles were removed under reduced pressure and the resulting residue loaded onto an Isolute® SCX-2 cartridge and washed with MeOH followed by 2M NH$_3$/MeOH. The basic fractions were combined, concentrated in vacuo and the resulting residue was purified by column chromatography (Si—PCC, gradient 0-5% MeOH in DCM) to afford 377 as a white solid (214 mg, 71%). LCMS (Method K): R$_T$ 3.59 min [M+H]$^+$ 453.1. $^1$H NMR (DMSO-d$_6$, 400 MHz): δ 12.43 (1H, s), 8.23 (1H, br s), 8.14 (1H, br s), 7.96 (1H, d, J=7.67 Hz), 7.68 (1H, dd, J=8.83, 5.02 Hz), 7.36 (1H, dd, J=9.41, 2.45 Hz), 7.11 (1H, td, J=9.29, 2.36 Hz), 5.79 (1H, br s), 5.70-5.60 (1H, m), 4.48-4.34 (2H, m), 4.31-4.19 (2H, m), 1.65 (3H, d, J=6.67 Hz), 1.44 (9H, s)

Example 378

N-[1-[1-(azetidin-3-yl)-6-fluoro-benzimidazol-2-yl]ethyl]-9H-purin-6-amine 378

To a solution of 3-{6-fluoro-2-[(S)-1-(9H-purin-6-ylamino)ethyl]benzoimidazol-1-yl}azetidine-1-carboxylic acid tert-butyl ester (214 mg, 0.47 mmol) in DCM (5 mL) at 0° C. was added TFA (1.7 mL) dropwise. The mixture was stirred at 0° C. for 20 min then slowly warmed to RT. Stirring was continued at RT for 1.5 h. The volatiles were removed under reduced pressure and the resulting residue was loaded onto an Isolute® SCX-2 cartridge, washed with MeOH followed by 2M NH$_3$/MeOH. The basic fractions were combined and concentrated in vacuo to afford 378 as a white solid (160 mg, 96%). LCMS (Method K): R$_T$ 1.73 min [M+H]$^+$ 353.0. $^1$H NMR (DMSO-d$_6$, 400 MHz): δ 8.25 (1H, br s), 8.17-8.07 (2H, m), 7.95 (1H, br s), 7.64 (1H, dd, J=8.82, 5.08 Hz), 7.08 (1H, td, J=9.27, 2.42 Hz), 5.80 (1H, br s), 5.63-5.53

(1H, m), 4.14-4.06 (1H, m), 4.01 (2H, d, J=7.20 Hz), 3.93-3.74 (2H, m), 1.63 (3H, d, J=6.71 Hz)

Example 379

N-[1-(6-fluoro-1-isopropyl-benzimidazol-2-yl) ethyl]-9H-purin-6-amine 379

(S)-1-(6-Fluoro-1-isopropyl-1H-benzoimidazol-2-yl) ethylamine (0.5 g, 2.26 mmol) was dissolved in n-butanol (5 mL) and 6-chloro-9-(tetrahydropyran-2-yl)-9H-purine (0.54 g, 2.26 mmol) and DIPEA (2 mL, 11.3 mmol) added. The resultant dark red solution was heated to 100° C. overnight. The mixture was allowed to cool to RT and was concentrated in vacuo. The residue was purified by column chromatography (silica gel, gradient 0-10% MeOH in DCM) to afford 379 as a pale red solid (207 mg, 27%). LCMS (Method K): $R_T$ 2.68 min [M+H]+ 340.1 $^1$H NMR (DMSO-$d_6$, 400 MHz): δ 8.24 (1H, s), 8.15 (1H, s), 8.00-7.90 (1H, m), 7.64-7.55 (2H, m), 7.02 (1H, td, J=9.31, 2.40 Hz), 5.96-5.77 (1H, m), 4.98-4.85 (1H, m), 1.67 (3H, d, J=6.71 Hz), 1.57 (3H, d, J=6.91 Hz), 1.46 (3H, d, J=6.78 Hz)

Example 380

N-[(1S)-1-[6-fluoro-1-(1-isopropylazetidin-3-yl) benzimidazol-2-yl]ethyl]-9H-purin-6-amine 380

To a solution of [(S)-1-(1-azetidin-3-yl-6-fluoro-1H-benzoimidazol-2-yl)ethyl]-(9H-Aurin-6-yl)amine (80 mg, 0.23 mmol) in DCM (1.5 mL) were added acetone (50 μL, 0.68 mmol) and AcOH (26 μL, 0.45 mmol) followed by MeOH (4 drops). After 10 min stirring at 0° C., NaBH(OAc)$_3$ (96 mg, 0.45 mmol) was added in two portions and the mixture was allowed to warm to RT. Stirring at RT was continued for 3 h then the reaction mixture partitioned between DCM and a saturated aqueous solution of NaHCO$_3$. The aqueous phase was further extracted with DCM and the combined organic fractions washed with water, then brine, dried (Na$_2$SO$_4$) and concentrated in vacuo. The resulting residue was purified by column chromatography (Si—PCC, gradient 0-5% MeOH in DCM) to afford 380 as a white solid (61 mg, 68%). LCMS (Method K): $R_T$ 1.99 min [M+H]+ 395.1. $^1$H NMR (DMSO-$d_6$, 400 MHz): δ 12.25 (1H, s), 8.23 (1H, br s), 8.13 (1H, s), 8.07 (1H, dd, J=10.04, 2.53 Hz), 7.92 (1H, br d, J=7.36 Hz), 7.62 (1H, dd, J=8.81, 5.10 Hz), 7.05 (1H, td, J=9.25, 2.46 Hz), 5.74 (1H, br s), 5.28-5.18 (1H, m), 3.71 (1H, t, J=7.92 Hz), 3.64-3.49 (3H, m), 2.51-2.44 (1H, m), 1.62 (3H, d, J=6.69 Hz), 0.92-0.87 (6H, dd, J=6.14, 4.75 Hz)

Example 381

2-(dimethylamino)-1-[3-[6-fluoro-2-[1-(9H-purin-6-ylamino)ethyl]benzimidazol-1-yl]azetidin-1-yl]ethanone 381

A mixture of [(S)-1-(1-azetidin-3-yl-6-fluoro-1H-benzoimidazol-2-yl)ethyl]-(9H-purin-6-yl)amine (75 mg, 0.21 mmol) dimethylaminoacetic acid (25 mg. 0.23 mmol), 4-methylmorpholine (70 μL, 0.64 mmol) and HATU (93 mg, 0.24 mmol) in DMF (2 mL) was stirred at RT for 4 h. The crude mixture was partitioned between EtOAc and a saturated aqueous solution of NaHCO$_3$. The aqueous phase was further extracted with EtOAc and the combined organic fractions washed with water, followed by brine, dried (MgSO$_4$) and concentrated in vacuo. The resulting residue was purified by column chromatography (Si—PCC, gradient 0-10% 2N NH$_3$/MeOH in DCM) followed by reverse phase HPLC (Phenomenex Gemini 5 μm C18 on a gradient 5-60%, 0.1% NH$_4$OH in acetonitrile/water) to afford 381 as a white solid (20 mg, 22%). LCMS (Method K): $R_T$ 1.86 min [M+H]+ 438.1. $^1$H NMR (DMSO-$d_6$, 400 MHz): δ 8.30-7.92 (3H, m), 7.71-7.63 (1H, m), 7.45-7.34 (1H, m), 7.11 (1H, t, J=9.36 Hz), 5.93-5.58 (2H, m), 4.82-4.69 (1H, m), 4.67-4.56 (1H, m), 4.49-4.34 (1H, m), 4.25-4.26 (1H, m), 3.14 (1H, d, J=14.18 Hz), 2.89 (1H, dd, J=14.18, 3.84 Hz), 2.23 (3H, s), 2.22 (3H, s), 1.67 (3H, d, J=6.66 Hz)

Example 382

5-[6-fluoro-2-[1-(9H-purin-6-ylamino)ethyl]benzimidazol-1-yl]-1H-pyridin-2-one 382

A mixture of (S)—N-[4-fluoro-2-(6-fluoropyridin-3-ylamino)phenyl]-2-(9H-purin-6-ylamino)propionamide (255 mg, 0.62 mmol) in AcOH (10 mL) was heated at 100° C. for 24 h. After cooling to RT, the volatiles were removed under reduced pressure and the residue was partitioned between EtOAc and a saturated aqueous solution of NaHCO$_3$. The aqueous phase was extracted with EtOAc and the combined organic fractions washed with water, followed by brine, dried (Na$_2$SO$_4$) and concentrated in vacuo. The resulting residue was purified by column chromatography (Si—PCC, gradient 0-20% 2M NH$_3$/MeOH in DCM) to afford 382 as a pink solid (38 mg, 16%). LCMS (Method K): $R_T$ 2.40 min [M+H]+ 391.0. $^1$H NMR (DMSO-$d_6$+TFA-D, 400 MHz, 80° C.): δ 8.58-8.49 (2H, m), 7.82 (1H, d, J=2.96 Hz), 7.75 (1H, dd, J=8.81, 4.70 Hz), 7.51 (1H, dd, J=9.59, 2.99 Hz), 7.21-7.07 (2H, m), 6.40 (1H, d, J=9.60 Hz), 5.86 (1H, br d), 1.79 (3H, d, J=6.82 Hz)

Example 383

2-[3-[6-fluoro-2-[1-(9H-purin-6-ylamino)ethyl]benzimidazol-1-yl]azetidin-1-yl]ethanol 383

To a solution of [(S)-1-(1-azetidin-3-yl-6-fluoro-1H-benzoimidazol-2-yl)ethyl]-(9H-purin-6-yl)amine (200 mg, 0.57 mmol) in DCE (7 mL) were added (tert-butyldimethylsilyloxy)acetaldehyde (132 μL, 0.62 mmol) and AcOH (39 μL, 0.68 mmol) followed by MeOH (4 drops). After 10 min stirring at 0° C., NaBH(OAc)$_3$ (168 mg, 0.79 mmol) was added in two portions and the mixture allowed to warm to RT. Stirring at RT was continued for 18 h and then the reaction mixture was partitioned between DCM and a saturated aqueous solution of NaHCO$_3$. The aqueous phase was extracted with DCM and the combined organic fractions washed with water, then brine, dried (Na$_2$SO$_4$) and concentrated in vacuo. The resulting residue was purified by column chromatography (Si—PCC, gradient 0-10% 2N NH$_3$/MeOH in DCM) to afford [(S)-1-(1-{1-[2-(tert-butyldimethylsilanyloxy)ethyl]azetidin-3-yl}-6-fluoro-1H-benzoimidazol-2-yl)ethyl]-(9H-Aurin-6-yl)amine (211 mg, 73%).

A solution of the material thus obtained (211 mg) in tetra-n-butylammonium fluoride (1M in THF, 0.38 mL, 0.38 mmol) was stirred for 4 h at RT. The volatiles were removed under reduced pressure and the resulting residue purified by column chromatography (Si—PCC, gradient 0-15% 2N NH$_3$/MeOH in DCM) followed by reverse phase HPLC (Phenomenex Gemini 5 μm C18 on a 30 min gradient 5-60%, 0.1% NH$_4$OH in acetonitrile/water) to afford 383 as a white solid (118 mg, 72%). LCMS (Method K): $R_T$ 1.78 min [M+H]+ 397.0. $^1$H NMR (DMSO-$d_6$, 400 MHz): δ 8.25 (1H, br s), 8.17-8.11 (2H, m), 7.93 (1H, d, J=7.85 Hz), 7.63 (1H, dd, J=8.81, 5.10 Hz), 7.07 (1H, td, J=9.25, 2.46 Hz), 5.76 (1H, br s), 5.40-5.31 (1H, m), 4.48 (1H, br s), 3.80-3.71 (2H, m), 3.69-3.55 (2H, m), 3.46-3.39 (2H, br m), 2.64 (2H, t, J=5.88 Hz), 1.63 (3H, d, J=6.69 Hz)

Example 386 methyl 3-cyclopropyl-5-fluoro-2-[(1S)-1-(9H-purin-6-ylamino)ethyl]benzimidazole-4-carboxylate 386

A solution of 3-cyclopropyl-5-fluoro-2-{(S)-1-[9-(tetrahydro-pyran-2-yl)-9H-purin-6-ylamino]ethyl}-3H-benzoimidazole-4-carboxylic acid methyl ester (178 mg, 0.37 mmol) in DCM was loaded onto an Isolute® SCX-2 cartridge which was washed with MeOH followed by 2M NH$_3$/MeOH. The basic fractions were combined, concentrated in vacuo and the resulting residue subjected to a second SCX-2 cartridge purification. The basic fractions were combined, concentrated in vacuo and the resulting residue purified by column chromatography (Si—PCC, gradient 0-10% MeOH in DCM) to afford 386 as a white solid (36 mg, 25%). LCMS (Method K): R$_T$ 3.03 min [M+H]$^+$ 396.04. $^1$H NMR (DMSO-d$_6$, 400 MHz): δ 8.25-8.11 (2H, m), 8.03 (1H, s), 7.73 (1H, dd, J=8.81, 4.72 Hz), 7.13 (1H, t, J=9.78 Hz), 5.98 (1H, s), 3.94 (3H, s), 1.68 (3H, d, J=6.74 Hz), 1.17-0.84 (4H, m)

Example 389

[3-cyclopropyl-5-fluoro-2-[(1S)-1-(9H-purin-6-ylamino)ethyl]benzimidazol-4-yl]-morpholino-methanone 389

A mixture of 3-cyclopropyl-5-fluoro-2-{(S)-1-[9-(tetrahydropyran-2-yl)-9H-purin-6-ylamino]ethyl}-3H-benzoimidazole-4-carboxylic acid (64 mg, 0.14 mmol), HATU (63 mg, 0.17 mmol), morpholine (18 μL, 0.216 mmol) and DIPEA (47 μL, 0.28 mmol) in DCM (2 mL) was stirred at RT for 1 h. The crude mixture was loaded onto an Isolute® SCX-2 cartridge which was washed with MeOH followed by 2M NH$_3$/MeOH. The basic fractions were combined, concentrated in vacuo and the resulting residue purified by column chromatography (Si—PCC, gradient 0-10% MeOH in DCM) to afford 389 (46 mg, 75%) as a white solid. LCMS (Method K): R$_T$ 2.49 and 2.53 min [M+H]$^+$ 451.05. $^1$H NMR (DMSO-d$_6$, 400 MHz): δ 8.24-7.83 (3H, m), 7.69-7.60 (1H, m), 7.10 (1H, t, J=9.53 Hz), 6.07-5.84 (1H, m), 3.90-3.83 (1H, m), 3.80-3.72 (1H, m), 3.69-3.59 (2H, m), 3.59-3.50 (2H, m), 3.41-3.35 (2H, m), 3.28-3.20 (1H, m), 1.72-1.63 (3H, m), 1.26-0.85 (4H, m)

Example 390

3-[6-fluoro-2-[(1S)-1-(9H-purin-6-ylamino)ethyl]benzimidazol-1-yl]cyclobutanol 390

A mixture of [(S)-1-[1-(3-benzyloxycyclobutyl)-6-fluoro-1H-benzoimidazol-2-yl]ethyl]-(9H-purin-6-yl)amine (0.13 g, 0.29 mmol) in DCM (5 mL) was cooled to 0° C. To this mixture was added boron tribromide (2.1 mL, 1.43 mmol) dropwise and the resultant mixture stirred at RT for 2 h. The reaction mixture was quenched with MeOH (2 mL) and concentrated in vacuo. The resulting yellow solid was purified by column chromatography (Si—PCC, gradient 0-10% MeOH in DCM) to afford 390 as an off-white glassy solid (50 mg, 50%). $^1$H NMR (DMSO-d$_6$): δ 8.98 (1H, s), 8.55-8.37 (2H, m), 7.93 (1H, d, J=9.74 Hz), 7.69 (1H, dd, J=8.92, 4.99 Hz), 7.21 (1H, t, J=9.90 Hz), 5.89 (1H, s), 4.86-4.75 (1H, m), 4.05-3.95 (1H, m), 2.97-2.62 (4H, m), 1.70 (3H, d, J=6.75 Hz)

Example 391

3-[6-fluoro-2-[(1S)-1-(9H-purin-6-ylamino)ethyl]benzimidazol-1-yl]cyclobutanol 391

A mixture of [(S)-1-[1-(cis-3-benzyloxycyclobutyl)-6-fluoro-1H-benzoimidazol-2-yl]ethyl]-(9H-purin-6-yl)amine (0.12 g, 0.26 mmol) in DCM (5 mL) cooled to 0° C. To this mixture was added boron tribromide (1M in DCM, 0.53 mL, 0.53 mmol) dropwise and the resultant mixture stirred at RT for 2 h. The reaction mixture was quenched with MeOH (2 mL) and concentrated in vacuo. The resulting yellow was solid purified by column chromatography (Si—PCC, gradient 0-10% MeOH in DCM) to afford 391 as an off-white glassy solid (50 mg, 50%). LCMS (Method K): R$_T$ 2.21 min [M+H]$^+$ 368.3. $^1$H NMR (DMSO-d$_6$): δ 12.8 (1H, br s), 8.21 (1H, s), 8.09 (1H, s), 7.78-7.89 (1H, m), 7.47-7.61 (2H, m), 6.95-7.04 (1H, m), 5.78 (1H, br s), 5.43 (1H, qn, J=8.82 Hz), 5.11 1H, d, J=4.2 Hz), 4.41-4.50 (1H, m), 2.86-3.04 (2H, m), 2.26-2.38 (1H, m), 2.08-2.20 (1H, m), 1.59 (1H, d, J=6.7 Hz)

Example 392

4-amino-6-[[(1S)-1-[6-fluoro-1-(3-hydroxycyclobutyl)benzimidazol-2-yl]ethyl]amino]pyrimidine-5-carbonitrile 392

4-Amino-6-[(S)-1-[1-(trans-3-benzyloxycyclobutyl)-6-fluoro-1H-benzoimidazol-2-yl]ethylamino]-pyrimidine-5-carbonitrile (0.06 g, 0.13 mmol) in DCM (5 mL) cooled to 0° C. To this mixture was added boron tribromide (1M solution in DCM, 0.26 mL, 0.23 mmol) dropwise and the resulting mixture stirred at RT for 2 h. The reaction mixture was quenched with MeOH (2 mL) and concentrated in vacuo. The resulting yellow solid was purified by column chromatography (Si—PCC, gradient 0-10% MeOH in DCM) to afford 392 as a colourless glassy solid (75 mg, quantitative). LCMS (Method K): R$_T$ 2.41 min [M+H]$^+$ 368.3. $^1$H NMR (DMSO-d$_6$): δ 8.17 (1H, d, J=6.44 Hz), 8.07 (1H, s), 7.92 (1H, d, J=9.28 Hz), 7.81 (1H, dd, J=8.98, 4.77 Hz), 7.59 (2H, s), 7.41 (1H, t, J=9.27 Hz), 5.83-5.75 (1H, m), 5.49-5.39 (1H, m), 4.59-4.53 (1H, m), 3.16-2.97 (2H, m), 2.46-2.28 (2H, m), 1.67 (3H, d, J=6.81 Hz Example 393

N-[(1S)-1-(1-benzyl-6-fluoro-benzimidazol-2-yl)ethyl]-9H-purin-6-amine 393

A mixture of (S)-1-(1-benzyl-6-fluoro-1H-benzoimidazol-2-yl)ethylamine (322 mg, 1.20 mmol), 6-chloro-9-(tetrahydropyran-2-yl)-9H-purine (286 mg, 1.20 mmol) and DIPEA (1.07 mL, 5.98 mmol) in IPA (5 mL) was heated at 90° C. in a sealed vial overnight. The resultant mixture was allowed to cool to RT and then concentrated in vacuo. The residue was passed down an Isolute® SCX-2 cartridge, eluting with DCM, MeOH and 2M NH$_3$ in MeOH solution to afford a pale red gum. This was purified by column chromatography (silica gel, gradient 0-10% [2M NH$_3$ in MeOH] in DCM) to afford 393 as a white solid (140 mg, 31%). LCMS (Method K): R$_T$ 3.21 min [M+H]$^+$ 388.1 $^1$H NMR (DMSO-d$_6$, 400 MHz): δ 8.20 (1H, s), 8.13 (1H, s), 8.04-7.93 (1H, s), 7.63 (1H, dd, J=8.80, 4.92 Hz), 7.35-7.17 (4H, m), 7.16-7.10

(2H, m), 7.03 (1H, ddd, J=9.91, 8.78, 2.52 Hz), 5.93-5.75 (1H, m), 5.61 (2H, s), 1.59 (3H, d, J=6.77 Hz)

Example 394

4-amino-6-[[(1S)-1-(1-benzyl-6-fluoro-benzimidazol-2-yl)ethyl]amino]pyrimidine-5-carbonitrile 394

A mixture of (S)-1-(1-benzyl-6-fluoro-1H-benzoimidazol-2-yl)ethylamine (320 mg, 1.19 mmol), 4-amino-6-chloropyrimidine-5-carbonitrile (184 mg, 1.19 mmol) and DIPEA (1.06 mL, 5.95 mmol) in IPA (5 mL) was heated at 90° C. in a sealed vial overnight. The resultant mixture was allowed to cool to RT and then concentrated in vacuo. The residue was purified by column chromatography (silica gel, gradient 0-10% [2M NH$_3$ in MeOH] in DCM) to afford 394 as a white solid (164 mg, 36%). LCMS (Method K): R$_T$ 3.58 min [M+H]$^+$ 388.1 $^1$H NMR (DMSO-d$_6$, 400 MHz): δ 7.94 (1H, s), 7.69 (1H, d, J=7.9 Hz), 7.61 (1H, dd, J=8.9, 4.5 Hz), 7.13-7.28 (5H, m), 6.95-7.05 (3H, m), 5.65 (1H, qn, J=7.9 Hz), 5.46 (2H, q, J=9.91, 5.5 Hz), 3.12 (1H, d, J=5.5 Hz), 1.49 (3H, d, J=6.77 Hz)

Example 395

4-amino-6-[[(1S)-1-(7-bromo-1-cyclopropyl-6-fluoro-benzimidazol-2-yl)ethyl]amino]pyrimidine-5-carbonitrile 395

A mixture of (S)-1-(7-bromo-1-cyclopropyl-6-fluoro-1H-benzoimidazol-2-yl)ethylamine (80 mg, 0.27 mmol), 4-amino-6-chloropyrimidine-5-carbonitrile (41 mg, 0.27 mmol) and DIPEA (140 µL, 0.80 mmol) in IPA (1 mL) was heated at 90° C. in a sealed vial for 16 h. After cooling to RT, the reaction mixture was diluted with MeOH and loaded onto an Isolute® SCX-2 cartridge. The cartridge was washed with MeOH followed by 2M NH$_3$/MeOH. The basic fractions were combined, concentrated in vacuo and the resulting residue purified by column chromatography (Si—PCC, gradient 0-100% EtOAc in cyclohexane) to afford 395 as a white solid (86 mg, 77%). LCMS (Method K): R$_T$ 4.10 min [M+H]$^+$ 415.95. $^1$H NMR (CDCl$_3$, 400 MHz): δ 8.20 (1H, s), 7.56 (1H, dd, J=8.73, 4.57 Hz), 7.10-7.04 (1H, m), 6.27 (1H, d, J=7.81 Hz), 6.06-5.98 (1H, m), 5.32 (2H, s), 3.52-3.46 (1H, m), 1.68 (3H, d, J=6.75 Hz), 1.45-1.33 (3H, m), 1.20-1.14 (1H, m)

Example 396

N-[(1S)-1-[6-fluoro-1-(3-methoxycyclobutyl)benzimidazol-2-yl]ethyl]-9H-purin-6-amine 396

To a solution of (S)-1-[6-fluoro-1-(cis-3-methoxycyclobutyl)-1H-benzoimidazol-2-yl]ethylamine (160 mg, 0.61 mmol) in IPA (1.5 mL) was added 6-chloro-9-(tetrahydropyran-2-yl)-9H-purine (150 mg, 0.61 mmol) and DIPEA (0.53 mL, 3.1 mmol) and the reaction mixture heated at 90° C. for 16 h. After cooling to RT, the volatiles were removed under reduced pressure and the resulting residue loaded onto an Isolute® SCX-2 cartridge. The cartridge was washed with MeOH followed by 2M NH$_3$/MeOH. The basic fractions were combined, concentrated in vacuo and the resulting residue purified by column chromatography (Si—PCC, gradient 0-5% MeOH in DCM) to afford 396 as a white solid (120 mg, 52%). $^1$H NMR 6 (DMSO-d$_6$): 8.24 (1H, s), 8.14 (1H, s), 7.90 (1H, d, J=7.84 Hz), 7.63 (1H, dd, J=8.82, 5.11 Hz), 7.54 (1H, dd, J=9.80, 2.47 Hz), 7.11-7.02 (1H, m), 5.84 (1H, s), 4.99-4.89 (1H, m), 3.81-3.72 (1H, m), 3.23 (3H, s), 2.96-2.59 (4H, m), 1.64 (3H, d, J=6.70 Hz)

Example 397

N-[(1S)-1-[6-fluoro-1-(3-methoxycyclobutyl)benzimidazol-2-yl]ethyl]-9H-purin-6-amine 397

To a solution of (S)-1-[6-fluoro-1-(trans-3-methoxycyclobutyl)-1Hbenzoimidazol-2-yl]ethylamine (79 mg, 0.3 mmol) in IPA (1 mL) was added 6-chloro-9-(tetrahydropyran-2-yl)-9H-purine (72 mg, 0.3 mmol) and DIPEA (0.26 mL, 1.5 mmol) and the reaction mixture heated at 90° C. for 16 h. After cooling to RT, the volatiles were removed under reduced pressure and the resulting residue was loaded onto an Isolute® SCX-2 cartridge. The cartridge was washed with MeOH followed by 2M NH$_3$/MeOH. The basic fractions were combined, concentrated in vacuo and the resulting residue purified by column chromatography (Si—PCC, gradient 0-5% MeOH in DCM) to afford 397 as a white solid (37 mg, 32%). $^1$H NMR δ (DMSO-d$_6$): 12.82 (1H, s), 8.25 (1H, s), 8.14 (1H, s), 7.92 (1H, s), 7.67-7.57 (2H, m), 7.05 (1H, td, J=9.30, 2.38 Hz), 5.86 (1H, s), 5.44-5.33 (1H, m), 4.17 (1H, t, J=6.72 Hz), 3.12 (3H, s), 3.07-2.96 (1H, m), 2.88-2.86 (1H, m), 2.56-2.45 (1H, m), 2.27-2.18 (1H, m), 1.65 (3H, d, J=6.69 Hz)

Example 398

(S)—N-(1-(7-fluoro-5,6-dihydro-4H-imidazo[4,5,1-ij]quinolin-2-yl)ethyl)-9H-purin-6-amine 398

A mixture of (5)-1-(7-fluoro-5,6-dihydro-4H-imidazo[4,5,1-ij]quinolin-2-yl)ethylamine (48.5 mg, 0.221 mmol), 6-chloro-9-(tetrahydropyran-2-yl)-9H-purine (52.9 mg, 0.221 mmol), and DIPEA (0.113 mL, 0.663 mmol) in n-butanol (1 mL) was stirred in a sealed vial at 90° C. for 16 h. After cooling to RT, volatiles were removed under reduced pressure. The residue was dissolved in MeOH (3 mL) and the resulting solution was cooled in an ice bath. HCl in isopropanol (1.25 M, 2 mL) was added and the mixture stirred at 0° C. for 1 h and then concentrated under reduced pressure. The residue was dissolved in MeOH and loaded onto an Isolute® SCX-2 cartridge. The cartridge was washed with MeOH and the product eluted with 0.5 M NH$_3$ in MeOH, further purification by column chromatography (Si—PCC, gradient 2-14% 2M NH$_3$/MeOH in DCM) afforded 398 as a white solid (43.4 mg, 58%). LCMS (Method J): R$_T$ 4.80 min [M+H]$^+$ 338.2. $^1$H NMR ((CD$_3$)$_2$SO, 400 MHz): 12.81 (1H, bs), 8.23 (1H, s), 8.15 (1H, s), 7.96 (1H, d, J=7.8 Hz), 7.37 (1H, dd, J=8.8, 4.2 Hz), 6.92 (1H, dd, J=10.5, 8.8 Hz), 5.80 (1H, bs), 4.29-4.16 (2H, m), 2.87 (2H, t, J=6.1 Hz), 2.16-2.05 (2H, m), 1.68 (3H, d, J=6.8 Hz)

Example 399

3-[6-fluoro-2-[(1S)-1-(9H-purin-6-ylamino)ethyl] benzimidazol-1-yl]cyclobutanecarbonitrile 399

3-[2-((S)-1-Aminoethyl)-6-fluorobenzoimidazol-1-yl]cyclobutanecarbonitrile (0.075 g, 0.29 mmol), 6-chloro-9-(tetrahydropyran-2-yl)-9H-purine (0.070 g, 0.29 mmol) and DIPEA (0.26 mL, 1.45 mmol) in 2-propanol (5 mL) was stirred at 90° C. in a sealed microwave tube for 16 hours. After cooling, the reaction mixture was concentrated in vacuo and the residue loaded onto an Isolute® SCX-2 cartridge which was washed with DCM and MeOH, then the product eluted with 2M NH$_3$/MeOH then concentrated in vacuo. The residue was purified by silica gel chromatography, eluting with 100% DCM—10% methanol in DCM to give 399 as a solid (0.035 g, 32%). LCMS (Method K): R$_T$ 2.76 min [M+H]$^+$ 376.0. $^1$H NMR (MeOD-d$_4$) δ: 8.33 (1H, br s), 8.05 (1H, br s), 7.53-7.61 (2H, m), 6.97-7.04 (1H, m), 6.02 (1H, br s), 5.76-5.87 (1H, m), 3.38-3.49 (2H, m), 3.21-3.30 (2H, m), 2.76-2.88 (1H, m), 2.37-2.47 (1H, m), 1.76 (3H, d, J=6.1 Hz)

Example 400

[3-cyclopropyl-5-fluoro-2-[(1S)-1-(thiazolo[5,4-d] pyrimidin-7-ylamino)ethyl]benzimidazol-4-yl]-morpholino-methanone 400

A mixture of [2-((S)-1-aminoethyl)-3-cyclopropyl-5-fluoro-3H-benzoimidazol-4-yl]-morpholin-4-yl-methanone (108 mg, 0.33 mmol), 7-chloro-thiazolo[5,4-d]pyrimidine (61 mg, 0.36 mmol) and DIPEA (170 µL, 0.98 mmol) in IPA (1 mL) was heated at 90° C. in a sealed vial for 17 h. After cooling to RT, the reaction mixture was diluted with MeOH and loaded onto an Isolute® SCX-2 cartridge. The cartridge was washed with MeOH followed by 2M NH$_3$/MeOH. The basic fractions were combined, concentrated in vacuo and the resulting residue purified by column chromatography (Si—PCC, gradient 0-10% MeOH in DCM) to afford 400 as a pale yellow solid (110 mg, 39%). LCMS (Method K): R$_T$ 3.16 min [M+H]$^+$ 468.02. $^1$H NMR (CDCl$_3$, 400 MHz): δ 8.82 (0.7H, s), 8.77 (0.3H, s), 8.54 (0.3H, s), 8.52 (0.7H, s), 7.73-7.65 (1H, m), 7.17 (0.7H, d, J=8.02 Hz), 7.05-6.95 (1H, m), 6.67 (0.3H, d, J=8.45 Hz), 6.31-6.23 (0.3H, m), 6.14-6.04 (0.7H, m), 4.23-4.14 (1H, m), 3.93-3.72 (4H, m), 3.68-3.51 (2H, m), 3.47-3.33 (2H, m), 1.84 (1H, d, J=6.77 Hz), 1.75 (2H, d, J=6.76 Hz), 1.54-1.46 (0.7H, m), 1.41-1.29 (1H, m), 1.20-1.10 (0.3H, m), 1.03-0.93 (1H, m), 0.86-0.71 (1H, m)

Example 401

4-amino-6-[[(1S)-1-[1-cyclopropyl-6-fluoro-7-(morpholine-4-carbonyl)benzimidazol-2-yl]ethyl]amino] pyrimidine-5-carbonitrile 401

A mixture of [2-((S)-1-aminoethyl)-3-cyclopropyl-5-fluoro-3H-benzoimidazol-4-yl]-morpholin-4-yl-methanone (106 mg, 0.32 mmol), 4-amino-6-chloropyrimidine-5-carbonitrile (54 mg, 0.35 mmol) and DIPEA (170 µL, 0.98 mmol) in IPA (1 mL) was heated at 90° C. in a sealed vial for 17 h. After cooling to RT, the reaction mixture was diluted with MeOH and loaded onto an Isolute® SCX-2 cartridge. The cartridge was washed with MeOH followed by 2M NH$_3$/MeOH. The basic fractions were combined, concentrated in vacuo and the resulting residue purified by column chromatography (Si—PCC, gradient 0-10% MeOH in EtOAc) followed by trituration with EtOAc to afford 401 as a white solid (60 mg, 31%). LCMS (Method K): R$_T$ 2.81 min [M+H]$^+$ 451.06. $^1$H NMR (CDCl$_3$, 400 MHz): δ 8.18 (1H, s), 7.71-7.65 (1H, m), 7.05-6.97 (1H, m), 6.47-6.40 (0.7H, m), 6.15-6.05 (0.3H, m), 5.98-5.88 (1H, m), 5.38-5.31 (2H, m), 4.22-4.14 (1H, m), 3.93-3.72 (4H, m), 3.69-3.52 (2H, m), 3.44-3.33 (2H, m), 1.73 (1H, d, J=6.78 Hz), 1.65 (2H, d, J=6.76 Hz), 1.43-1.24 (2H, m), 1.11-0.93 (1H, m), 0.86-0.69 (1H, m)

Example 402

4-amino-6-[[(1S)-1-[6-fluoro-1-(1-methylpyrazol-3-yl)benzimidazol-2-yl]ethyl]amino]pyrimidine-5-carbonitrile 402

TFA (1 mL) was added to a stirring solution of {(S)-1-[6-fluoro-1-(1-methyl-1H-pyrazol-3-yl)-1H-benzoimidazol-2-yl]ethyl}carbamic acid tert-butyl ester (126 mg, 0.35 mmol) in DCM (3 mL). After stirring at RT for 3 h, the reaction mixture was diluted with MeOH and loaded onto an Isolute® SCX-2 cartridge. The cartridge was washed with MeOH followed by 2M NH$_3$/MeOH. The basic fractions were combined and concentrated in vacuo to give a brown oil. A mixture of this residue, 4-amino-6-chloropyrimidine-5-carbonitrile (60 mg, 0.39 mmol) and DIPEA (205 µL, 1.17 mmol) in IPA (1 mL) was heated at 90° C. in a sealed vial for 16 h. After cooling to RT, the crude mixture was diluted with MeOH and loaded onto an Isolute® SCX-2 cartridge. The cartridge was washed with MeOH followed by 2M NH$_3$/MeOH. The basic fractions were combined, concentrated in vacuo and the resulting residue purified by column chromatography (Si—PCC, gradient 0-10% MeOH in EtOAc) followed by trituration with EtOAc to afford 402 as a white solid (71 mg, 54% over 2 steps). LCMS (Method K): R$_T$ 3.27 min [M+H]$^+$ 378.04. $^1$H NMR (DMSO-d$_6$, 400 MHz): δ 7.97 (1H, s), 7.91 (1H, d, J=2.31 Hz), 7.73 (1H, dd, J=8.66, 4.85 Hz), 7.61 (1H, d, J=7.64 Hz), 7.25 (2H, s), 7.17-7.08 (2H, m), 6.54 (1H, d, J=2.31 Hz), 5.77-5.67 (1H, m), 3.89 (3H, s), 1.52 (3H, d, J=6.87 Hz)

Example 403

N-[(1S)-1-[6-fluoro-1-(1-methylpyrazol-3-yl)benzimidazol-2-yl]ethyl]-9H-purin-6-amine 403

TFA (1 mL) was added to a stirring solution of {(S)-1-[6-fluoro-1-(1-methyl-1H-pyrazol-3-yl)-1H-benzoimidazol-2-yl]ethyl}carbamic acid tert-butyl ester (187 mg, 0.52 mmol) in DCM (3 mL). After stirring at RT for 3 h, the reaction mixture was diluted with MeOH and loaded onto an Isolute® SCX-2 cartridge. The cartridge was washed with MeOH followed by 2M NH$_3$/MeOH. The basic fractions were combined and concentrated in vacuo to give a brown oil. A mixture of this residue, 6-chloro-9-(tetrahydropyran-2-yl)-9H-purine (126 mg, 0.53 mmol) and DIPEA (280 µL, 1.59 mmol) in IPA (1 mL) was heated at 90° C. in a sealed vial for 24 h. After cooling to RT, the reaction mixture was diluted with MeOH and loaded onto an Isolute® SCX-2 cartridge. The cartridge was washed with MeOH followed by 2M NH$_3$/MeOH. The basic fractions were combined, concentrated in vacuo and the resulting residue purified by column chromatography (Si—PCC, gradient 0-10% MeOH in DCM) followed by trituration with EtOAc to afford 403 as a pale brown solid (98 mg, 50% over 2 steps). LCMS (Method K): R$_T$ 2.84 min [M+H]$^+$ 378.03. $^1$H NMR (DMSO-d$_6$, 400 MHz): δ 8.21-8.11 (2H, m), 7.94-7.81 (2H, m), 7.75-7.66 (1H, m), 7.19-7.08 (2H, m), 6.61 (1H, d, J=2.29 Hz), 5.89-5.73 (1H, m), 3.89 (3H, s), 1.61 (3H, d, J=6.84 Hz)

Example 404

4-amino-6-[[(1S)-1-[6-fluoro-1-(3-hydroxycyclobutyl)benzimidazol-2-yl]ethyl]amino]pyrimidine-5-carbonitrile 404

A mixture of 4-amino-6-{(S)-1-[1-(3-benzyloxycyclobutyl)-6-fluoro-1H-benzoimidazol-2-yl] ethylamino}pyrimidine-5-carbonitrile (0.05 g, 0.11 mmol) in DCM (3 mL) was cooled to 0° C. To this mixture was added boron tribromide (0.22 mL, 0.22 mmol) dropwise and the resultant mixture stirred at RT for 2 h. The reaction mixture was quenched with MeOH (2 mL) and concentrated in vacuo. The resulting yellow solid was purified by column chromatography (Si—PCC, gradient 0-10% MeOH in DCM) to afford 404 as an off-white glassy solid (50 mg, 99%). $^1$H NMR (DMSO-d$_6$): δ 7.97-8.09 (3H, m), 7.74 (1H, dd, J=7.75, 4.8 Hz), 7.50 (2H, br s), 7.26-7.36 (1H, m), 5.67 (1H, qn, J=6.7 Hz), 4.70 (1H, qn, J=8.5 Hz), 3.96 (1H, m), 2.72-2.91 (2H, m), 2.55-2.72 (2H, m), 1.6 (3H, d, 7.2 Hz). LCMS (Method K): R$_T$ 2.36 min [M+H]$^+$ 368

Example 405

[(S)-1-(5-Fluoro-6,7,8,9-tetrahydro-2,9a-diazabenzo[cd]azulen-1-yl)ethyl]-(9H-purin-6-yl)amine 405

A mixture of (S)-1-(5-fluoro-6,7,8,9-tetrahydro-2,9a-diazabenzo[cd]azulen-1-yl)ethylamine (70 mg, 0.30 mmol), 6-chloro-9-(tetrahydropyran-2-yl)-9H-purine (71.8 mg, 0.30 mmol), and DIPEA (0.153 mL, 0.90 mmol) in n-butanol (1.5 mL) was stirred in a sealed vial at 90° C. for 16 h. After cooling to RT, volatiles were removed under reduced pressure. The residue was dissolved in MeOH (5 mL) and cooled in an ice bath. HCl in isopropanol (1.25 M, 3 mL) was added and the mixture stirred at 0° C. for 1.5 h and then concentrated under reduced pressure. The residue was dissolved in MeOH and loaded onto an Isolute® SCX-2 cartridge. The cartridge was washed with MeOH and the product eluted with 0.5 M NH$_3$ in MeOH, further purification by column chromatography (Si—PCC, gradient 2-12% 2M NH$_3$/MeOH in DCM) afforded 405 as a white solid (72.8 mg, 69%). LCMS (Method K): R$_T$ 2.68 min [M+H]$^+$ 352.0. $^1$H NMR ((CD$_3$)$_2$SO, 400 MHz): 12.93 (1H, bs), 8.24 (1H, s), 8.15 (1H, s), 7.89 (1H, d, J=7.9 Hz), 7.43 (1H, dd, J=8.7, 4.8 Hz), 6.99 (1H, dd, J=10.8, 8.8 Hz), 5.83 (1H, bs), 4.31-4.29 (2H, m), 3.04-3.01 (2H, m), 2.08-1.94 (4H, m), 1.66 (3H, d, J=6.7 Hz)

Example 406

4-Amino-6-[(S)-1-(5-fluoro-6,7,8,9-tetrahydro-2,9a-diazabenzo[cd]azulen-1-yl)ethylamino]pyrimidine-5-carbonitrile 406

A mixture of (S)-1-(5-fluoro-6,7,8,9-tetrahydro-2,9a-diazabenzo[cd]azulen-1-yl)ethylamine (70 mg, 0.30 mmol), 4-amino-6-chloropyrimidine-5-carbonitrile (46.4 mg, 0.30 mmol), and DIPEA (102 μL, 0.60 mmol) in isopropanol (1.5 mL) was stirred at 90° C. for 3 h. After cooling to RT, volatiles were removed under reduced pressure and the resulting residue was purified by column chromatography (Si—PCC, gradient 2-7% 2M NH$_3$/MeOH in DCM). Crystallisation from MeOH (5 mL) afforded 406 as a white solid (43.2 mg, 41%). LCMS (Method K): R$_T$ 2.91 min [M+H]$^+$ 352.1. $^1$H NMR ((CD$_3$)$_2$SO, 400 MHz): 8.07 (1H, s), 7.69 (1H, d, J=7.5 Hz), 7.45 (1H, dd, J=8.8, 4.8 Hz), 7.31 (2H, bs), 7.00 (1H, dd, J=10.8, 8.7 Hz), 5.67 (1H, quintet, J=6.9 Hz), 4.25-4.14 (2H, m), 3.05-3.01 (2H, m), 2.08-1.93 (4H, m), 1.58 (3H, d, J=6.7 Hz)

Example 407

[(S)-1-(7-Fluoro-4-methyl-5,6-dihydro-4H-imidazo[4,5,1-ij]quinolin-2-yl)ethyl]-(9H-purin-6-yl)amine 407

A mixture of (S)-1-(7-fluoro-4-methyl-5,6-dihydro-4H-imidazo[4,5,1-ij]quinolin-2-yl)ethylamine (15.8 mg, 0.0677 mmol), 6-chloro-9-(tetrahydropyran-2-yl)-9H-purine (17.8 mg, 0.0745 mmol), and DIPEA (0.0346 mL, 0.20 mmol) in n-butanol (0.5 mL) was stirred in a sealed vial at 90° C. for 16 h. After cooling to RT, volatiles were removed under reduced pressure. The residue was dissolved in MeOH (1.5 mL) and cooled in an ice bath. HCl in isopropanol (1.25 M, 1 mL) was added and the mixture stirred at 0° C. for 90 min and then concentrated under reduced pressure. The residue was dissolved in MeOH and loaded onto an Isolute® SCX-2 cartridge. The cartridge was washed with MeOH and the product eluted with 0.5 M NH$_3$ in MeOH, further purification by column chromatography (Si—PCC, gradient 2-12% 2M NH$_3$/MeOH in DCM) afforded 407 as a white solid (8 mg, 34%). Analytical data shows the product to be a mixture of diastereomers (ratio ~1:1) which could be separated. LCMS (Method K): R$_T$ 2.59 & 2.62 min [M+H]$^+$ 352. $^1$H NMR (CD$_3$OD, 400 MHz): 8.25 & 8.24 (1H, 2 s), 8.10 & 8.08 (1H, 2 s), 7.39-7.35 (1H, m), 6.96-6.91 (1H, m), 5.93 & 5.82 (1H, 2 bs), 5.26-5.21 & 4.93-4.87 (1H, 2 m), 3.09-3.03 (1H, m), 2.97-2.88 (1H, m), 2.27-2.21 (1H, m), 2.15-2.03 (1H, m), 1.83 & 1.78 (3H, 2 d, J=6.9 Hz), 1.45 & 1.41 (3H, 2 d, J=6.7 Hz)

Example 408

4-amino-6-[[(1S)-1-[6-fluoro-1-isopropyl-7-(2-pyridyl)benzimidazol-2-yl]ethyl]amino]pyrimidine-5-carbonitrile 408

(S)-1-(6-Fluoro-1-isopropyl-7-pyridin-2-yl-1H-benzoimidazol-2-yl)ethylamine (0.166 g, 0.56 mmol), 4-amino-6-chloropyrimidine-5-carbonitrile (86 mg, 0.56 mmol) and DIPEA (497 μL, 2.78 mmol) in IPA (5 mL) were added and the reaction mixture heated at 90° C. for 16 h. The reaction mixture was concentrated in vacuo and the resultant residue purified by flash chromatography (SiO$_2$, eluting with 0-10% methanol in DCM) to give 408 as a white solid (140 mg, 61%). LCMS (Method K): R$_T$ 3.28 min [M+H]$^+$ 417. $^1$H NMR (DMSO-d$_6$, 400 MHz): δ 8.70 (1H, ddd, J=4.8, 1.7, 0.8 Hz), 7.99 (1H, s), 7.93 (1H, td, J=7.8, 1.8 Hz), 7.67 (1H, dd, J=8.8, 4.9 Hz), 7.61 (1H, d, J=7.6 Hz), 7.48 (1H, ddd, J=7.6, 4.8, 1.2 Hz), 7.29 (3H, br s), 7.12 (1H, dd, J=10.3, 8.8 Hz), 5.64 (1H, sept, J=7.1 Hz), 4.01-3.89 (1H, m), 1.55 (3H, d, J=6.6 Hz), 1.27-1.11 (6H, m)

Example 409

N-[(1S)-1-[6-fluoro-1-isopropyl-7-(2-pyridyl)benzimidazol-2-yl]ethyl]-9H-purin-6-amine 409

(S)-1-(6-Fluoro-1-isopropyl-7-pyridin-2-yl-1H-benzoimidazol-2-yl)ethylamine (0.18 g, 0.6 mmol), 6-chloro-9-(tetrahydropyran-2-yl)-9H-purine (145 mg, 0.60 mmol) and DIPEA (543 μL, 3.0 mmol) were added and the reaction mixture heated at 90° C. for 16 hours. The reaction mixture was loaded onto an SCX column to remove the THP group. The column was washed with MeOH and the product was eluted with 2M NH$_3$ in MeOH. The product fractions were collected, concentrated in vacuo and the resultant residue was subjected to flash chromatography (SiO$_2$, eluting with 0-10% methanol in DCM) to give 409 as a white solid (23 mg, 10%). LCMS (Method K): R$_T$ 2.94 min [M+H]$^+$ 417. $^1$H NMR (DMSO-d$_6$, 400 MHz): δ 12.69 (1H, br s), 8.69 (1H, d, J=4.4 Hz), 8.17 (1H, br s), 8.13 (1H, s), 7.93 (1H, td, J=7.8, 1.8 Hz), 7.66 (1H, dd, J=8.8, 5.0 Hz), 7.64 (1H, br s), 7.62 (1H, d, J=7.8 Hz), 7.47 (1H, ddd, J=7.7, 4.9, 1.1 Hz), 7.11 (1H, dd, J=10.2, 8.9 Hz), 5.90-5.78 (1H, m), 4.11-3.87 (1H, m), 1.62 (3H, d, J=6.6 Hz), 1.35-1.15 (6H, m)

Example 410

4-amino-6-[[(1S)-1-[1-ethyl-6-fluoro-7-(2-pyridyl) benzimidazol-2-yl]ethyl]amino]pyrimidine-5-carbonitrile 410

A mixture of (S)-1-(1-ethyl-6-fluoro-7-pyridin-2-yl-1H-benzoimidazol-2-yl)ethylamine (0.203 g, 0.715 mmol), 4-amino-6-chloropyrimidine-5-carbonitrile (0.11 g, 0.715 mmol) and DIPEA (0.65 mL, 3.58 mmol) in IPA (5 mL) was stirred at 80° C. in a sealed microwave tube for 16 hours. After cooling, the mixture was concentrated in vacuo and the residue was purified chromatography, (Si—PPC, gradient 0-5% MeOH in DCM), to give 410 as a solid (0.095 g, 33%). LCMS (Method K): $R_T$ 3.03 min [M+H]+ 403. $^1$H NMR (DMSO-$d_6$, 400 MHz): δ 8.71-8.67 (1H, m), 7.96 (1H, s), 7.92 (1H, td, J=7.8, 1.9 Hz), 7.73 (1H, d, J=7.7 Hz), 7.70-7.62 (2H, m), 7.47 (1H, ddd, J=7.7, 5.0, 1.1 Hz), 7.25 (2H, br s), 7.12 (1H, dd, J=10.4, 8.8 Hz), 5.60 (1H, quin, J=7.2 Hz), 3.80-3.67 (2H, m), 1.55 (3H, d, J=6.8 Hz), 0.69 (3H, t, J=7.1 Hz)

Example 411

4-amino-6-[[(1S)-1-[6-fluoro-1-methyl-7-(2-pyridyl) benzimidazol-2-yl]ethyl]amino]pyrimidine-5-carbonitrile 411

(S)-1-(6-Fluoro-1-methyl-7-pyridin-2-yl-1H-benzoimidazol-2-yl)ethylamine (0.093 g, 0.35 mmol), 4-amino-6-chloropyrimidine-5-carbonitrile (53 mg, 0.35 mmol) and DIPEA (313 µL, 1.72 mmol) in IPA (5 mL) were added and the reaction mixture heated at 90° C. for 16 h. The reaction mixture was concentrated in vacuo and the resultant residue purified by flash chromatography (Si—PPC, gradient 0-10% methanol in DCM) to give 411 as a white solid (95 mg, 72%). LCMS (Method K): $R_T$ 2.76 min [M+H]+ 389. $^1$H NMR (DMSO-$d_6$, 400 MHz): δ 8.70 (1H, ddd, J=4.8, 1.7, 0.9 Hz), 7.98 (1H, s), 7.91 (1H, td, J=7.8, 1.8 Hz), 7.71-7.64 (2H, m), 7.60 (1H, dq, J=7.7, 0.9 Hz), 7.46 (1H, ddd, J=7.6, 4.9, 1.0 Hz), 7.26 (2H, br s), 7.11 (1H, dd, J=10.5, 8.8 Hz), 5.59 (1H, quin, J=7.3 HZ), 3.09 (3H, s), 1.53 (3H, d, J=6.8 Hz)

Example 412

N-[(1S)-1-[1-ethyl-6-fluoro-7-(2-pyridyl)benzimidazol-2-yl]ethyl]-9H-purin-6-amine 412

A mixture of (S)-1-(1-ethyl-6-fluoro-7-pyridin-2-yl-1H-benzoimidazol-2-yl)ethylamine (0.203 g, 0.715 mmol), 6-chloro-9-(tetrahydropyran-2-yl)-9H-purine (145 mg, 0.60 mmol) and DIPEA (543 µL, 3.0 mmol) were added and the reaction mixture heated at 90° C. for 16 hours. The reaction mixture was loaded onto an SCX column to remove the THP group. The column was washed with MeOH and the product was eluted with 2M NH$_3$ in MeOH. The product fractions were collected, concentrated in vacuo and the resultant residue was subjected to flash chromatography (Si—PPC, gradient 0-7% MeOH in DCM) to give 412 as a white solid (75 mg, 25%). LCMS (Method K): $R_T$ 2.76 min [M+H]+ 403. $^1$H NMR (DMSO, 400 MHz): δ 12.83 (1H, br s), 8.68 (1H, d, J=4.8 Hz), 8.12 (2H, d, J=14.3 Hz), 7.95 (1H, br s), 7.91 (1H, td, J=7.7, 1.7 Hz), 7.68-7.62 (2H, m), 7.46 (1H, d, J=7.2, 5.0 Hz), 7.11 (1H, dd, J=10.4, 9.0 Hz), 5.78-5.67 (1H, m), 3.91-3.71 (2H, m), 1.63 (3H, d, J=6.8 Hz), 0.71 (3H, t, J=6.9 Hz)

Example 413

N-[(1S)-1-[6-fluoro-1-methyl-7-(2-pyridyl)benzimidazol-2-yl]ethyl]-9H-purin-6-amine 413

A mixture of (S)-1-(6-fluoro-1-methyl-7-pyridin-2-yl-1H-benzoimidazol-2-yl)ethylamine (100 mg, 0.37 mmol), 6-chloro-9-(tetrahydropyran-2-yl)-9H-purine (88 mg, 0.37 mmol) and DIPEA (340 µL, 1.85 mmol) in IPA (5 mL) were added and the reaction mixture heated at 90° C. for 16 h. The reaction mixture was loaded onto an SCX column to remove the THP group. The column was washed with MeOH and the product was eluted with 2M NH$_3$ in MeOH. The product fractions were collected, concentrated in vacuo and the resultant residue was subjected to flash chromatography (Si—PPC, gradient 0-5% MeOH in DCM) to give 413 as a white solid (67 mg, 47%). LCMS (Method K): $R_T$ 2.53 min [M+H]+ 389. $^1$H NMR (DMSO-$d_6$, 400 MHz): δ 12.7 (1H, br s), 8.68 (1H, ddd, J=4.8, 1.7, 0.8 Hz), 8.13 (2H, d, J=21.9 Hz), 7.91 (1H, br s), 7.90 (1H, td, J=7.8, 1.8 Hz), 7.65 (1H, dd, J=8.8, 4.8 Hz), 7.60 (1H, tq, J=7.7, 1.1 Hz), 7.44 (1H, ddd, J=7.5, 4.8, 1.1 Hz), 7.10 (1H, dd, J=10.4, 8.8 Hz), 5.82-5.67 (1H, m), 3.15 (3H, s), 1.61 (3H, d, J=6.7 Hz)

Example 414

4-amino-6-[[(1S)-1-[1-cyclopropyl-6-fluoro-7-(3-pyridyl)benzimidazol-2-yl]ethyl]amino]pyrimidine-5-carbonitrile 414

A mixture of 4-amino-6-[(S)-1-(7-bromo-1-cyclopropyl-6-fluoro-1H-benzoimidazol-2-yl)ethylamino]pyrimidine-5-carbonitrile (68 mg, 0.16 mmol), pyridine-3-boronic acid (26 mg, 0.21 mmol), tetrakis(triphenylphosphine)palladium (19 mg, 10 mol %) and caesium carbonate (106 mg, 0.33 mol) in dioxane (3 mL) and H$_2$O (1.5 mL) was purged with argon gas then heated at 140° C., for 30 min, by microwave irradiation. After cooling to RT, the reaction mixture was diluted with MeOH and loaded into an Isolute® SCX-2 cartridge. The cartridge was washed with MeOH followed by 2M NH$_3$/MeOH. The basic fractions were combined, concentrated in vacuo and the resulting residue purified by column chromatography (Si—PCC, gradient 0-10% MeOH in EtOAc) followed by reverse phase HPLC (Phenomenex Gemini 5 µm C18 on a gradient 10-90%, 0.1% NH$_4$OH in acetonitrile/water) to afford 414 as a white solid (29 mg, 43%). LCMS (Method K): $R_T$ 2.80 min [M+H]+ 415.06. $^1$H NMR (CDCl$_3$ 400 MHz): δ 8.74 (1H, s), 8.66 (1H, dd, J=4.86, 1.69 Hz), 8.17 (1H, s), 7.86 (1H, s), 7.70 (1H, dd, J=8.79, 4.66 Hz), 7.43 (1H, dd, J=7.83, 4.85 Hz), 7.13 (1H, dd, J=10.24, 8.78 Hz), 6.45-6.14 (1H, br m), 5.97 (1H, m), 5.36 (2H, s), 2.95 (1H, m), 1.70 (3H, d, J=6.73 Hz), 1.02-0.09 (4H, m)

Example 415

4-amino-6-[[(1S)-1-(1-cyclopropyl-6-fluoro-7-phenyl-benzimidazol-2-yl)ethyl]amino]pyrimidine-5-carbonitrile 415

A mixture of 4-amino-6-[(S)-1-(7-bromo-1-cyclopropyl-6-fluoro-1H-benzoimidazol-2-yl)ethylamino]pyrimidine-5-carbonitrile (68 mg, 0.16 mmol), phenylboronic acid (26 mg, 0.21 mmol), tetrakis(triphenylphosphine)palladium (19 mg, 10 mol %) and caesium carbonate (106 mg, 0.33 mol) in dioxane (3 mL) and H₂O (1.5 mL) was purged with argon gas then heated at 140° C., for 30 min, by microwave irradiation. After cooling to RT, the reaction mixture was diluted with MeOH and loaded into an Isolute® SCX-2 cartridge. The cartridge was washed with MeOH followed by 2M NH₃/MeOH. The basic fractions were combined, concentrated in vacuo and the resulting residue purified by column chromatography (Si—PCC, gradient 0-100% EtOAc in DCM) followed by recrystallisation from EtOAc/cyclohexane to afford 415 as a white solid (10 mg, 15%). LCMS (Method K): $R_T$ 4.08 min [M+H]⁺ 414.08. ¹H NMR (CDCl₃ 400 MHz): δ 8.17 (1H, s), 7.65 (1H, dd, J=8.89, 4.63 Hz), 7.43-7.42 (5H, m), 7.09 (1H, dd, J=10.20, 8.76 Hz), 6.35 (1H, d, J=7.83 Hz), 5.96 (1H, m), 5.32 (2H, s), 2.89-2.83 (1H, m), 1.69 (3H, d, J=6.74 Hz), 0.79 (1H, m), 0.61 (1H, m), 0.47 (1H, m), 0.23 (1H, m)

Example 416

4-amino-6-[[(1S)-1-[6-fluoro-1-(2-methylpyrazol-3-yl)benzimidazol-2-yl]ethyl]amino]pyrimidine-5-carbonitrile 416

A mixture of (S)-1-[6-fluoro-1-(2-methyl-2H-pyrazol-3-yl)-1H-benzoimidazol-2-yl]ethylamine, (0.093 g, 0.359 mmol), 4-amino-6-chloropyrimidine-5-carbonitrile (0.078 g, 0.502 mmol) and DIPEA (0.12 mL, 0.646 mmol) in IPA (2 mL) was stirred at 80° C. in a sealed microwave tube for 16 h. After cooling, mixture was loaded onto an Isolute® SCX-2 cartridge which was washed with MeOH and the product eluted with 2M NH₃/MeOH then concentrated in vacuo. Residue was purified by silica gel chromatography eluting with 100% DCM—8% (2M ammonia in methanol) in DCM to give 416 as a white solid (0.107 g, 79%). LCMS (Method K): $R_T$ 3.16, 3.28 min [M+H]⁺ 378.0. ¹H NMR (DMSO-d₆, 400 MHz): δ 7.92-7.87 (1H, s), 7.87-7.84 (1H, m), 7.75-7.75 (1H, m), 7.60-7.54 (1H, m), 7.30-7.19 (3H, m), 6.96 (1H, m), 6.61-6.44 (1H, m), 5.47-5.38 (1H, m), 3.59-3.53 (3H, m), 3.17 (0H, d, J=5.25 Hz), 1.58-1.51 (3H, m). Signals split due to presence of rotamers/tautomers Example 417

N-[(1S)-1-[6-fluoro-1-(2-methylpyrazol-3-yl)benzimidazol-2-yl]ethyl]-9H-purin-6-amine 417

A mixture of (S)-1-[6-fluoro-1-(2-methyl-2H-pyrazol-3-yl)-1H-benzoimidazol-2-yl]-ethylamine, (0.093 g, 0.36 mmol), 6-chloro-9-(tetrahydropyran-2-yl)-9H-purine (0.119 g, 0.50 mmol) and DIPEA (0.12 mL, 0.65 mmol) in IPA (2 mL) was stirred at 80° C. in a sealed tube for 16 h. After cooling, the reaction mixture was concentrated in vacuo and the residue purified by chromatography (SiO₂, 0-8% (2M ammonia in methanol) in DCM). The product was dissolved in methanol (4 mL) and treated with HCl/dioxane (4M, 0.6 mL, 2.4 mmol) then stirred for 30 minutes. The resulting mixture was concentrated in vacuo and residue loaded onto an Isolute® SCX-2 cartridge and washed with MeOH. The product was eluted with 2M NH₃/MeOH then concentrated in vacuo to give 417 as a white solid (0.078 g, 58%). LCMS (Method K): $R_T$ 2.79, 2.95 min [M+H]⁺ 378.0. ¹H NMR (DMSO-d₆, 400 MHz): δ 12.91-12.00 (1H, m), 8.30-7.81 (3H, m), 7.78-7.71 (1H, m), 7.50 (1H, s), 7.23-7.03 (1H, m), 7.03-6.92 (1H, m), 6.69-6.51 (1H, m), 5.60-5.22 (1H, m), 3.62-3.55 (3H, m), 1.65-1.54 (3H, m). Signals split due to presence of rotamers/tautomers Example 418

4-amino-6-[[(1S)-1-[6-fluoro-1-(1-methylpyrazol-4-yl)benzimidazol-2-yl]ethyl]amino]pyrimidine-5-carbonitrile 418

A mixture of (S)-1-[6-fluoro-1-(1-methyl-1H-pyrazol-4-yl)-1H-benzoimidazol-2-yl]-ethylamine, (0.055 g, 0.21 mmol), 4-amino-6-chloropyrimidine-5-carbonitrile (0.046 g, 0.30 mmol) and DIPEA (0.07 mL, 0.38 mmol) in IPA (1.5 mL) was stirred at 80° C. in a sealed tube for 16 h. After cooling, the reaction mixture was concentrated in vacuo and the residue purified by chromatography (SiO₂, 0-10% (2M ammonia in methanol) in DCM) to give 418 as a white solid (0.060 g, 75%). LCMS (Method K): $R_T$ 2.94 min [M+H]⁺ 378.0. ¹H NMR (DMSO-d₆, 400 MHz): δ 8.12 (1H, s), 7.96 (1H, s), 7.70-7.60 (3H, m), 7.25 (2H, s), 7.09 (1H, m), 6.96 (1H, m), 5.46 (1H, m), 3.88 (3H, s), 1.51 (3H, d, J=6.85 Hz)

Example 419

N-[(1S)-1-[6-fluoro-1-(1-methylpyrazol-4-yl)benzimidazol-2-yl]ethyl]-9H-purin-6-amine 419

A mixture of (S)-1-[6-fluoro-1-(1-methyl-1H-pyrazol-4-yl)-1H-benzoimidazol-2-yl]ethylamine, (0.055 g, 0.21 mmol), 6-chloro-9-(tetrahydropyran-2-yl)-9H-purine (0.070 g, 0.30 mmol) and DIPEA (0.07 mL, 0.38 mmol) in IPA (1.5 mL) was stirred at 80° C. in a sealed tube for 16 h. After cooling, the reaction mixture was concentrated in vacuo and the residue purified by chromatography (SiO₂, 0-10% (2M ammonia in methanol) in DCM). The product was dissolved in methanol (4 mL) and treated with HCl/dioxane (4M, 0.5 mL, 2.0 mmol) then stirred for 15 minutes. The resulting mixture was concentrated in vacuo and the residue loaded onto an Isolute® SCX-2 cartridge and washed with MeOH then the product eluted with 2M NH₃/MeOH and concentrated in vacuo to give 419 as a white solid (0.050 g, 63%). LCMS (Method K): $R_T$ 2.65 min [M+H]⁺ 378.0. ¹H NMR (DMSO-d₆, 400 MHz): δ 12.90 (1H, s), 8.22-8.03 (3H, m), 7.89-7.81 (1H, m), 7.76 (1H, s), 7.66-7.62 (1H, m), 7.09-7.05 (1H, m), 7.00-6.91 (1H, m), 5.61-5.42 (1H, m), 3.86 (3H, s), 1.57 (3H, d, J=6.84 Hz)

Example 420

4-amino-6-[[(1S)-1-[6-fluoro-1-(2-methoxyethyl)-7-(2-pyridyl)benzimidazol-2-yl]ethyl]amino]pyrimidine-5-carbonitrile 420

A mixture of (S)-1-[6-fluoro-1-(2-methoxyethyl)-7-pyridin-2-yl-1H-benzoimidazol-2-yl]ethylamine (167 mg, 0.53 mmol), 4-amino-6-chloropyrimidine-5-carbonitrile (86 mg, 0.56 mmol) and DIPEA (0.28 mL, 1.6 mmol) in IPA (1 mL) was heated for 16 h at 90° C. After cooling to RT, the volatiles were removed under reduced pressure and the resulting residue loaded onto an Isolute® SCX-2 cartridge. The cartridge was washed with MeOH, followed by 2M NH₃/MeOH. The basic fractions were combined, concentrated in vacuo and the resulting residue was purified by column chromatography (Si—PPC, gradient 0-10% 2M NH₃ in MeOH/DCM) to afford 420 as a white solid (146 mg, 63%). LCMS (Method K): $R_T$ 3.15 min [M+H]⁺ 433. ¹H NMR (DMSO-d₆, 400 MHz): δ 8.73 (1H, ddd, J=5.0, 2.0, 1.0 Hz), 8.03 (1H, s), 7.97 (1H, ddd, J=7.5, 7.5, 2.0 Hz), 7.74 (1H, dd, J=9.0, 5.0 Hz), 7.70-7.66 (2H, m), 7.51 (1H, ddd, J=7.5, 5.0, 1.0 Hz), 7.30 (2H, bs), 7.18 (1H, dd, J=10.5, 9.0), 5.69 (1H, dq, J=6.5, 6.5

Hz), 4.14-4.07 (1H, m), 3.82 (1H, ddd, J=15.0, 5.0, 5.0 Hz), 3.07-2.99 (2H, m), 2.93 (1H, s), 1.59 (3H, d, J=6.5 Hz)

Example 421

4-amino-6-[[(1S)-1-(7-bromo-1-methyl-benzimidazol-2-yl)ethyl]amino]pyrimidine-5-carbonitrile 421

A mixture of (S)-1-(7-bromo-1-methyl-1H-benzoimidazol-2-yl)ethylamine (1 g, 3.9 mmol), 4-amino-6-chloropyrimidine-5-carbonitrile (0.64 g, 4.1 mmol) and DIPEA (2.1 mL, 4.1 mmol) in IPA (7.8 mL) was heated for 16 h at 90° C. After cooling to RT, the reaction mixture was filtered and the solid washed with MeOH and DCM to afford 421 as a cream solid (1.05 g, 72%). LCMS (Method K): $R_T$ 3.27 min [M+H]$^+$ 372 (for $^{79}$Br) $^1$H NMR (DMSO-d$_6$, 400 MHz): δ 8.07 (1H, s), 7.79 (1H, d, J=7.5 Hz), 7.63 (1H, d, J=8.0 Hz), 7.41 (1H, d, J=4.0 Hz), 7.32 (2H, bs), 7.11 (1H, dd, J=8.0, 8.0 Hz), 5.70 (1H, dq, J=7.5, 7.0 Hz), 4.01 (3H, s), 1.60 (3H, d, J=7.0 Hz)

Example 422

4-amino-6-[[(1S)-1-[7-(3-cyanophenyl)-1-methyl-benzimidazol-2-yl]ethyl]amino]pyrimidine-5-carbonitrile 422

A mixture of 4-amino-6-[(S)-1-(7-bromo-1-methyl-1H-benzoimidazol-2-yl)ethylamino]pyrimidine-5-carbonitrile (100 mg, 0.27 mmol), 3-cyanobenzeneboronic acid (51 mg, 0.35 mmol), Pd(PPh$_3$)$_4$ (31 mg, 0.03 mmol) and Cs$_2$CO$_3$ (175 mg, 0.54 mmol) in dioxane (3 mL) and H$_2$O (1.5 mL) was heated for 30 min by microwave irradiation at 140° C. The reaction solution was loaded onto an Isolute® SCX-2 cartridge. The cartridge was washed with MeOH, followed by 2M NH$_3$ in MeOH. The basic fractions were combined and concentrated in vacuo. The resulting residue was purified by column chromatography (Si—PPC, gradient 0-10% 2M NH$_3$ in MeOH/DCM) to afford 422 as a white solid (41 mg, 39%). LCMS (Method K): $R_T$ 3.08 min [M+H]$^+$ 395. $^1$H NMR (DMSO-d$_6$, 400 MHz): δ 8.03 (1H, s), 7.97 (1H, s), 7.94-7.91 (1H, m), 7.82-7.80 (1H, m), 7.72-7.66 (3H, m), 7.32 (2H, bs), 7.26 (1H, dd, J=8.0, 7.5 Hz), 7.07 (1H, dd, J=7.5, 1.0 Hz), 5.65 (1H, dq, J=7.0, 7.0 Hz), 3.29 (3H, s), 1.60 (3H, d, J=7.0 Hz)

Example 423

4-amino-6-[[(1S)-1-[7-(4-cyanophenyl)-1-methyl-benzimidazol-2-yl]ethyl]amino]pyrimidine-5-carbonitrile 423

A mixture of 4-amino-6-[(S)-1-(7-bromo-1-methyl-1H-benzoimidazol-2-yl)ethylamino]pyrimidine-5-carbonitrile (100 mg, 0.27 mmol), 4-cyanobenzeneboronic acid (51 mg, 0.35 mmol), Pd(PPh$_3$)$_4$ (31 mg, 0.03 mmol) and Cs$_2$CO$_3$ (175 mg, 0.54 mmol) in dioxane (3 mL) and H$_2$O (1.5 mL) was heated for 30 min by microwave irradiation at 140° C. The reaction solution was loaded onto an Isolute® SCX-2 cartridge. The cartridge was washed with MeOH, followed by 2M NH$_3$ in MeOH. The basic fractions were combined and concentrated in vacuo. The resulting residue was dissolved in DCM and the fine precipitate filtered and washed with DCM. The filtrate was concentrated in vacuo and purified by column chromatography (Si—PPC, gradient 0-10% 2M NH$_3$ in MeOH/DCM) to afford 423 as a white solid (36 mg, 34%). LCMS (Method K): $R_T$ 2.30 min [M+H]$^+$ 395. $^1$H NMR (DMSO-d$_6$, 400 MHz): δ 8.04 (1H, s), 7.96-7.94 (2H, m), 7.72-7.67 (4H, m), 7.32 (2H, bs), 7.27, (1H, dd, J=8.0, 7.5 Hz), 7.07 (1H, dd, J=7.5, 1.0 Hz), 5.66 (1H, dq, J=7.0, 7.0 Hz), 3.28 (3H, s), 1.60 (3H, d, J=7.0 Hz)

Example 424

4-amino-6-[[(1S)-1-(6-fluoro-1-methyl-7-phenyl-benzimidazol-2-yl)ethyl]amino]pyrimidine-5-carbonitrile 424

A mixture of 4-amino-6-[(S)-1-(7-bromo-6-fluoro-1-methyl-1H-benzoimidazol-2-yl)ethylamino]pyrimidine-5-carbonitrile, (0.10 g, 0.26 mmol), phenylboronic acid (0.041 g, 0.33 mmol), tetrakis(triphenylphosphine)palladium(0) (0.015 g, 0.013 mmol) and caesium carbonate (0.17 g, 0.51 mmol) in dioxane (3 mL) and water (1.5 mL) was placed in a sealed tube and degassed with nitrogen for 5 min, then heated for 30 minutes at 140° C. by microwave irradiation. The resulting mixture was loaded onto an Isolute® SCX-2 cartridge and washed with MeOH then the product eluted with 2M NH$_3$/MeOH. then concentrated in vacuo. The resulting residue was purified by chromatography (SiO$_2$, 0-7% (2M ammonia in methanol) in DCM) then by preparative HPLC (Phenomenex Gemini 5 μm C18 on a 78 min gradient 20-98% 0.1% HCO$_2$H in acetonitrile/water). The relevant fractions were concentrated to approximately ⅓ volume and partitioned between DCM (3×) and saturated aqueous NaHCO$_3$. The combined DCM extracts were dried (Na$_2$SO$_4$) and concentrated in vacuo to give 424 as a white solid (0.058 g, 58%). LCMS (Method K): $R_T$ 3.55 min [M+H]$^+$ 388.0. $^1$H NMR (DMSO-d$_6$, 400 MHz): δ 8.03 (1H, s), 7.66-7.62 (2H, m), 7.52-7.41 (5H, m), 7.30 (2H, s), 7.13 (1H, m), 5.61 (1H, m), 3.15 (3H, s), 1.57 (3H, d, J=6.72 Hz)

Example 425

4-amino-6-[[(1S)-1-[6-fluoro-1-methyl-7-(3-pyridyl) benzimidazol-2-yl]ethyl]amino]pyrimidine-5-carbonitrile 425

A mixture of 4-amino-6-[(S)-1-(7-bromo-6-fluoro-1-methyl-1H-benzoimidazol-2-yl)ethylamino]-pyrimidine-5-carbonitrile, (0.10 g, 0.26 mmol), 3-pyridylboronic acid (0.041 g, 0.33 mmol), tetrakis(triphenylphosphine)palladium(0) (0.015 g, 0.013 mmol) and caesium carbonate (0.17 g, 0.51 mmol) in dioxane (3 mL) and water (1.5 mL) was placed in a sealed tube and degassed with nitrogen for 5 min, then heated for 30 minutes at 140° C. by microwave irradiation. The resulting mixture was loaded onto an Isolute® SCX-2 cartridge then washed with MeOH and the product eluted with 2M NH$_3$/MeOH and concentrated in vacuo. The resulting residue was purified by chromatography (SiO$_2$, 0-10% (2M ammonia in methanol) in DCM) then by preparative HPLC (Phenomenex Gemini 5 μm C18 on a 78 min gradient 20-98% 0.1% HCO$_2$H in acetonitrile/water) to give 425 as a white solid (0.066 g, 66%). LCMS (Method K): $R_T$ 2.50 min [M+H]$^+$ 389.1. $^1$H NMR (DMSO-d$_6$, 400 MHz): δ 8.72-8.64 (2H, m), 8.22-8.03 (1H, m), 7.97-7.90 (1H, m), 7.75-7.65 (2H, m), 7.57-7.53 (1H, m), 7.30 (2H, s), 7.21-7.17 (1H, m), 5.63 (1H, m), 3.19-3.17 (3H, m), 1.58 (3H, d, J=6.72 Hz)

Example 426

4-amino-6-[[(1S)-1-[6-fluoro-7-(1H-indazol-4-yl)-1-methyl-benzimidazol-2-yl]ethyl]amino]pyrimidine-5-carbonitrile 426

A mixture of 4-amino-6-[(S)-1-(7-bromo-6-fluoro-1-methyl-1H-benzoimidazol-2-yl)ethylamino]pyrimidine-5-carbonitrile, (0.10 g, 0.26 mmol), 1H-indazole-4-boronic acid (0.054 g, 0.33 mmol), tetrakis(triphenylphosphine)palladium (0) (0.015 g, 0.013 mmol) and caesium carbonate (0.17 g, 0.51 mmol) in dioxane (3 mL) and water (1.5 mL) was placed in a sealed tube and degassed with nitrogen for 5 minutes, then heated for 30 min at 140° C. by microwave irradiation. 1H-indazole-4-boronic acid (0.054 g, 0.33 mmol) and tetrakis(triphenylphosphine)palladium(0) (0.015 g, 0.01 mmol) were added and the resultant mixture heated for 30 min at 140° C. by microwave irradiation. The resulting mixture was loaded onto an Isolute® SCX-2 cartridge then washed with MeOH and the product eluted with 2M $NH_3$/MeOH and concentrated in vacuo. The residue was purified by preparative HPLC (Phenomenex Gemini 5 μm C18 on a 78 min gradient 20-98% 0.1% $HCO_2H$ in acetonitrile/water) to give 426 as a white solid (0.044 g, 40%). LCMS (Method K): $R_T$ 2.82, 2.99 min [M+H]$^+$ 428.1. $^1H$ NMR (DMSO-$d_6$, 400 MHz): δ 13.30 (1H, s), 8.23-7.98 (1H, m), 7.77-7.60 (4H, m), 7.51-7.48 (1H, m), 7.36-7.24 (2H, m), 7.23-7.08 (2H, m), 5.59-5.54 (1H, m), 3.00 (3H, d, J=8.05 Hz), 1.57 (3H, dd, J=6.69, 1.65 Hz). Signals split due to presence of rotamers/tautomers Example 427

4-amino-6-[[(1S)-1-[6-fluoro-1-methyl-7-(1-methylpyrazol-4-yl)benzimidazol-2-yl]ethyl]amino]pyrimidine-5-carbonitrile 427

A mixture of 4-Amino-6-[(S)-1-(7-bromo-6-fluoro-1-methyl-1H-benzoimidazol-2-yl)ethylamino]-pyrimidine-5-carbonitrile, (0.10 g, 0.26 mmol), 1-methyl-4-(4,4,5,5-tetramethyl-[1,3,2]dioxaborolan-2-yl)-1H-pyrazole (0.069 g, 0.33 mmol), tetrakis(triphenylphosphine)palladium(0) (0.015 g, 0.01 mmol) and caesium carbonate (0.17 g, 0.51 mmol) in dioxane (3 mL) and water (1.5 mL) was placed in a sealed tube and degassed with nitrogen for 5 minutes, then heated for 30 minutes at 140° C. by microwave irradiation. The resulting mixture was loaded onto an Isolute® SCX-2 cartridge then washed with MeOH and the product eluted with 2M $NH_3$/MeOH and concentrated in vacuo. The resulting residue was purified by chromatography ($SiO_2$, 0-10% (2M ammonia in methanol) in DCM) then by preparative HPLC (Phenomenex Gemini 5 μm C18 on a 78 min gradient 20-98% 0.1% $HCO_2H$ in acetonitrile/water) to give 427 as a white solid (0.081 g, 81%). LCMS (Method K): $R_T$ 2.50 min [M+H]$^+$ 392.1. $^1H$ NMR (DMSO-$d_6$, 400 MHz): δ 8.24 (1H, s), 7.92 (1H, s), 7.67-7.59 (2H, m), 7.31 (2H, s), 7.12-7.08 (1H, m), 5.64 (1H, m), 3.93 (3H, s), 3.17 (3H, s), 1.58 (3H, d, J=6.74 Hz)

Example 428

4-amino-6-[[(1S)-1-[6-fluoro-1-methyl-7-(1H-pyrazol-4-yl)benzimidazol-2-yl]ethyl]amino]pyrimidine-5-carbonitrile 428

A mixture of 4-Amino-6-[(S)-1-(7-bromo-6-fluoro-1-methyl-1H-benzoimidazol-2-yl)ethylamino]-pyrimidine-5-carbonitrile, (0.10 g, 0.26 mmol), 4-(4,4,5,5-tetramethyl-[1,3,2]dioxaborolan-2-yl)-1H-pyrazole (0.065 g, 0.33 mmol), tetrakis(triphenylphosphine)palladium(0) (0.015 g, 0.01 mmol) and caesium carbonate (0.17 g, 0.51 mmol) in dioxane (3 mL) and water (1.5 mL) was placed in a sealed tube and degassed with nitrogen for 5 minutes, then heated for 40 minutes at 140° C. by microwave irradiation. 4-(4,4,5,5-Tetramethyl-[1,3,2]dioxaborolan-2-yl)-1H-pyrazole (0.10 g, 0.52 mmol) and tetrakis(triphenylphosphine)palladium(0) (0.015 g, 0.01 mmol) were added and the resultant mixture heated for 80 minutes at 140° C. by microwave irradiation. The resulting mixture was loaded onto an Isolute® SCX-2 cartridge then washed with MeOH and the product eluted with 2M $NH_3$/MeOH then concentrated in vacuo. The residue was purified by chromatography eluting with ($SiO_2$, 0-10% (2M ammonia in methanol) in DCM) then by preparative HPLC (Phenomenex Gemini 5 μm C18 on a 78 min gradient 20-98% 0.1% $HCO_2H$ in acetonitrile/water) to give 428 as a white solid (0.019 g, 20%). LCMS (Method K): $R_T$ 2.23 min [M+H]$^+$ 378.0. $^1H$ NMR (DMSO-$d_6$, 400 MHz): δ 13.10 (1H, s), 8.28 (1H, s), 8.04 (1H, s), 7.83 (1H, s), 7.66-7.64 (1H, m), 7.60 (1H, dd, J=8.74, 4.77 Hz), 7.31 (2H, s), 7.12-7.06 (1H, m), 5.66-5.61 (1H, m), 3.66 (3H, s), 1.57 (3H, d, J=6.73 Hz)

Example 429

4-amino-6-[[(1S)-1-[6-fluoro-1-methyl-7-(4-pyridyl)benzimidazol-2-yl]ethyl]amino]pyrimidine-5-carbonitrile 429

A mixture of 4-Amino-6-[(S)-1-(7-bromo-6-fluoro-1-methyl-1H-benzoimidazol-2-yl)ethylamino]pyrimidine-5-carbonitrile, (0.10 g, 0.26 mmol), 4-pyridyl boronic acid (0.041 g, 0.33 mmol), tetrakis(triphenylphosphine)palladium(0) (0.015 g, 0.01 mmol) and caesium carbonate (0.17 g, 0.51 mmol) in dioxane (3 mL) and water (1.5 mL) was placed in a sealed tube and degassed with nitrogen for 5 minutes, then heated for 40 minutes at 140° C. by microwave irradiation. The resulting mixture was loaded onto an Isolute® SCX-2 cartridge then washed with MeOH and the product eluted with 2M $NH_3$/MeOH then concentrated in vacuo. The residue was purified by chromatography eluting with ($SiO_2$, 0-10% (2M ammonia in methanol) in DCM) then by preparative HPLC (Phenomenex Gemini 5 μm C18 on a 78 min gradient 20-98% 0.1% $HCO_2H$ in acetonitrile/water). The relevant fractions were concentrated to approximately ⅓ volume then partitioned between DCM (3×) and saturated aqueous $NaHCO_3$. The combined DCM extracts were dried ($Na_2SO_4$) and concentrated in vacuo to give 429 as a white solid (0.066 g, 66%). LCMS (Method K): $R_T$ 2.32 min [M+H]$^+$ 389.1. $^1H$ NMR (DMSO-$d_6$, 400 MHz): δ 8.72 (2H, d, J=5.05 Hz), 8.03 (1H, s), 7.71-7.70 (2H, m), 7.53 (2H, d, J=13.97 Hz), 7.31 (2H, s), 7.18 (1H, dd, J=10.45, 8.79 Hz), 5.64 (1H, m), 3.21 (3H, s), 1.58 (3H, d, J=6.74 Hz)

Example 430

N-[(1S)-1-(7-bromo-6-fluoro-1-methyl-benzimidazol-2-yl)ethyl]-9H-purin-6-amine 430

A mixture of (S)-1-(7-Bromo-6-fluoro-1-methyl-1H-benzoimidazol-2-yl)ethylamine, (0.50 g, 1.84 mmol), 6-chloro-9-(tetrahydropyran-2-yl)-9H-purine (0.61 g, 2.57 mmol) and DIPEA (0.60 mL, 3.31 mmol) in IPA (7 mL) was stirred at 85° C. in a sealed tube for 21 h. After cooling, the was mixture partitioned between DCM (3×) and saturated aqueous $NaHCO_3$. The combined DCM extracts were dried ($Na_2SO_4$), concentrated in vacuo and the residue purified by chromatography ($SiO_2$, 0-5% (2M ammonia in methanol) in DCM). The product was dissolved in methanol (15 mL), treated with HCl/dioxane (4M, 2.0 mL, 8.0 mmol) then stirred for 10 minutes. The reaction mixture was concentrated in vacuo and the residue loaded onto an Isolute® SCX-2 cartridge which was washed with MeOH and the product eluted with 2M $NH_3$/MeOH then concentrated in vacuo to give 430 as a white solid (0.45 g, 63%). LCMS (Method K): $R_T$ 3.12 min [M+H]$^+$ 390.0. ¹H NMR (DMSO-d$_6$, 400 MHz): δ 12.99 (1H, s), 8.27-7.97 (3H, m), 7.62 (1H, dd, J=8.72, 4.66 Hz), 7.23-7.16 (1H, m), 5.76 (1H, m), 4.09 (3H, s), 1.67 (3H, d, J=6.76 Hz). Signals split due to presence of tautomers Example 431

N-[(1S)-1-(6-fluoro-1-methyl-7-phenyl-benzimidazol-2-yl)ethyl]-9H-purin-6-amine 431

A mixture of [(S)-1-(7-bromo-6-fluoro-1-methyl-1H-benzoimidazol-2-yl)ethyl]-(9H-purin-6-yl)amine, (0.10 g, 0.26 mmol), phenylboronic acid (0.041 g, 0.33 mmol), tetrakis(triphenylphosphine)palladium(0) (0.015 g, 0.01 mmol) and caesium carbonate (0.17 g, 0.51 mmol) in dioxane (3 mL) and water (1.5 mL) was placed in a sealed tube and degassed with nitrogen for 5 minutes, then heated for 45 minutes at 140° C. by microwave irradiation. The resulting mixture was loaded onto an Isolute® SCX-2 cartridge then washed with MeOH and the product eluted with 2M NH$_3$/MeOH and concentrated in vacuo. The residue was purified by chromatography (SiO$_2$, 0-10% (2M ammonia in methanol) in DCM) then by preparative HPLC (Phenomenex Gemini 5 μm C18 on a 78 min gradient 20-98% 0.1% HCO$_2$H in acetonitrile/water). The relevant fractions were concentrated to approximately ⅓ volume and partitioned between DCM (3×) and saturated aqueous NaHCO$_3$. The combined DCM extracts were dried (Na$_2$SO$_4$) and concentrated in vacuo to give 431 as a white solid (0.075 g, 76%). LCMS (Method K): R$_T$ 3.21 min [M+H]⁺ 388.0. ¹H NMR (DMSO-d$_6$, 400 MHz): δ 12.98 (1H, s), 8.26-8.11 (2H, m), 7.93-7.86 (1H, m), 7.64 (1H, dd, J=8.82, 4.74 Hz), 7.54-7.39 (5H, m), 7.15-7.08 (1H, m), 5.82-5.71 (1H, m), 3.21 (3H, s), 1.65 (3H, d, J=6.74 Hz). Signals split due to presence of tautomers Example 432

4-amino-6-[[(1S)-1-[7-(3,6-dihydro-2H-pyran-4-yl)-6-fluoro-1-methyl-benzimidazol-2-yl]ethyl]amino]pyrimidine-5-carbonitrile 432

A mixture of 4-amino-6-[(S)-1-(7-bromo-6-fluoro-1-methyl-1H-benzoimidazol-2-yl)ethylamino]pyrimidine-5-carbonitrile (122 mg, 0.31 mmol), 4-(4,4,5,5-tetramethyl-[1,3,2]dioxaborolan-2-yl)-3,6-dihydro-2H-pyran (85 mg, 0.41 mmol), tetrakis(triphenylphosphine)palladium (36 mg, 10 mol %) and caesium carbonate (204 mg, 0.63 mol) in dioxane (3 mL) and H$_2$O (1.5 mL) was purged with argon gas then heated at 140° C., for 30 min, by microwave irradiation. After cooling to RT, the reaction mixture was diluted with MeOH and loaded into an Isolute® SCX-2 cartridge. The cartridge was washed with MeOH followed by 2M NH$_3$/MeOH. The basic fractions were combined, concentrated in vacuo and the resulting residue purified by column chromatography (Si—PCC, gradient 0-100% EtOAc in DCM) followed by reverse phase HPLC (Phenomenex Gemini 5 μm C18 on a gradient 5-75%, 0.1% NH$_4$OH in acetonitrile/water) to afford 432 as a white solid (19 mg, 15%). LCMS (Method K): R$_T$ 2.79 min [M+H]⁺ 394.16. ¹H NMR (DMSO-d$_6$, 400 MHz): δ 8.07 (1H, s), 7.69 (1H, m), 7.55 (1H, dd, J=8.76, 4.82 Hz), 7.30 (2H, br s), 7.04 (1H, dd, J=10.42, 8.75 Hz), 5.87 (1H br s), 5.70 (1H, m), 4.24 (2H, s), 3.86 (2H, m), 3.73 (3H, s), 2.45-2.23 (2H, m), 1.58 (3H, d, J=6.72 Hz)

Example 433

N-[(1S)-1-[6-fluoro-1-methyl-7-(4-pyridyl)benzimidazol-2-yl]ethyl]-9H-purin-6-amine 433

A mixture of [(S)-1-(7-bromo-6-fluoro-1-methyl-1H-benzoimidazol-2-yl)ethyl]-(9H-purin-6-yl)amine, (0.10 g, 0.26 mmol), 4-pyridylboronic acid (0.041 g, 0.33 mmol), tetrakis(triphenylphosphine)palladium(0) (0.015 g, 0.01 mmol) and caesium carbonate (0.17 g, 0.51 mmol) in dioxane (3 mL) and water (1.5 mL) was placed in a sealed tube and degassed with nitrogen for 5 minutes, then heated for 45 minutes at 140° C. by microwave irradiation. The resulting mixture was loaded onto an Isolute® SCX-2 cartridge then washed with MeOH and the product eluted with 2M NH$_3$/MeOH and concentrated in vacuo. The residue was purified by chromatography (SiO$_2$, 0-10% (2M ammonia in methanol) in DCM) then by preparative HPLC (Phenomenex Gemini 5 μm C18 on a 78 min gradient 20-98% 0.1% HCO$_2$H in acetonitrile/water) to give 433 as a white solid (0.019 g, 20%). LCMS (Method K): R$_T$ 2.10 min [M+H]⁺ 389.1. ¹H NMR (DMSO-d$_6$, 400 MHz): δ 12.70 (1H, s), 8.70 (2H, s), 8.25-8.13 (2H, m), 7.95 (1H, d), 7.71 (1H, dd, J=8.80, 4.80 Hz), 7.53 (2H, d, J=17.59 Hz), 7.17 (1H, dd, J=10.45, 8.79 Hz), 5.85-5.73 (1H, m), 3.30 (3H, s), 1.66 (3H, d, J=6.75 Hz). Signals split due to presence of tautomers Example 434

4-Amino-6-[1-(6-fluoro-3,4-dihydro-5-oxa-1,2a-diazaacenaphthylen-2-yl)ethylamino]pyrimidine-5-carbonitrile 434

A mixture of 1-(6-fluoro-3,4-dihydro-5-oxa-1,2a-diazaacenaphthylen-2-yl)ethylamine (108 mg, 0.49 mmol), 4-amino-6-chloro-5-cyanopyrimidine (75 mg, 0.49 mmol) and DIPEA (171 μL, 0.98 mmol) in IPA (1 mL) was heated for 18 h at 100° C. After cooling to RT, the volatiles were removed in vacuo and the resulting residue was taken up in MeOH and acidified with TFA, at which point the solution became homogenous. The reaction mixture was passed through a 2 g Isolute® SCX-2 cartridge, eluting with 2M NH$_3$/MeOH. The basic fraction was concentrated in vacuo and the resulting brown residue was purified by column chromatography (Si—PPC, gradient 0-8% 2M NH$_3$/MeOH in DCM) to afford 434 as a pale yellow solid (125 mg, 75%). LCMS (Method K): R$_T$ 2.49 min [M+H]⁺ 340.1. ¹H NMR (DMSO, 400 MHz): δ 8.02 (1H, s), 7.74 (1H, d, J=7.4 Hz), 7.27 (2H, br s), 7.09 (1H, dd, J=8.7, 3.3 Hz), 6.95 (1H, dd, J=12.3, 8.8 Hz), 5.60 (1H, dq, J=7.4, 6.8 Hz), 4.50-4.41 (2H, m), 4.36-4.27 (2H, m), 1.58 (3H, d, J=6.8 Hz)

Example 435

[1-(6-Fluoro-3,4-dihydro-5-oxa-1,2a-diazaacenaphthylen-2-yl)ethyl]-(9H-purin-6-yl)amine 435

Hydrogen chloride, HCl (384 μL of a 4M solution in dioxane) was added to a solution of [1-(6-fluoro-3,4-dihydro-5-oxa-1,2a-diazaacenaphthylen-2-yl)ethyl]-[9-(tetrahydropyran-2-yl)-9H-purin-6-yl]amine (130 mg, 0.31 mmol) in MeOH (1 mL) and the reaction was stirred at RT for 20 min. The crude reaction mixture was passed through a 2 g Isolute® SCX-2 cartridge, eluting with 2M NH$_3$/MeOH. The basic fraction was concentrated in vacuo to give 435 (92 mg, 87%) as a pale yellow solid. LCMS (Method K): R$_T$ 2.28 min [M+H]⁺ 340.0. ¹H NMR (CD$_3$OD, 400 MHz): δ 8.22 (1H, s), 8.06 (1H, s), 7.06 (1H, dd, J=8.9, 3.1 Hz), 6.91 (1H, dd, J=12.0, 8.9 Hz), 5.78 (1H, br s), 4.63-4.38 (4H, m), 1.79 (3H, d, J=7.0 Hz)

Example 436

4-Amino-6-[(S)-1-(5-fluoro-8,9-dihydro-7H-6-oxa-2,9a-diazabenzo[c,d]azulen-1-yl)ethylamino]pyrimidine-5-carbonitrile 436

A mixture of (S)-1-(5-fluoro-8,9-dihydro-7H-6-oxa-2,9a-diazabenzo[c,d]azulen-1-yl)ethylamine (51 mg, 0.22 mmol), 4-amino-6-chloro-5-cyanopyrimidine (34 mg, 0.22 mmol) and DIPEA (77 µL, 0.98 mmol) in IPA (0.5 mL) was heated for 24 h at 100° C. After cooling to RT, the volatiles were removed in vacuo and the resulting residue was taken up in MeOH and acidified with TFA, at which point the solution became homogenous. The reaction mixture was passed through a 2 g Isolute® SCX-2 cartridge, eluting with 2M $NH_3$/MeOH. The basic fraction was concentrated in vacuo and the resulting brown residue was purified by column chromatography (Si—PPC, gradient 0-8% 2M $NH_3$/MeOH in DCM) to afford 436 as a white solid (58 mg, 75%). LCMS (Method K): $R_T$ 2.63 min [M+H]$^+$ 354.0

Example 437

[(S)-1-(5-Fluoro-8,9-dihydro-7H-6-oxa-2,9a-diazabenzo[c,d]azulen-1-yl)ethyl]-(9H-purin-6-yl)amine 437

Hydrogen chloride HCl (250 µL of a 4M solution in dioxane) was added to a solution of [(S)-1-(5-fluoro-8,9-dihydro-7H-6-oxa-2,9a-diazabenzo[c,d]azulen-1-yl)ethyl]-[9-(tetrahydropyran-2-yl)-9H-purin-6-yl]amine (86 mg, 0.20 mmol) in MeOH (1 mL) and the reaction was stirred at RT for 10 min. The crude reaction mixture was passed through a 2 g Isolute® SCX-2 cartridge, eluting with 2M $NH_3$/MeOH. The basic fraction was concentrated in vacuo to give 437 (65 mg, 92%) as a white solid. LCMS (Method K): $R_T$ 2.40 min [M+H]$^+$ 354.0. $^1$H NMR (DMSO, 400 MHz): δ 12.93 (1H, s), 8.19 (1H, br s), 8.08 (1H, s), 7.92-7.7.80 (1H, m), 7.11 (1H, dd, J=8.6, 3.9 Hz), 7.01 (1H, dd, J=11.7, 8.6 Hz), 5.79 (1H, br s), 4.42-4.26 (4H, m), 2.34-2.27 (2H, m), 1.63 (3H, d, J=6.6 Hz)

Example 438

4-Amino-6-[(S)-1-(R)-6-fluoro-3-methyl-3,4-dihydro-5-oxa-1,2a-diazaacenaphthylen-2-yl)ethylamino]pyrimidine-5-carbonitrile 438

A mixture of (S)-1-((R)-6-fluoro-3-methyl-3,4-dihydro-5-oxa-1,2a-diazaacenaphthylen-2-yl)ethylamine (62 mg, 0.26 mmol), 4-amino-6-chloro-5-cyanopyrimidine (41 mg, 0.26 mmol) and DIPEA (91 µL, 0.52 mmol) in IPA (1 mL) was heated for 18 h at 100° C. After cooling to RT, the volatiles were removed in vacuo and the resulting brown residue was purified by column chromatography (Si—PPC, gradient 0-8% 2M $NH_3$/MeOH in DCM) to afford 438 as a white solid (77 mg, 84%). LCMS (Method K): $R_T$ 2.74 min [M+H]$^+$ 354.1. $^1$H NMR (DMSO, 400 MHz): δ 7.98 (1H, s), 7.07 (1H, dd, J=8.6, 3.0 Hz), 6.93 (1H, dd, J=12.1, 8.6 Hz), 5.77 (1H, q, J=7.0 Hz), 4.84-4.81 (1H, m), 4.46 (1H, dd, J=11.4, 1.3 Hz), 4.22 (1H, dd, J=11.4, 2.2 Hz), 1.67 (3H, d, J=7.0 Hz), 1.47 (3H, d, J=6.6 Hz)

Example 439

[(S)-1-((R)-6-Fluoro-3-methyl-3,4-dihydro-5-oxa-1,2a-diazaacenaphthylen-2-yl)ethyl](9H-purin-6-yl)amine 439

HCl (260 µL of a 4M solution in dioxane) was added to a solution of [(S)-1-((R)-6-fluoro-3-methyl-3,4-dihydro-5-oxa-1,2a-diazaacenaphthylen-2-yl)ethyl][9-(tetrahydropyran-2-yl)-9H-purin-6-yl]amine (93 mg, 0.21 mmol) in MeOH (1 mL) and the reaction was stirred at RT for 30 min. The crude reaction mixture was passed through a 2 g Isolute® SCX-2 cartridge, eluting with 2M $NH_3$/MeOH. The basic fraction was concentrated in vacuo to give 439 (71 mg, 96%) as a white solid. LCMS (Method K): $R_T$ 2.50 min [M+H]$^+$ 354.0. $^1$H NMR (CD$_3$OD, 400 MHz): δ 8.21 (1H, s), 8.07 (1H, s), 7.07 (1H, dd, J=8.8, 3.1 Hz), 6.93 (1H, dd, J=11.9, 8.8 Hz), 5.89 (1H, br s), 4.88 (1H, qdd, J=6.6, 2.3, 1.6 Hz), 4.45 (1H, dd, J=11.8, 1.6 Hz), 4.22 (1H, dd, J=11.8, 2.3 Hz), 1.76 (3H, d, J=7.0 Hz), 1.44 (3H, d, J=6.6 Hz)

Example 440

4-Amino-6-[(S)-1-((S)-6-fluoro-3-methyl-3,4-dihydro-5-oxa-1,2a-diazaacenaphthylen-2-yl)ethylamino]pyrimidine-5-carbonitrile 440

A mixture of (S)-1-((S)-6-fluoro-3-methyl-3,4-dihydro-5-oxa-1,2a-diazaacenaphthylen-2-yl)ethylamine (86 mg, 0.36 mmol), 4-amino-6-chloro-5-cyanopyrimidine (56 mg, 0.36 mmol) and DIPEA (125 µL, 0.92 mmol) in IPA (1 mL) was heated for 18 h at 100° C. After cooling to RT, the volatiles were removed in vacuo and the resulting brown residue was purified by column chromatography (Si—PPC, gradient 0-5% 2M $NH_3$/MeOH in DCM) to afford 440 as a white solid (100 mg, 79%). LCMS (Method K): $R_T$ 2.86 min [M+H]$^+$ 354.1. $^1$H NMR (DMSO, 400 MHz): δ 8.01 (1H, s), 7.08 (1H, dd, J=8.8, 3.1 Hz), 6.94 (1H, dd, J=12.3, 8.8 Hz), 5.67 (1H, q, J=7.0 Hz), 5.04 (1H, qdd, J=6.6, 2.6, 1.7 Hz), 4.47 (1H, dd, J=11.9, 1.7 Hz), 4.20 (1H, dd, J=11.9, 2.6 Hz), 1.71 (3H, d, J=7.0 Hz), 1.45 (3H, d, J=6.6 Hz)

Example 441

[(S)-1-((S)-6-Fluoro-3-methyl-3,4-dihydro-5-oxa-1,2a-diazaacenaphthylen-2-yl)ethyl](9H-purin-6-yl)amine 441

Hydrogen chloride HCl (340 µL of a 4M solution in dioxane) was added to a solution of [(S)-1-((S)-6-fluoro-3-methyl-3,4-dihydro-5-oxa-1,2a-diazaacenaphthylen-2-yl)ethyl][9-(tetrahydropyran-2-yl)-9H-purin-6-yl]amine (117 mg, 0.27 mmol) in MeOH (1 mL) and the reaction was stirred at RT for 30 min. The crude reaction mixture was passed through a 2 g Isolute® SCX-2 cartridge, eluting with 2M $NH_3$/MeOH. The basic fraction was concentrated in vacuo to give 441 (88 mg, 92%) as an off-white solid. LCMS (Method K): $R_T$ 2.61 min [M+H]$^+$ 354.0. $^1$H NMR (CD$_3$OD, 400 MHz): δ 8.23 (1H, s), 8.05 (1H, s), 7.08 (1H, dd, J=8.8, 3.1 Hz), 6.93 (1H, dd, J=12.1, 8.8 Hz), 5.77 (1H, br s), 5.19 (1H, qdd, J=6.7, 2.6, 1.8 Hz), 4.48 (1H, dd, J=11.5, 1.8 Hz), 4.20 (1H, dd, J=11.5, 2.6 Hz), 1.80 (3H, d, J=7.0 Hz), 1.47 (3H, d, J=6.7 Hz)

Example 442

4-Amino-6-[(S)-1-(1-cyclopropyl-6-fluoro-7-pyridin-2-yl-1H-benzoimidazol-2-yl)ethylamino]-pyrimidine-5-carbonitrile 442

A mixture of 4-amino-6-[(S)-1-(7-bromo-1-cyclopropyl-6-fluoro-1H-benzoimidazol-2-yl)ethylamino]pyrimidine-5-carbonitrile (70 mg, 0.17 mmol), 2-(tributylstannyl)pyridine (0.06 mL, 0.19 mmol), tetrakis(triphenylphosphine)palladium (19 mg, 10 mol %) and copper(I)-thiophene-2-carboxylate (6 mg, 20 mol %) in dioxane (1 mL) was purged with argon gas then heated at 150° C., for 20 min, in a microwave reactor (Biotage). After cooling to RT, the reaction mixture was diluted with MeOH and loaded onto an Isolute® SCX-2 cartridge. The cartridge was washed with MeOH followed by 2M NH$_3$/MeOH. The basic fractions were combined, concentrated in vacuo and the resulting residue purified by column chromatography (Si—PCC, gradient 0-10% MeOH in EtOAc) to afford 442 as a pale yellow solid (17 mg, 24%). LCMS (Method K): R$_T$ 3.05 min [M+H]$^+$ 415.07. $^1$H NMR (DMSO-d$_6$, 400 MHz): δ 8.72 (1H, ddd, J=4.87, 1.81, 0.94 Hz), 8.02 (1H, s), 7.94 (1H, td, J=7.71, 1.84 Hz), 7.73-7.66 (3H, m), 7.45 (1H, ddd, J=7.59, 4.87, 1.16 Hz), 7.30 (2H, s), 7.16 (1H, dd, J=10.65, 8.75 Hz), 5.84-5.75 (1H, m), 3.02-2.95 (1H, m), 1.61 (3H, d, J=6.76 Hz), 1.25-1.20 (1H, m), 0.79-0.69 (1H, m), 0.52-0.43 (1H, m), 0.41-0.28 (1H, m)

Example 443

(6-Fluoro-1-phenyl-1H-benzoimidazol-2-ylmethyl)-(9H-purin-6-yl)amine 443

(6-Fluoro-1-phenyl-1H-benzoimidazol-2-ylmethyl)[9-(tetrahydropyran-2-yl)-9H-purin-6-yl]amine (0.125 g, 0.28 mmol) in MeOH (2 mL) was treated with 4M HCl in dioxane (0.35 mL). After 15 min at 20° C. the reaction was poured onto a 10 g SCX cartridge which was eluted first with methanol then with 1:1 MeOH/2M NH$_3$ in isopropanol. Product containing fractions were evaporated to a white solid. This was triturated with diethyl ether and dried to give 443 as a white solid, (86 mg, 85%). LCMS (Method C): R$_T$ 3.16 min [M+H]$^+$ 360.02. NMR δ (ppm) (DMSO-d$_6$): 12.9 (1H, s), 8.11 (2H, s), 7.92 (1H, s), 7.66-7.60 (6H, m), 7.09 (1H, td, J=9.31, 2.45 Hz), 6.93 (1H, dd, J=8.96, 2.50 Hz), 4.8 (2H, bs)

Example 901

PI3K Isoform Inhibition Assay (p110 alpha, beta, gamma, delta: α, β, γ, δ)

PI3K enzymatic activity was assayed by measuring the amount of product phosphatidylinositol 3,4,5-phosphate (PIP3) formed from substrate 4,5 phosphatidylinositol 4,5-phosphate (PIP2) using a fluorescence polarization displacement assay. The decrease in fluorescence polarization of a fluorescent PIP$_3$ probe is measured as it is displaced from a PIP$_3$-binding protein GRP-1detector by PI3K-catalyzed product. Assays were conducted in 384-well black Proxi-plates in the presence of 10 mM Tris (pH 7.5), 50 mM NaCl, 4 mM MgCl$_2$, 5% glycerol, 25 μM ATP, 10 μM PIP$_2$ (Echelon Biosciences), 0.05% 3-[(3-cholamidopropyl)dimethylammonio]-1-propanesulfonate, 1 mM dithiothreitol, and 2% DMSO. The kinase reactions were initiated by the addition of 40 ng/mL p110α/p85α, 300 ng/mL p110β/p85α, 40 ng/mL p110γ, or 40 ng/mL p110δ/p85α (Upstate Group, Millipore; Dundee, UK), and 10 μM PIP$_2$ (Echelon Biosciences) to the wells. The reactions were stopped at timepoints that yielded a fixed change in fluorescence polarization consistent with initial rate conditions (typically 30 minutes), by the addition of 12.5 mM EDTA, 100 nM GRP-1 detector, and 5 nM tetramethylrhodamine-labeled PIP$_3$ (TAMRA-PIP$_3$; Echelon Biosciences). After 60 minutes of incubation at room temperature to allow equilibration of labeled and unlabeled PIP3 binding, the parallel and perpendicular components of the fluorescence emissions from each sample were measured at an excitation wavelength of 530 nm and an emission wavelength of 590 nm using an Envision fluorescent plate reader with a rhodamine filter (PerkinElmer Life and Analytical Sciences; Wellesley, Mass.). The assay is capable of detecting 0.1-2.0 μM PIP$_3$ product. The IC$_{50}$ values were obtained by fitting the dose-dependent inhibition data to a 4-parameter equation using Assay Explorer software (MDL, San Ramon, Calif.).

Alternatively, inhibition of PI3K was determined in a radiometric assay using purified, recombinant enzyme and ATP at a concentration of 1 uM. The Formula I compound was serially diluted in 100% DMSO. The kinase reaction was incubated for 1 h at room temperature, and the reaction was terminated by the addition of PBS. IC$_{50}$ values were subsequently determined using sigmoidal dose-response curve fit (variable slope).

The same protocol may be used to establish IC$_{50}$ values for p110α (alpha) PI3K binding.

Recombinant PI3K p110 isoforms alpha, beta, and delta may be prepared and purified according to US 2008/0275067 from recombinant PI3K heterodimeric complexes consisting of a p110 catalytic subunit and a p85 regulatory subunit overexpressed using the BAC-TO-BAC® HT baculovirus expression system (GIBCO/BRL), and then purified for use in biochemical assays. The four Class I PI 3-kinases are cloned into baculovirus vectors as follows:

p110 delta: A FLAG™-tagged (Eastman Kodak Co., U.S. Pat. No. 4,703,004; U.S. Pat. No. 4,782,137; U.S. Pat. No. 4,851,341) version of human p110.delta (Chantry et al., J. Biol. Chem. (1997) 272:19236-41) is subcloned using standard recombinant DNA techniques into the BamHI-XbaI site of the insect cell expression vector pFastbac HTb (Life Technologies, Gaithersburg, Md.), such that the clone is in frame with the His tag of the vector.

p110 alpha: Similar to the method used for p110 delta, described above, a FLAG™-tagged version of p110 alpha (Volinia et al (1994) Genomics, 24(3):427-77) was subcloned in BamH1-HindIII sites of pFastbac HTb (Life Technologies) such that the clone was in frame with the His tag of the vector.

p110 beta: A p110 beta (see Hu et al (1993) Mol. Cell. Biol., 13:7677-88) clone was amplified from the human MARATHON™ Ready spleen cDNA library (Clontech, Palo Alto Calif.) according to the manufacturer's protocol using the specified primers.

The p110 delta binding IC$_{50}$ values and delta/alpha selectivity of selected compounds from Table 1 include:

| Compound No. | p110 delta IC50 (micromolar) | IC50 p110 alpha/IC50 p110 delta (greater than or equal to, ≥) |
| --- | --- | --- |
| 101 | 0.0523 | 40 |
| 102 | 0.0091 | 230 |
| 103 | 0.033 | 64 |
| 106 | 0.189 | 11 |
| 114 | 0.0201 | 104 |
| 115 | 0.0137 | 153 |
| 119 | 0.00159 | 1320 |
| 120 | 0.00446 | 470 |
| 123 | 0.000854 | 2459 |
| 128 | 0.0362 | 58 |
| 129 | 0.0634 | 33 |
| 139 | 0.302 | 7 |
| 142 | 0.278 | 8 |
| 143 | 0.0879 | 24 |

Example 902

Collagen Induced Arthritis Efficacy Test

The efficacy of Formula I compound inhibitors of PI3K delta to inhibit the induction and/or progression of collagen induced arthritis was tested in mice. DBA1/J male mice (Jackson Labs; 5-6 weeks of age) are acclimatized for one week and are then injected intra-dermally at the base of the tail with 0.1 ml of an emulsion of Bovine Type II Collagen (100 mg) and an equal volume of Complete Freunds Adjuvant (200 mg *Mycobacterium tuberculosis*). Three weeks later, mice are injected intra-dermally at the base of the tail with 0.1 ml of an emulsion of Bovine Type II Collagen (100 mg) and an equal volume of Incomplete Freunds Adjuvant for boost. Dosing generally starts as soon as animals display signs of joint inflammation or clinical score 1-2.

All mice are evaluated 2-3 times a week for arthritis using a macroscopic scoring system for each paw. At the end of the experiment clinical scores are obtained to evaluate the intensity of edema in the four paws. A score of 0 to 4 is assigned to each paw. Animals are scored 0 when no inflammatory signs (swelling and redness) are observed in any of the small joints (intraphalangeal, metacarpophalangeal, metatarsophalangeal) or large joints (wrist/carpus, ankle/tarsus). Animals are scored 1 when very slight to slight inflammation was observed (swelling and/or redness of paw or one digit), 2 moderate edema (swelling in two or more joint), 3 severe edema (gross swelling of the paw with more than two joints involved), and 4 when very severe edema (severe arthritis of the entire paw and digits) is present. The arthritic index for each mouse is evaluated by adding the four scores of the individual paws, giving a maximum score of 16. Plasma and serum samples are taken at 1 hour (orbital bleed) post dose and 24 hrs (cardiac puncture) post dose. Samples are stored at −20° C. until analysis. At termination, the hind paws are transected at the distal tibia, just proximal to the tarsal joint. The left and right hind paws are placed in the histology cassettes individually and fixed in 10% formalin. These paws are sent to histology dept for further process.

Materials: Bovine Type II collagen, immunization grade, 2 mg/ml (5 ml/vial) in 0.05 M acetic acid (solution), store at −20° C., from Chondrex, LLC, Seattle, Wash. Adjuvant complete H37 Ra, 6×10 ml/box, contains 1 mg/ml *Mycobacterium tuberculosis*. For use in animal immunological studies, for laboratory use, store at +4° C., from Difco Laboratories, Detroit, Mich. 48232-7058 USA. Adjuvant Incomplete H37 Ra, 6×10 ml/box: For use in animal immunological studies, for laboratory use, store at +4° C., from Difco Laboratories.

Example 903

CD69 Whole Blood Assay

Human blood is obtained from healthy volunteers, with the following restrictions: 1 week drug-free, non-smokers. Blood (approximately 20 mls to test 8 compounds) is collected by venipuncture into Vacutainer tubes with sodium heparin.

Cynomolgus monkey blood is obtained courtesy of the LAT group from monkeys not previously exposed to, or after a washout period from, chemical dosing. Additional cyno blood draws may be collected during the course of pharmacokinetic or toxicology studies. Blood (25-30 mls for naïve monkeys or 3-4 mls from monkeys on studies requiring repeated draws) is collected by venipuncture into Vacutainer tubes with sodium heparin.

Solutions of Formula I compounds at 1000 or 2000 µM in PBS (20×), are diluted by three-fold serial dilutions in 10% DMSO in PBS for a nine point dose-response curve. An aliquot of 5.5 µl of each compound is added in duplicate to a 2 ml 96-well plate; 5.5 µl of 10% DMSO in PBS is added as control and no-stimulus wells. Human whole blood—HWB (100 µl) is added to each well. After mixing the plates are incubated at 37° C., 5% $CO_2$, 100% humidity for 30 minutes.

Goat F(ab')2 anti-human IgM (10 µl of a 500 µg/ml solution, 50 µg/ml final) is added to each well (except the no-stimulus wells) with mixing and the plates are incubated for an additional 20 hours. At the end of the 20 hour incubation, samples are incubated with fluorescent labeled antibodies for 30 minutes, at 37° C., 5% $CO_2$, 100% humidity. Include induced control, unstained and single stains for compensation adjustments and initial voltage settings. Samples are then lysed with Pharmingen Lyse according to the manufacturer's instructions. Samples are then transferred to a 96 well plate suitable to be run on the AMS 96 well system on the BD Calibur FACs machine. Data acquired and Mean Fluorescence Intensity values were obtained using Cell Quest Software. Results are initially analyzed by FACS analysis software (Flow Jo). The IC50 for test compounds is defined as the concentration which decreases by 50% the percent positive of CD69 cells that are also CD20 positive stimulated by anti-IgM (average of 8 control wells, after subtraction of the average of 8 wells for the no-stimulus background). The 1050 values are calculated by ActivityBase using Xlfit version 3, equation 201.

The 1050 values of selected compounds from Table 1 in the CD69 Whole Blood Assay include:

| Compound No. | IC50 (micromolar) |
| --- | --- |
| 114 | 0.0834 |
| 123 | 0.0291 |
| 124 | 0.0671 |
| 138 | 0.0876 |
| 160 | 0.179 |

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents a) may be considered to fall within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

We claim:
1. A compound selected from the group consisting of:
   9-((1-phenyl-1H-benzo[d]imidazol-2-yl)methyl)-9H-purin-6-amine;
   4-amino-8-((1-phenyl-1H-benzo[d]imidazol-2-yl)methyl)pyrido[2,3-d]pyrimidin-5(8H)-one;
   7-((1-phenyl-1H-benzo[d]imidazol-2-yl)methyl)-7H-pyrrolo[2,3-d]pyrimidin-4-amine;
   5-iodo-7-((1-phenyl-1H-benzo[d]imidazol-2-yl)methyl)-7H-pyrrolo[2,3-d]pyrimidin-4-amine;
   3-iodo-1-((1-phenyl-1H-benzo[d]imidazol-2-yl)methyl)-1H-pyrazolo[3,4-d]pyrimidin-4-amine;
   3-methyl-1-((1-phenyl-1H-benzo[d]imidazol-2-yl)methyl)-1H-pyrazolo[3,4-d]pyrimidin-4-amine;
   3-(4-amino-1-((1-phenyl-1H-benzo[d]imidazol-2-yl)methyl)-1H-pyrazolo[3,4-d]pyrimidin-3-yl)prop-2-yn-1-ol;
   3-(4-amino-1-((1-phenyl-1H-benzo[d]imidazol-2-yl)methyl)-1H-pyrazolo[3,4-d]pyrimidin-3-yl)-5-fluorophenol;

3-(1H-indol-3-yl)-1-((1-phenyl-1H-benzo[d]imidazol-2-yl)methyl)-1H-pyrazolo[3,4-d]pyrimidin-4-amine;

4-(4-amino-1-((1-phenyl-1H-benzo[d]imidazol-2-yl)methyl)-1H-pyrazolo[3,4-d]pyrimidin-3-yl)-2-fluorophenol;

N-(6-(4-amino-1-((1-phenyl-1H-benzo[d]imidazol-2-yl)methyl)-1H-pyrazolo[3,4-d]pyrimidin-3-yl)benzo[d]thiazol-2-yl)acetamide;

1-((1-phenyl-1H-benzo[d]imidazol-2-yl)methyl)-1H-pyrazolo[3,4-d]pyrimidin-6-amine;

9-((3-phenyl-1H-indol-2-yl)methyl)-9H-purin-6-amine;

9-((3-phenylbenzofuran-2-yl)methyl)-9H-purin-6-amine;

1-((3-phenylbenzo[b]thiophen-2-yl)methyl)-1H-pyrazolo[3,4-d]pyrimidin-4-amine;

9-((3-phenylbenzo[b]thiophen-2-yl)methyl)-9H-purin-6-amine; and 9-((3-o-tolylbenzo[b]thiophen-2-yl)methyl)-9H-purin-6-amine.

2. A pharmaceutical composition comprised of a compound of claim 1 and a pharmaceutically acceptable carrier, glidant, diluent, or excipient.

3. A process for making a pharmaceutical composition which comprises combining a compound of claim 1 with a pharmaceutically acceptable carrier.

* * * * *